US012611442B2

(12) United States Patent
Wooster et al.

(10) Patent No.: US 12,611,442 B2
(45) Date of Patent: Apr. 28, 2026

(54) mRNA ENCODING ENGINEERED CFTR

(71) Applicant: Translate Bio, Inc., Lexington, MA (US)

(72) Inventors: Richard Wooster, Lexington, MA (US); Frank DeRosa, Lexington, MA (US); Lianne Boeglin, Lexington, MA (US); Priyaanka Nanduri, Lexington, MA (US); Anusha Dias, Lexington, MA (US); Khang Anh Tran, Lexington, MA (US)

(73) Assignee: TRANSLATE BIO, INC., Waltham, MA (US)

( * ) Notice: Subject to any disclaimer, the term of this patent is extended or adjusted under 35 U.S.C. 154(b) by 1072 days.

(21) Appl. No.: 17/761,893

(22) PCT Filed: Sep. 17, 2020

(86) PCT No.: PCT/US2020/051277

§ 371 (c)(1),
(2) Date: Mar. 18, 2022

(87) PCT Pub. No.: WO2021/055609

PCT Pub. Date: Mar. 25, 2021

(65) Prior Publication Data

US 2024/0197825 A1 Jun. 20, 2024

Related U.S. Application Data

(60) Provisional application No. 63/021,263, filed on May 7, 2020, provisional application No. 62/984,632, filed on Mar. 3, 2020, provisional application No. 62/903,047, filed on Sep. 20, 2019.

(51) Int. Cl.
*A61K 38/17* (2006.01)
*A61K 48/00* (2006.01)

(52) U.S. Cl.
CPC ........ *A61K 38/177* (2013.01); *A61K 48/0033* (2013.01); *A61K 48/005* (2013.01)

(58) Field of Classification Search
CPC ........ A61K 38/177; A61P 11/00; C12N 15/00
See application file for complete search history.

(56) References Cited

U.S. PATENT DOCUMENTS 2,647,121 A 7/1953 Jacoby
2,717,909 A 9/1955 Kosmin
2,819,718 A 1/1958 Goldman
2,844,629 A 7/1958 William et al.
3,096,560 A 7/1963 Liebig
3,535,289 A 10/1970 Yoshihara et al.
3,614,954 A 10/1971 Mirowski et al.
3,614,955 A 10/1971 Mirowski
3,656,185 A 4/1972 Carpentier
3,805,301 A 4/1974 Liebig
3,945,052 A 3/1976 Liebig
3,995,623 A 12/1976 Blake et al.
4,013,507 A 3/1977 Rembaum
4,072,146 A 2/1978 Howes
4,096,860 A 6/1978 McLaughlin
4,099,528 A 7/1978 Sorenson et al.
4,106,129 A 8/1978 Carpentier et al.
4,134,402 A 1/1979 Mahurkar
4,140,126 A 2/1979 Choudhury
4,180,068 A 12/1979 Jacobsen et al.
4,182,833 A 1/1980 Hicks
4,227,533 A 10/1980 Godfrey
4,284,459 A 8/1981 Patel et al.
4,308,085 A 12/1981 Horhold et al.
4,323,525 A 4/1982 Bornat
4,335,723 A 6/1982 Patel
4,339,369 A 7/1982 Hicks et al.
4,355,426 A 10/1982 MacGregor
4,375,817 A 3/1983 Engle et al.
4,385,631 A 5/1983 Uthmann
4,401,472 A 8/1983 Gerber
4,406,656 A 9/1983 Hattler et al.
4,475,972 A 10/1984 Wong
4,530,113 A 7/1985 Matterson
4,550,447 A 11/1985 Seiler, Jr. et al.
4,562,596 A 1/1986 Kornberg
4,568,329 A 2/1986 Mahurkar
4,571,241 A 2/1986 Christopher
4,601,718 A 7/1986 Possis et al.
4,647,416 A 3/1987 Seiler, Jr. et al.
4,662,382 A 5/1987 Sluetz et al.
4,701,162 A 10/1987 Rosenberg
4,710,169 A 12/1987 Christopher (Continued)

FOREIGN PATENT DOCUMENTS

CA 2518132 A1 3/2006
CA 2807552 A1 2/2012

(Continued)

OTHER PUBLICATIONS

U.S. Appl. No. 60/083,294, filed Apr. 28, 1998, Chen et al.

(Continued)

*Primary Examiner* — Valarie E Bertoglio

(74) *Attorney, Agent, or Firm* — LATHROP GPM LLP; James H. Velema, Esq.

(57) ABSTRACT

The present invention provides, among other things, improved methods and pharmaceutical compositions for treating cystic fibrosis based on codon optimized mRNA encoding an engineered or mutant Cystic Fibrosis Transmembrane Conductance Regulator (CFTR) protein.

10 Claims, 35 Drawing Sheets

Specification includes a Sequence Listing.

(56) References Cited

U.S. PATENT DOCUMENTS

| | | | |
|---|---|---|---|
| 4,720,517 | A | 1/1988 | Ravichandran et al. |
| 4,737,323 | A | 4/1988 | Martin et al. |
| 4,762,915 | A | 8/1988 | Kung et al. |
| 4,782,836 | A | 11/1988 | Alt |
| 4,856,521 | A | 8/1989 | Irnich |
| 4,860,751 | A | 8/1989 | Callaghan |
| 4,878,908 | A | 11/1989 | Martin et al. |
| 4,892,540 | A | 1/1990 | Vallana |
| 4,897,355 | A | 1/1990 | Eppstein et al. |
| 4,920,016 | A | 4/1990 | Allen et al. |
| 4,946,683 | A | 8/1990 | Forssen |
| 4,946,857 | A | 8/1990 | Kanehira et al. |
| 4,960,409 | A | 10/1990 | Catalano |
| 4,966,945 | A | 10/1990 | Drawert et al. |
| 5,024,671 | A | 6/1991 | Tu et al. |
| 5,025,005 | A | 6/1991 | Nomura et al. |
| 5,047,540 | A | 9/1991 | Kamata et al. |
| 5,101,824 | A | 4/1992 | Lekholm |
| 5,104,399 | A | 4/1992 | Lazarus |
| 5,116,360 | A | 5/1992 | Pinchuk et al. |
| 5,138,067 | A | 8/1992 | Kamata et al. |
| 5,151,105 | A | 9/1992 | Kwan-Gett |
| 5,171,678 | A | 12/1992 | Behr et al. |
| 5,176,661 | A | 1/1993 | Evard et al. |
| 5,194,654 | A | 3/1993 | Hostetler et al. |
| 5,200,395 | A | 4/1993 | Eto et al. |
| 5,223,263 | A | 6/1993 | Hostetler et al. |
| 5,261,419 | A | 11/1993 | Osypka |
| 5,264,618 | A | 11/1993 | Felgner et al. |
| 5,279,833 | A | 1/1994 | Rose |
| 5,282,824 | A | 2/1994 | Gianturco |
| 5,284,491 | A | 2/1994 | Sutton et al. |
| 5,300,022 | A | 4/1994 | Klapper et al. |
| 5,314,430 | A | 5/1994 | Bardy |
| 5,330,768 | A | 7/1994 | Park et al. |
| 5,334,761 | A | 8/1994 | Gebeyehu et al. |
| 5,395,619 | A | 3/1995 | Zalipsky et al. |
| 5,405,363 | A | 4/1995 | Kroll et al. |
| 5,405,379 | A | 4/1995 | Lane |
| 5,455,352 | A | 10/1995 | Huellmann et al. |
| 5,464,924 | A | 11/1995 | Silvis et al. |
| 5,503,852 | A | 4/1996 | Steiner et al. |
| 5,528,023 | A | 6/1996 | Butturini et al. |
| 5,552,155 | A | 9/1996 | Bailey et al. |
| 5,595,756 | A | 1/1997 | Bally et al. |
| 5,607,385 | A | 3/1997 | Francischelli et al. |
| 5,609,624 | A | 3/1997 | Kalis |
| 5,610,283 | A | 3/1997 | Buechler |
| 5,614,548 | A | 3/1997 | Piantadosi et al. |
| 5,626,869 | A | 5/1997 | Nyqvist et al. |
| 5,631,018 | A | 5/1997 | Zalipsky et al. |
| 5,677,124 | A | 10/1997 | DuBois et al. |
| 5,693,088 | A | 12/1997 | Lazarus |
| 5,697,953 | A | 12/1997 | Kroll et al. |
| 5,700,437 | A | 12/1997 | Fujii et al. |
| 5,705,188 | A | 1/1998 | Junichi et al. |
| 5,705,385 | A | 1/1998 | Bally et al. |
| 5,736,573 | A | 4/1998 | Galat |
| 5,744,335 | A | 4/1998 | Wolff et al. |
| 5,772,694 | A | 6/1998 | Bokros et al. |
| 5,776,165 | A | 7/1998 | Ripart |
| 5,776,747 | A | 7/1998 | Schinstine et al. |
| 5,783,383 | A | 7/1998 | Kondo et al. |
| 5,844,107 | A | 12/1998 | Hanson et al. |
| 5,874,105 | A | 2/1999 | Watkins et al. |
| 5,885,613 | A | 3/1999 | Holland et al. |
| 5,910,168 | A | 6/1999 | Myers et al. |
| 5,916,208 | A | 6/1999 | Luther et al. |
| 5,965,434 | A | 10/1999 | Wolff et al. |
| 5,976,567 | A | 11/1999 | Wheeler et al. |
| 5,976,569 | A | 11/1999 | Milstein |
| 5,981,501 | A | 11/1999 | Wheeler et al. |
| 6,055,454 | A | 4/2000 | Heemels |
| 6,067,471 | A | 5/2000 | Warren |
| 6,090,384 | A | 7/2000 | Ra et al. |
| 6,096,070 | A | 8/2000 | Ragheb et al. |
| 6,096,075 | A | 8/2000 | Bokros et al. |
| 6,120,799 | A | 9/2000 | McDonald et al. |
| 6,147,055 | A | 11/2000 | Hobart et al. |
| 6,152,955 | A | 11/2000 | KenKnight et al. |
| 6,165,763 | A | 12/2000 | Brown et al. |
| 6,169,923 | B1 | 1/2001 | Kroll |
| 6,176,877 | B1 | 1/2001 | Buchanan et al. |
| 6,204,297 | B1 | 3/2001 | Tracy et al. |
| 6,210,892 | B1 | 4/2001 | Bennett et al. |
| 6,214,804 | B1 | 4/2001 | Felgner et al. |
| 6,271,208 | B1 | 8/2001 | Bischoff |
| 6,271,209 | B1 | 8/2001 | Smith et al. |
| 6,287,591 | B1 | 9/2001 | Semple et al. |
| 6,299,604 | B1 | 10/2001 | Ragheb et al. |
| 6,335,199 | B1 | 1/2002 | Bischoff et al. |
| 6,358,278 | B1 | 3/2002 | Brendzel et al. |
| 6,370,434 | B1 | 4/2002 | Zhang et al. |
| 6,371,983 | B1 | 4/2002 | Lane |
| 6,417,326 | B1 | 7/2002 | Cullis et al. |
| 6,468,793 | B1 | 10/2002 | Teem |
| 6,485,726 | B1 | 11/2002 | Blumberg et al. |
| 6,534,484 | B1 | 3/2003 | Wheeler et al. |
| 6,585,410 | B1 | 7/2003 | Ryan |
| 6,586,410 | B1 | 7/2003 | Wheeler et al. |
| 6,670,178 | B1 | 12/2003 | Selden et al. |
| 6,696,424 | B1 | 2/2004 | Wheeler |
| 6,733,777 | B2 | 5/2004 | Erbacher et al. |
| 6,743,823 | B1 | 6/2004 | Summar et al. |
| 6,756,055 | B2 | 6/2004 | McDonald et al. |
| 6,790,838 | B2 | 9/2004 | Alison et al. |
| 6,815,432 | B2 | 11/2004 | Wheeler et al. |
| 6,821,530 | B2 | 11/2004 | Koob et al. |
| 6,835,395 | B1 | 12/2004 | Semple et al. |
| 6,858,224 | B2 | 2/2005 | Wheeler et al. |
| 6,858,225 | B2 | 2/2005 | Semple et al. |
| 6,887,665 | B2 | 5/2005 | Trulson et al. |
| 6,998,115 | B2 | 2/2006 | Langer et al. |
| 7,022,214 | B2 | 4/2006 | Olech |
| 7,067,697 | B2 | 6/2006 | Gao |
| 7,084,303 | B2 | 8/2006 | Watanabe et al. |
| 7,341,738 | B2 | 3/2008 | Semple et al. |
| 7,422,902 | B1 | 9/2008 | Wheeler et al. |
| 7,427,394 | B2 | 9/2008 | Anderson et al. |
| 7,507,859 | B2 | 3/2009 | Grinstaff et al. |
| 7,556,684 | B2 | 7/2009 | Bury et al. |
| 7,745,651 | B2 | 6/2010 | Heyes et al. |
| 7,799,565 | B2 | 9/2010 | MacLachlan et al. |
| 7,803,397 | B2 | 9/2010 | Heyes et al. |
| 7,901,708 | B2 | 3/2011 | MacLachlan et al. |
| 7,972,435 | B2 | 7/2011 | Bury et al. |
| 8,021,686 | B2 | 9/2011 | Semple et al. |
| 8,071,082 | B2 | 12/2011 | Zugates et al. |
| 8,101,741 | B2 | 1/2012 | MacLachlan et al. |
| 8,106,022 | B2 | 1/2012 | Manoharan et al. |
| 8,158,601 | B2 | 4/2012 | Chen et al. |
| 8,188,263 | B2 | 5/2012 | MacLachlan et al. |
| RE43,612 | E | 8/2012 | Anderson et al. |
| 8,236,943 | B2 | 8/2012 | Lee et al. |
| 8,278,036 | B2 | 10/2012 | Kariko et al. |
| 8,287,849 | B2 | 10/2012 | Langer et al. |
| 8,329,070 | B2 | 12/2012 | MacLachlan et al. |
| 8,389,238 | B2 | 3/2013 | Cooper et al. |
| 8,450,298 | B2 | 5/2013 | Mahon et al. |
| 8,450,467 | B2 | 5/2013 | Manoharan et al. |
| 8,513,403 | B2 | 8/2013 | MacLachlan et al. |
| 8,557,231 | B2 | 10/2013 | Langer et al. |
| 8,562,966 | B2 | 10/2013 | Zugates et al. |
| 8,569,256 | B2 | 10/2013 | Heyes et al. |
| 8,652,512 | B2 | 2/2014 | Schmehl et al. |
| 8,691,966 | B2 | 4/2014 | Kariko et al. |
| 8,710,200 | B2 | 4/2014 | Schrum et al. |
| 8,748,089 | B2 | 6/2014 | Kariko et al. |
| 8,802,644 | B2 | 8/2014 | Chen et al. |
| 8,808,681 | B2 | 8/2014 | Anderson et al. |
| 8,808,982 | B2 | 8/2014 | Dahl et al. |
| 8,822,663 | B2 | 9/2014 | Schrum et al. |
| 8,828,956 | B2 | 9/2014 | Manoharan et al. |
| 8,835,108 | B2 | 9/2014 | Kariko et al. |

(56) References Cited

U.S. PATENT DOCUMENTS 8,846,348 B2 9/2014 Jendrisak et al.
8,853,377 B2 10/2014 Guild et al.
8,859,229 B2 10/2014 Rabinovich et al.
8,883,202 B2 11/2014 Manoharan et al.
8,936,942 B2 1/2015 Heyes et al.
8,969,353 B2 3/2015 Mahon et al.
8,980,864 B2 3/2015 Hoge et al.
8,999,351 B2 4/2015 Manoharan et al.
8,999,950 B2 4/2015 MacLachlan et al.
9,005,930 B2 4/2015 Jendrisak et al.
9,012,219 B2 4/2015 Kariko et al.
9,012,498 B2 4/2015 Manoharan et al.
9,018,187 B2 4/2015 Heyes et al.
9,040,256 B2 5/2015 Grunenwald et al.
9,051,567 B2 6/2015 Fitzgerald et al.
9,061,021 B2 6/2015 Guild et al.
9,061,059 B2 6/2015 Chakraborty et al.
9,074,208 B2 7/2015 MacLachlan et al.
9,080,211 B2 7/2015 Grunenwald et al.
9,085,801 B2 7/2015 Grunenwald et al.
9,089,604 B2 7/2015 Chakraborty et al.
9,095,552 B2 8/2015 Chakraborty et al.
9,107,886 B2 8/2015 Chakraborty et al.
9,114,113 B2 8/2015 Chakraborty et al.
9,181,319 B2 11/2015 Schrum et al.
9,181,321 B2 11/2015 Heartlein et al.
9,186,325 B2 11/2015 Manoharan et al.
9,186,372 B2 11/2015 de Fougerolles et al.
9,187,748 B2 11/2015 Geisbert et al.
9,192,651 B2 11/2015 Chakraborty et al.
9,220,682 B2 12/2015 Manoharan et al.
9,220,683 B2 12/2015 Manoharan et al.
9,220,755 B2 12/2015 Chakraborty et al.
9,220,792 B2 12/2015 Chakraborty et al.
9,233,141 B2 1/2016 Chakraborty et al.
9,254,311 B2 2/2016 Bancel et al.
9,295,689 B2 3/2016 de Fougerolles et al.
9,301,993 B2 4/2016 Chakraborty et al.
9,303,079 B2 4/2016 Chakraborty et al.
9,334,328 B2 5/2016 Schrum et al.
9,345,780 B2 5/2016 Manoharan et al.
9,352,042 B2 5/2016 Heyes et al.
9,352,048 B2 5/2016 Manoharan et al.
9,364,435 B2 6/2016 Yaworski et al.
9,394,234 B2 7/2016 Chen et al.
9,404,127 B2 8/2016 Yaworski et al.
9,428,751 B2 8/2016 MacDonald et al.
9,464,124 B2 10/2016 Bancel et al.
9,492,386 B2 11/2016 MacLachlan et al.
9,504,651 B2 11/2016 MacLachlan et al.
9,504,734 B2 11/2016 Bancel et al.
9,518,272 B2 12/2016 Yaworksi et al.
9,572,874 B2 2/2017 Fotin-Mleczek et al.
9,587,003 B2 3/2017 Bancel et al.
9,616,084 B2 4/2017 Mutzke
10,471,153 B2 11/2019 DeRosa et al.
2002/0022721 A1 2/2002 Trulson et al.
2002/0094528 A1 7/2002 Salafsky
2002/0192651 A1 12/2002 Wheeler et al.
2002/0192721 A1 12/2002 Rizzuto et al.
2002/0193622 A1 12/2002 Watanabe et al.
2003/0082154 A1 5/2003 Leamon
2003/0083272 A1 5/2003 Wiederholt et al.
2003/0104044 A1 6/2003 Semple et al.
2003/0181410 A1 9/2003 Wheeler et al.
2003/0215395 A1 11/2003 Yu et al.
2004/0110709 A1 6/2004 Li et al.
2004/0132683 A1 7/2004 Felgner et al.
2004/0142025 A1 7/2004 MacLachlan et al.
2004/0224912 A1 11/2004 Dobie et al.
2004/0235982 A1 11/2004 Rabasco et al.
2005/0004058 A1 1/2005 Benoit et al.
2005/0008689 A1 1/2005 Semple et al.
2005/0032730 A1 2/2005 Von Der Mulbe et al.
2005/0054026 A1 3/2005 Atsushi et al.
2005/0059005 A1 3/2005 Tuschl et al.
2005/0059624 A1 3/2005 Hoerr et al.
2005/0065107 A1 3/2005 Hobart et al.
2005/0069590 A1 3/2005 Buehler et al.
2005/0079212 A1 4/2005 Wheeler et al.
2005/0143332 A1 6/2005 Monahan et al.
2005/0148786 A1 7/2005 Ikeda et al.
2005/0158302 A1 7/2005 Faustman et al.
2005/0244961 A1 11/2005 Short et al.
2005/0250723 A1 11/2005 Hoerr et al.
2006/0008910 A1 1/2006 MacLachlan et al.
2006/0059576 A1 3/2006 Pasinetti et al.
2006/0069225 A1 3/2006 Wintermantel et al.
2006/0083780 A1 4/2006 Heyes et al.
2006/0172003 A1 8/2006 Meers et al.
2006/0204566 A1 9/2006 Smyth-Templeton et al.
2006/0216343 A1 9/2006 Panzner et al.
2006/0223939 A1 10/2006 Lange et al.
2006/0228404 A1 10/2006 Anderson et al.
2006/0241071 A1 10/2006 Grinstaff et al.
2007/0135372 A1 6/2007 MacLachlan et al.
2007/0142628 A1 6/2007 Ghoshal et al.
2007/0172950 A1 7/2007 Wheeler et al.
2007/0252295 A1 11/2007 Panzner et al.
2007/0275923 A1 11/2007 Chen et al.
2007/0281336 A1 12/2007 Jendrisak et al.
2008/0145338 A1 6/2008 Anderson et al.
2008/0160048 A1 7/2008 Fuller
2008/0242626 A1 10/2008 Zugates et al.
2008/0260706 A1 10/2008 Rabinovich et al.
2009/0023673 A1 1/2009 Manoharan et al.
2009/0093433 A1 4/2009 Woolf et al.
2009/0163705 A1 6/2009 Manoharan et al.
2009/0186805 A1 7/2009 Tabor et al.
2009/0221684 A1 9/2009 Grinstaff et al.
2009/0263407 A1 10/2009 Dande et al.
2009/0270481 A1 10/2009 MacLachlan et al.
2009/0286852 A1 11/2009 Kariko et al.
2009/0326051 A1 12/2009 Corey et al.
2010/0028943 A1 2/2010 Thomas et al.
2010/0035249 A1 2/2010 Hayashizaki et al.
2010/0036084 A1 2/2010 Langer et al.
2010/0041152 A1 2/2010 Wheeler et al.
2010/0047261 A1 2/2010 Hoerr et al.
2010/0120129 A1 5/2010 Amshey et al.
2010/0178699 A1 7/2010 Gao et al.
2010/0189729 A1 7/2010 Hoerr et al.
2010/0267806 A1 10/2010 Bumcrot et al.
2010/0323356 A1 12/2010 Inoue et al.
2010/0331234 A1 12/2010 Mahon et al.
2011/0009641 A1 1/2011 Anderson et al.
2011/0035819 A1 2/2011 Cooper et al.
2011/0038941 A1 2/2011 Lee et al.
2011/0092739 A1 4/2011 Chen et al.
2011/0143397 A1 6/2011 Kariko et al.
2011/0200582 A1 8/2011 Baryza et al.
2011/0244026 A1 10/2011 Guild et al.
2011/0256175 A1 10/2011 Hope et al.
2011/0287435 A1 11/2011 Grunenwald et al.
2011/0293703 A1 12/2011 Mahon et al.
2011/0311583 A1 12/2011 Manoharan et al.
2012/0007803 A1 1/2012 Takatsuka
2012/0009222 A1 1/2012 Nguyen et al.
2012/0065252 A1 3/2012 Schrum et al.
2012/0065358 A1 3/2012 Langer et al.
2012/0114831 A1 5/2012 Semple et al.
2012/0128760 A1 5/2012 Manoharan et al.
2012/0129910 A1 5/2012 Thompson et al.
2012/0142756 A1 6/2012 Guild et al.
2012/0195936 A1 8/2012 Rudolph et al.
2012/0202871 A1 8/2012 Heyes et al.
2012/0237975 A1 9/2012 Schrum et al.
2012/0251560 A1 10/2012 Dahlman et al.
2012/0251618 A1 10/2012 Schrum et al.
2012/0328668 A1 12/2012 MacLachlan et al.
2013/0017223 A1 1/2013 Hope et al.
2013/0158021 A1 6/2013 Dong et al.
2013/0195967 A1 8/2013 Guild et al.
2013/0237594 A1 9/2013 de Fougerolles et al.

(56) References Cited

U.S. PATENT DOCUMENTS

| | | | |
|---|---|---|---|
| 2013/0259923 | A1 | 10/2013 | Bancel et al. |
| 2013/0259924 | A1 | 10/2013 | Bancel et al. |
| 2013/0266640 | A1 | 10/2013 | de Fougerolles et al. |
| 2013/0302401 | A1 | 11/2013 | Ma et al. |
| 2014/0010861 | A1 | 1/2014 | Bancel et al. |
| 2014/0044772 | A1 | 2/2014 | MacLachlan et al. |
| 2014/0094399 | A1 | 4/2014 | Langer et al. |
| 2014/0105964 | A1 | 4/2014 | Bancel et al. |
| 2014/0105965 | A1 | 4/2014 | Bancel et al. |
| 2014/0147432 | A1 | 5/2014 | Bancel et al. |
| 2014/0147454 | A1 | 5/2014 | Chakraborty et al. |
| 2014/0148502 | A1 | 5/2014 | Bancel et al. |
| 2014/0155472 | A1 | 6/2014 | Bancel et al. |
| 2014/0155473 | A1 | 6/2014 | Bancel et al. |
| 2014/0155474 | A1 | 6/2014 | Bancel et al. |
| 2014/0155475 | A1 | 6/2014 | Bancel et al. |
| 2014/0161830 | A1 | 6/2014 | Anderson et al. |
| 2014/0162897 | A1 | 6/2014 | Grunenwald et al. |
| 2014/0171485 | A1 | 6/2014 | Bancel et al. |
| 2014/0179756 | A1 | 6/2014 | MacLachlan et al. |
| 2014/0179771 | A1 | 6/2014 | Bancel et al. |
| 2014/0186432 | A1 | 7/2014 | Bancel et al. |
| 2014/0193482 | A1 | 7/2014 | Bancel et al. |
| 2014/0194494 | A1 | 7/2014 | Bancel et al. |
| 2014/0199371 | A1 | 7/2014 | Bancel et al. |
| 2014/0200163 | A1 | 7/2014 | Mikkelsen et al. |
| 2014/0200261 | A1 | 7/2014 | Hoge et al. |
| 2014/0200262 | A1 | 7/2014 | Bancel et al. |
| 2014/0200263 | A1 | 7/2014 | Bancel et al. |
| 2014/0200264 | A1 | 7/2014 | Bancel et al. |
| 2014/0206752 | A1 | 7/2014 | Afeyan et al. |
| 2014/0206753 | A1 | 7/2014 | Guild et al. |
| 2014/0206755 | A1 | 7/2014 | Bancel et al. |
| 2014/0206852 | A1 | 7/2014 | Hoge et al. |
| 2014/0221248 | A1 | 8/2014 | Jendrisak et al. |
| 2014/0221465 | A1 | 8/2014 | Bancel et al. |
| 2014/0227300 | A1 | 8/2014 | Chin et al. |
| 2014/0243399 | A1 | 8/2014 | Schrum et al. |
| 2014/0249208 | A1 | 9/2014 | Bancel et al. |
| 2014/0255467 | A1 | 9/2014 | Bancel et al. |
| 2014/0255468 | A1 | 9/2014 | Bancel et al. |
| 2014/0275227 | A1 | 9/2014 | Hoge et al. |
| 2014/0275229 | A1 | 9/2014 | Bancel et al. |
| 2014/0288160 | A1 | 9/2014 | Guild et al. |
| 2014/0294937 | A1 | 10/2014 | MacLachlan et al. |
| 2014/0294938 | A1 | 10/2014 | Guild et al. |
| 2014/0294939 | A1 | 10/2014 | Guild et al. |
| 2014/0294940 | A1 | 10/2014 | Guild et al. |
| 2014/0329884 | A1 | 11/2014 | Dong et al. |
| 2014/0343129 | A1 | 11/2014 | de Fougerolles et al. |
| 2014/0363876 | A1 | 12/2014 | Jendrisak et al. |
| 2015/0004217 | A1 | 1/2015 | Guild et al. |
| 2015/0005372 | A1 | 1/2015 | Hoge et al. |
| 2015/0011615 | A1 | 1/2015 | Manoharan et al. |
| 2015/0011633 | A1 | 1/2015 | Shorr et al. |
| 2015/0017211 | A1 | 1/2015 | de Fougerolles et al. |
| 2015/0038556 | A1 | 2/2015 | Heartlein et al. |
| 2015/0038558 | A1 | 2/2015 | Kariko et al. |
| 2015/0044277 | A1 | 2/2015 | Bancel et al. |
| 2015/0050354 | A1 | 2/2015 | Bouchon et al. |
| 2015/0051268 | A1 | 2/2015 | Bancel et al. |
| 2015/0056253 | A1 | 2/2015 | Bancel et al. |
| 2015/0064235 | A1 | 3/2015 | Bancel et al. |
| 2015/0064236 | A1 | 3/2015 | Bancel et al. |
| 2015/0064242 | A1 | 3/2015 | Heyes et al. |
| 2015/0064725 | A1 | 3/2015 | Schrum et al. |
| 2015/0086614 | A1 | 3/2015 | Bancel et al. |
| 2015/0110857 | A1 | 4/2015 | DeRosa et al. |
| 2015/0110858 | A1 | 4/2015 | DeRosa et al. |
| 2015/0110859 | A1 | 4/2015 | Heartlein et al. |
| 2015/0111248 | A1 | 4/2015 | Bancel et al. |
| 2015/0111945 | A1 | 4/2015 | Geisbert et al. |
| 2015/0119444 | A1 | 4/2015 | Manoharan et al. |
| 2015/0119445 | A1 | 4/2015 | Manoharan et al. |
| 2015/0157565 | A1 | 6/2015 | Heartlein et al. |
| 2015/0166465 | A1 | 6/2015 | Chen et al. |
| 2015/0190515 | A1 | 7/2015 | Manoharan et al. |
| 2015/0191760 | A1 | 7/2015 | Jendrisak et al. |
| 2015/0265708 | A1 | 9/2015 | Manoharan et al. |
| 2015/0267192 | A1 | 9/2015 | Heartlein et al. |
| 2015/0315541 | A1 | 11/2015 | Bancel et al. |
| 2015/0315584 | A1 | 11/2015 | MacDonald et al. |
| 2015/0366997 | A1 | 12/2015 | Guild et al. |
| 2016/0095924 | A1 | 4/2016 | Hope et al. |
| 2016/0114011 | A1 | 4/2016 | Bancel et al. |
| 2016/0115477 | A1 | 4/2016 | MacLachlan et al. |
| 2016/0115483 | A1 | 4/2016 | MacLachlan et al. |
| 2016/0136236 | A1 | 5/2016 | Hoge et al. |
| 2016/0151284 | A1 | 6/2016 | Heyes et al. |
| 2016/0158385 | A1 | 6/2016 | Bancel et al. |
| 2016/0193299 | A1 | 7/2016 | de Fougerolles et al. |
| 2016/0194368 | A1 | 7/2016 | Hoge et al. |
| 2016/0194625 | A1 | 7/2016 | Hoge et al. |
| 2016/0199485 | A1 | 7/2016 | Manoharan et al. |
| 2016/0213785 | A1 | 7/2016 | Manoharan et al. |
| 2016/0237108 | A1 | 8/2016 | Fraley et al. |
| 2016/0237134 | A1 | 8/2016 | Hoge et al. |
| 2016/0250354 | A1 | 9/2016 | Manoharan et al. |
| 2016/0251681 | A1 | 9/2016 | Yaworski et al. |
| 2016/0256567 | A1 | 9/2016 | Heyes et al. |
| 2016/0256568 | A1 | 9/2016 | Heyes et al. |
| 2016/0256573 | A1 | 9/2016 | de Fougerolles et al. |
| 2016/0264971 | A1 | 9/2016 | Geisbert et al. |
| 2016/0264975 | A1 | 9/2016 | Schrum et al. |
| 2016/0274089 | A1 | 9/2016 | Ciufolini et al. |
| 2016/0304552 | A1 | 10/2016 | Roy et al. |
| 2016/0317647 | A1 | 11/2016 | Ciaramella et al. |
| 2016/0317676 | A1 | 11/2016 | Hope et al. |
| 2016/0331828 | A1 | 11/2016 | Ciaramella et al. |
| 2016/0348099 | A1 | 12/2016 | Roy et al. |
| 2016/0354490 | A1 | 12/2016 | Roy et al. |
| 2016/0354491 | A1 | 12/2016 | Roy et al. |
| 2016/0354492 | A1 | 12/2016 | Roy et al. |
| 2016/0354493 | A1 | 12/2016 | Roy et al. |
| 2016/0367687 | A1 | 12/2016 | Manoharan et al. |
| 2016/0367702 | A1 | 12/2016 | Hoge et al. |
| 2016/0375134 | A1 | 12/2016 | Bancel et al. |
| 2016/0375137 | A9 | 12/2016 | Manoharan et al. |
| 2017/0000858 | A1 | 1/2017 | Fotin-Mleczek et al. |
| 2017/0000870 | A1 | 1/2017 | Hoerr et al. |
| 2017/0000871 | A1 | 1/2017 | Probst et al. |
| 2017/0002060 | A1 | 1/2017 | Bolen et al. |
| 2017/0007702 | A1 | 1/2017 | Heyes et al. |
| 2017/0014496 | A1 | 1/2017 | Fotin-Mleczek et al. |
| 2017/0028059 | A1 | 2/2017 | Baumhof et al. |
| 2017/0029847 | A1 | 2/2017 | Thess |
| 2017/0056528 | A1 | 3/2017 | De Fougerolles et al. |
| 2017/0056529 | A1 | 3/2017 | Thess et al. |
| 2017/0065727 | A1 | 3/2017 | Fotin-Mleczek et al. |
| 2018/0161451 | A1 | 6/2018 | Fotin-Mleczek et al. |
| 2019/0248855 | A1 | 8/2019 | Kappes et al. |

FOREIGN PATENT DOCUMENTS

| | | | |
|---|---|---|---|
| CN | 100569877 | C | 12/2009 |
| CN | 101863544 | A | 10/2010 |
| DE | 24 30 998 | A1 | 1/1975 |
| DE | 2520814 | A1 | 11/1976 |
| DE | 3728917 | A1 | 3/1989 |
| EP | 6 73 637 | A1 | 9/1995 |
| EP | 0783297 | A1 | 7/1997 |
| EP | 0853123 | A1 | 7/1998 |
| EP | 0959092 | A1 | 11/1999 |
| EP | 1519714 | B1 | 4/2005 |
| EP | 1979364 | A2 | 10/2008 |
| EP | 2045251 | A1 | 4/2009 |
| EP | 2338478 | B1 | 6/2011 |
| EP | 2338520 | A1 | 6/2011 |
| EP | 2449106 | A1 | 5/2012 |
| EP | 2532649 | A1 | 12/2012 |
| EP | 2578685 | A2 | 4/2013 |
| EP | 2823809 | A1 | 1/2015 |
| FR | 1 378 382 | A | 11/1964 |
| FR | 2 235 112 | A1 | 1/1975 |

(56) References Cited

FOREIGN PATENT DOCUMENTS

| | | | |
|---|---|---|---|
| GB | 1072118 | A | 6/1967 |
| GB | 1602085 | A | 11/1981 |
| JP | H07-053535 | | 2/1955 |
| JP | S48-022365 | | 3/1973 |
| JP | S49-127908 | A | 12/1974 |
| JP | S51-023537 | | 2/1976 |
| JP | 51-125144 | | 11/1976 |
| JP | S52-010847 | | 1/1977 |
| JP | S63125144 | A | 5/1988 |
| JP | 63-154788 | A | 6/1988 |
| JP | H09-505593 | A | 6/1997 |
| JP | H10-197978 | A | 7/1998 |
| JP | 11-005786 | A | 1/1999 |
| JP | 11-080142 | | 3/1999 |
| JP | 2001-523215 | A | 11/2001 |
| JP | 2002-167368 | A | 6/2002 |
| JP | 2003-519199 | A | 6/2003 |
| JP | 4-108173 | B2 | 6/2008 |
| JP | 2008-247749 | A | 10/2008 |
| JP | 50-24216 | B2 | 9/2012 |
| WO | WO-90/11092 | A1 | 10/1990 |
| WO | WO-93/18229 | A1 | 9/1993 |
| WO | WO-93/18754 | A1 | 9/1993 |
| WO | WO-95/11004 | A1 | 4/1995 |
| WO | WO-95/14651 | A1 | 6/1995 |
| WO | WO-95/27478 | A1 | 10/1995 |
| WO | WO-96/18372 | A2 | 6/1996 |
| WO | WO-96/26179 | A1 | 8/1996 |
| WO | WO-96/37211 | A1 | 11/1996 |
| WO | WO-96/40964 | A2 | 12/1996 |
| WO | WO-97/46223 | A1 | 12/1997 |
| WO | WO-98/10748 | A1 | 3/1998 |
| WO | WO-98/16202 | A2 | 4/1998 |
| WO | WO-98/51278 | A2 | 11/1998 |
| WO | WO-99/14346 | A2 | 3/1999 |
| WO | WO-00/03044 | A1 | 1/2000 |
| WO | WO-00/62813 | A2 | 10/2000 |
| WO | WO-00/64484 | A2 | 11/2000 |
| WO | WO-00/69913 | A1 | 11/2000 |
| WO | WO-01/05375 | A1 | 1/2001 |
| WO | WO-01/07599 | A1 | 2/2001 |
| WO | WO-02/00870 | A2 | 1/2002 |
| WO | WO-02/22709 | A1 | 3/2002 |
| WO | WO-02/31025 | A2 | 4/2002 |
| WO | WO-02/34236 | A2 | 5/2002 |
| WO | WO-02/42317 | A2 | 5/2002 |
| WO | WO-03/040288 | A2 | 5/2003 |
| WO | WO-03/070735 | A2 | 8/2003 |
| WO | WO-2004/043588 | A2 | 5/2004 |
| WO | WO-2004/048345 | A2 | 6/2004 |
| WO | WO-2004/106411 | A2 | 12/2004 |
| WO | WO-2005/026372 | A1 | 3/2005 |
| WO | WO-2005/028619 | A2 | 3/2005 |
| WO | WO-2005/037226 | A2 | 4/2005 |
| WO | WO-2005/121348 | A1 | 12/2005 |
| WO | WO-2006/000448 | A2 | 1/2006 |
| WO | WO-2006/016097 | A2 | 2/2006 |
| WO | WO-2006/082088 | A1 | 8/2006 |
| WO | WO-2006/105043 | A2 | 10/2006 |
| WO | WO-2006/138380 | A2 | 12/2006 |
| WO | WO-2007/024708 | A2 | 3/2007 |
| WO | WO-2007/031091 | A2 | 3/2007 |
| WO | WO-2007/120863 | A2 | 10/2007 |
| WO | WO-2007/126386 | A1 | 11/2007 |
| WO | WO-2007/137237 | A2 | 11/2007 |
| WO | WO-2007/143659 | A2 | 12/2007 |
| WO | WO-2008/011561 | A2 | 1/2008 |
| WO | WO-2008/042973 | A2 | 4/2008 |
| WO | WO-2008/045548 | A2 | 4/2008 |
| WO | WO-2008/083949 | A2 | 7/2008 |
| WO | WO-2008/113364 | A2 | 9/2008 |
| WO | WO-2009/046220 | A2 | 4/2009 |
| WO | WO-2009/127060 | A1 | 10/2009 |
| WO | WO-2009/127230 | A1 | 10/2009 |
| WO | WO-2010/037408 | A1 | 4/2010 |
| WO | WO-2010/042877 | A1 | 4/2010 |
| WO | WO-2010/045512 | A2 | 4/2010 |
| WO | WO-2010/053572 | A2 | 5/2010 |
| WO | WO-2010/054401 | A1 | 5/2010 |
| WO | WO-2010/054405 | A1 | 5/2010 |
| WO | WO-2010/056403 | A1 | 5/2010 |
| WO | WO-2010/099387 | A1 | 9/2010 |
| WO | WO-2010/114789 | A1 | 10/2010 |
| WO | WO-2010/119256 | A1 | 10/2010 |
| WO | WO-2010/129709 | A1 | 11/2010 |
| WO | WO-2010/144740 | A1 | 12/2010 |
| WO | WO-2010/147992 | A1 | 12/2010 |
| WO | WO-2010/148013 | A2 | 12/2010 |
| WO | WO-2011/012316 | A2 | 2/2011 |
| WO | WO-2011/012746 | A2 | 2/2011 |
| WO | WO-2011/039144 | A1 | 4/2011 |
| WO | WO-2011/068810 | A1 | 6/2011 |
| WO | WO-2011/075656 | A1 | 6/2011 |
| WO | WO-2011/141705 | A1 | 11/2011 |
| WO | WO-2012/019168 | A2 | 2/2012 |
| WO | WO-2012/019630 | A1 | 2/2012 |
| WO | WO-2012/019780 | A1 | 2/2012 |
| WO | WO-2012/027675 | A2 | 3/2012 |
| WO | WO-2012/045075 | A1 | 4/2012 |
| WO | WO-2012/045082 | A2 | 4/2012 |
| WO | WO-2012/075040 | A2 | 6/2012 |
| WO | WO-2012/133737 | A1 | 10/2012 |
| WO | WO-2012/135025 | A2 | 10/2012 |
| WO | WO-2012/135805 | A2 | 10/2012 |
| WO | WO-2012/170889 | A1 | 12/2012 |
| WO | WO-2012/170930 | A1 | 12/2012 |
| WO | WO-2013/039857 | A1 | 3/2013 |
| WO | WO-2013/039861 | A2 | 3/2013 |
| WO | WO-2013/063468 | A1 | 5/2013 |
| WO | WO-2013/090186 | A1 | 6/2013 |
| WO | WO-2013/101690 | A1 | 7/2013 |
| WO | WO-2013/102203 | A1 | 7/2013 |
| WO | WO-2013/126803 | A1 | 8/2013 |
| WO | WO-2013/130161 | A1 | 9/2013 |
| WO | WO-2013/149140 | A1 | 10/2013 |
| WO | WO-2013/149141 | A1 | 10/2013 |
| WO | WO-2013/151663 | A1 | 10/2013 |
| WO | WO-2013/151664 | A1 | 10/2013 |
| WO | WO-2013/151666 | A2 | 10/2013 |
| WO | WO-2013/151667 | A1 | 10/2013 |
| WO | WO-2013/151668 | A2 | 10/2013 |
| WO | WO-2013/151670 | A2 | 10/2013 |
| WO | WO-2013/151671 | A1 | 10/2013 |
| WO | WO-2013/151672 | A2 | 10/2013 |
| WO | WO-2013/151736 | A2 | 10/2013 |
| WO | WO-2013/182683 | A1 | 12/2013 |
| WO | WO-2013/185067 | A1 | 12/2013 |
| WO | WO-2013/185069 | A1 | 12/2013 |
| WO | WO-2014/028487 | A1 | 2/2014 |
| WO | WO-2014/089486 | A1 | 6/2014 |
| WO | WO-2014/113089 | A2 | 7/2014 |
| WO | WO-2014/143884 | A2 | 9/2014 |
| WO | WO-2014/144039 | A1 | 9/2014 |
| WO | WO-2014/144196 | A1 | 9/2014 |
| WO | WO-2014/144711 | A1 | 9/2014 |
| WO | WO-2014/144767 | A1 | 9/2014 |
| WO | WO-2014/152027 | A1 | 9/2014 |
| WO | WO-2014/152030 | A1 | 9/2014 |
| WO | WO-2014/152031 | A1 | 9/2014 |
| WO | WO-2014/152211 | A1 | 9/2014 |
| WO | WO-2014/152513 | A1 | 9/2014 |
| WO | WO-2014/152540 | A1 | 9/2014 |
| WO | WO-2014/152659 | A1 | 9/2014 |
| WO | WO-2014/152673 | A1 | 9/2014 |
| WO | WO-2014/152774 | A1 | 9/2014 |
| WO | WO-2014/152940 | A1 | 9/2014 |
| WO | WO-2014/152966 | A1 | 9/2014 |
| WO | WO-2014/153052 | A2 | 9/2014 |
| WO | WO-2014/158795 | A1 | 10/2014 |
| WO | WO-2014/159813 | A1 | 10/2014 |
| WO | WO-2014/179562 | A1 | 11/2014 |
| WO | WO-2014/210356 | A1 | 12/2014 |
| WO | WO-2015/006747 | A2 | 1/2015 |
| WO | WO-2015/011633 | A1 | 1/2015 |

(56) References Cited

FOREIGN PATENT DOCUMENTS

| | | | |
|---|---|---|---|
| WO | WO-2015/048744 | A2 | 4/2015 |
| WO | WO-2015/051169 | A2 | 4/2015 |
| WO | WO-2015/051173 | A2 | 4/2015 |
| WO | WO-2015/058069 | A1 | 4/2015 |
| WO | WO-2015/061467 | A1 | 4/2015 |
| WO | WO-2015/085318 | A2 | 6/2015 |
| WO | WO-2015/089511 | A2 | 6/2015 |
| WO | WO-2016/054421 | A1 | 4/2016 |
| WO | WO-2016/071857 | A1 | 5/2016 |
| WO | WO-2016/077123 | A1 | 5/2016 |
| WO | WO-2016/077125 | A1 | 5/2016 |
| WO | WO-2016/118724 | A1 | 7/2016 |
| WO | WO-2016/118725 | A1 | 7/2016 |
| WO | WO-2016/154127 | A2 | 9/2016 |
| WO | WO-2016/164762 | A1 | 10/2016 |
| WO | WO-2016/183366 | A2 | 11/2016 |
| WO | WO-2016/197132 | A1 | 12/2016 |
| WO | WO-2016/197133 | A1 | 12/2016 |
| WO | WO-2016/201377 | A1 | 12/2016 |
| WO | WO-2017/019891 | A2 | 2/2017 |
| WO | WO-2017/049074 | A1 | 3/2017 |
| WO | WO-2017/049275 | A2 | 3/2017 |
| WO | WO-2017/049286 | A1 | 3/2017 |
| WO | WO-2017/099823 | A1 | 6/2017 |
| WO | WO-2017/106799 | A1 | 6/2017 |
| WO | WO-2017/177169 | A1 | 10/2017 |
| WO | WO-2018/089790 | A1 | 5/2018 |
| WO | WO-2018/089801 | A1 | 5/2018 |
| WO | WO-2018/157154 | A2 | 8/2018 |
| WO | WO-2018/213476 | A1 | 11/2018 |
| WO | WO-2018/232357 | A1 | 12/2018 |
| WO | WO-2019/046809 | A1 | 3/2019 |
| WO | WO-2019/207060 | A1 | 10/2019 |
| WO | WO-2020/047061 | A1 | 3/2020 |
| WO | WO-2020/106946 | A1 | 5/2020 |
| WO | WO-2021/021988 | A1 | 2/2021 |
| WO | WO-2021/055609 | A1 | 3/2021 |
| WO | WO-2021/226468 | A1 | 11/2021 |

OTHER PUBLICATIONS

U.S. Appl. No. 61/494,714, filed Jun. 8, 2011, Guild.

Adami, R.C. et al., An amino acid-based amphoteric liposomal delivery system for systemic administration of siRNA. Molecular Therapy 19(6):1141-1151 (2011).

Akinc, A. et al., A combinatorial library of lipid-like materials for delivery of RNAi therapeutics. Nature Biotechnology 26(5):561-569 (2008).

Akinc, A. et al., Development of lipidoid-siRNA formulations for systemic delivery to the liver. Molecular Therapy 17(5):872-879 (2009).

Alton, E.W.F.W. et al., Cationic Lipid-Mediated CFTR Gene Transfer to the Lungs and Nose of Patients with Cystic Fibrosis: a Double-Blind Placebo-Controlled Trial, Lancet, 353:947-954 (1999).

Alton et al., "A randomised, double-blind, placebo-controlled trial of repeated nebulisation of non-viral cystic fibrosis transmembrane conductance regulator (CFTR) gene therapy in patients with cystic fibrosis", National Institute for Health Research, vol. 3, Issue 5, (2016). 240 pages.

Anderson, D.G. et al., Structure/property studies of polymeric gene delivery using a library of poly(beta-amino esters). Molecular Therapy 11(3):426-434 (2005).

Anderson, D.M. et al., Stability of mRNA/Cationic Lipid Lipoplexes in Human and Rat Cerebrospinal Fluid: Methods and Evidence for Nonviral mRNA Gene Delivery to the Central Nervous System, Human Gene Therapy, 14:191-202 (2003).

Anderson, J. Biological Responses to Materials. Annual Review of Materials Research 31:81-110 (2001).

Anderson, W. French, Human gene therapy, Nature, 392, 25-30 (1998).

Andries, O. et al., Comparison of the Gene Transfer Efficiency of mRNA/GL67 and pDNA/GL67 Complexes in Respiratory Cells, Mol. Pharmaceut., 9: 2136-2145 (2012).

Auffray, C. et al., Purification of Mouse Immunoglubulin Heavy-Chain Messenger RNAs from Total Myeloma Tumor RNA, European Journal of Biochemistry, 107(2):303-314 (1980).

Author Unknown, Blood Proteins, published by Wikipedia, San Francisco, CA, 2 pages, <http://en.wikipedia.org/wiki/Blood_proteins> downloaded May 17, 2015.

Bajaj, A. et al., Synthesis and gene transfection efficacies of PEI-cholesterol-based lipopolymers. Bioconjugate Chemistry 19(8):1640-516511 (2008).

Barreau, C. et al., Liposome-mediated RNA transfection should be used with caution, RNA, 12:1790-1793 (2006).

Behlke, M. A. et al., Progress towards in vivo use of siRNAs, Molecular Therapy, 13:644-670 (2006).

Behr, J. et al., Efficient Gene Transfer into Mammalian Primary Endocrine Cells with Lipo Polyamine-Coated DNA, Proc. Nat.'l Acad. Sci., 86: 6982-6986 (1989).

Bennett, J. Immune response following intraocular delivery of recombinant viral vectors, Gene Therapy, 10: 977-982 (2003).

Bhaduri, S. et al., Procedure for the preparation of milligram quantities of adenovirus messenger ribonucleic acid, J. Virol., 10(6): 1126-1129 (1972).

Bloomfield, V.A., Quasi-Elastic Light Scattering Applications in Biochemistry and Biology, Ann. Rev. Biophys. Bioeng. 10:421-450 (1981).

Boussif, O. et al., A versatile vector for gene and oligonucleotide transfer into cells in culture and in vivo: polyethylenimine. Proceedings of the National Academy of Sciences of the USA. 92(16):7297-7301 (1995).

Braun, C.S. et al., Structure/function relationships of polyamidoamine/DNA dendrimers as gene delivery vehicles. Journal of Pharmaceutical Sciences 94(2):423-436 (2005).

Breunig, M. et al., Breaking up the correlation between efficacy and toxicity for nonviral gene delivery. Proceedings of the National Academy of Sciences of the U S A. 104(36):14454-14459 (2007).

Breunig, M. et al., Mechanistic investigation of poly(ethylene imine)-based siRNA delivery: disulfide bonds boost intracellular release of the cargo. Journal of Controlled Release 130(1):57-63 (2008).

Brey, D.M. et al., Controlling poly(beta-amino ester) network properties through macromer branching. Acta Biomaterialia 4(2):207-217 (2008).

Brey, D.M. et al., Influence of macromer molecular weight and chemistry on poly(beta-amino ester) network properties and initial cell interactions. Journal of Biomedical Materials Research Part A 85(3):731-741 (2007).

Broadbent, S. et al., "The cystic fibrosis transmembrane conductance regulator is an extracellular chloride sensor," Pfluegers Archiv: European Journal of Physiology, Springer Verlag, Berlin, DE, vol. 467, No. 8, Oct. 4, 2014, pp. 1783-1794.

Brown, M.D. et al., Gene Delivery with synthetic (non viral) carriers, Int. J. Pharm., 1-21 (2001).

Budker, V. et al., Protein/Amphipathic Polyamine Complexes Enable Highly Efficient Transfection with Minimal Toxicity, BioTechniques, 23: 139-147 (1997).

Burger, G. et al., Sequencing complete mitochondrial and plastid genomes, Nature Protocols, 2: 603-614 (2007).

Burnett, J.C. et al., Current progress of siRNA/shRNA therapeutics in clinical trials. Biotechnology Journal 6(9):1130-1146 (2011).

Byk, G. et al., Synthesis, activity, and structure—activity relationship studies of novel cationic lipids for DNA transfer. Journal of Medical Chemistry 41(2):224-235 (1998).

Caplen, N.J. et al., In vitro liposome-mediated DNA transfection of epithelial cell lines using the cationic liposome DC-Chol/DOPE, Gene Therapy, 2:603-613 (1995).

Cassiman, D. Gene transfer for inborn errors of metabolism of the liver: the clinical perspective, Current Pharmaceutical Design, 17(24):2550-2557 (2011).

Castanotto, D. et al., The promises and pitfalls of RNA-interference-based therapeutics. Nature 457(7228):426-433 (2009).

Chakraborty, C. Potentiality of Small Interfering RNAs (siRNA) as Recent Therapeutic Targets for Gene-Silencing. Current Drug Targets 8(3):469-82 (2007).

(56) References Cited

OTHER PUBLICATIONS

Chandler, R. et al., Liver-directed adeno-associated virus serotype 8 gene transfer rescues a lethal murine model of citrullinemmia type 1, Gene Therapy, 20:1188-1191 (2013).
Chau, Y. et al., Investigation of targeting mechanism of new dextran-peptide-methotrexate conjugates using biodistribution study in matrix-metalloproteinase-overexpressing tumor xenograft model, J. Pharm. Sci., 95(3): 542-551 (2006).
Chen, D. et al., Rapid discovery of potent siRNA-containing lipid nanoparticles enabled by controlled microfluidic formulation. Journal of the American Chemical Society 134(16):6948-6951 (2012).
Chen, Y. and Huang, L., Tumor-targeted delivery of siRNA by non-viral vector: safe and effective cancer therapy. Expert Opinion on Drug Delivery 5(12):1301-1311 (2008).
Chiou, H.C. et al., Enhanced resistance to nuclease degradation of nucleic acids complexed to; asialoglycoprotein-polylysine carriers, Nucleic Acids Research, 22(24):5439-5446 (1994).
Christensen, U.B. et al., Intercalating nucleic acids containing insertions of 1-O-(1-pyrenylmethyl)glycerol: stabilisation of dsDNA and discrimination of DNA over RNA, Nucl. Acids. Res., 30(22): 4918-4925 (2002).
Conese, M. et al., Gene and Cell Therapy for Cystic Fibrosis: From Bench to Bedside, J. Cyst. Fibros., 10 Suppl 2:S114-s128 (2011).
Cotten, M. et al., Receptor-mediated transport of DNA into eukaryotic cells. Methods in Enzymology 217 (H):618-644 (1993).
Cowling, V.H., Regulation of mRNA cap methylation, Biochemical Journal, 425:295-302 (2010).
Creusat, G. et al., Proton sponge trick for pH-sensitive disassembly of polyethylenimine-based siRNA delivery systems. Bioconjugate Chemistry 21(5):994-1002 (2010).
Crooke, S.T. Molecular mechanisms of action of antisense drugs. Biochimica et Biophysica Acta 1489(1):31-44. Review (1999).
Crystal, R.G. Transfer of genes to humans: early lessons and obstacles to success. Science 270(5235):404-410. Review (1995).
Damen, M. et al., Delivery of DNA and siRNA by novel gemini-like amphiphilic peptides. Journal of Controlled Release 145(1):33-39 (2010).
Dande, P. et al., Improving RNA interference in mammalian cells by 4'-thio-modified small interfering RNA (siRNA): effect on siRNA activity and nuclease stability when used in combination with 2'-0-alkyl modifications, Journal of Medicinal Chemistry, 49(5):1624-1634 (2006).
Davis, M. E., The first targeted delivery of siRNA in humans via a self-assembling, cyclodextrin polymer-based nanoparticle: from concept to clinic. Molecular Pharmacuetics 6(3):659-668 (2009).
Davis, M.E. et al., Evidence of RNAi in humans from systemically administered siRNA via targeted nanoparticles. Nature 464(7291):1067-1070 (2010).
Debus, H. et al., Delivery of Messenger RNA Using Poly(ethylene imine)-poly(ethylene glycol)-Copolymer Blends for Polyplex Formation: Biophysical Characterization and In Vitro Transfection Properties, J. Control. Rel., 148:334-343 (2010).
Decher, G. Fuzzy Nanoassemblies: Toward Layered Polymeric Multicomposites. Science 277: 1232-1237 (1997).
Demeshkina, N. et al., Interactions of the ribosome with mRNA and tRNA, Current Opinion in Structural Biology, 20(3):325-332 (2010).
Denardo, S.J. et al., Enhanced Therapeutic Index of Radioimmunotherapy (RIT) in Prostate Cancer Patients Comparison of Radiation Dosimetry for 1,4,7,10-Tetraazacyclododecane-N,N', N'', N'''-Tetraacetic Acid (DOTA)-Peptide versus 2IT-DOTA Monoclonal Antibody Linkage for RIT1, Clin. Cancer Res., 9: 3665s (2003). 7 pages.
Dern, R.J. et al., Toxicity studies of pyrimethamine (daraprim). The American Journal of Tropical Medicine and Hygiene 4(2):217-220 (1955).
Deshmukh, H. M and Huang, L., Liposome and polylysine mediated gene therapy. New Journal of Chemistry 21:113-124 (1997).
Ding et al., "Systemic Messenger RNA Therapy as a Treatment for Methylmalonic Acidemia," vol. 1, No. 12, pp. 3548-3558, (2017).
Discher, B.M. et al., Polymersomes: tough vesicles made from diblock copolymers. Science 284(5417):1143-1146 (1999).
Discher, D.E. and Eisenberg, A., Polymer vesicles. Science 297(5583):967-973. Review (2002).
Dong, Y. et al., Lipopeptide nanoparticles for potent and selective siRNA delivery in rodents and nonhuman primates, Proceedings of the National Academy of Sciences, 111(11): 3955-3960 (2014).
Driscoll, K.E. et al., Intratracheal instillation as an exposure technique for the evaluation of respiratory tract toxicity: uses and limitations, Toxicol. Sci., 55(1): 24-35 (2000).
Drummond, D.C. et al., Optimizing Liposomes for Delivery of Chemotherapeutic Agents to Solid Tumors, Pharmacological Reviews, 51(4): 691-743 (1999).
Dwarki, V. et al., Cationic liposome-mediated RNA transfection, Methods in Enzymology, 217:644-654 (1993).
Eck, et al., Goodman & Gilman's The Pharmacological Basis of Therapeutics, McGraw-Hill, New York, 77-101 (1996).
Elbashir, S.M. et al., RNA interference is mediated by 21- and 22-nucleotide RNAs. Genes & Development 15: 188-200 (2001).
Elton, C., The Next Next Big Thing, Boston Magazine, 106-118 (Mar. 2013).
Emlen, W. et al., Effect of DNA size and strandedness on the in vivo clearance and organ localization of DNA, Clinical & Experimental Immunology, 56:185-192 (1984).
Eon-Duval, A. et al., Removal of RNA impurities by tangential flow filtration in an RNase-free plasmid DNA purification process, Analytical Biochemistry, 316(1):66-73 (2003).
Ernst, N. et al., Interaction of Liposomal and Polycationic Transfection Complexes with Pulmonary Surfactant, J. Gene. Med., 1:331-340 (1999).
Estimated Number of Animal and Plant Species on Earth, http://www.factmonster.com/ipka/A0934288.html, 2000-2014, 3 pages, (Retrieved Aug. 2, 2014).
Ewert, K. et al., Cationic lipid-DNA complexes for gene therapy: understanding the relationship between complex structure and gene delivery pathways at the molecular level. Current Medicinal Chemistry 11(2): 133-149 (2004).
Fath, S. et al., Multiparameter RNA and Codon Optimization: A Standardized Tool to Assess and Enhance Autologous Mammalian Gene Expression, PLoS One, 6(3):e17596 (14 pages) 2011.
Fechter, P. and Brownlee, G. G., Recognition of mRNA cap structures by viral and cellular proteins, Journal of General Virology, 86:1239-1249 (2005).
Felgner, P.L. and Ringold, G.M., Cationic liposome-mediated transfection, Nature, 337(6205):387-388 (1989).
Felgner, P.L. et al., Lipofection: A Highly Efficient, Lipid-Mediated DNA-Transfection Procedure, Proc. Natl. Acad., 84:7413-7417 (1987).
Fenske, D.B. and Cullis, P., Liposomal nanomedicines. Expert Opinion on Drug Delivery 5(1):25-44 (2008).
Fernandez, V. et al., Cross Flow Filtration of RNA Extracts by Hollow Fiber Membrane, Acta Biotechnologica, 12(1):49-56 (1992).
Ferruti, P.F. and Barbucci, R. , Linear amino polymers: Synthesis, protonation and complex formation. Advances in Polymer Science 58:55-92 (1984).
Ferruti, P.F et al., A novel modification of poly(l-lysine) leading to a soluble cationic polymer with reduced toxicity and with potential as a transfection agent. Macromolecular Chemistry and Physics 199:2565-2575 (1998).
Fire, A. et al., Potent and specific genetic interference by double-stranded RNA in Caenorhabditis elegans. Nature 391(6669):806-811 (1998).
Fischer, D. et al., Effect of poly(ethylene imine) molecular weight and pegylation on organ distribution and pharmacokinetics; of polyplexes with oligodeoxynucleotides in mice, Drug Metabolism and Disposition, 32(9):983-992 (2004).
Fumoto, S. et al., Targeted Gene Delivery: Importance of Administration Routes, Novel Gene Therapy Approaches, 3-31 (2013).
Furgeson, D.Y. et al., Modified linear polyethylenimine-cholesterol conjugates for DNA complexation. Bioconjugate Chemistry 14(4):840-847 (2003).
Furgeson, D.Y. et al., Novel water insoluble lipoparticulates for gene delivery. Pharmaceutical Research 19(4): 382-390 (2002).

(56) References Cited

OTHER PUBLICATIONS

Galipon, J. et al., Stress-induced 1ncRNAs evade nuclear degradation and enter the translational machinery, Genes to Cells, 18(5):353-368 (2013).
Gao, X. and Huang, L., A novel cationic liposome reagent for efficient transfection of mammalian cells, Biochem. Biophys. Res. Comm., 179(1): 280-285 (1991).
Garbuzenko, O.B. et al., Intratracheal Versus Intravenous Liposomal Delivery of siRNA, Antisense Oligonucleotides and Anticancer Drug, Pharmaceutical Research, 26(2):382-394 (2009).
Geraerts, M. et al., Upscaling of lentiviral vector production by tangential flow filtration, Journal of Gene Medicine, 7(10):1299-1310 (2005).
Godbey, W.T. et al., Size matters: molecular weight affects the efficiency of poly(ethylenimine) as a gene delivery vehicle. Journal of Biomedical Materials Research 45(3):268-275 (1998).
Gonzalez, H. et al., New class of polymers for the delivery of macromolecular therapeutics. Bioconjugate Chemistry 10(6):1068-1074 (1999).
Gonzalez-Aseguinolaza, G. et al., Gene therapy of liver diseases: A 2011 perspective, Clinics and Research in Hepatology and Gastroenterology, 35(11):699-708 (2011).
Gordon, N. Ornithine transcarbamylase deficiency: a urea cycle defect, European Journal of Paediatric Neurology, 7:115-121 (2003).
Gorecki, et al., Prospects and problems of gene therapy: an update, Expert Opin. Emerging Drugs, 6(2): 187-198 (2001).
Grayson, A.C.R. et al., Biophysical and structural characterization of polyethylenimine-mediated siRNA delivery in vitro. Pharmaceutical Research 23(8): 1868-1876 (2006).
Grudzien, E. et al., Novel cap analogs for in vitro synthesis of mRNAs with high translational efficiency, RNA Biology, 10(9):1479-1487 (2004).
Grunlan, M.A. et al., Synthesis of 1,9-bis[glycidyloxypropyl]penta(1'H, 1'H, 2'H, 2'H-perfluoroalkylmethylsiloxane)s and copolymerization with piperazine. Polymer 45:2517-2523 (2004).
Gupta, U. et al., A review of in vitro-in vivo investigations on dendrimers: the novel nanoscopic drug carriers. Nanomedicine: Nanotechnology, Biology, and Medicine 2(2):66-73 (2006).
Gust, T.C. et al., RNA-containing adenovirus/polyethylenimine transfer complexes effectively transduce dendritic cells and induce antigen-specific T cell responses, The Journal of Gene Medicine, 6(4): 464-470 (2004).
Guttman, M. et al., Chromatin signature reveals over a thousand highly conserved large non-coding RNAs in mammals, Nature, 458:223-227 (2009).
Haensler, J. and Szoka, F., Polyamidoamine cascade polymers mediate efficient transfection of cells in culture. Bioconjugate Chemistry 4(5):372-379 (1993).
Harada-Shiba, M. et al., Polyion complex micelles as vectors in gene therapy—pharmacokinetics and in vivo; gene transfer, Gene Therapy, 9(6):407-414 (2002).
Haskins M., Gene Therapy for Lysosomal Storage Disorders (LDSs) in Large Animal Models, Ilar J., 50(2):112-121 (2009).
Hata, A. et al., Isolation and Characterization of the Human Ornithine Transcarbamylase Gene: Structure of the 5'-End Region, Journal of Biochemistry, 100:717-725 (1986).
Hecker, J. et al., Advances in Self-Limited Gene Expression of Protective Intracellular Proteins In-Vivo in Rat Brain Using mRNA / Cationic Lipid Complexes, Anesthesia and Analgesia, 86(2S):346S (1994). 3 pages.
Heidenreich, O. et al., High Activity and Stability of Hammerhead Ribozymes Containing 2'-Modified Pyrimidine Nucleosides and Phosphorothioates, The Journal of Biological Chemistry, 269(3):2131-2138 (1994).
Henkin, R. I. et al., Inhaled Insulin-Intrapulmonary, intranasal, and other routes of administration: Mechanisms of action, Nutrition, 26: 33-39 (2010).
Hess, P. R. et al., Vaccination with mRNAs Encoding Tumor-Associated Antigens and Granulocyte-Macrophage Colony-Stimulating Factor Efficiently Primes CTL Responses, but is Insufficient to Overcome Tolerance to a Model Tumor/Self Antigen, Cancer Immunology, Immunotherapy:CII, 55(6): 672-683 (2006).
Heyes, J. et al., Cationic Lipid Saturation Influences Intracellular Delivery of Encapsulated Nucleic Acids, J. Controlled Release, 107:276-287 (2005).
Higman, M.A. et al., The mRNA (Guanine-7-)methyltransferase Domain of the Vaccinia Virus mRNA Capping Enzyme, The Journal of Biological Chemistry, 269(21):14974-14981 (1994).
Hill, I.R.C. et al., In vitro cytotoxicity of poly(amidoamine)s: relevance to DNA delivery. Biochimica et Biophysica Acta 1427: 161-174 (1999).
Hill, J.G. et al., Enantioselective Epoxidation of Allylic Alcohols: (2S,3S)-3-Propyloxiranemethanol. Organic Syntheses Collection 7: 461 (1990) and 63: 66 (1985) (8 pages).
Hillery, A.M. et al., Drug Delivery and Targeting for Pharmacists and Pharmaceutical Scientists, Taylor and Francis (2005). 448 pages.
Hoerr, I. et al., In Vivo Application of RNA Leads to Induction of Specific Cytotoxic T Lymphocytes and Antibodies, European Journal of Immunology, 30(1):1-7 (2000).
Hofland, H.E.J et al., Formation of stable cationic lipid/DNA complexes for gene transfer. Proceedings of the National Academy of Sciences of the USA 93 (14): 7305-7309 (1996).
Holtkamp S. et al., "Modification Antigen-encoding RNA Increases Stability, Translational Efficacy, and T-cell Stimulatory Capacity of Dendritic Cells," Blood, 108(13), pp. 4009-4017.
*Homo sapiens* galactosidase, alpha (GLA) mRNA, NCBI Reference Sequence NM_000169.1, Modification Date: Nov. 17, 2006. 3 pages.
Hope, M.J. et al., Cationic Lipids, Phosphatidylethanolamine and the Intracellular Delivery of Polymeric, Nucleic Acid-Based Drugs. Molecular Membrane Technology 15:1-14 (1998).
Hope, M.J. et al., Reduction of Liposome Size and Preparation of Unilamellar Vesicles by Extrusion Techniques, In: Liposome Technology, 1:123-139 (1993).
Hornung, V. et al., Quantitative expression of toll-like receptor 1-10 mRNA in cellular subsets of human peripheral blood mononuclear cells and sensitivity to CpG oligodeoxynucleotides. The Journal of Immunology 168: 4531-4537 (2002).
Horwich, A.L. et al., Structure and Expression of a Complementary DNA for the Nuclear Coded Precursor of Human Mitochondrial Ornithine Transcarbamylase, Science, 224(4653):1068-1074 (1984).
Horwich, A.L. et al., Targeting of Pre-Ornithine Transcarbamylase to Mitochondria: Definition of Critical Regions and Residues in the Leader Peptide, Cell, 44:451-459 (1986).
Howard, K.A. Delivery of RNA interference therapeutics using polycation-based nanoparticles. Advanced Drug Delivery Reviews 61: 710-720 (2009).
Huang, Z. et al., Thiocholesterol-based lipids for ordered assembly of bioresponsive gene carriers, Molecular Therapy, 11(3):409-417 (2005).
Huttenhofer, A. and Noller, H., Footprinting mRNA-ribosome complexes with chemical probes, The EMBO Journal, 13(16):3892-3901 (1994).
Incani, V. et al., Lipid and hydrophobic modification of cationic carriers on route to superior gene vectors. Soft Matter 6: 2124-2138 (2010).
International Preliminary Report on Patentability for PCT/US2010/058457, 12 pages (Jun. 14, 2012).
International Preliminary Report on Patentability for PCT/US18/33011, 6 pages (Nov. 28, 2019).
International Preliminary Report on Patentability for PCT/US18/20011, 19 pages (Aug. 27, 2019).
International Preliminary Report on Patentability for PCT/US2019/062592, 6 pages (Jun. 3, 2021).
International Preliminary Report on Patentability for PCT/US20/44158, 9 pages (Feb. 10, 2022).
International Preliminary Report on Patentability for PCT/US2020/51277, 8 pages (Mar. 31, 2022).
International Search Report for PCT/US15/27563, 5 pages (Sep. 18, 2015).
International Search Report for PCT/US2010/058457, 4 pages (May 6, 2011).

(56) References Cited

OTHER PUBLICATIONS

International Search Report for PCT/US2011/062459, 3 pages (Apr. 11, 2012).
International Search Report for PCT/US2012/041663, 4 pages (Oct. 8, 2012).
International Search Report for PCT/US2012/041724, 5 pages (Oct. 25, 2012).
International Search Report for PCT/US2013/034602, 2 pages (Jun. 17, 2013).
International Search Report for PCT/US2013/034604, 4 pages (Jun. 17, 2013).
International Search Report for PCT/US2013/044769, 4 pages (Nov. 12, 2013).
International Search Report for PCT/US2013/044771, 6 pages (Nov. 1, 2013).
International Search Report for PCT/US2013/073672, 6 pages (Mar. 3, 2014).
International Search Report for PCT/US2014/027422, 5 pages (Jul. 31, 2014).
International Search Report for PCT/US2014/027585, 3 pages (Jul. 14, 2014).
International Search Report for PCT/US2014/027587, 6 pages (Jul. 24, 2014).
International Search Report for PCT/US2014/027602, 6 pages (Jul. 28, 2014).
International Search Report for PCT/US2014/027717, 5 pages (Jul. 16, 2014).
International Search Report for PCT/US2014/028330, 5 pages (Jul. 22, 2014).
International Search Report for PCT/US2014/028441, 6 pages (Jul. 22, 2014).
International Search Report for PCT/US2014/028498, 5 pages (Jul. 28, 2014).
International Search Report for PCT/US2014/028849, 6 pages (Jul. 17, 2015).
International Search Report for PCT/US2014/061786, 6 pages (Feb. 6, 2015).
International Search Report for PCT/US2014/061793, 4 pages (Feb. 6, 2015).
International Search Report for PCT/US2014/061830, 5 pages (Feb. 4, 2015).
International Search Report for PCT/US2014/061841, 6 pages (Feb. 24, 2015).
International Search Report for PCT/US2015/039004, 4 pages (Oct. 6, 2015).
International Search Report for PCT/US2015/21403 (4 pages) mailed Jun. 15, 2015.
International Search Report for PCT/US18/20011, 7 pages (Sep. 12, 2018).
International Search Report and Written Opinion for PCT/US18/33011, 19 pages (Aug. 9, 2018).
International Search Report and Written Opinion for PCT/US2019/062592, 13 pages (Feb. 26, 2020).
International Search Report and Written Opinion for PCT/US20/44158, 15 pages (Nov. 13, 2020).
International Search Report and Written Opinion for PCT/US20/51277, 16 pages (Dec. 18, 2020).
International Search Report and Written Opinion for PCT/US21/31313, 17 pages (Oct. 18, 2021).
Jakobsen, K. et al., Purification of MRNA Directly From Crude Plant Tissues in 15 Minutes Using Magnetic Oligo DT Microsheres, Nucleic Acids Research, 18(12):3669 (1990).
Jeffs, L.B. et al., A scalable, extrusion-free method for efficient liposomal encapsulation of plasmid DNA, Pharmacol. Res., 22(3): 362-372 (2005).
Jemielity, J. et al., Novel "anti-reverse" cap analogs with superior translational properties, Cold Spring Harbor Laboratory Press, 9(9):1108-1122 (2003).
Jiang, G. et al., Hyaluronic acid-polyethyleneimine conjugate for target specific intracellular delivery of siRNA. Biopolymers 89 (7): 635-642 (2008).
Jiang, M. et al., Electrochemically controlled release of lipid/DNA complexes: a new tool for synthetic gene delivery system. Electrochemistry Communications (6): 576-582 (2004).
Jiang, S. and Cao, Z., Ultralow-fouling, functionalizable, and hydrolyzable zwitterionic materials and their derivatives for biological applications. Advanced Materials 22(9):920-932 (2010).
Jolck, R.I. et al., Solid-phase synthesis of PEGylated lipopeptides using click chemistry. Bioconjugate Chemistry 21(5):807-810 (2010).
Jon, S. et al., Degradable poly(amino alcohol esters) as potential DNA vectors with low cytotoxicity. Biomacromolecules 4(6):1759-1762 (2003).
Jones, G. et al., Duplex- and Triplex-Forming Properties of 4'-Thio-Modified Oligodeoxynucleotides, Bioorganic & Medicinal Chemistry Letters, 7(10):1275-1278 (1997).
Kabanov, A.V. and Kabanov, V.A., DNA complexes with polycations for the delivery of genetic material into cells. Bioconjugate Chemistry 6(1): 7-20 (1995).
Kamath, S. et al., Surface chemistry influences implant-mediated host tissue responses. Journal of Biomedical Materials Research A 86(3):617-626 (2007).
Kariko, K. et al., In vivo protein expression from mRNA delivered into adult rat brain, Journal of Neuroscience Methods, 105:77-86 (2001).
Kariko, K. et al., Incorporation of Pseudouridine Into mRNA Yields Superior Nonimmunogenic Vector With Increased Translational Capacity and Biological Stability, Molecular Therapy, 16(11): 1833-1840 (2008).
Kasuya, T. et al., In Vivo Delivery of Bionanocapsules Displaying Phaseolus vulgaris Agglutinin-L4 Isolectin to Malignant Tumors Overexpressing N-Acetylglucosaminyltransferase V, Human Gene Therapy, 19:887-895 (2008).
Kaur, N. et al., A delineation of diketopiperazine self-assembly processes: understanding the molecular events involved in Nepsilon-(fumaroyl)diketopiperazine of L-Lys (FDKP) interactions. Molecular Pharmaceutics 5(2):294-315 (2007).
Kaur, T. et al., Addressing the Challenge: Current and Future Directions in Ovarian Cancer Therapy, Current Gene Therapy, 9: 434-458 (2009).
Kiew, L.V. et al., Effect of antisense oligodeoxynucleotides for ICAM-1 on renal ischaemia-reperfusion injury in the anaesthetised rat, The Journal of Physiology, 557(3):981-989 (2004).
Kim, S.H. et al., Comparative evaluation of target-specific GFP gene silencing efficiencies for antisense ODN, synthetic siRNA, and siRNA plasmid complexed with PEI-PEG-FOL conjugate. Bioconjugate Chemistry 17(1): 241-244 (2006).
Kim, T. et al., Synthesis of biodegradable cross-linked poly(beta-amino ester) for gene delivery and its modification, inducing enhanced transfection efficiency and stepwise degradation. Bioconjugate Chemistry 16(5):1140-1148 (2005).
Klibanov, A.L. et al., Amphipathic polyethyleneglycols effectively prolong the circulation time of liposomes, FEBS, 268(1): 235-237 (1990).
Kober, L. et al., Optimized Signal Peptides for the Development of High Expressing CHO Cell Lines, Biotechnol. Bioeng., 110:1164-1173 (2012).
Kodama, K. et al., The Features and Shortcomings for Gene Delivery of Current Non-Viral Carriers, Current Medicinal Chemistry, 13: 2155-2161 (2006).
Kore, A. and Charles, I., Synthesis and evaluation of 2'-O-allyl substituted dinucleotide cap analog for mRNA translation, Bioorganics & Medicinal Chemistry, 18:8061-8065 (2010).
Kore, A. and Shanmugasundaram, M., Synthesis and biological evaluation of trimethyl-substituted cap analogs, Bioorganic & Medicinal Chemistry, 18:880-884 (2008).
Kormann, M.S.D. et al., Expression of therapeutic proteins after delivery of chemically modified mRNA in mice, Nature Biotechnology, 29(2):154-157 (2011).
Kozak, M. An analysis of 5'-noncoding sequences from 699 vertebrate messenger RNAs, Nucleic Acid Research, 15(20):8125-8148 (1987).

(56) References Cited

OTHER PUBLICATIONS

Krieg, P.A. et al., In vitro RNA synthesis with SP6 RNA polymerase, Methods in Enzymology, 155:397-415 (1987).
Kvasnica, M. et al., Platinum(II) complexes with steroidal esters of L-methionine and L-histidine: Synthesis, characterization and cytotoxic activity, Bioorganic & Medicinal Chemistry, 16:3704-3713 (2008).
Lam, J.K.W et al., Pulmonary delivery of therapeutic siRNA, Advanced Drug Delivery Reviews (2011). 15 pages.
Lasic, D.D. et al., Gelation of liposome interior: A novel method for drug encapsulation, FEBS, 312(2,3):255-258 (1992).
Lasic, D.D. Novel applications of liposomes, Trends in Biotechnology, 16:307-321 (1998).
Lechardeur, et al., Metabolic instability of plasmid DNA in the cytosol: a potential barrier to gene transfer, Gene Therapy, 6: 482-497 (1999).
Lee, S. et al., Stability and cellular uptake of polymerized siRNA (poly-siRNA)/polyethylenimine (PEI) complexes for efficient gene silencing. Journal of Controlled Release 141: 339-346 (2010).
Li, L. et al., Preparation and Gene Delivery of Alkaline Amino Acids-Based Cationic Liposomes, Archives of Pharmaceutical Research, 31(7):924-931 (2008).
Li, S. et al., In vivo gene transfer via intravenous administration of cationic lipid-protamine-DNA (LPD) complexes, Gene Therapy, 4:891-900 (1997).
Li, W. et al., Lipid-based Nanoparticles for Nucleic Acid Delivery, Pharmaceutical Research, 24(3):438-449 (2007).
Liebhaber, S.A. et al., Translation inhibition by an mRNA coding region secondary structure is determined by its proximity to the AUG initiation codon, Journal of Molecular Biology, 226(3):609-621 (1992).
Lim, Y. et al., A self-destroying polycationic polymer: biodegradable poly(4-hydroxy-I-proline ester). Journal of American Chemical Society 121: 5633-5639 (1999).
Lindgren, V. et al., Human Ornithine Transcarbamylase Locus Mapped to Band Xp21.1 Near the Duchenne Muscular Dystrophy Locus, Science, 226(2675):698-700 (1984).
Liu, X. et al., COStar: a D-star Lite-based Dynamic Search Algorithm for Codon Optimization, Journal of Theoretical Biology, 344:19-30 (2014).
Liu, Y. and Huang, L., Designer Lipids Advance Systematic siRNA Delivery, Molecular Therapy, 18(4):669-670 (2010).
Liu, Y. et al., Factors influencing the efficiency of cationic liposome-mediated intravenous gene delivery, Nature Biotechnology, 15:167-173 (1997).
Lo, K-M et al., High level expression and secretion of Fc-X fusion proteins in mammalian cells, Protein Engineering, 11(6):495-500 (1998).
Lorenzi, J. C. C. et al., Intranasal Vaccination with Messenger RNA as a New Approach in Gene Therapy: Use Against Tuberculosis, BMC Biotechnology, 10(77):1-11 (2010).
Love, K.T. et al., Lipid-like materials for low-dose, in vivo gene silencing, PNAS, 107(5):1864-1869 (2010).
Lu, D. et al., Optimization of methods to achieve mRNA-mediated transfection of tumor cells in vitro and in vivo employing cationic liposome vectors, Cancer Gene Therapy, 1(4):245-252 (1994).
Lukyanov, A.N. and Torchilin, V.P., Micelles from lipid derivatives of water-soluble polymers as delivery systems for poorly soluble drugs. Advanced Drug Delivery Reviews 56: 1273-1289 (2004).
Luo, D. and Saltzman, M., Synthetic DNA delivery systems. Nature Biotechnology 18: 33-37. Review (2000).
Lynn, D.M. and Langer, R., Degradable Poly(β-amino esters) :? Synthesis, Characterization, and Self-Assembly with Plasmid DNA. Journal of American Chemical Society 122(44): 10761-10768 (2000).
Lynn, D.M. et al., Accelerated discovery of synthetic transfection vectors: parallel synthesis and screening of a degradable polymer library. Journal of American Chemical Society 123 (33): 8155-8156 (2001).
Lynn, D.M. et al., pH-Responsive Polymer Microspheres: Rapid Release of Encapsulated Material within the Range of Intracellular pH. Angewandte Chemie International Edition 40(9): 1707-1710 (2001).
Ma, M. et al., Development of Cationic Polymer Coatings to Regulate Foreign Body Responses. Advanced Healthcare Materials 23: H189-H194. Reviews (2011).
MacLachlan, I., Lipid nanoparticle-mediated delivery of messenger RNA, 1st International mRNA Health Conference; Tubingen Germany, (Oct. 24, 2013) Retrieved from the Internet: URL: <http://files.shareholder.com/downloads/ABEA-50QJTB/2628241206x0x699789/47543d12-db34-4e6e-88a9-f3ae5d97b1d2/MacLachlan_mRNA_Conf_2013>. 32 pages.
Maeda-Mamiya, R. et al., In vivo gene delivery by cationic tetraamino; fullerene. Proceedings of National Academy of Sciences U S A, 107(12):5339-5344 (2010).
Malone, R.W., et al., Cationic liposome-mediated RNA transfection, PNAS, 86:6077-6081 (1989).
Mammal, http://en.wikipedia.org/wiki/Mammal, 2007, Pearson Education, NY, NY, Author unknown (Source: The international union for conservation of nature and natural resources), 2 pages, (Retrieved Aug. 2, 2014).
Mansour, H.M. et al., Nanomedicine in pulmonary delivery, International Journal of Nanomedicine, 4:299-319 (2009).
Margus, H. et al., Cell-penetrating peptides as versatile vehicles for oligonucleotide delivery. Molecular Therapy 20 (3): 525-533 (2012).
Martell, A.E. and Chaberek, S., The Preparation and the Properties of Some N,N'-Disubstituted-ethylenediaminedipropionic Acids. Journal of the American Chemical Society 72: 5357-5361 (1950).
Martinon, F. et al., Induction of Virus-Specific Cytotoxic T Lymphocytes in Vivo by Liposome-Entrapped mRNA, European Journal of Immunology, 23(7):1719-1722 (1993).
Mathiowitz, E. and Langer, R., Polyanhydride microspheres as drug carriers I. Hot-melt microencapsulation. Journal of Controlled Release 5: 13-22 (1987).
Mathiowitz, E. et al., Novel microcapsules for delivery systems. Reactive Polymers 6: 275-283 (1987).
Mathiowitz, E. et al., Polyanhydride microspheres as drug carriers II. Microencapsulation by solvent removal. Journal of Applied Polymer Sciences 35: 755-774 (1988).
Matsumura, Y. et al., "In vitro methods for CFTR biogenesis," in Cystic Fibrosis, pp. 233-253. Humana Press, 2011.
Mauro, V., "Codon Optimization in the Production of Recombinant Biotherapeutics: Potential Risks and Considerations," Biodrugs, vol. 32, No. 1, Feb. 1, 2018, pp. 69-81.
McCracken, S. et al., 5'-Capping Enzymes are Targeted to Pre-MRNA by Binding to the Phosphorylated Carboxy-Terminal Domain of RNA Polymerase II, Genes and Development, 22(24):3306-3318 (1997).
Mcivor, R. S., Therapeutic Delivery of mRNA: The Medium is the Message, Molecular Therapy, 19(5):822-823 (2011).
Melton, D.A. et al., Efficient in vitro synthesis of biologically active RNA and RNA hybridization probes from; plasmids containing a bacteriophage SP6 promoter, Nucleic Acids Research, 12(18):7035-7056 (1984).
Mendelsohn, J.D. et al., Rational design of cytophilic and cytophobic polyelectrolyte multilayer thin films. Biomacromolecules 4(1): 96-106 (2003).
Merkel, O.M. and Kissel, T., Nonviral Pulmonary Delivery of siRNA, Accounts of Chemical Research, 45(7):961-970 (2012).
Merten, O. et al., Large-Scale Manufacture and Characterization of a Lentiviral Vector Produced for Clinical Ex Vivo Gene Therapy Application, Human Gene Therapy, 22(3):343-356 (2011).
Miller, A. Cationic Liposomes for Gene Therapy. Angewandte Chemie International Edition 37: 1768-1785 (1998).
Monia, B.P. et al., Evaluation of 2'-Modified Oligonucleotides Containing 2'-Deoxy Gaps as Antisense Inhibitors of Gene Epression, The Journal of Biological Chemistry, 268(19):14514-14522 (1993).
Morrissey, D.V. et al., Potent and Persistent in vivo Anti-HBV Activity of Chemically Modified siRNAs, Nat. Biotechnol., 23(8): 1003-1007 (2005).

(56) References Cited

OTHER PUBLICATIONS

Narang, A.S. et al., Cationic lipids with increased DNA binding affinity for nonviral gene transfer in dividing and nondividing cells. Bioconjugate Chemistry 16(1): 156-168 (2005).
Navarro, G. et al., Phospholipid-polyethylenimine conjugate-based micelle-like nanoparticles for siRNA delivery. Drug Delivery and Translational Research 1: 25-33 (2011).
Neamnark, A. et al., Aliphatic lipid substitution on 2 kDa polyethylenimine improves plasmid delivery and transgene expression. Molecular Pharmaceutics 6(6): 1798-1815 (2009).
Ng, J. et al., LincRNAs join the pluripotency alliance, Nature Genetics, 42:1035-1036 (2010).
Nguyen, D.N. et al., A novel high-throughput cell-based method for integrated quantification of type I interferons and in vitro screening of immunostimulatory RNA drug delivery. Biotechnology and Bioengineering 103(4): 664-675 (2009).
Nguyen, D.N. et al., Drug delivery-mediated control of RNA immunostimulation. Molecular Therapy 17(9): 1555-1562 (2009).
Nojima, T. et al., The Interaction between Cap-binding Complex and RNA Export Factor is Required for Intronless mRNA Export, Journal of Biological Chemistry, 282(21):15645-15651 (2007).
Nori, A. et al., Tat-conjugated synthetic macromolecules facilitate cytoplasmic drug delivery to human ovarian carcinoma cells, Bioconj. Chem., 14(1): 44-50 (2003).
Okumura, K. et al., Bax mRNA therapy using cationic liposomes for human malignant melanoma, The Journal of Gene Medicine, 10:910-917 (2008).
Otsuka, Y. et al., Identification of a Cytoplasmic Complex That Adds a Cap onto 5'-Monophosphate RNA, Molecular and Cellular Biology, 29(8):2155-2167 (2009).
Ozer, A., Alternative applications for drug delivery: nasal and pulmonary routes, Nanomaterials and Nanosystems for Biomedical Applications, M.R. Mozafari (ed.): 99-112 (2007).
Painter, H. et al, Topical Delivery of mRNA to the Murine Lung and Nasal Epithelium, Gene Medicine Group and the Medical Informatics Unit, Nuffield Department of Clinical Laboratory Sciences, University of Oxford, 1 page.
Painter, H. et al., Topical Delivery of mRNA to the Murine Lung and Nasal Epithelium, Molecular Therapy, 9:S187 (2004). 1 page.
Painter, H., An Investigation of mRNA as a Gene Transfer Agent, Gene Medicine Research Group Nuffield Department of Clinical Laboratory Sciences and Merton College, University of Oxford, 1-282 (2007).
Painter, H., An Investigation of mRNA as a Gene Transfer Agent, Oxford University GeneMedicine, Abstract Only, 1 page (2007).
Parrish, D.A. and Mathias, L.J., Five- and six-membered ring opening of pyroglutamic diketopiperazine. Journal of Organic Chemistry 67(6): 1820-1826 (2002).
Patton, J., Market Trends in Pulmonary Therapies, Trends and Opportunities, VI: 372-377.
Paulus, C. and Nevels, M., The Human Cytomegalovirus Major Immediate-Early Proteins as Antagonists of Intrinsic and Innate Antiviral Host Responses, Viruses, 1:760-779 (2009).
Pearson, H. "One gene, twenty years: when the cystic fibrosis gene was found in 1989, therapy seemed around the corner. Two decades on, biologists still have a long way to go," Nature, vol. 460, Issue 7252, pp. 164-169 (2009).
Peppas, N.A. et al., Hydrogels in Biology and Medicine: From Molecular Principles to Bionanotechnology. Advanced Materials 18: 1345-1360 (2006).
Philipp, A. et al., Hydrophobically modified oligoethylenimines as highly efficient transfection agents for siRNA delivery. Bioconjugate Chemistry 20(11): 2055-2061 (2009).
Plotkin, J. et al., "Synonymous but not the same: the causes and consequences of codon bias," Nature Reviews Genetics, Nature Publishing Group, GB, vol. 12, No. 1, Jan. 1, 2011, pp. 32-42.
Pons, M. et al., Liposomes obtained by the ethanol injection method, Int. J. Pharm., 95: 51-56. (1993).
Prata, C.A. et al., Lipophilic peptides for gene delivery. Bioconjugate Chemistry 19(2): 418-420 (2008).
Probst, J. et al., Spontaneous cellular uptake of exogenous messenger RNA in vivo is nucleic acid-specific, saturable and ion dependent, Gene Therapy, 14:1175-1180 (2007).
Promega, PolyATtract mRNA Isolation Systems, Instructions for Use of Products Z5200, Z5210, Z2300 and Z5310, Technical Manual (2012). 16 pages.
Putnam, D. Polymers for gene delivery across length scales. Nature Materials 5: 439-451 (2006).
Putnam, D. and Langer, R., Poly(4-hydroxy-I-proline ester): Low-Temperature Polycondensation and Plasmid DNA Complexation. Macromolecules 32(11): 3658-3662 (1999).
Qiagen, Oligotex Handbook, Second Edition (2002).
Rabinovich, P.M. et al., Synthetic Messenger RNA as a Tool for Gene Therapy, Human Gene Therapy, 17:1027-1035 (2006).
Ramjeesingh, M. et al., "The intact CFTR protein mediates ATPase rather than adenylate kinase activity," Biochemical Journal, vol. 412, No. 2, Jun. 1, 2008, pp. 315-321.
Raper, S.E. et al., Developing adenoviral-mediated in vivo gene therapy for ornithine transcarbamylase deficiency, Journal of Inherited Metabolic Disease, 21:119-137 (1998).
Ratajczak, J. et al., Membrane-derived microvesicles: important and underappreciated mediators of cell-to-cell communication, Leukemia, 20:1487-1495 (2006).
Ratner, B.D. and Bryant, S., Biomaterials: where we have been and where we are going. Annual Review of Biomedical Engineering 6: 41-75 (2004).
Reddy, A. et al., The Effect of Labour and Placental Separation on the Shedding of Syncytiotrophoblast Microparticles, Cell-free DNA and mRNA in Normal Pregnancy and Pre-eclampsia, Placenta, 29: 942-949 (2008).
Rejman, J. et al., Characterization and transfection properties of lipoplexes stabilized with novel exchangeable polyethylene glycol-lipid conjugates, Biochimica et Biophysica Acta, 1660:41-52 (2004).
Remington: The Science and Practice of Pharmacy, 21st Edition, Philadelphia, PA. Lippincott Williams & Wilkins (2005). 3 pages.
Robinson et al., "Lipid Nanoparticle-Delivered Chemically Modified mRNA Restores Chloride Secretion in Cystic Fibrosis," Molecular Therapy, 26(8): 1-13 (2018).
Rosenecker et al., "Gene therapy for cystic fibrosis lung disease: Current status and future perspectives," Current Opinion in Molecular Therapeutics 2006 8(5): 439-445.
Rosenecker et al., "Interaction of bronchoalveolar lavage fluid with polyplexes and lipoplexes: analysing the role of proteins and glycoproteins," J Gene Med. 5, 49-60 (2003).
Rowe et al., "Cystic Fibrosis," New Engl J Med 352 2005, 1992-2001.
Rudolph, C. et al., Aerosolized Nanogram Quantities of Plasmid DNA Mediate Highly Efficient Gene Delivery to Mouse Airway Epithelium, Molecular Therapy, 12(3): 493-501 (2005).
Rudolph, C. et al., Methodological optimization of polyethylenimine (PEI)-based gene delivery to the lungs of mice via aerosol application, Journal of Gene Medicine, 7(1): 59-66 (2005).
Ruiz et al., "A Clinical Inflammatory Syndrome Attributed to Aerosolized Lipid-DNA Administration in Cystic Fibrosis," Human Gene Therapy, Liebert, US, vol. 12, No. 7, pp. 751-761, May 1, 2001.
Ryng, S. et al., Synthesis and structure elucidation of 5-aminomethinimino-3-methyl-4-isoxazolecarboxylic acid phenylamides and their immunological activity. Arch. Pharm. Pharm. Med. Chem 330(11):319-26 (1997).
Sahay, G. et al., Endocytosis of nanomedicines. Journal of Controlled Release 145: 182-195 (2010).
Sakiyama-Elbert, S.E. and Hubbell, J.A., Functional Biomaterials: Design of Novel Biomaterials. Annual Review of Materials Research 31: 183-201 (2001).
Schnierle, B.S. et al., Cap-specific mRNA (nucleoside-O2'-)-methyltransferase and poly(A) polymerase stimulatory activities of vaccinia virus are mediated by a single protein, Proceedings of the National Academy of Sciences, 89:2897-2901 (1992).
Schreier, H., The new frontier: gene and oligonucleotide therapy, Pharmaceutica Acta Helvetiae, 68(3):145-159 (1994).
Semple, S.C. et al., Rational design of cationic lipids for siRNA delivery, Nature Biotechnology, 28(2): 172-176 (2010).

(56) References Cited

OTHER PUBLICATIONS

Shchori E., Poly(secondary Amine)s from Diacrylates and Diamines. Journal of Polymer Science 21(6):413-15 (1983).
Sherwood, R.F. Advanced drug delivery reviews: enzyme prodrug therapy, Adv. Drug Del. Rev., 22: 269-288 (1996).
Shimada, A. et al., Translocation Pathway of the Intratracheally Instilled Ultrafine Particles from the Lung into the Blood Circulation in the Mouse, Toxicologic Pathology, 34:949-957 (2006).
Siegwart, D.J. et al., Combinatorial synthesis of chemically diverse core-shell nanoparticles for intracellular delivery. Proceedings of the National Academy of the Sciences of the USA 108(32):12996-123001 (2011).
Smisterova, J. et al., Molecular Shape of the Cationic Lipid Controls the Structure of Cationic Lipid/Dioleylphosphatidylethanolamine-DNA Complexes and the Efficiency of Gene Delivery, The Journal of Biological Chemistry, 276(50):47615-47622 (2001).
Stern, L. et al., A novel antitumor prodrug platform designed to be cleaved by the endoprotease legumain, Bioconj. Chem., 20: 500-510 (2009).
Su, X. et al., Cytosolic Delivery Mediated Via Electrostatic Surface Binding of mRNA to Degradable Lipid-Coated Polymeric Nanoparticles, Polymer Preprints, 51(2):668-669 (2010).
Su, X. et al., In Vitro and in Vivo mRNA Delivery Using Lipid-Enveloped pH-Responsive Polymer Nanoparticles, Molecular Pharmaceutics, 8(3):774-787 (2011).
Suri, M. et al., Genetics for Pediatricians, Remedica Publishing, (2005). 5 pages.
Szoka, F. and Papahadjopoulos, D., Comparative properties and methods of preparation of lipid vesicles (liposomes). Annual Review of Biophysics Bioengineering 9: 467-508 (1980).
Tagawa, M. et al., Gene expression and active virus replication in the liver after injection of duck hepatitis B virus DNA into the peripheral vein of ducklings, Journal of Hepatology, 24:328-334 (1996).
Takahashi, Y. et al., Development of safe and effective nonviral gene therapy by eliminating CpG motifs from plasmid DNA vector, Frontiers in Bioscience, S4: 133-141 (2012).
Tan, S. et al., Engineering Nanocarriers for siRNA Delivery. Small 7(7): 841-856 (2011).
Tang, F. and Hughes, J. et al., Introduction of a Disulfide Bond into a Cationic Lipid Enhances Transgene Expression of Plasmid DNA, Biochemical and Biophysical Research Communications, 242(1):141-145 (1998).
Tang, M.X. et al., In vitro gene delivery by degraded polyamidoamine dendrimers. Bioconjugate Chemistry 7(6): 703-714 (1996).
Tarcha, P.J. et al., Synthesis and characterization of chemically condensed oligoethylenimine containing beta-aminopropionamide linkages for siRNA delivery. Biomaterials 28: 3731-3740 (2007).
Tavernier, G. et al., mRNA as gene therapeutic: How to control protein expression, Journal of Controlled Release, 150:238-247 (2011).
Tcherepanova, I. et al., Ectopic expression of a truncated CD40L protein from synthetic post-transcriptionally capped RNA in dendritic cells induces high levels of IL-12 secretion, BMC Molecular Biology, 9(1):pp. 1-13 (2008).
Theus, S. and Liarakos, C., A Simple Assay for Determining the Capping Efficiencies of RNA Polymerases Used for In Vitro Transcription, BioChromatography, 9(5):610-614 (1990).
Third Party Preissuance Submission Under 37 CFR § 1.290 (Oct. 25, 2013). 9 pages.
Thomas, C. E. et al., Progress and problems with the use of viral vectors for gene therapy, Nature Reviews/Genetics, 4: 346-358 (2003).
Thompson, P.E. et al., Antiamebic action of 5-chloro-7-diethylaminomethyl-8-quinolinol and of other substituted 8-quinolinols in vitro and in experimental animals. American Journal of Tropical Medicine and Hygiene 2(4): 224-248 (1955).
Toki, B.E. et al., Protease-mediated fragmentation of p-amidobenzyl ethers: a new strategy for the activation of anticancer prodrugs, J. Org. Chem., 67(6): 1866-1872 (2002).
Tranchant, I. et al., Physicochemical optimisation of plasmid delivery by cationic lipids. Journal of Gene Medicine 6: S24-S35 (2004).
Tsui, N.B. et al., Stability of endogenous and added RNA in blood specimens, serum, and plasma, Clinical Chemistry, 48(10):1647-1653 (2002).
Tsvetkov, D.E. et al., Neoglycoconjugates based on dendrimeric poly(aminoamides). Russian Journal of Bioorganic Chemistry 28(6): 470-486 (2002).
Tuschl, T. et al., Targeted mRNA degradation by double-stranded RNA in vitro, Genes and Development, 13(24):3191-3197 (1999).
Urban-Klein, B. et al., RNAi-mediated gene-targeting through systemic application of polyethylenimine (PEI)-complexed siRNA in vivo. Gene Therapy 12(5): 461-466 (2005).
Van Balen, G.P. et al., Liposome/water lipophilicity: methods, information content, and pharmaceutical applications. Medicinal Research Reviews 24(3): 299-324 (2004).
Van De Wetering, P. et al., Structure-activity relationships of water-soluble cationic methacrylate/methacrylamide polymers for nonviral gene delivery. Bioconjugate Chemistry 10(4): 589-597 (1999).
Van Der Gun, B.T.F et al., Serum insensitive, intranuclear protein delivery by the multipurpose cationic lipid Saint-2, Journal of Controlled Release, 123:228-238 (2007).
Van Tendeloo, V.F.I et al., mRNA-based gene transfer as a tool for gene and cell therapy, Current Opinion in Molecular Therapeutics, 9(5):423-431 (2007).
Vandenbroucke, R.E. et al., Prolonged gene silencing in hepatoma cells and primary hepatocytes after small interfering RNA delivery with biodegradable poly(beta-amino esters). Journal of Gene Medicine 10: 783-794 (2008).
Varambally, S. et al., Genomic Loss of microRNA-101 Leads to Overexpression of Histone Methyltransferase EZH2 in Cancer, Science, 322:1695-1699 (2008).
Veronese, F.M. et al., PEG-doxorubicin conjugates: influence of polymer structure on drug release, in vitro cytotoxicity, biodistribution, and antitumor activity, Bioconj. Chem., 16(4): 775-784 (2005).
Viecelli, H. et al., Gene Therapy for Hepatic Diseases Using Non-Viral Minicircle-DNA Vector, Journal of Inherited Metabolic Disease, 35(1):S144 (2012). 1 page.
Viecelli, H. et al., Gene therapy for liver diseases using non-viral minicircle-DNA vector, Human Gene Therapy, 23(10):A145 (2012). 1 page.
Viecelli, H. et al., Gene therapy for liver diseases using non-viral minicircle-DNA vector, Molecular Therapy, 21(1):S136 (2013). 1 page.
Villalobos, A. et al., "Gene Designer: a synthetic biology tool for constructing artificial DNA segments," BMC Bioinformatics, Biomed Central, London, GB, vol. 7, No. 1, Jun. 6, 2006, pp. 1-8.
Vomelova, I. et al., Methods of RNA Purification. All Ways (Should) Lead to Rome, Folia Biologica, 55(6):242-251 (2009).
Von Harpe et al., Characterization of commercially available and synthesized polyethylenimines for gene delivery. Journal of Controlled Release 69(2):309-322 (2000).
Walde, P. et al., Preparation of Vesicles (Liposomes). Encyclopedia of Nanoscience and Nanotechnology. Nalwa, ed. American Scientific Publishers, Los Angeles 9:43-79 (2004).
Wang, H. et al., N-acetylgalactosamine functionalized mixed micellar nanoparticles for targeted delivery of siRNA to liver, Journal of Controlled Release, 166(2):106-114 (2013).
Wang, Y. et al., Systemic delivery of modified mRNA encoding herpes simplex virus 1 thymidine kinase for targeted cancer gene therapy, Molecular Therapy, 21(2):358-367 (2013).
Webb, M. et al., Sphinogomyeline-cholesterol liposomes significantly enhance the pharmacokinetic and therapeutic properties of vincristine in murine and human tumour models, British Journal of Cancer, 72(4):896-904 (1995).
Werth, S. et al., A low molecular weight fraction of polyethylenimine (PEI) displays increased transfection efficiency of DNA and siRNA in fresh or lyophilized complexes. Journal of Controlled Release 112: 257-270 (2006).
Wetzer, B. et al., Reducible cationic lipids for gene transfer, Biochem. J., 356:747-756 (2001).

(56) References Cited

OTHER PUBLICATIONS

White, J.E. et al., Poly(hydroxyaminoethers): A New Family of Epoxy-Based Thermoplastics. Advanced Materials 12(23): 1791-1800 (2000).
White, J.E. et al., Step-growth polymerization of 10,11-epoxyundecanoic acid. Synthesis and properties of a new hydroxy-functionalized thermopastic polyester. Advanced Materials 48: 3990-3998 (2007).
Whitehead, K.A. et al., Knocking down barriers: advances in siRNA delivery. Nature Reviews Drug Discovery 8(2): 129-139 (2009).
Wiehe, J.M. et al., mRNA-mediated gene delivery into human progenitor cells promotes highly efficient protein expression, Journal of Cellular and Molecular Medicine, 11(3):521-530 (2007).
Williams, D. et al., A simple, highly efficient method for heterologous expression in mammalian primary neurons using cationic lipid-mediated mRNA transfection, Frontiers in Neuroscience, 4(181):1-20 (2010).
Written Opinion for PCT/US15/27563, 12 pages (Sep. 18, 2015).
Written Opinion for PCT/US2010/058457, 14 pages (May 6, 2011).
Written Opinion for PCT/US2011/062459, 9 pages (Apr. 11, 2012).
Written Opinion for PCT/US2012/041663, 7 pages (Oct. 8, 2012).
Written Opinion for PCT/US2012/041724, 11 pages (Oct. 25, 2012).
Written Opinion for PCT/US2013/034602, 4 pages (Jun. 17, 2013).
Written Opinion for PCT/US2013/034604, 9 pages (Jun. 17, 2013).
Written Opinion for PCT/US2013/044769, 8 pages (Nov. 12, 2013).
Written Opinion for PCT/US2013/044771, 7 pages (Nov. 1, 2013).
Written Opinion for PCT/US2013/073672, 7 pages (Mar. 3, 2014).
Written Opinion for PCT/US2014/027422, 6 pages (Jul. 31, 2014).
Written Opinion for PCT/US2014/027587, 5 pages (Jul. 24, 2014).
Written Opinion for PCT/US2014/027602, 7 pages (Jul. 28, 2014).
Written Opinion for PCT/US2014/027717, 5 pages (Jul. 16, 2014).
Written Opinion for PCT/US2014/028330, 7 pages (Jul. 22, 2014).
Written Opinion for PCT/US2014/028441, 6 pages (Jul. 22, 2014).
Written Opinion for PCT/US2014/028498, 6 pages (Jul. 28, 2014).
Written Opinion for PCT/US2014/028849, 7 pages (Jul. 17, 2015).
Written Opinion for PCT/US2014/061786, 5 pages (Feb. 6, 2015).
Written Opinion for PCT/US2014/061793, 4 pages (Feb. 6, 2015).
Written Opinion for PCT/US2014/061830, 7 pages (Feb. 4, 2015).
Written Opinion for PCT/US2014/061841, 8 pages (Feb. 24, 2015).
Written Opinion for PCT/US2015/039004, 8 pages (Oct. 6, 2015).
Written Opinion for PCT/US2015/21403 (7 pages) mailed Jun. 15, 2015.
Wu, J. and Zern, M., Modification of liposomes for liver targeting, Journal of Hepatology, 24(6):757-763 (1996).
Wu, J. et al., Cationic lipid polymerization as a novel approach for constructing new DNA delivery agents. Bioconjugate Chemistry 12(2): 251-257 (2001).
Wurdinger, T. et al., A secreted luciferase for ex-vivo monitoring of in vivo processes, Nat. Methods, 5(2):171-173 (2008).
Xiong et al., "Biomedical applications of mRNA nanomedicine," Nano Research, vol. 11, No. 10, pp. 5281-5309, (2018).
Yamamoto, A. et al., Current prospects for mRNA gene delivery, European Journal of Pharmaceutics and Biopharmaceutics, 71(3): 484-489 (2009).
Yamamoto, Y. et al., Important Role of the Proline Residue in the Signal Sequence that Directs the Secretion of Human Lysozyme in *Saccharomyces cerevisiae*, Biochemistry, 28:2728-2732 (1989).
Yasuda, M. et al., Fabry Disease: Novel [alpha]-Galactosidase A 3-terminal Mutations Result in Multiple Transcripts Due to Aberrant 3-End Formation, American Journal of Human Genetics, 73:162-173 (2003).
Ye, X. et al., Nucleic Acids, Protein Synthesis, and Molecular Genetics: Prolonged Metabolic Correction in Adult Ornithine Transcarbamylase-deficient Mice with Adenoviral Vectors, The Journal of Biological Chemistry, 271:3639-3646 (1996).
Yokoe, H. et al., Spatial dynamics of GFP-tagged proteins investigated by local fluorescence enhancement, Nature Biotechnology, 14(10):1252-1256 (1996).
Yoneda et al., A cell-penetrating peptidic GRP78 ligand for tumor cell-specific prodrug therapy, Bioorg. Med. Chern. Lett., 18(5): 1632-1636 (2008).
Yoshioka, Y. and Calvert, P., Epoxy-based Electroactive Polymer Gels. Experimental Mechanics 42(4): 404-408 (2002).
Zagridullin, P.H. et al., Monobasic amines. II. Cycloalkylation and hydroxyalkylation of cyclic and acyclic di- and polyamines. Journal of Organic Chemistry, 26(1):184-88. Russian (1990).
Zaugg, H.E. et al., 3-Carboxy-2,5-piperazinedione and Derivatives. Journal of American Chemical Society 78(11):2626-2631 (1956).
Zauner, W.et al., Polylysine-based transfection systems utilizing receptor-mediated delivery. Advanced Drug Delivery Reviews 30(1-3):97-113(1998).
Zintchenko, A. et al., Simple modifications of branched PEI lead to highly efficient siRNA carriers with low toxicity. Bioconjugate Chemistry 19(7):1448-1455 (2008).
Zou, S. et al., Lipid-mediated delivery of RNA is more efficient than delivery of DNA in non-dividing cells, International Journal of Pharmaceutics, 389(1-2):232-243 (2010).
Lee et al., "Interference with Ubiquitination in CFTR Modifies Stability of Core Glycosylated and Cell Surface Pools", Molecular and Cellular Biology, Jul. 2014, 34(14): 2554-2565.
Rich et al., "Regulation of the cystic fibrosis transmembrane conductance regulator CI-channel by negative charge in the R domain", J Biol Chem., Sep. 25, 1993, 268(27): 20259-20267.
Chang et al., "Protein kinase A (PKA) still activates CFTR chloride channel after mutagenesis of all 10 PKA consensus phosphorylation sites", J Biol Chem., May 25, 1993, 268(15): 11304-11311.

| Transfection mRNA Test Groups: | Baseline Current (Pre-Amphotericin B) Mean ± SEM (n) (µA/cm²) | Forskolin Response Mean ± SEM (n) (µA/cm²) | VX-770 Response Mean ± SEM (n) (µA/cm²) | ∑(Forskolin, VX-770) Responses Mean ± SEM (n) (µA/cm²) | CFTRinh-172 Response Mean ± SEM (n) (µA/cm²) |
|---|---|---|---|---|---|
| WT | -4.65±1.43 (4) $^{A}$ | -80.30±3.43 (4) $^{C}$ | -15.13±0.89 (4) $^{C}$ | -95.43±4.19 (4) $^{D}$ | 94.25±3.93 (4) $^{A}$ |
| 15A | -1.01±0.11 (4) $^{A}$ | -10.91±0.41 (4) $^{A}$ | -36.41±1.48 (4) $^{D}$ | -47.33±1.87 (4) $^{B}$ | 47.01±1.79 (4) $^{D}$ |
| 15A/E1371Q | -65.01±1.34 (4) $^{B}$ | -8.81±0.21 (4) $^{A}$ | -4.02±0.27 (4) $^{A}$ | -12.83±0.44 (4) $^{A}$ | 70.62±1.33 (4) $^{B}$ |
| 15D/E1371Q | -64.76±1.32 (3) $^{C}$ | -4.33±0.14 (3) $^{A}$ | -5.46±0.11 (3) $^{A}$ | -9.79±0.07 (3) $^{A}$ | 71.51±1.84 (3) $^{B}$ |

FIG. 12A

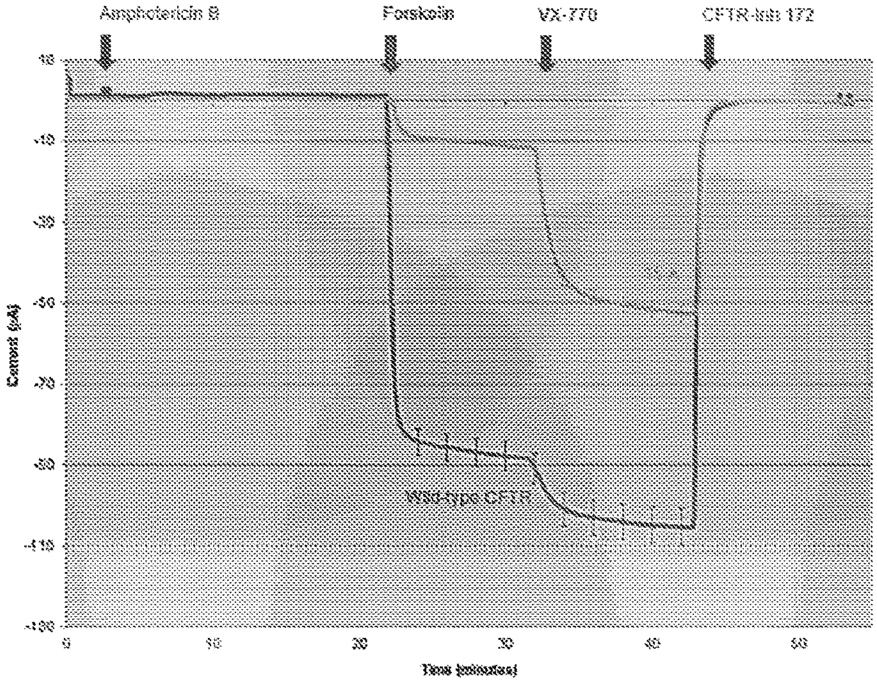

FIG. 12B

ATP interacts with identified residues in NBD1 and NBD2

Alterations in identified resides modulate channel relaxation time

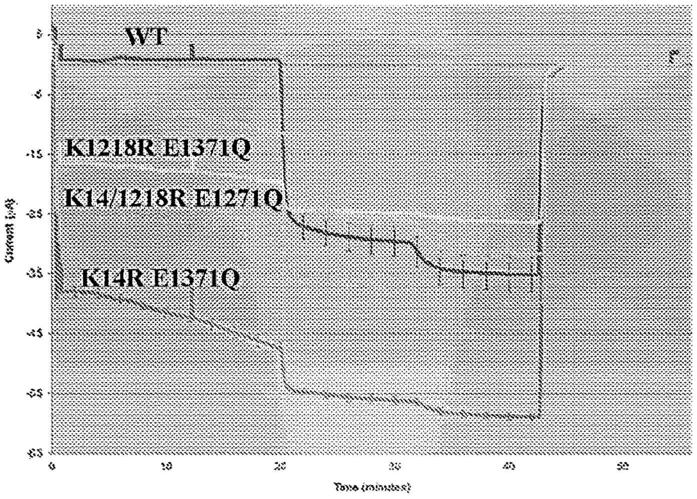
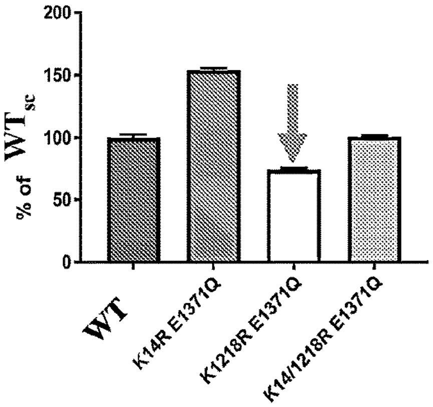
FIG. 15C mRNA ENCODING ENGINEERED CFTR

CROSS-REFERENCE TO RELATED APPLICATIONS

This application is a 35 U.S.C. § 371 National Stage Application of International Application No. PCT/US20/51277, filed on Sep. 17, 2020, which claims benefit of, and priority to U.S. Provisional Patent Application Ser. No. 62/903,047 filed on Sep. 20, 2019, U.S. Provisional Patent Application Ser. No. 62/984,632, filed on Mar. 3, 2020, and U.S. Provisional Patent Application No. 63/021,263, filed on May 7, 2020, the contents of each of which are incorporated herein in its entirety.

INCORPORATION-BY-REFERENCE OF SEQUENCE LISTING

The contents of the text file named "MRT-2115US-_SL.txt", which was created on Oct. 11, 2022 and is 261 KB in size, are hereby incorporated by reference in its entirety.

BACKGROUND

Cystic fibrosis is an autosomal inherited disorder resulting from mutation of the CFTR gene, which encodes a chloride ion channel believed to be involved in regulation of multiple other ion channels and transport systems in epithelial cells. Loss of function of CFTR results in chronic lung disease, aberrant mucus production, and dramatically reduced life expectancy. See generally Rowe et al., New Engl. J. Med. 352, 1992-2001 (2005).

Currently there is no cure for cystic fibrosis. The literature has documented numerous difficulties encountered in attempting to induce expression of CFTR in the lung. For example, viral vectors comprising CFTR DNA triggered immune responses and CF symptoms persisted after administration. Conese et al., J. Cyst. Fibros. 10 Suppl 2, S114-28 (2011); Rosenecker et al., Curr. Opin. Mol. Ther. 8, 439-45 (2006). Non-viral delivery of DNA, including CFTR DNA, has also been reported to trigger immune responses. Alton et al., Lancet 353, 947-54 (1999); Rosenecker et al., J Gene Med. 5, 49-60 (2003). Furthermore, non-viral DNA vectors encounter the additional problem that the machinery of the nuclear pore complex does not ordinarily import DNA into the nucleus, where transcription would occur. Pearson, Nature 460, 164-69 (2009).

SUMMARY OF THE INVENTION

The present invention provides, among other things, pharmaceutical compositions comprising messenger RNA (mRNA) encoding an engineered or mutant Cystic Fibrosis Transmembrane Conductance Regulator (CFTR) protein and methods of making and using thereof. Notably, engineered or mutant CFTR proteins described herein contain mutations that enhance the activity or stability of the protein. These pharmaceutical compositions can be used for improved treatment of cystic fibrosis.

In one aspect, the present invention provides a pharmaceutical composition for treating cystic fibrosis, comprising an mRNA encoding a Cystic Fibrosis Transmembrane Conductance Regulator (CFTR), wherein the CFTR comprises one or more mutations that produce an activated CFTR protein.

In one aspect, a pharmaceutical composition is provided herein for treating cystic fibrosis, comprising an mRNA encoding a Cystic Fibrosis Transmembrane Conductance Regulator (CFTR), wherein the CFTR comprises one or more mutations that produce a CFTR protein that is more stable than a wild type CFTR protein.

For example, in some embodiments, the mutant CFTR protein has a greater half-life in comparison to wild type CFTR. In some embodiments, the mutant CFTR protein has about the same half-life as a wild type CFTR. In some embodiments, the mutant CFTR protein has about 5 minutes, 10 minutes, 15 minutes, 30 minutes, 45 minutes, 60 minutes, 90 minutes, 2 hours, 4 hours, 6 hours, 8 hours, 10 hours, 12 hours, 14 hours, 16 hours, 18 hours, 20 hours, 22 hours, or 24 hours greater half-life in comparison to wild type CFTR. In some embodiments, the mutant CFTR protein has more than 24 hours half-life in comparison to wild type CFTR.

In some embodiments, one or more mutations are located within the CFTR regulatory domain, a membrane-spanning domain (MSD), and/or a nucleotide-binding domain (NBD). In some embodiments, one or more mutations are located within the CFTR regulatory domain amino acid residues 634-835. In some embodiments, mutations are located within different domains.

In some embodiments, the engineered CFTR protein comprising one or more mutations results in increased activity in comparison to wild type CFTR protein.

In some embodiments, the engineered CFTR protein comprising one or more mutations results in increased trafficking in comparison to wild type CFTR protein.

In some embodiments, the engineered CFTR protein comprising one or more mutations results in increased conductivity in comparison to wild type CFTR protein. In some embodiments, the engineered CFTR protein comprising one or more mutations results in increased conductivity in the presence of modulators in comparison to wild type CFTR protein. For example, the engineered CFTR protein has increased conductivity in the presence of a potentiator, corrector and/or activator in comparison to conductivity in a wild type CFTR protein.

In some embodiments, the engineered CFTR protein comprising one or more mutations has improved pharmacokinetic properties in comparison to wild type CFTR protein.

In some embodiments, the engineered CFTR protein comprising one or more mutations produces an activated CFTR protein that is more stable than a wild type CFTR protein.

In some embodiments, the engineered CFTR protein comprising one or more mutations produces a CFTR protein that is more therapeutically effective for the treatment of cystic fibrosis in comparison to a wild type CFTR protein. For example, the engineered CFTR protein has one or more of improved activity, trafficking, synergistic conductivity in the presence of modulators (e.g., potentiators, correctors and/or activators), pharmacokinetic properties, and stability in comparison to wild type CFTR protein.

In some embodiments, the CFTR comprises at least 2 mutations in amino acid residues in comparison to wild type CFTR protein. In some embodiments, the CFTR comprises at least 3 mutations in amino acid residues in comparison to wild type CFTR protein. In some embodiments, the CFTR comprises at least 4 mutations in amino acid residues in comparison to wild type CFTR protein. In some embodiments, the CFTR comprises at least 5 mutations in amino acid residues in comparison to wild type CFTR protein. In some embodiments, the CFTR comprises at least 6 mutations in amino acid residues in comparison to wild type CFTR protein. In some embodiments, the CFTR comprises at least 7 mutations in amino acid residues in comparison to wild type CFTR protein. In some embodiments, the CFTR comprises at least 10 mutations in amino acid residues in comparison to wild type CFTR protein. In some embodiments, the CFTR comprises at least 11 mutations in amino acid residues in comparison to wild type CFTR protein. In some embodiments, the CFTR comprises at least 12 mutations in amino acid residues in comparison to wild type CFTR protein. In some embodiments, the CFTR comprises at least 13 mutations in amino acid residues in comparison to wild type CFTR protein. In some embodiments, the CFTR comprises at least 14 mutations in amino acid residues in comparison to wild type CFTR protein. In some embodiments, the CFTR comprises at least 15 mutations in amino acid residues in comparison to wild type CFTR protein. In some embodiments, the CFTR comprises at least 16 mutations in amino acid residues in comparison to wild type CFTR protein. In some embodiments, the CFTR comprises at least 17 mutations in amino acid residues in comparison to wild type CFTR protein. In some embodiments, the CFTR comprises at least 18 mutations in amino acid residues in comparison to wild type CFTR protein. In some embodiments, the CFTR comprises at least 19 mutations in amino acid residues in comparison to wild type CFTR protein. In some embodiments, the CFTR comprises at least 20 mutations in amino acid residues in comparison to wild type CFTR protein.

In some embodiments, the CFTR comprises between 1 and 20 mutations in amino acid residues in comparison to wild type CFTR protein. In some embodiments, the CFTR comprises between 2 and 15 mutations in amino acid residues in comparison to wild type CFTR protein. In some embodiments, the CFTR comprises between 3 and 12 mutations in amino acid residues in comparison to wild type CFTR protein. In some embodiments, the CFTR comprises between 5 and 10 mutations in amino acid residues in comparison to wild type CFTR protein.

In some embodiments, the mutation is an amino acid substitution. In some embodiments, the mutation is a deletion of one or more amino acids. In some embodiments, the mutation is an insertion of one or more amino acids. In some embodiments, the mutation is an amino acid inversion. In some embodiments, the mutation is a combination of amino acid substitution, a deletion of one or more amino acids, an insertion of one or more amino acids, an amino acid inversion.

In some embodiments, one or more mutations are made at residues K14, K68, S422, S660, S670, S686, T690, S700, K710, S712, K716, S737, S753, S768, T787, T788, S790, S795, S813, K978, K1041, K1080, K1218, E1371, K190, G550, R553, R555, K1250, K464, W401, F409, F430, and combinations thereof. In some embodiments, a mutation is made at residue K14. In some embodiments, a mutation is made at residue K68. In some embodiments, a mutation is made at residue S422. In some embodiments, a mutation is made at residue S660. In some embodiments, a mutation is made at residue S670. In some embodiments, a mutation is made at residue S686. In some embodiments, a mutation is made at residue S700. In some embodiments, a mutation is made at residue K710. In some embodiments, a mutation is made at residue S712. In some embodiments, a mutation is made at residue K716. In some embodiments, a mutation is made at residue S737. In some embodiments, a mutation is made at residue S753. In some embodiments, a mutation is made at residue S768. In some embodiments, a mutation is made at residue T787. In some embodiments, a mutation is made at residue T788. In some embodiments, a mutation is made at residue S790. In some embodiments, a mutation is made at residue S795. In some embodiments, a mutation is made at residue S813. In some embodiments, a mutation is made at residue K978. In some embodiments, a mutation is made at residue K1041. In some embodiments, a mutation is made at residue K1080. In some embodiments, a mutation is made at residue K1218. In some embodiments, a mutation is made at residue E1371. In some embodiments, a mutation is made at residue K190. In some embodiments, a mutation is made at residue G550. In some embodiments, a mutation is made at residue R553. In some embodiments, a mutation is made at residue R555. In some embodiments, a mutation is made at residue K1250. In some embodiments, a mutation is made at residue K464. In some embodiments, a mutation is made at residue W401. In some embodiments, a mutation is made at residue F409. In some embodiments, a mutation is made at residue F430. Accordingly, in some embodiments, one or more CFTR lysine residues are mutated. In some embodiments, one or more CFTR serine residues are mutated. In some embodiments, one or more CFTR glycine residues are mutated. In some embodiments, one or more CFTR threonine residues are mutated. In some embodiments, one or more CFTR arginine residues are mutated. In some embodiments, one or more CFTR tryptophan residues are mutated. In some embodiments, one or more CFTR threonine residues are mutated. In some embodiments, one or more CFTR glutamic acid residues are mutated. In some embodiments, one or more CFTR phenylalanine residues are mutated.

In some embodiments, CFTR comprises one or more ATP gating cycle mutations. In some embodiments, CFTR comprises mutations at residues W401 and E1371. In some embodiments, CFTR comprises mutations at residues K464 and E1371. In some embodiments, CFTR comprises mutations at W401, F409, and E1371. In some embodiments, CFTR comprises mutations at W401, F409, F430 and E1371. In some embodiments, CFTR comprises a mutation at K978. In some embodiments, CFTR comprises a mutation at E1371. In some embodiments, CFTR comprises mutations at residues W401 and E1371. In some embodiments, CFTR comprises mutations at W401, F409, and E1371. In some embodiments, CFTR comprises mutations at W401, F409, F430, and E1371. In some embodiments, CFTR comprises mutations at K464 and E1371.

In some embodiments, the one or more mutations result in a substitution to an alanine residue. In some embodiments, the one or more mutations result in a substitution to an arginine residue. In some embodiments, the one or more mutations result in a substitution to an asparagine residue. In some embodiments, the one or more mutations result in a substitution to an aspartate residue. In some embodiments, the one or more mutations result in a substitution to a cysteine residue. In some embodiments, the one or more mutations result in a substitution to a glutamate residue. In some embodiments, the one or more mutations result in a substitution to a glutamine residue. In some embodiments, the one or more mutations result in a substitution to a glycine residue. In some embodiments, the one or more mutations result in a substitution to a histidine residue. In some embodiments, the one or more mutations result in a substitution to an isoleucine residue. In some embodiments, the one or more mutations result in a substitution to a leucine residue. In some embodiments, the one or more mutations result in a substitution to a lysine residue. In some embodiments, the one or more mutations result in a substitution to a methionine residue. In some embodiments, the one or more mutations result in a substitution to a phenylalanine residue. In some embodiments, the one or more mutations result in a substitution to a proline residue. In some embodiments, the one or more mutations result in a substitution to a serine residue. In some embodiments, the one or more mutations result in a substitution to a threonine residue. In some embodiments, the one or more mutations result in a substitution to a tryptophan residue. In some embodiments, the one or more mutations result in a substitution to a tyrosine residue.

In some embodiments, one or more mutations are selected from K14R, K68R, K710R, K716R, K1041R, K1080R, K1218R, and combinations thereof.

In some embodiments, the CFTR comprises mutations selected from K14R, K68R, K1218R, K14R/K68R, K14R/K1218R, K68R/K1218R, and K14R/K68R/K1218R. Accordingly, in some embodiments, the one or more mutations is a K14R mutation. In some embodiments, the one or more mutations is a K68R mutation. In some embodiments, the one or more mutations is a K1218R mutation. In some embodiments, the one or more mutations is a K14R/K68R mutation. In some embodiments, the one or more mutations is a K14R/K1218R mutation. In some embodiments, the one or more mutations is a K68R/K1218R mutation. In some embodiments, the one or more mutations is a K14R/K68R/K1218R mutation.

In some embodiments, the CFTR comprises mutations S660D/S737D/S795D/S813D, S660DD/S686D/S700D/S737D/S795D/S813D, K978C, or E1371Q. In some embodiments, the CFTR comprises mutations S660D/S737D/S795D/S813D. In some embodiments, the CFTR comprises mutations S660DD/S686D/S700D/S737D/S795D/S813D. In some embodiments, the one or more mutations is a K978C mutation. In some embodiments, the one or more mutations is a E1371Q mutation. In some embodiments, the CFTR comprises mutations S422D/S660D/S670D/S686D/T690D/S700D/S712D/S753D/T787D/T788D/S790D/S795D/S813 D. In some embodiments, the CFTR comprises mutations S422D/S660D/S670D/S686D/T690D/S700D/S712D/S737D/S753D/S768D/T787D/T788D/S790 D/S795D/S813D.

In some embodiments, the one or more mutations made at residues S422, S660, S670, S686, T690, S700, S712, S737, S753, 5768, T787, T788, 5790, S795, 5813 is an amino acid substitution to glutamic acid (E). In some embodiments, the CFTR comprises mutations S422E/S660E/S670E/S686E/T690E/S700E/S712E/S753E/T787E/T788E/S790E/S795E/S813E. In some embodiments, the CFTR comprises mutations S422E/S660E/S670E/S686E/T690E/S700E/S712E/S737E/S753E/S768E/T787E/T788E/S790E/S795E/S813E.

In some embodiments, the CFTR further comprises K14R mutation. In some embodiments, the CFTR further comprises E1371Q mutation. In some embodiments, the CFTR comprises mutations K14R/S422D/S660D/S670D/S686D/T690D/S700D/S712D/S753D/T787D/T788D/S790D/S795D/S813D. In some embodiments, the CFTR comprises mutations K14R/S422D/S660D/S670D/S686D/T690D/S700D/S712D/S737D/S753D/S768D/T787D/T788 D/S790D/S795D/S813D. In some embodiments, the CFTR comprises mutations K14R/S422E/S660E/S670E/S686E/T690E/S700E/S712E/S753E/T787E/T788E/S790E/S795E/S813E. In some embodiments, the CFTR comprises mutations K14R/S422E/S660E/S670E/S686E/T690E/S700E/S712E/S737E/S753E/S768E/T787E/T788E/S790E/S795E/S813E.

In some embodiments, the mRNA encoding CFTR is codon optimized. In some embodiments, the mRNA encoding CFTR is not codon optimized.

In some embodiments, the codon optimized CFTR mRNA further comprises a 5' untranslated region (UTR) sequence of SEQ ID NO: 4.

In some embodiments, the codon optimized CFTR mRNA further comprises a 3' untranslated region (UTR) sequence of SEQ ID NO: 5 of SEQ ID NO: 6.

In some embodiments, the codon optimized CFTR mRNA is encapsulated within a nanoparticle. In some embodiments, the nanoparticle is a liposome. In some embodiments, the liposome comprises one or more cationic lipids, one or more non-cationic lipids, one or more cholesterol-based lipids and one or more PEG-modified lipids. In some embodiments, the liposome comprises no more than three distinct lipid components. In some embodiments, one distinct lipid component is a sterol-based cationic lipid. In some embodiments, a sterol-based cationic lipid is imidazole cholesterol ester (ICE).

In some embodiments, the liposome has a size of less than about 200 nm. In some embodiments, the liposome has a size of less than about 150 nm. In some embodiments, the liposome has a size of less than about 120 nm. In some embodiments, the liposome has a size of less than about 110 nm. In some embodiments, the liposome has a size of less than about 100 nm. In some embodiments, the liposome has a size of less than about 80 nm. In some embodiments, the liposome has a size of less than about 60 nm. In some embodiments, the liposome has a size of less than about 50 nm.

In some embodiments, the pharmaceutical composition further comprises a CFTR potentiator. In some embodiments, the pharmaceutical composition further comprises a CFTR corrector. In some embodiments, the pharmaceutical composition further comprises a CFTR activator. In some embodiments, the pharmaceutical composition further comprises a CFTR potentiator, corrector and/or activator. Suitable CFTR potentiators, correctors and/or activators include ivacaftor (trade name Kalydeco®), lumacaftor (trade name Orkambi®), tezacaftor, vX-659, VX-445, VX-152, VX-440, VX-371, VX-561, GLPG1837, GLPG2222, GLPG2737, GLPG2451, GLPG1837, PTI-428, PTI-801, PTI-808, and eluforsen. In some embodiments, the pharmaceutical composition further comprises ivacaftor. In some embodiments, the pharmaceutical composition further comprises lumacaftor. In some embodiments, the pharmaceutical composition further comprises tezacaftor. In some embodiments, the pharmaceutical composition further comprises ivacaftor, lumacaftor, tezacaftor, or a combination. In some embodiments, the pharmaceutical composition further comprises VX-659. In some embodiments, the pharmaceutical composition further comprises VX-445. In some embodiments, the pharmaceutical composition further comprises VX-152. In some embodiments, the pharmaceutical composition further comprises VX-440. In some embodiments, the pharmaceutical composition further comprises VX-371. In some embodiments, the pharmaceutical composition further comprises VX-561. In some embodiments, the pharmaceutical composition further comprises GLPG1837. In some embodiments, the pharmaceutical composition further comprises GLPG2222. In some embodiments, the pharmaceutical composition further comprises GLPG2737. In some embodiments, the pharmaceutical composition further comprises GLPG2451. In some embodiments, the pharmaceutical composition further comprises GLPG1837. In some embodiments, the pharmaceutical composition further comprises PTI-428. In some embodiments, the pharmaceutical composition further comprises PTI-801. In some embodiments, the pharmaceutical composition further comprises PTI-808. In some embodiments, the pharmaceutical composition further comprises eluforsen. In some embodiments, the pharmaceutical composition further comprises any combination of CFTR potentiators, correctors, and/or activators.

In one aspect, the invention provides, among other things, a polynucleotide comprising a sequence complementary to the sequence of the mRNA of the present invention.

In some embodiments, the polynucleotide is a linear or circular polynucleotide comprising deoxyribonucleotide residues.

In one aspect, the invention provides, among other things, a cultured cell comprising the polynucleotide of the present invention.

In one aspect, the invention provides a method of inducing CFTR expression in epithelial cells in a lung of a mammal comprising a step of contacting the epithelial cells in the lung of the mammal with a pharmaceutical composition of the present invention.

In some embodiments, the codon optimized CFTR mRNA is administered via pulmonary delivery. In some embodiments, the codon optimized CFTR mRNA is administered via intravenous delivery. In some embodiments, the codon optimized CFTR mRNA is administered via oral, rectal, vaginal, transmucosal, or intestinal administration; parenteral delivery, including intradermal, transdermal (topical), intramuscular, subcutaneous, intramedullary injections, as well as intrathecal, direct intraventricular, intravenous, intraperitoneal, and/or intranasal administration.

In some embodiments, the pulmonary delivery is nebulization. In some embodiments, the codon optimized CFTR mRNA is administered via aerosolization.

In some embodiments, treating the subject is achieved at a lower therapeutically effective dose in comparison to treating the subject with an mRNA encoding a wild type CFTR.

In some embodiments, treating the subject in need results in shorter nebulization times to administer a therapeutically effective dose in comparison to treating with an mRNA encoding wild type CFTR.

In one aspect, the invention provides, among other things, a nucleic acid encoding a modified Cystic Fibrosis Transmembrane Conductance Regulator (CFTR) protein, wherein the modified CFTR protein comprises one or more amino acid substitutions to glutamic acid.

In some embodiments, one or more amino acid substitutions occur at serine residues. In some embodiments, one or more amino acid substitutions occur at threonine residues.

In some embodiments, one or more amino acid substitutions are located within the CFTR regulatory domain. In some embodiments, one or more amino acid substitutions are located at amino acid residues 440-820. In some embodiments, one or more amino acid substitutions occur at residue S422, S660, S670, S686, T690, S700, S712, S737, S753, S768, T787, T788, S790, S795, and/or S813.

In some embodiments, a modified CFTR protein comprises one or more mutations of S422E, S660E, S670E, S686E, T690E, S700E, S712E, S737E, S753E, S768E, T787E, T788E, S790E, S795E, and/or S813E. In some embodiments, a modified CFTR protein comprises mutations S422E/S660E/S670E/S686E/T690E/S700E/S712E/S753E/T787E/T788E/S790E/S795E/S813E. In some embodiments, a modified CFTR protein comprises mutations S422E/S660E/S670E/S686E/T690E/S700E/S712E/S737E/S753E/S768E/T787E/T788E/S790E/S795E/S813E.

In some embodiments, a modified CFTR protein further comprises K14R mutation. In some embodiments, a modified CFTR protein further comprises E1371Q mutation.

In one aspect, the invention provides, among other things, a nucleic acid encoding a modified Cystic Fibrosis Transmembrane Conductance Regulator (CFTR) protein, wherein the modified CFTR protein comprises K14R and E1371Q mutations.

In some embodiments, a modified CFTR protein further comprises one or more mutations in the CFTR regulatory domain, a membrane-spanning domain (MSD), and/or a nucleotide-binding domain.

In some embodiments, a nucleic acid is DNA, cDNA, RNA, mRNA or PNA. In some embodiments, a nucleic acid is DNA. In some embodiments, a nucleic acid is cDNA. In some embodiments, a nucleic acid is RNA. In some embodiments, a nucleic acid is mRNA. In some embodiments, a nucleic acid is PNA. In some embodiments, a nucleic acid is PCNA. In some embodiments, a nucleic acid is MCNA.

In one aspect, the invention provides, among other things, an adeno-associated virus (AAV) vector comprising a nucleic acid encoding a modified Cystic Fibrosis Transmembrane Conductance Regulator (CFTR) protein.

In some embodiments, an AAV vector is packaged in a virus or viral particle. In some embodiments, a virus particle is pseudotyped. In some embodiments, a virus is a retrovirus, adenovirus, adeno-associate virus, herpes virus, or lentivirus.

In one aspect, the invention provides, among other things, a modified CFTR protein comprising one or more amino acid substitutions to glutamic acid.

In one aspect, the invention provides, among other things, a method of treating cystic fibrosis comprising administering to a subject in need of treatment a modified CFTR protein.

In one aspect, the invention provides, among other things, a method of inducing CFTR expression in a subject, the method comprising administering the AAV vector. In one aspect, the invention provides, among other things, a method of treating cystic fibrosis comprising administering to a subject in need of treatment the AAV vector.

BRIEF DESCRIPTION OF THE DRAWING

The drawings are for illustration purposes only not for limitation.

FIG. 2A shows a schematic model and exemplary R domain phosphomimetic mutations. FIG. 2B shows a schematic model of ATP-gating mutations.

FIG. 12A is a table of currents depicting chloride ion flux at baseline and after forskolin, VX-770, and CFTRinh-172 additions. FIG. 12B is an exemplary graph of short-circuit conductivity illustrating, among other things, that alanine substitution at phosphomimetic sites reduces forskolin-induced chloride conductance in FRT cells.

FIG. 15C depicts a series of graphs that show measurements of short-circuit conductivity measured by Ussing chamber of CFTR variants.

DEFINITIONS

Figure 1:
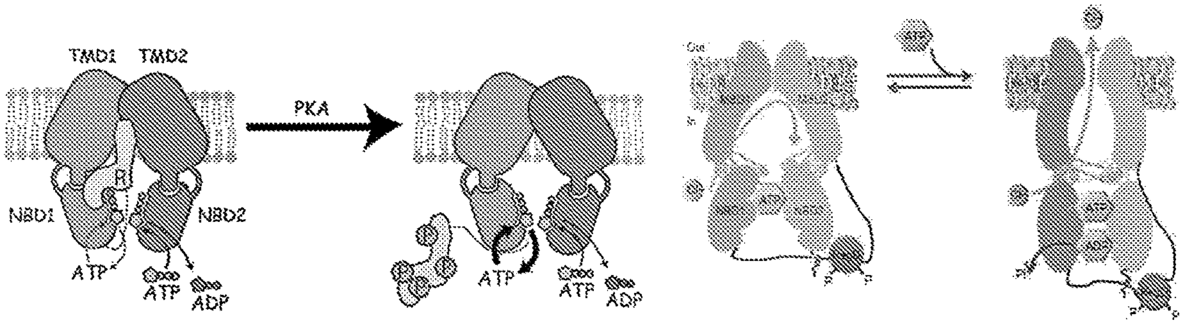
FIG. 1 shows a schematic that illustrates the regulation of Cystic Fibrosis Transmembrane Conductance Regulator (CFTR) channel activity.

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, the term "batch" refers to a quantity or amount of mRNA synthesized at one time, e.g., produced according to a single manufacturing order during the same cycle of manufacture. A batch may refer to an amount of mRNA synthesized in one reaction that occurs via a single aliquot of enzyme and/or a single aliquot of DNA template for continuous synthesis under one set of conditions. In some embodiments, a batch would include the mRNA produced from a reaction in which not all reagents and/or components are supplemented and/or replenished as the reaction progresses. The term "not in a single batch" would not mean mRNA synthesized at different times that are combined to achieve the desired amount.

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery). In some embodiments, delivery is pulmonary delivery, e.g., comprising nebulization.

Encapsulation: As used herein, the term "encapsulation," or grammatical equivalent, refers to the process of confining an mRNA molecule within a nanoparticle.

Engineered or mutant: As used herein, the terms "engineered" or "mutant", or grammatical equivalents refer to a nucleotide or protein sequence comprising one or more modifications compared to its naturally-occurring sequence, including but not limited to deletions, insertions of heterologous nucleic acids or amino acids, inversions, substitutions, or combinations thereof.

Expression: As used herein, "expression" of a nucleic acid sequence refers to translation of an mRNA into a polypeptide, assemble multiple polypeptides (e.g., heavy chain or light chain of antibody) into an intact protein (e.g., antibody) and/or post-translational modification of a polypeptide or fully assembled protein (e.g., antibody). In this application, the terms "expression" and "production," and grammatical equivalents, are used interchangeably.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

Impurities: As used herein, the term "impurities" refers to substances inside a confined amount of liquid, gas, or solid, which differ from the chemical composition of the target material or compound. Impurities are also referred to as contaminants.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

messenger RNA (mRNA): As used herein, the term "messenger RNA (mRNA)" refers to a polynucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated.

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery. In some embodiments, the nucleotides T and U are used interchangeably in sequence descriptions.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Stable: As used herein, the term "stable" protein or its grammatical equivalents refer to protein that retains its physical stability and/or biological activity. In one embodiment, protein stability is determined based on the percentage of monomer protein in the solution, at a low percentage of degraded (e.g., fragmented) and/or aggregated protein. In one embodiment, a stable engineered protein retains or exhibits an enhanced half-life as compared to a wild-type protein. In one embodiment, a stable engineered protein is less prone to ubiquitination that leads to proteolysis as compared to a wild-type protein.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, improved methods and pharmaceutical compositions for treating cystic fibrosis using messenger RNA (mRNA) encoding an engineered or mutant Cystic Fibrosis Transmembrane Conductance Regulator (CFTR) protein. In some embodiments, the mRNA is a codon-optimized mRNA. In particular embodiments, the engineered or mutant CFTR proteins achieve higher activity or stability than the wild-type CFTR protein. mRNAs disclosed herein encoding engineered or mutant CFTR proteins are particularly useful for treating cystic fibrosis by mRNA therapeutics.

Cystic Fibrosis

The present invention may be used to treat a subject who is suffering from or susceptible to cystic fibrosis. Cystic fibrosis is a genetic disorder characterized by mutations in the gene for Cystic Fibrosis Transmembrane Conductance Regulator (CFTR). The CFTR protein functions as a channel across the membrane of cells that produce mucus, sweat, saliva, tears, and digestive enzymes. The channel transports negatively charged particles called chloride ions into and out of cells. The transport of chloride ions helps control the movement of water in tissues, which is necessary for the production of thin, freely flowing mucus. Mucus is a slippery substance that lubricates and protects the lining of the airways, digestive system, reproductive system, and other organs and tissues.

Respiratory symptoms of cystic fibrosis include: a persistent cough that produces thick mucus (sputum), wheezing, breathlessness, exercise intolerance, repeated lung infections and inflamed nasal passages or a stuffy nose. Digestive symptoms of cystic fibrosis include: foul-smelling, greasy stools, poor weight gain and growth, intestinal blockage, particularly in newborns (meconium ileus), and severe constipation.

Codon Optimized mRNA Encoding CFTR

In some embodiments, the present invention provides methods and compositions for delivering codon optimized mRNA encoding CFTR to a subject for the treatment of cystic fibrosis. A suitable codon optimized CFTR mRNA encodes any full length, fragment or portion of a CFTR protein which can be substituted for naturally-occurring CFTR protein activity and/or reduce the intensity, severity, and/or frequency of one or more symptoms associated with cystic fibrosis.

In some embodiments, a suitable codon optimized mRNA sequence is an mRNA sequence encoding a human CFTR (hCFTR) protein. Exemplary codon optimized CFTR mRNA coding sequence and the corresponding amino acid sequence are shown in Table 1:

TABLE 1

| Exemplary Codon-Optimized Human CFTR | |
|---|---|
| SEQ ID NO: 1 | **AUG**CAACGCUCUCCUCUUGAAAAGGCCUCGGUGGUGUCCAAGCUCUU<br>CUUCUCGUGGACUAGACCCAUCCUGAGAAAGGGGUACAGACAGCGCU<br>UGGAGCUGUCCGAUAUCUAUCAAAUCCCUUCCGUGGACUCCGCGGAC |

TABLE 1-continued

| Exemplary Codon-Optimized Human CFTR |
| --- |
| AACCUGUCCGAGAAGCUCGAGAGAGAAUGGGACAGAGAACUCGCCUC<br>AAAGAAGAACCCGAAGCUGAUUAAUGCGCUUAGGCGGUGCUUUUUC<br>UGGCGGUUCAUGUUCUACGGCAUCUUCCUCUACCUGGGAGAGGUCAC<br>CAAGGCCGUGCAGCCCCUGUUGCUGGGACGGAUUAUUGCCUCCUACG<br>ACCCCGACAACAAGGAAGAAAGAAGCAUCGCUAUCUACUUGGGCAUC<br>GGUCUGUGCCUGCUUUUCAUCGUCCGGACCCUCUUGUUGCAUCCUGC<br>UAUUUUCGGCCUGCAUCACAUUGGCAUGCAGAUGAGAAUUGCCAUG<br>UUUUCCCUGAUCUACAAGAAAACUCUGAAGCUCUCGAGCCGCGUGCU<br>UGACAAGAUUUCCAUCGGCCAGCUCGUGUCCCUGCUCUCCAACAAUC<br>UGAACAAGUUCGACGAGGGCCUCGCCCUGGCCCACUUCGUGUGGAUC<br>GCCCCUCUGCAAGUGGCGCUUCUGAUGGGCCUGAUCUGGGAGCUGCU<br>GCAAGCCUCGGCAUUCUGUGGGCUUGGAUUCCUGAUCGUGCUGGCAC<br>UGUUCCAGGCCGGACUGGGGCGGAUGAUGAUGAAGUACAGGGACCA<br>GAGAGCCGGAAAGAUUUCCGAACGGCUGGUGAUCACUUCGGAAAUG<br>AUCGAAAACAUCCAGUCAGUGAAGGCCUACUGCUGGGAAGAGGCCAU<br>GGAAAAGAUGAUUGAAAACCUCCGGCAAACCGAGCUGAAGCUGACCC<br>GCAAGGCCGCUUACGUGCGCUAUUUCAACUCGUCCGCUUUCUUCUUC<br>UCCGGGUUCUUCGUGGUGUUUCUCUCCGUGCUCCCCUACGCCCUGAU<br>UAAGGGAAUCAUCCUCAGGAAGAUCUUCACCACCAUUUCCUUCUGUA<br>UCGUGCUCCGCAUGGCCGUGACCCGGCAGUUCCCAUGGGCCGUGCAG<br>ACUUGGUACGACUCCCUGGGAGCCAUUAACAAGAUCCAGGACUUCCU<br>UCAAAAGCAGGAGUACAAGACCCUCGAGUACAACCUGACUACUACCG<br>AGGUCGUGAUGGAAAACGUCACCGCCUUUUGGGAGGAGGGAUUUGG<br>CGAACUGUUCGAGAAGGCCAAGCAGAACAACAACAACCGCAAGACCU<br>CGAACGGUGACGACUCCCUCUUCUUUUCAAACUUCAGCCUGCUCGGG<br>ACGCCCGUGCUGAAGGACAUUAACUUCAAGAUCGAAAGAGGACAGCU<br>CCUGGCGGUGGCCGGAUCGACCGGAGCCGGAAAGACUUCCCUGCUGA<br>UGGUGAUCAUGGGAGAGCUUGAACCUAGCGAGGGAAAGAUCAAGCA<br>CUCCGGCCGCAUCAGCUUCUGUAGCCAGUUUUCCUGGAUCAUGCCCG<br>GAACCAUUAAGGAAAACAUCAUCUUCGGCGUGUCCUACGAUGAAUAC<br>CGCUACCGGUCCGUGAUCAAAGCCUGCCAGCUGGAAGAGGAUAUUUC<br>AAAGUUCGCGGAGAAAGAUAACAUCGUGCUGGGCGAAGGGGGUAUU<br>ACCUUGUCGGGGGGCCAGCGGGCUAGAAUCUCGCUGGCCAGAGCCGU<br>GUAUAAGGACGCCGACCUGUAUCUCCUGGACUCCCCCUUCGGAUACC<br>UGGACGUCCUGACCGAAAAGGAGAUCUUCGAAUCGUGCGUGUGCAA<br>GCUGAUGGCUAACAAGACUCGCAUCCUCGUGACCUCCAAAAUGGAGC<br>ACCUGAAGAAGGCAGACAAGAUUCUGAUUCUGCAUGAGGGGUCCUCC<br>UACUUUUACGGCACCUUCUCGGAGUUGCAGAACUUGCAGCCCGACUU<br>CUCAUCGAAGCUGAUGGGUUGCGACAGCUUCGACCAGUUCUCCGCCG<br>AAAGAAGGAACUCGAUCCUGACGGAAACCUUGCACCGCUUCUCUUUG<br>GAAGGCGACGCCCCUGUGUCAUGGACCGAGACUAAGAAGCAGAGCUU<br>CAAGCAGACCGGGGAAUUCGGCGAAAAGAGGAAGAACAGCAUCUUG<br>AACCCCAUUAACUCCAUCCGCAAGUUCUCAAUCGUGCAAAAGACGCC<br>ACUGCAGAUGAACGGCAUUGAGGAGGACUCCGACGAACCCCUUGAGA<br>GGCGCCUGUCCCUGGUGCCGGACAGCGAGCAGGGAGAAGCCAUCCUG<br>CCUCGGAUUUCCGUGAUCUCCACUGGUCCGACGCUCCAAGCCCGGCG<br>GCGGCAGUCCGUGCUGAACCUGAUGACCCACAGCGUGAACCAGGGCC<br>AAAACAUUCACCGCAAGACUACCGCAUCCACCCGGAAAGUGUCCCUG<br>GCACCUCAAGCGAAUCUUACCGAGCUCGACAUCUACUCCCGGAGACU<br>GUCGCAGGAAACCGGGCUCGAAAUUUCCGAAGAAAUCAACGAGGAG<br>GAUCUGAAAGAGUGCUUCUUCGACGAUAUGGAGUCGAUACCCGCCGU<br>GACGACUUGGAACACUUAUCUGCGGUACAUCACUGUGCACAAGUCAU<br>UGAUCUUCGUGCUGAUUUGGUGCCUGGUGAUUUUCCUGGCCGAGGU<br>CGCGGCCUCACUGGUGGUGCUCUGGCUGUUGGGAAACACGCCUCUGC<br>AAGACAAGGGAAACUCCACGCACUCGAGAAACAACAGCUAUGCCGUG<br>AUUAUCACUUCCACCUCCUCUUAUUACGUGUUCUACAUCUACGUCGG<br>AGUGGCGGAUACCCUGCUCGCGAUGGGUUUCUUCAGAGGACUGCCGC<br>UGGUCCACACCUUGAUCACCGUCAGCAAGAUUCUUCACCACAAGAUG<br>UUGCAUAGCGUGCUGCAGGCCCCCAUGUCCACCCUCAACACUCUGAA<br>GGCCGGAGGCAUUCUGAACAGAUUCUCCAAGGACAUCGCUAUCCUGG<br>ACGAUCUCCUGCCGCUUACCAUCUUUGACUUCAUCCAGCUGCUGCUG<br>AUCGUGAUUGGAGCAAUCGCAGUGGUGGCGGUGCUGCAGCCUUACA<br>UUUUCGUGGCCACUGUGCCGGUCAUUGUGGCGUUCAUCAUGCUGCGG<br>GCCUACUUCCUCCAAACCAGCCAGCAGCUGAAGCAACUGGAAUCCGA<br>GGGACGAUCCCCCAUCUUCACUCACCUUGUGACGUCGUUGAAGGGAC<br>UGUGGACCCUCCGGGCUUUCGGACGGCAGCCCUACUUCGAAACCCUC<br>UUCCACAAGGCCCUGAACCUCCACACCGCCAAUUGGUUCCUGUACCU<br>GUCCACCCUGCGGUGGUUCCAGAUGCGCAUCGAGAUGAUUUUCGUCA<br>UCUUCUUCAUCGCGGUCACAUUCAUCAGCAUCCUGACUACCGGAGAG<br>GGAGAGGGACGGGUCGGAAUAAUCCUGACCCUCGCCAUGAACAUUAU<br>GAGCACCCUGCAGUGGGCAGUGAACAGCUCGAUCGACGUGGACAGCC<br>UGAUGCGAAGCGUCAGCCGCGUGUUCAAGUUCAUCGACAUGCCUACU<br>GAGGGAAAACCCACUAAGUCCACUAAGCCCUACAAAAAUGGCCAGCU<br>GAGCAAGGUCAUGAUCAUCGAAAACUCCCACGUGAAGAAGGACGAU<br>AUUUGGCCCUCCGGAGGUCAAAUGACCGUGAAGGACCUGACCGCAAA<br>GUACACCGAGGGAGGAAACGCCAUUCUCGAAAACAUCAGCUUCUCCA<br>UUUCGCCGGGACAGCGGGUCGGCCUUCUCGGGCGGACCGGUUCCGGG<br>AAGUCAACUCUGCUGUCGGCUUUCCUCCGGCUGCUGAAUACCGAGGG |

TABLE 1-continued

| | Exemplary Codon-Optimized Human CFTR |
|---|---|
| | GGAAAUCCAAAUUGACGGCGUGUCUUGGGAUUCCAUUACUCUGCAGC<br>AGUGGCGGAAGGCCUUCGGCGUGAUCCCCCAGAAGGUGUUCAUCUUC<br>UCGGGUACCUUCCGGAAGAACCUGGAUCCUUACGAGCAGUGGAGCGA<br>CCAAGAAAUCUGGAAGGUCGCCGACGAGGUCGGCCUGCGCUCCGUGA<br>UUGAACAAUUUCCUGGAAAGCUGGACUUCGUGCUCGUCGACGGGGG<br>AUGUGUCCUGUCGCACGGACAUAAGCAGCUCAUGUGCCUCGCACGGU<br>CCGUGCUCUCCAAGGCCAAGAUUCUGCUGCUGGACGAACCUUCGGCC<br>CACCUGGAUCCGGUCACCUACCAGAUCAUCAGGAGGACCCUGAAGCA<br>GGCCUUUGCCGAUUGCACCGUGAUUCUCUGCGAGCACCGCAUCGAGG<br>CCAUGCUGGAGUGCCAGCAGUUCCUGGUCAUCGAGGAGAACAAGGUC<br>CGCCAAUACGACUCCAUUCAAAAGCUCCUCAACGAGCGGUCGCUGUU<br>CAGACAAGCUAUUUCACCGUCCGAUAGAGUGAAGCUCUUCCCGCAUC<br>GGAACAGCUCAAAGUGCAAAUCGAAGCCGCAGAUCGCAGCCUUGAAG<br>GAAGAGACUGAGGAAGAGGUGCAGGACACCCGGCUU**UAA** |
| SEQ ID NO: 2 | **AUG**CAGCGGUCCCCGCUCGAAAAGGCCAGUGUCGUGUCCAAACUCUU<br>CUUCUCAUGGACUCGGCCUAUCCUUAGAAAGGGGUAUCGGCAGAGGC<br>UUGAGUUGUCUGACAUCUACCAGAUCCCCUCGGUAGAUUCGGCGGAU<br>AACCUCUCGGAGAAGCUCGAACGGGAAUGGGACCGCGAACUCGCGUC<br>UAAGAAAAACCCGAAGCUCAUCAACGCACUGAGAAGGUGCUUCUUCU<br>GGCGGUUCAUGUUCUACGGUAUCUUCUUGUAUCUCGGGGAGGUCAC<br>AAAAGCAGUCCAACCCCUGUUGUUGGGUCGCAUUAUCGCCUCGUACG<br>ACCCCGAUAACAAAGAAGAACGGAGCAUCGCGAUCUACCUCGGGAUC<br>GGACUGUGUUUGCUUUUCAUCGUCAGAACACUUUUGUUGCAUCCAGC<br>AAUCUUCGGCCUCCAUCACAUCGGUAUGCAGAUGCGAAUCGCUAUGU<br>UUAGCUUGAUCUACAAAAAGACACUGAAACUCUCGUCGCGGGUGUU<br>GGAUAAGAUUUCCAUCGGUCAGUUGGUGUCCCUGCUUAGUAAUAAC<br>CUCAACAAAUUCGAUGAGGGACUGGCGCUGGCACAUUUCGUGUGGA<br>UUGCCCCGUUGCAAGUCGCCCUUUUGAUGGGCCUUAUUUGGGAGCUG<br>UUGCAGGCAUCUGCCUUUUGUGGCCUGGGAUUUCUGAUUGUGUUGG<br>CAUUGUUUCAGGCUGGGCUUGGGCGGAUGAUGAUGAAGUAUCGCGA<br>CCAGAGAGCGGGUAAAAUCUCGGAAAGACUCGUCAUCACUUCGGAAA<br>UGAUCGAAAACAUCCAGUCGGUCAAAGCCUAUUGCUGGGAAGAAGC<br>UAUGGAGAAGAUGAUUGAAAACCUCCGCCAAACUGAGCUGAAACUG<br>ACCCGCAAGGCGGCGUAUGUCCGGUAUUUCAAUUCGUCAGCGUUCUU<br>CUUUUCCGGGUUCUUCGUUGUCUUUCUCUCGGUUUUGCCUUAUGCCU<br>UGAUUAAGGGGAUUAUCCUCCGCAAGAUUUUCACCACGAUUUCGUUC<br>UGCAUUGUAUUGCGCAUGGCAGUGACACGGCAAUUUCCGUGGGCCGU<br>GCAGACAUGGUAUGACUCGCUUGGAGCGAUCAACAAAAUCCAAGACU<br>UCUUGCAAAAGCAAGAGUACAAGACCCUGGAGUACAAUCUUACUACU<br>ACGGAGGUAGUAAUGGAGAAUGUGACGGCUUUUUGGGAAGAGGGUU<br>UUGGAGAACUGUUUGAGAAAGCAAAGCAGAAUAACAACAACCGCAA<br>GACCUCAAAUGGGGACGAUUCCCUGUUUUUCUCGAACUUCUCCCUGC<br>UCGGAACACCCGUGUUGAAGGACAUCAAUUUCAAGAUUGAGAGGGG<br>ACAGCUUCUCGCGGUAGCGGGAAGCACUGGUGCGGAAAAACUAGCC<br>UCUUGAUGGUGAUUAUGGGGGAGCUUGAGCCCAGCGAGGGGAAGAU<br>UAAACACUCCGGGCGUAUCUCAUUCUGUAGCCAGUUUUCAUGGAUCA<br>UGCCCGGAACCAUUAAAGAGAACAUCAUUUUCGGAGUAUCCUAUGA<br>UGAGUACCGAUACAGAUCGGUCAUUAAGGCGUGCCAGUUGGAAGAG<br>GACAUUUCUAAGUUCGCCGAGAAGGAUAACAUCGUCUUGGGAGAAG<br>GGGGUAUUACAUUGUCGGGAGGGCAGCGAGCGCGGAUCAGCCUCGCG<br>AGAGCGGUAUACAAAGAUGCAGAUUUGUAUCUGCUUGAUUCACCGU<br>UUGGAUACCUCGACGUAUUGACAGAAAAAGAAAUCUUCGAGUCGUG<br>CGUGUGUAAACUUAUGGCUAAUAAGACGAGAAUCCUGGUGACAUCA<br>AAAAUGGAACACCUUAAGAAGGCGGACAAGAUCCUGAUCCUCCACGA<br>AGGAUCGUCCUACUUUUACGGCACUUUCUCAGAGUUGCAAAACUUGC<br>AGCCGGACUUCUCAAGCAAACUCAUGGGGUGUGACUCAUUCGACCAG<br>UUCAGCGCGGAACGGCGGAACUCGAUCUUGACGGAAACGCUGCACCG<br>AUUCUCGCUUGAGGGUGAUGCCCCGGUAUCGUGGACCGAGACAAAGA<br>AGCAGUCGUUUAAGCAGACAGGAGAAUUUGGUGAGAAAAGAAAGAA<br>CAGUAUCUUGAAUCCUAUUAACUCAAUUCGCAAGUUCUCAAUCGUCC<br>AGAAAACUCCACUGCAGAUGAAUGGAAUUGAAGAGGAUUCGGACGA<br>ACCCCUGGAGCGCAGGCUUAGCCUCGUGCCGGAUUCAGAGCAAGGGG<br>AGGCCAUUCUUCCCCGGAUUUCGGUGAUUUCAACCGGACCUACACUU<br>CAGGCGAGGCGAAGGCAAUCCGUGCUCAACCUCAUGACGCAUUCGGU<br>AAACCAGGGGCAAAACAUUCACCGCAAAACGACGGCCUCAACGAGAA<br>AAGUGUCACUUGCACCCCAGGCGAAUUUGACUGAACUCGACAUCUAC<br>AGCCGUAGGCUUUCGCAAGAAACCGGACUUGAGAUCAGCGAAGAAA<br>UCAAUGAAGAAGAUUUGAAAGAGUGUUUCUUUGAUGACAUGGAAUC<br>AAUCCCAGCGGUGACAACGUGGAACACAUACUUGCGUUACAUCACGG<br>UGCACAAGUCCUUGAUUUUCGUCCUCAUCUGGUGUCUCGUGAUCUUU<br>CUCGCUGAGGUCGCAGCGUCACUUGUGGUCCUCUGGCUGCUUGGUAA<br>UACGCCCUUGCAAGACAAAGGCAAUUCUACACACUCAAGAAACAAUU<br>CCUAUGCCGUGAUUAUCACUUCUACAAGCUCGUAUUACGUGUUUUAC<br>AUCUACGUAGGAGUGGCCGACACUCUGCUCGCGAUGGGUUUCUUCCG<br>AGGACUCCCACUCGUUCACACGCUUAUCACUGUCUCCAAGAUUCUCC<br>ACCAUAAGAUGCUUCAUAGCGUACUGCAGGCUCCCAUGUCCACCUUG<br>AAUACGCUCAAGGCGGGAGGUAUUUUGAAUCGCUUCUCAAAAGAUA |

TABLE 1-continued

| Exemplary Codon-Optimized Human CFTR | |
|---|---|
| | UUGCAAUUUUGGAUGACCUUCUGCCCCUGACGAUCUUCGACUUCAUC<br>CAGUUGUUGCUGAUCGUGAUUGGGGCUAUUGCAGUAGUCGCUGUCC<br>UCCAGCCUUACAUUUUUGUCGCGACCGUUCCGGUGAUCGUGGCGUUU<br>AUCAUGCUGCGGGCCUAUUUCUUGCAGACGUCACAGCAGCUUAAGCA<br>ACUGGAGUCUGAAGGGAGGUCGCCUAUCUUUACGCAUCUUGUGACCA<br>GUUUGAAGGGAUUGUGGACGUUGCGCGCCUUUGGCAGGCAGCCCUAC<br>UUUGAAACACUGUUCCACAAAGCGCUGAAUCUCCAUACGGCAAAUUG<br>GUUUUUGUAUUUGAGUACCCUCCGAUGGUUUCAGAUGCGCAUUGAG<br>AUGAUUUUUGUGAUCUUCUUUAUCGCGGUGACUUUUAUCUCCAUCU<br>UGACCACGGGAGAGGGCGAGGGACGGGUCGGUAUUAUCCUGACACUC<br>GCCAUGAACAUUAUGAGCACUUUGCAGUGGGCAGUGAACAGCUCGA<br>UUGAUGUGGAUAGCCUGAUGAGGUCCGUUUCGAGGGUCUUUAAGUU<br>CAUCGACAUGCCGACGGAGGGAAAGCCCACAAAAAGUACGAAACCCU<br>AUAAGAAUGGGCAAUUGAGUAAGGUAAUGAUCAUCGAGAACAGUCA<br>CGUGAAGAAGGAUGACAUCUGGCCUAGCGGGGGUCAGAUGACCGUG<br>AAGGACCUGACGGCAAAAUACACCGAGGGAGGGAACGCAAUCCUUGA<br>AAACAUCUCGUUCAGCAUUAGCCCCGGUCAGCGUGUGGGUUGCUCG<br>GGAGGACCGGGUCAGGAAAAUCGACGUUGCUGUCGGCCUUCUUGAG<br>ACUUCUGAAUACAGAGGGUGAGAUCCAGAUCGACGGCGUUUCGUGG<br>GAUAGCAUCACCUUGCAGCAGUGGCGGAAAGCGUUUGGAGUAAUCCC<br>CCAAAAGGUCUUUAUCUUUAGCGGAACCUUCCGAAAGAAUCUCGAUC<br>CUUAUGAACAGUGGUCAGAUCAAGAGAUUUGGAAAGUCGCGGACGA<br>GGUUGGCCUUCGGAGUGUAAUCGAGCAGUUUCCGGGAAAACUCGAC<br>UUUGUCCUUGUAGAUGGGGGAUGCGUCCUGUCGCAUGGGCACAAGC<br>AGCUCAUGUGCCUGGCGCGAUCCGUCCUCUCUAAAGCGAAAAUUCUU<br>CUCUUGGAUGAACCUUCGGCCCAUCUGGACCCGGUAACGUAUCAGAU<br>CAUCAGAAGGACACUUAAGCAGGCGUUUGCCGACUGCACGGUGAUUC<br>UCUGUGAGCAUCGUAUCGAGGCCAUGCUCGAAUGCCAGCAAUUUCUU<br>GUCAUCGAAGAGAAUAAGGUCCGCCAGUACGACUCCAUCCAGAAGCU<br>GCUUAAUGAGAGAUCAUUGUUCCGGCAGGCGAUUUCACCAUCCGAUA<br>GGGUGAAACUUUUUCCACACAGAAAUUCGUCGAAGUGCAAGUCCAA<br>ACCGCAGAUCGCGGCCUUGAAAGAAGAGACUGAAGAAGAAGUUCAA<br>GACACGCGUCUU**UAA** |
| Human CFTR Protein Sequence | MQRSPLEKASVVSKLFFSWTRPILRKGYRQRLELSDIYQIPSVDSADNLSEK<br>LEREWDRELASKKNPKLINALRRCFFWRFMFYGIFLYLGEVTKAVQPLLL<br>GRIIASYDPDNKEERSIAIYLGIGLCLLFIVRTLLLHPAIFGLHHIGMQMRIA<br>MFSLIYKKTLKLSSRVLDKISIGQLVSLLSNNLNKFDEGLALAHFVWIAPLQ<br>VALLMGLIWELLQASAFCGLGFLIVLALFQAGLGRMMMKYRDQRAGKIS<br>ERLVITSEMIENIQSVKAYCWEEAMEKMIENLRQTELKLTRKAAYVRYFN<br>SSAFFFSGFFVVFLSVLPYALIKGIILRKIFTTISFCIVLRMAVTRQFPWAVQT<br>WYDSLGAINKIQDFLQKQEYKTLEYNLTTTEVVMENVTAFWEEGFGELFE<br>KAKQNNNNRKTSNGDDSLFFSNFSLLGTPVLKDINFKIERGQLLAVAGSTG<br>AGKTSLLMVIMGELEPSEGKIKHSGRISFCSQFSWIMPGTIKENIIFGVSYDE<br>YRYRSVIKACQLEEDISKFAEKDNIVLGEGGITLSGGQRARISLARAVYKD<br>ADLYLLDSPFGYLDVLTEKEIFESCVCKLMANKTRILVTSKMEHLKKADKI<br>LILHEGSSYFYGTFSELQNLQPDFSSKLMGCDSFDQFSAERRNSILTETLHR<br>FSLEGDAPVSWTETKKQSFKQTGEFGEKRKNSILNPINSIRKFSIVQKTPLQ<br>MNGIEEDSDEPLERRLSLVPDSEQGEAILPRISVISTGPTLQARRRQSVLNL<br>MTHSVNQGQNIHRKTTASTRKVSLAPQANLTELDIYSRRLSQETGLEISEEI<br>NEEDLKECFFDDMESIPAVTTWNTYLRYITVHKSLIFVLIWCLVIFLAEVAA<br>SLVVLWLLGNTPLQDKGNSTHSRNNSYAVIITSTSSYYVFYIYVGVADTLL<br>AMGFFRGLPLVHTLITVSKILHHKMLHSVLQAPMSTLNTLKAGGILNRFSK<br>DIAILDDLLPLTIFDFIQLLLIVIGAIAVVAVLQPYIFVATVPVIVAFIMLRAY<br>FLQTSQQLKQLESEGRSPIFTHLVTSLKGLWTLRAFGRQPYFETLFHKALN<br>LHTANWFLYLSTLRWFQMRIEMIFVIFFIAVTFISILTTGEGEGRVGIILTLA<br>MNIMSTLQWAVNSSIDVDSLMRSVSRVFKFIDMPTEGKPTKSTKPYKNGQ<br>LSKVMIIENSHVKKDDIWPSGGQMTVKDLTAKYTEGGNAILENISFSISPGQ<br>RVGLLGRTGSGKSTLLSAFLRLLNTEGEIQIDGVSWDSITLQQWRKAFGVIP<br>QKVFIFSGTFRKNLDPYEQWSDQEIWKVADEVGLRSVIEQFPGKLDFVLVD<br>GGCVLSHGHKQLMCLARSVLSKAKILLLDEPSAHLDPVTYQIIRRTLKQAF<br>ADCTVILCEHRIEAMLECQQFLVIEENKVRQYDSIQKLLNERSLFRQAISPS<br>DRVKLFPHRNSSKCKSKPQIAALKEETEEEVQDTRL (SEQ ID NO: 3) |

Additional exemplary codon optimized mRNA sequences are described below, for example, SEQ ID NO: 7 and SEQ ID NO: 8, both of which include 5' and 3' untranslated regions framing a codon-optimized hCFTR-encoding mRNA and SEQ ID NO: 27 to SEQ ID NO: 40.

Engineered or Mutant CFTR Proteins

In some embodiments, a suitable mRNA sequence encodes an engineered or mutant CFTR protein. In some embodiments, the mRNA sequence may be codon optimized. In some embodiments, an engineered or mutant CFTR protein may be a modified CFTR protein containing one or more amino acid substitutions, deletions, and/or insertions that increases the activity and/or stability as compared to a wild-type or naturally-occurring CFTR protein. Accordingly, in some embodiments, the modified CFTR amino acid sequence has 70%, 75%, 80%, 85%, 90%, 95, 98%, 99% or more identity to wild type CFTR. Furthermore, in some embodiments, the modified CFTR is encoded by an mRNA that has 70%, 75%, 80%, 85%, 90%, 95, 98%, 99% or more identity to an mRNA that encodes a wild type CFTR protein.

Activated CFTR Protein Mutations

CFTR is a single polypeptide containing an N-terminal lasso motif, two transmembrane domains (TMDs), and two nucleotide-binding domains (NBDs). Distinct from other ATP-binding cassette (ABC) transporters, CFTR also contains an ~200-residue cytoplasmic regulatory (R) domain that regulates the activity of CFTR. The activity of CFTR is regulated by protein kinase A-dependent phosphorylation and ATP. The R domain contains 19 predicted sites for protein kinase A (PKA); up to six have been found phosphorylated in vivo. Phosphorylation of the R domain increases the open probability of the CFTR channel and also stimulates ATP hydrolysis by CFTR. Additionally, eliminating ATP hydrolysis prolongs the lifetime of the open CFTR channel (activated CFTR), and mutating the cytosolic loops promotes CFTR activity independent of ATP.

In some embodiments, an engineered CFTR protein may contain one or more modifications that provide constitutive CFTR activity. In some embodiments, the one or more modifications provide a more CFTR activity in comparison to wild type CFTR protein activity. In particular, an engineered CFTR protein may contain one or more modifications that mimic phosphorylated residue in the R domain (R Domain Phosphomimetic mutation). In some embodiments, serine (S) or threonine (T) residues are substituted with aspartic acid (D) residues to mimic phosphorylation states. In some embodiments, serine (S) or threonine (T) residues are substituted with glutamic acid (E) residues. In some embodiments, an engineered CFTR protein may contain one or more modifications at residues S422, S660, S670, S686, T690, S700, S712, S737, S753, S768, T787, T788, S790, S795 and S813. In some embodiments, an engineered CFTR protein may contain one or more modifications that include S422D, S660D, S670D, S686D, T690D, S700D, S712D, S737D, S753D, S768D, T787D, T788D, S790D, S795D and S813D. In some embodiments, an engineered CFTR protein contains modifications of S660D, S737D, S795D and S813D. In some embodiments, an engineered CFTR protein contains modifications of S660D, S686D, S700D, S737D, S795D and S813D. In some embodiments, an engineered CFTR protein contains modifications of S660D, S686D, S700D, S712D, S737D, S768D, S795D and S813D. In some embodiments, an engineered CFTR protein contains modifications of S422D, S660D, S670D, S686D, T690D, S700D, S712D, S753D, T787D, T788D, S790D, S795D and S813D. In some embodiments, an engineered CFTR protein contains modifications of S422D, S660D, S670D, S686D, T690D, S700D, S712D, S737D, S753D, S768D, T787D, T788D, S790D, S795D and S813D.

In some embodiments, increasing the number of phosphomimetic CFTR mutations results in increased sensitivity to activation. In some embodiments, increasing the number of phosphomimetic CFTR mutations results in increased sensitivity to activation by forskolin. In some embodiments, the number of phosphomimetic CFTR mutations include 1, 2, 3, 4, 5, 6, 7, 8, 9, 10, 11, 12, 13, 14, 15, 16, 17, 18, 19 or 20 amino acid substitutions.

In some embodiments, an engineered CFTR protein has low or no immunogenic potential. Accordingly, in some embodiments, an engineered CFTR protein has low immunogenic potential. In some embodiments, an engineered CFTR protein has no immunogenic potential. In some embodiments, an engineered CFTR protein does not create or enhance the potential of cytotoxic T cell lymphocyte epitopes. Accordingly, in some embodiments, an engineered CFTR protein does not create the potential of cytotoxic T cell lymphocyte epitopes. In some embodiments, an engineered CFTR protein does not enhance the potential of cytotoxic T cell lymphocyte epitopes. In some embodiments, an engineered CFTR protein does not cause increased cytotoxicity in comparison to a vehicle control.

In some embodiments, engineered, codon-optimized CFTR has increased activity in comparison to non-codon optimized CFTR.

In some embodiments, an engineered CFTR protein contains modifications at residues S660 and S737, S795 and S813. In some embodiments an engineered CFTR protein contains modifications at residues S660, S686, S700, S737, and S795. In some embodiments an engineered CFTR protein contains modifications at residues S660, S686, S700, S737, S795, and S813. In some embodiments an engineered CFTR protein contains modifications at residues S422, S660, S670, S686, S690, S700, S712, S737, S753, S768, S787, S788, S790, S795, and S813. In some embodiments an engineered CFTR protein contains modifications at residues S422, S660, S670, S686, S690, S700, S712, S753, S787, S788, S790, S795, and S813. In some embodiments an engineered CFTR protein contains modifications at residues S660, S686, S700, S712, S737, S768, S795, and S813. In some embodiments an engineered CFTR protein contains modifications at residue K978. In some embodiments an engineered CFTR protein contains modifications at residue E1371. In some embodiments an engineered CFTR protein contains modifications at residues S422, S660, S670, S686, S690, S700, S712, S753, S787, S788, S790, S795, S813, and E1371. In some embodiments, an engineered CFTR protein contains S660D and S737D, S795D and S813D mutations. In some embodiments an engineered CFTR protein contains S660D, S686D, S700D, S737D, and S795D mutations. In some embodiments an engineered CFTR protein contains S660D, S686D, S700D, S737D, S795D, and S813D mutations. In some embodiments an engineered CFTR protein contains S422D, S660D, S670D, S686D, S690D, S700D, S712D, S737D, S753D, S768D, S787D, S788D, S790D, S795D, and S813D mutations. In some embodiments an engineered CFTR protein contains S422A, S660A, S670A, S686A, S690A, S700A, S712A, S737A, S753A, S768A, S787A, S788A, S790A, S795A, and S813A mutations. In some embodiments an engineered CFTR protein contains S422D, S660D, S670D, S686D, S690D, S700D, S712D, S753D, S787D, S788D, S790D, S795D, and S813D mutations. In some embodiments an engineered CFTR protein contains S660D, S686D, S700D, S712D, S737D, S768D, S795D, and S813D mutations. In some embodiments an engineered CFTR protein contains K978C mutation. In some embodiments an engineered CFTR protein contains E1371Q mutation. In some embodiments an engineered CFTR protein contains S422A, S660A, S670A, S686A, S690A, S700A, S712A, S753A, S787A, S788A, S790A, S795A, S813A, and E1371Q mutations. In some embodiments an engineered CFTR protein contains S422D, S660D, S670D, S686D, S690D, S700D, S712D, S753D, S787D, S788D, S790D, S795D, S813D, and E1371Q mutations.

In some embodiments, an engineered CFTR protein may contain one more modifications to abolish its ATPase activity (ATP Hydrolysis-Deficient mutation). In some embodiments, a catalytic residue in NBD2 domain of CFTR is replaced to abolish its ATPase activity. In particular embodiments, a catalytic residue is E1371. In some embodiment, an engineered CFTR protein contains an E1371Q modification.

In some embodiments, an engineered CFTR protein may contain a modification in the cytosolic loops that promote CFTR channel activity in the absence of ATP (ATP-Independent Activity mutation). In some embodiments, K978 residue in the cytosolic loop is modified to achieve constitutive activity. In some embodiments, K978 is substituted with cysteine, serine, or proline. In particular embodiments, an engineered CFTR protein contains a K978C mutation.

In some embodiments, an engineered CFTR protein may contain any combinations of modifications to achieve a CFTR protein that has greater activity as compared to wild type CFTR protein.

Stable Trafficking CFTR Protein Mutations

Posttranslational modification can occur at multiple intracellular sites and modify the fate of native and damaged proteins. Both wild-type and mutant CFTR proteins undergo ubiquitination at multiple lysines in the proteins and in one or more subcellular locations. There are several potential lysines to which ubiquitin can be added in CFTR to stabilize the protein. There are additional sites on the CFTR protein that are involved in proteolysis initiation. For example, the ubiquitinated K710, K716, and K1041 residues stabilize wild-type CFTR, protecting it from proteolysis. Modifications K14R and K68R lead to increased mature band C CFTR, which can be augmented by proteasomal (but not lysosomal) inhibition, allowing trafficking to the surface. The amount of CFTR in the K1041R mutant was drastically reduced and consisted of bands A/B. The K1218R mutant increases total and cell surface CFTR, which is further accumulated by proteasomal and lysosomal inhibition.

In some embodiments, an engineered CFTR protein may contain one or more modifications that provide an increased stability for CFTR protein compared to the naturally-occurring CFTR protein (Stability mutant). In particular, an engineered CFTR protein may contain one or more modifications that remove an ubiquitination site in a CFTR protein. In some embodiments, an ubiquitination site is K14, K68, K710, K716, K1041, K1080 or K1218. In some embodiments, a lysine residue is substituted with an arginine residue to remove ubiquitination sites. In some embodiments an engineered CFTR protein contains one or more modifications of K14R, K68R, K710R, K716R, K1041R, K1080R, and K1218R.

In some embodiments, an engineered CFTR protein contains modifications at residue K14. In some embodiments, an engineered CFTR protein contains modifications at residue K68. In some embodiments, an engineered CFTR protein contains modifications at residues K14 and K68. In some embodiments, an engineered CFTR protein contains modifications at residue K1218. In some embodiments, an engineered CFTR protein contains modifications at residues K68 and K1218. In some embodiments, an engineered CFTR protein contains modifications at residues K14 and K1218. In some embodiments, an engineered CFTR protein contains modifications at residues K14, K68, and K1218. In some embodiments, an engineered CFTR protein contains modifications at residue K710. In some embodiments, an engineered CFTR protein contains modifications at residue K716. In some embodiments, an engineered CFTR protein contains modifications at residues K710 and K716. In some embodiments, an engineered CFTR protein contains modifications at residue K1041. In some embodiments, an engineered CFTR protein contains modifications at residues K710, R716, and K1041.

In some embodiments, an engineered CFTR protein contains K14R mutation. In some embodiments, an engineered CFTR protein contains K68R mutation. In some embodiments, an engineered CFTR protein contains K14R and K68R mutations. In some embodiments, an engineered CFTR protein contains K1218R mutation. In some embodiments, an engineered CFTR protein contains K68R and K1218R mutations. In some embodiments, an engineered CFTR protein contains K14R and K1218R mutations. In some embodiments, an engineered CFTR protein contains K14R, K68R, and K1218R mutations. In some embodiments, an engineered CFTR protein contains K710R mutation. In some embodiments, an engineered CFTR protein contains K716R mutation. In some embodiments, an engineered CFTR protein contains K710R and K716R mutations. In some embodiments, an engineered CFTR protein contains K1041R mutation. In some embodiments, an engineered CFTR protein contains K710R, R716R, and K1041R mutations.

In some embodiments, an engineered CFTR protein may contain any combination of Phosphorylated R Domain Mimic, ATP-Independent Activity, ATP Hydrolysis-Deficient, and Stability mutant modifications. In some embodiments, an engineered CFTR protein comprises one or more mutations at residues K14, K68, S422, S660, S670, S686, S700, K710, S712, K716, S737, S753, S768, T787, T786, S790, S795, S813, K978, K1041, K1080, K1218, E1371, and combinations thereof. In particular embodiments, an engineered CFTR protein comprises a combination of mutations listed in Table 2.

In some embodiments, an engineered CFTR protein contains modifications at residues S660, S737, S795, S813, and K14. In some embodiments, an engineered CFTR protein contains modifications at residues S660, S737, S795, S813, and K68. In some embodiments, an engineered CFTR protein contains modifications at residues S660, S737, S795, S813, and K1218. In some embodiments, an engineered CFTR protein contains modifications at residues S660, S737, S795, S813, K14, and K68. In some embodiments, an engineered CFTR protein contains modifications at residues S660, S737, S795, S813, K14, and K1218. In some embodiments, an engineered CFTR protein contains modifications at residues S660, S737, S795, S813, K68, and K1218. In some embodiments, an engineered CFTR protein contains modifications at residues S660, S737, S795, S813, K14, K68, and K1218. In some embodiments, an engineered CFTR protein contains modifications at residues S660, S686, S700, S737, S795, and K14. In some embodiments, an engineered CFTR protein contains modifications at residues S660, S686, S700, S737, S795, and K68. In some embodiments, an engineered CFTR protein contains modifications at residues S660, S686, S700, S737, S795, and K1218. In some embodiments, an engineered CFTR protein contains modifications at residues S660, S686, S700, S737, S795, K14, and K68. In some embodiments, an engineered CFTR protein contains modifications at residues S660, S686, S700, S737, S795, K14, and K1218. In some embodiments, an engineered CFTR protein contains modifications at residues S660, S686, S700, S737, S795, K68, and K1218. In some embodiments, an engineered CFTR protein contains modifications at residues S660, S686, S700, S737, S795, K14, K68, and K1218. In some embodiments, an engineered CFTR protein contains modifications at residues K978, and K14. In some embodiments, an engineered CFTR protein contains modifications at residues K978, and K68. In some embodiments, an engineered CFTR protein contains modifications at residues K978 and K1218. In some embodiments, an engineered CFTR protein contains modifications at residues K978, K14, and K68. In some embodiments, an engineered CFTR protein contains modifications at residues K978, K14, and K1218. In some embodiments, an engineered CFTR protein contains modifications at residues K978, K68, and K1218. In some embodiments, an engineered CFTR protein contains modifications at residues K978, K14, K68, and K1218. In some embodiments, an engineered CFTR protein contains modifications at residues E1371, K14, K68, and K1218. In some embodiments, an engineered CFTR protein contains modifications at residues E1371, and K14. In some embodiments, an engineered CFTR protein contains modifications at residues E1371, and K68. In some embodiments, an engineered CFTR protein contains modifications at residues E1371, and K1218. In some embodiments, an engineered CFTR protein contains modifications at residues E1371, K14, and K68. In some embodiments, an engineered CFTR protein contains modifications at residues E1371, K14, and K1218. In some embodiments, an engineered CFTR protein contains modifications at residues E1371, K68, and K1218. In some embodiments, an engineered CFTR protein contains modifications at residues S660, S686, S700, S737, S795, and E1371. In some embodiments, an engineered CFTR protein contains modifications at residues S660, S686, S700, S737, S795, E1371, and K14. In some embodiments, an engineered CFTR protein contains modifications at residues S660, S686, S700, S737, S795, E1371, and K68. In some embodiments, an engineered CFTR protein contains modifications at residues S660, S686, S700, S737, S795, E1371, and K1218. In some embodiments, an engineered CFTR protein contains modifications at residues S660, S686, S700, S737, S795, E1371, K14, and K68. In some embodiments, an engineered CFTR protein contains modifications at residues S660, S686, S700, S737, S795, E1371, K14, and K1218. In some embodiments, an engineered CFTR protein contains modifications at residues S660, S686, S700, S737, S795, E1371, K68, and K1218. In some embodiments, an engineered CFTR protein contains modifications at residues S660, S686, S700, S737, S795, E1371, K14, K68, and K1218. In some embodiments, an engineered CFTR protein contains modifications at residues S660, S686, S700, S737, S795, K978, E1371, and K14. In some embodiments, an engineered CFTR protein contains modifications at residues S660, S686, S700, S737, S795, K978, E1371, and K68. In some embodiments, an engineered CFTR protein contains modifications at residues S660, S686, S700, S737, S795, K978, E1371, and K1218. In some embodiments, an engineered CFTR protein contains modifications at residues S660, S686, S700, S737, S795, K978, E1371, K14, and K68. In some embodiments, an engineered CFTR protein contains modifications at residues S660, S686, S700, S737, S795, K978, E1371, K14, and K1218. In some embodiments, an engineered CFTR protein contains modifications at residues S660, S686, S700, S737, S795, K978, E1371, K68, and K1218. In some embodiments, an engineered CFTR protein contains modifications at residues S660, S686, S700, S737, S795, E1371, K14, K68, K978, and K1218.

In some embodiments, an engineered CFTR protein contains S660D, S73D7, S795D, S813D, and K14R mutations. In some embodiments, an engineered CFTR protein contains S660D, S737D, S795D, S813D, and K68R mutations. In some embodiments, an engineered CFTR protein contains S660D, S737D, S795D, S813D, and K1218R mutations. In some embodiments, an engineered CFTR protein contains S660D, S737D, S795D, S813D, K14R, and K68R mutations. In some embodiments, an engineered CFTR protein contains S660D, S737D, S795D, S813D, K14R, and K1218R mutations. In some embodiments, an engineered CFTR protein contains S660D, S737D, S795D, S813D, K68R, and K1218R mutations. In some embodiments an engineered CFTR protein contains S660D, S737D, S795D, S813D, K14R, K68R, and K1218R mutations. In some embodiments, an engineered CFTR protein contains S660D, S686D, S700D, S737D, S795D, and K14R mutations. In some embodiments, an engineered CFTR protein contains S660D, S686D, S700D, S737D, S795D, and K68R mutations. In some embodiments, an engineered CFTR protein contains S660D, S686D, S700D, S737D, S795D, and K1218R mutations. In some embodiments, an engineered CFTR protein contains S660D, S686D, S700D, S737D, S795D, K14R, and K68R mutations. In some embodiments, an engineered CFTR protein contains S660D, S686D, S700D, S737D, S795D, K14R, and K1218R mutations. In some embodiments, an engineered CFTR protein contains S660D, S686D, S700D, S737D, S795D, K68R, and K1218R mutations. In some embodiments, an engineered CFTR protein contains S660D, S686D, S700D, S737D, S795D, K14R, K68R, and K1218R mutations. In some embodiments, an engineered CFTR protein contains K978C, and K14R mutations. In some embodiments, an engineered CFTR protein contains K978C, and K68R mutations. In some embodiments, an engineered CFTR protein contains K978C and K1218R mutations. In some embodiments, an engineered CFTR protein contains K978C, K14R, and K68R mutations. In some embodiments, an engineered CFTR protein contains K978C, K14R, and K1218R mutations. In some embodiments, an engineered CFTR protein contains K978C, K68R, and K1218R mutations. In some embodiments, an engineered CFTR protein contains K978C, K14R, K68R, and K1218R mutations. In some embodiments, an engineered CFTR protein contains E1371Q, and K14R mutations. In some embodiments, an engineered CFTR protein contains E1371Q, and K68R mutations. In some embodiments, an engineered CFTR protein contains E1371Q, and K1218R mutations. In some embodiments, an engineered CFTR protein contains E1371Q, K14R, and K68R mutations. In some embodiments, an engineered CFTR protein contains E1371Q, K14R, and K1218R mutations. In some embodiments, an engineered CFTR protein contains E1371Q, K68R, and K1218R mutations. In some embodiments, an engineered CFTR protein contains E1371Q, K14R, K68R, and K1218R mutations. In some embodiments, an engineered CFTR protein contains S660D, S686D, S700D, S737D, S795D, E1371Q, and K14R mutations. In some embodiments, an engineered CFTR protein contains S660D, S686D, S700D, S737D, S795D, E1371Q, and K68R mutations. In some embodiments, an engineered CFTR protein contains S660D, S686D, S700D, S737D, S795D, E1371Q, and K1218R mutations. In some embodiments, an engineered CFTR protein contains S660D, S686D, S700D, S737D, S795D, E1371Q, K14R, and K68R mutations. In some embodiments, an engineered CFTR protein contains S660D, S686D, S700D, S737D, S795D, E1371Q, K14R, and K1218R mutations. In some embodiments, an engineered CFTR protein contains S660D, S686D, S700D, S737D, S795D, E1371D, K68R, and K1218R mutations. In some embodiments, an engineered CFTR protein contains S660D, S686D, S700D, S737D, S795D, and E1371Q mutations. In some embodiments, an engineered CFTR protein contains S660D, S686D, S700D, S737D, S795D, K978C, E1371Q, and K14R mutations. In some embodiments, an engineered CFTR protein contains S660D, S686D, S700D, S737D, S795D, K978C, E1371Q, and K68R mutations. In some embodiments, an engineered CFTR protein contains S660D, S686D, S700D, S737D, S795D, K978C, E1371Q, and K1218R mutations. In some embodiments, an engineered CFTR protein contains S660D, S686D, S700D, S737D, S795D, K978C, E1371Q, K14R, and K68R mutations. In some embodiments, an engineered CFTR protein contains S660D, S686D, S700D, S737D, S795D, K978C, E1371Q, K14R, and K1218R mutations. In some embodiments, an engineered CFTR protein contains S660D, S686D, S700D, S737D, S795D, K978C, E1371Q, K68R, and K1218R mutations. In some embodiments, an engineered CFTR protein contains S660D, S686D, S700D, S737D, S795D, E1371Q, K14R, K68R, and K1218R mutations. In some embodiments, an engineered CFTR protein contains S660D, S686D, S700D, S737D, S795D, E1371Q, K14R, K68R, K978C, and K1218R mutations.

70%, 75%, 80%, 85%, 90%, 91%, 92%, 93%, 94%, 95%, 96%, 97%, 98%, 99% or more identical SEQ ID NO: 46.

In some embodiments, an engineered CFTR protein comprises K978C mutation. In some embodiments, an mRNA suitable for the present invention encodes an amino acid sequence at least 80%, 85%, 90%, 91%, 92%, 93%, 94%, 95%, 96%, 97%, 98%, 99% or more homologous to SEQ TD NO: 43. In some embodiments, an mRNA suitable for the present invention has a nucleotide sequence at least 50%,

TABLE 2

Engineered CFTR Proteins

| Engineered | Activated CFTR Mutation | | | | | | | | Stable CFTR Mutation | | |
|---|---|---|---|---|---|---|---|---|---|---|---|
| CFTR | S660 | S686 | S700 | S737 | S795 | S813 | K978 | E1371 | K14 | K68 | K1218 |
| A | | | | | | | | | | | |
| B | D | | | D | D | D | | | | | |
| C | D | D | D | D | D | | | | | | |
| D | | | | | | | C | | | | |
| E | | | | | | | | Q | | | |
| F | | | | | | | | | R | | |
| G | | | | | | | | | | R | |
| H | | | | | | | | | R | R | |
| I | | | | | | | | | | | R |
| J | | | | | | | | | | R | R |
| K | | | | | | | | | R | | R |
| L | | | | | | | | | R | R | R |
| M | D | | | D | D | D | | | R | R | R |
| N | D | D | D | D | D | | | | R | R | R |
| O | | | | | | | C | | R | R | R |
| P | | | | | | | | Q | R | R | R |
| Q | D | D | D | D | D | D | | Q | | | |
| R | D | D | D | D | D | D | | Q | R | R | R |
| S | D | D | D | D | D | D | C | Q | R | R | R |
| T | X | X | X | X | X | X | X | X | X | X | X |

*X = any amino acid

In some embodiments, an engineered CFTR protein comprises S660D, S737D, S795D and S813D mutations. In some embodiments, an mRNA suitable for the present invention encodes an amino acid sequence at least 80%, 85%, 90%, 91%, 92%, 93%, 94%, 95%, 96%, 97%, 98%, 99% or more homologous to SEQ ID NO: 41. In some embodiments, an mRNA suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical SEQ ID NO: 45.

In some embodiments, an engineered CFTR protein comprises S660D, S686D, S700D, S737D, S795D and S813D mutations. In some embodiments, an mRNA suitable for the present invention encodes an amino acid sequence at least 80%, 85%, 90%, 91%, 92%, 93%, 94%, 95%, 96%, 97%, 98%, 99% or more homologous to SEQ ID NO: 42. In some embodiments, an mRNA suitable for the present invention has a nucleotide sequence at least 50%, 55%, 60%, 65%, 55%, 60%, 65%, 70%, 75%, 80%, 85%, 90%, 91%, 92%, 93%, 94%, 95%, 96%, 97%, 98%, 99% or more identical SEQ TD NO: 47.

In some embodiments, an engineered CFTR protein comprises E1371Q mutation. In some embodiments, an mRNA suitable for the present invention encodes an amino acid sequence at least 80%, 85%, 90%, 91%, 92%, 93%, 94%, 95%, 96%, 97%, 98%, 99% or more homologous to SEQ TD NO: 44. In some embodiments, an mRNA suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical SEQ TD NO: 48.

TABLE 3

| | Exemplary Engineered CFTR Protein Sequences |
|---|---|
| SEQ ID NO: 41 | MQRSPLEKASVVSKLFFSWTRPILRKGYRQRLELSDIYQIPSVDSADNLSEK<br>LEREWDRELASKKNPKLINALRRCFFWRFMFYGIFLYLGEVTKAVQPLLL<br>GRIIASYDPDNKEERSIAIYLGIGLCLLFIVRTLLLHPAIFGLHHIGMQMRIA<br>MFSLIYKKTLKLSSRVLDKISIGQLVSLLSNNLNKFDEGLALAHFVWIAPLQ<br>VALLMGLIWELLQASAFCGLGFLIVLALFQAGLGRMMMKYRDQRAGKIS<br>ERLVITSEMIENIQSVKAYCWEEAMEKMIENLRQTELKLTRKAAYVRYFN<br>SSAFFFSGFFVVFLSVLPYALIKGIILRKIFTTISFCIVLRMAVTRQFPWAVQT<br>WYDSLGAINKIQDFLQKQEYKTLEYNLTTTEVVMENVTAFWEEGFGELFE<br>KAKQNNNNRKTSNGDDSLFFSNFSLLGTPVLKDINFKIERGQLLAVAGSTG<br>AGKTSLLMVIMGELEPSEGKIKHSGRISFCSQFSWIMPGTIKENIIFGVSYDE<br>YRYRSVIKACQLEEDISKFAEKDNIVLGEGGITLSGGQRARISLARAVYKD<br>ADLYLLDSPFGYLDVLTEKEIFESCVCKLMANKTRILVTSKMEHLKKADKI<br>LILHEGSSYFYGTFSELQNLQPDFSSKLMGCDSFDQFSAERRNDILTETLHR<br>FSLEGDAPVSWTETKKQSFKQTGEFGEKRKNSILNPINSIRKFSIVQKTPLQ<br>MNGIEEDSDEPLERRLDLVPDSEQGEAILPRISVISTGPTLQARRRQSVLNL<br>MTHSVNQGQNIHRKTTASTRKVDLAPQANLTELDIYSRRLDQETGLEISEEI<br>NEEDLKECFFDDMESIPAVTTWNTYLRYITVHKSLIFVLIWCLVIFLAEVAA<br>SLVVLWLLGNTPLQDKGNSTHSRNNSYAVIITSTSSYYVFYIYVGVADTLL<br>AMGFFRGLPLVHTLITVSKILHHKMLHSVLQAPMSTLNTLKAGGILNRFSK<br>DIAILDDLLPLTIFDFIQLLLIVIGAIAVVAVLQPYIFVATVPVIVAFIMLRAY<br>FLQTSQQLKQLESEGRSPIFTHLVTSLKGLWTLRAFGRQPYFETLFHK<br>ALNLHTANWFLYLSTLRWFQMRIEMIFVIFFIAVTFISILTTGEGEGRVGIIL<br>TLAMNIMSTLQWAVNSSIDVDSLMRSVSRVFKFIDMPTEGKPTKSTKPYK<br>NGQLSKVMIIENSHVKKDDIWPSGGQMTVKDLTAKYTEGGNAILENISFSI<br>SPGQRVGLLGRTGSGKSTLLSAFLRLLNTEGEIQIDGVSWDSITLQQWRKA<br>FGVIPQKVFIFSGTFRKNLDPYEQWSDQEIWKVADEVGLRSVIEQFPGKLD<br>FVLVDGGCVLSHGHKQLMCLARSVLSKAKILLLDEPSAHLDPVTYQIIRRT<br>LKQAFADCTVILCEHRIEAMLECQQFLVIEENKVRQYDSIQKLLNERSLFR<br>QAISPSDRVKLFPHRNSSKCKSKPQIAALKEETEEEVQDTRL (SEQ ID NO:<br>41) |
| SEQ ID NO: 42 | MQRSPLEKASVVSKLFFSWTRPILRKGYRQRLELSDIYQIPSVDSADNLSEK<br>LEREWDRELASKKNPKLINALRRCFFWRFMFYGIFLYLGEVTKAVQPLLL<br>GRIIASYDPDNKEERSIAIYLGIGLCLLFIVRTLLLHPAIFGLHHIGMQMRIA<br>MFSLIYKKTLKLSSRVLDKISIGQLVSLLSNNLNKFDEGLALAHFVWIAPLQ<br>VALLMGLIWELLQASAFCGLGFLIVLALFQAGLGRMMMKYRDQRAGKIS<br>ERLVITSEMIENIQSVKAYCWEEAMEKMIENLRQTELKLTRKAAYVRYFN<br>SSAFFFSGFFVVFLSVLPYALIKGIILRKIFTTISFCIVLRMAVTRQFPWAVQT<br>WYDSLGAINKIQDFLQKQEYKTLEYNLTTTEVVMENVTAFWEEGFGELFE<br>KAKQNNNNRKTSNGDDSLFFSNFSLLGTPVLKDINFKIERGQLLAVAGSTG<br>AGKTSLLMVIMGELEPSEGKIKHSGRISFCSQFSWIMPGTIKENIIFGVSYDE<br>YRYRSVIKACQLEEDISKFAEKDNIVLGEGGITLSGGQRARISLARAVYKD<br>ADLYLLDSPFGYLDVLTEKEIFESCVCKLMANKTRILVTSKMEHLKKADKI<br>LILHEGSSYFYGTFSELQNLQPDFSSKLMGCDSFDQFSAERRNDILTETLHR<br>FSLEGDAPVSWTETKKQDFKQTGEFGEKRKNDILNPINSIRKFSIVQKTPLQ<br>MNGIEEDSDEPLERRLDLVPDSEQGEAILPRISVISTGPTLQARRRQSVLNL<br>MTHSVNQGQNIHRKTTASTRKVDLAPQANLTELDIYSRRLDQETGLEISEEI<br>NEEDLKECFFDDMESIPAVTTWNTYLRYITVHKSLIFVLIWCLVIFLAEVAA<br>SLVVLWLLGNTPLQDKGNSTHSRNNSYAVIITSTSSYYVFYIYVGVADTLL<br>AMGFFRGLPLVHTLITVSKILHHKMLHSVLQAPMSTLNTLKAGGILNRFSK<br>DIAILDDLLPLTIFDFIQLLLIVIGAIAVVAVLQPYIFVATVPVIVAFIMLRAY<br>FLQTSQQLKQLESEGRSPIFTHLVTSLKGLWTLRAFGRQPYFETLFHKALN<br>LHTANWFLYLSTLRWFQMRIEMIFVIFFIAVTFISILTTGEGEGRVGIILTLA<br>MNIMSTLQWAVNSSIDVDSLMRSVSRVFKFIDMPTEGKPTKSTKPYKNGQ<br>LSKVMIIENSHVKKDDIWPSGGQMTVKDLTAKYTEGGNAILENISFSISPGQ<br>RVGLLGRTGSGKSTLLSAFLRLLNTEGEIQIDGVSWDSITLQQWRKAFGVIP<br>QKVFIFSGTFRKNLDPYEQWSDQEIWKVADEVGLRSVIEQFPGKLDFVLVD<br>GGCVLSHGHKQLMCLARSVLSKAKILLLDEPSAHLDPVTYQIIRRTLKQAF<br>ADCTVILCEHRIEAMLECQQFLVIEENKVRQYDSIQKLLNERSLFRQAISPS<br>DRVKLFPHRNSSKCKSKPQIAALKEETEEEVQDTRL (SEQ ID NO: 42) |
| SEQ ID NO: 43 | MQRSPLEKASVVSKLFFSWTRPILRKGYRQRLELSDIYQIPSVDSADNLSEK<br>LEREWDRELASKKNPKLINALRRCFFWRFMFYGIFLYLGEVTKAVQPLLL<br>GRIIASYDPDNKEERSIAIYLGIGLCLLFIVRTLLLHPAIFGLHHIGMQMRIA<br>MFSLIYKKTLKLSSRVLDKISIGQLVSLLSNNLNKFDEGLALAHFVWIAPLQ<br>VALLMGLIWELLQASAFCGLGFLIVLALFQAGLGRMMMKYRDQRAGKIS<br>ERLVITSEMIENIQSVKAYCWEEAMEKMIENLRQTELKLTRKAAYVRYFN<br>SSAFFFSGFFVVFLSVLPYALIKGIILRKIFTTISFCIVLRMAVTRQFPWAVQT<br>WYDSLGAINKIQDFLQKQEYKTLEYNLTTTEVVMENVTAFWEEGFGELFE<br>KAKQNNNNRKTSNGDDSLFFSNFSLLGTPVLKDINFKIERGQLLAVAGSTG<br>AGKTSLLMVIMGELEPSEGKIKHSGRISFCSQFSWIMPGTIKENIIFGVSYDE<br>YRYRSVIKACQLEEDISKFAEKDNIVLGEGGITLSGGQRARISLARAVYKD<br>ADLYLLDSPFGYLDVLTEKEIFESCVCKLMANKTRILVTSKMEHLKKADKI<br>LILHEGSSYFYGTFSELQNLQPDFSSKLMGCDSFDQFSAERRNSILTETLHR<br>FSLEGDAPVSWTETKKQSFKQTGEFGEKRKNSILNPINSIRKFSIVQKTPLQ<br>MNGIEEDSDEPLERRLSLVPDSEQGEAILPRISVISTGPTLQARRRQSVLNL<br>MTHSVNQGQNIHRKTTASTRKVSLAPQANLTELDIYSRRLSQETGLEISEEI<br>NEEDLKECFFDDMESIPAVTTWNTYLRYITVHKSLIFVLIWCLVIFLAEVAA |

TABLE 3-continued

| Exemplary Engineered CFTR Protein Sequences | |
|---|---|
| | SLVVLWLLGNTPLQDKGNSTHSRNNSYAVIITSTSSYYVFYIYVGVADTLL<br>AMGFFRGLPLVHTLITVSKILHHKMLHSVLQAPMSTLNTLKAGGILNRFSC<br>DIAILDDLLPLTIFDFIQLLLIVIGAIAVVAVLQPYIFVATVPVIVAFIMLRAY<br>FLQTSQQLKQLESEGRSPIFTHLVTSLKGLWTLRAFGRQPYFETLFHKALN<br>LHTANWFLYLSTLRWFQMRIEMIFVIFFIAVTFISILTTGEGEGRVGIILTLA<br>MNIMSTLQWAVNSSIDVDSLMRSVSRVFKFIDMPTEGKPTKSTKPYKNGQ<br>LSKVMIIENSHVKKDDIWPSGGQMTVKDLTAKYTEGGNAILENISFSISPGQ<br>RVGLLGRTGSGKSTLLSAFLRLLNTEGEIQIDGVSWDSITLQQWRKAFGVIP<br>QKVFIFSGTFRKNLDPYEQWSDQEIWKVADEVGLRSVIEQFPGKLDFVLVD<br>GGCVLSHGHKQLMCLARSVLSKAKILLLDEPSAHLDPVTYQIIRRTLKQAF<br>ADCTVILCEHRIEAMLECQQFLVIEENKVRQYDSIQKLLNERSLFRQAISPS<br>DRVKLFPHRNSSKCKSKPQIAALKEETEEEVQDTRL (SEQ ID NO: 43) |
| SEQ ID NO: 44 | MQRSPLEKASVVSKLFFSWTRPILRKGYRQRLELSDIYQIPSVDSADNLSEK<br>LEREWDRELASKKNPKLINALRRCFFWRFMFYGIFLYLGEVTKAVQPLLL<br>GRIIASYDPDNKEERSIAIYLGIGLCLLFIVRTLLLHPAIFGLHHIGMQMRIA<br>MFSLIYKKTLKLSSRVLDKISIGQLVSLLSNNLNKFDEGLALAHFVWIAPLQ<br>VALLMGLIWELLQASAFCGLGFLIVLALFQAGLGRMMMKYRDQRAGKIS<br>ERLVITSEMIENIQSVKAYCWEEAMEKMIENLRQTELKLTRKAAYVRYFN<br>SSAFFFSGFFVVFLSVLPYALIKGIILRKIFTTISFCIVLRMAVTRQFPWAVQT<br>WYDSLGAINKIQDFLQKQEYKTLEYNLTTTEVVMENVTAFWEEGFGELFE<br>KAKQNNNNRKTSNGDDSLFFSNFSLLGTPVLKDINFKIERGQLLAVAGSTG<br>AGKTSLLMVIMGELEPSEGKIKHSGRISFCSQFSWIMPGTIKENIIFGVSYDE<br>YRYRSVIKACQLEEDISKFAEKDNIVLGEGGITLSGGQRARISLARAVYKD<br>ADLYLLDSPFGYLDVLTEKEIFESCVCKLMANKTRILVTSKMEHLKKADKI<br>LILHEGSSYFYGTFSELQNLQPDFSSKLMGCDSFDQFSAERRNSILTETLHR<br>FSLEGDAPVSWTETKKQSFKQTGEFGEKRKNSILNPINSIRKFSIVQKTPLQ<br>MNGIEEDSDEPLERRLSLVPDSEQGEAILPRISVISTGPTLQARRRQSVLNL<br>MTHSVNQGQNIHRKTTASTRKVSLAPQANLTELDIYSRRLSQETGLEISEEI<br>NEEDLKECFFDDMESIPAVTTWNTYLRYITVHKSLIFVLIWCLVIFLAEVAA<br>SLVVLWLLGNTPLQDKGNSTHSRNNSYAVIITSTSSYYVFYIYVGVADTLL<br>AMGFFRGLPLVHTLITVSKILHHKMLHSVLQAPMSTLNTLKAGGILNRFSK<br>DIAILDDLLPLTIFDFIQLLLIVIGAIAVVAVLQPYIFVATVPVIVAFIMLRAY<br>FLQTSQQLKQLESEGRSPIFTHLVTSLKGLWTLRAFGRQPYFETLFHKALN<br>LHTANWFLYLSTLRWFQMRIEMIFVIFFIAVTFISILTTGEGEGRVGIILTLA<br>MNIMSTLQWAVNSSIDVDSLMRSVSRVFKFIDMPTEGKPTKSTKPYKNGQ<br>LSKVMIIENSHVKKDDIWPSGGQMTVKDLTAKYTEGGNAILENISFSISPGQ<br>RVGLLGRTGSGKSTLLSAFLRLLNTEGEIQIDGVSWDSITLQQWRKAFGVIP<br>QKVFIFSGTFRKNLDPYEQWSDQEIWKVADEVGLRSVIEQFPGKLDFVLVD<br>GGCVLSHGHKQLMCLARSVLSKAKILLLDQPSAHLDPVTYQIIRRTLKQAF<br>ADCTVILCEHRIEAMLECQQFLVIEENKVRQYDSIQKLLNERSLFRQAISPS<br>DRVKLFPHRNSSKCKSKPQIAALKEETEEEVQDTRL (SEQ ID NO: 44) |

TABLE 4

| Exemplary Codon Optimized mRNA Sequences Encoding an Engineered CFTR Protein | |
|---|---|
| SEQ ID NO: 45 | ATGCAACGCTCTCCTCTTGAAAAGGCCTCGGTGGTGTCCAAGCTCTTCT<br>TCTCGTGGACTAGACCCATCCTGAGAAAGGGGTACAGACAGCGCTTGG<br>AGCTGTCCGATATCTATCAAATCCCTTCCGTGGACTCCGCGGACAACCT<br>GTCCGAGAAGCTCGAGAGAGAATGGGACAGAGAACTCGCCTCAAAGA<br>AGAACCCGAAGCTGATTAATGCGCTTAGGCGGTGCTTTTTCTGGCGGTT<br>CATGTTCTACGGCATCTTCCTCTACCTGGGAGAGGTCACCAAGGCCGTG<br>CAGCCCCTGTTGCTGGGACGGATTATTGCCTCCTACGACCCCGACAACA<br>AGGAAGAAAGAAGCATCGCTATCTACTTGGGCATCGGTCTGTGCCTGC<br>TTTTCATCGTCCGGACCCTCTTGTTGCATCCTGCTATTTTCGGCCTGCAT<br>CACATTGGCATGCAGATGAGAATTGCCATGTTTTCCCTGATCTACAAGA<br>AAACTCTGAAGCTCTCGAGCCGCGTGCTTGACAAGATTTCCATCGGCCA<br>GCTCGTGTCCCTGCTCTCCAACAATCTGAACAAGTTCGACGAGGGCCTC<br>GCCCTGGCCCACTTCGTGTGGATCGCCCCTCTGCAAGTGGCGCTTCTGA<br>TGGGCCTGATCTGGGAGCTGCTGCAAGCCTCGGCATTCTGTGGGCTTGG<br>ATTCCTGATCGTGCTGGCACTGTTCCAGGCCGGACTGGGGCGGATGAT<br>GATGAAGTACAGGGACCAGAGAGCCGGAAAGATTTCCGAACGGCTGG<br>TGATCACTTCGGAAATGATCGAAAACATCCAGTCAGTGAAGGCCTACT<br>GCTGGGAAGAGGCCATGGAAAAGATGATTGAAAACCTCCGGCAAACC<br>GAGCTGAAGCTGACCCGCAAGGCCGCTTACGTGCGCTATTTCAACTCGT<br>CCGCTTTCTTCTTCTCCGGGTTCTTCGTGGTGTTTCTCTCCGTGCTCCCCT<br>ACGCCCTGATTAAGGGAATCATCCTCAGGAAGATCTTCACCACCATTTC<br>CTTCTGTATCGTGCTCCGCATGGCCGTGACCCGGCAGTTCCCATGGGCC<br>GTGCAGACTTGGTACGACTCCCTGGGAGCCATTAACAAGATCCAGGAC<br>TTCCTTCAAAAGCAGGAGTACAAGACCCTCGAGTACAACCTGACTACT<br>ACCGAGGTCGTGATGGAAAACGTCACCGCCTTTTGGGAGGAGGGATTT<br>GGCGAACTGTTCGAGAAGGCCAAGCAGAACAACAACAACCGCAAGAC<br>CTCGAACGGTGACGACTCCCTCTTCTTTTCAAACTTCAGCCTGCTCGGG |

TABLE 4-continued

| Exemplary Codon Optimized mRNA Sequences Encoding an Engineered CFTR Protein | |
|---|---|
| | ACGCCCGTGCTGAAGGACATTAACTTCAAGATCGAAAGAGGACAGCTC<br>CTGGCGGTGGCCGGATCGACCGGAGCCGGAAAGACTTCCCTGCTGATG<br>GTGATCATGGGAGAGCTTGAACCTAGCGAGGGAAAGATCAAGCACTCC<br>GGCCGCATCAGCTTCTGTAGCCAGTTTTCCTGGATCATGCCCGGAACCA<br>TTAAGGAAAACATCATCTTCGGCGTGTCCTACGATGAATACCGCTACCG<br>GTCCGTGATCAAAGCCTGCCAGCTGGAAGAGGATATTTCAAAGTTCGC<br>GGAGAAAGATAACATCGTGCTGGGCGAAGGGGGTATTACCTTGTCGGG<br>GGGCCAGCGGGCTAGAATCTCGCTGGCCAGAGCCGTGTATAAGGACGC<br>CGACCTGTATCTCCTGGACTCCCCCTTCGGATACCTGGACGTCCTGACC<br>GAAAAGGAGATCTTCGAATCGTGCGTGTGCAAGCTGATGGCTAACAAG<br>ACTCGCATCCTCGTGACCTCCAAAATGGAGCACCTGAAGAAGGCAGAC<br>AAGATTCTGATTCTGCATGAGGGGTCCTCCTACTTTTACGGCACCTTCT<br>CGGAGTTGCAGAACTTGCAGCCCGACTTCTCATCGAAGCTGATGGGTT<br>GCGACAGCTTCGACCAGTTCTCCGCCGAAAGAAGGAACGATATCCTGA<br>CGGAAACCTTGCACCGCTTCTCTTTGGAAGGCGACGCCCCTGTGTCATG<br>GACCGAGACTAAGAAGCAGAGCTTCAAGCAGACCGGGGAATTCGGCG<br>AAAAGAGGAAGAACAGCATCTTGAACCCCATTAACTCCATCCGCAAGT<br>TCTCAATCGTGCAAAAGACGCCACTGCAGATGAACGGCATTGAGGAGG<br>ACTCCGACGAACCCCTTGAGAGGCGCCTGGATCTGGTGCCGGACAGCG<br>AGCAGGGAGAAGCCATCCTGCCTCGGATTTCCGTGATCTCCACTGGTCC<br>GACGCTCCAAGCCCGGCGGCGGCAGTCCGTGCTGAACCTGATGACCCA<br>CAGCGTGAACCAGGGCCAAAACATTCACCGCAAGACTACCGCATCCAC<br>CCGGAAAGTGGATCTGGCACCTCAAGCGAATCTTACCGAGCTCGACAT<br>CTACTCCCGGAGACTGGATCAGGAAACCGGGCTCGAAATTTCCGAAGA<br>AATCAACGAGGAGGATCTGAAAGAGTGCTTCTTCGACGATATGGAGTC<br>GATACCCGCCGTGACGACTTGGAACACTTATCTGCGGTACATCACTGTG<br>CACAAGTCATTGATCTTCGTGCTGATTTGGTGCCTGGTGATTTTCCTGG<br>CCGAGGTCGCGGCCTCACTGGTGGTGCTCTGGCTGTTGGGAAACACGC<br>CTCTGCAAGACAAGGGAAACTCCACGCACTCGAGAAACAACAGCTATG<br>CCGTGATTATCACTTCCACCTCCTCTTATTACGTGTTCTACATCTACGTC<br>GGAGTGGCGGATACCCTGCTCGCGATGGGTTTCTTCAGAGGACTGCCG<br>CTGGTCCACACCTTGATCACCGTCAGCAAGATTCTTCACCACAAGATGT<br>TGCATAGCGTGCTGCAGGCCCCCATGTCCACCCTCAACACTCTGAAGGC<br>CGGAGGCATTCTGAACAGATTCTCCAAGGACATCGCTATCCTGGACGA<br>TCTCCTGCCGCTTACCATCTTTGACTTCATCCAGCTGCTGCTGATCGTGA<br>TTGGAGCAATCGCAGTGGTGGCGGTGCTGCAGCCTTACATTTTCGTGGC<br>CACTGTGCCGGTCATTGTGGCGTTCATCATGCTGCGGGCCTACTTCCTC<br>CAAACCAGCCAGCAGCTGAAGCAACTGGAATCCGAGGGACGATCCCCC<br>ATCTTCACTCACCTTGTGACGTCGTTGAAGGGACTGTGGACCCTCCGGG<br>CTTTCGGACGGCAGCCCTACTTCGAAACCCTCTTCCACAAGGCCCTGAA<br>CCTCCACACCGCCAATTGGTTCCTGTACCTGTCCACCCTGCGGTGGTTC<br>CAGATGCGCATCGAGATGATTTTCGTCATCTTCTTCATCGCGGTCACAT<br>TCATCAGCATCCTGACTACCGGAGAGGGAGAGGGACGGGTCGGAATAA<br>TCCTGACCCTCGCCATGAACATTATGAGCACCCTGCAGTGGGCAGTGA<br>ACAGCTCGATCGACGTGGACAGCCTGATGCGAAGCGTCAGCCGCGTGT<br>TCAAGTTCATCGACATGCCTACTGAGGGAAAACCCACTAAGTCCACTA<br>AGCCCTACAAAAATGGCCAGCTGAGCAAGGTCATGATCATCGAAAACT<br>CCCACGTGAAGAAGGACGATATTTGGCCCTCCGGAGGTCAAATGACCG<br>TGAAGGACCTGACCGCAAAGTACACCGAGGGAGGAAACGCCATTCTCG<br>AAAACATCAGCTTCTCCATTTCGCCGGGACAGCGGGTCGGCCTTCTCGG<br>GCGGACCGGTTCCGGGAAGTCAACTCTGCTGTCGGCTTTCCTCCGGCTG<br>CTGAATACCGAGGGGGAAATCCAAATTGACGGCGTGTCTTGGGATTCC<br>ATTACTCTGCAGCAGTGGCGGAAGGCCTTCGGCGTGATCCCCCAGAAG<br>GTGTTCATCTTCTCGGGTACCTTCCGGAAGAACCTGGATCCTTACGAGC<br>AGTGGAGCGACCAAGAAATCTGGAAGGTCGCCGACGAGGTCGGCCTGC<br>GCTCCGTGATTGAACAATTTCCTGGAAAGCTGGACTTCGTGCTCGTCGA<br>CGGGGGATGTGTCCTGTCGCACGGACATAAGCAGCTCATGTGCCTCGC<br>ACGGTCCGTGCTCTCCAAGGCCAAGATTCTGCTGCTGGACGAACCTTCG<br>GCCCACCTGGATCCGGTCACCTACCAGATCATCAGGAGGACCCTGAAG<br>CAGGCCTTTGCCGATTGCACCGTGATTCTCTGCGAGCACCGCATCGAGG<br>CCATGCTGGAGTGCCAGCAGTTCCTGGTCATCGAGGAGAACAAGGTCC<br>GCCAATACGACTCCATTCAAAAGCTCCTCAACGAGCGGTCGCTGTTCA<br>GACAAGCTATTTCACCGTCCGATAGAGTGAAGCTCTTCCCGCATCGGA<br>ACAGCTCAAAGTGCAAATCGAAGCCGCAGATCGCAGCCTTGAAGGAAG<br>AGACTGAGGAAGAGGTGCAGGACACCCGGCTTTAA (SEQ ID NO: 45) |
| SEQ ID NO: 46 | ATGCAACGCTCTCCTCTTGAAAAGGCCTCGGTGGTGTCCAAGCTCTTCT<br>TCTCGTGGACTAGACCCATCCTGAGAAAGGGGTACAGACAGCGCTTGG<br>AGCTGTCCGATATCTATCAAATCCCTTCCGTGGACTCCGCGGACAACCT<br>GTCCGAGAAGCTCGAGAGAGAATGGGACAGAGAACTCGCCTCAAAGA<br>AGAACCCGAAGCTGATTAATGCGCTTAGGCGGTGCTTTTTCTGGCGGTT<br>CATGTTCTACGGCATCTTCCTCTACCTGGGAGAGGTCACCAAGGCCGTG<br>CAGCCCCTGTTGCTGGGACGGATTATTGCCTCCTACGACCCCGACAACA<br>AGGAAGAAAGAAGCATCGCTATCTACTTGGGCATCGGTCTGTGCCTGC<br>TTTTCATCGTCCGGACCCTCTTGTTGCATCCTGCTATTTTCGGCCTGCAT<br>CACATTGGCATGCAGATGAGAATTGCCATGTTTTCCCTGATCTACAAGA<br>AAACTCTGAAGCTCTCGAGCCGCGTGCTTGACAAGATTTCCATCGGCCA |

TABLE 4-continued

| Exemplary Codon Optimized mRNA Sequences Encoding an Engineered CFTR Protein |
|---|
| GCTCGTGTCCCTGCTCTCCAACAATCTGAACAAGTTCGACGAGGGCCTC<br>GCCCTGGCCCACTTCGTGTGGATCGCCCCTCTGCAAGTGGCGCTTCTGA<br>TGGGCCTGATCTGGGAGCTGCTGCAAGCCTCGGCATTCTGTGGGCTTGG<br>ATTCCTGATCGTGCTGGCACTGTTCCAGGCCGGACTGGGGCGGATGAT<br>GATGAAGTACAGGGACCAGAGAGCCGGAAAGATTTCCGAACGGCTGG<br>TGATCACTTCGGAAATGATCGAAAACATCCAGTCAGTGAAGGCCTACT<br>GCTGGGAAGAGGCCATGGAAAAGATGATTGAAAACCTCCGGCAAACC<br>GAGCTGAAGCTGACCCGCAAGGCCGCTTACGTGCGCTATTTCAACTCGT<br>CCGCTTTCTTCTTCTCCGGGTTCTTCGTGGTGTTTCTCTCCGTGCTCCCCT<br>ACGCCCTGATTAAGGGAATCATCCTCAGGAAGATCTTCACCACCATTTC<br>CTTCTGTATCGTGCTCCGCATGGCCGTGACCCGGCAGTTCCCATGGGCC<br>GTGCAGACTTGGTACGACTCCCTGGGAGCCATTAACAAGATCCAGGAC<br>TTCCTTCAAAAGCAGGAGTACAAGACCCTCGAGTACAACCTGACTACT<br>ACCGAGGTCGTGATGGAAAACGTCACCGCCTTTTGGGAGGAGGGATTT<br>GGCGAACTGTTCGAGAAGGCCAAGCAGAACAACAACAACCGCAAGAC<br>CTCGAACGGTGACGACTCCCTCTTCTTTTCAAACTTCAGCCTGCTCGGG<br>ACGCCCGTGCTGAAGGACATTAACTTCAAGATCGAAAGAGGACAGCTC<br>CTGGCGGTGGCCGGATCGACCGGAGCCGGAAAGACTTCCCTGCTGATG<br>GTGATCATGGGAGAGCTTGAACCTAGCGAGGGAAAGATCAAGCACTCC<br>GGCCGCATCAGCTTCTGTAGCCAGTTTTCCTGGATCATGCCCGGAACCA<br>TTAAGGAAAACATCATCTTCGGCGTGTCCTACGATGAATACCGCTACCG<br>GTCCGTGATCAAAGCCTGCCAGCTGGAAGAGGATATTTCAAAGTTCGC<br>GGAGAAAGATAACATCGTGCTGGGCGAAGGGGGTATTACCTTGTCGGG<br>GGGCCAGCGGGCTAGAATCTCGCTGGCCAGAGCCGTGTATAAGGACGC<br>CGACCTGTATCTCCTGGACTCCCCCTTCGGATACCTGGACGTCCTGACC<br>GAAAAGGAGATCTTCGAATCGTGCGTGTGCAAGCTGATGGCTAACAAG<br>ACTCGCATCCTCGTGACCTCCAAAATGGAGCACCTGAAGAAGGCAGAC<br>AAGATTCTGATTCTGCATGAGGGGTCCTCCTACTTTTACGGCACCTTCT<br>CGGAGTTGCAGAACTTGCAGCCCGACTTCTCATCGAAGCTGATGGGTT<br>GCGACAGCTTCGACCAGTTCTCCGCCGAAAGAAGGAACGATATCCTGA<br>CGGAAACCTTGCACCGCTTCTCTTTGGAAGGCGACGCCCCTGTGTCATG<br>GACCGAGACTAAGAAGCAGGATTTCAAGCAGACCGGGGAATTCGGCG<br>AAAAGAGGAAGAACGACATCTTGAACCCCATTAACTCCATCCGCAAGT<br>TCTCAATCGTGCAAAAGACGCCACTGCAGATGAACGGCATTGAGGAG<br>ACTCCGACGAACCCCTTGAGAGGCGCCTGGATCTGGTGCCGGACAGCG<br>AGCAGGGAGAAGCCATCCTGCCTCGGATTTCCGTGATCTCCACTGGTCC<br>GACGCTCCAAGCCCGGCGGCGGCAGTCCGTGCTGAACCTGATGACCCA<br>CAGCGTGAACCAGGGCCAAAACATTCACCGCAAGACTACCGCATCCAC<br>CCGGAAAGTGGATCTGGCACCTCAAGCGAATCTTACCGAGCTCGACAT<br>CTACTCCCGGAGACTGGATCAGGAAACCGGGCTCGAAATTTCCGAAGA<br>AATCAACGAGGAGGATCTGAAAGAGTGCTTCTTCGACGATATGGAGTC<br>GATACCCGCCGTGACGACTTGGAACACTTATCTGCGGTACATCACTGTG<br>CACAAGTCATTGATCTTCGTGCTGATTTGGTGCCTGGTGATTTTCCTGG<br>CCGAGGTCGCGGCCTCACTGGTGGTGCTCTGGCTGTTGGGAAACACGC<br>CTCTGCAAGACAAGGGAAACTCCACGCACTCGAGAAACAACAGCTATG<br>CCGTGATTATCACTTCCACCTCCTCTTATTACGTGTTCTACATCTACGTC<br>GGAGTGGCGGATACCCTGCTCGCGATGGGTTTCTTCAGAGGACTGCCG<br>CTGGTCCACACCTTGATCACCGTCAGCAAGATTCTTCACCACAAGATGT<br>TGCATAGCGTGCTGCAGGCCCCCATGTCCACCCTCAACACTCTGAAGGC<br>CGGAGGCATTCTGAACAGATTCTCCAAGGACATCGCTATCCTGGACGA<br>TCTCCTGCCGCTTACCATCTTTGACTTCATCCAGCTGCTGCTGATCGTGA<br>TTGGAGCAATCGCAGTGGTGGCGGTGCTGCAGCCTTACATTTTCGTGGC<br>CACTGTGCCGGTCATTGTGGCGTTCATCATGCTGCGGGCCTACTTCCTC<br>CAAACCAGCCAGCAGCTGAAGCAACTGGAATCCGAGGGACGATCCCCC<br>ATCTTCACTCACCTTGTGACGTCGTTGAAGGGACTGTGGACCCTCCGGG<br>CTTTCGGACGGCAGCCCTACTTCGAAACCCTCTTCCACAAGGCCCTGAA<br>CCTCCACACCGCCAATTGGTTCCTGTACCTGTCCACCCTGCGGTGGTTC<br>CAGATGCGCATCGAGATGATTTTCGTCATCTTCTTCATCGCGGTCACAT<br>TCATCAGCATCCTGACTACCGGAGAGGGAGAGGGACGGGTCGGAATAA<br>TCCTGACCCTCGCCATGAACATTATGAGCACCCTGCAGTGGGCAGTGA<br>ACAGCTCGATCGACGTGGACAGCCTGATGCGAAGCGTCAGCCGCGTGT<br>TCAAGTTCATCGACATGCCTACTGAGGGAAAACCCACTAAGTCCACTA<br>AGCCCTACAAAAATGGCCAGCTGAGCAAGGTCATGATCATCGAAAACT<br>CCCACGTGAAGAAGGACGATATTTGGCCCTCCGGAGGTCAAATGACCG<br>TGAAGGACCTGACCGCAAAGTACACCGAGGGAGGAAACGCCATTCTCG<br>AAAACATCAGCTTCTCCATTTCGCCGGGACAGCGGGTCGGCCTTCTCGG<br>GCGGACCGGTTCCGGGAAGTCAACTCTGCTGTCGGCTTTCCTCCGGCTG<br>CTGAATACCGAGGGGGAAATCCAAATTGACGGCGTGTCTTGGGATTCC<br>ATTACTCTGCAGCAGTGGCGGAAGGCCTTCGGCGTGATCCCCCAGAAG<br>GTGTTCATCTTCTCGGGTACCTTCCGGAAGAACCTGGATCCTTACGAGC<br>AGTGGAGCGACCAAGAAATCTGGAAGGTCGCCGACGAGGTCGGCCTGC<br>GCTCCGTGATTGAACAATTTCCTGGAAAGCTGGACTTCGTGCTCGTCGA<br>CGGGGGATGTGTCCTGTCGCACGGACATAAGCAGCTCATGTGCCTCGC<br>ACGGTCCGTGCTCTCCAAGGCCAAGATTCTGCTGCTGGACGAACCTTCG<br>GCCCACCTGGATCCGGTCACCTACCAGATCATCAGGAGGACCCTGAAG<br>CAGGCCTTTGCCGATTGCACCGTGATTCTCTGCGAGCACCGCATCGAGG<br>CCATGCTGGAGTGCCAGCAGTTCCTGGTCATCGAGGAGAACAAGGTCC |

TABLE 4-continued

| Exemplary Codon Optimized mRNA Sequences Encoding an Engineered CFTR Protein | |
|---|---|
| | GCCAATACGACTCCATTCAAAAGCTCCTCAACGAGCGGTCGCTGTTCA<br>GACAAGCTATTTCACCGTCCGATAGAGTGAAGCTCTTCCCGCATCGGA<br>ACAGCTCAAAGTGCAAATCGAAGCCGCAGATCGCAGCCTTGAAGGAAG<br>AGACTGAGGAAGAGGTGCAGGACACCCGGCTTTAA (SEQ ID NO: 46) |
| SEQ ID NO: 47 | ATGCAACGCTCTCCTCTTGAAAAGGCCTCGGTGGTGTCCAAGCTCTTCT<br>TCTCGTGGACTAGACCCATCCTGAGAAAGGGGTACAGACAGCGCTTGG<br>AGCTGTCCGATATCTATCAAATCCCTTCCGTGGACTCCGCGGACAACCT<br>GTCCGAGAAGCTCGAGAGAGAATGGGACAGAGAACTCGCCTCAAAGA<br>AGAACCCGAAGCTGATTAATGCGCTTAGGCGGTGCTTTTTCTGGCGGTT<br>CATGTTCTACGGCATCTTCCTCTACCTGGGAGAGGTCACCAAGGCCGTG<br>CAGCCCCTGTTGCTGGGACGGATTATTGCCTCCTACGACCCCGACAACA<br>AGGAAGAAAGAAGCATCGCTATCTACTTGGGCATCGGTCTGTGCCTGC<br>TTTTCATCGTCCGGACCCTCTTGTTGCATCCTGCTATTTTCGGCCTGCAT<br>CACATTGGCATGCAGATGAGAATTGCCATGTTTTCCCTGATCTACAAGA<br>AAACTCTGAAGCTCTCGAGCCGCGTGCTTGACAAGATTTCCATCGGCCA<br>GCTCGTGTCCCTGCTCTCCAACAATCTGAACAAGTTCGACGAGGGCCTC<br>GCCCTGGCCCACTTCGTGTGGATCGCCCCTCTGCAAGTGGCGCTTCTGA<br>TGGGCCTGATCTGGGAGCTGCTGCAAGCCTCGGCATTCTGTGGGCTTGG<br>ATTCCTGATCGTGCTGGCACTGTTCCAGGCCGGACTGGGGCGGATGAT<br>GATGAAGTACAGGGACCAGAGAGCCGGAAAGATTTCCGAACGGCTGG<br>TGATCACTTCGGAAATGATCGAAAACATCCAGTCAGTGAAGGCCTACT<br>GCTGGGAAGAGGCCATGGAAAAGATGATTGAAAACCTCCGGCAAACC<br>GAGCTGAAGCTGACCCGCAAGGCCGCTTACGTGCGCTATTTCAACTCGT<br>CCGCTTTCTTCTTCTCCGGGTTCTTCGTGGTGTTTCTCTCCGTGCTCCCCT<br>ACGCCCTGATTAAGGGAATCATCCTCAGGAAGATCTTCACCACCATTTC<br>CTTCTGTATCGTGCTCCGCATGGCCGTGACCCGGCAGTTCCCATGGGCC<br>GTGCAGACTTGGTACGACTCCCTGGGAGCCATTAACAAGATCCAGGAC<br>TTCCTTCAAAAGCAGGAGTACAAGACCCTCGAGTACAACCTGACTACT<br>ACCGAGGTCGTGATGGAAAACGTCACCGCCTTTTGGGAGGAGGGATTT<br>GGCGAACTGTTCGAGAAGGCCAAGCAGAACAACAACAACCGCAAGAC<br>CTCGAACGGTGACGACTCCCTCTTCTTTTCAAACTTCAGCCTGCTCGGG<br>ACGCCCGTGCTGAAGGACATTAACTTCAAGATCGAAAGAGGACAGCTC<br>CTGGCGGTGGCCGGATCGACCGGAGCCGGAAAGACTTCCCTGCTGATG<br>GTGATCATGGGAGAGCTTGAACCTAGCGAGGGAAAGATCAAGCACTCC<br>GGCCGCATCAGCTTCTGTAGCCAGTTTTCCTGGATCATGCCCGGAACCA<br>TTAAGGAAAACATCATCTTCGGCGTGTCCTACGATGAATACCGCTACCG<br>GTCCGTGATCAAAGCCTGCCAGCTGGAAGAGGATATTTCAAAGTTCGC<br>GGAGAAAGATAACATCGTGCTGGGCGAAGGGGGTATTACCTTGTCGGG<br>GGGCCAGCGGGCTAGAATCTCGCTGGCCAGAGCCGTGTATAAGGACGC<br>CGACCTGTATCTCCTGGACTCCCCCTTCGGATACCTGGACGTCCTGACC<br>GAAAAGGAGATCTTCGAATCGTGCGTGTGCAAGCTGATGGCTAACAAG<br>ACTCGCATCCTCGTGACCTCCAAAATGGAGCACCTGAAGAAGGCAGAC<br>AAGATTCTGATTCTGCATGAGGGGTCCTCCTACTTTTACGGCACCTTCT<br>CGGAGTTGCAGAACTTGCAGCCCGACTTCTCATCGAAGCTGATGGGTT<br>GCGACAGCTTCGACCAGTTCTCCGCCGAAAGAAGGAACTCGATCCTGA<br>CGGAAACCTTGCACCGCTTCTCTTTGGAAGGCGACGCCCCTGTGTCATG<br>GACCGAGACTAAGAAGCAGAGCTTCAAGCAGACCGGGGAATTCGGCG<br>AAAAGAGGAAGAACAGCATCTTGAACCCCATTAACTCCATCCGCAAGT<br>TCTCAATCGTGCAAAAGACGCCACTGCAGATGAACGGCATTGAGGAGG<br>ACTCCGACGAACCCCTTGAGAGGCGCCTGTCCCTGGTGCCGGACAGCG<br>AGCAGGGAGAAGCCATCCTGCCTCGGATTTCCGTGATCTCCACTGGTCC<br>GACGCTCCAAGCCCGGCGGCGGCAGTCCGTGCTGAACCTGATGACCCA<br>CAGCGTGAACCAGGGCCAAAACATTCACCGCAAGACTACCGCATCCAC<br>CCGGAAAGTGTCCCTGGCACCTCAAGCGAATCTTACCGAGCTCGACAT<br>CTACTCCCGGAGACTGTCGCAGGAAACCGGGCTCGAAATTTCCGAAGA<br>AATCAACGAGGAGGATCTGAAAGAGTGCTTCTTCGACGATATGGAGTC<br>GATACCCGCCGTGACGACTTGGAACACTTATCTGCGGTACATCACTGTG<br>CACAAGTCATTGATCTTCGTGCTGATTTGGTGCCTGGTGATTTTCCTGG<br>CCGAGGTCGCGGCCTCACTGGTGGTGCTCTGGCTGTTGGGAAACACGC<br>CTCTGCAAGACAAGGGAAACTCCACGCACTCGAGAAACAACAGCTATG<br>CCGTGATTATCACTTCCACCTCCTCTTATTACGTGTTCTACATCTACGTC<br>GGAGTGGCGGATACCCTGCTCGCGATGGGTTTCTTCAGAGGACTGCCG<br>CTGGTCCACACCTTGATCACCGTCAGCAAGATTCTTCACCACAAGATGT<br>TGCATAGCGTGCTGCAGGCCCCCATGTCCACCCTCAACACTCTGAAGGC<br>CGGAGGCATTCTGAACAGATTCTCCTGCGACATCGCTATCCTGGACGAT<br>CTCCTGCCGCTTACCATCTTTGACTTCATCCAGCTGCTGCTGATCGTGAT<br>TGGAGCAATCGCAGTGGTGGCGGTGCTGCAGCCTTACATTTTCGTGGCC<br>ACTGTGCCGGTCATTGTGGCGTTCATCATGCTGCGGGCCTACTTCCTCC<br>AAACCAGCCAGCAGCTGAAGCAACTGGAATCCGAGGGACGATCCCCCA<br>TCTTCACTCACCTTGTGACGTCGTTGAAGGGACTGTGGACCCTCCGGGC<br>TTTCGGACGGCAGCCCTACTTCGAAACCCTCTTCCACAAGGCCCTGAAC<br>CTCCACACCGCCAATTGGTTCCTGTACCTGTCCACCCTGCGGTGGTTCC<br>AGATGCGCATCGAGATGATTTTCGTCATCTTCTTCATCGCGGTCACATT<br>CATCAGCATCCTGACTACCGGAGAGGGAGAGGGACGGGTCGGAATAAT<br>CCTGACCCTCGCCATGAACATTATGAGCACCCTGCAGTGGGCAGTGAA<br>CAGCTCGATCGACGTGGACAGCCTGATGCGAAGCGTCAGCCGCGTGTT |

TABLE 4-continued

| Exemplary Codon Optimized mRNA Sequences Encoding an Engineered CFTR Protein | |
|---|---|
| | CAAGTTCATCGACATGCCTACTGAGGGAAAACCCACTAAGTCCACTAA GCCCTACAAAAATGGCCAGCTGAGCAAGGTCATGATCATCGAAAACTC CCACGTGAAGAAGGACGATATTTGGCCCTCCGGAGGTCAAATGACCGT GAAGGACCTGACCGCAAAGTACACCGAGGGAGGAAACGCCATTCTCG AAAACATCAGCTTCTCCATTTCGCCGGGACAGCGGGTCGGCCTTCTCGG GCGGACCGGTTCCGGGAAGTCAACTCTGCTGTCGGCTTTCCTCCGGCTG CTGAATACCGAGGGGGAAATCCAAATTGACGGCGTGTCTTGGGATTCC ATTACTCTGCAGCAGTGGCGGAAGGCCTTCGGCGTGATCCCCCAGAAG GTGTTCATCTTCTCGGGTACCTTCCGGAAGAACCTGGATCCTTACGAGC AGTGGAGCGACCAAGAAATCTGGAAGGTCGCCGACGAGGTCGGCCTGC GCTCCGTGATTGAACAATTTCCTGGAAAGCTGGACTTCGTGCTCGTCGA CGGGGGATGTGTCCTGTCGCACGGACATAAGCAGCTCATGTGCCTCGC ACGGTCCGTGCTCTCCAAGGCCAAGATTCTGCTGCTGGACGAACCTTCG GCCCACCTGGATCCGGTCACCTACCAGATCATCAGGAGGACCCTGAAG CAGGCCTTTGCCGATTGCACCGTGATTCTCTGCGAGCACCGCATCGAGG CCATGCTGGAGTGCCAGCAGTTCCTGGTCATCGAGGAGAACAAGGTCC GCCAATACGACTCCATTCAAAAGCTCCTCAACGAGCGGTCGCTGTTCA GACAAGCTATTTCACCGTCCGATAGAGTGAAGCTCTTCCCGCATCGGA ACAGCTCAAAGTGCAAATCGAAGCCGCAGATCGCAGCCTTGAAGGAAG AGACTGAGGAAGAGGTGCAGGACACCCGGCTTTAA (SEQ ID NO: 47) |
| SEQ ID NO: 48 | ATGCAACGCTCTCCTCTTGAAAAGGCCTCGGTGGTGTCCAAGCTCTTCT TCTCGTGGACTAGACCCATCCTGAGAAAGGGGTACAGACAGCGCTTGG AGCTGTCCGATATCTATCAAATCCCTTCCGTGGACTCCGCGGACAACCT GTCCGAGAAGCTCGAGAGAGAATGGGACAGAGAACTCGCCTCAAAGA AGAACCCGAAGCTGATTAATGCGCTTAGGCGGTGCTTTTTCTGGCGGTT CATGTTCTACGGCATCTTCCTCTACCTGGGAGAGGTCACCAAGGCCGTG CAGCCCCTGTTGCTGGGACGGATTATTGCCTCCTACGACCCCGACAACA AGGAAGAAAGAAGCATCGCTATCTACTTGGGCATCGGTCTGTGCCTGC TTTTCATCGTCCGGACCCTCTTGTTGCATCCTGCTATTTTCGGCCTGCAT CACATTGGCATGCAGATGAGAATTGCCATGTTTTCCCTGATCTACAAGA AAACTCTGAAGCTCTCGAGCCGCGTGCTTGACAAGATTTCCATCGGCCA GCTCGTGTCCCTGCTCTCCAACAATCTGAACAAGTTCGACGAGGGCCTC GCCCTGGCCCACTTCGTGTGGATCGCCCCTCTGCAAGTGGCGCTTCTGA TGGGCCTGATCTGGGAGCTGCTGCAAGCCTCGGCATTCTGTGGGCTTGG ATTCCTGATCGTGCTGGCACTGTTCCAGGCCGGACTGGGGCGGATGAT GATGAAGTACAGGGACCAGAGAGCCGGAAAGATTTCCGAACGGCTGG TGATCACTTCGGAAATGATCGAAAACATCCAGTCAGTGAAGGCCTACT GCTGGGAAGAGGCCATGGAAAAGATGATTGAAAACCTCCGGCAAACC GAGCTGAAGCTGACCCGCAAGGCCGCTTACGTGCGCTATTTCAACTCGT CCGCTTTCTTCTTCTCCGGGTTCTTCGTGGTGTTTCTCTCCGTGCTCCCCT ACGCCCTGATTAAGGGAATCATCCTCAGGAAGATCTTCACCACCATTTC CTTCTGTATCGTGCTCCGCATGGCCGTGACCCGGCAGTTCCCATGGGCC GTGCAGACTTGGTACGACTCCCTGGGAGCCATTAACAAGATCCAGGAC TTCCTTCAAAAGCAGGAGTACAAGACCCTCGAGTACAACCTGACTACT ACCGAGGTCGTGATGGAAAACGTCACCGCCTTTTGGGAGGAGGGATTT GGCGAACTGTTCGAGAAGGCCAAGCAGAACAACAACAACCGCAAGAC CTCGAACGGTGACGACTCCCTCTTCTTTTCAAACTTCAGCCTGCTCGGG ACGCCCGTGCTGAAGGACATTAACTTCAAGATCGAAAGAGGACAGCTC CTGGCGGTGGCCGGATCGACCGGAGCCGGAAAGACTTCCCTGCTGATG GTGATCATGGGAGAGCTTGAACCTAGCGAGGGAAAGATCAAGCACTCC GGCCGCATCAGCTTCTGTAGCCAGTTTTCCTGGATCATGCCCGGAACCA TTAAGGAAAACATCATCTTCGGCGTGTCCTACGATGAATACCGCTACCG GTCCGTGATCAAAGCCTGCCAGCTGGAAGAGGATATTTCAAAGTTCGC GGAGAAAGATAACATCGTGCTGGGCGAAGGGGGTATTACCTTGTCGGG GGGCCAGCGGGCTAGAATCTCGCTGGCCAGAGCCGTGTATAAGGACGC CGACCTGTATCTCCTGGACTCCCCCTTCGGATACCTGGACGTCCTGACC GAAAAGGAGATCTTCGAATCGTGCGTGTGCAAGCTGATGGCTAACAAG ACTCGCATCCTCGTGACCTCCAAAATGGAGCACCTGAAGAAGGCAGAC AAGATTCTGATTCTGCATGAGGGGTCCTCCTACTTTTACGGCACCTTCT CGGAGTTGCAGAACTTGCAGCCCGACTTCTCATCGAAGCTGATGGGTT GCGACAGCTTCGACCAGTTCTCCGCCGAAAGAAGGAACTCGATCCTGA CGGAAACCTTGCACCGCTTCTCTTTGGAAGGCGACGCCCCTGTGTCATG GACCGAGACTAAGAAGCAGAGCTTCAAGCAGACCGGGGAATTCGGCG AAAAGAGGAAGAACAGCATCTTGAACCCCATTAACTCCATCCGCAAGT TCTCAATCGTGCAAAAGACGCCACTGCAGATGAACGGCATTGAGGAGG ACTCCGACGAACCCCTTGAGAGGCGCCTGTCCCTGGTGCCGGACAGCG AGCAGGGAGAAGCCATCCTGCCTCGGATTTCCGTGATCTCCACTGGTCC GACGCTCCAAGCCCGGCGGCGGCAGTCCGTGCTGAACCTGATGACCCA CAGCGTGAACCAGGGCCAAAACATTCACCGCAAGACTACCGCATCCAC CCGGAAAGTGTCCCTGGCACCTCAAGCGAATCTTACCGAGCTCGACAT CTACTCCCGGAGACTGTCGCAGGAAACCGGGCTCGAAATTTCCGAAGA AATCAACGAGGAGGATCTGAAAGAGTGCTTCTTCGACGATATGGAGTC GATACCCGCCGTGACGACTTGGAACACTTATCTGCGGTACATCACTGTG CACAAGTCATTGATCTTCGTGCTGATTTGGTGCCTGGTGATTTTCCTGG CCGAGGTCGCGGCCTCACTGGTGGTGCTCTGGCTGTTGGGAAACACGC CTCTGCAAGACAAGGGAAACTCCACGCACTCGAGAAACAACAGCTATG |

TABLE 4-continued

| Exemplary Codon Optimized mRNA Sequences Encoding an Engineered CFTR Protein | |
|---|---|
| | CCGTGATTATCACTTCCACCTCCTCTTATTACGTGTTCTACATCTACGTC<br>GGAGTGGCGGATACCCTGCTCGCGATGGGTTTCTTCAGAGGACTGCCG<br>CTGGTCCACACCTTGATCACCGTCAGCAAGATTCTTCACCACAAGATGT<br>TGCATAGCGTGCTGCAGGCCCCCATGTCCACCCTCAACACTCTGAAGGC<br>CGGAGGCATTCTGAACAGATTCTCCAAGGACATCGCTATCCTGGACGA<br>TCTCCTGCCGCTTACCATCTTTGACTTCATCCAGCTGCTGCTGATCGTGA<br>TTGGAGCAATCGCAGTGGTGGCGGTGCTGCAGCCTTACATTTTCGTGGC<br>CACTGTGCCGGTCATTGTGGCGTTCATCATGCTGCGGGCCTACTTCCTC<br>CAAACCAGCCAGCAGCTGAAGCAACTGGAATCCGAGGGACGATCCCCC<br>ATCTTCACTCACCTTGTGACGTCGTTGAAGGGACTGTGGACCCTCCGGG<br>CTTTCGGACGGCAGCCCTACTTCGAAACCCTCTTCCACAAGGCCCTGAA<br>CCTCCACACCGCCAATTGGTTCCTGTACCTGTCCACCCTGCGGTGGTTC<br>CAGATGCGCATCGAGATGATTTTCGTCATCTTCTTCATCGCGGTCACAT<br>TCATCAGCATCCTGACTACCGGAGAGGGAGAGGGACGGGTCGGAATAA<br>TCCTGACCCTCGCCATGAACATTATGAGCACCCTGCAGTGGGCAGTGA<br>ACAGCTCGATCGACGTGGACAGCCTGATGCGAAGCGTCAGCCGCGTGT<br>TCAAGTTCATCGACATGCCTACTGAGGGAAAACCCACTAAGTCCACTA<br>AGCCCTACAAAAATGGCCAGCTGAGCAAGGTCATGATCATCGAAAACT<br>CCCACGTGAAGAAGGACGATATTTGGCCCTCCGGAGGTCAAATGACCG<br>TGAAGGACCTGACCGCAAAGTACACCGAGGGAGGAAACGCCATTCTCG<br>AAAACATCAGCTTCTCCATTTCGCCGGGACAGCGGGTCGGCCTTCTCGG<br>GCGGACCGGTTCCGGGAAGTCAACTCTGCTGTCGGCTTTCCTCCGGCTG<br>CTGAATACCGAGGGGGAAATCCAAATTGACGGCGTGTCTTGGGATTCC<br>ATTACTCTGCAGCAGTGGCGGAAGGCCTTCGGCGTGATCCCCCAGAAG<br>GTGTTCATCTTCTCGGGTACCTTCCGGAAGAACCTGGATCCTTACGAGC<br>AGTGGAGCGACCAAGAAATCTGGAAGGTCGCCGACGAGGTCGGCCTGC<br>GCTCCGTGATTGAACAATTTCCTGGAAAGCTGGACTTCGTGCTCGTCGA<br>CGGGGGATGTGTCCTGTCGCACGGACATAAGCAGCTCATGTGCCTCGC<br>ACGGTCCGTGCTCTCCAAGGCCAAGATTCTGCTGCTGGACCAACCTTCG<br>GCCCACCTGGATCCGGTCACCTACCAGATCATCAGGAGGACCCTGAAG<br>CAGGCCTTTGCCGATTGCACCGTGATTCTCTGCGAGCACCGCATCGAGG<br>CCATGCTGGAGTGCCAGCAGTTCCTGGTCATCGAGGAGAACAAGGTCC<br>GCCAATACGACTCCATTCAAAAGCTCCTCAACGAGCGGTCGCTGTTCA<br>GACAAGCTATTTCACCGTCCGATAGAGTGAAGCTCTTCCCGCATCGGA<br>ACAGCTCAAAGTGCAAATCGAAGCCGCAGATCGCAGCCTTGAAGGAAG<br>AGACTGAGGAAGAGGTGCAGGACACCCGGCTTTAA (SEQ ID NO: 48) |
| SEQ ID NO: 49 Codon Optimized hCFTR - K14R E1371Q | ATGCAGCGCTCGCCTCTGGAAAAGGCGAGCGTCGTGTCACGGCTATTC<br>TTTTCTTGGACCCGGCCCATTCTCAGGAAGGGCTACAGGCAGAGGCTG<br>GAGTTGAGCGACATCTATCAGATTCCTTCCGTGGACAGCGCCGACAAC<br>CTGAGCGAGAAGCTGGAAAGGGAGTGGGACCGCGAACTGGCAAGCAA<br>AAAGAACCCCAAGCTGATCAATGCCCTGAGAAGGTGTTTCTTTTGGAG<br>ATTCATGTTCTACGGGATCTTTCTGTATCTGGGCGAGGTTACAAAGGCT<br>GTGCAGCCCCTGCTGCTCGGCAGAATCATCGCCTCATACGATCCAGAC<br>AACAAGGAAGAAAGAAGCATCGCCATCTACCTGGGCATTGGCCTCTGC<br>CTCCTGTTTATTGTGCGGACTCTGCTGCTGCACCCAGCAATTTTCGGGTT<br>GCATCATATTGGCATGCAGATGCGCATTGCTATGTTTTCCCTCATCTAC<br>AAAAAGACACTGAAACTCAGCTCCCGGGTGCTGGACAAGATCTCCATC<br>GGCCAACTGGTGTCTCTCCTGAGCAATAACTTGAATAAGTTCGACGAA<br>GGGCTGGCCCTGGCACACTTCGTGTGGATTGCCCCCCTGCAGGTGGCCC<br>TGCTGATGGGACTGATTTGGGAACTGCTGCAGGCTAGCGCTTTCTGCGG<br>CCTGGGGTTCCTGATCGTGCTGGCACTGTTTCAGGCAGGCCTGGGCCGT<br>ATGATGATGAAGTACAGAGACCAGAGGGCCGGGAAGATCTCCGAACG<br>GCTCGTTATTACCTCTGAGATGATCGAGAACATTCAGTCTGTGAAAGCC<br>TACTGCTGGGAGGAGGCTATGGAGAAGATGATCGAGAATCTGAGACAG<br>ACCGAGCTGAAGCTGACCAGAAAGGCCGCCTACGTGAGGTACTTCAAC<br>AGCAGTGCCTTCTTCTTCTCTGGCTTCTTCGTTGTGTTTCTGAGCGTGCT<br>GCCATACGCTCTCATCAAAGGCATCATCCTGCGGAAGATCTTCACCACC<br>ATCAGCTTTTGCATCGTGCTTAGAATGGCCGTGACCCGGCAGTTCCCAT<br>GGGCCGTGCAAACTTGGTATGATTCCCTGGGCGCCATCAACAAAATCC<br>AGGATTTCCTGCAGAAGCAGGAATACAAGACACTCGAATATAATCTCA<br>CAACTACTGAGGTGGTTATGGAGAACGTGACTGCCTTCTGGGAGGAGG<br>GGTTCGGAGAGCTTTTTGAGAAGGCAAAACAGAATAACAACAACCGCA<br>AAACCAGCAACGGCGACGACAGCCTGTTCTTCTCCAATTTTTCTCTCCT<br>GGGAACACCCGTCCTCAAAGACATCAACTTTAAGATCGAGAGGGGACA<br>GCTGCTCGCAGTCGCCGGATCCACAGGCGCCGGCAAGACCTCTCTGCT<br>GATGGTTATCATGGGCGAACTGGAGCCATCCGAGGGCAAGATTAAGCA<br>CAGTGGAAGAATCTCCTTTTGTAGCCAGTTCAGTTGGATTATGCCCGGC<br>ACTATTAAGGAGAATATCATTTTTGGGGTGAGCTATGATGAGTATCGGT<br>ATCGGAGCGTTATCAAAGCCTGTCAGCTGGAGGAGGATATCAGCAAAT<br>TCGCAGAGAAGGATAATATCGTGCTGGGGGAGGGGGGAATCACCCTGA<br>GCGGAGGCCAGAGAGCCAGAATCTCACTGGCCCGGGCCGTCTACAAGG<br>ACGCCGACCTTTACCTTCTGGACAGTCCCTTTGGATATCTGGATGTGCT<br>GACTGAAAAGGAGATCTTCGAGTCTTGTGTGTGCAAGCTGATGGCTAA<br>TAAGACCCGGATCCTAGTGACCAGTAAGATGGAGCACCTGAAGAAGGC<br>AGACAAGATCTTGATTCTGCACGAGGGATCCTCTTACTTTTACGGCACC<br>TTTAGCGAGCTGCAGAATCTCCAGCCCGATTTCTCATCTAAGCTGATGG |

TABLE 4-continued

| Exemplary Codon Optimized mRNA Sequences Encoding an Engineered CFTR Protein | |
|---|---|
| | GCTGTGATAGCTTCGACCAGTTCTCTGCCGAGCGCAGAAACAGCATCCT<br>GACAGAGACACTGCACCGGTTTTCACTGGAGGGCGACGCCCCTGTCAG<br>CTGGACCGAGACCAAAAAGCAGTCTTTCAAGCAGACAGGCGAGTTCGG<br>CGAGAAGCGCAAAAACAGCATCCTGAATCCAATCAACTCTATAAGGAA<br>GTTTAGCATCGTGCAGAAGACACCCCTCCAGATGAACGGCATCGAAGA<br>GGACAGTGACGAGCCCCTGGAGCGGCGCCTGAGCCTCGTGCCTGACAG<br>CGAACAGGGCGAGGCCATCCTGCCTAGGATCAGCGTGATTTCAACCGG<br>GCCAACACTGCAGGCTAGGAGAAGACAGTCAGTGCTTAACCTGATGAC<br>ACATAGCGTGAATCAGGGACAGAACATCCATCGAAAAACCACAGCCTC<br>TACTCGCAAAGTGTCACTGGCTCCTCAGGCTAATCTGACAGAGCTGGA<br>CATCTATAGCAGGAGGCTGAGCCAGGAGACAGGCCTGGAGATCAGTGA<br>GGAGATCAACGAAGAGGACCTGAAGGAGTGCTTTTTCGATGACATGGA<br>GAGTATCCCCGCCGTCACCACCTGGAATACCTACCTCCGGTACATCACA<br>GTGCACAAGTCCCTCATCTTTGTGCTGATTTGGTGCCTCGTGATCTTTCT<br>CGCAGAAGTGGCCGCCTCCCTGGTGGTGCTGTGGCTGTTGGGGAATAC<br>TCCACTGCAGGACAAAGGCAATTCTACACACAGCAGGAATAATTCCTA<br>TGCCGTGATTATCACCAGCACATCCTCTTACTACGTGTTCTACATCTAC<br>GTGGGAGTGGCAGATACTCTGCTTGCAATGGGCTTCTTCAGGGGGCTG<br>CCCCTGGTGCACACACTGATCACAGTGTCCAAGATCCTCCACCATAAA<br>ATGCTCCACAGCGTGCTGCAGGCACCCATGAGCACCCTGAACACACTG<br>AAGGCCGGCGGCATCCTGAATCGCTTTTCCAAAGACATCGCCATCCTCG<br>ACGATCTCCTGCCACTGACCATCTTCGATTTTATCCAGCTGCTGCTGAT<br>CGTGATCGGGGCCATCGCCGTGGTGGCCGTGCTGCAGCCATACATTTTC<br>GTGGCTACAGTGCCCGTGATCGTTGCCTTTATCATGCTGAGAGCCTACT<br>TCCTGCAGACTTCTCAGCAGCTGAAGCAGCTGGAGAGCGAAGGGAGAA<br>GCCCCATCTTCACTCACCTGGTGACAAGCCTGAAGGGACTCTGGACCCT<br>GAGAGCCTTCGGCCGGCAGCCCTATTTCGAGACCCTGTTTCACAAGGCC<br>CTCAACCTGCACACAGCCAACTGGTTTCTCTACCTGTCCACCCTGAGGT<br>GGTTCCAGATGAGGATTGAAATGATCTTCGTGATTTTTTTCATCGCCGT<br>GACATTCATTAGCATTCTGACCACCGGCGAGGGGGAGGGGAGAGTGGG<br>CATCATCCTGACCCTTGCCATGAACATTATGTCCACACTGCAGTGGGCC<br>GTGAATAGTTCAATCGACGTGGACAGTCTGATGAGGTCCGTGAGCCGG<br>GTGTTCAAGTTCATTGACATGCCCACAGAGGGGAAACCCACCAAAAGC<br>ACCAAGCCCTACAAGAACGGGCAGCTGTCCAAGGTTATGATCATCGAG<br>AACTCTCACGTGAAGAAGGACGACATTTGGCCCAGCGGCGGCCAGATG<br>ACAGTGAAAGATCTGACCGCCAAATACACCGAGGGAGGCAACGCCATC<br>CTCGAAAACATTAGCTTCTCTATCAGCCCTGGACAGAGGGTGGGCCTG<br>CTGGGCCGGACAGGCTCAGGGAAGAGTACTCTGCTGTCAGCATTCCTG<br>AGGCTCCTGAACACAGAGGGCGAGATCCAGATTGACGGCGTGTCCTGG<br>GACTCCATCACCCTGCAGCAGTGGCGGAAGGCTTTCGGGGTGATCCCC<br>CAGAAGGTGTTCATCTTTAGCGGCACTTTCAGAAAGAATCTGGACCCTT<br>ATGAGCAGTGGAGTGACCAGGAGATCTGGAAAGTGGCCGATGAGGTC<br>GGACTGAGGAGCGTGATCGAGCAGTTTCCAGGGAAGCTGGACTTTGTG<br>CTGGTGGATGGCGGATGCGTGCTGTCTCACGGCCATAAACAGCTGATG<br>TGTCTGGCCCGGTCCGTGCTGTCTAAGGCCAAGATCCTGCTGCTGGACC<br>AACCCTCCGCCCACCTGGACCCCGTGACATACCAGATCATCAGGAGAA<br>CTCTCAAGCAGGCCTTCGCCGACTGTACCGTGATTCTGTGCGAGCACCG<br>CATTGAAGCTATGCTGGAGTGTCAGCAGTTCCTGGTGATCGAGGAAAA<br>TAAGGTGAGGCAGTACGACAGCATCCAGAAGCTGCTGAACGAGCGCTC<br>CCTGTTCCGCCAGGCTATCTCCCCATCAGACCGGGTGAAGCTCTTTCCC<br>CACAGAAACTCCTCAAAGTGCAAGTCCAAGCCCCAGATCGCCGCCCTG<br>AAGGAGGAGACCGAGGAGGAGGTGCAGGACACCAGGCTGTGA (SEQ<br>ID NO: 49) |
| SEQ ID NO: 50 Codon Optimized - hCFTR-13E K14R | ATGCAGCGCTCGCCTCTGGAAAAGGCGAGCGTCGTGTCACGGCTATTC<br>TTTTCTTGGACCCGGCCCATTCTCAGGAAGGGCTACAGGCAGAGGCTG<br>GAGTTGAGCGACATCTATCAGATTCCTTCCGTGGACAGCGCCGACAAC<br>CTGAGCGAGAAGCTGGAAAGGGAGTGGGACCGCGAACTGGCAAGCAA<br>AAAGAACCCCAAGCTGATCAATGCCCTGAGAAGGTGTTTCTTTTGGAG<br>ATTCATGTTCTACGGGATCTTTCTGTATCTGGGCGAGGTTACAAAGGCT<br>GTGCAGCCCCTGCTGCTCGGCAGAATCATCGCCTCATACGATCCAGAC<br>AACAAGGAAGAAAGAAGCATCGCCATCTACCTGGGCATTGGCCTCTGC<br>CTCCTGTTTATTGTGCGGACTCTGCTGCTGCACCCAGCAATTTTCGGGTT<br>GCATCATATTGGCATGCAGATGCGCATTGCTATGTTTTCCCTCATCTAC<br>AAAAAGACACTGAAACTCAGCTCCCGGGTGCTGGACAAGATCTCCATC<br>GGCCAACTGGTGTCTCTCCTGAGCAATAACTTGAATAAGTTCGACGAA<br>GGGCTGGCCCTGGCACACTTCGTGTGGATTGCCCCCCTGCAGGTGGCCC<br>TGCTGATGGGACTGATTTGGGAACTGCTGCAGGCTAGCGCTTTCTGCGG<br>CCTGGGGTTCCTGATCGTGCTGGCACTGTTTCAGGCAGGCCTGGGCCGT<br>ATGATGATGAAGTACAGAGACCAGAGGGCCGGGAAGATCTCCGAACG<br>GCTCGTTATTACCTCTGAGATGATCGAGAACATTCAGTCTGTGAAAGCC<br>TACTGCTGGGAGGAGGCTATGGAGAAGATGATCGAGAATCTGAGACAG<br>ACCGAGCTGAAGCTGACCAGAAAGGCCGCCTACGTGAGGTACTTCAAC<br>AGCAGTGCCTTCTTCTTCTCTGGCTTCTTCGTTGTGTTTCTGAGCGTGCT<br>GCCATACGCTCTCATCAAAGGCATCATCCTGCGGAAGATCTTCACCACC<br>ATCAGCTTTTGCATCGTGCTTAGAATGGCCGTGACCCGGCAGTTCCCAT<br>GGGCCGTGCAAACTTGGTATGATTCCCTGGGCGCCATCAACAAAATCC |

TABLE 4-continued

| Exemplary Codon Optimized mRNA Sequences Encoding an Engineered CFTR Protein | |
|---|---|
| | AGGATTTCCTGCAGAAGCAGGAATACAAGACACTCGAATATAATCTCA<br>CAACTACTGAGGTGGTTATGGAGAACGTGACTGCCTTCTGGGAGGAGG<br>GGTTCGGAGAGCTTTTTGAGAAGGCAAAACAGAATAACAACAACCGCA<br>AAACCGAGAACGGCGACGACAGCCTGTTCTTCTCCAATTTTTCTCTCCT<br>GGGAACACCCGTCCTCAAAGACATCAACTTTAAGATCGAGAGGGGACA<br>GCTGCTCGCAGTCGCCGGATCCACAGGCGCCGGCAAGACCTCTCTGCT<br>GATGGTTATCATGGGCGAACTGGAGCCATCCGAGGGCAAGATTAAGCA<br>CAGTGGAAGAATCTCCTTTTGTAGCCAGTTCAGTTGGATTATGCCCGGC<br>ACTATTAAGGAGAATATCATTTTTGGGGTGAGCTATGATGAGTATCGGT<br>ATCGGAGCGTTATCAAAGCCTGTCAGCTGGAGGAGGATATCAGCAAAT<br>TCGCAGAGAAGGATAATATCGTGCTGGGGGAGGGGGGAATCACCCTGA<br>GCGGAGGCCAGAGAGCCAGAATCTCACTGGCCCGGGCCGTCTACAAGG<br>ACGCCGACCTTTACCTTCTGGACAGTCCCTTTGGATATCTGGATGTGCT<br>GACTGAAAAGGAGATCTTCGAGTCTTGTGTGTGCAAGCTGATGGCTAA<br>TAAGACCCGGATCCTAGTGACCAGTAAGATGGAGCACCTGAAGAAGGC<br>AGACAAGATCTTGATTCTGCACGAGGGATCCTCTTACTTTTACGGCACC<br>TTTAGCGAGCTGCAGAATCTCCAGCCCGATTTCTCATCTAAGCTGATGG<br>GCTGTGATAGCTTCGACCAGTTCTCTGCCGAGCGCAGAAACGAAATCC<br>TGACAGAGACACTGCACCGGTTTGAGCTGGAGGGCGACGCCCCTGTCA<br>GCTGGACCGAGACCAAAAAGCAGGAATTCAAGCAGGAGGGCGAGTTC<br>GGCGAGAAGCGCAAAAACGAAATCCTGAATCCAATCAACTCTATAAGG<br>AAGTTTGAAATCGTGCAGAAGACACCCCTCCAGATGAACGGCATCGAA<br>GAGGACAGTGACGAGCCCCTGGAGCGGCGCCTGAGCCTCGTGCCTGAC<br>AGCGAACAGGGCGAGGCCATCCTGCCTAGGATCGAGGTGATTTCAACC<br>GGGCCAACACTGCAGGCTAGGAGAAGACAGTCAGTGCTTAACCTGATG<br>ACACATAGCGTGAATCAGGGACAGAACATCCATCGAAAAGAAGAAGC<br>CGAAACTCGCAAAGTGGAGCTGGCTCCTCAGGCTAATCTGACAGAGCT<br>GGACATCTATAGCAGGAGGCTGGAACAGGAGACAGGCCTGGAGATCA<br>GTGAGGAGATCAACGAAGAGGACCTGAAGGAGTGCTTTTTCGATGACA<br>TGGAGAGTATCCCCGCCGTCACCACCTGGAATACCTACCTCCGGTACAT<br>CACAGTGCACAAGTCCCTCATCTTTGTGCTGATTTGGTGCCTCGTGATC<br>TTTCTCGCAGAAGTGGCCGCCTCCCTGGTGGTGCTGTGGCTGTTGGGGA<br>ATACTCCACTGCAGGACAAAGGCAATTCTACACACAGCAGGAATAATT<br>CCTATGCCGTGATTATCACCAGCACATCCTCTTACTACGTGTTCTACAT<br>CTACGTGGGAGTGGCAGATACTCTGCTTGCAATGGGCTTCTTCAGGGG<br>GCTGCCCCTGGTGCACACACTGATCACAGTGTCCAAGATCCTCCACCAT<br>AAAATGCTCCACAGCGTGCTGCAGGCACCCATGAGCACCCTGAACACA<br>CTGAAGGCCGGCGGCATCCTGAATCGCTTTTCCAAAGACATCGCCATCC<br>TCGACGATCTCCTGCCACTGACCATCTTCGATTTTATCCAGCTGCTGCT<br>GATCGTGATCGGGGCCATCGCCGTGGTGGCCGTGCTGCAGCCATACAT<br>TTTCGTGGCTACAGTGCCCGTGATCGTTGCCTTTATCATGCTGAGAGCC<br>TACTTCCTGCAGACTTCTCAGCAGCTGAAGCAGCTGGAGAGCGAAGGG<br>AGAAGCCCCATCTTCACTCACCTGGTGACAAGCCTGAAGGGACTCTGG<br>ACCCTGAGAGCCTTCGGCCGGCAGCCCTATTTCGAGACCCTGTTTCACA<br>AGGCCCTCAACCTGCACACAGCCAACTGGTTTCTCTACCTGTCCACCCT<br>GAGGTGGTTCCAGATGAGGATTGAAATGATCTTCGTGATTTTTTTCATC<br>GCCGTGACATTCATTAGCATTCTGACCACCGGCGAGGGGGAGGGGAGA<br>GTGGGCATCATCCTGACCCTTGCCATGAACATTATGTCCACACTGCAGT<br>GGGCCGTGAATAGTTCAATCGACGTGGACAGTCTGATGAGGTCCGTGA<br>GCCGGGTGTTCAAGTTCATTGACATGCCCACAGAGGGGAAACCCACCA<br>AAAGCACCAAGCCCTACAAGAACGGGCAGCTGTCCAAGGTTATGATCA<br>TCGAGAACTCTCACGTGAAGAAGGACGACATTTGGCCCAGCGGCGGCC<br>AGATGACAGTGAAAGATCTGACCGCCAAATACACCGAGGGAGGCAAC<br>GCCATCCTCGAAAACATTAGCTTCTCTATCAGCCCTGGACAGAGGGTG<br>GGCCTGCTGGGCCGGACAGGCTCAGGGAAGAGTACTCTGCTGTCAGCA<br>TTCCTGAGGCTCCTGAACACAGAGGGCGAGATCCAGATTGACGGCGTG<br>TCCTGGGACTCCATCACCCTGCAGCAGTGGCGGAAGGCTTTCGGGGTG<br>ATCCCCCAGAAGGTGTTCATCTTTAGCGGCACTTTCAGAAAGAATCTGG<br>ACCCTTATGAGCAGTGGAGTGACCAGGAGATCTGGAAAGTGGCCGATG<br>AGGTCGGACTGAGGAGCGTGATCGAGCAGTTTCCAGGGAAGCTGGACT<br>TTGTGCTGGTGGATGGCGGATGCGTGCTGTCTCACGGCCATAAACAGCT<br>GATGTGTCTGGCCCGGTCCGTGCTGTCTAAGGCCAAGATCCTGCTGCTG<br>GACGAACCCTCCGCCCACCTGGACCCCGTGACATACCAGATCATCAGG<br>AGAACTCTCAAGCAGGCCTTCGCCGACTGTACCGTGATTCTGTGCGAGC<br>ACCGCATTGAAGCTATGCTGGAGTGTCAGCAGTTCCTGGTGATCGAGG<br>AAAATAAGGTGAGGCAGTACGACAGCATCCAGAAGCTGCTGAACGAG<br>CGCTCCCTGTTCCGCCAGGCTATCTCCCCATCAGACCGGGTGAAGCTCT<br>TTCCCCACAGAAACTCCTCAAAGTGCAAGTCCAAGCCCCAGATCGCCG<br>CCCTGAAGGAGGAGACCGAGGAGGAGGTGCAGGACACCAGGCTGTGA<br>(SEQ ID NO: 50) |
| SEQ ID NO: 51 Codon Optimized-hCFTR-15E K14R | ATGCAGCGCTCGCCTCTGGAAAAGGCGAGCGTCGTGTCACGGCTATTC<br>TTTTCTTGGACCCGGCCCATTCTCAGGAAGGGCTACAGGCAGAGGCTG<br>GAGTTGAGCGACATCTATCAGATTCCTTCCGTGGACAGCGCCGACAAC<br>CTGAGCGAGAAGCTGGAAAGGGAGTGGGACCGCGAACTGGCAAGCAA<br>AAAGAACCCCAAGCTGATCAATGCCCTGAGAAGGTGTTTCTTTTGGAG<br>ATTCATGTTCTACGGGATCTTTCTGTATCTGGGCGAGGTTACAAAGGCT |

TABLE 4-continued

| Exemplary Codon Optimized mRNA Sequences Encoding an Engineered CFTR Protein |
|---|
| GTGCAGCCCCTGCTGCTCGGCAGAATCATCGCCTCATACGATCCAGAC<br>AACAAGGAAGAAAGAAGCATCGCCATCTACCTGGGCATTGGCCTCTGC<br>CTCCTGTTTATTGTGCGGACTCTGCTGCTGCACCCAGCAATTTTCGGGTT<br>GCATCATATTGGCATGCAGATGCGCATTGCTATGTTTTCCCTCATCTAC<br>AAAAAGACACTGAAACTCAGCTCCCGGGTGCTGGACAAGATCTCCATC<br>GGCCAACTGGTGTCTCTCCTGAGCAATAACTTGAATAAGTTCGACGAA<br>GGGCTGGCCCTGGCACACTTCGTGTGGATTGCCCCCCTGCAGGTGGCCC<br>TGCTGATGGGACTGATTTGGGAACTGCTGCAGGCTAGCGCTTTCTGCGG<br>CCTGGGGTTCCTGATCGTGCTGGCACTGTTTCAGGCAGGCCTGGGCCGT<br>ATGATGATGAAGTACAGAGACCAGAGGGCCGGGAAGATCTCCGAACG<br>GCTCGTTATTACCTCTGAGATGATCGAGAACATTCAGTCTGTGAAAGCC<br>TACTGCTGGGAGGAGGCTATGGAGAAGATGATCGAGAATCTGAGACAG<br>ACCGAGCTGAAGCTGACCAGAAAGGCCGCCTACGTGAGGTACTTCAAC<br>AGCAGTGCCTTCTTCTTCTCTGGCTTCTTCGTTGTGTTTCTGAGCGTGCT<br>GCCATACGCTCTCATCAAAGGCATCATCCTGCGGAAGATCTTCACCACC<br>ATCAGCTTTTGCATCGTGCTTAGAATGGCCGTGACCCGGCAGTTCCCAT<br>GGGCCGTGCAAACTTGGTATGATTCCCTGGGCGCCATCAACAAAATCC<br>AGGATTTCCTGCAGAAGCAGGAATACAAGACACTCGAATATAATCTCA<br>CAACTACTGAGGTGGTTATGGAGAACGTGACTGCCTTCTGGGAGGAGG<br>GGTTCGGAGAGCTTTTTGAGAAGGCAAAACAGAATAACAACAACCGCA<br>AAACCGAGAACGGCGACGACAGCCTGTTCTTCTCCAATTTTTCTCTCCT<br>GGGAACACCCGTCCTCAAAGACATCAACTTTAAGATCGAGAGGGGACA<br>GCTGCTCGCAGTCGCCGGATCCACAGGCGCCGGCAAGACCTCTCTGCT<br>GATGGTTATCATGGGCGAACTGGAGCCATCCGAGGGCAAGATTAAGCA<br>CAGTGGAAGAATCTCCTTTTGTAGCCAGTTCAGTTGGATTATGCCCGGC<br>ACTATTAAGGAGAATATCATTTTTGGGGTGAGCTATGATGAGTATCGGT<br>ATCGGAGCGTTATCAAAGCCTGTCAGCTGGAGGAGGATATCAGCAAAT<br>TCGCAGAGAAGGATAATATCGTGCTGGGGGAGGGGGGAATCACCCTGA<br>GCGGAGGCCAGAGAGCCAGAATCTCACTGGCCCGGGCCGTCTACAAGG<br>ACGCCGACCTTTACCTTCTGGACAGTCCCTTTGGATATCTGGATGTGCT<br>GACTGAAAAGGAGATCTTCGAGTCTTGTGTGTGCAAGCTGATGGCTAA<br>TAAGACCCGGATCCTAGTGACCAGTAAGATGGAGCACCTGAAGAAGGC<br>AGACAAGATCTTGATTCTGCACGAGGGATCCTCTTACTTTTACGGCACC<br>TTTAGCGAGCTGCAGAATCTCCAGCCCGATTTCTCATCTAAGCTGATGG<br>GCTGTGATAGCTTCGACCAGTTCTCTGCCGAGCGCAGAAACGAAATCC<br>TGACAGAGACACTGCACCGGTTTGAGCTGGAGGGCGACGCCCCTGTCA<br>GCTGGACCGAGACCAAAAAGCAGGAATTCAAGCAGGAGGGCGAGTTC<br>GGCGAGAAGCGCAAAAACGAAATCCTGAATCCAATCAACTCTATAAGG<br>AAGTTTGAAATCGTGCAGAAGACACCCCTCCAGATGAACGGCATCGAA<br>GAGGACAGTGACGAGCCCCTGGAGCGGCGCCTGGAACTCGTGCCTGAC<br>AGCGAACAGGGCGAGGCCATCCTGCCTAGGATCGAGGTGATTTCAACC<br>GGGCCAACACTGCAGGCTAGGAGAAGACAGGAAGTGCTTAACCTGATG<br>ACACATAGCGTGAATCAGGGACAGAACATCCATCGAAAAGAAGAAGC<br>CGAAACTCGCAAAGTGGAGCTGGCTCCTCAGGCTAATCTGACAGAGCT<br>GGACATCTATAGCAGGAGGCTGGAACAGGAGACAGGCCTGGAGATCA<br>GTGAGGAGATCAACGAAGAGGACCTGAAGGAGTGCTTTTTCGATGACA<br>TGGAGAGTATCCCCGCCGTCACCACCTGGAATACCTACCTCCGGTACAT<br>CACAGTGCACAAGTCCCTCATCTTTGTGCTGATTTGGTGCCTCGTGATC<br>TTTCTCGCAGAAGTGGCCGCCTCCCTGGTGGTGCTGTGGCTGTTGGGGA<br>ATACTCCACTGCAGGACAAAGGCAATTCTACACACAGCAGGAATAATT<br>CCTATGCCGTGATTATCACCAGCACATCCTCTTACTACGTGTTCTACAT<br>CTACGTGGGAGTGGCAGATACTCTGCTTGCAATGGGCTTCTTCAGGGG<br>GCTGCCCCTGGTGCACACACTGATCACAGTGTCCAAGATCCTCCACCAT<br>AAAATGCTCCACAGCGTGCTGCAGGCACCCATGAGCACCCTGAACACA<br>CTGAAGGCCGGCGGCATCCTGAATCGCTTTTCCAAAGACATCGCCATCC<br>TCGACGATCTCCTGCCACTGACCATCTTCGATTTTATCCAGCTGCTGCT<br>GATCGTGATCGGGGCCATCGCCGTGGTGGCCGTGCTGCAGCCATACAT<br>TTTCGTGGCTACAGTGCCCGTGATCGTTGCCTTTATCATGCTGAGAGCC<br>TACTTCCTGCAGACTTCTCAGCAGCTGAAGCAGCTGGAGAGCGAAGGG<br>AGAAGCCCCATCTTCACTCACCTGGTGACAAGCCTGAAGGGACTCTGG<br>ACCCTGAGAGCCTTCGGCCGGCAGCCCTATTTCGAGACCCTGTTTCACA<br>AGGCCCTCAACCTGCACACAGCCAACTGGTTTCTCTACCTGTCCACCCT<br>GAGGTGGTTCCAGATGAGGATTGAAATGATCTTCGTGATTTTTTTCATC<br>GCCGTGACATTCATTAGCATTCTGACCACCGGCGAGGGGGAGGGGAGA<br>GTGGGCATCATCCTGACCCTTGCCATGAACATTATGTCCACACTGCAGT<br>GGGCCGTGAATAGTTCAATCGACGTGGACAGTCTGATGAGGTCCGTGA<br>GCCGGGTGTTCAAGTTCATTGACATGCCCACAGAGGGGAAACCCACCA<br>AAAGCACCAAGCCCTACAAGAACGGGCAGCTGTCCAAGGTTATGATCA<br>TCGAGAACTCTCACGTGAAGAAGGACGACATTTGGCCCAGCGGCGGCC<br>AGATGACAGTGAAAGATCTGACCGCCAAATACACCGAGGGAGGCAAC<br>GCCATCCTCGAAAACATTAGCTTCTCTATCAGCCCTGGACAGAGGGTG<br>GGCCTGCTGGGCCGGACAGGCTCAGGGAAGAGTACTCTGCTGTCAGCA<br>TTCCTGAGGCTCCTGAACACAGAGGGCGAGATCCAGATTGACGGCGTG<br>TCCTGGGACTCCATCACCCTGCAGCAGTGGCGGAAGGCTTTCGGGGTG<br>ATCCCCCAGAAGGTGTTCATCTTTAGCGGCACTTTCAGAAAGAATCTGG<br>ACCCTTATGAGCAGTGGAGTGACCAGGAGATCTGGAAAGTGGCCGATG<br>AGGTCGGACTGAGGAGCGTGATCGAGCAGTTTCCAGGGAAGCTGGACT |

TABLE 4-continued

| Exemplary Codon Optimized mRNA Sequences Encoding an Engineered CFTR Protein | |
|---|---|
| | TTGTGCTGGTGGATGGCGGATGCGTGCTGTCTCACGGCCATAAACAGCT GATGTGTCTGGCCCGGTCCGTGCTGTCTAAGGCCAAGATCCTGCTGCTG GACGAACCCTCCGCCCACCTGGACCCCGTGACATACCAGATCATCAGG AGAACTCTCAAGCAGGCCTTCGCCGACTGTACCGTGATTCTGTGCGAGC ACCGCATTGAAGCTATGCTGGAGTGTCAGCAGTTCCTGGTGATCGAGG AAAATAAGGTGAGGCAGTACGACAGCATCCAGAAGCTGCTGAACGAG CGCTCCCTGTTCCGCCAGGCTATCTCCCCATCAGACCGGGTGAAGCTCT TTCCCCACAGAAACTCCTCAAAGTGCAAGTCCAAGCCCCAGATCGCCG CCCTGAAGGAGGAGACCGAGGAGGAGGTGCAGGACACCAGGCTGTGA (SEQ ID NO: 51) |
| SEQ ID NO: 52 Codon Optimized-hCFTR-13E | ATGCAGCGCTCGCCTCTGGAAAAGGCGAGCGTCGTGTCAAAGCTATTC TTTTCTTGGACCCGGCCCATTCTCAGGAAGGGCTACAGGCAGAGGCTG GAGTTGAGCGACATCTATCAGATTCCTTCCGTGGACAGCGCCGACAAC CTGAGCGAGAAGCTGGAAAGGGAGTGGGACCGCGAACTGGCAAGCAA AAAGAACCCCAAGCTGATCAATGCCCTGAGAAGGTGTTTCTTTTGGAG ATTCATGTTCTACGGGATCTTTCTGTATCTGGGCGAGGTTACAAAGGCT GTGCAGCCCCTGCTGCTCGGCAGAATCATCGCCTCATACGATCCAGAC AACAAGGAAGAAAGAAGCATCGCCATCTACCTGGGCATTGGCCTCTGC CTCCTGTTTATTGTGCGGACTCTGCTGCTGCACCCAGCAATTTTCGGGTT GCATCATATTGGCATGCAGATGCGCATTGCTATGTTTTCCCTCATCTAC AAAAAGACACTGAAACTCAGCTCCCGGGTGCTGGACAAGATCTCCATC GGCCAACTGGTGTCTCTCCTGAGCAATAACTTGAATAAGTTCGACGAA GGGCTGGCCCTGGCACACTTCGTGTGGATTGCCCCCCTGCAGGTGGCCC TGCTGATGGGACTGATTTGGGAACTGCTGCAGGCTAGCGCTTTCTGCGG CCTGGGGTTCCTGATCGTGCTGGCACTGTTTCAGGCAGGCCTGGGCCGT ATGATGATGAAGTACAGAGACCAGAGGGCCGGGAAGATCTCCGAACG GCTCGTTATTACCTCTGAGATGATCGAGAACATTCAGTCTGTGAAAGCC TACTGCTGGGAGGAGGCTATGGAGAAGATGATCGAGAATCTGAGACAG ACCGAGCTGAAGCTGACCAGAAAGGCCGCCTACGTGAGGTACTTCAAC AGCAGTGCCTTCTTCTTCTCTGGCTTCTTCGTTGTGTTTCTGAGCGTGCT GCCATACGCTCTCATCAAAGGCATCATCCTGCGGAAGATCTTCACCACC ATCAGCTTTTGCATCGTGCTTAGAATGGCCGTGACCCGGCAGTTCCCAT GGGCCGTGCAAACTTGGTATGATTCCCTGGGCGCCATCAACAAAATCC AGGATTTCCTGCAGAAGCAGGAATACAAGACACTCGAATATAATCTCA CAACTACTGAGGTGGTTATGGAGAACGTGACTGCCTTCTGGGAGGAGG GGTTCGGAGAGCTTTTTGAGAAGGCAAAACAGAATAACAACAACCGCA AAACCGAGAACGGCGACGACAGCCTGTTCTTCTCCAATTTTTCTCTCCT GGGAACACCCGTCCTCAAAGACATCAACTTTAAGATCGAGAGGGGACA GCTGCTCGCAGTCGCCGGATCCACAGGCGCCGGCAAGACCTCTCTGCT GATGGTTATCATGGGCGAACTGGAGCCATCCGAGGGCAAGATTAAGCA CAGTGGAAGAATCTCCTTTTGTAGCCAGTTCAGTTGGATTATGCCCGGC ACTATTAAGGAGAATATCATTTTTGGGGTGAGCTATGATGAGTATCGGT ATCGGAGCGTTATCAAAGCCTGTCAGCTGGAGGAGGATATCAGCAAAT TCGCAGAGAAGGATAATATCGTGCTGGGGGAGGGGGGAATCACCCTGA GCGGAGGCCAGAGAGCCAGAATCTCACTGGCCCGGGCCGTCTACAAGG ACGCCGACCTTTACCTTCTGGACAGTCCCTTTGGATATCTGGATGTGCT GACTGAAAAGGAGATCTTCGAGTCTTGTGTGTGCAAGCTGATGGCTAA TAAGACCCGGATCCTAGTGACCAGTAAGATGGAGCACCTGAAGAAGGC AGACAAGATCTTGATTCTGCACGAGGGATCCTCTTACTTTTACGGCACC TTTAGCGAGCTGCAGAATCTCCAGCCCGATTTCTCATCTAAGCTGATGG GCTGTGATAGCTTCGACCAGTTCTCTGCCGAGCGCAGAAACGAAATCC TGACAGAGACACTGCACCGGTTTGAGCTGGAGGGCGACGCCCCTGTCA GCTGGACCGAGACCAAAAAGCAGGAATTCAAGCAGGAGGGCGAGTTC GGCGAGAAGCGCAAAAACGAAATCCTGAATCCAATCAACTCTATAAGG AAGTTTGAAATCGTGCAGAAGACACCCCTCCAGATGAACGGCATCGAA GAGGACAGTGACGAGCCCCTGGAGCGGCGCCTGAGCCTCGTGCCTGAC AGCGAACAGGGCGAGGCCATCCTGCCTAGGATCGAGGTGATTTCAACC GGGCCAACACTGCAGGCTAGGAGAAGACAGTCAGTGCTTAACCTGATG ACACATAGCGTGAATCAGGGACAGAACATCCATCGAAAAGAAGAAGC CGAAACTCGCAAAGTGGAGCTGGCTCCTCAGGCTAATCTGACAGAGCT GGACATCTATAGCAGGAGGCTGGAACAGGAGACAGGCCTGGAGATCA GTGAGGAGATCAACGAAGAGGACCTGAAGGAGTGCTTTTTCGATGACA TGGAGAGTATCCCCGCCGTCACCACCTGGAATACCTACCTCCGGTACAT CACAGTGCACAAGTCCCTCATCTTTGTGCTGATTTGGTGCCTCGTGATC TTTCTCGCAGAAGTGGCCGCCTCCCTGGTGGTGCTGTGGCTGTTGGGGA ATACTCCACTGCAGGACAAAGGCAATTCTACACACAGCAGGAATAATT CCTATGCCGTGATTATCACCAGCACATCCTCTTACTACGTGTTCTACAT CTACGTGGGAGTGGCAGATACTCTGCTTGCAATGGGCTTCTTCAGGGG GCTGCCCCTGGTGCACACACTGATCACAGTGTCCAAGATCCTCCACCAT AAAATGCTCCACAGCGTGCTGCAGGCACCCATGAGCACCCTGAACACA CTGAAGGCCGGCGGCATCCTGAATCGCTTTTCCAAAGACATCGCCATCC TCGACGATCTCCTGCCACTGACCATCTTCGATTTTATCCAGCTGCTGCT GATCGTGATCGGGGCCATCGCCGTGGTGGCCGTGCTGCAGCCATACAT TTTCGTGGCTACAGTGCCCGTGATCGTTGCCTTTATCATGCTGAGAGCC TACTTCCTGCAGACTTCTCAGCAGCTGAAGCAGCTGGAGAGCGAAGGG AGAAGCCCCATCTTCACTCACCTGGTGACAAGCCTGAAGGGACTCTGG |

TABLE 4-continued

| Exemplary Codon Optimized mRNA Sequences Encoding an Engineered CFTR Protein |
|---|
| ACCCTGAGAGCCTTCGGCCGGCAGCCCTATTTCGAGACCCTGTTTCACA<br>AGGCCCTCAACCTGCACACAGCCAACTGGTTTCTCTACCTGTCCACCCT<br>GAGGTGGTTCCAGATGAGGATTGAAATGATCTTCGTGATTTTTTTCATC<br>GCCGTGACATTCATTAGCATTCTGACCACCGGCGAGGGGGAGGGGAGA<br>GTGGGCATCATCCTGACCCTTGCCATGAACATTATGTCCACACTGCAGT<br>GGGCCGTGAATAGTTCAATCGACGTGGACAGTCTGATGAGGTCCGTGA<br>GCCGGGTGTTCAAGTTCATTGACATGCCCACAGAGGGGAAACCCACCA<br>AAAGCACCAAGCCCTACAAGAACGGGCAGCTGTCCAAGGTTATGATCA<br>TCGAGAACTCTCACGTGAAGAAGGACGACATTTGGCCCAGCGGCGGCC<br>AGATGACAGTGAAAGATCTGACCGCCAAATACACCGAGGGAGGCAAC<br>GCCATCCTCGAAAACATTAGCTTCTCTATCAGCCCTGGACAGAGGGTG<br>GGCCTGCTGGGCCGGACAGGCTCAGGGAAGAGTACTCTGCTGTCAGCA<br>TTCCTGAGGCTCCTGAACACAGAGGGCGAGATCCAGATTGACGGCGTG<br>TCCTGGGACTCCATCACCCTGCAGCAGTGGCGGAAGGCTTTCGGGGTG<br>ATCCCCCAGAAGGTGTTCATCTTTAGCGGCACTTTCAGAAAGAATCTGG<br>ACCCTTATGAGCAGTGGAGTGACCAGGAGATCTGGAAAGTGGCCGATG<br>AGGTCGGACTGAGGAGCGTGATCGAGCAGTTTCCAGGGAAGCTGGACT<br>TTGTGCTGGTGGATGGCGGATGCGTGCTGTCTCACGGCCATAAACAGCT<br>GATGTGTCTGGCCCGGTCCGTGCTGTCTAAGGCCAAGATCCTGCTGCTG<br>GACGAACCCTCCGCCCACCTGGACCCCGTGACATACCAGATCATCAGG<br>AGAACTCTCAAGCAGGCCTTCGCCGACTGTACCGTGATTCTGTGCGAGC<br>ACCGCATTGAAGCTATGCTGGAGTGTCAGCAGTTCCTGGTGATCGAGG<br>AAAATAAGGTGAGGCAGTACGACAGCATCCAGAAGCTGCTGAACGAG<br>CGCTCCCTGTTCCGCCAGGCTATCTCCCCATCAGACCGGGTGAAGCTCT<br>TTCCCCACAGAAACTCCTCAAAGTGCAAGTCCAAGCCCCAGATCGCCG<br>CCCTGAAGGAGGAGACCGAGGAGGAGGTGCAGGACACCAGGCTGTGA<br>(SEQ ID NO: 52) |

In some embodiments, a suitable mRNA sequence may be an mRNA sequence encoding a homolog or an analog of human CFTR (hCFTR) protein. For example, a homolog or an analog of hCFTR protein may be a modified hCFTR protein containing one or more amino acid substitutions, deletions, and/or insertions as compared to a wild-type or naturally-occurring hCFTR protein while retaining substantial hCFTR protein activity. In some embodiments, an mRNA suitable for the present invention encodes an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO: 3, SEQ ID NO: 41, SEQ ID NO: 42, SEQ ID NO: 43, or SEQ ID NO: 44. In some embodiments, an mRNA suitable for the present invention encodes a protein substantially identical to an engineered hCFTR protein. In some embodiments, an mRNA suitable for the present invention encodes an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 41, SEQ ID NO: 42, SEQ ID NO: 43, or SEQ ID NO: 44. In some embodiments, an mRNA suitable for the present invention encodes a fragment or a portion of an engineered hCFTR protein. In some embodiments, an mRNA suitable for the present invention encodes a fragment or a portion of an engineered hCFTR protein, wherein the fragment or portion of the protein still maintains CFTR activity similar to that of the full-length engineered protein. In some embodiments, an mRNA suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical SEQ ID NO: 1, SEQ ID NO: 7, SEQ ID NO: 8, SEQ ID NO: 45, SEQ ID NO: 46, SEQ ID NO: 47, or SEQ ID NO: 48.

In some embodiments, an mRNA suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical to any one of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39 or SEQ ID NO: 40.

In some embodiments, a suitable mRNA encodes a fusion protein comprising a full length, fragment or portion of an engineered hCFTR protein fused to another protein (e.g., an N or C terminal fusion). In some embodiments, the protein fused to the mRNA encoding a full length, fragment or portion of an engineered hCFTR protein encodes a signal or a cellular targeting sequence.

(SEQ ID NO: 21)

```
ATGCAGAGGAGCCCACTGGAGAAAGCCTCCGTGGTGAGTAAACTCTTTTTTAGTTGG
ACCAGACCCATCCTGCGAAAAGGATACAGGCAGCGCCTCGAGTTGTCAGATATCTA
CCAGATTCCTTCTGTGGACTCAGCTGACAATTTGAGTGAGAAGCTGGAGCGGGAGTG
GGATAGAGAGCTGGCGAGCAAAAAAAACCCCAAGCTTATCAATGCTCTGCGCCGCT
GCTTTTTCTGGAGGTTCATGTTTTATGGGATCTTCCTGTACCTGGGGGAGGTCACCAA
AGCTGTTCAGCCGCTCCTTCTTGGCCGCATCATCGCCAGCTATGACCCTGATAATAA
AGAAGAAAGGTCTATTGCTATTTATCTGGGAATTGGCCTCTGCTTGCTCTTCATCGTC
CGCACCCTTCTGCTGCACCCTGCCATTTTTGGCCTTCACCACATCGGCATGCAAATG
AGAATTGCCATGTTCTCCCTCATTTACAAAAAGACCCTGAAACTTTCCTCAAGAGTG
TTAGATAAAATATCCATTGGTCAGCTGGTCAGCCTGCTGTCCAACAATCTTAACAAA
TTTGATGAAGGCTTGGCGCTGGCCCACTTCGTGTGGATTGCACCTCTGCAGGTGGCC
CTGTTGATGGGACTTATATGGGAGCTGCTTCAAGCCTCTGCTTTCTGTGGGCTGGGCT
```

-continued

TTTTGATTGTACTGGCACTTTTTCAGGCTGGGCTCGGAAGAATGATGATGAAATACA
GAGATCAGCGGGCCGGGAAGATATCAGAGCGACTTGTGATCACCAGTGAAATGATT
GAAAATATTCAGAGCGTGAAAGCCTACTGCTGGGAAGAAGCCATGGAGAAGATGAT
TGAGAACCTGAGGCAGACAGAGCTCAAGCTCACTCGGAAGGCTGCTTATGTTCGCT
ATTTCAACAGCAGCGCCTTCTTCTTCAGTGGCTTCTTTGTTGTCTTCCTGTCTGTTCTG
CCATATGCACTGATAAAAGGCATTATTTTACGAAAGATCTTCACCACCATCAGTTTT
TGCATCGTTCTCAGGATGGCCGTCACAAGACAGTTCCCCTGGGCTGTGCAGACCTGG
TACGATTCCTTGGGGGCCATCAACAAGATTCAAGATTTCTTGCAAAAACAAGAATAT
AAAACTTTAGAATACAACCTCACCACCACTGAAGTGGTCATGGAAAATGTGACAGC
CTTTTGGGAGGAGGGTTTTGGAGAATTGTTCGAGAAGGCAAAGCAGAATAACAACA
ACAGGAAGACGAGCAATGGGGACGACTCTCTCTTCTTCAGCAACTTTTCACTGCTCG
GGACCCCTGTGTTGAAAGATATAAACTTCAAGATCGAGAGGGGCCAGCTCTTGGCT
GTGGCAGGCTCCACTGGAGCTGGTAAAACATCTCTTCTCATGGTGATCATGGGGGAA
CTGGAGCCTTCCGAAGGAAAAATCAAGCACAGTGGGAGAATCTCATTCTGCAGCCA
GTTTTCCTGGATCATGCCCGGCACCATTAAGGAAAACATCATATTTGGAGTGTCCTA
TGATGAGTACCGCTACCGGTCAGTCATCAAAGCCTGTCAGTTGGAGGAGGACATCTC
CAAGTTTGCAGAGAAAGACAACATTGTGCTTGGAGAGGGGGGTATCACTCTTTCTGG
AGGACAAAGAGCCAGGATCTCTTTGGCCCGGGCAGTCTACAAGGATGCAGACCTCT
ACTTGTTGGACAGTCCCTTCGGCTACCTCGACGTGCTGACTGAAAAAGAAATTTTTG
AAAGCTGTGTGTGCAAACTGATGGCAAACAAGACCAGGATTCTTGTCACCAGCAAG
ATGGAACATCTGAAGAAAGCGGACAAAATTCTGATTCTGCATGAAGGGAGCTCCTA
CTTCTATGGAACATTTAGCGAGCTTCAGAACCTACAGCCAGACTTCTCCTCCAAATT
AATGGGCTGTGACTCCTTCGACCAGTTCTCTGCAGAAAGAAGAAACTCTATACTCAC
AGAGACCCTCCACCGCTTCTCCCTTGAGGGAGATGCCCCAGTTTCTTGGACAGAAAC
CAAGAAGCAGTCCTTTAAGCAGACTGGCGAGTTTGGTGAAAAGAGGAAAAATTCAA
TTCTCAATCCAATTAACAGTATTCGCAAGTTCAGCATTGTCCAGAAGACACCCCTCC
AGATGAATGGCATCGAAGAAGATAGTGACGAGCCGCTGGAGAGACGGCTGAGTCTG
GTGCCAGATTCAGAACAGGGGGAGGCCATCCTGCCCCGGATCAGCGTCATTTCCAC
AGGCCCCACATTACAAGCACGGCGCCGGCAGAGTGTTTTAAATCTCATGACCCATTC
AGTGAACCAGGGCCAAAATATCCACAGGAAGACTACAGCTTCTACCCGGAAAGTGT
CTCTGGCCCCTCAGGCCAATCTGACCGAGCTGGACATCTACAGCAGGAGGCTCTCCC
AGGAAACAGGGCTGGAAATATCTGAAGAGATTAATGAAGAGGATCTTAAAGAGTGC
TTCTTTGATGACATGGAGAGCATCCCCGCGGTGACCACATGGAACACCTACCTTAGA
TATATTACTGTCCACAAGAGCCTCATATTTGTCCTCATCTGGTGCCTGGTTATTTTCC
TCGCTGAGGTGGCGGCCAGTCTTGTTGTGCTCTGGCTGCTGGGCAACACTCCTCTCC
AGGACAAGGGCAATAGTACTCACAGCAGAAATAATTCTTATGCCGTCATCATTACA
AGCACCTCCAGCTACTACGTGTTCTACATCTATGTGGGCGTGGCTGACACCCTCCTG
GCCATGGGTTTCTTCCGGGGCCTGCCTTTGGTGCACACCCTCATCACAGTGTCAAAA
ATTCTGCACCATAAAATGCTTCATTCTGTCCTGCAGGCACCCATGAGCACTTTGAAC
ACATTGAAGGCTGGCGGCATCCTCAACAGATTTTCTAAAGATATTGCTATCCTGGAT
GATCTCCTCCCCCTGACAATCTTTGACTTTATCCAGCTTCTGCTGATCGTGATTGGAG
CCATAGCAGTGGTTGCTGTCCTGCAGCCCTACATTTTTGTGGCCACCGTGCCCGTGAT
TGTTGCCTTTATTATGCTCAGAGCTTACTTCCTGCAAACTTCTCAACAGCTCAAACAG
CTAGAATCTGAGGGCCGGAGCCCCATTTTTACCCACCTGGTGACTTCCCTGAAGGGA
CTGTGGACTCTGAGAGCATTCGGGCGACAGCCTTACTTTGAGACACTGTTCCACAAG
GCCCTGAACTTGCACACTGCCAACTGGTTTCTTTACCTGAGCACACTCCGCTGGTTCC
AGATGCGGATAGAGATGATCTTCGTCATCTTTTTTATAGCTGTAACCTTCATTTCTAT
CCTTACAACAGGAGAAGGAGAGGGCAGGGTGGGAATCATCCTCACGCTGGCTATGA
ACATAATGTCCACCTTGCAGTGGGCCGTGAATTCCAGTATAGATGTGGATTCTCTAA
TGAGGAGTGTCTCCCGGGTGTTTAAATTCATTGATATGCCTACTGAGGGGAAACCCA
CCAAGTCAACAAAACCTTATAAGAATGGACAGCTGAGCAAGGTGATGATAATTGAG
AACAGCCACGTGAAGAAGGATGACATTTGGCCCAGCGGGGGCCAGATGACTGTGAA
GGACCTGACGGCCAAGTACACCGAAGGTGGAAATGCCATTTTGGAAAACATCAGCT
TCTCAATCTCTCCTGGGCAGAGAGTTGGATTGCTGGGTCGCACGGGCAGCGGCAAAT
CAACCCTGCTCAGTGCCTTCCTTCGGCTCCTGAATACAGAAGGCGAAATCCAAATTG
ACGGGGTGAGCTGGGACAGCATCACCCTGCAGCAGTGGAGAAAAGCATTTGGGGTC
ATTCCACAGAAAGTTTTCATCTTCTCTGGCACTTTCAGAAAGAACCTGGACCCCTAT
GAGCAGTGGAGCGACCAGGAGATCTGGAAGGTTGCAGATGAAGTTGGCCTGCGGAG
TGTGATAGAACAATTTCCTGGCAAGCTGGATTTTGTGCTGGTAGATGGAGGCTGCGT
GCTGTCCCACGGCCACAAACAGCTGATGTGCCTCGCCCGCTCCGTTCTTTCAAAGGC
CAAAATCTTGCTTTTGGATGAGCCCAGTGCTCACCTCGACCCAGTGACCTATCAGAT
AATCCGCAGGACCTTAAAGCAAGCTTTTGCCGACTGCACCGTCATACTGTGTGAGCA
CCGGATTGAAGCAATGCTGGAATGCCAGCAGTTTCTGGTGATCGAGGAGAATAAGG
TCCGGCAGTACGACAGCATCCAGAAGTTGTTGAATGAGCGCAGCCTTTTCCGCCAGG
CCATCTCCCCATCTGACAGAGTCAAGCTGTTTCCACATAGGAACTCCTCTAAGTGCA
AGTCCAAGCCCCAGATCGCTGCCCTCAAGGAGGAAACTGAGGAAGAGGTGCAGGAT
ACCCGCCTGTGA (SEQ ID NO: 22)

ATGCAGAGGAGCCCACTGGAGAAAGCCTCCGTGGTGAGTAAACTCTTTTTTAGTTGG
ACCAGACCCATCCTGCGAAAAGGATACAGGCAGCGCCTCGAGTTGTCTGATATCTA
CCAGATTCCTTCTGTGGACTCAGCTGACAATTTGAGTGAGAAGCTGGAGCGGGAGTG
GGATAGAGAGCTGGCGAGCAAAAAAAACCCCAAGCTTATCAATGCTCTGCGCCGCT
GCTTTTTCTGGAGGTTCATGTTTTATGGGATCTTCCTGTACCTGGGGGAGGTCACCAA
AGCTGTTCAGCCGCTCCTTCTTGGCCGCATCATCGCCAGCTATGACCCTGATAATAA
AGAAGAAAGGTCTATTGCTATTTATCTGGGAATTGGCCTCTGCTTGCTCTTCATCGTC
CGCACCCTTCTGCTGCACCCTGCCATTTTTGGCCTTCACCACATCGGCATGCAAATG
AGAATTGCCATGTTCTCCCTCATTTACAAAAAGACCCTGAAACTTTCCTCAAGAGTG
TTAGATAAAATATCCATTGGTCAGCTGGTCAGCCTGCTGTCCAACAATCTTAACAAA
TTTGATGAAGGCTTGGCGCTGGCCCACTTCGTGTGGATTGCACCTCTGCAGGTGGCC
CTGTTGATGGGACTTATATGGGAGCTGCTTCAAGCCTCTGCTTTCTGTGGGCTGGGCT

-continued

TTTTGATTGTACTGGCACTTTTTCAGGCTGGGCTCGGAAGAATGATGATGAAATACA
GAGATCAGCGGGCCGGGAAGATTTCAGAGCGACTTGTGATCACCAGTGAAATGATT
GAAAATATTCAGAGCGTGAAAGCCTACTGCTGGGAAGAAGCCATGGAGAAGATGAT
TGAGAACCTGAGGCAGACAGAGCTCAAGCTCACTCGGAAGGCTGCTTATGTTCGCT
ATTTCAACAGCAGCGCCTTCTTCTTCAGTGGCTTCTTTGTTGTCTTCCTGTCTGTTCTG
CCATATGCACTGATAAAAGGCATTATTTTACGAAAGATCTTCACCACCATCAGTTTT
TGCATCGTTCTCAGGATGGCCGTCACAAGACAGTTCCCCTGGGCTGTGCAGACCTGG
TACGATTCCTTGGGGGCCATCAACAAGATTCAAGATTTCTTGCAAAAACAAGAATAT
AAAACTTTAGAATACAACCTCACCACCACTGAAGTGGTCATGGAAAATGTGACAGC
CTTTTGGGAGGAGGGTTTTGGAGAATTGTTCGAGAAGGCAAAGCAGAATAACAACA
ACAGGAAGACGAGCAATGGGGACGACTCTCTCTTCTTCAGCAACTTTTCACTGCTCG
GGACCCCTGTGTTGAAAGATATAAACTTCAAGATCGAGAGGGGCCAGCTCTTGGCT
GTGGCAGGCTCCACTGGAGCTGGTAAAACATCTCTTCTCATGGTGATCATGGGGGAA
CTGGAGCCTTCCGAAGGAAAAATCAAGCACAGTGGGAGAATCTCATTCTGCAGCCA
GTTTTCCTGGATCATGCCCGGCACCATTAAGGAAAACATCATATTTGGAGTGTCCTA
TGATGAGTACCGCTACCGGTCAGTCATCAAAGCCTGTCAGTTGGAGGAGGACATCTC
CAAGTTTGCAGAGAAAGACAACATTGTGCTTGGAGAGGGGGGTATCACTCTTTCTGG
AGGACAAAGAGCCAGGATCTCTTTGGCCCGGGCAGTCTACAAGGATGCAGACCTCT
ACTTGTTGGACAGTCCCTTCGGCTACCTCGACGTGCTGACTGAAAAAGAAATTTTTG
AAAGCTGTGTGTGCAAACTGATGGCAAACAAGACCAGGATTCTTGTCACCAGCAAG
ATGGAACATCTGAAGAAAGCGGACAAAATTCTGATTCTGCATGAAGGGAGCTCCTA
CTTCTATGGAACATTTAGCGAGCTTCAGAACCTACAGCCAGACTTCTCCTCCAAATT
AATGGGCTGTGACTCCTTCGACCAGTTCTCTGCAGAAAGAAGAAACTCTATACTCAC
AGAGACCCTCCACCGCTTCTCCCTTGAGGGAGATGCCCCAGTTTCTTGGACAGAAAC
CAAGAAGCAGTCCTTTAAGCAGACTGGCGAGTTTGGTGAAAAGAGGAAAAATTCAA
TTCTCAATCCAATTAACAGTATTCGCAAGTTCAGCATTGTCCAGAAGACACCCCTCC
AGATGAATGGCATCGAAGAAGATAGTGACGAGCCGCTGGAGAGACGGCTGAGTCTG
GTGCCAGATTCAGAACAGGGGGAGGCCATCCTGCCCCGGATCAGCGTCATTTCCAC
AGGCCCCACATTACAAGCACGGCGCCGGCAGAGTGTTTTAAATCTCATGACCCATTC
AGTGAACCAGGGCCAAAATATCCACAGGAAGACTACAGCTTCTACCCGGAAAGTGT
CTCTGGCCCCTCAGGCCAATCTGACCGAGCTGGACATCTACAGCAGGAGGCTCTCCC
AGGAAACAGGGCTGGAAATATCTGAAGAGATTAATGAAGAGGATCTTAAAGAGTGC
TTCTTTGATGACATGGAGAGCATCCCCGCGGTGACCACATGGAACACCTACCTTAGA
TATATTACTGTCCACAAGAGCCTCATATTTGTCCTCATCTGGTGCCTGGTTATTTTCC
TCGCTGAGGTGGCGGCCAGTCTTGTTGTGCTCTGGCTGCTGGGCAACACTCCTCTCC
AGGACAAGGGCAATAGTACTCACAGCAGAAATAATTCTTATGCCGTCATCATTACA
AGCACCTCCAGCTACTACGTGTTCTACATCTATGTGGGCGTGGCTGACACCCTCCTG
GCCATGGGTTTCTTCCGGGGCCTGCCTTTGGTGCACACCCTCATCACAGTGTCAAAA
ATTCTGCACCATAAAATGCTTCATTCTGTCCTGCAGGCACCCATGAGCACTTTGAAC
ACATTGAAGGCTGGCGGCATCCTCAACAGATTTTCTAAAGATATTGCTATCCTGGAT
GATCTCCTCCCCCTGACAATCTTTGACTTTATCCAGCTTCTGCTGATCGTGATTGGAG
CCATAGCAGTGGTTGCTGTCCTGCAGCCCTACATTTTTGTGGCCACCGTGCCCGTGAT
TGTTGCCTTTATTATGCTCAGAGCTTACTTCCTGCAAACTTCTCAACAGCTCAAACAG
CTAGAATCTGAGGGCCGGAGCCCCATTTTTACCCACCTGGTGACTTCCCTGAAGGGA
CTGTGGACTCTGAGAGCATTCGGGCGACAGCCTTACTTTGAGACACTGTTCCACAAG
GCCCTGAACTTGCACACTGCCAACTGGTTTCTTTACCTGAGCACACTCCGCTGGTTCC
AGATGCGGATAGAGATGATCTTCGTCATCTTTTTTATAGCTGTAACCTTCATTTCTAT
CCTTACAACAGGAGAAGGAGAGGGCAGGGTGGGAATCATCCTCACGCTGGCTATGA
ACATAATGTCCACCTTGCAGTGGGCCGTGAATTCCAGTATAGATGTGGATTCTCTAA
TGAGGAGTGTCTCCCGGGTGTTTAAATTCATTGATATGCCTACTGAGGGGAAACCCA
CCAAGTCAACAAAACCTTATAAGAATGGACAGCTGAGCAAGGTGATGATAATTGAG
AACAGCCACGTGAAGAAGGATGACATTTGGCCCAGCGGGGGCCAGATGACTGTGAA
GGACCTGACGGCCAAGTACACCGAAGGTGGAAATGCCATTTTGGAAAACATCAGCT
TCTCAATCTCTCCTGGCCAGAGAGTTGGATTGCTGGGTCGCACGGGCAGCGGCAAAT
CAACCCTGCTCAGTGCCTTCCTTCGGCTCCTGAATACAGAAGGCGAAATCCAAATTG
ACGGGGTGAGCTGGGACAGCATCACCCTGCAGCAGTGGAGAAAAGCATTTGGGGTC
ATTCCACAGAAAGTTTTCATCTTCTCTGGCACTTTCAGAAAGAACCTGGACCCCTAT
GAGCAGTGGAGCGACCAGGAGATCTGGAAGGTTGCAGATGAAGTTGGCCTGCGGAG
TGTGATAGAACAATTTCCTGGCAAGCTGGATTTTGTGCTGGTAGATGGAGGCTGCGT
GCTGTCCCACGGCCACAAACAGCTGATGTGCCTCGCCCGCTCCGTTCTTTCAAAGGC
CAAAATCTTGCTTTTGGATGAGCCCAGTGCTCACCTTGACCCAGTGACCTATCAGAT
AATCCGCAGGACCTTAAAGCAAGCTTTTGCCGACTGCACCGTCATACTGTGTGAGCA
CCGGATTGAAGCAATGCTGGAATGCCAGCAGTTTCTGGTGATCGAGGAGAATAAGG
TCCGGCAGTACGACAGCATCCAGAAGTTGTTGAATGAGCGCAGCCTTTTCCGCCAGG
CCATCTCCCCATCTGACAGAGTCAAGCTGTTTCCACATAGGAACTCCTCTAAGTGCA
AGTCCAAGCCCCAGATCGCTGCCCTCAAGGAGGAAACTGAGGAAGAGGTGCAGGAT
ACCCGCCTGTGA (SEQ ID NO: 23)

ATGCAGAGGAGCCCACTGGAGAAAGCCTCCGTGGTGAGTAAACTCTTTTTTAGTTGG
ACCAGACCCATCCTGCGAAAAGGATACAGGCAGCGCCTCGAGTTGTCAGATATCTA
CCAGATTCCTTCTGTGGACTCAGCTGACAATTTGAGTGAGAAGCTGGAGCGGGAGTG
GGATAGAGAGCTGGCGAGCAAAAAAAACCCCAAGCTTATCAATGCTCTGCGCCGCT
GCTTTTTCTGGAGGTTCATGTTTTATGGGATCTTCCTGTACCTGGGGGAGGTCACCAA
AGCTGTTCAGCCGCTCCTTCTTGGCCGCATCATCGCCAGCTATGACCCTGATAATAA
AGAAGAAAGGTCTATTGCTATTTATCTGGGAATTGGCCTCTGCTTGCTCTTCATCGTC
CGCACCCTTCTGCTGCACCCTGCCATTTTTGGCCTTCACCACATCGGCATGCAAATG
AGAATTGCCATGTTCTCCCTCATTTACAAAAAGACCCTGAAACTTTCCTCAAGAGTG
TTAGATAAAATATCCATTGGTCAGCTGGTCAGCCTGCTGTCCAACAATCTTAACAAA
TTTGATGAAGGCTTGGCGCTGGCCCACTTCGTGTGGATTGCACCTCTGCAGGTGGCC
CTGTTGATGGGACTTATATGGGAGCTGCTTCAAGCCTCTGCTTTCTGTGGGCTGGGCT

-continued

TTTTGATTGTACTGGCACTTTTTCAGGCTGGGCTCGGAAGAATGATGATGAAATACA
GAGATCAGCGGGCCGGGAAGATATCAGAGCGACTTGTGATCACCAGTGAAATGATT
GAAAATATTCAGAGCGTGAAAGCCTACTGCTGGGAAGAAGCCATGGAGAAGATGAT
TGAGAACCTGAGGCAGACAGAGCTCAAGCTCACTCGGAAGGCTGCTTATGTTCGCT
ATTTCAACAGCAGCGCCTTCTTCTTCAGTGGCTTCTTTGTTGTCTTCCTGTCTGTTCTG
CCATATGCACTGATAAAAGGCATTATTTTACGAAAGATCTTCACCACCATCAGTTTT
TGCATCGTTCTCAGGATGGCCGTCACAAGACAGTTCCCCTGGGCTGTGCAGACCTGG
TACGATTCCTTGGGGGCCATCAACAAGATTCAAGATTTCTTGCAAAAACAAGAATAT
AAAACTTTAGAATACAACCTCACCACCACTGAAGTGGTCATGGAAAATGTGACAGC
CTTTTGGGAGGAGGGTTTTGGAGAATTGTTCGAGAAGGCAAAGCAGAATAACAACA
ACAGGAAGACGAGCAATGGGGACGACTCTCTCTTCTTCAGCAACTTTTCACTGCTCG
GGACCCCTGTGTTGAAAGATATAAACTTCAAGATCGAGAGGGGCCAGCTCTTGGCT
GTGGCAGGCTCCACTGGAGCTGGTAAAACATCTCTTCTCATGGTGATCATGGGGGAA
CTGGAGCCTTCCGAAGGAAAAATCAAGCACAGTGGGAGAATCTCATTCTGCAGCCA
GTTTTCCTGGATCATGCCCGGCACCATTAAGGAAAACATCATATTTGGAGTGTCCTA
TGATGAGTACCGCTACCGGTCAGTCATCAAAGCCTGTCAGTTGGAGGAGGACATCTC
CAAGTTTGCAGAGAAAGACAACATTGTGCTTGGAGAGGGGGGTATCACTCTTTCTGG
AGGACAAAGAGCCAGGATCTCTTTGGCCCGGGCAGTCTACAAGGATGCAGACCTCT
ACTTGTTGGACAGTCCCTTCGGCTACCTCGACGTGCTGACTGAAAAAGAAATTTTTG
AAAGCTGTGTGTGCAAACTGATGGCAAACAAGACCAGGATTCTTGTCACCAGCAAG
ATGGAACATCTGAAGAAAGCGGACAAAATTCTGATTCTGCATGAAGGGAGCTCCTA
CTTCTATGGAACATTTAGCGAGCTTCAGAACCTACAGCCAGACTTCTCCTCCAAATT
AATGGGCTGTGACTCCTTCGACCAGTTCTCTGCAGAAAGAAGAAACTCTATACTCAC
AGAGACCCTCCACCGCTTCTCCCTTGAGGGAGATGCCCCAGTTTCTTGGACAGAAAC
CAAGAAGCAGTCCTTTAAGCAGACTGGCGAGTTTGGTGAAAAGAGGAAAAATTCAA
TTCTCAATCCAATTAACAGTATTCGCAAGTTCAGCATTGTCCAGAAGACACCCCTCC
AGATGAATGGCATCGAAGAAGATAGTGACGAGCCGCTGGAGAGACGGCTGAGTCTG
GTGCCAGATTCAGAACAGGGGGAGGCCATCCTGCCCCGGATCAGCGTCATTTCCAC
AGGCCCCACATTACAAGCACGGCGCCGGCAGAGTGTTTTAAATCTCATGACCCATTC
AGTGAACCAGGGCCAAAATATCCACAGGAAGACTACAGCTTCTACCCGGAAAGTGT
CTCTGGCCCCTCAGGCCAATCTGACCGAGCTGGACATCTACAGCAGGAGGCTCTCCC
AGGAAACAGGGCTTGAAATATCTGAAGAGATTAATGAAGAGGATCTTAAAGAGTGC
TTCTTTGATGACATGGAGAGCATCCCCGCGGTGACCACATGGAACACCTACCTTAGA
TATATTACTGTCCACAAGAGCCTCATATTTGTCCTCATCTGGTGCCTGGTTATTTTCC
TCGCTGAGGTGGCGGCCAGTCTTGTTGTGCTCTGGCTGCTGGGCAACACTCCTCTCC
AGGACAAGGGCAATAGTACACACAGCAGAAATAATTCTTATGCCGTCATCATTACA
AGCACCTCCAGCTACTACGTGTTCTACATCTATGTGGGCGTGGCTGACACCCTCCTG
GCCATGGGTTTCTTCCGGGGCCTGCCTTTGGTGCACACCCTCATCACAGTGTCAAAA
ATTCTGCACCATAAAATGCTTCATTCTGTCCTGCAGGCACCCATGAGCACTTTGAAC
ACATTGAAGGCTGGCGGCATCCTCAACAGATTTTCTAAAGATATTGCTATCCTGGAT
GATCTCCTCCCCCTGACAATCTTTGACTTTATCCAGCTTCTGCTGATCGTGATTGGAG
CCATAGCAGTGGTTGCTGTCCTGCAGCCCTACATTTTTGTGGCCACCGTGCCCGTGAT
TGTTGCCTTTATTATGCTCAGAGCTTACTTCCTGCAAACTTCTCAACAGCTCAAACAG
CTAGAATCTGAGGGCCGGAGCCCCATTTTTACCCACCTGGTGACTTCCCTGAAGGGA
CTGTGGACTCTGAGAGCATTCGGGCGACAGCCTTACTTTGAGACACTGTTCCACAAG
GCCCTGAACTTGCACACTGCCAACTGGTTTCTTTACCTGAGCACACTCCGCTGGTTCC
AGATGCGGATAGAGATGATCTTCGTCATCTTTTTTATAGCTGTAACCTTCATTTCTAT
CCTTACAACAGGAGAAGGAGAGGGCAGGGTGGGAATCATCCTCACGCTGGCTATGA
ACATAATGTCCACCTTGCAGTGGGCCGTGAATTCCAGTATAGATGTGGATTCTCTAA
TGAGGAGTGTCTCCCGGGTGTTTAAATTCATTGATATGCCTACTGAGGGGAAACCCA
CCAAGTCAACAAAACCTTATAAGAATGGACAGCTGAGCAAGGTGATGATAATTGAG
AACAGCCACGTGAAGAAGGATGACATTTGGCCCAGCGGGGGCCAGATGACTGTGAA
GGACCTGACGGCCAAGTACACCGAAGGTGGAAATGCCATTTTGGAAAACATCAGCT
TCTCAATCTCTCCTGGGCAGAGAGTTGGATTGCTGGGTCGCACGGGCAGCGGCAAAT
CAACCCTGCTCAGTGCCTTCCTTCGGCTCCTGAATACAGAAGGCGAAATCCAAATTG
ACGGGGTGAGCTGGGACAGCATCACCCTGCAGCAGTGGAGAAAAGCATTTGGGGTC
ATTCCACAGAAAGTTTTCATCTTCTCTGGCACTTTCAGAAAGAACCTGGACCCCTAT
GAGCAGTGGAGCGACCAGGAGATCTGGAAGGTTGCAGATGAAGTTGGCCTGCGGAG
TGTGATAGAACAATTTCCTGGCAAGCTGGATTTTGTGCTGGTAGATGGAGGCTGCGT
GCTGTCCCACGGCCACAAACAGCTGATGTGCCTCGCCCGCTCCGTTCTTTCAAAGGC
CAAAATCTTGCTTTTGGATGAGCCCAGTGCTCACCTTGACCCAGTGACCTATCAGAT
AATCCGCAGGACCTTAAAGCAAGCTTTTGCCGACTGCACCGTCATACTGTGTGAGCA
CCGGATTGAAGCAATGCTGGAATGCCAGCAGTTTCTGGTGATCGAGGAGAATAAGG
TCCGGCAGTACGACAGCATCCAGAAGTTGTTGAATGAGCGCAGCCTTTTCCGCCAGG
CCATCTCCCCATCTGACAGAGTCAAGCTGTTTCCACATAGGAACTCCTCTAAGTGCA
AGTCCAAGCCCCAGATCGCTGCCCTCAAGGAGGAAACTGAGGAAGAGGTGCAGGAT
ACCCGCCTGTGA (SEQ ID NO: 24)

ATGCAGAGGAGCCCACTGGAGAAAGCCTCCGTGGTGAGTAAACTCTTTTTTAGTTGG
ACCAGACCCATCCTGCGAAAAGGATACAGGCAGCGCCTCGAGTTGTCAGATATCTA
CCAGATTCCTTCTGTGGACTCAGCTGACAATTTGAGTGAGAAGCTGGAGCGGGAGTG
GGATAGAGAGCTGGCGAGCAAAAAAAACCCCAAGCTTATCAATGCTCTGCGCCGCT
GCTTTTTCTGGAGGTTCATGTTTTATGGGATCTTCCTGTACCTGGGGGAGGTCACCAA
AGCTGTTCAGCCGCTCCTTCTTGGCCGCATCATCGCCAGCTATGACCCTGATAATAA
AGAAGAAAGGTCTATTGCTATTTATCTGGGAATTGGCCTCTGCTTGCTCTTCATCGTC
CGCACCCTTCTGCTGCACCCTGCCATTTTTGGCCTTCACCACATCGGCATGCAAATG
AGAATTGCCATGTTCTCCCTCATTTACAAAAAGACCCTGAAACTTTCCTCAAGAGTG
TTAGATAAAATATCCATTGGTCAGCTGGTCAGCCTGCTGTCCAACAATCTTAACAAA
TTTGATGAAGGCTTGGCGCTGGCCCACTTCGTGTGGATTGCACCTCTGCAGGTGGCC
CTGTTGATGGGACTTATATGGGAGCTGCTTCAAGCCTCTGCTTTCTGTGGGCTGGGCT

-continued

TTTTGATTGTACTGGCACTTTTTCAGGCTGGGCTCGGAAGAATGATGATGAAATACA
GAGATCAGCGGGCCGGGAAGATATCAGAGCGACTTGTGATCACCAGTGAAATGATT
GAAAATATTCAGAGCGTGAAAGCCTACTGCTGGGAAGAAGCCATGGAGAAGATGAT
TGAGAACCTGAGGCAGACAGAGCTCAAGCTCACTCGGAAGGCTGCTTATGTTCGCT
ATTTCAACAGCAGCGCCTTCTTCTTCAGTGGCTTCTTTGTTGTCTTCCTGTCTGTTCTG
CCATATGCACTGATAAAAGGCATTATTTTACGAAAGATCTTCACCACCATCAGTTTT
TGCATCGTTCTCAGGATGGCCGTCACAAGACAGTTCCCCTGGGCTGTGCAGACCTGG
TACGATTCCTTGGGGGCCATCAACAAGATTCAAGATTTCTTGCAAAAACAAGAATAT
AAAACTTTAGAATACAACCTCACCACCACTGAAGTGGTCATGGAAAATGTGACAGC
CTTTTGGGAGGAGGGTTTTGGAGAATTGTTCGAGAAGGCAAAGCAGAATAACAACA
ACAGGAAGACGAGCAATGGGGACGACTCTCTCTTCTTCAGCAACTTTTCACTGCTCG
GGACCCCTGTGTTGAAAGATATAAACTTCAAGATCGAGAGGGGCCAGCTCTTGGCT
GTGGCAGGCTCCACTGGAGCTGGTAAAACATCTCTTCTCATGGTGATCATGGGGGAA
CTGGAGCCTTCCGAAGGAAAAATCAAGCACAGTGGGAGAATCTCATTCTGCAGCCA
GTTTTCCTGGATCATGCCCGGCACCATTAAGGAAAACATCATATTTGGAGTGTCCTA
TGATGAGTACCGCTACCGGTCAGTCATCAAAGCCTGTCAGTTGGAGGAGGACATCTC
CAAGTTTGCAGAGAAAGACAACATTGTGCTTGGAGAGGGGGGTATCACTCTTTCTGG
AGGACAAAGAGCCAGGATCTCTTTGGCCCGGGCAGTCTACAAGGATGCAGACCTCT
ACTTGTTGGACAGTCCCTTCGGCTACCTCGACGTGCTGACTGAAAAAGAAATTTTTG
AAAGCTGTGTGTGCAAACTGATGGCAAACAAGACCAGGATTCTTGTCACCAGCAAG
ATGGAACATCTGAAGAAAGCGGACAAAATTCTGATTCTGCATGAAGGGAGCTCCTA
CTTCTATGGAACATTTAGCGAGCTTCAGAACCTACAGCCAGACTTCTCCTCCAAATT
AATGGGCTGTGACTCCTTCGACCAGTTCTCTGCAGAAAGAAGAAACTCTATACTCAC
AGAGACCCTCCACCGCTTCTCCCTTGAGGGAGATGCCCCAGTTTCTTGGACAGAAAC
CAAGAAGCAGTCCTTTAAGCAGACTGGCGAGTTTGGTGAAAAGAGGAAAAATTCAA
TTCTCAATCCAATTAACAGTATTCGCAAGTTCAGCATTGTCCAGAAGACACCCCTCC
AGATGAATGGCATCGAAGAAGATAGTGACGAGCCGCTGGAGAGACGGCTGAGTCTG
GTGCCAGATTCAGAACAGGGGGAGGCCATCCTGCCCCGGATCAGCGTCATTTCCAC
AGGCCCCACATTACAAGCACGGCGCCGGCAGAGTGTTTTAAATCTCATGACCCATTC
AGTGAACCAGGGCCAAAATATCCACAGGAAGACTACAGCTTCTACCCGGAAAGTGT
CTCTGGCCCCTCAGGCCAATCTGACCGAGCTGGACATCTACAGCAGGAGGCTCTCCC
AGGAAACAGGGCTGGAAATATCTGAAGAGATTAATGAAGAGGATCTTAAAGAGTGC
TTCTTTGATGACATGGAGAGCATCCCCGCGGTGACCACATGGAACACCTACCTTAGA
TATATTACTGTCCACAAGAGCCTCATATTTGTCCTCATCTGGTGCCTGGTTATTTTCC
TCGCTGAGGTGGCGGCCAGTCTTGTTGTGCTCTGGCTGCTGGGCAACACTCCTCTCC
AGGACAAGGGCAATAGTACTCACAGCAGAAATAATTCTTATGCCGTCATCATTACA
AGCACCTCCAGCTACTACGTGTTCTACATCTATGTGGGCGTGGCTGACACCCTCCTG
GCCATGGGTTTCTTCCGGGGCCTGCCTTTGGTGCACACCCTCATCACAGTGTCAAAA
ATTCTGCACCATAAAATGCTTCATTCTGTCCTGCAGGCACCCATGAGCACTTTGAAC
ACATTGAAGGCTGGCGGCATCCTCAACAGATTTTCTAAAGATATTGCTATCCTGGAT
GATCTCCTCCCCCTGACAATCTTTGACTTTATCCAGCTTCTGCTGATCGTGATTGGAG
CCATAGCAGTGGTTGCTGTCCTGCAGCCCTACATTTTTGTGGCCACCGTGCCCGTGAT
TGTTGCCTTTATTATGCTCAGAGCTTACTTCCTGCAAACTTCTCAACAGCTCAAACAG
CTAGAATCTGAGGGCCGGAGCCCCATTTTTACCCACCTGGTGACTTCCCTGAAGGGA
CTGTGGACTCTGAGAGCATTCGGGCGACAGCCTTACTTTGAGACACTGTTCCACAAG
GCCCTGAACTTGCACACTGCCAACTGGTTTCTTTACCTGAGCACACTCCGCTGGTTCC
AGATGCGGATAGAGATGATCTTCGTCATCTTTTTTATAGCTGTAACCTTCATTTCTAT
CCTTACAACAGGAGAAGGAGAGGGCAGGGTGGGAATCATCCTCACGCTGGCTATGA
ACATAATGTCCACCTTGCAGTGGGCCGTGAATTCCAGTATAGATGTGGATTCTCTAA
TGAGGAGTGTCTCCCGGGTGTTTAAATTCATTGATATGCCAACTGAGGGGAAACCCA
CCAAGTCAACAAAACCTTATAAGAATGGACAGCTGAGCAAGGTGATGATAATTGAG
AACAGCCACGTGAAGAAGGATGACATTTGGCCCAGCGGGGGCCAGATGACTGTGAA
GGACCTGACGGCCAAGTACACCGAAGGTGGAAATGCCATTTTGGAAAACATCAGCT
TCTCAATCTCTCCTGGGCAGAGAGTTGGATTGCTGGGTCGCACGGGCAGCGGCAAAT
CAACCCTGCTCAGTGCCTTCCTTCGGCTCCTGAATACAGAAGGCGAAATCCAAATTG
ACGGGGTGAGCTGGGACAGCATCACCCTGCAGCAGTGGAGAAAAGCATTTGGGGTC
ATTCCACAGAAAGTTTTCATCTTCTCTGGCACTTTCAGAAAGAACCTGGACCCCTAT
GAGCAGTGGAGCGACCAGGAGATCTGGAAGGTTGCAGATGAAGTTGGCCTGCGGAG
TGTGATAGAACAATTTCCTGGCAAGCTGGATTTTGTGCTGGTAGATGGAGGCTGCGT
GCTGTCCCACGGCCACAAACAGCTGATGTGCCTCGCCCGCTCCGTTCTTTCAAAGGC
CAAAATCTTGCTTTTGGATGAGCCCAGTGCTCACCTCGACCCAGTGACCTATCAGAT
AATCCGCAGGACCTTAAAGCAAGCTTTTGCCGACTGCACCGTCATACTGTGTGAGCA
CCGGATTGAAGCAATGCTGGAATGCCAGCAGTTTCTGGTGATCGAGGAGAATAAGG
TCCGGCAGTACGACAGCATCCAGAAGTTGTTGAATGAGCGCAGCCTTTTCCGCCAGG
CCATCTCCCCATCTGACAGAGTCAAGCTGTTTCCACATAGGAACTCCTCTAAGTGCA
AGTCCAAGCCCCAGATCGCTGCCCTCAAGGAGGAAACTGAGGAAGAGGTGCAGGAT
ACCCGCCTGTGA (SEQ ID NO: 25)

ATGCAGAGGAGCCCACTGGAGAAAGCCTCCGTGGTGAGTAAACTCTTTTTTAGTTGG
ACCAGACCCATCCTGCGAAAAGGATACAGGCAGCGCCTCGAGTTGTCAGATATCTA
CCAGATTCCTTCTGTGGACTCAGCTGACAATTTGAGTGAGAAGCTGGAGCGGGAGTG
GGATAGAGAGCTGGCGAGCAAAAAAAACCCCAAGCTTATCAATGCTCTGCGCCGCT
GCTTTTTCTGGAGGTTCATGTTTTATGGGATCTTCCTGTACCTGGGGGAGGTCACCAA
AGCTGTTCAGCCGCTCCTTCTTGGCCGCATCATCGCCAGCTATGACCCTGATAATAA
AGAAGAAAGGTCTATTGCTATTTATCTGGGAATTGGCCTCTGCTTGCTCTTCATCGTC
CGCACCCTTCTGCTGCACCCTGCCATTTTTGGCCTTCACCACATCGGCATGCAAATG
AGAATTGCCATGTTCTCCCTCATTTACAAAAAGACCCTGAAACTTTCCTCAAGAGTG
TTAGATAAAATATCCATTGGTCAGCTGGTCAGCCTGCTGTCCAACAATCTTAACAAA
TTTGATGAAGGCTTGGCGCTGGCCCACTTCGTGTGGATTGCACCTCTGCAGGTGGCC
CTGTTGATGGGACTTATATGGGAGCTGCTTCAAGCCTCTGCTTTCTGTGGGCTGGGCT

-continued

TTTTGATTGTACTGGCACTTTTTCAGGCTGGGCTCGGAAGAATGATGATGAAATACA
GAGATCAGCGGGCCGGGAAGATATCAGAGCGACTTGTGATCACCAGTGAAATGATT
GAAAATATTCAGAGCGTGAAAGCCTACTGCTGGGAAGAAGCCATGGAGAAGATGAT
TGAGAACCTGAGGCAGACAGAGCTCAAGCTCACTCGGAAGGCTGCTTATGTTCGCT
ATTTCAACAGCAGCGCCTTCTTCTTCAGTGGCTTCTTTGTTGTCTTCCTGTCTGTTCTG
CCATATGCACTGATAAAAGGCATTATTTTACGAAAGATCTTCACCACCATCAGTTTT
TGCATCGTTCTCAGGATGGCCGTCACAAGACAGTTCCCCTGGGCTGTGCAGACCTGG
TACGATTCCTTGGGGGCCATCAACAAGATTCAAGATTTCTTGCAAAAACAAGAATAT
AAAACTTTAGAATACAACCTCACCACCACTGAAGTGGTCATGGAAAATGTGACAGC
CTTTTGGGAGGAGGGTTTTGGAGAATTGTTCGAGAAGGCAAAGCAGAATAACAACA
ACAGGAAGACGAGCAATGGGGACGACTCTCTCTTCTTCAGCAACTTTTCACTGCTCG
GGACCCCTGTGTTGAAAGATATAAACTTCAAGATCGAGAGGGGCCAGCTCTTGGCT
GTGGCAGGCTCCACTGGAGCTGGTAAAACATCTCTTCTCATGGTGATCATGGGGGAA
CTGGAGCCTTCCGAAGGAAAAATCAAGCACAGTGGGAGAATCTCATTCTGCAGCCA
GTTTTCCTGGATCATGCCCGGCACCATTAAGGAAAACATCATATTTGGAGTGTCCTA
TGATGAGTACCGCTACCGGTCAGTCATCAAAGCCTGTCAGTTGGAGGAGGACATCTC
CAAGTTTGCAGAGAAAGACAACATTGTGCTTGGAGAGGGGGGTATCACTCTTTCTGG
AGGACAAAGAGCCAGGATCTCTTTGGCCCGGGCAGTCTACAAGGATGCAGACCTCT
ACTTGTTGGACAGTCCCTTCGGCTACCTCGACGTGCTGACTGAAAAAGAAATTTTTG
AAAGCTGTGTGTGCAAACTGATGGCAAACAAGACCAGGATTCTTGTCACCAGCAAG
ATGGAACATCTGAAGAAAGCGGACAAAATTCTGATTCTGCATGAAGGGAGCTCCTA
CTTCTATGGAACATTTAGCGAGCTTCAGAACCTACAGCCAGACTTCTCCTCCAAATT
AATGGGCTGTGACTCCTTCGACCAGTTCTCTGCAGAAAGAAGAAACTCTATACTCAC
AGAGACCCTCCACCGCTTCTCCCTTGAGGGAGATGCCCCAGTTTCTTGGACAGAAAC
CAAGAAGCAGTCCTTTAAGCAGACTGGCGAGTTTGGTGAAAAGAGGAAAAATTCAA
TTCTCAATCCTATTAACAGTATTCGCAAGTTCAGCATTGTCCAGAAGACACCCCTCC
AGATGAATGGCATCGAAGAAGATAGTGACGAGCCGCTGGAGAGACGGCTGAGTCTG
GTGCCAGATTCAGAACAGGGGGAGGCCATCCTGCCCCGGATCAGCGTCATTTCCAC
AGGCCCCACATTACAAGCACGGCGCCGGCAGAGTGTTTTAAATCTCATGACCCATTC
AGTGAACCAGGGCCAAAATATCCACAGGAAGACTACAGCTTCTACCCGGAAAGTGT
CTCTGGCCCCTCAGGCCAATCTGACCGAGCTGGACATCTACAGCAGGAGGCTCTCCC
AGGAAACAGGGCTTGAAATATCTGAAGAGATTAATGAAGAGGATCTTAAAGAGTGC
TTCTTTGATGACATGGAGAGCATCCCCGCGGTGACCACATGGAACACCTACCTTAGA
TATATTACTGTCCACAAGAGCCTCATATTTGTCCTCATCTGGTGCCTGGTTATTTTCC
TCGCTGAGGTGGCGGCCAGTCTTGTTGTGCTCTGGCTGCTGGGCAACACTCCTCTCC
AGGACAAGGGCAATAGTACTCACAGCAGAAATAATTCTTATGCCGTCATCATTACA
AGCACCTCCAGCTACTACGTGTTCTACATCTATGTGGGCGTGGCTGACACCCTCCTG
GCCATGGGTTTCTTCCGGGGCCTGCCTTTGGTGCACACCCTCATCACAGTGTCAAAA
ATTCTGCACCATAAAATGCTTCATTCTGTCCTGCAGGCACCCATGAGCACTTTGAAC
ACATTGAAGGCTGGCGGCATCCTCAACAGATTTTCTAAAGATATTGCTATCCTGGAT
GATCTCCTCCCCCTGACAATCTTTGACTTTATCCAGCTTCTGCTGATCGTGATTGGAG
CCATAGCAGTGGTTGCTGTCCTGCAGCCCTACATTTTTGTGGCCACCGTGCCCGTGAT
TGTTGCCTTTATTATGCTCAGAGCTTACTTCCTGCAAACTTCTCAACAGCTCAAACAG
CTAGAATCTGAGGGCCGGAGCCCCATTTTTACCCACCTGGTGACTTCCCTGAAGGGA
CTGTGGACTCTGAGAGCATTCGGGCGACAGCCTTACTTTGAGACACTGTTCCACAAG
GCCCTGAACTTGCACACTGCCAACTGGTTTCTTTACCTGAGCACACTCCGCTGGTTCC
AGATGCGGATAGAGATGATCTTCGTCATCTTTTTTATAGCTGTAACCTTCATTTCTAT
CCTTACAACAGGAGAAGGAGAGGGCAGGGTGGGAATCATCCTCACGCTGGCTATGA
ACATAATGTCCACCTTGCAGTGGGCCGTGAATTCCAGTATAGATGTGGATTCTCTAA
TGAGGAGTGTCTCCCGGGTGTTTAAATTCATTGATATGCCTACTGAGGGGAAACCCA
CCAAGTCAACAAAACCTTATAAGAATGGACAGCTGAGCAAGGTGATGATAATTGAG
AACAGCCACGTGAAGAAGGATGACATTTGGCCCAGCGGGGGCCAGATGACTGTGAA
GGACCTGACGGCCAAGTACACCGAAGGTGGAAATGCCATTTTGGAAAACATCAGCT
TCTCAATCTCTCCTGGGCAGAGAGTTGGATTGCTGGGTCGCACGGGCAGCGGCAAAT
CAACCCTGCTCAGTGCCTTCCTTCGGCTCCTGAATACAGAAGGCGAAATCCAAATTG
ACGGGGTGAGCTGGGACAGCATCACCCTGCAGCAGTGGAGAAAAGCATTTGGGGTC
ATTCCACAGAAAGTTTTCATCTTCTCTGGCACTTTCAGAAAGAACCTGGACCCCTAT
GAGCAGTGGAGCGACCAGGAGATCTGGAAGGTTGCAGATGAAGTTGGCCTGCGGAG
TGTGATAGAACAATTTCCTGGCAAGCTGGATTTTGTGCTGGTAGATGGAGGCTGCGT
GCTGTCCCACGGCCACAAACAGCTGATGTGCCTCGCCCGCTCCGTTCTTTCAAAGGC
CAAAATCTTGCTTTTGGATGAGCCCAGTGCTCACCTCGACCCAGTGACCTATCAGAT
AATCCGCAGGACCTTAAAGCAAGCTTTTGCCGACTGCACCGTCATACTGTGTGAGCA
CCGGATTGAAGCAATGCTGGAATGCCAGCAGTTTCTGGTGATCGAGGAGAATAAGG
TCCGGCAGTACGACAGCATCCAGAAGTTGTTGAATGAGCGCAGCCTTTTCCGCCAGG
CCATCTCCCCATCTGACAGAGTCAAGCTGTTTCCACATAGGAACTCCTCTAAGTGCA
AGTCCAAGCCCCAGATCGCTGCCCTCAAGGAGGAAACTGAGGAAGAGGTGCAGGAT
ACCCGCCTGTGA (SEQ ID NO: 26)

ATGCAGAGGAGCCCACTGGAGAAAGCCTCCGTGGTGAGTAAACTCTTTTTTAGTTGG
ACCAGACCCATCCTGCGAAAAGGATACAGGCAGCGCCTCGAGTTGTCAGATATCTA
CCAGATTCCTTCTGTGGACTCAGCTGACAATTTGAGTGAGAAGCTGGAGCGGGAGTG
GGATAGAGAGCTGGCGAGCAAAAAAAACCCCAAGCTTATCAATGCTCTGCGCCGCT
GCTTTTTCTGGAGGTTCATGTTTTATGGGATCTTCCTGTACCTGGGGGAGGTCACCAA
AGCTGTTCAGCCGCTCCTTCTTGGCCGCATCATCGCCAGCTATGACCCTGATAATAA
AGAAGAAAGGTCTATTGCTATTTATCTGGGAATTGGCCTCTGCTTGCTCTTCATCGTC
CGCACCCTTCTGCTGCACCCTGCCATTTTTGGCCTTCACCACATCGGCATGCAAATG
AGAATTGCCATGTTCTCCCTCATTTACAAAAAGACCCTGAAACTTTCCTCAAGAGTG
TTAGATAAAATATCCATTGGTCAGCTGGTCAGCCTGCTGTCCAACAATCTTAACAAA
TTTGATGAAGGCTTGGCGCTGGCCCACTTCGTGTGGATTGCACCTCTGCAGGTGGCC
CTGTTGATGGGACTTATATGGGAGCTGCTTCAAGCCTCTGCTTTCTGTGGGCTGGGCT

-continued

TTTTGATTGTACTGGCACTTTTTCAGGCTGGGCTCGGAAGAATGATGATGAAATACA
GAGATCAGCGGGCCGGGAAGATTTCAGAGCGACTTGTGATCACCAGTGAAATGATT
GAAAATATTCAGAGCGTGAAAGCCTACTGCTGGGAAGAAGCCATGGAGAAGATGAT
TGAGAACCTGAGGCAGACAGAGCTCAAGCTCACTCGGAAGGCTGCTTATGTTCGCT
ATTTCAACAGCAGCGCCTTCTTCTTCAGTGGCTTCTTTGTTGTCTTCCTGTCTGTTCTG
CCATATGCACTGATAAAAGGCATTATTTTACGAAAGATCTTCACCACCATCAGTTTT
TGCATCGTTCTCAGGATGGCCGTCACAAGACAGTTCCCCTGGGCTGTGCAGACCTGG
TACGATTCCTTGGGGGCCATCAACAAGATTCAAGATTTCTTGCAAAAACAAGAATAT
AAAACTTTAGAATACAACCTCACCACCACTGAAGTGGTCATGGAAAATGTGACAGC
CTTTTGGGAGGAGGGTTTTGGAGAATTGTTCGAGAAGGCAAAGCAGAATAACAACA
ACAGGAAGACGAGCAATGGGGACGACTCTCTCTTCTTCAGCAACTTTTCACTGCTCG
GGACCCCTGTGTTGAAAGATATAAACTTCAAGATCGAGAGGGGCCAGCTCTTGGCT
GTGGCAGGCTCCACTGGAGCTGGTAAAACATCTCTTCTCATGGTGATCATGGGGGAA
CTGGAGCCTTCCGAAGGAAAAATCAAGCACAGTGGGAGAATCTCATTCTGCAGCCA
GTTTTCCTGGATCATGCCCGGCACCATTAAGGAAAACATCATATTTGGAGTGTCCTA
TGATGAGTACCGCTACCGGTCAGTCATCAAAGCCTGTCAGTTGGAGGAGGACATCTC
CAAGTTTGCAGAGAAAGACAACATTGTGCTTGGAGAGGGGGGTATCACTCTTTCTGG
AGGACAAAGAGCCAGGATCTCTTTGGCCCGGGCAGTCTACAAGGATGCAGACCTCT
ACTTGTTGGACAGTCCCTTCGGCTACCTCGACGTGCTGACTGAAAAAGAAATTTTTG
AAAGCTGTGTGTGCAAACTGATGGCAAACAAGACCAGGATTCTTGTCACCAGCAAG
ATGGAACATCTGAAGAAAGCGGACAAAATTCTGATTCTGCATGAAGGGAGCTCCTA
CTTCTATGGAACATTTAGCGAGCTTCAGAACCTACAGCCAGACTTCTCCTCCAAATT
AATGGGCTGTGACTCCTTCGACCAGTTCTCTGCAGAAAGAAGAAACTCTATACTCAC
AGAGACCCTCCACCGCTTCTCCCTTGAGGGAGATGCCCCAGTTTCTTGGACAGAAAC
CAAGAAGCAGTCCTTTAAGCAGACTGGCGAGTTTGGTGAAAAGAGGAAAAATTCAA
TTCTCAATCCAATTAACAGTATTCGCAAGTTCAGCATTGTCCAGAAGACACCCCTCC
AGATGAATGGCATCGAAGAAGATAGTGACGAGCCGCTGGAGAGACGGCTGAGTCTG
GTGCCAGATTCAGAACAGGGGGAGGCCATCCTGCCCCGGATCAGCGTCATTTCCAC
AGGCCCCACATTACAAGCACGGCGCCGGCAGAGTGTTTTAAATCTCATGACCCATTC
AGTGAACCAGGGCCAAAATATCCACAGGAAGACTACAGCTTCTACCCGGAAAGTGT
CTCTGGCCCCTCAGGCCAATCTGACCGAGCTGGACATCTACAGCAGGAGGCTCTCCC
AGGAAACAGGGCTGGAAATATCTGAAGAGATTAATGAAGAGGATCTTAAAGAGTGC
TTCTTTGATGACATGGAGAGCATCCCCGCGGTGACCACATGGAACACCTACCTTAGA
TATATTACTGTCCACAAGAGCCTCATATTTGTCCTCATCTGGTGCCTGGTTATTTTCC
TCGCTGAGGTGGCGGCCAGTCTTGTTGTGCTCTGGCTGCTGGGCAACACTCCTCTCC
AGGACAAGGGCAATAGTACTCACAGCAGAAATAATTCTTATGCCGTCATCATTACA
AGCACCTCCAGCTACTACGTGTTCTACATCTATGTGGGCGTGGCTGACACCCTCCTG
GCCATGGGTTTCTTCCGGGGCCTGCCTTTGGTGCACACCCTCATCACAGTGTCAAAA
ATTCTGCACCATAAAATGCTTCATTCTGTCCTGCAGGCACCCATGAGCACTTTGAAC
ACATTGAAGGCTGGCGGCATCCTCAACAGATTTTCTAAAGATATTGCTATCCTGGAT
GATCTCCTCCCCCTGACAATCTTTGACTTTATCCAGCTTCTGCTGATCGTGATTGGAG
CCATAGCAGTGGTTGCTGTCCTGCAGCCCTACATTTTTGTGGCCACCGTGCCCGTGAT
TGTTGCCTTTATTATGCTCAGAGCTTACTTCCTGCAAACTTCTCAACAGCTCAAACAG
CTAGAATCTGAGGGCCGGAGCCCCATTTTTACCCACCTGGTGACTTCCCTGAAGGGA
CTGTGGACTCTGAGAGCATTCGGGCGACAGCCTTACTTTGAGACACTGTTCCACAAG
GCCCTGAACTTGCACACTGCCAACTGGTTTCTTTACCTGAGCACACTCCGCTGGTTCC
AGATGCGGATAGAGATGATCTTCGTCATCTTTTTTATAGCTGTAACCTTCATTTCTAT
CCTTACAACAGGAGAAGGAGAGGGCAGGGTGGGAATCATCCTCACGCTGGCTATGA
ACATAATGTCCACCTTGCAGTGGGCCGTGAATTCCAGTATAGATGTGGATTCTCTAA
TGAGGAGTGTCTCCCGGGTGTTTAAATTCATTGATATGCCAACTGAGGGGAAACCCA
CCAAGTCAACAAAACCTTATAAGAATGGACAGCTGAGCAAGGTGATGATAATTGAG
AACAGCCACGTGAAGAAGGATGACATTTGGCCCAGCGGGGGCCAGATGACTGTGAA
GGACCTGACGGCCAAGTACACCGAAGGTGGAAATGCCATTTTGGAAAACATCAGCT
TCTCAATCTCTCCTGGGCAGAGAGTTGGATTGCTGGGTCGCACGGGCAGCGGCAAAT
CAACCCTGCTCAGTGCCTTCCTTCGGCTCCTGAATACAGAAGGCGAAATCCAAATTG
ACGGGGTGAGCTGGGACAGCATCACCCTGCAGCAGTGGAGAAAAGCATTTGGGGTC
ATTCCACAGAAAGTTTTCATCTTCTCTGGCACTTTCAGAAAGAACCTGGACCCCTAT
GAGCAGTGGAGCGACCAGGAGATCTGGAAGGTTGCAGATGAAGTTGGCCTGCGGAG
TGTGATAGAACAATTTCCTGGCAAGCTGGATTTTGTGCTGGTAGATGGAGGCTGCGT
GCTGTCCCACGGCCACAAACAGCTGATGTGCCTCGCCCGCTCCGTTCTTTCAAAGGC
CAAAATCTTGCTTTTGGATGAGCCCAGTGCTCACCTCGACCCAGTGACCTATCAGAT
AATCCGCAGGACCTTAAAGCAAGCTTTTGCCGACTGCACCGTCATACTGTGTGAGCA
CCGGATTGAAGCAATGCTGGAATGCCAGCAGTTTCTGGTGATCGAGGAGAATAAGG
TCCGGCAGTACGACAGCATCCAGAAGTTGTTGAATGAGCGCAGCCTTTTCCGCCAGG
CCATCTCCCCATCTGACAGAGTCAAGCTGTTTCCACATAGGAACTCCTCTAAGTGCA
AGTCCAAGCCCCAGATCGCTGCCCTCAAGGAGGAAACTGAGGAAGAGGTGCAGGAT
ACCCGCCTGTGA (SEQ ID NO: 27)

ATGCAGAGGAGCCCACTGGAGAAAGCCTCCGTGGTGAGTAAACTCTTTTTTAGTTGG
ACCAGACCCATCCTGCGAAAAGGATACAGGCAGCGCCTCGAGTTGTCTGATATCTA
CCAGATTCCTTCTGTGGACTCAGCTGACAATTTGAGTGAGAAGCTGGAGCGGGAGTG
GGATAGAGAGCTGGCGAGCAAAAAAAACCCCAAGCTTATCAATGCTCTGCGCCGCT
GCTTTTTCTGGAGGTTCATGTTTTATGGGATCTTCCTGTACCTGGGGGAGGTCACCAA
AGCTGTTCAGCCGCTCCTTCTTGGCCGCATCATCGCCAGCTATGACCCTGATAATAA
AGAAGAAAGGTCTATTGCTATTTATCTGGGAATTGGCCTCTGCTTGCTCTTCATCGTC
CGCACCCTTCTGCTGCACCCTGCCATTTTTGGCCTTCACCACATCGGCATGCAAATG
AGAATTGCCATGTTCTCCCTCATTTACAAAAAGACCCTGAAACTTTCCTCAAGAGTG
TTAGATAAAATATCCATTGGTCAGCTGGTCAGCCTGCTGTCCAACAATCTTAACAAA
TTTGATGAAGGCTTGGCGCTGGCCCACTTCGTGTGGATTGCACCTCTGCAGGTGGCC
CTGTTGATGGGACTTATATGGGAGCTGCTTCAAGCCTCTGCTTTCTGTGGGCTGGGCT

-continued

TTTTGATTGTACTGGCACTTTTTCAGGCTGGGCTCGGAAGAATGATGATGAAATACA
GAGATCAGCGGGCCGGGAAGATATCAGAGCGACTTGTGATCACCAGTGAAATGATT
GAAAATATTCAGAGCGTGAAAGCCTACTGCTGGGAAGAAGCCATGGAGAAGATGAT
TGAGAACCTGAGGCAGACAGAGCTCAAGCTCACTCGGAAGGCTGCTTATGTTCGCT
ATTTCAACAGCAGCGCCTTCTTCTTCAGTGGCTTCTTTGTTGTCTTCCTGTCTGTTCTG
CCATATGCACTGATAAAAGGCATTATTTTACGAAAGATCTTCACCACCATCAGTTTT
TGCATCGTTCTCAGGATGGCCGTCACAAGACAGTTCCCCTGGGCTGTGCAGACCTGG
TACGATTCCTTGGGGGCCATCAACAAGATTCAAGATTTCTTGCAAAAACAAGAATAT
AAAACTTTAGAATACAACCTCACCACCACTGAAGTGGTCATGGAAAATGTGACAGC
CTTTTGGGAGGAGGGTTTTGGAGAATTGTTCGAGAAGGCAAAGCAGAATAACAACA
ACAGGAAGACGAGCAATGGGGACGACTCTCTCTTCTTCAGCAACTTTTCACTGCTCG
GGACCCCTGTGTTGAAAGATATAAACTTCAAGATCGAGAGGGGCCAGCTCTTGGCT
GTGGCAGGCTCCACTGGAGCTGGTAAAACATCTCTTCTCATGGTGATCATGGGGGAA
CTGGAGCCTTCCGAAGGAAAAATCAAGCACAGTGGGAGAATCTCATTCTGCAGCCA
GTTTTCCTGGATCATGCCCGGCACCATTAAGGAAAACATCATATTTGGAGTGTCCTA
TGATGAGTACCGCTACCGGTCCGTCATCAAAGCCTGTCAGTTGGAGGAGGACATCTC
CAAGTTTGCAGAGAAAGACAACATTGTGCTTGGAGAGGGGGGTATCACTCTTTCTGG
AGGACAAAGAGCCAGGATCTCTTTGGCCCGGGCAGTCTACAAGGATGCAGACCTCT
ACTTGTTGGACAGTCCCTTCGGCTACCTCGACGTGCTGACTGAAAAAGAAATTTTTG
AAAGCTGTGTGTGCAAACTGATGGCAAACAAGACCAGGATTCTTGTCACCAGCAAG
ATGGAACATCTGAAGAAAGCGGACAAAATTCTGATTCTGCATGAAGGGAGCTCCTA
CTTCTATGGAACATTTAGCGAGCTTCAGAACCTACAGCCAGACTTCTCCTCCAAATT
AATGGGCTGTGACTCCTTCGACCAGTTCTCTGCAGAAAGAAGAAACTCTATACTCAC
AGAGACCCTCCACCGCTTCTCCCTTGAGGGAGATGCCCCAGTTTCTTGGACAGAAAC
CAAGAAGCAGTCCTTTAAGCAGACTGGCGAGTTTGGTGAAAAGAGGAAAAATTCAA
TTCTCAATCCAATTAACAGTATTCGCAAGTTCAGCATTGTCCAGAAGACACCCCTCC
AGATGAATGGCATCGAAGAAGATAGTGACGAGCCGCTGGAGAGACGGCTGAGTCTG
GTGCCAGATTCAGAACAGGGGGAGGCCATCCTGCCCCGGATCAGCGTCATTTCCAC
AGGCCCCACATTACAAGCACGGCGCCGGCAGAGTGTTTTAAATCTCATGACCCATTC
AGTGAACCAGGGCCAAAATATCCACAGGAAGACTACAGCTTCTACCCGGAAAGTGT
CTCTGGCCCCTCAGGCCAATCTGACCGAGCTGGACATCTACAGCAGGAGGCTCTCCC
AGGAAACAGGGCTTGAAATATCTGAAGAGATTAATGAAGAGGATCTTAAAGAGTGC
TTCTTTGATGACATGGAGAGCATCCCCGCGGTGACCACATGGAACACCTACCTTAGA
TATATTACTGTCCACAAGAGCCTCATATTTGTCCTCATCTGGTGCCTGGTTATTTTCC
TCGCTGAGGTGGCGGCCAGTCTTGTTGTGCTCTGGCTGCTGGGCAACACTCCTCTCC
AGGACAAGGGCAATAGTACTCACAGCAGAAATAATTCTTATGCCGTCATCATTACA
AGCACCTCCAGCTACTACGTGTTCTACATCTATGTGGGCGTGGCTGACACCCTCCTG
GCCATGGGTTTCTTCCGGGGCCTGCCTTTGGTGCACACCCTCATCACAGTGTCAAAA
ATTCTGCACCATAAAATGCTTCATTCTGTCCTGCAGGCACCCATGAGCACTTTGAAC
ACATTGAAGGCTGGCGGCATCCTCAACAGATTTTCTAAAGATATTGCTATCCTGGAT
GATCTCCTCCCCCTGACAATCTTTGACTTTATCCAGCTTCTGCTGATCGTGATTGGAG
CCATAGCAGTGGTTGCTGTCCTGCAGCCCTACATTTTTGTGGCCACCGTGCCCGTGAT
TGTTGCCTTTATTATGCTCAGAGCTTACTTCCTGCAAACTTCTCAACAGCTCAAACAG
CTAGAATCTGAGGGCCGGAGCCCCATTTTTACCCACCTGGTGACTTCCCTGAAGGGA
CTGTGGACTCTGAGAGCATTCGGGCGACAGCCTTACTTTGAGACACTGTTCCACAAG
GCCCTGAACTTGCACACTGCCAACTGGTTTCTTTACCTGAGCACACTCCGCTGGTTCC
AGATGCGGATAGAGATGATCTTCGTCATCTTTTTTATAGCTGTAACCTTCATTTCTAT
CCTTACAACAGGAGAAGGAGAGGGCAGGGTGGGAATCATCCTCACGCTGGCTATGA
ACATAATGTCCACCTTGCAGTGGGCCGTGAATTCCAGTATAGATGTGGATTCTCTAA
TGAGGAGTGTCTCCCGGGTGTTTAAATTCATTGATATGCCTACTGAGGGGAAACCCA
CCAAGTCAACAAAGCCTTATAAGAATGGACAGCTGAGCAAGGTGATGATAATTGAG
AACAGCCACGTGAAGAAGGATGACATTTGGCCCAGCGGGGGCCAGATGACTGTGAA
GGACCTGACGGCCAAGTACACCGAAGGTGGAAATGCCATTTTGGAAAACATCAGCT
TCTCAATCTCTCCTGGGCAGAGAGTTGGATTGCTGGGTCGCACGGGCAGCGGCAAAT
CAACCCTGCTCAGTGCCTTCCTTCGGCTCCTGAATACAGAAGGCGAAATCCAAATTG
ACGGGGTGAGCTGGGACAGCATCACCCTGCAGCAGTGGAGAAAAGCATTTGGGGTC
ATTCCACAGAAAGTTTTCATCTTCTCTGGCACTTTCAGAAAGAACCTGGACCCCTAT
GAGCAGTGGAGCGACCAGGAGATCTGGAAGGTTGCAGATGAAGTTGGCCTGCGGAG
TGTGATAGAACAATTTCCTGGCAAGCTGGATTTTGTGCTGGTAGATGGAGGCTGCGT
GCTGTCCCACGGCCACAAACAGCTGATGTGCCTCGCCCGCTCCGTTCTTTCAAAGGC
CAAAATCTTGCTTTTGGATGAGCCCAGTGCTCACCTCGACCCAGTGACCTATCAGAT
AATCCGCAGGACCTTAAAGCAAGCTTTTGCCGACTGCACCGTCATACTGTGTGAGCA
CCGGATTGAAGCAATGCTGGAATGCCAGCAGTTTCTGGTGATCGAGGAGAATAAGG
TCCGGCAGTACGACAGCATCCAGAAGTTGTTGAATGAGCGCAGCCTTTTCCGCCAGG
CCATCTCCCCATCTGACAGAGTCAAGCTGTTTCCACATAGGAACTCCTCTAAGTGCA
AGTCCAAGCCCCAGATCGCTGCCCTCAAGGAGGAAACTGAGGAAGAGGTGCAGGAT
ACCCGCCTGTGA (SEQ ID NO: 28)

ATGCAGAGGAGCCCACTGGAGAAAGCCTCCGTGGTGAGTAAACTCTTTTTTAGTTGG
ACCAGACCCATCCTGCGAAAAGGATACAGGCAGCGCCTCGAGTTGTCAGATATCTA
CCAGATTCCTTCTGTGGACTCAGCTGACAATTTGAGTGAGAAGCTGGAGCGGGAGTG
GGATAGAGAGCTGGCGAGCAAAAAAAACCCCAAGCTTATCAATGCTCTGCGCCGCT
GCTTTTTCTGGAGGTTCATGTTTTATGGGATCTTCCTGTACCTGGGGGAGGTCACCAA
AGCTGTTCAGCCGCTCCTTCTTGGCCGCATCATCGCCAGCTATGACCCTGATAATAA
AGAAGAAAGGTCTATTGCTATTTATCTGGGAATTGGCCTCTGCTTGCTCTTCATCGTC
CGCACCCTTCTGCTGCACCCTGCCATTTTTGGCCTTCACCACATCGGCATGCAAATG
AGAATTGCCATGTTCTCCCTCATTTACAAAAAGACCCTGAAACTTTCCTCAAGAGTG
TTAGATAAAATATCCATTGGTCAGCTGGTCAGCCTGCTGTCCAACAATCTTAACAAA
TTTGATGAAGGCTTGGCGCTGGCCCACTTCGTGTGGATTGCACCTCTGCAGGTGGCC
CTGTTGATGGGACTTATATGGGAGCTGCTTCAAGCCTCTGCTTTCTGTGGGCTGGGCT

-continued

TTTTGATTGTACTGGCACTTTTTCAGGCTGGGCTCGGAAGAATGATGATGAAATACA
GAGATCAGCGGGCCGGGAAGATATCAGAGCGACTTGTGATCACCAGTGAAATGATT
GAAAATATTCAGAGCGTGAAAGCCTACTGCTGGGAAGAAGCCATGGAGAAGATGAT
TGAGAACCTGAGGCAGACAGAGCTCAAGCTCACTCGGAAGGCTGCTTATGTTCGCT
ATTTCAACAGCAGCGCCTTCTTCTTCAGTGGCTTCTTTGTTGTCTTCCTGTCTGTTCTG
CCATATGCACTGATAAAAGGCATTATTTTACGAAAGATCTTCACCACCATCAGTTTT
TGCATCGTTCTCAGGATGGCCGTCACAAGACAGTTCCCCTGGGCTGTGCAGACCTGG
TACGATTCCTTGGGGGCCATCAACAAGATTCAAGATTTCTTGCAAAAACAAGAATAT
AAAACTTTAGAATACAACCTCACCACCACTGAAGTGGTCATGGAAAATGTGACAGC
CTTTTGGGAGGAGGGTTTTGGAGAATTGTTCGAGAAGGCAAAGCAGAATAACAACA
ACAGGAAGACGAGCAATGGGGACGACTCTCTCTTCTTCAGCAACTTTTCACTGCTCG
GGACCCCTGTGTTGAAAGATATAAACTTCAAGATCGAGAGGGGCCAGCTCTTGGCT
GTGGCAGGCTCCACTGGAGCTGGTAAAACATCTCTTCTCATGGTGATCATGGGGGAA
CTGGAGCCTTCCGAAGGAAAAATCAAGCACAGTGGGAGAATCTCATTCTGCAGCCA
GTTTTCCTGGATCATGCCCGGCACCATTAAGGAAAACATCATATTTGGAGTGTCCTA
TGATGAGTACCGCTACCGGTCAGTCATCAAAGCCTGTCAGTTGGAGGAGGACATCTC
CAAGTTTGCAGAGAAAGACAACATTGTGCTTGGAGAGGGGGGTATCACTCTTTCTGG
AGGACAAAGAGCCAGGATCTCTTTGGCCCGGGCAGTCTACAAGGATGCAGACCTCT
ACTTGTTGGACAGTCCCTTCGGCTACCTCGACGTGCTGACTGAAAAAGAAATTTTTG
AAAGCTGTGTGTGCAAACTGATGGCAAACAAGACCAGGATTCTTGTCACCAGCAAG
ATGGAACATCTGAAGAAAGCGGACAAAATTCTGATTCTGCATGAAGGGAGCTCCTA
CTTCTATGGAACATTTAGCGAGCTTCAGAACCTACAGCCAGACTTCTCCTCCAAATT
AATGGGCTGTGACTCCTTCGACCAGTTCTCTGCAGAAAGAAGAAACTCTATACTCAC
AGAGACCCTCCACCGCTTCTCCCTTGAGGGAGATGCCCCAGTTTCTTGGACAGAAAC
CAAGAAGCAGTCCTTTAAGCAGACTGGCGAGTTTGGTGAAAAGAGGAAAAATTCAA
TTCTCAATCCTATTAACAGTATTCGCAAGTTCAGCATTGTCCAGAAGACACCCCTCC
AGATGAATGGCATCGAAGAAGATAGTGACGAGCCGCTGGAGAGACGGCTGAGTCTG
GTGCCAGATTCAGAACAGGGGGAGGCCATCCTGCCCCGGATCAGCGTCATTTCCAC
AGGCCCCACATTACAAGCACGGCGCCGGCAGAGTGTTTTAAATCTCATGACCCATTC
AGTGAACCAGGGCCAAAATATCCACAGGAAGACTACAGCTTCTACCCGGAAAGTGT
CTCTGGCCCCTCAGGCCAATCTGACCGAGCTGGACATCTACAGCAGGAGGCTCTCCC
AGGAAACAGGGCTTGAAATATCTGAAGAGATTAATGAAGAGGATCTTAAAGAGTGC
TTCTTTGATGACATGGAGAGCATCCCCGCGGTGACCACATGGAACACCTACCTTAGA
TATATTACTGTCCACAAGAGCCTCATATTTGTCCTCATCTGGTGCCTGGTTATTTTCC
TCGCTGAGGTGGCGGCCAGTCTTGTTGTGCTCTGGCTGCTGGGCAACACTCCTCTCC
AGGACAAGGGCAATAGTACACACAGCAGAAATAATTCTTATGCCGTCATCATTACA
AGCACCTCCAGCTACTACGTGTTCTACATCTATGTGGGCGTGGCTGACACCCTCCTG
GCCATGGGTTTCTTCCGGGGCCTGCCTTTGGTGCACACCCTCATCACAGTGTCAAAA
ATTCTGCACCATAAAATGCTTCATTCTGTCCTGCAGGCACCCATGAGCACTTTGAAC
ACATTGAAGGCTGGCGGCATCCTCAACAGATTTTCTAAAGATATTGCTATCCTGGAT
GATCTCCTCCCCCTGACAATCTTTGACTTTATCCAGCTTCTGCTGATCGTGATTGGAG
CCATAGCAGTGGTTGCTGTCCTGCAGCCCTACATTTTTGTGGCCACCGTGCCCGTGAT
TGTTGCCTTTATTATGCTCAGAGCTTACTTCCTGCAAACTTCTCAACAGCTCAAACAG
CTAGAATCTGAGGGCCGGAGCCCCATTTTTACCCACCTGGTGACTTCCCTGAAGGGA
CTGTGGACTCTGAGAGCATTCGGGCGACAGCCTTACTTTGAGACACTGTTCCACAAG
GCCCTGAACTTGCACACTGCCAACTGGTTTCTTTACCTGAGCACACTCCGCTGGTTCC
AGATGCGGATAGAGATGATCTTCGTCATCTTTTTTATAGCTGTAACCTTCATTTCTAT
CCTTACAACAGGAGAAGGAGAGGGCAGGGTGGGAATCATCCTCACGCTGGCTATGA
ACATAATGTCCACCTTGCAGTGGGCCGTGAATTCCAGTATAGATGTGGATTCTCTAA
TGAGGAGTGTCTCCCGGGTGTTTAAATTCATTGATATGCCTACTGAGGGGAAACCCA
CCAAGTCAACAAAACCTTATAAGAATGGACAGCTGAGCAAGGTGATGATAATTGAG
AACAGCCACGTGAAGAAGGATGACATTTGGCCCAGCGGGGGCCAGATGACTGTGAA
GGACCTGACGGCCAAGTACACCGAAGGTGGAAATGCCATTTTGGAAAACATCAGCT
TCTCAATCTCTCCTGGGCAGAGAGTTGGATTGCTGGGTCGCACGGGCAGCGGCAAAT
CAACCCTGCTCAGTGCCTTCCTTCGGCTCCTGAATACAGAAGGCGAAATCCAAATTG
ACGGGGTGAGCTGGGACAGCATCACCCTGCAGCAGTGGAGAAAAGCATTTGGGGTC
ATTCCACAGAAAGTTTTCATCTTCTCTGGCACTTTCAGAAAGAACCTGGACCCCTAT
GAGCAGTGGAGCGACCAGGAGATCTGGAAGGTTGCAGATGAAGTTGGCCTGCGGAG
TGTGATAGAACAATTTCCTGGCAAGCTGGATTTTGTGCTGGTAGATGGAGGCTGCGT
GCTGTCCCACGGCCACAAACAGCTGATGTGCCTCGCCCGCTCCGTTCTTTCAAAGGC
CAAAATCTTGCTTTTGGATGAGCCCAGTGCTCACCTCGACCCAGTGACCTATCAGAT
AATCCGCAGGACCTTAAAGCAAGCTTTTGCCGACTGCACCGTCATACTGTGTGAGCA
CCGGATTGAAGCAATGCTGGAATGCCAGCAGTTTCTGGTGATCGAGGAGAATAAGG
TCCGGCAGTACGACAGCATCCAGAAGTTGTTGAATGAGCGCAGCCTTTTCCGCCAGG
CCATCTCCCCATCTGACAGAGTCAAGCTGTTTCCACATAGGAACTCCTCTAAGTGCA
AGTCCAAGCCCCAGATCGCTGCCCTCAAGGAGGAAACTGAGGAAGAGGTGCAGGAT
ACCCGCCTGTGA (SEQ ID NO: 29)

ATGCAGAGGAGCCCACTGGAGAAAGCCTCCGTGGTGAGTAAACTCTTTTTTAGTTGG
ACCAGACCCATCCTGCGAAAAGGATACAGGCAGCGCCTCGAGTTGTCAGATATCTA
CCAGATTCCTTCTGTGGACTCAGCTGACAATTTGAGTGAGAAGCTGGAGCGGGAGTG
GGATAGAGAGCTGGCGAGCAAAAAAAACCCCAAGCTTATCAATGCTCTGCGCCGCT
GCTTTTTCTGGAGGTTCATGTTTTATGGGATCTTCCTGTACCTGGGGGAGGTCACCAA
AGCTGTTCAGCCGCTCCTTCTTGGCCGCATCATCGCCAGCTATGACCCTGATAATAA
AGAAGAAAGGTCTATTGCTATTTATCTGGGAATTGGCCTCTGCTTGCTCTTCATCGTC
CGCACCCTTCTGCTGCACCCTGCCATTTTTGGCCTTCACCACATCGGCATGCAAATG
AGAATTGCCATGTTCTCCCTCATTTACAAAAAGACCCTGAAACTTTCCTCAAGAGTG
TTAGATAAAATATCCATTGGTCAGCTGGTCAGCCTGCTGTCCAACAATCTTAACAAA
TTTGATGAAGGCTTGGCGCTGGCCCACTTCGTGTGGATTGCACCTCTGCAGGTGGCC
CTGTTGATGGGACTTATATGGGAGCTGCTTCAAGCCTCTGCTTTCTGTGGGCTGGGCT

-continued

TTTTGATTGTACTGGCACTTTTTCAGGCTGGGCTCGGAAGAATGATGATGAAATACA
GAGATCAGCGGGCCGGGAAGATATCAGAGCGACTTGTGATCACCAGTGAAATGATT
GAAAATATTCAGAGCGTGAAAGCCTACTGCTGGGAAGAAGCCATGGAGAAGATGAT
TGAGAACCTGAGGCAGACAGAGCTCAAGCTCACTCGGAAGGCTGCTTATGTTCGCT
ATTTCAACAGCAGCGCCTTCTTCTTCAGTGGCTTCTTTGTTGTCTTCCTGTCTGTTCTG
CCATATGCACTGATAAAAGGCATTATTTTACGAAAGATCTTCACCACCATCAGTTTT
TGCATCGTTCTCAGGATGGCCGTCACAAGACAGTTCCCCTGGGCTGTGCAGACCTGG
TACGATTCCTTGGGGGCCATCAACAAGATTCAAGATTTCTTGCAAAAACAAGAATAT
AAAACTTTAGAATACAACCTCACCACCACTGAAGTGGTCATGGAAAATGTGACAGC
CTTTTGGGAGGAGGGTTTTGGAGAATTGTTCGAGAAGGCAAAGCAGAATAACAACA
ACAGGAAGACGAGCAATGGGGACGACTCTCTCTTCTTCAGCAACTTTTCACTGCTCG
GGACCCCTGTGTTGAAAGATATAAACTTCAAGATCGAGAGGGGCCAGCTCTTGGCT
GTGGCAGGCTCCACTGGAGCTGGTAAAACATCTCTTCTCATGGTGATCATGGGGGAA
CTGGAGCCTTCCGAAGGAAAAATCAAGCACAGTGGGAGAATCTCATTCTGCAGCCA
GTTTTCCTGGATCATGCCCGGCACCATTAAGGAAAACATCATATTTGGAGTGTCCTA
TGATGAGTACCGCTACCGGTCCGTCATCAAAGCCTGTCAGTTGGAGGAGGACATCTC
CAAGTTTGCAGAGAAAGACAACATTGTGCTTGGAGAGGGGGGTATCACTCTTTCTGG
AGGACAAAGAGCCAGGATCTCTTTGGCCCGGGCAGTCTACAAGGATGCAGACCTCT
ACTTGTTGGACAGTCCCTTCGGCTACCTCGACGTGCTGACTGAAAAAGAAATTTTTG
AAAGCTGTGTGTGCAAACTGATGGCAAACAAGACCAGGATTCTTGTCACCAGCAAG
ATGGAACATCTGAAGAAAGCGGACAAAATTCTGATTCTGCATGAAGGGAGCTCCTA
CTTCTATGGAACATTTAGCGAGCTTCAGAACCTACAGCCAGACTTCTCCTCCAAATT
AATGGGCTGTGACTCCTTCGACCAGTTCTCTGCAGAAAGAAGAAACTCTATACTCAC
AGAGACCCTCCACCGCTTCTCCCTTGAGGGAGATGCCCCAGTTTCTTGGACAGAAAC
CAAGAAGCAGTCCTTTAAGCAGACTGGCGAGTTTGGTGAAAAGAGGAAAAATTCAA
TTCTCAATCCAATTAACAGTATTCGCAAGTTCAGCATTGTCCAGAAGACACCCCTCC
AGATGAATGGCATCGAAGAAGATAGTGACGAGCCGCTGGAGAGACGGCTGAGTCTG
GTGCCAGATTCAGAACAGGGGGAGGCCATCCTGCCCCGGATCAGCGTCATTTCCAC
AGGCCCCACATTACAAGCACGGCGCCGGCAGAGTGTTTTAAATCTCATGACCCATTC
AGTGAACCAGGGCCAAAATATCCACAGGAAGACTACAGCTTCTACCCGGAAAGTGT
CTCTGGCCCCTCAGGCCAATCTGACCGAGCTGGACATCTACAGCAGGAGGCTCTCCC
AGGAAACAGGGCTGGAAATATCTGAAGAGATTAATGAAGAGGATCTTAAAGAGTGC
TTCTTTGATGACATGGAGAGCATCCCCGCGGTGACCACATGGAACACCTACCTTAGA
TATATTACTGTCCACAAGAGCCTCATATTTGTCCTCATCTGGTGCCTGGTTATTTTCC
TCGCTGAGGTGGCGGCCAGTCTTGTTGTGCTCTGGCTGCTGGGCAACACTCCTCTCC
AGGACAAGGGCAATAGTACTCACAGCAGAAATAATTCTTATGCCGTCATCATTACA
AGCACCTCCAGCTACTACGTGTTCTACATCTATGTGGGCGTGGCTGACACCCTCCTG
GCCATGGGTTTCTTCCGGGGCCTGCCTTTGGTGCACACCCTCATCACAGTGTCAAAA
ATTCTGCACCATAAAATGCTTCATTCTGTCCTGCAGGCACCCATGAGCACTTTGAAC
ACATTGAAGGCTGGCGGCATCCTCAACAGATTTTCTAAAGATATTGCTATCCTGGAT
GATCTCCTCCCCCTGACAATCTTTGACTTTATCCAGCTTCTGCTGATCGTGATTGGAG
CCATAGCAGTGGTTGCTGTCCTGCAGCCCTACATTTTTGTGGCCACCGTGCCCGTGAT
TGTTGCCTTTATTATGCTCAGAGCTTACTTCCTGCAAACTTCTCAACAGCTCAAACAG
CTAGAGTCTGAGGGCCGGAGCCCCATTTTTACCCACCTGGTGACTTCCCTGAAGGGA
CTGTGGACTCTGAGAGCATTCGGGCGACAGCCTTACTTTGAGACACTGTTCCACAAG
GCCCTGAACTTGCACACTGCCAACTGGTTTCTTTACCTGAGCACACTCCGCTGGTTCC
AGATGCGGATAGAGATGATCTTCGTCATCTTTTTTATAGCTGTAACCTTCATTTCTAT
CCTTACAACAGGAGAAGGAGAGGGCAGGGTGGGAATCATCCTCACGCTGGCTATGA
ACATAATGTCCACCTTGCAGTGGGCCGTGAATTCCAGTATAGATGTGGATTCTCTAA
TGAGGAGTGTCTCCCGGGTGTTTAAATTCATTGATATGCCTACTGAGGGGAAACCCA
CCAAGTCAACAAAACCTTATAAGAATGGACAGCTGAGCAAGGTGATGATAATTGAG
AACAGCCACGTGAAGAAGGATGACATTTGGCCCAGCGGGGGCCAGATGACTGTGAA
GGACCTGACGGCCAAGTACACCGAAGGTGGAAATGCCATTTTGGAAAACATCAGCT
TCTCAATCTCTCCTGGGCAGAGAGTTGGATTGCTGGGTCGCACGGGCAGCGGCAAAT
CAACCCTGCTCAGTGCCTTCCTTCGGCTCCTGAATACAGAAGGCGAAATCCAAATTG
ACGGGGTGAGCTGGGACAGCATCACCCTGCAGCAGTGGAGAAAAGCATTTGGGGTC
ATTCCACAGAAAGTTTTCATCTTCTCTGGCACTTTCAGAAAGAACCTGGACCCCTAT
GAGCAGTGGAGCGACCAGGAGATCTGGAAGGTTGCAGATGAAGTTGGCCTGCGGAG
TGTGATAGAACAATTTCCTGGCAAGCTGGATTTTGTGCTGGTAGATGGAGGCTGCGT
GCTGTCCCACGGCCACAAACAGCTGATGTGCCTCGCCCGCTCCGTTCTTTCAAAGGC
CAAAATCTTGCTTTTGGATGAGCCCAGTGCTCACCTCGACCCAGTGACCTATCAGAT
AATCCGCAGGACCTTAAAGCAAGCTTTTGCCGACTGCACCGTCATACTGTGTGAGCA
CCGGATTGAAGCAATGCTGGAATGCCAGCAGTTTCTGGTGATCGAGGAGAATAAGG
TCCGGCAGTACGACAGCATCCAGAAGTTGTTGAATGAGCGCAGCCTTTTCCGCCAGG
CCATCTCCCCATCTGACAGAGTCAAGCTGTTTCCACATAGGAACTCCTCTAAGTGCA
AGTCCAAGCCCCAGATCGCTGCCCTCAAGGAGGAAACTGAGGAAGAGGTGCAGGAT
ACCCGCCTGTGA (SEQ ID NO: 30)

ATGCAGAGGAGCCCACTGGAGAAAGCCTCCGTGGTGAGTAAACTCTTTTTTAGTTGG
ACCAGACCCATCCTGCGAAAAGGATACAGGCAGCGCCTCGAGTTGTCTGATATCTA
CCAGATTCCTTCTGTGGACTCAGCTGACAATTTGAGTGAGAAGCTGGAGCGGGAGTG
GGATAGAGAGCTGGCGAGCAAAAAAAACCCCAAGCTTATCAATGCTCTGCGCCGCT
GCTTTTTCTGGAGGTTCATGTTTTATGGGATCTTCCTGTACCTGGGGGAGGTCACCAA
AGCTGTTCAGCCGCTCCTTCTTGGCCGCATCATCGCCAGCTATGACCCTGATAATAA
AGAAGAAAGGTCTATTGCTATTTATCTGGGAATTGGCCTCTGCTTGCTCTTCATCGTC
CGCACCCTTCTGCTGCACCCTGCCATTTTTGGCCTTCACCACATCGGCATGCAAATG
AGAATTGCCATGTTCTCCCTCATTTACAAAAAGACCCTGAAACTTTCCTCAAGAGTG
TTAGATAAAATATCCATTGGTCAGCTGGTCAGCCTGCTGTCCAACAATCTTAACAAA
TTTGATGAAGGCTTGGCGCTGGCCCACTTCGTGTGGATTGCACCTCTGCAGGTGGCC
CTGTTGATGGGACTTATATGGGAGCTGCTTCAAGCCTCTGCTTTCTGTGGGCTGGGCT

-continued

TTTTGATTGTACTGGCACTTTTTCAGGCTGGGCTCGGAAGAATGATGATGAAATACA
GAGATCAGCGGGCCGGGAAGATTTCAGAGCGACTTGTGATCACCAGTGAAATGATT
GAAAATATTCAGAGCGTGAAAGCCTACTGCTGGGAAGAAGCCATGGAGAAGATGAT
TGAGAACCTGAGGCAGACAGAGCTCAAGCTCACTCGGAAGGCTGCTTATGTTCGCT
ATTTCAACAGCAGCGCCTTCTTCTTCAGTGGCTTCTTTGTTGTCTTCCTGTCTGTTCTG
CCATATGCACTGATAAAAGGCATTATTTTACGAAAGATCTTCACCACCATCAGTTTT
TGCATCGTTCTCAGGATGGCCGTCACAAGACAGTTCCCCTGGGCTGTGCAGACCTGG
TACGATTCCTTGGGGGCCATCAACAAGATTCAAGATTTCTTGCAAAAACAAGAATAT
AAAACTTTAGAATACAACCTCACCACCACTGAAGTGGTCATGGAAAATGTGACAGC
CTTTTGGGAGGAGGGTTTTGGAGAATTGTTCGAGAAGGCAAAGCAGAATAACAACA
ACAGGAAGACGAGCAATGGGGACGACTCTCTCTTCTTCAGCAACTTTTCACTGCTCG
GGACCCCTGTGTTGAAAGATATAAACTTCAAGATCGAGAGGGGCCAGCTCTTGGCT
GTGGCAGGCTCCACTGGAGCTGGTAAAACATCTCTTCTCATGGTGATCATGGGGGAA
CTGGAGCCTTCCGAAGGAAAAATCAAGCACAGTGGGAGAATCTCATTCTGCAGCCA
GTTTTCCTGGATCATGCCCGGCACCATTAAGGAAAACATCATATTTGGAGTGTCCTA
TGATGAGTACCGCTACCGGTCAGTCATCAAAGCCTGTCAGTTGGAGGAGGACATCTC
CAAGTTTGCAGAGAAAGACAACATTGTGCTTGGAGAGGGGGGTATCACTCTTTCTGG
AGGACAAAGAGCCAGGATCTCTTTGGCCCGGGCAGTCTACAAGGATGCAGACCTCT
ACTTGTTGGACAGTCCCTTCGGCTACCTCGACGTGCTGACTGAAAAAGAAATTTTTG
AAAGCTGTGTGTGCAAACTGATGGCAAACAAGACCAGGATTCTTGTCACCAGCAAG
ATGGAACATCTGAAGAAAGCGGACAAAATTCTGATTCTGCATGAAGGGAGCTCCTA
CTTCTATGGAACATTTAGCGAGCTTCAGAACCTACAGCCAGACTTCTCCTCCAAATT
AATGGGCTGTGACTCCTTCGACCAGTTCTCTGCAGAAAGAAGAAACTCTATACTCAC
AGAGACCCTCCACCGCTTCTCCCTTGAGGGAGATGCCCCAGTTTCTTGGACAGAAAC
CAAGAAGCAGTCCTTTAAGCAGACTGGCGAGTTTGGTGAAAAGAGGAAAAATTCAA
TTCTCAATCCTATTAACAGTATTCGCAAGTTCAGCATTGTCCAGAAGACACCCCTCC
AGATGAATGGCATCGAAGAAGATAGTGACGAGCCGCTGGAGAGACGGCTGAGTCTG
GTGCCAGATTCAGAACAGGGGGAGGCCATCCTGCCCCGGATCAGCGTCATTTCCAC
AGGCCCCACATTACAAGCACGGCGCCGGCAGAGTGTTTTAAATCTCATGACCCATTC
AGTGAACCAGGGCCAAAATATCCACAGGAAGACTACAGCTTCTACCCGGAAAGTGT
CTCTGGCCCCTCAGGCCAATCTGACCGAGCTGGACATCTACAGCAGGAGGCTCTCCC
AGGAAACAGGGCTGGAAATATCTGAAGAGATTAATGAAGAGGATCTTAAAGAGTGC
TTCTTTGATGACATGGAGAGCATCCCCGCGGTGACCACATGGAACACCTACCTTAGA
TATATTACTGTCCACAAGAGCCTCATATTTGTCCTCATCTGGTGCCTGGTTATTTTCC
TCGCTGAGGTGGCGGCCAGTCTTGTTGTGCTCTGGCTGCTGGGCAACACTCCTCTCC
AGGACAAGGGCAATAGTACACACAGCAGAAATAATTCTTATGCCGTCATCATTACA
AGCACCTCCAGCTACTACGTGTTCTACATCTATGTGGGCGTGGCTGACACCCTCCTG
GCCATGGGTTTCTTCCGGGGCCTGCCTTTGGTGCACACCCTCATCACAGTGTCAAAA
ATTCTGCACCATAAAATGCTTCATTCTGTCCTGCAGGCACCCATGAGCACTTTGAAC
ACATTGAAGGCTGGCGGCATCCTCAACAGATTTTCTAAAGATATTGCTATCCTGGAT
GATCTCCTCCCCCTGACAATCTTTGACTTTATCCAGCTTCTGCTGATCGTGATTGGAG
CCATAGCAGTGGTTGCTGTCCTGCAGCCCTACATTTTTGTGGCCACCGTGCCCGTGAT
TGTTGCCTTTATTATGCTCAGAGCTTACTTCCTGCAAACTTCTCAACAGCTCAAACAG
CTAGAATCTGAGGGCCGGAGCCCCATTTTTACCCACCTGGTGACTTCCCTGAAGGGA
CTGTGGACTCTGAGAGCATTCGGGCGACAGCCTTACTTTGAGACACTGTTCCACAAG
GCCCTGAACTTGCACACTGCCAACTGGTTTCTTTACCTGAGCACACTCCGCTGGTTCC
AGATGCGGATAGAGATGATCTTCGTCATCTTTTTTATAGCTGTAACCTTCATTTCTAT
CCTTACAACAGGAGAAGGAGAGGGCAGGGTGGGAATCATCCTCACGCTGGCTATGA
ACATAATGTCCACCTTGCAGTGGGCCGTGAATTCCAGTATAGATGTGGATTCTCTAA
TGAGGAGTGTCTCCCGGGTGTTTAAATTCATTGATATGCCTACTGAGGGGAAACCCA
CCAAGTCAACAAAACCTTATAAGAATGGACAGCTGAGCAAGGTGATGATAATTGAG
AACAGCCACGTGAAGAAGGATGACATTTGGCCCAGCGGGGGCCAGATGACTGTGAA
GGACCTGACGGCCAAGTACACCGAAGGTGGAAATGCCATTTTGGAAAACATCAGCT
TCTCAATCTCTCCTGGGCAGAGAGTTGGATTGCTGGGTCGCACGGGCAGCGGCAAAT
CAACCCTGCTCAGTGCCTTCCTTCGGCTCCTGAATACAGAAGGCGAAATCCAAATTG
ACGGGGTGAGCTGGGACAGCATCACCCTGCAGCAGTGGAGAAAAGCATTTGGGGTC
ATTCCACAGAAAGTTTTCATCTTCTCTGGCACTTTCAGAAAGAACCTGGACCCCTAT
GAGCAGTGGAGCGACCAGGAGATCTGGAAGGTTGCAGATGAAGTTGGCCTGCGGAG
TGTGATAGAACAATTTCCTGGCAAGCTGGATTTTGTGCTGGTAGATGGAGGCTGCGT
GCTGTCCCACGGCCACAAACAGCTGATGTGCCTCGCCCGCTCCGTTCTTTCAAAGGC
CAAAATCTTGCTTTTGGATGAGCCCAGTGCTCACCTCGACCCAGTGACCTATCAGAT
AATCCGCAGGACCTTAAAGCAAGCTTTTGCCGACTGCACCGTCATACTGTGTGAGCA
CCGGATTGAAGCAATGCTGGAATGCCAGCAGTTTCTGGTGATCGAGGAGAATAAGG
TCCGGCAGTACGACAGCATCCAGAAGTTGTTGAATGAGCGCAGCCTTTTCCGCCAGG
CCATCTCCCCATCTGACAGAGTCAAGCTGTTTCCACATAGGAACTCCTCTAAGTGCA
AGTCCAAGCCCCAGATCGCTGCCCTCAAGGAGGAAACTGAGGAAGAGGTGCAGGAT
ACCCGCCTGTGA (SEQ ID NO: 31)

ATGCAGAGAAGCCCCCTGGAGAAGGCCTCTGTGGTGAGCAAGCTGTTCTTCAGCTG
GACCAGACCCATCCTGAGAAAGGGCTACAGACAGAGACTGGAGCTGTCTGACATCT
ACCAGATCCCCTCTGTGGACTCTGCCGACAACCTGTCTGAGAAGCTGGAGAGAGAG
TGGGACAGAGAGCTGGCCAGCAAGAAGAACCCCAAGCTGATCAATGCCCTGAGAA
GATGCTTCTTCTGGAGATTCATGTTCTATGGCATCTTCCTGTACCTGGGAGAGGTGAC
CAAGGCCGTGCAGCCCCTGCTGCTGGGCAGGATCATTGCCAGCTATGACCCTGACA
ACAAGGAGGAGAGAAGCATTGCCATCTACCTGGGCATTGGCCTGTGCCTGCTGTTCA
TTGTGAGAACCCTGCTGCTGCACCCTGCCATCTTTGGCCTGCACCACATTGGCATGC
AGATGAGAATTGCCATGTTCAGCCTGATCTACAAGAAGACCCTGAAGCTGAGCAGC
AGAGTGCTGGACAAGATCAGCATTGGCCAGCTGGTGAGCCTGCTGAGCAACAACCT
GAACAAGTTTGATGAGGGCCTGGCCCTGGCCCACTTTGTGTGGATTGCCCCCCTGCA
GGTGGCCCTGCTGATGGGCCTGATCTGGGAGCTGCTGCAGGCCTCTGCCTTCTGTGG

-continued

CCTGGGCTTCCTGATTGTGCTGGCCCTGTTCCAGGCCGGCCTGGGCAGAATGATGAT
GAAGTACAGAGACCAGAGAGCCGGCAAGATCTCTGAGAGACTGGTGATCACCTCTG
AGATGATTGAGAACATCCAGTCTGTGAAGGCCTACTGCTGGGAGGAGGCCATGGAG
AAGATGATTGAGAACCTGAGACAGACAGAGCTGAAGCTGACCAGGAAGGCCGCCTA
TGTGAGATACTTCAACAGCTCTGCCTTCTTCTTCTCTGGCTTCTTTGTGGTGTTCCTGT
CTGTGCTGCCCTATGCCCTGATCAAGGGCATCATCCTGAGGAAGATCTTCACCACCA
TCAGCTTCTGCATTGTGCTGAGGATGGCCGTGACCAGGCAGTTCCCCTGGGCCGTGC
AGACCTGGTATGACAGCCTGGGGGCCATCAACAAGATCCAGGACTTCCTGCAGAAG
CAGGAGTACAAGACCCTGGAGTACAACCTGACCACCACAGAGGTGGTGATGGAGAA
TGTGACAGCCTTCTGGGAGGAGGGCTTTGGAGAGCTGTTTGAGAAGGCCAAGCAGA
ACAACAACAACAGAAAGACCAGCAATGGAGATGACAGCCTGTTCTTCAGCAACTTC
AGCCTGCTGGGCACCCCTGTGCTGAAGGACATCAACTTCAAGATTGAGAGGGGCCA
GCTGCTGGCCGTGGCCGGCAGCACAGGAGCCGGCAAGACCAGCCTGCTGATGGTGA
TCATGGGAGAGCTGGAGCCCTCTGAGGGCAAGATCAAGCACTCTGGCAGAATCAGC
TTCTGCAGCCAGTTCAGCTGGATCATGCCTGGCACCATCAAGGAGAACATCATCTTT
GGGGTGAGCTATGATGAGTACAGGTACAGATCTGTGATCAAGGCCTGCCAGCTGGA
GGAGGACATCTCCAAGTTTGCCGAGAAGGACAACATTGTGCTGGGGGAGGGAGGCA
TCACCCTGTCTGGGGGCCAGAGAGCCAGAATCAGCCTGGCCAGAGCCGTGTACAAG
GATGCCGACCTGTACCTGCTGGACAGCCCCTTTGGCTACCTGGATGTGCTGACAGAG
AAGGAGATCTTTGAGAGCTGTGTGTGCAAGCTGATGGCCAACAAGACCAGGATCCT
GGTGACCAGCAAGATGGAGCACCTGAAGAAGGCCGACAAGATCCTGATCCTGCATG
AGGGCAGCAGCTACTTCTATGGCACCTTCTCTGAGCTGCAGAACCTGCAGCCTGACT
TCAGCAGCAAGCTGATGGGCTGTGACAGCTTTGACCAGTTCTCTGCTGAGAGAAGA
AACAGCATCCTGACAGAGACCCTGCACAGGTTCAGCCTGGAGGGGGATGCCCCTGT
GAGCTGGACAGAGACCAAGAAGCAGAGCTTCAAGCAGACAGGAGAGTTTGGGGAG
AAGAGGAAGAACAGCATCCTGAACCCCATCAACAGCATCAGGAAGTTCAGCATTGT
GCAGAAGACCCCCCTGCAGATGAATGGCATTGAGGAGGACTCTGATGAGCCCCTGG
AGAGAAGACTGAGCCTGGTGCCAGACTCTGAGCAGGGAGAGGCCATCCTGCCCAGG
ATCTCTGTGATCAGCACAGGCCCCACCCTGCAGGCCAGAAGAAGACAGTCTGTGCT
GAACCTGATGACCCACTCTGTGAACCAGGGCCAGAATATCCACAGAAAGACCACAG
CCAGCACCAGAAAGGTGAGCCTGGCCCCCCAGGCCAACCTGACAGAGCTGGACATC
TACAGCAGAAGGCTGAGCCAGGAGACAGGCCTGGAGATCTCTGAGGAGATCAATGA
GGAGGACCTGAAGGAGTGCTTCTTTGATGACATGGAGAGCATCCCTGCCGTGACCA
CCTGGAACACCTACCTGAGATACATCACAGTGCACAAGAGCCTGATCTTTGTGCTGA
TCTGGTGCCTGGTGATCTTCCTGGCCGAGGTGGCCGCCAGCCTGGTGGTGCTGTGGC
TGCTGGGCAACACCCCCCTGCAGGACAAGGGCAACAGCACCCACAGCAGAAACAAC
AGCTATGCTGTGATCATCACCAGCACCAGCAGCTACTATGTGTTCTACATCTATGTG
GGAGTGGCTGACACCCTGCTGGCCATGGGCTTCTTCAGAGGCCTGCCCCTGGTGCAC
ACCCTGATCACAGTGAGCAAGATCCTGCACCACAAGATGCTGCACTCTGTGCTGCAG
GCCCCCATGAGCACCCTGAACACCCTGAAGGCTGGAGGCATCCTGAACAGATTCAG
CAAGGACATTGCCATCCTGGATGACCTGCTGCCCCTGACCATCTTTGACTTCATCCA
GCTGCTGCTGATTGTGATTGGAGCCATTGCCGTGGTGGCCGTGCTGCAGCCCTACAT
CTTTGTGGCCACAGTGCCTGTGATTGTGGCCTTCATCATGCTGAGGGCCTACTTCCTG
CAGACCAGCCAGCAGCTGAAGCAGCTGGAGTCTGAGGGCAGAAGCCCCATCTTCAC
CCACCTGGTGACCAGCCTGAAGGGCCTGTGGACCCTGAGGGCCTTTGGCAGACAGC
CCTACTTTGAGACCCTGTTCCACAAGGCCCTGAACCTGCACACAGCCAACTGGTTCC
TGTACCTGAGCACCCTGAGATGGTTCCAGATGAGGATTGAGATGATCTTTGTGATCT
TCTTCATTGCCGTGACCTTCATCAGCATCCTGACCACAGGGGAGGGCGAGGGCAGA
GTGGGCATCATCCTGACCCTGGCCATGAACATCATGAGCACCCTGCAGTGGGCCGTG
AACAGCAGCATTGATGTGGACAGCCTGATGAGATCTGTGAGCAGAGTGTTCAAGTT
CATTGACATGCCCACAGAGGGCAAGCCCACCAAGAGCACCAAGCCCTACAAGAATG
GCCAGCTGAGCAAGGTGATGATCATTGAGAACAGCCATGTGAAGAAGGATGACATC
TGGCCCTCTGGAGGCCAGATGACAGTGAAGGACCTGACAGCCAAGTACACAGAGGG
GGGCAATGCCATCCTGGAGAACATCAGCTTCAGCATCAGCCCTGGCCAGAGGGTGG
GCCTGCTGGGCAGAACAGGCTCTGGCAAGAGCACCCTGCTGTCTGCCTTCCTGAGGC
TGCTGAACACAGAGGGAGAGATCCAGATTGATGGGGTGAGCTGGGACAGCATCACC
CTGCAGCAGTGGAGGAAGGCCTTTGGGGTGATCCCCCAGAAGGTGTTCATCTTCTCT
GGCACCTTCAGGAAGAACCTGGACCCCTATGAGCAGTGGTCTGACCAGGAGATCTG
GAAGGTGGCCGATGAGGTGGGCCTGAGATCTGTGATTGAGCAGTTCCCTGGCAAGC
TGGACTTTGTGCTGGTGGATGGAGGCTGTGTGCTGAGCCATGGCCACAAGCAGCTGA
TGTGCCTGGCCAGATCTGTGCTGAGCAAGGCCAAGATCCTGCTGCTGGATGAGCCCT
CTGCCCACCTGGACCCTGTGACCTACCAGATCATCAGAAGAACCCTGAAGCAGGCC
TTTGCCGACTGCACAGTGATCCTGTGTGAGCACAGAATTGAGGCCATGCTGGAGTGC
CAGCAGTTCCTGGTGATTGAGGAGAACAAGGTGAGGCAGTATGACAGCATCCAGAA
GCTGCTGAATGAGAGAAGCCTGTTCAGACAGGCCATCAGCCCCTCTGACAGAGTGA
AGCTGTTCCCCCACAGGAACAGCAGCAAGTGCAAGAGCAAGCCCCAGATTGCCGCC
CTGAAGGAGGAGACAGAGGAGGAGGTGCAGGACACCAGACTGTGA (SEQ ID NO: 32)

ATGCAGAGGAGCCCCCTGGAGAAGGCCAGCGTGGTGAGCAAGCTGTTCTTCAGCTG
GACCAGGCCCATCCTGAGGAAGGGCTACAGGCAGAGGCTGGAGCTGAGCGACATCT
ACCAGATCCCCAGCGTGGACAGCGCCGACAACCTGAGCGAGAAGCTGGAGAGGGA
GTGGGACAGGGAGCTGGCCAGCAAGAAGAACCCCAAGCTGATCAACGCCCTGAGG
AGGTGCTTCTTCTGGAGGTTCATGTTCTACGGCATCTTCCTGTACCTGGGCGAGGTG
ACCAAGGCCGTGCAGCCCCTGCTGCTGGGCAGGATCATCGCCAGCTACGACCCCGA
CAACAAGGAGGAGAGGAGCATCGCCATCTACCTGGGCATCGGCCTGTGCCTGCTGT
TCATCGTGAGGACCCTGCTGCTGCACCCCGCCATCTTCGGCCTGCACCACATCGGCA
TGCAGATGAGGATCGCCATGTTCAGCCTGATCTACAAGAAGACCCTGAAGCTGAGC
AGCAGGGTGCTGGACAAGATCAGCATCGGCCAGCTGGTGAGCCTGCTGAGCAACAA
CCTGAACAAGTTCGACGAGGGCCTGGCCCTGGCCCACTTCGTGTGGATCGCCCCCCT
GCAGGTGGCCCTGCTGATGGGCCTGATCTGGGAGCTGCTGCAGGCCAGCGCCTTCTG

-continued

CGGCCTGGGCTTCCTGATCGTGCTGGCCCTGTTCCAGGCCGGCCTGGGCAGGATGAT
GATGAAGTACAGGGACCAGAGGGCCGGCAAGATCAGCGAGAGGCTGGTGATCACC
AGCGAGATGATCGAGAACATCCAGAGCGTGAAGGCCTACTGCTGGGAGGAGGCCAT
GGAGAAGATGATCGAGAACCTGAGGCAGACCGAGCTGAAGCTGACCAGGAAGGCC
GCCTACGTGAGGTACTTCAACAGCAGCGCCTTCTTCTTCAGCGGCTTCTTCGTGGTGT
TCCTGAGCGTGCTGCCCTACGCCCTGATCAAGGGCATCATCCTGAGGAAGATCTTCA
CCACCATCAGCTTCTGCATCGTGCTGAGGATGGCCGTGACCAGGCAGTTCCCCTGGG
CCGTGCAGACCTGGTACGACAGCCTGGGCGCCATCAACAAGATCCAGGACTTCCTG
CAGAAGCAGGAGTACAAGACCCTGGAGTACAACCTGACCACCACCGAGGTGGTGAT
GGAGAACGTGACCGCCTTCTGGGAGGAGGGCTTCGGCGAGCTGTTCGAGAAGGCCA
AGCAGAACAACAACAACAGGAAGACCAGCAACGGCGACGACAGCCTGTTCTTCAGC
AACTTCAGCCTGCTGGGCACCCCCGTGCTGAAGGACATCAACTTCAAGATCGAGAG
GGGCCAGCTGCTGGCCGTGGCCGGCAGCACCGGCGCCGGCAAGACCAGCCTGCTGA
TGGTGATCATGGGCGAGCTGGAGCCCAGCGAGGGCAAGATCAAGCACAGCGGCAG
GATCAGCTTCTGCAGCCAGTTCAGCTGGATCATGCCCGGCACCATCAAGGAGAACA
TCATCTTCGGCGTGAGCTACGACGAGTACAGGTACAGGAGCGTGATCAAGGCCTGC
CAGCTGGAGGAGGACATCAGCAAGTTCGCCGAGAAGGACAACATCGTGCTGGGCGA
GGGCGGCATCACCCTGAGCGGCGGCCAGAGGGCCAGGATCAGCCTGGCCAGGGCCG
TGTACAAGGACGCCGACCTGTACCTGCTGGACAGCCCCTTCGGCTACCTGGACGTGC
TGACCGAGAAGGAGATCTTCGAGAGCTGCGTGTGCAAGCTGATGGCCAACAAGACC
AGGATCCTGGTGACCAGCAAGATGGAGCACCTGAAGAAGGCCGACAAGATCCTGAT
CCTGCACGAGGGCAGCAGCTACTTCTACGGCACCTTCAGCGAGCTGCAGAACCTGC
AGCCCGACTTCAGCAGCAAGCTGATGGGCTGCGACAGCTTCGACCAGTTCAGCGCC
GAGAGGAGGAACAGCATCCTGACCGAGACCCTGCACAGGTTCAGCCTGGAGGGCGA
CGCCCCCGTGAGCTGGACCGAGACCAAGAAGCAGAGCTTCAAGCAGACCGGCGAGT
TCGGCGAGAAGAGGAAGAACAGCATCCTGAACCCCATCAACAGCATCAGGAAGTTC
AGCATCGTGCAGAAGACCCCCCTGCAGATGAACGGCATCGAGGAGGACAGCGACG
AGCCCCTGGAGAGGAGGCTGAGCCTGGTGCCCGACAGCGAGCAGGGCGAGGCCATC
CTGCCCAGGATCAGCGTGATCAGCACCGGCCCCACCCTGCAGGCCAGGAGGAGGCA
GAGCGTGCTGAACCTGATGACCCACAGCGTGAACCAGGGCCAGAACATCCACAGGA
AGACCACCGCCAGCACCAGGAAGGTGAGCCTGGCCCCCCAGGCCAACCTGACCGAG
CTGGACATCTACAGCAGGAGGCTGAGCCAGGAGACCGGCCTGGAGATCAGCGAGG
AGATCAACGAGGAGGACCTGAAGGAGTGCTTCTTCGACGACATGGAGAGCATCCCC
GCCGTGACCACCTGGAACACCTACCTGAGGTACATCACCGTGCACAAGAGCCTGAT
CTTCGTGCTGATCTGGTGCCTGGTGATCTTCCTGGCCGAGGTGGCCGCCAGCCTGGT
GGTGCTGTGGCTGCTGGGCAACACCCCCCTGCAGGACAAGGGCAACAGCACCCACA
GCAGGAACAACAGCTACGCCGTGATCATCACCAGCACCAGCAGCTACTACGTGTTC
TACATCTACGTGGGCGTGGCCGACACCCTGCTGGCCATGGGCTTCTTCAGGGGCCTG
CCCCTGGTGCACACCCTGATCACCGTGAGCAAGATCCTGCACCACAAGATGCTGCAC
AGCGTGCTGCAGGCCCCCATGAGCACCCTGAACACCCTGAAGGCCGGCGGCATCCT
GAACAGGTTCAGCAAGGACATCGCCATCCTGGACGACCTGCTGCCCCTGACCATCTT
CGACTTCATCCAGCTGCTGCTGATCGTGATCGGCGCCATCGCCGTGGTGGCCGTGCT
GCAGCCCTACATCTTCGTGGCCACCGTGCCCGTGATCGTGGCCTTCATCATGCTGAG
GGCCTACTTCCTGCAGACCAGCCAGCAGCTGAAGCAGCTGGAGAGCGAGGGCAGGA
GCCCCATCTTCACCCACCTGGTGACCAGCCTGAAGGGCCTGTGGACCCTGAGGGCCT
TCGGCAGGCAGCCCTACTTCGAGACCCTGTTCCACAAGGCCCTGAACCTGCACACCG
CCAACTGGTTCCTGTACCTGAGCACCCTGAGGTGGTTCCAGATGAGGATCGAGATGA
TCTTCGTGATCTTCTTCATCGCCGTGACCTTCATCAGCATCCTGACCACCGGCGAGG
GCGAGGGCAGGGTGGGCATCATCCTGACCCTGGCCATGAACATCATGAGCACCCTG
CAGTGGGCCGTGAACAGCAGCATCGACGTGGACAGCCTGATGAGGAGCGTGAGCAG
GGTGTTCAAGTTCATCGACATGCCCACCGAGGGCAAGCCCACCAAGAGCACCAAGC
CCTACAAGAACGGCCAGCTGAGCAAGGTGATGATCATCGAGAACAGCCACGTGAAG
AAGGACGACATCTGGCCCAGCGGCGGCCAGATGACCGTGAAGGACCTGACCGCCAA
GTACACCGAGGGCGGCAACGCCATCCTGGAGAACATCAGCTTCAGCATCAGCCCCG
GCCAGAGGGTGGGCCTGCTGGGCAGGACCGGCAGCGGCAAGAGCACCCTGCTGAGC
GCCTTCCTGAGGCTGCTGAACACCGAGGGCGAGATCCAGATCGACGGCGTGAGCTG
GGACAGCATCACCCTGCAGCAGTGGAGGAAGGCCTTCGGCGTGATCCCCCAGAAGG
TGTTCATCTTCAGCGGCACCTTCAGGAAGAACCTGGACCCCTACGAGCAGTGGAGC
GACCAGGAGATCTGGAAGGTGGCCGACGAGGTGGGCCTGAGGAGCGTGATCGAGC
AGTTCCCCGGCAAGCTGGACTTCGTGCTGGTGGACGGCGGCTGCGTGCTGAGCCAC
GGCCACAAGCAGCTGATGTGCCTGGCCAGGAGCGTGCTGAGCAAGGCCAAGATCCT
GCTGCTGGACGAGCCCAGCGCCCACCTGGACCCCGTGACCTACCAGATCATCAGGA
GGACCCTGAAGCAGGCCTTCGCCGACTGCACCGTGATCCTGTGCGAGCACAGGATC
GAGGCCATGCTGGAGTGCCAGCAGTTCCTGGTGATCGAGGAGAACAAGGTGAGGCA
GTACGACAGCATCCAGAAGCTGCTGAACGAGAGGAGCCTGTTCAGGCAGGCCATCA
GCCCCAGCGACAGGGTGAAGCTGTTCCCCCACAGGAACAGCAGCAAGTGCAAGAGC
AAGCCCCAGATCGCCGCCCTGAAGGAGGAGACCGAGGAGGAGGTGCAGGACACCA
GGCTGTGA (SEQ ID NO: 33)

ATGCAGAGATCCCCTCTGGAGAAGGCCTCAGTGGTGTCCAAGCTTTTCTTCTCCTGG
ACCAGGCCCATTTTAAGAAAGGGCTACAGGCAGAGACTTGAGCTGTCTGACATCTAT
CAGATCCCTTCTGTGGATTCTGCTGACAATCTTAGTGAAAAATTGGAAAGGGAGTGG
GACAGAGAGCTGGCAAGTAAAAAGAACCCCAAGCTGATTAATGCCCTGAGGCGCTG
CTTTTTTTGGAGATTCATGTTCTATGGCATATTCCTCTACCTTGGAGAAGTAACCAAA
GCTGTACAGCCTCTCCTCCTTGGCAGAATCATTGCCTCCTATGATCCTGATAACAAG
GAGGAGAGAAGCATAGCCATCTACCTGGGCATTGGGCTGTGCCTCTTGTTTATTGTG
AGGACCCTTCTCTTGCACCCTGCCATCTTTGGCCTTCATCACATTGGCATGCAAATGA
GAATAGCAATGTTTAGTCTTATTTACAAAAAAACATTAAAACTCTCTTCCAGGGTGT
TGGACAAGATCAGTATTGGACAACTGGTCAGCCTGCTGAGCAACAACCTGAACAAG
TTTGATGAAGGACTGGCCCTGGCCCACTTTGTCTGGATTGCCCCCCTTCAGGTGGCTC

-continued

TTTTGATGGGCCTGATCTGGGAACTCCTGCAGGCCTCTGCCTTCTGTGGGTTAGGCTT
CCTGATAGTGCTAGCTCTCTTTCAGGCAGGGTTGGGTAGAATGATGATGAAGTACAG
AGACCAGAGGGCTGGGAAGATATCTGAGAGGCTGGTCATTACTTCTGAAATGATAG
AAAACATCCAGTCTGTTAAAGCTTACTGCTGGGAGGAGGCTATGGAAAAGATGATT
GAGAACTTGAGGCAAACAGAGCTCAAGCTGACTAGGAAGGCAGCCTATGTCAGGTA
TTTCAACAGCAGTGCTTTCTTCTTCTCAGGCTTTTTCGTGGTCTTCTTGAGTGTTCTGC
CCTATGCCCTCATCAAGGGGATAATTTTGAGAAAGATTTTCACCACTATTTCCTTTTG
CATTGTCCTGAGGATGGCTGTCACCAGGCAATTCCCCTGGGCTGTGCAGACATGGTA
TGACTCTCTGGGGGCCATCAACAAAATCCAAGATTTCCTGCAGAAGCAGGAGTACA
AGACCCTGGAATACAACCTCACCACCACAGAAGTTGTGATGGAGAATGTGACTGCA
TTCTGGGAGGAAGGATTTGGGGAGCTGTTTGAGAAAGCAAAACAAAACAATAATAA
CAGGAAAACCAGCAATGGAGATGACTCCCTGTTCTTTTCCAACTTCTCTTTGTTGGG
CACCCCTGTCCTGAAAGATATAAACTTTAAAATTGAAAGAGGGCAGCTGTTGGCAGT
TGCTGGCTCCACAGGAGCTGGAAAAACTTCACTACTGATGGTGATCATGGGGGAGTT
AGAACCCTCTGAAGGGAAAATAAAACATTCTGGGAGGATTAGTTTCTGCAGCCAGT
TCAGCTGGATCATGCCTGGGACCATTAAAGAAAATATTATATTTGGAGTGAGCTATG
ATGAATATAGATATAGGAGTGTCATCAAAGCCTGTCAGTTGGAGGAAGACATCAGC
AAATTTGCAGAGAAAGACAACATTGTTCTGGGTGAAGGTGGCATCACCCTGTCAGG
AGGGCAAAGGGCCAGGATCAGCTTGGCCAGAGCAGTCTATAAAGATGCTGATCTGT
ACCTCCTGGATAGCCCTTTTGGCTATCTGGATGTTTTGACAGAGAAGGAAATTTTTG
AGTCCTGTGTCTGCAAGTTAATGGCAAATAAAACAAGGATACTTGTGACCTCAAAA
ATGGAACACCTGAAGAAGGCTGACAAAATTCTGATCCTGCATGAGGGCAGCAGCTA
CTTTTATGGAACATTTTCTGAACTGCAGAATTTGCAACCAGACTTTTCATCAAAGCTC
ATGGGATGTGACAGTTTTGATCAGTTTTCTGCAGAAAGGAGAAACTCCATTTTGACT
GAGACCCTGCACAGGTTCAGTCTGGAGGGGGATGCCCCAGTGAGTTGGACTGAGAC
AAAGAAACAGAGCTTCAAGCAGACTGGAGAGTTTGGAGAAAAGAGGAAAAACTCA
ATTCTCAATCCCATCAATAGCATCAGGAAGTTCAGCATAGTTCAGAAGACTCCTTTG
CAGATGAATGGGATTGAAGAGGACTCAGATGAGCCCCTGGAAAGGAGACTCTCCTT
GGTGCCAGATTCAGAGCAGGGGGAAGCCATACTGCCAAGGATCTCTGTGATTTCTAC
AGGGCCCACCCTCCAAGCAAGAAGGAGACAGTCAGTTTTAAACCTGATGACCCACT
CTGTCAACCAGGGACAGAACATTCATAGAAAGACAACAGCATCTACAAGAAAAGTT
TCACTGGCCCCTCAAGCCAATTTAACTGAACTAGATATCTACAGCAGGAGGCTCAGC
CAAGAAACAGGCCTGGAGATCTCAGAAGAAATAAATGAGGAGGATTTGAAGGAAT
GCTTCTTTGATGATATGGAGAGCATCCCAGCTGTCACAACCTGGAACACCTACCTGA
GATACATCACAGTGCACAAATCCCTCATCTTTGTACTTATATGGTGCCTTGTCATCTT
CTTAGCTGAGGTGGCTGCTTCCCTGGTGGTGCTGTGGCTGCTGGGAAACACACCCCT
CCAGGATAAAGGGAACTCTACTCACAGCAGGAACAACAGTTATGCTGTGATCATCA
CCAGTACCTCCTCCTACTATGTGTTCTACATTTATGTTGGAGTTGCAGACACATTGCT
TGCCATGGGTTTTTTTAGAGGACTCCCCCTGGTGCATACTCTCATCACTGTTTCCAAA
ATCCTTCACCACAAGATGCTGCACAGTGTACTACAGGCTCCCATGAGCACCCTCAAC
ACTCTTAAAGCAGGAGGAATCTTGAACAGATTTAGCAAGGACATTGCAATTCTTGAT
GACCTGCTTCCACTGACCATCTTTGACTTCATCCAGCTTCTGCTCATTGTAATTGGTG
CCATTGCTGTGGTAGCAGTGCTCCAGCCATATATTTTTGTGGCCACTGTGCCTGTTAT
TGTGGCCTTCATTATGTTGAGAGCCTACTTCCTGCAGACCTCTCAGCAGCTCAAGCA
ACTTGAAAGTGAGGGCAGGAGCCCCATATTTACACACTTGGTCACTTCCCTCAAAGG
CCTCTGGACACTCAGAGCTTTTGGAAGACAACCTTATTTTGAAACTCTCTTCCACAA
GGCTCTGAATCTCCACACAGCCAACTGGTTTCTGTATCTTTCAACACTGCGCTGGTTC
CAGATGAGGATTGAGATGATCTTTGTTATCTTCTTCATAGCTGTTACCTTCATCTCTA
TTCTGACAACTGGTGAGGGGGAAGGGAGAGTAGGCATCATCCTCACACTAGCCATG
AACATAATGTCTACCTTACAATGGGCCGTGAACAGCTCCATAGATGTGGACAGCCTC
ATGAGAAGTGTGTCAAGAGTTTTCAAATTCATTGACATGCCCACAGAAGGCAAACC
AACCAAGAGCACAAAACCCTACAAGAATGGCCAGCTGAGTAAGGTCATGATCATTG
AAAATTCTCATGTGAAGAAGGATGATATTTGGCCCAGTGGGGGCCAGATGACAGTC
AAGGACCTCACTGCCAAATACACAGAGGGTGGAAATGCTATCCTAGAGAACATCTC
CTTCTCCATCTCCCCAGGCCAAAGAGTTGGCTTGCTGGGCAGGACTGGCAGTGGCAA
GTCCACCTTGCTCTCAGCATTTCTCAGGCTTTTAAATACAGAGGGAGAGATTCAAAT
TGATGGGGTGTCTTGGGATAGTATAACACTTCAACAGTGGAGGAAAGCCTTTGGTGT
GATTCCTCAGAAAGTGTTTATCTTCTCTGGCACTTTCAGAAAAAATCTGGACCCCTAT
GAACAGTGGAGTGACCAGGAAATCTGGAAGGTGGCAGATGAAGTGGGCCTAAGATC
AGTCATAGAGCAGTTTCCTGGAAAGTTGGATTTTGTGCTTGTAGATGGAGGCTGTGT
GCTGTCCCATGGCCATAAACAGCTAATGTGCCTGGCTAGGTCAGTGCTGAGCAAGGC
CAAGATCCTGCTGTTAGATGAGCCTTCAGCCCATCTGGACCCTGTGACATACCAGAT
TATCAGAAGAACTCTGAAGCAGGCCTTTGCTGACTGCACTGTCATCCTGTGTGAGCA
CAGAATTGAGGCCATGCTGGAGTGCCAGCAGTTCCTTGTTATAGAAGAGAATAAGG
TTAGGCAGTATGACAGCATTCAGAAACTGCTAAATGAAAGATCTCTCTTCAGGCAAG
CTATTTCACCATCTGATAGAGTGAAACTTTTTCCCCACAGAAATTCCTCTAAATGTAA
ATCTAAGCCCCAGATAGCTGCCTTGAAAGAGGAGACTGAAGAAGAAGTCCAGGACA
CCAGACTGTGA (SEQ ID NO: 34)

ATGCAGAGATCCCCGCTGGAGAAGGCATCTGTGGTGTCAAAACTGTTCTTTAGCTGG
ACAAGGCCCATCCTTAGGAAAGGGTACAGACAGAGGTTGGAGCTGTCAGACATATA
TCAGATCCCTTCAGTGGACTCTGCAGACAACCTCTCTGAAAAGCTGGAGAGGGAAT
GGGACAGGGAACTGGCCAGCAAAAAAAACCCTAAACTGATTAATGCCCTGAGGAGG
TGCTTCTTTTGGAGATTCATGTTCTATGGGATCTTCCTTTACCTGGGGGAGGTGACTA
AAGCTGTTCAGCCTCTTCTTCTGGGGAGGATTATTGCCTCCTATGACCCAGACAACA
AAGAAGAAAGAAGCATAGCCATTTACTTAGGCATAGGCCTCTGCTTGCTCTTCATAG
TTAGAACCCTCCTACTCCACCCAGCCATCTTTGGTCTCCACCACATAGGTATGCAGA
TGAGAATAGCAATGTTCTCCTTGATCTACAAGAAGACCCTCAAGCTGTCCAGCAGGG
TGCTGGACAAGATCTCCATAGGCCAGTTAGTCAGTCTACTGTCCAATAACTTAAATA
AGTTTGATGAGGGACTGGCACTGGCACATTTTGTGTGGATTGCCCCCCTCCAAGTGG

-continued

CCCTTCTTATGGGCCTTATCTGGGAGCTGTTGCAGGCCTCTGCTTTCTGTGGCCTGGG
TTTCCTCATAGTCCTAGCCTTATTCCAGGCTGGACTGGGCAGAATGATGATGAAGTA
TAGGGACCAAAGAGCAGGGAAGATTTCTGAAAGGCTGGTTATAACTTCTGAGATGA
TTGAGAACATTCAGTCAGTGAAAGCTTACTGCTGGGAAGAAGCTATGGAAAAAATG
ATTGAAAATCTCAGACAGACTGAATTAAAGTTGACCAGGAAAGCTGCTTATGTCAG
ATACTTCAACTCCTCAGCCTTCTTTTTTTCTGGCTTCTTTGTTGTATTCCTTTCAGTCC
TCCCCTATGCCCTGATTAAGGGCATTATCTTGAGGAAAATTTTCACAACCATCTCCTT
TTGTATTGTCCTCAGGATGGCTGTTACAAGGCAATTTCCTTGGGCTGTGCAAACTTG
GTATGATAGCCTTGGAGCAATCAACAAGATCCAGGATTTCCTGCAAAAGCAGGAGT
ACAAGACATTGGAATACAACCTTACCACCACTGAGGTGGTGATGGAAAATGTGACT
GCCTTCTGGGAGGAGGGGTTTGGAGAGCTGTTTGAGAAAGCCAAACAGAACAACAA
CAATAGAAAGACCTCTAATGGTGATGATTCCCTGTTCTTTTCTAACTTTAGTCTTCTG
GGGACCCCAGTTCTGAAAGATATTAACTTTAAAATTGAAAGGGGACAGTTGCTGGCT
GTGGCTGGGTCCACTGGGGCTGGGAAGACAAGCCTGCTCATGGTGATCATGGGAGA
GCTGGAACCCAGTGAAGGAAAGATCAAACACTCAGGCAGGATCTCCTTCTGCAGCC
AGTTCTCATGGATTATGCCAGGCACTATTAAAGAAAATATCATCTTTGGTGTAAGCT
ATGATGAGTACAGGTATAGATCTGTAATTAAAGCCTGCCAGCTGGAGGAAGACATC
TCTAAGTTTGCTGAGAAGGATAACATTGTGTTGGGGGAAGGGGGCATCACCCTTTCT
GGTGGGCAGAGGGCTAGGATCTCCCTTGCTAGGGCAGTATACAAGGATGCTGACTT
GTACCTCTTGGATAGTCCTTTTGGCTACCTAGATGTGCTGACAGAGAAAGAAATATT
TGAAAGCTGTGTGTGTAAGCTCATGGCTAACAAGACCAGGATCCTGGTCACCAGTA
AAATGGAACACCTCAAAAAAGCAGACAAGATCCTTATTCTCCATGAGGGCTCCTCCT
ACTTCTATGGGACCTTCAGTGAGCTGCAGAATCTGCAGCCAGACTTCTCCTCAAAAC
TTATGGGCTGTGACTCCTTTGACCAATTCTCTGCAGAAAGAAGGAATAGCATACTGA
CAGAAACACTGCATAGATTCTCCCTGGAAGGAGATGCCCCAGTGAGTTGGACAGAA
ACCAAAAAGCAGAGCTTCAAGCAGACTGGTGAGTTTGGTGAAAAGAGGAAGAATTC
TATCCTGAACCCCATCAATAGCATCAGGAAATTTAGCATAGTCCAAAAGACCCCCCT
CCAGATGAATGGAATAGAGGAGGATAGTGATGAGCCTCTTGAGAGAAGGCTGTCCC
TGGTTCCAGACAGTGAACAGGGTGAAGCCATTCTTCCGAGGATCAGTGTCATCTCCA
CTGGGCCCACATTGCAGGCCAGAAGAAGACAGTCTGTTCTGAATTTGATGACACATT
CTGTGAATCAAGGCCAGAATATCCATAGAAAAACCACTGCCAGCACCAGAAAAGTT
TCTCTAGCCCCCCAGGCTAACCTGACTGAGTTAGACATCTACAGCAGAAGGCTGAGC
CAAGAGACTGGCTTGGAAATATCTGAGGAGATCAATGAGGAGGACCTCAAGGAGTG
CTTCTTTGATGACATGGAGTCAATCCCTGCAGTCACTACATGGAACACTTACCTAAG
GTACATCACAGTTCATAAGAGCCTCATCTTTGTCCTCATATGGTGTCTGGTCATCTTT
TTAGCAGAAGTGGCTGCCAGCCTAGTTGTGCTGTGGTTACTGGGCAATACACCTCTT
CAGGACAAAGGCAATAGCACACACAGCAGAAACAACTCCTATGCAGTGATCATCAC
CTCTACAAGCTCTTACTATGTATTCTATATATATGTGGGAGTGGCAGATACTCTCCTG
GCCATGGGATTCTTCAGGGGATTACCTCTAGTTCACACATTGATCACAGTGTCAAAA
ATTCTCCACCACAAGATGTTACACAGTGTCCTGCAAGCCCCAATGTCTACTCTGAAC
ACACTTAAGGCAGGTGGAATTTTGAATAGGTTTAGCAAGGACATAGCTATCCTGGAT
GATCTCCTCCCTCTGACCATCTTTGACTTCATCCAGTTACTGCTCATTGTAATTGGAG
CCATTGCAGTGGTAGCAGTCCTACAGCCTTACATTTTTGTGGCTACTGTTCCTGTTAT
TGTGGCCTTCATTATGCTAAGAGCTTACTTCCTGCAAACAAGCCAACAGTTGAAACA
GCTAGAAAGTGAGGGAAGGTCCCCCATCTTCACCCACCTGGTGACATCACTCAAGG
GGCTATGGACTCTTAGGGCTTTTGGGAGACAGCCGTACTTTGAGACCTTATTCCATA
AGGCCCTTAACCTCCATACAGCAAACTGGTTCTTATACCTGAGTACTCTGAGGTGGT
TTCAAATGAGGATTGAAATGATTTTTGTGATCTTCTTCATTGCTGTGACCTTCATCTC
AATCTTGACCACAGGAGAGGGGGAGGGCAGGGTGGGCATCATACTGACCTTGGCCA
TGAACATTATGTCAACCCTGCAGTGGGCTGTCAATAGCTCCATTGATGTGGACAGTC
TGATGAGGAGTGTCTCCAGGGTCTTCAAGTTTATTGACATGCCAACTGAGGGCAAAC
CCACCAAAAGCACTAAGCCATATAAAAATGGCCAACTGTCCAAAGTGATGATCATT
GAAAATTCACATGTAAAGAAGGATGATATCTGGCCCTCTGGAGGACAGATGACAGT
GAAAGACCTGACTGCCAAGTACACAGAGGGTGGTAATGCCATTCTTGAGAACATTA
GTTTCAGTATTTCCCCGGGGCAAAGGGTGGGCCTCCTTGGCAGAACAGGCTCTGGCA
AGAGTACCCTGCTGTCAGCCTTTTTAAGACTGTTGAACACTGAGGGAGAAATTCAGA
TTGATGGTGTCTCCTGGGATAGCATCACCCTCCAGCAGTGGAGAAAAGCTTTTGGAG
TGATCCCGCAAAAGGTTTTCATCTTTTCAGGCACCTTCCGGAAGAACCTGGACCCCT
ATGAGCAGTGGTCTGACCAGGAAATATGGAAGGTAGCTGATGAAGTTGGGCTTAGG
TCAGTCATAGAGCAGTTCCCAGGCAAACTGGACTTTGTCCTGGTGGATGGTGGATGT
GTACTGAGTCATGGGCACAAACAGCTGATGTGCCTAGCCAGGTCTGTGCTCAGCAA
GGCAAAGATATTGCTGCTTGATGAACCCAGTGCCCATCTGGACCCAGTCACATATCA
GATCATCAGAAGAACATTGAAGCAGGCCTTTGCTGATTGCACAGTTATCCTCTGTGA
GCACAGGATTGAGGCCATGCTGGAGTGCCAGCAGTTTCTGGTGATTGAGGAGAATA
AAGTAAGGCAGTATGACTCCATCCAGAAGCTGCTCAATGAAAGAAGCCTCTTTAGA
CAAGCTATCTCCCCCTCAGACAGGGTCAAATTGTTCCCTCACAGAAACAGCAGCAA
GTGCAAGAGCAAGCCCCAAATTGCAGCCTTGAAAGAGGAGACAGAGGAAGAGGTG
CAGGACACCAGACTCTGA (SEQ ID NO: 35)

ATGCAGAGAAGCCCCCTGGAGAAGGCCAGCGTGGTGAGCAAGCTGTTCTTCAGCTG
GACCAGACCCATCCTGAGAAAGGGCTACAGACAGAGACTGGAGCTGAGCGACATCT
ACCAGATCCCCAGCGTGGACAGCGCCGACAACCTGAGCGAGAAGCTGGAGAGAGA
GTGGGACAGAGAGCTGGCCAGCAAGAAGAACCCCAAGCTGATCAACGCCCTGAGA
AGATGCTTCTTCTGGAGATTCATGTTCTACGGCATCTTCCTGTACCTGGGCGAGGTG
ACCAAGGCCGTGCAGCCCCTGCTGCTGGGCAGAATCATCGCCAGCTACGACCCCGA
CAACAAGGAGGAGAGAAGCATCGCCATCTACCTGGGCATCGGCCTGTGCCTGCTGT
TCATCGTGAGAACCCTGCTGCTGCACCCCGCCATCTTCGGCCTGCACCACATCGGCA
TGCAGATGAGAATCGCCATGTTCAGCCTGATCTACAAGAAGACCCTGAAGCTGAGC
AGCAGAGTGCTGGACAAGATCAGCATCGGCCAGCTGGTGAGCCTGCTGAGCAACAA
CCTGAACAAGTTCGACGAGGGCCTGGCCCTGGCCCACTTCGTGTGGATCGCCCCCCT

-continued

GCAGGTGGCCCTGCTGATGGGCCTGATCTGGGAGCTGCTGCAGGCCAGCGCCTTCTG
CGGCCTGGGCTTCCTGATCGTGCTGGCCCTGTTCCAGGCCGGCCTGGGCAGAATGAT
GATGAAGTACAGAGACCAGAGAGCCGGCAAGATCAGCGAGAGACTGGTGATCACC
AGCGAGATGATCGAGAACATCCAGAGCGTGAAGGCCTACTGCTGGGAGGAGGCCAT
GGAGAAGATGATCGAGAACCTGAGACAGACCGAGCTGAAGCTGACCAGAAAGGCC
GCCTACGTGAGATACTTCAACAGCAGCGCCTTCTTCTTCAGCGGCTTCTTCGTGGTGT
TCCTGAGCGTGCTGCCCTACGCCCTGATCAAGGGCATCATCCTGAGAAAGATCTTCA
CCACCATCAGCTTCTGCATCGTGCTGAGAATGGCCGTGACCAGACAGTTCCCCTGGG
CCGTGCAGACCTGGTACGACAGCCTGGGCGCCATCAACAAGATCCAGGACTTCCTG
CAGAAGCAGGAGTACAAGACCCTGGAGTACAACCTGACCACCACCGAGGTGGTGAT
GGAGAACGTGACCGCCTTCTGGGAGGAGGGCTTCGGCGAGCTGTTCGAGAAGGCCA
AGCAGAACAACAACAACAGAAAGACCAGCAACGGCGACGACAGCCTGTTCTTCAGC
AACTTCAGCCTGCTGGGCACCCCCGTGCTGAAGGACATCAACTTCAAGATCGAGAG
AGGCCAGCTGCTGGCCGTGGCCGGCAGCACCGGCGCCGGCAAGACCAGCCTGCTGA
TGGTGATCATGGGCGAGCTGGAGCCCAGCGAGGGCAAGATCAAGCACAGCGGCAG
AATCAGCTTCTGCAGCCAGTTCAGCTGGATCATGCCCGGCACCATCAAGGAGAACA
TCATCTTCGGCGTGAGCTACGACGAGTACAGATACAGAAGCGTGATCAAGGCCTGC
CAGCTGGAGGAGGACATCAGCAAGTTCGCCGAGAAGGACAACATCGTGCTGGGCGA
GGGCGGCATCACCCTGAGCGGCGGCCAGAGAGCCAGAATCAGCCTGGCCAGAGCCG
TGTACAAGGACGCCGACCTGTACCTGCTGGACAGCCCCTTCGGCTACCTGGACGTGC
TGACCGAGAAGGAGATCTTCGAGAGCTGCGTGTGCAAGCTGATGGCCAACAAGACC
AGAATCCTGGTGACCAGCAAGATGGAGCACCTGAAGAAGGCCGACAAGATCCTGAT
CCTGCACGAGGGCAGCAGCTACTTCTACGGCACCTTCAGCGAGCTGCAGAACCTGC
AGCCCGACTTCAGCAGCAAGCTGATGGGCTGCGACAGCTTCGACCAGTTCAGCGCC
GAGAGAAGAAACAGCATCCTGACCGAGACCCTGCACAGATTCAGCCTGGAGGGCGA
CGCCCCCGTGAGCTGGACCGAGACCAAGAAGCAGAGCTTCAAGCAGACCGGCGAGT
TCGGCGAGAAGAGAAAGAACAGCATCCTGAACCCCATCAACAGCATCAGAAAGTTC
AGCATCGTGCAGAAGACCCCCCTGCAGATGAACGGCATCGAGGAGGACAGCGACG
AGCCCCTGGAGAGAAGACTGAGCCTGGTGCCCGACAGCGAGCAGGGCGAGGCCATC
CTGCCCAGAATCAGCGTGATCAGCACCGGCCCCACCCTGCAGGCCAGAAGAAGACA
GAGCGTGCTGAACCTGATGACCCACAGCGTGAACCAGGGCCAGAACATCCACAGAA
AGACCACCGCCAGCACCAGAAAGGTGAGCCTGGCCCCCCAGGCCAACCTGACCGAG
CTGGACATCTACAGCAGAAGACTGAGCCAGGAGACCGGCCTGGAGATCAGCGAGG
AGATCAACGAGGAGGACCTGAAGGAGTGCTTCTTCGACGACATGGAGAGCATCCCC
GCCGTGACCACCTGGAACACCTACCTGAGATACATCACCGTGCACAAGAGCCTGAT
CTTCGTGCTGATCTGGTGCCTGGTGATCTTCCTGGCCGAGGTGGCCGCCAGCCTGGT
GGTGCTGTGGCTGCTGGGCAACACCCCCCTGCAGGACAAGGGCAACAGCACCCACA
GCAGAAACAACAGCTACGCCGTGATCATCACCAGCACCAGCAGCTACTACGTGTTC
TACATCTACGTGGGCGTGGCCGACACCCTGCTGGCCATGGGCTTCTTCAGAGGCCTG
CCCCTGGTGCACACCCTGATCACCGTGAGCAAGATCCTGCACCACAAGATGCTGCAC
AGCGTGCTGCAGGCCCCCATGAGCACCCTGAACACCCTGAAGGCCGGCGGCATCCT
GAACAGATTCAGCAAGGACATCGCCATCCTGGACGACCTGCTGCCCCTGACCATCTT
CGACTTCATCCAGCTGCTGCTGATCGTGATCGGCGCCATCGCCGTGGTGGCCGTGCT
GCAGCCCTACATCTTCGTGGCCACCGTGCCCGTGATCGTGGCCTTCATCATGCTGAG
AGCCTACTTCCTGCAGACCAGCCAGCAGCTGAAGCAGCTGGAGAGCGAGGGCAGAA
GCCCCATCTTCACCCACCTGGTGACCAGCCTGAAGGGCCTGTGGACCCTGAGAGCCT
TCGGCAGACAGCCCTACTTCGAGACCCTGTTCCACAAGGCCCTGAACCTGCACACCG
CCAACTGGTTCCTGTACCTGAGCACCCTGAGATGGTTCCAGATGAGAATCGAGATGA
TCTTCGTGATCTTCTTCATCGCCGTGACCTTCATCAGCATCCTGACCACCGGCGAGG
GCGAGGGCAGAGTGGGCATCATCCTGACCCTGGCCATGAACATCATGAGCACCCTG
CAGTGGGCCGTGAACAGCAGCATCGACGTGGACAGCCTGATGAGAAGCGTGAGCAG
AGTGTTCAAGTTCATCGACATGCCCACCGAGGGCAAGCCCACCAAGAGCACCAAGC
CCTACAAGAACGGCCAGCTGAGCAAGGTGATGATCATCGAGAACAGCCACGTGAAG
AAGGACGACATCTGGCCCAGCGGCGGCCAGATGACCGTGAAGGACCTGACCGCCAA
GTACACCGAGGGCGGCAACGCCATCCTGGAGAACATCAGCTTCAGCATCAGCCCCG
GCCAGAGAGTGGGCCTGCTGGGCAGAACCGGCAGCGGCAAGAGCACCCTGCTGAGC
GCCTTCCTGAGACTGCTGAACACCGAGGGCGAGATCCAGATCGACGGCGTGAGCTG
GGACAGCATCACCCTGCAGCAGTGGAGAAAGGCCTTCGGCGTGATCCCCCAGAAGG
TGTTCATCTTCAGCGGCACCTTCAGAAAGAACCTGGACCCCTACGAGCAGTGGAGC
GACCAGGAGATCTGGAAGGTGGCCGACGAGGTGGGCCTGAGAAGCGTGATCGAGC
AGTTCCCCGGCAAGCTGGACTTCGTGCTGGTGGACGGCGGCTGCGTGCTGAGCCAC
GGCCACAAGCAGCTGATGTGCCTGGCCAGAAGCGTGCTGAGCAAGGCCAAGATCCT
GCTGCTGGACGAGCCCAGCGCCCACCTGGACCCCGTGACCTACCAGATCATCAGAA
GAACCCTGAAGCAGGCCTTCGCCGACTGCACCGTGATCCTGTGCGAGCACAGAATC
GAGGCCATGCTGGAGTGCCAGCAGTTCCTGGTGATCGAGGAGAACAAGGTGAGACA
GTACGACAGCATCCAGAAGCTGCTGAACGAGAGAAGCCTGTTCAGACAGGCCATCA
GCCCCAGCGACAGAGTGAAGCTGTTCCCCCACAGAAACAGCAGCAAGTGCAAGAGC
AAGCCCCAGATCGCCGCCCTGAAGGAGGAGACCGAGGAGGAGGTGCAGGACACCA
GACTGTGA (SEQ ID NO: 36)

ATGCAGCGCAGCCCCCTGGAGAAGGCCAGCGTGGTGAGCAAGCTGTTCTTCAGCTG
GACCCGCCCCATCCTGCGCAAGGGCTACCGCCAGCGCCTGGAGCTGAGCGACATCT
ACCAGATCCCCAGCGTGGACAGCGCCGACAACCTGAGCGAGAAGCTGGAGCGCGA
GTGGGACCGCGAGCTGGCCAGCAAGAAGAACCCCAAGCTGATCAACGCCCTGCGCC
GCTGCTTCTTCTGGCGCTTCATGTTCTACGGCATCTTCCTGTACCTGGGCGAGGTGAC
CAAGGCCGTGCAGCCCCTGCTGCTGGGCCGCATCATCGCCAGCTACGACCCCGACA
ACAAGGAGGAGCGCAGCATCGCCATCTACCTGGGCATCGGCCTGTGCCTGCTGTTCA
TCGTGCGCACCCTGCTGCTGCACCCCGCCATCTTCGGCCTGCACCACATCGGCATGC
AGATGCGCATCGCCATGTTCAGCCTGATCTACAAGAAGACCCTGAAGCTGAGCAGC
CGCGTGCTGGACAAGATCAGCATCGGCCAGCTGGTGAGCCTGCTGAGCAACAACCT

-continued
GAACAAGTTCGACGAGGGCCTGGCCCTGGCCCACTTCGTGTGGATCGCCCCCCTGCA
GGTGGCCCTGCTGATGGGCCTGATCTGGGAGCTGCTGCAGGCCAGCGCCTTCTGCGG
CCTGGGCTTCCTGATCGTGCTGGCCCTGTTCCAGGCCGGCCTGGGCCGCATGATGAT
GAAGTACCGCGACCAGCGCGCCGGCAAGATCAGCGAGCGCCTGGTGATCACCAGCG
AGATGATCGAGAACATCCAGAGCGTGAAGGCCTACTGCTGGGAGGAGGCCATGGAG
AAGATGATCGAGAACCTGCGCCAGACCGAGCTGAAGCTGACCCGCAAGGCCGCCTA
CGTGCGCTACTTCAACAGCAGCGCCTTCTTCTTCAGCGGCTTCTTCGTGGTGTTCCTG
AGCGTGCTGCCCTACGCCCTGATCAAGGGCATCATCCTGCGCAAGATCTTCACCACC
ATCAGCTTCTGCATCGTGCTGCGCATGGCCGTGACCCGCCAGTTCCCCTGGGCCGTG
CAGACCTGGTACGACAGCCTGGGCGCCATCAACAAGATCCAGGACTTCCTGCAGAA
GCAGGAGTACAAGACCCTGGAGTACAACCTGACCACCACCGAGGTGGTGATGGAGA
ACGTGACCGCCTTCTGGGAGGAGGGCTTCGGCGAGCTGTTCGAGAAGGCCAAGCAG
AACAACAACAACCGCAAGACCAGCAACGGCGACGACAGCCTGTTCTTCAGCAACTT
CAGCCTGCTGGGCACCCCCGTGCTGAAGGACATCAACTTCAAGATCGAGCGCGGCC
AGCTGCTGGCCGTGGCCGGCAGCACCGGCGCCGGCAAGACCAGCCTGCTGATGGTG
ATCATGGGCGAGCTGGAGCCCAGCGAGGGCAAGATCAAGCACAGCGGCCGCATCA
GCTTCTGCAGCCAGTTCAGCTGGATCATGCCCGGCACCATCAAGGAGAACATCATCT
TCGGCGTGAGCTACGACGAGTACCGCTACCGCAGCGTGATCAAGGCCTGCCAGCTG
GAGGAGGACATCAGCAAGTTCGCCGAGAAGGACAACATCGTGCTGGGCGAGGGCG
GCATCACCCTGAGCGGCGGCCAGCGCGCCCGCATCAGCCTGGCCCGCGCCGTGTAC
AAGGACGCCGACCTGTACCTGCTGGACAGCCCCTTCGGCTACCTGGACGTGCTGACC
GAGAAGGAGATCTTCGAGAGCTGCGTGTGCAAGCTGATGGCCAACAAGACCCGCAT
CCTGGTGACCAGCAAGATGGAGCACCTGAAGAAGGCCGACAAGATCCTGATCCTGC
ACGAGGGCAGCAGCTACTTCTACGGCACCTTCAGCGAGCTGCAGAACCTGCAGCCC
GACTTCAGCAGCAAGCTGATGGGCTGCGACAGCTTCGACCAGTTCAGCGCCGAGCG
CCGCAACAGCATCCTGACCGAGACCCTGCACCGCTTCAGCCTGGAGGGCGACGCCC
CCGTGAGCTGGACCGAGACCAAGAAGCAGAGCTTCAAGCAGACCGGCGAGTTCGGC
GAGAAGCGCAAGAACAGCATCCTGAACCCCATCAACAGCATCCGCAAGTTCAGCAT
CGTGCAGAAGACCCCCCTGCAGATGAACGGCATCGAGGAGGACAGCGACGAGCCCC
TGGAGCGCCGCCTGAGCCTGGTGCCCGACAGCGAGCAGGGCGAGGCCATCCTGCCC
CGCATCAGCGTGATCAGCACCGGCCCCACCCTGCAGGCCCGCCGCCGCCAGAGCGT
GCTGAACCTGATGACCCACAGCGTGAACCAGGGCCAGAACATCCACCGCAAGACCA
CCGCCAGCACCCGCAAGGTGAGCCTGGCCCCCCAGGCCAACCTGACCGAGCTGGAC
ATCTACAGCCGCCGCCTGAGCCAGGAGACCGGCCTGGAGATCAGCGAGGAGATCAA
CGAGGAGGACCTGAAGGAGTGCTTCTTCGACGACATGGAGAGCATCCCCGCCGTGA
CCACCTGGAACACCTACCTGCGCTACATCACCGTGCACAAGAGCCTGATCTTCGTGC
TGATCTGGTGCCTGGTGATCTTCCTGGCCGAGGTGGCCGCCAGCCTGGTGGTGCTGT
GGCTGCTGGGCAACACCCCCCTGCAGGACAAGGGCAACAGCACCCACAGCCGCAAC
AACAGCTACGCCGTGATCATCACCAGCACCAGCAGCTACTACGTGTTCTACATCTAC
GTGGGCGTGGCCGACACCCTGCTGGCCATGGGCTTCTTCCGCGGCCTGCCCCTGGTG
CACACCCTGATCACCGTGAGCAAGATCCTGCACCACAAGATGCTGCACAGCGTGCT
GCAGGCCCCCATGAGCACCCTGAACACCCTGAAGGCCGGCGGCATCCTGAACCGCT
TCAGCAAGGACATCGCCATCCTGGACGACCTGCTGCCCCTGACCATCTTCGACTTCA
TCCAGCTGCTGCTGATCGTGATCGGCGCCATCGCCGTGGTGGCCGTGCTGCAGCCCT
ACATCTTCGTGGCCACCGTGCCCGTGATCGTGGCCTTCATCATGCTGCGCGCCTACTT
CCTGCAGACCAGCCAGCAGCTGAAGCAGCTGGAGAGCGAGGGCCGCAGCCCCATCT
TCACCCACCTGGTGACCAGCCTGAAGGGCCTGTGGACCCTGCGCGCCTTCGGCCGCC
AGCCCTACTTCGAGACCCTGTTCCACAAGGCCCTGAACCTGCACACCGCCAACTGGT
TCCTGTACCTGAGCACCCTGCGCTGGTTCCAGATGCGCATCGAGATGATCTTCGTGA
TCTTCTTCATCGCCGTGACCTTCATCAGCATCCTGACCACCGGCGAGGGCGAGGGCC
GCGTGGGCATCATCCTGACCCTGGCCATGAACATCATGAGCACCCTGCAGTGGGCC
GTGAACAGCAGCATCGACGTGGACAGCCTGATGCGCAGCGTGAGCCGCGTGTTCAA
GTTCATCGACATGCCCACCGAGGGCAAGCCCACCAAGAGCACCAAGCCCTACAAGA
ACGGCCAGCTGAGCAAGGTGATGATCATCGAGAACAGCCACGTGAAGAAGGACGA
CATCTGGCCCAGCGGCGGCCAGATGACCGTGAAGGACCTGACCGCCAAGTACACCG
AGGGCGGCAACGCCATCCTGGAGAACATCAGCTTCAGCATCAGCCCCGGCCAGCGC
GTGGGCCTGCTGGGCCGCACCGGCAGCGGCAAGAGCACCCTGCTGAGCGCCTTCCT
GCGCCTGCTGAACACCGAGGGCGAGATCCAGATCGACGGCGTGAGCTGGGACAGCA
TCACCCTGCAGCAGTGGCGCAAGGCCTTCGGCGTGATCCCCCAGAAGGTGTTCATCT
TCAGCGGCACCTTCCGCAAGAACCTGGACCCCTACGAGCAGTGGAGCGACCAGGAG
ATCTGGAAGGTGGCCGACGAGGTGGGCCTGCGCAGCGTGATCGAGCAGTTCCCCGG
CAAGCTGGACTTCGTGCTGGTGGACGGCGGCTGCGTGCTGAGCCACGGCCACAAGC
AGCTGATGTGCCTGGCCCGCAGCGTGCTGAGCAAGGCCAAGATCCTGCTGCTGGAC
GAGCCCAGCGCCCACCTGGACCCCGTGACCTACCAGATCATCCGCCGCACCCTGAA
GCAGGCCTTCGCCGACTGCACCGTGATCCTGTGCGAGCACCGCATCGAGGCCATGCT
GGAGTGCCAGCAGTTCCTGGTGATCGAGGAGAACAAGGTGCGCCAGTACGACAGCA
TCCAGAAGCTGCTGAACGAGCGCAGCCTGTTCCGCCAGGCCATCAGCCCCAGCGAC
CGCGTGAAGCTGTTCCCCCACCGCAACAGCAGCAAGTGCAAGAGCAAGCCCCAGAT
CGCCGCCCTGAAGGAGGAGACCGAGGAGGAGGTGCAGGACACCCGCCTGTAA (SEQ ID NO: 37)
ATGCAGAGAAGCCCCCTGGAGAAGGCCAGCGTGGTGAGCAAGCTGTTCTTCAGCTG
GACCAGACCCATCCTGAGAAAGGGCTACAGACAGAGACTGGAGCTGAGCGACATCT
ACCAGATCCCCAGCGTGGACAGCGCCGACAACCTGAGCGAGAAGCTGGAGAGAGA
GTGGGACAGAGAGCTGGCCAGCAAGAAGAACCCCAAGCTGATCAACGCCCTGAGA
AGATGCTTCTTCTGGAGATTCATGTTCTACGGCATCTTCCTGTACCTGGGCGAGGTG
ACCAAGGCCGTGCAGCCCCTGCTGCTGGGCAGAATCATCGCCAGCTACGACCCCGA
CAACAAGGAGGAGAGAAGCATCGCCATCTACCTGGGCATCGGCCTGTGCCTGCTGT
TCATCGTGAGAACCCTGCTGCTGCACCCCGCCATCTTCGGCCTGCACCACATCGGCA
TGCAGATGAGAATCGCCATGTTCAGCCTGATCTACAAGAAGACCCTGAAGCTGAGC
AGCAGAGTGCTGGACAAGATCAGCATCGGCCAGCTGGTGAGCCTGCTGAGCAACAA -continued CCTGAACAAGTTCGACGAGGGCCTGGCCCTGGCCCACTTCGTGTGGATCGCCCCCCT
GCAGGTGGCCCTGCTGATGGGCCTGATCTGGGAGCTGCTGCAGGCCAGCGCCTTCTG
CGGCCTGGGCTTCCTGATCGTGCTGGCCCTGTTCCAGGCCGGCCTGGGCAGAATGAT
GATGAAGTACAGGGACCAGAGAGCCGGCAAGATCAGCGAGAGACTGGTGATCACC
AGCGAGATGATCGAGAACATCCAGAGCGTGAAGGCCTACTGCTGGGAGGAGGCCAT
GGAGAAGATGATCGAGAACCTGAGACAGACCGAGCTGAAGCTGACCAGAAAGGCC
GCCTACGTGAGATACTTCAACAGCAGCGCCTTCTTCTTCAGCGGCTTCTTCGTGGTGT
TCCTGAGCGTGCTGCCCTACGCCCTGATCAAGGGCATCATCCTGAGAAAGATCTTCA
CCACCATCAGCTTCTGCATCGTGCTGAGAATGGCCGTGACCAGACAGTTCCCCTGGG
CCGTGCAGACCTGGTACGACAGCCTGGGCGCCATCAACAAGATCCAGGACTTCCTG
CAGAAGCAGGAGTACAAGACCCTGGAGTACAACCTGACCACCACCGAGGTGGTGAT
GGAGAACGTGACCGCCTTCTGGGAGGAGGGCTTCGGCGAGCTGTTCGAGAAGGCCA
AGCAGAACAACAACAACAGAAAGACCAGCAACGGCGACGACAGCCTGTTCTTCAGC
AACTTCAGCCTGCTGGGCACCCCCGTGCTGAAGGACATCAACTTCAAGATCGAGAG
AGGCCAGCTGCTGGCCGTGGCCGGCAGCACCGGCGCCGGCAAGACCAGCCTGCTGA
TGGTGATCATGGGCGAGCTGGAGCCCAGCGAGGGCAAGATCAAGCACAGCGGCAG
AATCAGCTTCTGCAGCCAGTTCAGCTGGATCATGCCCGGCACCATCAAGGAGAACA
TCATCTTCGGCGTGAGCTACGACGAGTACAGATACAGAAGCGTGATCAAGGCCTGC
CAGCTGGAGGAGGACATCAGCAAGTTCGCCGAGAAGGACAACATCGTGCTGGGCGA
GGGCGGCATCACCCTGAGCGGCGGCCAGAGAGCCAGAATCAGCCTGGCCAGAGCCG
TGTACAAGGACGCCGACCTGTACCTGCTGGACAGCCCCTTCGGCTACCTGGACGTGC
TGACCGAGAAGGAGATCTTCGAGAGCTGCGTGTGCAAGCTGATGGCCAACAAGACC
AGAATCCTGGTGACCAGCAAGATGGAGCACCTGAAGAAGGCCGACAAGATCCTGAT
CCTGCACGAGGGCAGCAGCTACTTCTACGGCACCTTCAGCGAGCTGCAGAACCTGC
AGCCCGACTTCAGCAGCAAGCTGATGGGCTGCGACAGCTTCGACCAGTTCAGCGCC
GAGAGAAGAAACAGCATCCTGACCGAGACCCTGCACAGATTCAGCCTGGAGGGCGA
CGCCCCCGTGAGCTGGACCGAGACCAAGAAGCAGAGCTTCAAGCAGACCGGCGAGT
TCGGCGAGAAGAGAAAGAACAGCATCCTGAACCCCATCAACAGCATCAGAAAGTTC
AGCATCGTGCAGAAGACCCCCCTGCAGATGAACGGCATCGAGGAGGACAGCGACG
AGCCCCTGGAGAGAAGACTGAGCCTGGTGCCCGACAGCGAGCAGGGCGAGGCCATC
CTGCCCAGAATCAGCGTGATCAGCACCGGCCCCACCCTGCAGGCCAGAAGAAGACA
GAGCGTGCTGAACCTGATGACCCACAGCGTGAACCAGGGCCAGAACATCCACAGAA
AGACCACCGCCAGCACCAGAAAGGTGAGCCTGGCCCCCCAGGCCAACCTGACCGAG
CTGGACATCTACAGCAGAAGACTGAGCCAGGAGACCGGCCTGGAGATCAGCGAGG
AGATCAACGAGGAGGACCTGAAGGAGTGCTTCTTCGACGACATGGAGAGCATCCCC
GCCGTGACCACCTGGAACACCTACCTGAGATACATCACCGTGCACAAGAGCCTGAT
CTTCGTGCTGATCTGGTGCCTGGTGATCTTCCTGGCCGAGGTGGCCGCCAGCCTGGT
GGTGCTGTGGCTGCTGGGCAACACCCCCCTGCAGGACAAGGGCAACAGCACCCACA
GCAGAAACAACAGCTACGCCGTGATCATCACCAGCACCAGCAGCTACTACGTGTTC
TACATCTACGTGGGCGTGGCCGACACCCTGCTGGCCATGGGCTTCTTCAGAGGCCTG
CCCCTGGTGCACACCCTGATCACCGTGAGCAAGATCCTGCACCACAAGATGCTGCAC
AGCGTGCTGCAGGCCCCCATGAGCACCCTGAACACCCTGAAGGCCGGCGGCATCCT
GAACAGATTCAGCAAGGACATCGCCATCCTGGACGACCTGCTGCCCCTGACCATCTT
CGACTTCATCCAGCTGCTGCTGATCGTGATCGGCGCCATCGCCGTGGTGGCCGTGCT
GCAGCCCTACATCTTCGTGGCCACCGTGCCCGTGATCGTGGCCTTCATCATGCTGAG
AGCCTACTTCCTGCAGACCAGCCAGCAGCTGAAGCAGCTGGAGAGCGAGGGCAGGA
GCCCCATCTTCACCCACCTGGTGACCAGCCTGAAGGGCCTGTGGACCCTGAGAGCCT
TCGGCAGACAGCCCTACTTCGAGACCCTGTTCCACAAGGCCCTGAACCTGCACACCG
CCAACTGGTTCCTGTACCTGAGCACCCTGAGATGGTTCCAGATGAGAATCGAGATGA
TCTTCGTGATCTTCTTCATCGCCGTGACCTTCATCAGCATCCTGACCACCGGCGAGG
GCGAGGGCAGAGTGGGCATCATCCTGACCCTGGCCATGAACATCATGAGCACCCTG
CAGTGGGCCGTGAACAGCAGCATCGACGTGGACAGCCTGATGAGAAGCGTGAGCAG
AGTGTTCAAGTTCATCGACATGCCCACCGAGGGCAAGCCCACCAAGAGCACCAAGC
CCTACAAGAACGGCCAGCTGAGCAAGGTGATGATCATCGAGAACAGCCACGTGAAG
AAGGACGACATCTGGCCCAGCGGCGGCCAGATGACCGTGAAGGACCTGACCGCCAA
GTACACCGAGGGCGGCAACGCCATCCTGGAGAACATCAGCTTCAGCATCAGCCCCG
GCCAGAGAGTGGGCCTGCTGGGCAGAACCGGCAGCGGCAAGAGCACCCTGCTGAGC
GCCTTCCTGAGACTGCTGAACACCGAGGGCGAGATCCAGATCGACGGCGTGAGCTG
GGACAGCATCACCCTGCAGCAGTGGAGAAAGGCCTTCGGCGTGATCCCCCAGAAGG
TGTTCATCTTCAGCGGCACCTTCAGAAAGAACCTGGACCCCTACGAGCAGTGGAGC
GACCAGGAGATCTGGAAGGTGGCCGACGAGGTGGGCCTGAGAAGCGTGATCGAGC
AGTTCCCCGGCAAGCTGGACTTCGTGCTGGTGGACGGCGGCTGCGTGCTGAGCCAC
GGCCACAAGCAGCTGATGTGCCTGGCCAGAAGCGTGCTGAGCAAGGCCAAGATCCT
GCTGCTGGACGAGCCCAGCGCCCACCTGGACCCCGTGACCTACCAGATCATCAGAA
GAACCCTGAAGCAGGCCTTCGCCGACTGCACCGTGATCCTGTGCGAGCACAGAATC
GAGGCCATGCTGGAGTGCCAGCAGTTCCTGGTGATCGAGGAGAACAAGGTGAGACA
GTACGACAGCATCCAGAAGCTGCTGAACGAGAGAAGCCTGTTCAGACAGGCCATCA
GCCCCAGCGACAGAGTGAAGCTGTTCCCCCACAGAAACAGCAGCAAGTGCAAGAGC
AAGCCCCAGATCGCCGCCCTGAAGGAGGAGACCGAGGAGGAGGTGCAGGACACCA
GACTGTGA (SEQ ID NO: 38)

ATGCAGAGGTCACCTCTGGAAAAGGCTAGCGTGGTCAGCAAGCTATTTTTTTCCTGG
ACCCGCCCGATACTCAGGAAGGGCTACCGACAGCGGCTGGAGCTGAGTGACATTTA
TCAGATTCCCTCCGTCGATTCCGCTGACAACCTGTCTGAGAAACTGGAGCGGGAATG
GGATAGGGAACTGGCGTCCAAAAAAAACCCCAAACTCATCAATGCACTCCGCAGAT
GCTTCTTCTGGCGGTTTATGTTTTATGGCATATTCCTGTATCTGGGGGAGGTGACGAA
AGCCGTGCAGCCGCTGCTGCTTGGTCGCATTATCGCGTCATACGATCCAGATAACAA
GGAGGAAAGAAGTATCGCTATCTATCTCGGGATAGGGCTGTGCCTGCTCTTCATTGT
GCGGACTCTTCTCTTGCACCCCGCCATTTTCGGTCTGCATCATATAGGTATGCAGATG
AGAATTGCGATGTTCTCATTGATTTACAAAAAAACGCTTAAGCTAAGTTCAAGGGTG

-continued

CTAGATAAGATATCGATCGGCCAGCTGGTGTCTCTGCTTAGCAACAACCTCAATAAA
TTCGACGAAGGCCTTGCACTGGCCCACTTCGTGTGGATCGCCCCTCTGCAGGTGGCT
CTGCTGATGGGGTTAATATGGGAGCTGTTGCAGGCCTCCGCTTTTTGTGGCCTGGGG
TTTCTCATCGTGTTGGCCTTGTTTCAGGCAGGGCTGGGACGTATGATGATGAAATAT
AGGGATCAGAGGGCTGGCAAAATCTCTGAGCGCCTGGTTATTACGAGTGAAATGAT
TGAGAACATCCAGTCAGTGAAGGCCTATTGCTGGGAGGAGGCCATGGAAAAAATGA
TTGAGAACCTACGCCAGACTGAGCTGAAGTTAACCAGAAAAGCCGCCTATGTGCGC
TACTTTAACAGTAGCGCATTTTTCTTCTCCGGTTTTTTCGTGGTGTTTCTTAGTGTGTT
GCCGTATGCCTTAATCAAGGGAATAATACTCCGGAAGATTTTCACTACCATCAGCTT
CTGTATCGTGTTGCGGATGGCCGTCACCCGGCAGTTTCCCTGGGCAGTACAGACTTG
GTACGATTCTCTCGGAGCAATTAACAAAATCCAAGACTTTCTACAAAAGCAGGAGT
ACAAGACCCTGGAGTACAATCTGACCACCACAGAAGTCGTAATGGAGAATGTAACT
GCCTTCTGGGAAGAGGGCTTTGGCGAACTCTTTGAAAAGGCCAAGCAGAACAATAA
CAACCGGAAGACCTCCAACGGGGACGACAGCTTATTTTTCAGCAATTTTTCTTTGCT
CGGGACCCCTGTACTGAAAGATATTAACTTTAAGATCGAGCGCGGACAACTCCTGGC
TGTCGCCGGCAGCACTGGAGCTGGAAAAACATCACTGCTTATGGTGATAATGGGAG
AACTCGAACCAAGCGAGGGAAAAATAAAGCACTCTGGACGGATTAGTTTTTGCTCC
CAGTTCTCGTGGATAATGCCTGGCACCATTAAGGAGAATATCATCTTTGGAGTGAGT
TACGACGAATACCGGTACCGGTCCGTTATCAAGGCTTGTCAACTCGAGGAGGACATT
TCTAAATTCGCCGAAAAAGATAATATAGTGCTGGGCGAAGGAGGCATTACACTGAG
CGGGGGTCAGAGAGCTCGAATTAGCCTCGCCCGAGCAGTCTATAAAGACGCCGATC
TTTACCTGCTGGATTCCCCTTTTGGGTATTTGGATGTTCTGACAGAGAAGGAAATCTT
TGAATCATGTGTCTGTAAACTGATGGCCAATAAGACTAGGATTCTAGTGACTTCGAA
AATGGAGCACCTGAAAAAAGCGGACAAAATTCTGATACTCCATGAAGGGTCTTCCT
ACTTCTACGGCACCTTCTCAGAGTTGCAGAACTTACAACCTGATTTTTCATCTAAGCT
TATGGGGTGCGACTCGTTTGACCAGTTCTCCGCTGAAAGACGAAACAGCATCTTAAC
GGAAACTCTTCACAGGTTCTCATTAGAGGGAGATGCGCCGGTGTCCTGGACAGAGA
CAAAAAAACAGTCTTTCAAACAGACAGGAGAGTTTGGCGAGAAGAGAAAAAACTC
AATCCTCAATCCCATCAATTCTATTAGAAAGTTTAGCATCGTCCAAAAAACACCATT
GCAGATGAATGGGATTGAGGAGGACAGTGATGAGCCTTTGGAACGAAGACTGTCCC
TGGTACCCGATAGCGAACAGGGTGAGGCCATCCTTCCTAGGATCTCGGTCATAAGTA
CAGGGCCCACACTGCAGGCCAGGCGACGTCAAAGTGTCCTCAATCTTATGACGCAC
AGTGTGAATCAGGGGCAGAACATCCATCGTAAGACGACAGCTTCAACTCGAAAGGT
CAGTCTAGCTCCACAAGCCAATCTTACAGAGCTGGACATTTATTCCCGCCGCCTCAG
TCAGGAGACCGGATTGGAAATATCAGAGGAAATTAATGAAGAGGATCTGAAGGAAT
GCTTCTTTGATGACATGGAATCGATCCCCGCTGTTACTACCTGGAACACATATCTGA
GATATATTACCGTCCATAAGAGCTTAATCTTTGTACTGATATGGTGCTTGGTGATTTT
CCTGGCAGAGGTTGCGGCGAGTTTGGTCGTGCTATGGCTCCTTGGAAACACTCCCCT
GCAGGATAAGGGGAACTCCACTCATAGCAGGAATAACAGCTATGCCGTGATCATCA
CCTCTACCTCCTCTTATTACGTGTTTTACATATACGTCGGTGTTGCGGATACCCTGTT
GGCAATGGGGTTCTTTAGAGGACTACCCCTAGTTCACACCCTGATCACCGTTTCGAA
GATCTTGCACCACAAGATGCTTCATAGCGTTCTCCAAGCTCCTATGAGCACCCTTAA
TACACTGAAAGCAGGAGGTATCCTTAACCGCTTTTCCAAAGACATCGCTATACTCGA
CGATTTGCTCCCATTGACCATCTTCGACTTCATTCAGCTGCTCCTCATTGTGATCGGC
GCCATTGCCGTGGTCGCAGTGTTACAGCCATATATTTTCGTAGCCACCGTGCCCGTC
ATCGTGGCATTTATCATGCTGCGCGCATATTTCTTACAGACATCTCAGCAACTGAAG
CAGCTGGAATCTGAGGGCAGATCTCCTATTTTTACACACCTGGTTACCAGCCTGAAG
GGCCTGTGGACCCTGCGTGCTTTCGGTCGCCAACCCTACTTTGAGACTCTCTTCCATA
AGGCTCTGAATTTACATACTGCCAATTGGTTCCTATACCTTAGTACCCTTCGGTGGTT
CCAGATGCGGATAGAAATGATCTTCGTGATTTTCTTCATCGCAGTCACTTTCATCTCT
ATTTTGACGACCGGTGAGGGCGAGGGCAGGGTGGGCATCATTCTGACTTTGGCCATG
AACATTATGTCAACACTCCAGTGGGCCGTTAATTCAAGCATTGATGTGGATTCCTTG
ATGCGTTCCGTCAGCAGGGTATTTAAATTCATAGACATGCCCACCGAGGGCAAGCCA
ACAAAATCTACCAAGCCATACAAAAATGGCCAACTAAGCAAGGTCATGATTATCGA
GAATTCTCATGTGAAAAAGGACGACATTTGGCCTTCCGGGGGTCAAATGACTGTAA
AGGACCTGACGGCTAAATACACTGAGGGCGGTAATGCTATCTTGGAGAACATCTCTT
TCAGCATCTCCCCTGGCCAGAGAGTGGGACTGCTCGGGCGGACAGGCTCCGGAAAG
TCTACGCTCCTTTCAGCATTCCTTAGACTTCTGAACACCGAAGGTGAGATTCAGATT
GACGGGGTCTCTTGGGACTCCATCACACTTCAGCAATGGAGGAAGGCATTCGGTGTA
ATCCCCCAAAAGGTTTTTATCTTCTCCGGAACATTTCGTAAGAATCTGGACCCGTAC
GAGCAGTGGTCAGATCAGGAGATCTGGAAAGTAGCAGACGAGGTCGGGCTACGGA
GCGTTATTGAACAGTTTCCTGGCAAACTGGACTTCGTTTTGGTGGACGGAGGCTGTG
TGCTGAGTCACGGCCATAAACAACTGATGTGCTTAGCTAGGTCTGTTCTCAGCAAGG
CAAAGATTTTACTGCTGGATGAACCAAGCGCCCACCTTGATCCAGTGACATATCAAA
TCATCAGAAGAACTCTTAAACAGGCGTTCGCCGACTGCACAGTGATCCTGTGTGAGC
ACAGAATAGAAGCCATGCTGGAATGTCAACAGTTTCTCGTGATTGAGGAGAACAAG
GTGCGCCAGTACGATAGCATCCAGAAGTTACTCAATGAAAGGTCACTCTTCAGGCA
GGCCATCTCACCCAGCGACCGCGTTAAGCTGTTTCCACACCGAAACAGTTCCAAGTG
CAAAAGTAAGCCACAGATTGCTGCACTGAAGGAAGAGACAGAAGAAGAAGTTCAG
GACACTCGGCTCTGA (SEQ ID NO: 39)

ATGCAGAGGAGCCCACTGGAGAAAGCCTCCGTGGTGAGTAAACTCTTTTTTAGTTGG
ACCAGACCCATCCTGCGAAAAGGATACAGGCAGCGCCTCGAGTTGTCAGATATCTA
CCAGATTCCTTCTGTGGACTCAGCTGACAATTTGAGTGAGAAGCTGGAGCGGGAGTG
GGATAGAGAGCTGGCGAGCAAAAAAAACCCCAAGCTTATCAATGCTCTGCGCCGCT
GCTTTTTCTGGAGGTTCATGTTTTATGGGATCTTCCTGTACCTGGGGGAGGTCACCAA
AGCTGTTCAGCCGCTCCTTCTTGGCCGCATCATCGCCAGCTATGACCCTGATAATAA
AGAAGAAAGGTCTATTGCTATTTATCTGGGAATTGGCCTCTGCTTGCTCTTCATCGTC
CGCACCCTTCTGCTGCACCCTGCCATTTTTGGCCTTCACCACATCGGCATGCAAATG
AGAATTGCCATGTTCTCCCTCATTTACAAAAAGACCCTGAAACTTTCCTCAAGAGTG

-continued

TTAGATAAAATATCCATTGGTCAGCTGGTCAGCCTGCTGTCCAACAATCTTAACAAA
TTTGATGAAGGCTTGGCGCTGGCCCACTTCGTGTGGATTGCACCTCTGCAGGTGGCC
CTGTTGATGGGACTTATATGGGAGCTGCTTCAAGCCTCTGCTTTCTGTGGGCTGGGCT
TTTTGATTGTACTGGCACTTTTTCAGGCTGGGCTCGGAAGAATGATGATGAAATACA
GAGATCAGCGGGCCGGGAAGATATCAGAGCGACTTGTGATCACCAGTGAAATGATT
GAAAATATTCAGAGCGTGAAAGCCTACTGCTGGGAAGAAGCCATGGAGAAGATGAT
TGAGAACCTGAGGCAGACAGAGCTCAAGCTCACTCGGAAGGCTGCTTATGTTCGCT
ATTTCAACAGCAGCGCCTTCTTCTTCAGTGGCTTCTTTGTTGTCTTCCTGTCTGTTCTG
CCATATGCACTGATAAAAGGCATTATTTTACGAAAGATCTTCACCACCATCAGTTTT
TGCATCGTTCTCAGGATGGCCGTCACAAGACAGTTCCCCTGGGCTGTGCAGACCTGG
TACGATTCCTTGGGGGCCATCAACAAGATTCAAGATTTCTTGCAAAAACAAGAATAT
AAAACTTTAGAATACAACCTCACCACCACTGAAGTGGTCATGGAAAATGTGACAGC
CTTTTGGGAGGAGGGTTTTGGAGAATTGTTCGAGAAGGCAAAGCAGAATAACAACA
ACAGGAAGACGAGCAATGGGGACGACTCTCTCTTCTTCAGCAACTTTTCACTGCTCG
GGACCCCTGTGTTGAAAGATATAAACTTCAAGATCGAGAGGGGCCAGCTCTTGGCT
GTGGCAGGCTCCACTGGAGCTGGTAAAACATCTCTTCTCATGGTGATCATGGGGGAA
CTGGAGCCTTCCGAAGGAAAAATCAAGCACAGTGGGAGAATCTCATTCTGCAGCCA
GTTTTCCTGGATCATGCCCGGCACCATTAAGGAAAACATCATATTTGGAGTGTCCTA
TGATGAGTACCGCTACCGGTCAGTCATCAAAGCCTGTCAGTTGGAGGAGGACATCTC
CAAGTTTGCAGAGAAAGACAACATTGTGCTTGGAGAGGGGGGTATCACTCTTTCTGG
AGGACAAAGAGCCAGGATCTCTTTGGCCCGGGCAGTCTACAAGGATGCAGACCTCT
ACTTGTTGGACAGTCCCTTCGGCTACCTCGACGTGCTGACTGAAAAAGAAATTTTTG
AAAGCTGTGTGTGCAAACTGATGGCAAACAAGACCAGGATTCTTGTCACCAGCAAG
ATGGAACATCTGAAGAAAGCGGACAAAATTCTGATTCTGCATGAAGGGAGCTCCTA
CTTCTATGGAACATTTAGCGAGCTTCAGAACCTACAGCCAGACTTCTCCTCCAAATT
AATGGGCTGTGACTCCTTCGACCAGTTCTCTGCAGAAAGAAGAAACTCTATACTCAC
AGAGACCCTCCACCGCTTCTCCCTTGAGGGAGATGCCCCAGTTTCTTGGACAGAAAC
CAAGAAGCAGTCCTTTAAGCAGACTGGCGAGTTTGGTGAAAAGAGGAAAAATTCAA
TTCTCAATCCAATTAACAGTATTCGCAAGTTCAGCATTGTCCAGAAGACACCCCTCC
AGATGAATGGCATCGAAGAAGATAGTGACGAGCCGCTGGAGAGACGGCTGAGTCTG
GTGCCAGATTCAGAACAGGGGGAGGCCATCCTGCCCCGGATCAGCGTCATTTCCAC
AGGCCCCACATTACAAGCACGGCGCCGGCAGAGTGTTTTAAATCTCATGACCCATTC
AGTGAACCAGGGCCAAAATATCCACAGGAAGACTACAGCTTCTACCCGGAAAGTGT
CTCTGGCCCCTCAGGCCAATCTGACCGAGCTGGACATCTACAGCAGGAGGCTCTCCC
AGGAAACAGGGCTGGAAATATCTGAAGAGATTAATGAAGAGGATCTTAAAGAGTGC
TTCTTTGATGACATGGAGAGCATCCCCGCGGTGACCACATGGAACACCTACCTTAGA
TATATTACTGTCCACAAGAGCCTCATATTTGTCCTCATCTGGTGCCTGGTTATTTTCC
TCGCTGAGGTGGCGGCCAGTCTTGTTGTGCTCTGGCTGCTGGGCAACACTCCTCTCC
AGGACAAGGGCAATAGTACTCACAGCAGAAATAATTCTTATGCCGTCATCATTACA
AGCACCTCCAGCTACTACGTGTTCTACATCTATGTGGGCGTGGCTGACACCCTCCTG
GCCATGGGTTTCTTCCGGGGCCTGCCTTTGGTGCACACCCTCATCACAGTGTCAAAA
ATTCTGCACCATAAAATGCTTCATTCTGTCCTGCAGGCACCCATGAGCACTTTGAAC
ACATTGAAGGCTGGCGGCATCCTCAACAGATTTTCTAAAGATATTGCTATCCTGGAT
GATCTCCTCCCCCTGACAATCTTTGACTTTATCCAGCTTCTGCTGATCGTGATTGGAG
CCATAGCAGTGGTTGCTGTCCTGCAGCCCTACATTTTTGTGGCCACCGTGCCCGTGAT
TGTTGCCTTTATTATGCTCAGAGCTTACTTCCTGCAAACTTCTCAACAGCTCAAACAG
CTAGAATCTGAGGGCCGGAGCCCCATTTTTACCCACCTGGTGACTTCCCTGAAGGGA
CTGTGGACTCTGAGAGCATTCGGGCGACAGCCTTACTTTGAGACACTGTTCCACAAG
GCCCTGAACTTGCACACTGCCAACTGGTTTCTTTACCTGAGCACACTCCGCTGGTTCC
AGATGCGGATAGAGATGATCTTCGTCATCTTTTTTATAGCTGTAACCTTCATTTCTAT
CCTTACAACAGGAGAAGGAGAGGGCAGGGTGGGAATCATCCTCACGCTGGCTATGA
ACATAATGTCCACCTTGCAGTGGGCCGTGAATTCCAGTATAGATGTGGATTCTCTAA
TGAGGAGTGTCTCCCGGGTGTTTAAATTCATTGATATGCCTACTGAGGGGAAACCCA
CCAAGTCAACAAAACCTTATAAGAATGGACAGCTGAGCAAGGTGATGATAATTGAG
AACAGCCACGTGAAGAAGGATGACATTTGGCCCAGCGGGGGCCAGATGACTGTGAA
GGACCTGACGGCCAAGTACACCGAAGGTGGAAATGCCATTTTGGAAAACATCAGCT
TCTCAATCTCTCCTGGGCAGAGAGTTGGATTGCTGGGTCGCACGGGCAGCGGCAAAT
CAACCCTGCTCAGTGCCTTCCTTCGGCTCCTGAATACAGAAGGCGAAATCCAAATTG
ACGGGGTGAGCTGGGACAGCATCACCCTGCAGCAGTGGAGAAAAGCATTTGGGGTC
ATTCCACAGAAAGTTTTCATCTTCTCTGGCACTTTCAGAAAGAACCTGGACCCCTAT
GAGCAGTGGAGCGACCAGGAGATCTGGAAGGTTGCAGATGAAGTTGGCCTGCGGAG
TGTGATAGAACAATTTCCTGGCAAGCTGGATTTTGTGCTGGTAGATGGAGGCTGCGT
GCTGTCCCACGGCCACAAACAGCTGATGTGCCTCGCCCGCTCCGTTCTTTCAAAGGC
CAAAATCTTGCTTTTGGATGAGCCCAGTGCTCACCTCGACCCAGTGACCTATCAGAT
AATCCGCAGGACCTTAAAGCAAGCTTTTGCCGACTGCACCGTCATACTGTGTGAGCA
CCGGATTGAAGCAATGCTGGAATGCCAGCAGTTTCTGGTGATCGAGGAGAATAAGG
TCCGGCAGTACGACAGCATCCAGAAGTTGTTGAATGAGCGCAGCCTTTTCCGCCAGG
CCATCTCCCCATCTGACAGAGTCAAGCTGTTTCCACATAGGAACTCCTCTAAGTGCA
AGTCCAAGCCCCAGATCGCTGCCCTCAAGGAGGAAACTGAGGAAGAGGTGCAGGAT
ACCCGCCTGTGA (SEQ ID NO: 40)

ATGCAACGGAGTCCTCTGGAAAAAGCCTCTGTCGTATCTAAGCTTTTCTTCAGTTGG
ACACGCCCGATTTTGAGAAAGGGTTATCGGCAACGCTTGGAACTTAGTGACATCTAC
CAAATTCCAAGTGTAGACTCAGCCGATAACTTGAGCGAAAAGCTCGAACGAGAGTG
GGATCGAGAACTGGCTAGCAAAAAAAATCCCAAACTCATAAATGCCCTGCGACGCT
GTTTCTTTTGGCGATTTATGTTTTACGGTATTTTCCTTTATTTGGGTGAGGTCACGAA
GGCTGTACAGCCACTGCTGCTGGGTCGCATCATTGCCTCTTACGACCCTGACAACAA
AGAGGAGCGGTCAATAGCTATCTACCTTGGTATAGGACTTTGCTTGCTCTTCATAGT
CCGCACGTTGCTTCTCCACCCTGCTATATTTGGTCTCCATCACATTGGGATGCAAATG
CGGATCGCGATGTTCAGTCTTATATATAAAAAGACTCTTAAACTTTCCAGCCGGGTT

-continued

CTGGATAAGATCTCTATTGGTCAACTGGTATCTCTTTTGTCTAACAACCTGAATAAGT
TCGACGAGGGCCTTGCATTGGCCCATTTTGTATGGATTGCCCCTTTGCAAGTCGCCCT
CCTGATGGGATTGATCTGGGAACTCCTGCAAGCTAGTGCTTTTTGCGGATTGGGATT
CCTCATAGTCCTTGCGCTCTTTCAGGCGGGACTTGGACGCATGATGATGAAGTATCG
CGACCAACGAGCTGGCAAGATCAGTGAACGGCTTGTAATAACCAGTGAAATGATAG
AGAACATCCAGAGCGTAAAAGCTTACTGTTGGGAAGAAGCGATGGAAAAGATGATT
GAGAACCTTCGCCAGACAGAACTTAAACTTACACGAAAGGCCGCTTATGTCCGGTA
CTTCAACTCTTCAGCATTTTTTTTTAGTGGCTTCTTTGTAGTGTTCCTGTCCGTCCTTC
CGTATGCACTTATCAAGGGTATAATACTTAGGAAAATCTTCACAACAATCAGTTTTT
GCATAGTCCTTCGCATGGCAGTAACTCGCCAATTTCCCTGGGCAGTTCAGACGTGGT
ACGACTCACTTGGCGCAATTAACAAAATTCAAGATTTCCTCCAAAAGCAAGAGTATA
AAACCTTGGAATACAACCTTACCACCACAGAAGTTGTAATGGAAAATGTCACAGCC
TTCTGGGAGGAAGGTTTCGGCGAACTTTTTGAGAAGGCGAAGCAAAATAACAATAA
TCGGAAAACATCAAACGGTGACGATTCACTGTTCTTTTCTAACTTTAGCCTTCTTGGG
ACGCCCGTCCTGAAGGACATAAACTTTAAGATTGAACGGGGTCAACTTCTCGCGGTC
GCAGGGAGTACTGGAGCGGGGAAAACGAGCCTGCTGATGGTGATAATGGGGGAGTT
GGAGCCCTCAGAAGGCAAGATCAAGCATAGTGGTAGAATTAGCTTCTGCAGTCAAT
TTAGTTGGATTATGCCGGGCACGATCAAAGAAAATATAATCTTTGGGGTATCCTACG
ATGAATACAGGTACCGATCAGTGATAAAAGCGTGCCAGCTTGAAGAAGACATTTCA
AAGTTTGCTGAGAAGGATAATATCGTACTTGGAGAAGGAGGTATCACCCTGTCTGG
GGGTCAACGAGCGAGGATCTCCCTGGCACGCGCCGTCTACAAGGACGCGGACCTCT
ATCTGTTGGATTCACCGTTCGGATATTTGGACGTGCTTACGGAGAAAGAAATATTTG
AGAGCTGTGTTTGCAAGCTCATGGCAAATAAAACCAGAATATTGGTTACAAGCAAG
ATGGAGCATCTTAAGAAAGCAGATAAAATCCTGATATTGCACGAGGGCTCTTCATAC
TTCTACGGGACGTTTTCTGAGTTGCAGAACCTCCAGCCGGATTTCAGCTCTAAGCTG
ATGGGCTGTGATTCCTTTGATCAGTTTAGTGCGGAAAGACGAAACAGTATACTCACC
GAAACACTGCACAGGTTCTCTCTGGAGGGCGACGCCCCGGTTTCCTGGACAGAGAC
GAAGAAGCAGTCCTTCAAACAGACAGGCGAGTTTGGGGAGAAAAGGAAAAATAGC
ATACTCAACCCGATTAACAGCATTCGCAAGTTCAGTATAGTACAAAAGACCCCGTTG
CAGATGAACGGTATAGAGGAAGATTCTGATGAGCCACTGGAAAGACGGCTTTCTCT
CGTTCCGGACAGTGAACAGGGAGAGGCAATACTGCCTCGGATCAGCGTTATCTCTAC
AGGACCTACTTTGCAAGCTCGGCGCCGACAGTCAGTCTTGAATCTTATGACTCATAG
TGTTAATCAAGGCCAGAATATCCATCGCAAGACCACCGCAAGTACAAGGAAAGTGA
GCTTGGCACCTCAAGCAAACCTTACTGAACTTGATATCTACTCACGGCGACTTTCAC
AGGAGACCGGACTTGAAATTAGTGAAGAAATTAACGAGGAGGACCTCAAGGAGTGC
TTCTTCGATGACATGGAATCAATCCCCGCAGTCACAACCTGGAACACTTATCTGAGG
TATATAACAGTTCACAAGAGCCTCATTTTTGTACTTATTTGGTGTTTGGTAATTTTCC
TGGCGGAGGTTGCTGCTTCTTTGGTCGTCCTTTGGCTCCTCGGGAATACACCGCTCCA
AGACAAAGGCAACTCTACCCATAGTAGGAACAATTCATATGCAGTGATTATAACCA
GTACATCATCTTATTACGTTTTCTATATTTATGTCGGGGTAGCTGACACGCTGTTGGC
GATGGGCTTCTTTAGGGGCCTCCCCTTGGTACACACCCTTATCACGGTGAGTAAAAT
CCTGCATCACAAAATGCTTCATTCTGTACTCCAAGCGCCGATGAGTACGCTTAATAC
GCTGAAAGCAGGAGGGATACTGAATCGGTTCAGCAAGGACATCGCCATTCTGGATG
ACCTGCTTCCATTGACAATATTTGATTTCATTCAGCTCCTTCTCATAGTTATTGGAGC
CATAGCGGTGGTGGCTGTGCTTCAGCCTTATATATTCGTTGCCACAGTTCCCGTTATA
GTGGCATTTATAATGCTCAGGGCCTACTTTCTCCAGACTTCCCAGCAGTTGAAGCAA
CTCGAATCAGAAGGAAGGTCACCTATTTTCACACATCTTGTGACTTCCTTGAAGGGC
TTGTGGACGCTGCGGGCCTTCGGAAGACAACCATATTTGAAACTCTCTTCCACAAA
GCTTTGAATCTTCATACTGCGAACTGGTTCCTGTATTTGAGTACTTTGCGCTGGTTCC
AGATGAGGATAGAAATGATATTCGTTATCTTCTTTATCGCGGTTACGTTCATAAGTA
TCCTCACTACGGGGGAGGGTGAGGGTAGAGTGGGCATAATACTGACCCTCGCCATG
AACATTATGTCCACCCTGCAGTGGGCGGTAAACAGCAGCATAGATGTGGATTCTTTG
ATGCGCAGTGTGAGCAGGGTTTTTAAGTTTATCGATATGCCGACGGAAGGAAAGCC
CACTAAAAGCACGAAACCCTATAAAAATGGACAGCTTAGCAAAGTAATGATAATCG
AGAATAGCCATGTGAAAAAGGATGACATATGGCCTTCCGGAGGCCAAATGACTGTT
AAAGATCTGACCGCTAAATATACCGAGGGCGGCAACGCAATACTCGAAAACATAAG
CTTTTCCATAAGCCCCGGCCAACGCGTGGGTCTTCTGGGGAGGACTGGCTCCGGAAA
ATCAACGTTGCTTAGCGCGTTTTTGCGGCTCCTTAACACTGAAGGTGAGATCCAAAT
AGATGGCGTTAGTTGGGACTCTATAACACTGCAACAATGGCGGAAAGCTTTCGGCGT
CATACCTCAGAAGGTGTTCATCTTTAGCGGAACGTTCAGGAAGAACTTGGATCCCTA
CGAACAATGGAGTGATCAAGAAATATGGAAAGTGGCAGATGAGGTAGGCTTGCGCA
GTGTCATTGAACAATTCCCAGGGAAACTCGACTTTGTACTGGTGGACGGCGGTTGCG
TCTTGTCACACGGGCACAAACAGTTGATGTGTTTGGCCCGCAGTGTTTTGTCTAAGG
CGAAGATTCTGTTGCTCGACGAACCGAGTGCTCATCTTGATCCCGTCACCTACCAAA
TCATCAGAAGGACGTTGAAGCAAGCTTTCGCCGACTGCACTGTAATCCTTTGTGAGC
ATAGGATCGAAGCAATGCTCGAGTGCCAACAGTTCTTGGTTATAGAGGAGAATAAG
GTTCGGCAATACGACTCAATACAGAAACTGCTTAATGAGCGGTCACTCTTTCGACAA
GCTATCTCTCCTAGTGACAGGGTAAAGCTTTTTCCTCATCGGAATTCCAGCAAGTGT
AAGAGTAAACCACAGATCGCCGCCCTTAAAGAGGAGACCGAAGAAGAGGTGCAGG
ATACGAGACTTTAG

Synthesis of mRNA mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7, or SP6 RNA polymerase), DNAse I, pyrophosphatase, and/or RNAse inhibitor. The exact conditions will vary according to the specific application.

Exemplary Codon-Optimized Human Cystic Fibrosis Transmembrane Conductance Regulator (CFTR) mRNAs

```
Construct design:
X - SEQ ID NO: 1 - Y
5' and 3' UTR Sequences:
                                          (SEQ ID NO: 4)
X (5' UTR Sequence) =
GGACAGAUCGCCUGGAGACGCCAUCCACGCUGUUUUGACCUCCAUAGAAG
ACACCGGGACCGAUCCAGCCUCCGCGGCCGGGAACGGUGCAUUGGAACGC
GGAUUCCCCGUGCCAAGAGUGACUCACCGUCCUUGACACG
```

-continued

```
                                          (SEQ ID NO: 5)
Y (3' UTR Sequence) =
CGGGUGGCAUCCCUGUGACCCCUCCCCAGUGCCUCUCCUGGCCCUGGAAG
UUGCCACUCCAGUGCCCACCAGCCUUGUCCUAAUAAAAUUAAGUUGCAUC
AAGCU
OR
                                          (SEQ ID NO: 6)
GGGUGGCAUCCCUGUGACCCCUCCCCAGUGCCUCUCCUGGCCCUGGAAGU
UGCCACUCCAGUGCCCACCAGCCUUGUCCUAAUAAAAUUAAGUUGCAUCA
AAGCU
```

An exemplary codon-optimized human CFTR mRNA sequence includes SEQ ID NO: 1 as described in the detailed description section.

An exemplary full-length codon-optimized human CFTR mRNA sequence is shown below.

(SEQ ID NO: 7)

GGACAGAUCGCCUGGAGACGCCAUCCACGCUGUUUUGACCUCCAUAGAAGACACC

GGGACCGAUCCAGCCUCCGCGGCCGGGAACGGUGCAUUGGAACGCGGAUUCCCCG

UGCCAAGAGUGACUCACCGUCCUUGACACGAUGCAACGCUCUCCUCUUGAAAAGG

CCUCGGUGGUGUCCAAGCUCUUCUUCUCGUGGACUAGACCCAUCCUGAGAAAGGG

GUACAGACAGCGCUUGGAGCUGUCCGAUAUCUAUCAAAUCCCUUCCGUGGACUCC

GCGGACAACCUGUCCGAGAAGCUCGAGAGAGAAUGGGACAGAGAACUCGCCUCAA

AGAAGAACCCGAAGCUGAUUAAUGCGCUUAGGCGGUGCUUUUUCUGGCGGUUCA

UGUUCUACGGCAUCUUCCUCUACCUGGGAGAGGUCACCAAGGCCGUGCAGCCCCU

GUUGCUGGGACGGAUUAUUGCCUCCUACGACCCCGACAACAAGGAAGAAAGAAGC

AUCGCUAUCUACUUGGGCAUCGGUCUGUGCCUGCUUUUCAUCGUCCGGACCCUCU

UGUUGCAUCCUGCUAUUUUCGGCCUGCAUCACAUUGGCAUGCAGAUGAGAAUUG

CCAUGUUUUCCCUGAUCUACAAGAAAACUCUGAAGCUCUCGAGCCGCGUGCUUGA

CAAGAUUUCCAUCGGCCAGCUCGUGUCCCUGCUCUCCAACAAUCUGAACAAGUUC

GACGAGGGCCUCGCCCUGGCCCACUUCGUGUGGAUCGCCCCUCUGCAAGUGGCGC

UUCUGAUGGGCCUGAUCUGGGAGCUGCUGCAAGCCUCGGCAUUCUGUGGGCUUG

GAUUCCUGAUCGUGCUGGCACUGUUCCAGGCCGGACUGGGGCGGAUGAUGAUGA

AGUACAGGGACCAGAGAGCCGGAAAGAUUUCCGAACGGCUGGUGAUCACUUCGG

AAAUGAUCGAAAACAUCCAGUCAGUGAAGGCCUACUGCUGGGAAGAGGCCAUGG

AAAAGAUGAUUGAAAACCUCCGGCAAACCGAGCUGAAGCUGACCCGCAAGGCCGC

UUACGUGCGCUAUUUCAACUCGUCCGCUUUCUUCUUCUCCGGGUUCUUCGUGGUG

UUUCUCUCCGUGCUCCCCUACGCCCUGAUUAAGGGAAUCAUCCUCAGGAAGAUCU

UCACCACCAUUUCCUUCUGUAUCGUGCUCCGCAUGGCCGUGACCCGGCAGUUCCC

AUGGGCCGUGCAGACUUGGUACGACUCCCUGGGAGCCAUUAACAAGAUCCAGGAC

UUCCUUCAAAAGCAGGAGUACAAGACCCUCGAGUACAACCUGACUACUACCGAGG

UCGUGAUGGAAAACGUCACCGCCUUUUGGGAGGAGGGAUUUGGCGAACUGUUCG

-continued

AGAAGGCCAAGCAGAACAACAACAACCGCAAGACCUCGAACGGUGACGACUCCCU

CUUCUUUUCAAACUUCAGCCUGCUCGGGACGCCCGUGCUGAAGGACAUUAACUUC

AAGAUCGAAAGAGGACAGCUCCUGGCGGUGGCCGGAUCGACCGGAGCCGGAAAG

ACUUCCCUGCUGAUGGUGAUCAUGGGAGAGCUUGAACCUAGCGAGGGAAAGAUC

AAGCACUCCGGCCGCAUCAGCUUCUGUAGCCAGUUUUCCUGGAUCAUGCCCGGAA

CCAUUAAGGAAAACAUCAUCUUCGGCGUGUCCUACGAUGAAUACCGCUACCGGUC

CGUGAUCAAAGCCUGCCAGCUGGAAGAGGAUAUUUCAAAGUUCGCGGAGAAAGA

UAACAUCGUGCUGGGCGAAGGGGGUAUUACCUUGUCGGGGGGCCAGCGGGCUAG

AAUCUCGCUGGCCAGAGCCGUGUAUAAGGACGCCGACCUGUAUCUCCUGGACUCC

CCCUUCGGAUACCUGGACGUCCUGACCGAAAAGGAGAUCUUCGAAUCGUGCGUGU

GCAAGCUGAUGGCUAACAAGACUCGCAUCCUCGUGACCUCCAAAAUGGAGCACCU

GAAGAAGGCAGACAAGAUUCUGAUUCUGCAUGAGGGGUCCUCCUACUUUUACGG

CACCUUCUCGGAGUUGCAGAACUUGCAGCCCGACUUCUCAUCGAAGCUGAUGGGU

UGCGACAGCUUCGACCAGUUCUCCGCCGAAAGAAGGAACUCGAUCCUGACGGAAA

CCUUGCACCGCUUCUCUUUGGAAGGCGACGCCCCUGUGUCAUGGACCGAGACUAA

GAAGCAGAGCUUCAAGCAGACCGGGGAAUUCGGCGAAAAGAGGAAGAACAGCAU

CUUGAACCCCAUUAACUCCAUCCGCAAGUUCUCAAUCGUGCAAAAGACGCCACUG

CAGAUGAACGGCAUUGAGGAGGACUCCGACGAACCCCUUGAGAGGCGCCUGUCCC

UGGUGCCGGACAGCGAGCAGGGAGAAGCCAUCCUGCCUCGGAUUUCCGUGAUCUC

CACUGGUCCGACGCUCCAAGCCCGGCGGCGGCAGUCCGUGCUGAACCUGAUGACC

CACAGCGUGAACCAGGGCCAAAACAUUCACCGCAAGACUACCGCAUCCACCCGGA

AAGUGUCCCUGGCACCUCAAGCGAAUCUUACCGAGCUCGACAUCUACUCCCGGAG

ACUGUCGCAGGAAACCGGGCUCGAAAUUUCCGAAGAAAUCAACGAGGAGGAUCU

GAAAGAGUGCUUCUUCGACGAUAUGGAGUCGAUACCCGCCGUGACGACUUGGAA

CACUUAUCUGCGGUACAUCACUGUGCACAAGUCAUUGAUCUUCGUGCUGAUUUG

GUGCCUGGUGAUUUUCCUGGCCGAGGUCGCGGCCUCACUGGUGGUGCUCUGGCUG

UUGGGAAACACGCCUCUGCAAGACAAGGGAAACUCCACGCACUCGAGAAACAACA

GCUAUGCCGUGAUUAUCACUUCCACCUCCUCUUAUUACGUGUUCUACAUCUACGU

CGGAGUGGCGGAUACCCUGCUCGCGAUGGGUUUCUUCAGAGGACUGCCGCUGGUC

CACACCUUGAUCACCGUCAGCAAGAUUCUUCACCACAAGAUGUUGCAUAGCGUGC

UGCAGGCCCCCAUGUCCACCCUCAACACUCUGAAGGCCGGAGGCAUUCUGAACAG

AUUCUCCAAGGACAUCGCUAUCCUGGACGAUCUCCUGCCGCUUACCAUCUUUGAC

UUCAUCCAGCUGCUGCUGAUCGUGAUUGGAGCAAUCGCAGUGGUGGCGGUGCUG

CAGCCUUACAUUUUCGUGGCCACUGUGCCGGUCAUUGUGGCGUUCAUCAUGCUGC

GGGCCUACUUCCUCCAAACCAGCCAGCAGCUGAAGCAACUGGAAUCCGAGGGACG

AUCCCCCAUCUUCACUCACCUUGUGACGUCGUUGAAGGGACUGUGGACCCUCCGG

GCUUUCGGACGGCAGCCCUACUUCGAAACCCUCUUCCACAAGGCCCUGAACCUCC

ACACCGCCAAUUGGUUCCUGUACCUGUCCACCCUGCGGUGGUUCCAGAUGCGCAU

CGAGAUGAUUUUCGUCAUCUUCUUCAUCGCGGUCACAUUCAUCAGCAUCCUGACU

ACCGGAGAGGGAGAGGGACGGGUCGGAAUAAUCCUGACCCUCGCCAUGAACAUU

AUGAGCACCCUGCAGUGGGCAGUGAACAGCUCGAUCGACGUGGACAGCCUGAUGC

-continued

GAAGCGUCAGCCGCGUGUUCAAGUUCAUCGACAUGCCUACUGAGGGAAAACCCAC

UAAGUCCACUAAGCCCUACAAAAAUGGCCAGCUGAGCAAGGUCAUGAUCAUCGAA

AACUCCCACGUGAAGAAGGACGAUAUUUGGCCCUCCGGAGGUCAAAUGACCGUGA

AGGACCUGACCGCAAAGUACACCGAGGGAGGAAACGCCAUUCUCGAAAACAUCAG

CUUCUCCAUUUCGCCGGGACAGCGGGUCGGCCUUCUCGGGCGGACCGGUUCCGGG

AAGUCAACUCUGCUGUCGGCUUUCCUCCGGCUGCUGAAUACCGAGGGGGAAAUCC

AAAUUGACGGCGUGUCUUGGGAUUCCAUUACUCUGCAGCAGUGGCGGAAGGCCU

UCGGCGUGAUCCCCCAGAAGGUGUUCAUCUUCUCGGGUACCUUCCGGAAGAACCU

GGAUCCUUACGAGCAGUGGAGCGACCAAGAAAUCUGGAAGGUCGCCGACGAGGU

CGGCCUGCGCUCCGUGAUUGAACAAUUUCCUGGAAAGCUGGACUUCGUGCUCGUC

GACGGGGGAUGUGUCCUGUCGCACGGACAUAAGCAGCUCAUGUGCCUCGCACGGU

CCGUGCUCUCCAAGGCCAAGAUUCUGCUGCUGGACGAACCUUCGGCCCACCUGGA

UCCGGUCACCUACCAGAUCAUCAGGAGGACCCUGAAGCAGGCCUUUGCCGAUUGC

ACCGUGAUUCUCUGCGAGCACCGCAUCGAGGCCAUGCUGGAGUGCCAGCAGUUCC

UGGUCAUCGAGGAGAACAAGGUCCGCCAAUACGACUCCAUUCAAAAGCUCCUCAA

CGAGCGGUCGCUGUUCAGACAAGCUAUUUCACCGUCCGAUAGAGUGAAGCUCUUC

CCGCAUCGGAACAGCUCAAAGUGCAAAUCGAAGCCGCAGAUCGCAGCCUUGAAGG

AAGAGACUGAGGAAGAGGUGCAGGACACCCGGCUUUAACGGGUGGCAUCCCUGU

GACCCCUCCCCAGUGCCUCUCCUGGCCCUGGAAGUUGCCACUCCAGUGCCCACCA

GCCUUGUCCUAAUAAAAUUAAGUUGCAUCAAGCU

In another example, a full length codon-optimized human CFTR mRNA sequence is shown below:

(SEQ ID NO: 8)

GGACAGAUCGCCUGGAGACGCCAUCCACGCUGUUUUGACCUCCAUAGAAGACACC

GGGACCGAUCCAGCCUCCGCGGCCGGGAACGGUGCAUUGGAACGCGGAUUCCCCG

UGCCAAGAGUGACUCACCGUCCUUGACACGAUGCAACGCUCUCCUCUUGAAAAGG

CCUCGGUGGUGUCCAAGCUCUUCUUCUCGUGGACUAGACCCAUCCUGAGAAAGGG

GUACAGACAGCGCUUGGAGCUGUCCGAUAUCUAUCAAAUCCCUUCCGUGGACUCC

GCGGACAACCUGUCCGAGAAGCUCGAGAGAGAAUGGGACAGAGAACUCGCCUCAA

AGAAGAACCCGAAGCUGAUUAAUGCGCUUAGGCGGUGCUUUUUCUGGCGGUUCA

UGUUCUACGGCAUCUUCCUCUACCUGGGAGAGGUCACCAAGGCCGUGCAGCCCCU

GUUGCUGGGACGGAUUAUUGCCUCCUACGACCCCGACAACAAGGAAGAAAGAAGC

AUCGCUAUCUACUUGGGCAUCGGUCUGUGCCUGCUUUUCAUCGUCCGGACCCUCU

UGUUGCAUCCUGCUAUUUUCGGCCUGCAUCACAUUGGCAUGCAGAUGAGAAUUG

CCAUGUUUUCCCUGAUCUACAAGAAAACUCUGAAGCUCUCGAGCCGCGUGCUUGA

CAAGAUUUCCAUCGGCCAGCUCGUGUCCCUGCUCUCCAACAAUCUGAACAAGUUC

GACGAGGGCCUCGCCCUGGCCCACUUCGUGUGGAUCGCCCCUCUGCAAGUGGCGC

UUCUGAUGGGCCUGAUCUGGGAGCUGCUGCAAGCCUCGGCAUUCUGUGGGCUUG

GAUUCCUGAUCGUGCUGGCACUGUUCCAGGCCGGACUGGGGCGGAUGAUGAUGA

AGUACAGGGACCAGAGAGCCGGAAAGAUUUCCGAACGGCUGGUGAUCACUUCGG

-continued

AAAUGAUCGAAAACAUCCAGUCAGUGAAGGCCUACUGCUGGGAAGAGGCCAUGG

AAAAGAUGAUUGAAAACCUCCGGCAAACCGAGCUGAAGCUGACCCGCAAGGCCGC

UUACGUGCGCUAUUUCAACUCGUCCGCUUUCUUCUUCUCCGGGUUCUUCGUGGUG

UUUCUCUCCGUGCUCCCCUACGCCCUGAUUAAGGGAAUCAUCCUCAGGAAGAUCU

UCACCACCAUUUCCUUCUGUAUCGUGCUCCGCAUGGCCGUGACCCGGCAGUUCCC

AUGGGCCGUGCAGACUUGGUACGACUCCCUGGGAGCCAUUAACAAGAUCCAGGAC

UUCCUUCAAAAGCAGGAGUACAAGACCCUCGAGUACAACCUGACUACUACCGAGG

UCGUGAUGGAAAACGUCACCGCCUUUUGGGAGGAGGGAUUUGGCGAACUGUUCG

AGAAGGCCAAGCAGAACAACAACAACCGCAAGACCUCGAACGGUGACGACUCCCU

CUUCUUUUCAAACUUCAGCCUGCUCGGGACGCCCGUGCUGAAGGACAUUAACUUC

AAGAUCGAAAGAGGACAGCUCCUGGCGGUGGCCGGAUCGACCGGAGCCGGAAAG

ACUUCCCUGCUGAUGGUGAUCAUGGGAGAGCUUGAACCUAGCGAGGGAAAGAUC

AAGCACUCCGGCCGCAUCAGCUUCUGUAGCCAGUUUUCCUGGAUCAUGCCCGGAA

CCAUUAAGGAAAACAUCAUCUUCGGCGUGUCCUACGAUGAAUACCGCUACCGGUC

CGUGAUCAAAGCCUGCCAGCUGGAAGAGGAUAUUUCAAAGUUCGCGGAGAAAGA

UAACAUCGUGCUGGGCGAAGGGGGUAUUACCUUGUCGGGGGGCCAGCGGGCUAG

AAUCUCGCUGGCCAGAGCCGUGUAUAAGGACGCCGACCUGUAUCUCCUGGACUCC

CCCUUCGGAUACCUGGACGUCCUGACCGAAAAGGAGAUCUUCGAAUCGUGCGUGU

GCAAGCUGAUGGCUAACAAGACUCGCAUCCUCGUGACCUCCAAAAUGGAGCACCU

GAAGAAGGCAGACAAGAUUCUGAUUCUGCAUGAGGGGUCCUCCUACUUUUACGG

CACCUUCUCGGAGUUGCAGAACUUGCAGCCCGACUUCUCAUCGAAGCUGAUGGGU

UGCGACAGCUUCGACCAGUUCUCCGCCGAAAGAAGGAACUCGAUCCUGACGGAAA

CCUUGCACCGCUUCUCUUUGGAAGGCGACGCCCCUGUGUCAUGGACCGAGACUAA

GAAGCAGAGCUUCAAGCAGACCGGGGAAUUCGGCGAAAAGAGGAAGAACAGCAU

CUUGAACCCCAUUAACUCCAUCCGCAAGUUCUCAAUCGUGCAAAAGACGCCACUG

CAGAUGAACGGCAUUGAGGAGGACUCCGACGAACCCCUUGAGAGGCGCCUGUCCC

UGGUGCCGGACAGCGAGCAGGGAGAAGCCAUCCUGCCUCGGAUUUCCGUGAUCUC

CACUGGUCCGACGCUCCAAGCCCGGCGGCGGCAGUCCGUGCUGAACCUGAUGACC

CACAGCGUGAACCAGGGCCAAAACAUUCACCGCAAGACUACCGCAUCCACCCGGA

AAGUGUCCCUGGCACCUCAAGCGAAUCUUACCGAGCUCGACAUCUACUCCCGGAG

ACUGUCGCAGGAAACCGGGCUCGAAAUUUCCGAAGAAAUCAACGAGGAGGAUCU

GAAAGAGUGCUUCUUCGACGAUAUGGAGUCGAUACCCGCCGUGACGACUUGGAA

CACUUAUCUGCGGUACAUCACUGUGCACAAGUCAUUGAUCUUCGUGCUGAUUUG

GUGCCUGGUGAUUUUCCUGGCCGAGGUCGCGGCCUCACUGGUGGUGCUCUGGCUG

UUGGGAAACACGCCUCUGCAAGACAAGGGAAACUCCACGCACUCGAGAAACAACA

GCUAUGCCGUGAUUAUCACUUCCACCUCCUCUUAUUACGUGUUCUACAUCUACGU

CGGAGUGGCGGAUACCCUGCUCGCGAUGGGUUUCUUCAGAGGACUGCCGCUGGUC

CACACCUUGAUCACCGUCAGCAAGAUUCUUCACCACAAGAUGUUGCAUAGCGUGC

UGCAGGCCCCCAUGUCCACCCUCAACACUCUGAAGGCCGGAGGCAUUCUGAACAG

AUUCUCCAAGGACAUCGCUAUCCUGGACGAUCUCCUGCCGCUUACCAUCUUUGAC

-continued

```
UUCAUCCAGCUGCUGCUGAUCGUGAUUGGAGCAAUCGCAGUGGUGGCGGUGCUG

CAGCCUUACAUUUUCGUGGCCACUGUGCCGGUCAUUGUGGCGUUCAUCAUGCUGC

GGGCCUACUUCCUCCAAACCAGCCAGCAGCUGAAGCAACUGGAAUCCGAGGGACG

AUCCCCCAUCUUCACUCACCUUGUGACGUCGUUGAAGGGACUGUGGACCCUCCGG

GCUUUCGGACGGCAGCCCUACUUCGAAACCCUCUUCCACAAGGCCCUGAACCUCC

ACACCGCCAAUUGGUUCCUGUACCUGUCCACCCUGCGGUGGUUCCAGAUGCGCAU

CGAGAUGAUUUUCGUCAUCUUCUUCAUCGCGGUCACAUUCAUCAGCAUCCUGACU

ACCGGAGAGGGAGAGGGACGGGUCGGAAUAAUCCUGACCCUCGCCAUGAACAUU

AUGAGCACCCUGCAGUGGGCAGUGAACAGCUCGAUCGACGUGGACAGCCUGAUGC

GAAGCGUCAGCCGCGUGUUCAAGUUCAUCGACAUGCCUACUGAGGGAAAACCCAC

UAAGUCCACUAAGCCCUACAAAAAUGGCCAGCUGAGCAAGGUCAUGAUCAUCGAA

AACUCCCACGUGAAGAAGGACGAUAUUUGGCCCUCCGGAGGUCAAAUGACCGUGA

AGGACCUGACCGCAAAGUACACCGAGGGAGGAAACGCCAUUCUCGAAAACAUCAG

CUUCUCCAUUUCGCCGGGACAGCGGGUCGGCCUUCUCGGGCGGACCGGUUCCGGG

AAGUCAACUCUGCUGUCGGCUUUCCUCCGGCUGCUGAAUACCGAGGGGGAAAUCC

AAAUUGACGGCGUGUCUUGGGAUUCCAUUACUCUGCAGCAGUGGCGGAAGGCCU

UCGGCGUGAUCCCCCAGAAGGUGUUCAUCUUCUCGGGUACCUUCCGGAAGAACCU

GGAUCCUUACGAGCAGUGGAGCGACCAAGAAAUCUGGAAGGUCGCCGACGAGGU

CGGCCUGCGCUCCGUGAUUGAACAAUUUCCUGGAAAGCUGGACUUCGUGCUCGUC

GACGGGGGAUGUGUCCUGUCGCACGGACAUAAGCAGCUCAUGUGCCUCGCACGGU

CCGUGCUCUCCAAGGCCAAGAUUCUGCUGCUGGACGAACCUUCGGCCCACCUGGA

UCCGGUCACCUACCAGAUCAUCAGGAGGACCCUGAAGCAGGCCUUUGCCGAUUGC

ACCGUGAUUCUCUGCGAGCACCGCAUCGAGGCCAUGCUGGAGUGCCAGCAGUUCC

UGGUCAUCGAGGAGAACAAGGUCCGCCAAUACGACUCCAUUCAAAAGCUCCUCAA

CGAGCGGUCGCUGUUCAGACAAGCUAUUUCACCGUCCGAUAGAGUGAAGCUCUUC

CCGCAUCGGAACAGCUCAAAGUGCAAAUCGAAGCCGCAGAUCGCAGCCUUGAAGG

AAGAGACUGAGGAAGAGGUGCAGGACACCCGGCUUUAAGGGUGGCAUCCCUGUG

ACCCCUCCCCAGUGCCUCUCCUGGCCCUGGAAGUUGCCACUCCAGUGCCCACCAGC

CUUGUCCUAAUAAAAUUAAGUUGCAUCAAAGCU
```

In some embodiments, an activity of CFTR proteins is evaluated by an Ussing chamber assay. In some embodiments, duration of activity of CFTR proteins is evaluated by time-course Ussing assays. In some embodiments, protein expression and stability are evaluated by pulse-chase methods. In some embodiments, protein expression and stability are evaluated by surface biotinylation.

In some embodiments, for the preparation of mRNA according to the invention, a DNA template is transcribed in vitro. A suitable DNA template typically has a promoter, for example a T3, T7 or SP6 promoter, for in vitro transcription, followed by desired nucleotide sequence for desired mRNA and a termination signal.

Codon Optimization

According to an increasing amount of research, mRNAs contain numerous layers of information that overlap the amino acid code. Traditionally, codon optimization has been used to remove rare codons which were thought to be rate-limiting for protein expression. While fast growing bacteria and yeast both exhibit strong codon bias in highly expressed genes, higher eukaryotes exhibit much less codon bias, making it more difficult to discern codons that may be rate-limiting. In addition, it has been found that codon bias per se does not necessarily yield high expression but requires other features.

For example, rare codons have been implicated in slowing translation and forming pause sites, which may be required for correct protein folding. Therefore, variations in codon usage may provide a mechanism to fine-tune the temporal pattern of elongation and thus increase the time available for a protein to take on its correct confirmation. Codon optimization can interfere with this fine-tuning mechanism, resulting in less efficient protein translation or an increased amount of incorrectly folded proteins. Similarly, codon optimization may disrupt the normal patterns of cognate and wobble tRNA usage, thereby affecting protein structure and function because wobble-dependent slowing of elongation may likewise have been selected as a mechanism for achieving correct protein folding.

Various methods of performing codon optimization are known in the art, however, each has significant drawbacks and limitations from a computational and/or therapeutic point of view. In particular, known methods of codon optimization often involve, for each amino acid, replacing every codon with the codon having the highest usage for that amino acid, such that the "optimized" sequence contains only one codon encoding each amino acid (so may be referred to as a one-to-one sequence). The increase in expression is not limited to cell cultures of mammalian cells but was also observed in vivo in a mouse model. It is expected that the observed improvement in expression of the codon-optimised CFTR coding sequence, either wild type or activated CFTR, will result in an improved, more cost-effective mRNA replacement therapy for patients in need thereof, because it does not require the use of modified nucleotides for the preparation of the mRNA and allows treatment with a reduced dose and/or at extended dosing intervals.

In some embodiments, codon-optimized mRNA is produced in accordance with methods known in the art.

In some embodiments, codon-optimized mRNA sequences according to the present invention were further codon-optimized by a new process: the process first generates a list of codon-optimized sequences and then applies three filters to the list. Specifically, it applies a motif screen filter, guanine-cytosine (GC) content analysis filter, and codon adaptation index (CAI) analysis filter to produce an updated list of optimized nucleotide sequences. The updated list no longer includes nucleotide sequences containing features that are expected to interfere with effective transcription and/or translation of the encoded protein antigen.

Synthesis of mRNA Using SP6 RNA Polymerase

In some embodiments, CFTR mRNA is produced using SP6 RNA Polymerase. SP6 RNA Polymerase is a DNA-dependent RNA polymerase with high sequence specificity for SP6 promoter sequences. The SP6 polymerase catalyzes the 5'→3' in vitro synthesis of RNA on either single-stranded DNA or double-stranded DNA downstream from its promoter; it incorporates native ribonucleotides and/or modified ribonucleotides and/or labeled ribonucleotides into the polymerized transcript. Examples of such labeled ribonucleotides include biotin-, fluorescein-, digoxigenin-, aminoallyl-, and isotope-labeled nucleotides.

The sequence for bacteriophage SP6 RNA polymerase was initially described (GenBank: Y00105.1) as having the following amino acid sequence:

```
                                        (SEQ ID NO: 9)
MQDLHAIQLQLEEEMFNGGIRRFEADQQRQIAAGSESDTAWNRRLLSELI

APMAEGIQAYKEEYEGKKGRAPRALAFLQCVENEVAAYITMKVVMDMLNT

DATLQAIAMSVAERIEDQVRFSKLEGHAAKYFEKVKKSLKASRTKSYRHA

HNVAVVAEKSVAEKDADFDRWEAWPKETQLQIGTTLLEILEGSVFYNGEP

VFMRAMRTYGGKTIYYLQTSESVGQWISAFKEHVAQLSPAYAPCVIPPRP

WRTPFNGGFHTEKVASRIRLVKGNREHVRKLTQKQMPKVYKAINALQNTQ

WQINKDVLAVIEEVIRLDLGYGVPSFKPLIDKENKPANPVPVEFQHLRGR

ELKEMLSPEQWQQFINWKGECARLYTAETKRGSKSAAVVRMVGQARKYSA
```

-continued

```
FESIYFVYAMDSRSRVYVQSSTLSPQSNDLGKALLRFTEGRPVNGVEALK

WFCINGANLWGWDKKTFDVRVSNVLDEEFQDMCRDIAADPLTFTQWAKAD

APYEFLAWCFEYAQYLDLVDEGRADEFRTHLPVHQDGSCSGIQHYSAMLR

DEVGAKAVNLKPSDAPQDIYGAVAQVVIKKNALYMDADDATTFTSGSVTL

SGTELRAMASAWDSIGITRSLTKKPVMTLPYGSTRLTCRESVIDYIVDLE

EKEAQKAVAEGRTANKVHPFEDDRQDYLTPGAAYNYMTALIWPSISEVVK

APIVAMKMIRQLARFAAKRNEGLMYTLPTGFILEQKIMATEMLRVRTCLM

GDIKMSLQVETDIVDEAAMMGAAAPNFVHGHDASHLILTVCELVDKGVTS

IAVIHDSFGTHADNTLTLRVALKGQMVAMYIDGNALQKLLEEHEVRWMVD

TGIEVPEQGEFDLNEIMDSEYVFA.
```

An SP6 RNA polymerase suitable for the present invention can be any enzyme having substantially the same polymerase activity as bacteriophage SP6 RNA polymerase. Thus, in some embodiments, an SP6 RNA polymerase suitable for the present invention may be modified from SEQ ID NO: 9. For example, a suitable SP6 RNA polymerase may contain one or more amino acid substitutions, deletions, or additions. In some embodiments, a suitable SP6 RNA polymerase has an amino acid sequence about 99%, 98%, 97%, 96%, 95%, 94%, 93%, 92%, 91%, 90%, 89%, 88%, 87%, 86%, 85%, 84%, 83%, 82%, 81%, 80%, 75%, 70%, 65%, or 60% identical or homologous to SEQ ID NO: 9. In some embodiments, a suitable SP6 RNA polymerase may be a truncated protein (from N-terminus, C-terminus, or internally) but retain the polymerase activity. In some embodiments, a suitable SP6 RNA polymerase is a fusion protein.

An SP6 RNA polymerase suitable for the invention may be a commercially-available product, e.g., from Aldevron, Ambion, New England Biolabs (NEB), Promega, and Roche. The SP6 may be ordered and/or custom designed from a commercial source or a non-commercial source according to the amino acid sequence of SEQ ID NO: 9 or a variant of SEQ ID NO: 9 as described herein. The SP6 may be a standard-fidelity polymerase or may be a high-fidelity/high-efficiency/high-capacity which has been modified to promote RNA polymerase activities, e.g., mutations in the SP6 RNA polymerase gene or post-translational modifications of the SP6 RNA polymerase itself. Examples of such modified SP6 include SP6 RNA Polymerase-Plus™ from Ambion, HiScribe SP6 from NEB, and RiboMAX™ and Riboprobe® Systems from Promega.

In some embodiments, a suitable SP6 RNA polymerase is a fusion protein. For example, an SP6 RNA polymerase may include one or more tags to promote isolation, purification, or solubility of the enzyme. A suitable tag may be located at the N-terminus, C-terminus, and/or internally. Non-limiting examples of a suitable tag include Calmodulin-binding protein (CBP); *Fasciola hepatica* 8-kDa antigen (Fh8); FLAG tag peptide; glutathione-S-transferase (GST); Histidine tag (e.g., hexahistidine tag (His6)); maltose-binding protein (MBP); N-utilization substance (NusA); small ubiquitin related modifier (SUMO) fusion tag; Streptavidin binding peptide (STREP); Tandem affinity purification (TAP); and thioredoxin (TrxA). Other tags may be used in the present invention. These and other fusion tags have been described, e.g., Costa et al. Frontiers in Microbiology 5 (2014): 63 and in PCT/US16/57044, the contents of which are incorporated herein by reference in their entireties. In certain embodiments, a His tag is located at SP6's N-terminus.

SP6 Promoter

Any promoter that can be recognized by an SP6 RNA polymerase may be used in the present invention. Typically, an SP6 promoter comprises 5' ATTTAGGTGACACTATAG-3' (SEQ ID NO: 10). Variants of the SP6 promoter have been discovered and/or created to optimize recognition and/or binding of SP6 to its promoter. Non-limiting variants include but are not limited to: 5'-ATTTAGGGGACACTATAGAAGAG-3'; 5'-ATTTAGGGGACACTATAGAAGG-3'; 5'-ATTTAGGGGACACTATAGAAGGG-3'; 5'-ATTTAGGTGACACTATAGAA-3'; 5'-ATTTAGGTGACACTATAGAAGA-3'; 5'-ATTTAGGTGACACTATAGAAGAG-3'; 5'-ATTTAGGTGACACTATAGAAGG-3'; 5'-ATTTAGGTGACACTATAGAAGGG-3'; 5'-ATTTAGGTGACACTATAGAAGNG-3'; and 5'-CATACGATTTAGGTGACACTATAG-3' (SEQ ID NO: 11 to SEQ ID NO: 20).

In addition, a suitable SP6 promoter for the present invention may be about 95%, 90%, 85%, 80%, 75%, or 70% identical or homologous to any one of SEQ ID NO: 10 to SEQ ID NO: 20. Moreover, an SP6 promoter useful in the present invention may include one or more additional nucleotides 5' and/or 3' to any of the promoter sequences described herein.

DNA Template

Typically, a CFTR DNA template is either entirely double-stranded or mostly single-stranded with a double-stranded SP6 promoter sequence.

Linearized plasmid DNA (linearized via one or more restriction enzymes), linearized genomic DNA fragments (via restriction enzyme and/or physical means), PCR products, and/or synthetic DNA oligonucleotides can be used as templates for in vitro transcription with SP6, provided that they contain a double-stranded SP6 promoter upstream (and in the correct orientation) of the DNA sequence to be transcribed.

In some embodiments, the linearized DNA template has a blunt-end.

In some embodiments, the DNA sequence to be transcribed may be optimized to facilitate more efficient transcription and/or translation. For example, the DNA sequence may be optimized regarding cis-regulatory elements (e.g., TATA box, termination signals, and protein binding sites), artificial recombination sites, chi sites, CpG dinucleotide content, negative CpG islands, GC content, polymerase slippage sites, and/or other elements relevant to transcription; the DNA sequence may be optimized regarding cryptic splice sites, mRNA secondary structure, stable free energy of mRNA, repetitive sequences, RNA instability motif, and/or other elements relevant to mRNA processing and stability; the DNA sequence may be optimized regarding codon usage bias, codon adaptability, internal chi sites, ribosomal binding sites (e.g., IRES), premature polyA sites, Shine-Dalgarno (SD) sequences, and/or other elements relevant to translation; and/or the DNA sequence may be optimized regarding codon context, codon-anticodon interaction, translational pause sites, and/or other elements relevant to protein folding. Optimization methods known in the art may be used in the present invention, e.g., GeneOptimizer by ThermoFisher and OptimumGene™, which are described in US 20110081708, the contents of which are incorporated herein by reference in its entirety.

In some embodiments, the DNA template includes a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and/or 5' UTR sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

Large-Scale mRNA Synthesis

The present invention relates to large-scale production of codon optimized CFTR mRNA. In some embodiments, a method according to the invention synthesizes mRNA at least 100 mg, 150 mg, 200 mg, 300 mg, 400 mg, 500 mg, 600 mg, 700 mg, 800 mg, 900 mg, 1 g, 5 g, 10 g, 25 g, 50 g, 75 g, 100 g, 250 g, 500 g, 750 g, 1 kg, 5 kg, 10 kg, 50 kg, 100 kg, 1000 kg, or more at a single batch. As used herein, the term "batch" refers to a quantity or amount of mRNA synthesized at one time, e.g., produced according to a single manufacturing setting. A batch may refer to an amount of mRNA synthesized in one reaction that occurs via a single aliquot of enzyme and/or a single aliquot of DNA template for continuous synthesis under one set of conditions. mRNA synthesized at a single batch would not include mRNA synthesized at different times that are combined to achieve the desired amount. Generally, a reaction mixture includes SP6 RNA polymerase, a linear DNA template, and an RNA polymerase reaction buffer (which may include ribonucleotides or may require addition of ribonucleotides).

According to the present invention, 1-100 mg of SP6 polymerase is typically used per gram (g) of mRNA produced. In some embodiments, about 1-90 mg, 1-80 mg, 1-60 mg, 1-50 mg, 1-40 mg, 10-100 mg, 10-80 mg, 10-60 mg, 10-50 mg of SP6 polymerase is used per gram of mRNA produced. In some embodiments, about 5-20 mg of SP6 polymerase is used to produce about 1 gram of mRNA. In some embodiments, about 0.5 to 2 grams of SP6 polymerase is used to produce about 100 grams of mRNA. In some embodiments, about 5 to 20 grams of SP6 polymerase is used to about 1 kilogram of mRNA. In some embodiments, at least 5 mg of SP6 polymerase is used to produce at least 1 gram of mRNA. In some embodiments, at least 500 mg of SP6 polymerase is used to produce at least 100 grams of mRNA. In some embodiments, at least 5 grams of SP6 polymerase is used to produce at least 1 kilogram of mRNA. In some embodiments, about 10 mg, 20 mg, 30 mg, 40 mg, 50 mg, 60 mg, 70 mg, 80 mg, 90 mg, or 100 mg of plasmid DNA is used per gram of mRNA produced. In some embodiments, about 10-30 mg of plasmid DNA is used to produce about 1 gram of mRNA. In some embodiments, about 1 to 3 grams of plasmid DNA is used to produce about 100 grams of mRNA. In some embodiments, about 10 to 30 grams of plasmid DNA is used to about 1 kilogram of mRNA. In some embodiments, at least 10 mg of plasmid DNA is used to produce at least 1 gram of mRNA. In some embodiments, at least 1 gram of plasmid DNA is used to produce at least 100 grams of mRNA. In some embodiments, at least 10 grams of plasmid DNA is used to produce at least 1 kilogram of mRNA.

In some embodiments, the concentration of the SP6 RNA polymerase in the reaction mixture may be from about 1 to 100 nM, 1 to 90 nM, 1 to 80 nM, 1 to 70 nM, 1 to 60 nM, 1 to 50 nM, 1 to 40 nM, 1 to 30 nM, 1 to 20 nM, or about 1 to 10 nM. In certain embodiments, the concentration of the SP6 RNA polymerase is from about 10 to 50 nM, 20 to 50 nM, or 30 to 50 nM. A concentration of 100 to 10000 Units/ml of the SP6 RNA polymerase may be used, as examples, concentrations of 100 to 9000 Units/ml, 100 to 8000 Units/ml, 100 to 7000 Units/ml, 100 to 6000 Units/ml, 100 to 5000 Units/ml, 100 to 1000 Units/ml, 200 to 2000 Units/ml, 500 to 1000 Units/ml, 500 to 2000 Units/ml, 500 to 3000 Units/ml, 500 to 4000 Units/ml, 500 to 5000 Units/ml, 500 to 6000 Units/ml, 1000 to 7500 Units/ml, and 2500 to 5000 Units/ml may be used.

The concentration of each ribonucleotide (e.g., ATP, UTP, GTP, and CTP) in a reaction mixture is between about 0.1 mM and about 10 mM, e.g., between about 1 mM and about 10 mM, between about 2 mM and about 10 mM, between about 3 mM and about 10 mM, between about 1 mM and about 8 mM, between about 1 mM and about 6 mM, between about 3 mM and about 10 mM, between about 3 mM and about 8 mM, between about 3 mM and about 6 mM, between about 4 mM and about 5 mM. In some embodiments, each ribonucleotide is at about 5 mM in a reaction mixture. In some embodiments, the total concentration of rNTPs (for example, ATP, GTP, CTP and UTPs combined) used in the reaction range between 1 mM and 40 mM. In some embodiments, the total concentration of rNTPs (for example, ATP, GTP, CTP and UTPs combined) used in the reaction range between 1 mM and 30 mM, or between 1 mM and 28 mM, or between 1 mM to 25 mM, or between 1 mM and 20 mM. In some embodiments, the total rNTPs concentration is less than 30 mM. In some embodiments, the total rNTPs concentration is less than 25 mM. In some embodiments, the total rNTPs concentration is less than 20 mM. In some embodiments, the total rNTPs concentration is less than 15 mM. In some embodiments, the total rNTPs concentration is less than 10 mM.

The RNA polymerase reaction buffer typically includes a salt/buffering agent, e.g., Tris, HEPES, ammonium sulfate, sodium bicarbonate, sodium citrate, sodium acetate, potassium phosphate sodium phosphate, sodium chloride, and magnesium chloride.

The pH of the reaction mixture may be between about 6 to 8.5, from 6.5 to 8.0, from 7.0 to 7.5, and in some embodiments, the pH is 7.5.

Linear or linearized DNA template (e.g., as described above and in an amount/concentration sufficient to provide a desired amount of RNA), the RNA polymerase reaction buffer, and SP6 RNA polymerase are combined to form the reaction mixture. The reaction mixture is incubated at between about 37° C. and about 42° C. for thirty minutes to six hours, e.g., about sixty to about ninety minutes.

In some embodiments, about 5 mM NTPs, about 0.05 mg/mL SP6 polymerase, and about 0.1 mg/ml DNA template in a suitable RNA polymerase reaction buffer (final reaction mixture pH of about 7.5) is incubated at about 37° C. to about 42° C. for sixty to ninety minutes.

In some embodiments, a reaction mixture contains linearized double stranded DNA template with an SP6 polymerase-specific promoter, SP6 RNA polymerase, RNase inhibitor, pyrophosphatase, 29 mM NTPs, 10 mM DTT and a reaction buffer (when at 10× is 800 mM HEPES, 20 mM spermidine, 250 mM $MgCl_2$, pH 7.7) and quantity sufficient (QS) to a desired reaction volume with RNase-free water; this reaction mixture is then incubated at 37° C. for 60 minutes. The polymerase reaction is then quenched by addition of DNase I and a DNase I buffer (when at 10× is 100 mM Tris-HCl, 5 mM $MgCl_2$ and 25 mM $CaCl_2$), pH 7.6) to facilitate digestion of the double-stranded DNA template in preparation for purification. This embodiment has been shown to be sufficient to produce 100 grams of mRNA.

In some embodiments, a reaction mixture includes NTPs at a concentration ranging from 1-10 mM, DNA template at a concentration ranging from 0.01-0.5 mg/ml, and SP6 RNA polymerase at a concentration ranging from 0.01-0.1 mg/ml, e.g., the reaction mixture comprises NTPs at a concentration of 5 mM, the DNA template at a concentration of 0.1 mg/ml, and the SP6 RNA polymerase at a concentration of 0.05 mg/ml.

Nucleotides

Various naturally-occurring or modified nucleosides may be used to product mRNA according to the present invention. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, pseudouridine, (e.g., N-1-methyl-pseudouridine), 2-thiouridine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

In some embodiments, the mRNA comprises one or more nonstandard nucleotide residues. The nonstandard nucleotide residues may include, e.g., 5-methyl-cytidine ("5mC"), pseudouridine ("yU"), and/or 2-thio-uridine ("2sU"). See, e.g., U.S. Pat. No. 8,278,036 or WO2011012316 for a discussion of such residues and their incorporation into mRNA. The mRNA may be RNA, which is defined as RNA in which 25% of U residues are 2-thio-uridine and 25% of C residues are 5-methylcytidine. Teachings for the use of RNA are disclosed US Patent Publication US20120195936 and international publication WO2011012316, both of which are hereby incorporated by reference in their entirety. The presence of nonstandard nucleotide residues may render an mRNA more stable and/or less immunogenic than a control mRNA with the same sequence but containing only standard residues. In further embodiments, the mRNA may comprise one or more nonstandard nucleotide residues chosen from isocytosine, pseudoisocytosine, 5-bromouracil, 5-propynyluracil, 6-aminopurine, 2-aminopurine, inosine, diaminopurine and 2-chloro-6-aminopurine cytosine, as well as combinations of these modifications and other nucleobase modifications. Some embodiments may further include additional modifications to the furanose ring or nucleobase. Additional modifications may include, for example, sugar modifications or substitutions (e.g., one or more of a 2'-O-alkyl modification, a locked nucleic acid (LNA)). In some embodiments, the RNAs may be complexed or hybridized with additional polynucleotides and/or peptide polynucleotides (PNA). In some embodiments where the sugar modification is a 2'-O-alkyl modification, such modification may include, but are not limited to a 2'-deoxy-2'-fluoro modification, a 2'-O-methyl modification, a 2'-O-methoxyethyl modification and a 2'-deoxy modification. In some embodiments, any of these modifications may be present in 0-100% of the nucleotides—for example, more than 0%, 1%, 10%, 25%, 50%, 75%, 85%, 90%, 95%, or 100% of the constituent nucleotides individually or in combination.

Post-Synthesis Processing

Typically, a 5' cap and/or a 3' tail may be added after the synthesis. The presence of the cap is important in providing resistance to nucleases found in most eukaryotic cells. The presence of a "tail" serves to protect the mRNA from exonuclease degradation.

A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp(5'(A, G(5')ppp(5')A and G(5')ppp(5')G. Additional cap structures are described in published US Application No. US 2016/0032356 and U.S. Provisional Application 62/464,327, filed Feb. 27, 2017, which are incorporated herein by reference.

Typically, a tail structure includes a poly(A) and/or poly (C) tail. A poly-A or poly-C tail on the 3' terminus of mRNA typically includes at least 50 adenosine or cytosine nucleotides, at least 150 adenosine or cytosine nucleotides, at least 200 adenosine or cytosine nucleotides, at least 250 adenosine or cytosine nucleotides, at least 300 adenosine or cytosine nucleotides, at least 350 adenosine or cytosine nucleotides, at least 400 adenosine or cytosine nucleotides, at least 450 adenosine or cytosine nucleotides, at least 500 adenosine or cytosine nucleotides, at least 550 adenosine or cytosine nucleotides, at least 600 adenosine or cytosine nucleotides, at least 650 adenosine or cytosine nucleotides, at least 700 adenosine or cytosine nucleotides, at least 750 adenosine or cytosine nucleotides, at least 800 adenosine or cytosine nucleotides, at least 850 adenosine or cytosine nucleotides, at least 900 adenosine or cytosine nucleotides, at least 950 adenosine or cytosine nucleotides, or at least 1 kb adenosine or cytosine nucleotides, respectively. In some embodiments, a poly A or poly C tail may be about 10 to 800 adenosine or cytosine nucleotides (e.g., about 10 to 200 adenosine or cytosine nucleotides, about 10 to 300 adenosine or cytosine nucleotides, about 10 to 400 adenosine or cytosine nucleotides, about 10 to 500 adenosine or cytosine nucleotides, about 10 to 550 adenosine or cytosine nucleotides, about 10 to 600 adenosine or cytosine nucleotides, about 50 to 600 adenosine or cytosine nucleotides, about 100 to 600 adenosine or cytosine nucleotides, about 150 to 600 adenosine or cytosine nucleotides, about 200 to 600 adenosine or cytosine nucleotides, about 250 to 600 adenosine or cytosine nucleotides, about 300 to 600 adenosine or cytosine nucleotides, about 350 to 600 adenosine or cytosine nucleotides, about 400 to 600 adenosine or cytosine nucleotides, about 450 to 600 adenosine or cytosine nucleotides, about 500 to 600 adenosine or cytosine nucleotides, about 10 to 150 adenosine or cytosine nucleotides, about 10 to 100 adenosine or cytosine nucleotides, about 20 to 70 adenosine or cytosine nucleotides, or about 20 to 60 adenosine or cytosine nucleotides) respectively. In some embodiments, a tail structure includes is a combination of poly (A) and poly (C) tails with various lengths described herein. In some embodiments, a tail structure includes at least 50%, 55%, 65%, 70%, 75%, 80%, 85%, 90%, 92%, 94%, 95%, 96%, 97%, 98%, or 99% adenosine nucleotides. In some embodiments, a tail structure includes at least 50%, 55%, 65%, 70%, 75%, 80%, 85%, 90%, 92%, 94%, 95%, 96%, 97%, 98%, or 99% cytosine nucleotides.

As described herein, the addition of the 5' cap and/or the 3' tail facilitates the detection of abortive transcripts generated during in vitro synthesis because without capping and/or tailing, the size of those prematurely aborted mRNA transcripts can be too small to be detected. Thus, in some embodiments, the 5' cap and/or the 3' tail are added to the synthesized mRNA before the mRNA is tested for purity (e.g., the level of abortive transcripts present in the mRNA). In some embodiments, the 5' cap and/or the 3' tail are added to the synthesized mRNA before the mRNA is purified as described herein. In other embodiments, the 5' cap and/or the 3' tail are added to the synthesized mRNA after the mRNA is purified as described herein.

mRNA synthesized according to the present invention may be used without further purification. In particular, mRNA synthesized according to the present invention may be used without a step of removing shortmers. In some embodiments, mRNA synthesized according to the present invention may be further purified. Various methods may be used to purify mRNA synthesized according to the present invention. For example, purification of mRNA can be performed using centrifugation, filtration and/or chromatographic methods. In some embodiments, the synthesized mRNA is purified by ethanol precipitation or filtration or chromatography, or gel purification or any other suitable means. In some embodiments, the mRNA is purified by HPLC. In some embodiments, the mRNA is extracted in a standard phenol: chloroform: isoamyl alcohol solution, well known to one of skill in the art. In some embodiments, the mRNA is purified using Tangential Flow Filtration. Suitable purification methods include those described in US 2016/0040154, US 2015/0376220, PCT application PCT/US18/19954 entitled "METHODS FOR PURIFICATION OF MESSENGER RNA" filed on Feb. 27, 2018, and PCT application PCT/US18/19978 entitled "METHODS FOR PURIFICATION OF MESSENGER RNA" filed on Feb. 27, 2018, all of which are incorporated by reference herein and may be used to practice the present invention.

In some embodiments, the mRNA is purified before capping and tailing. In some embodiments, the mRNA is purified after capping and tailing. In some embodiments, the mRNA is purified both before and after capping and tailing.

In some embodiments, the mRNA is purified either before or after or both before and after capping and tailing, by centrifugation.

In some embodiments, the mRNA is purified either before or after or both before and after capping and tailing, by filtration.

In some embodiments, the mRNA is purified either before or after or both before and after capping and tailing, by Tangential Flow Filtration (TFF).

In some embodiments, the mRNA is purified either before or after or both before and after capping and tailing by chromatography.

Characterization of mRNA

Full-length or abortive transcripts of mRNA may be detected and quantified using any methods available in the art. In some embodiments, the synthesized mRNA molecules are detected using blotting, capillary electrophoresis, chromatography, fluorescence, gel electrophoresis, HPLC, silver stain, spectroscopy, ultraviolet (UV), or UPLC, or a combination thereof. Other detection methods known in the art are included in the present invention. In some embodiments, the synthesized mRNA molecules are detected using UV absorption spectroscopy with separation by capillary electrophoresis. In some embodiments, mRNA is first denatured by a Glyoxal dye before gel electrophoresis ("Glyoxal gel electrophoresis"). In some embodiments, synthesized mRNA is characterized before capping or tailing. In some embodiments, synthesized mRNA is characterized after capping and tailing.

In some embodiments, mRNA generated by the method disclosed herein comprises less than 10%, less than 9%, less than 8%, less than 7%, less than 6%, less than 5%, less than 4%, less than 3%, less than 2%, less than 1%, less than 0.5%, less than 0.1% impurities other than full length mRNA. The impurities include IVT contaminants, e.g., proteins, enzymes, free nucleotides and/or shortmers.

In some embodiments, mRNA produced according to the invention is substantially free of shortmers or abortive transcripts. In particular, mRNA produced according to the invention contains undetectable level of shortmers or abortive transcripts by capillary electrophoresis or Glyoxal gel electrophoresis. As used herein, the term "shortmers" or "abortive transcripts" refers to any transcripts that are less than full-length. In some embodiments, "shortmers" or "abortive transcripts" are less than 100 nucleotides in length, less than 90, less than 80, less than 70, less than 60, less than 50, less than 40, less than 30, less than 20, or less than 10 nucleotides in length. In some embodiments, shortmers are detected or quantified after adding a 5'-cap, and/or a 3'-poly A tail.

mRNA Solution

In some embodiments, mRNA may be provided in a solution to be mixed with a lipid solution such that the mRNA may be encapsulated in lipid nanoparticles. A suitable mRNA solution may be any aqueous solution containing mRNA to be encapsulated at various concentrations. For example, a suitable mRNA solution may contain an mRNA at a concentration of or greater than about 0.01 mg/ml, 0.05 mg/ml, 0.06 mg/ml, 0.07 mg/ml, 0.08 mg/ml, 0.09 mg/ml, 0.1 mg/ml, 0.15 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, or 1.0 mg/ml. In some embodiments, a suitable mRNA solution may contain an mRNA at a concentration ranging from about 0.01-1.0 mg/ml, 0.01-0.9 mg/ml, 0.01-0.8 mg/ml, 0.01-0.7 mg/ml, 0.01-0.6 mg/ml, 0.01-0.5 mg/ml, 0.01-0.4 mg/ml, 0.01-0.3 mg/ml, 0.01-0.2 mg/ml, 0.01-0.1 mg/ml, 0.05-1.0 mg/ml, 0.05-0.9 mg/ml, 0.05-0.8 mg/ml, 0.05-0.7 mg/ml, 0.05-0.6 mg/ml, 0.05-0.5 mg/ml, 0.05-0.4 mg/ml, 0.05-0.3 mg/ml, 0.05-0.2 mg/ml, 0.05-0.1 mg/ml, 0.1-1.0 mg/ml, 0.2-0.9 mg/ml, 0.3-0.8 mg/ml, 0.4-0.7 mg/ml, or 0.5-0.6 mg/ml. In some embodiments, a suitable mRNA solution may contain an mRNA at a concentration up to about 5.0 mg/ml, 4.0 mg/ml, 3.0 mg/ml, 2.0 mg/ml, 1.0 mg/ml, 0.09 mg/ml, 0.08 mg/ml, 0.07 mg/ml, 0.06 mg/ml, or 0.05 mg/ml.

Typically, a suitable mRNA solution may also contain a buffering agent and/or salt. Generally, buffering agents can include HEPES, ammonium sulfate, sodium bicarbonate, sodium citrate, sodium acetate, potassium phosphate and sodium phosphate. In some embodiments, suitable concentration of the buffering agent may range from about 0.1 mM to 100 mM, 0.5 mM to 90 mM, 1.0 mM to 80 mM, 2 mM to 70 mM, 3 mM to 60 mM, 4 mM to 50 mM, 5 mM to 40 mM, 6 mM to 30 mM, 7 mM to 20 mM, 8 mM to 15 mM, or 9 to 12 mM. In some embodiments, suitable concentration of the buffering agent is or greater than about 0.1 mM, 0.5 mM, 1 mM, 2 mM, 4 mM, 6 mM, 8 mM, 10 mM, 15 mM, 20 mM, 25 mM, 30 mM, 35 mM, 40 mM, 45 mM, or 50 mM.

Exemplary salts can include sodium chloride, magnesium chloride, and potassium chloride. In some embodiments, suitable concentration of salts in an mRNA solution may range from about 1 mM to 500 mM, 5 mM to 400 mM, 10 mM to 350 mM, 15 mM to 300 mM, 20 mM to 250 mM, 30 mM to 200 mM, 40 mM to 190 mM, 50 mM to 180 mM, 50 mM to 170 mM, 50 mM to 160 mM, 50 mM to 150 mM, or 50 mM to 100 mM. Salt concentration in a suitable mRNA solution is or greater than about 1 mM, 5 mM, 10 mM, 20 mM, 30 mM, 40 mM, 50 mM, 60 mM, 70 mM, 80 mM, 90 mM, or 100 mM.

In some embodiments, a suitable mRNA solution may have a pH ranging from about 3.5-6.5, 3.5-6.0, 3.5-5.5, 3.5-5.0, 3.5-4.5, 4.0-5.5, 4.0-5.0, 4.0-4.9, 4.0-4.8, 4.0-4.7, 4.0-4.6, or 4.0-4.5. In some embodiments, a suitable mRNA solution may have a pH of or no greater than about 3.5, 4.0, 4.1, 4.2, 4.3, 4.4, 4.5, 4.6, 4.7, 4.8, 4.9, 5.0, 5.2, 5.4, 5.6, 5.8, 6.0, 6.1, 6.3, and 6.5.

Various methods may be used to prepare an mRNA solution suitable for the present invention. In some embodiments, mRNA may be directly dissolved in a buffer solution described herein. In some embodiments, an mRNA solution may be generated by mixing an mRNA stock solution with a buffer solution prior to mixing with a lipid solution for encapsulation. In some embodiments, an mRNA solution may be generated by mixing an mRNA stock solution with a buffer solution immediately before mixing with a lipid solution for encapsulation. In some embodiments, a suitable mRNA stock solution may contain mRNA in water at a concentration at or greater than about 0.2 mg/ml, 0.4 mg/ml, 0.5 mg/ml, 0.6 mg/ml, 0.8 mg/ml, 1.0 mg/ml, 1.2 mg/ml, 1.4 mg/ml, 1.5 mg/ml, or 1.6 mg/ml, 2.0 mg/ml, 2.5 mg/ml, 3.0 mg/ml, 3.5 mg/ml, 4.0 mg/ml, 4.5 mg/ml, or 5.0 mg/ml.

In some embodiments, an mRNA stock solution is mixed with a buffer solution using a pump. Exemplary pumps include but are not limited to gear pumps, peristaltic pumps and centrifugal pumps.

Typically, the buffer solution is mixed at a rate greater than that of the mRNA stock solution. For example, the buffer solution may be mixed at a rate at least 1×, 2×, 3×, 4×, 5×, 6×, 7×, 8×, 9×, 10×, 15×, or 20× greater than the rate of the mRNA stock solution. In some embodiments, a buffer solution is mixed at a flow rate ranging between about 100-6000 ml/minute (e.g., about 100-300 ml/minute, 300-600 ml/minute, 600-1200 ml/minute, 1200-2400 ml/minute, 2400-3600 ml/minute, 3600-4800 ml/minute, 4800-6000 ml/minute, or 60-420 ml/minute). In some embodiments, a buffer solution is mixed at a flow rate of or greater than about 60 ml/minute, 100 ml/minute, 140 ml/minute, 180 ml/minute, 220 ml/minute, 260 ml/minute, 300 ml/minute, 340 ml/minute, 380 ml/minute, 420 ml/minute, 480 ml/minute, 540 ml/minute, 600 ml/minute, 1200 ml/minute, 2400 ml/minute, 3600 ml/minute, 4800 ml/minute, or 6000 ml/minute.

In some embodiments, an mRNA stock solution is mixed at a flow rate ranging between about 10-600 ml/minute (e.g., about 5-50 ml/minute, about 10-30 ml/minute, about 30-60 ml/minute, about 60-120 ml/minute, about 120-240 ml/minute, about 240-360 ml/minute, about 360-480 ml/minute, or about 480-600 ml/minute). In some embodiments, an mRNA stock solution is mixed at a flow rate of or greater than about 5 ml/minute, 10 ml/minute, 15 ml/minute, 20 ml/minute, 25 ml/minute, 30 ml/minute, 35 ml/minute, 40 ml/minute, 45 ml/minute, 50 ml/minute, 60 ml/minute, 80 ml/minute, 100 ml/minute, 200 ml/minute, 300 ml/minute, 400 ml/minute, 500 ml/minute, or 600 ml/minute.

Delivery Vehicles

According to the present invention, mRNA encoding a CFTR protein (e.g., a full length, fragment, or portion of a CFTR protein) as described herein may be delivered as naked RNA (unpackaged) or via delivery vehicles. As used herein, the terms "delivery vehicle," "transfer vehicle," "nanoparticle" or grammatical equivalent, are used interchangeably.

Delivery vehicles can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition. A particular delivery vehicle is selected based upon its ability to facilitate the transfection of a nucleic acid to a target cell.

In some embodiments, a delivery vehicle comprising CFTR mRNA is administered by pulmonary delivery, e.g., comprising nebulization. In these embodiments, the delivery vehicle may be in an aerosolized composition which can be inhaled. In some embodiments, the mRNA is expressed in the tissue in which the delivery vehicle was administered, e.g., nasal cavity, trachea, bronchi, bronchioles, and/or other pulmonary system-related cell or tissue. Additional teaching of pulmonary delivery and nebulization are described in the related international application PCT/US17/61100 filed Nov. 10, 2017 by Applicant entitled "NOVEL ICE-BASED LIPID NANOPARTICLE FORMULATION FOR DELIVERY OF MRNA", and the U. S. Provisional Application U.S. Ser. No. 62/507,061, each of which is incorporated by reference in its entirety.

In some embodiments, mRNAs encoding a CFTR protein may be delivered via a single delivery vehicle. In some embodiments, mRNAs encoding a CFTR protein may be delivered via one or more delivery vehicles each of a different composition. According to various embodiments, suitable delivery vehicles include, but are not limited to polymer based carriers, such as polyethyleneimine (PEI), lipid nanoparticles and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), sol-gels, nanodendrimers, starch-based delivery systems, micelles, emulsions, niosomes, multi-domain-block polymers (vinyl polymers, polypropyl acrylic acid polymers, dynamic polyconjugates), dry powder formulations, plasmids, viruses, calcium phosphate nucleotides, aptamers, peptides and other vectorial tags. Also contemplated is the use of bionanocapsules and other viral capsid proteins assemblies as a suitable transfer vehicle. (Hum. Gene Ther. 2008 September; 19(9):887-95).

A delivery vehicle comprising CFTR mRNA may be administered and dosed in accordance with current medical practice, taking into account the clinical condition of the subject, the site and method of administration (e.g., local and systemic, including oral, pulmonary, and via injection), the scheduling of administration, the subject's age, sex, body weight, and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient protein production.

In some embodiments, a CFTR mRNA is administered in combination with one or more CFTR potentiators and/or correctors. Suitable CFTR potentiators and/or correctors include ivacaftor (trade name Kalydeco®), lumacaftor (trade name Orkambi®) or the combination of ivacaftor and lumacaftor. In some embodiments, a CFTR mRNA is administered in combination with one or more other CF treatment such as hormone replacement therapies, thyroid hormone replacement therapy, non-steroidal inflammatory drugs, and prescription dronabinol (Marinol®) during treatment.

In some embodiments, the human subject receives concomitant CFTR modulator therapy. In some embodiments, the concomitant CFTR modulator therapy comprises ivacaftor. In some embodiments, the concomitant CFTR modulator therapy comprises lumacaftor. In some embodiments, the concomitant CFTR modulator therapy comprises tezacaftor. In some embodiments, the concomitant CFTR modulator therapy is selected from ivacaftor, lumacaftor, tezacaftor, or a combination. In some embodiments, the concomitant CFTR modulator therapy comprises VX-659. In some embodiments, the concomitant CFTR modulator therapy comprises VX-445. In some embodiments, the concomitant CFTR modulator therapy comprises VX-152. In some embodiments, the concomitant CFTR modulator therapy comprises VX-440. In some embodiments, the concomitant CFTR modulator therapy comprises VX-371. In some embodiments, the concomitant CFTR modulator therapy comprises VX-561. In some embodiments, the concomitant CFTR modulator therapy comprises GLPG1837. In some embodiments, the concomitant CFTR modulator therapy comprises GLPG2222. In some embodiments, the concomitant CFTR modulator therapy comprises GLPG2737. In some embodiments, the concomitant CFTR modulator therapy comprises GLPG2451. In some embodiments, the concomitant CFTR modulator therapy comprises GLPG1837. In some embodiments, the concomitant CFTR modulator therapy comprises PTI-428. In some embodiments, the concomitant CFTR modulator therapy comprises PTI-801. In some embodiments, the concomitant CFTR modulator therapy comprises PTI-808. In some embodiments, the concomitant CFTR modulator therapy comprises eluforsen.

In some embodiments, the human subject is not eligible for treatment with one or more of ivacaftor, lumacaftor, tezacaftor, VX-659, VX-445, VX-152, VX-440, VX-371, VX-561, VX-659 or combinations thereof. In some embodiments, the human subject is not eligible for treatment with one or more of ivacaftor, lumacaftor, tezacaftor, VX-659, VX-445, VX-152, VX-440, VX-371, VX-561, VX-659, GLPG1837, GLPG2222, GLPG2737, GLPG2451, GLPG1837, PTI-428, PTI-801, PTI-808, eluforsen, or combinations thereof.

In some embodiments, delivery vehicles are formulated such that they are suitable for extended-release of the mRNA contained therein. Such extended-release compositions may be conveniently administered to a subject at extended dosing intervals.

Liposomal Delivery Vehicles

In some embodiments, a suitable delivery vehicle is a liposomal delivery vehicle, e.g., a lipid nanoparticle. As used herein, liposomal delivery vehicles, e.g., lipid nanoparticles, are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphiphilic polymers and surfactants (e.g., polymerosomes, niosomes, etc.). In the context of the present invention, a liposomal delivery vehicle typically serves to transport a desired mRNA to a target cell or tissue. In some embodiments, a nanoparticle delivery vehicle is a liposome. In some embodiments, a liposome comprises one or more cationic lipids, one or more non-cationic lipids, one or more cholesterol-based lipids and one or more PEG-modified lipids. In some embodiments, a liposome comprises no more than three distinct lipid components. In some embodiments, one distinct lipid component is a sterol-based cationic lipid.

Cationic Lipids

As used herein, the phrase "cationic lipids" refers to any of a number of lipid species that have a net positive charge at a selected pH, such as physiological pH.

Suitable cationic lipids for use in the compositions and methods of the invention include the cationic lipids as described in International Patent Publication WO 2010/144740, which is incorporated herein by reference. In certain embodiments, the compositions and methods of the present invention include a cationic lipid, (6Z,9Z,28Z,31Z)-heptatriaconta-6,9,28,31-tetraen-19-yl 4-(dimethylamino) butanoate, having a compound structure of:

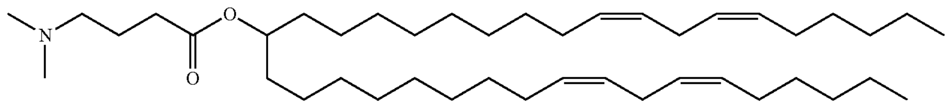 [SMILES: CCCCC/C=C\C/C=C\CCCCCCCCC(CCCCCCCC/C=C\C/C=C\CCCCC)OC(=O)CCCN(C)C]

and pharmaceutically acceptable salts thereof.

Other suitable cationic lipids for use in the compositions and methods of the present invention include ionizable cationic lipids as described in International Patent Publication WO 2013/149140, which is incorporated herein by reference. In some embodiments, the compositions and methods of the present invention include a cationic lipid of one of the following formulas:

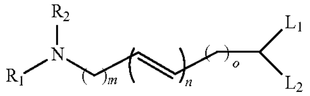

-continued

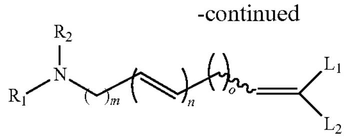

or a pharmaceutically acceptable salt thereof, wherein $R_1$ and $R_2$ are each independently selected from the group consisting of hydrogen, an optionally substituted, variably saturated or unsaturated $C_1$-$C_{20}$ alkyl and an optionally substituted, variably saturated or unsaturated $C_6$-$C_{20}$ acyl; wherein $L_1$ and $L_2$ are each independently selected from the group consisting of hydrogen, an optionally substituted $C_1$-$C_{30}$ alkyl, an optionally substituted variably unsaturated $C_1$-$C_{30}$ alkenyl, and an optionally substituted $C_1$-$C_{30}$ alkynyl; wherein m and o are each independently selected from the group consisting of zero and any positive integer (e.g., where m is three); and wherein n is zero or any positive integer (e.g., where n is one). In certain embodiments, the compositions and methods of the present invention include the cationic lipid (15Z, 18Z)—N,N-dimethyl-6-(9Z,12Z)-octadeca-9,12-dien-1-yl) tetracosa-15,18-dien-1-amine ("HGT5000"), having a compound structure of:

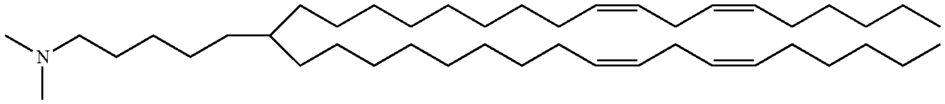

(HGT-5000)

and pharmaceutically acceptable salts thereof. In certain embodiments, the compositions and methods of the present invention include the cationic lipid (15Z, 18Z)—N,N-dimethyl-6-((9Z,12Z)-octadeca-9,12-dien-1-yl) tetracosa-4,15,18-trien-1-amine ("HGT5001"), having a compound structure of:

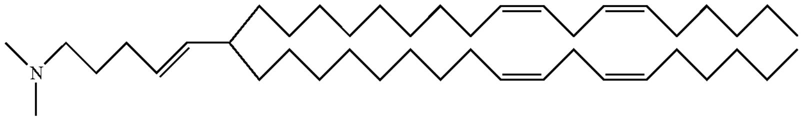

(HGT-5001)

and pharmaceutically acceptable salts thereof. In certain embodiments, the compositions and methods of the present invention include the cationic lipid and (15Z,18Z)—N,N-dimethyl-6-((9Z,12Z)-octadeca-9,12-dien-1-yl) tetracosa-5,15,18-trien-1-amine ("HGT5002"), having a compound structure of:

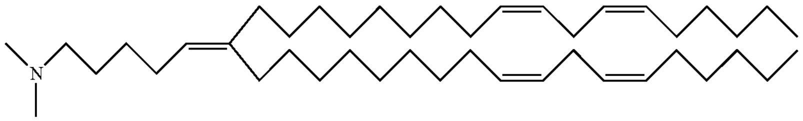

(HGT-5002)

and pharmaceutically acceptable salts thereof.

Other suitable cationic lipids for use in the compositions and methods of the invention include cationic lipids described as aminoalcohol lipidoids in International Patent Publication WO 2010/053572, which is incorporated herein by reference. In certain embodiments, the compositions and methods of the present invention include a cationic lipid having a compound structure of:

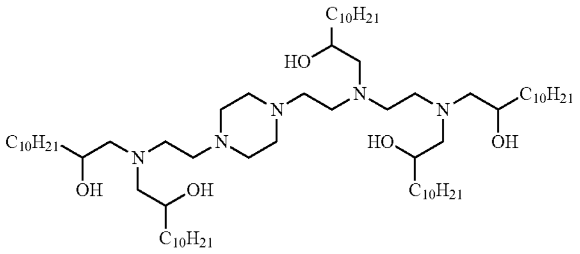

and pharmaceutically acceptable salts thereof.

Other suitable cationic lipids for use in the compositions and methods of the invention include the cationic lipids as described in International Patent Publication WO 2016/118725, which is incorporated herein by reference. In certain embodiments, the compositions and methods of the present invention include a cationic lipid having a compound structure of:

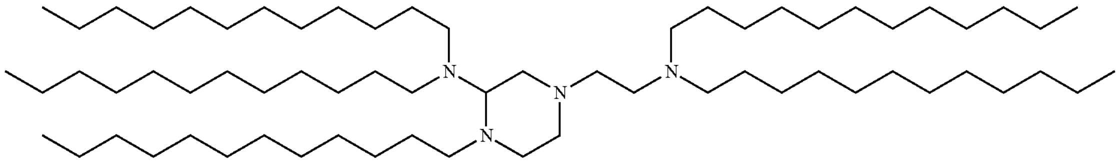 [SMILES: CCCCCCCCCCCCN(CCCCCCCCCCCC)CCN1CCN(CCCCCCCCCCCC)C(N(CCCCCCCCCCCC)CCCCCCCCCCCC)C1]

and pharmaceutically acceptable salts thereof.

Other suitable cationic lipids for use in the compositions and methods of the invention include the cationic lipids as described in International Patent Publication WO 2016/118724, which is incorporated herein by reference. In certain embodiments, the compositions and methods of the present invention include a cationic lipid having a compound structure of:

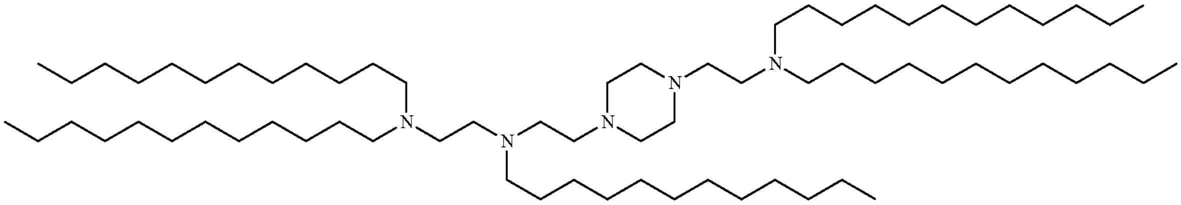 [SMILES: CCCCCCCCCCCCN(CCCCCCCCCCCC)CCN(CCCCCCCCCCCC)CCN1CCN(CCN(CCCCCCCCCCCC)CCCCCCCCCCCC)CC1]

and pharmaceutically acceptable salts thereof.

Other suitable cationic lipids for use in the compositions and methods of the invention include a cationic lipid having the formula of 14,25-ditridecyl 15,18,21,24-tetraaza-octatriacontane, and pharmaceutically acceptable salts thereof.

Other suitable cationic lipids for use in the compositions and methods of the invention include the cationic lipids as described in International Patent Publications WO 2013/063468 and WO 2016/205691, each of which are incorporated herein by reference. In some embodiments, the compositions and methods of the present invention include a cationic lipid of the following formula:

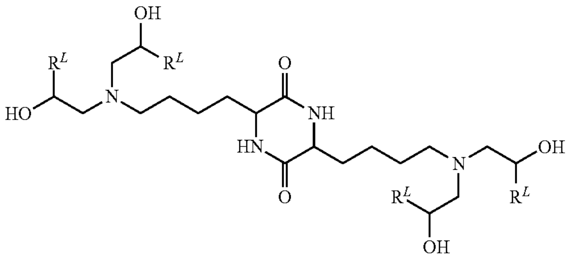

or pharmaceutically acceptable salts thereof, wherein each instance of $R^L$ is independently optionally substituted $C_6$-$C_{40}$ alkenyl. In certain embodiments, the compositions and methods of the present invention include a cationic lipid having a compound structure of:

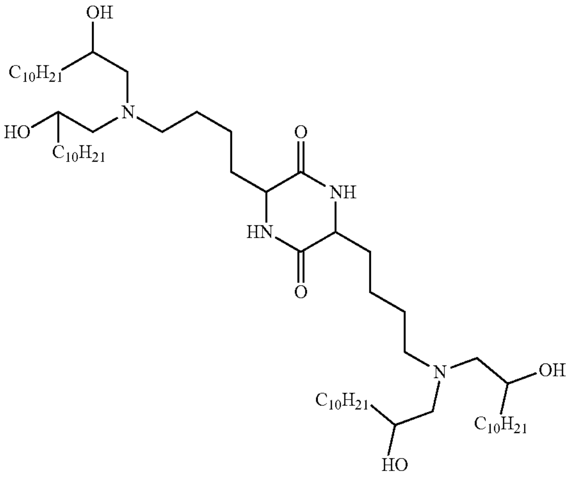

and pharmaceutically acceptable salts thereof. In certain embodiments, the compositions and methods of the present invention include a cationic lipid having a compound structure of:

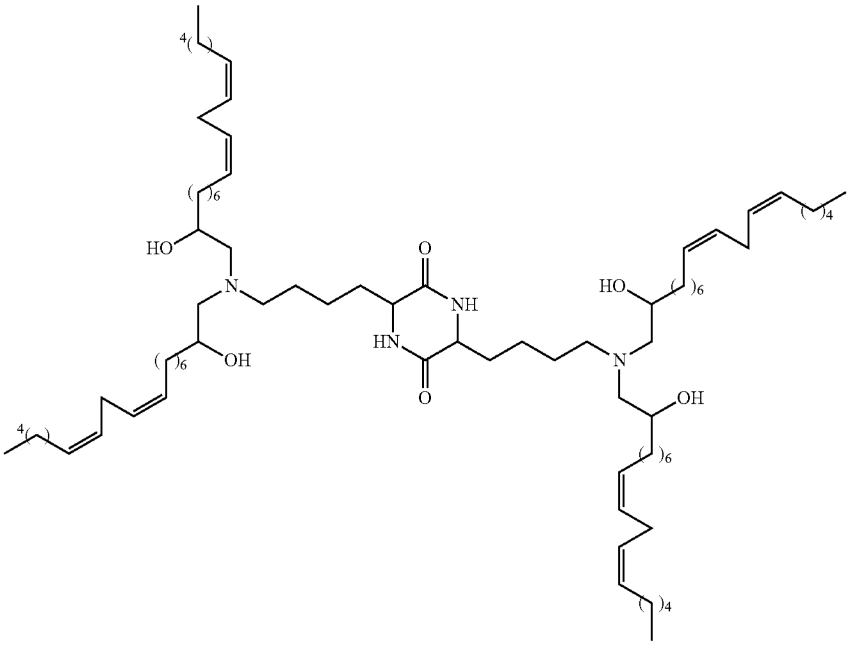

and pharmaceutically acceptable salts thereof. In certain embodiments, the compositions and methods of the present invention include a cationic lipid having a compound structure of:

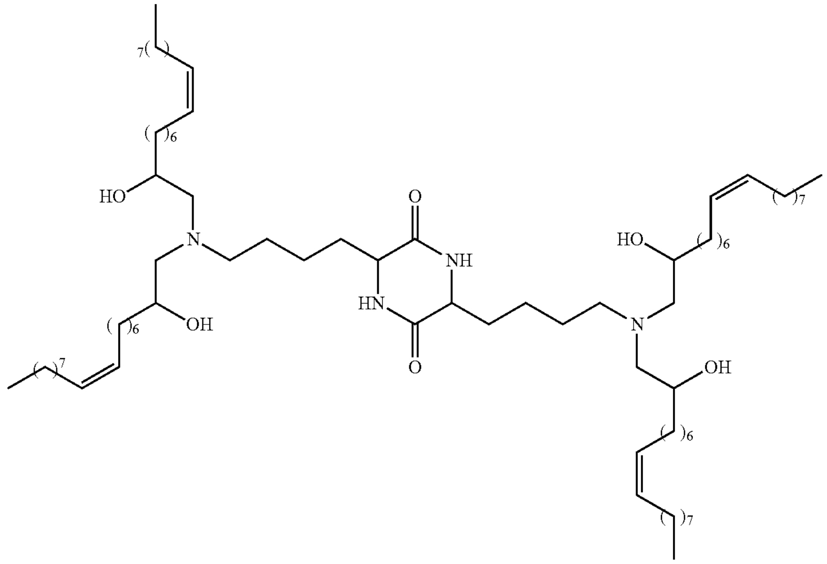

and pharmaceutically acceptable salts thereof. In certain embodiments, the compositions and methods of the present invention include a cationic lipid having a compound structure of.

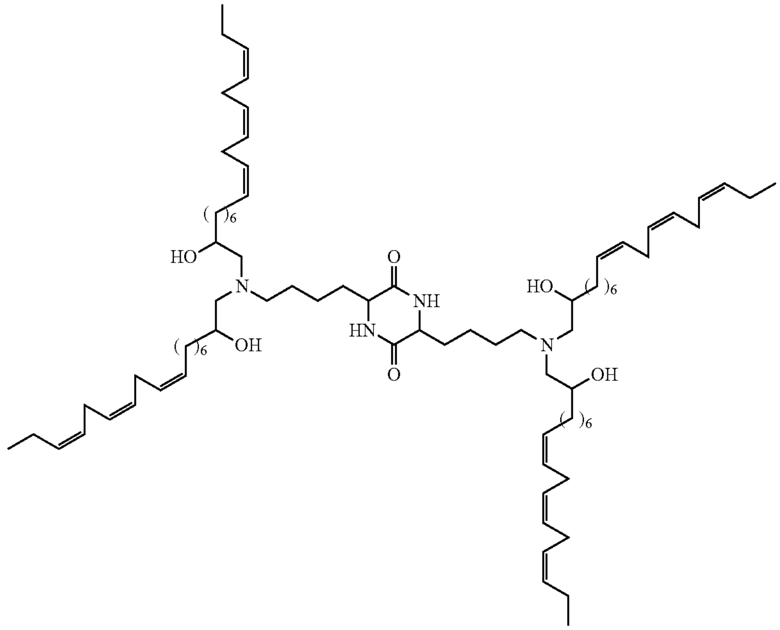

and pharmaceutically acceptable salts thereof.

Other suitable cationic lipids for use in the compositions and methods of the invention include the cationic lipids as described in International Patent Publication WO 2015/184256, which is incorporated herein by reference. In some embodiments, the compositions and methods of the present invention include a cationic lipid of the following formula:

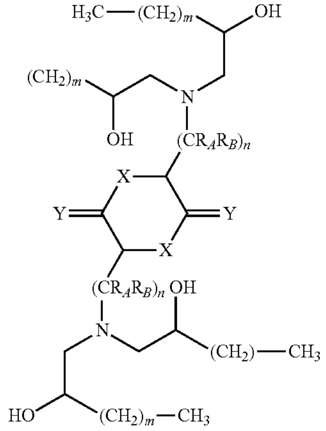

or a pharmaceutically acceptable salt thereof, wherein each X independently is O or S; each Y independently is O or S; each m independently is 0 to 20; each n independently is 1 to 6; each RA is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen; and each $R_B$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen. In certain embodiments, the compositions and methods of the present invention include a cationic lipid, "Target 23", having a compound structure of:

(Target 23)

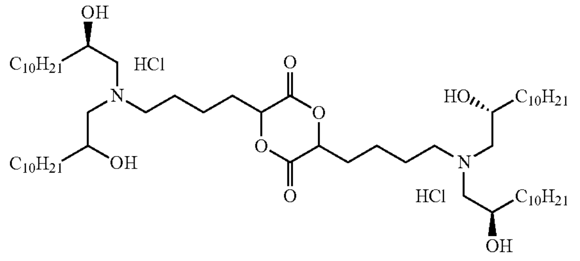

and pharmaceutically acceptable salts thereof.

Other suitable cationic lipids for use in the compositions and methods of the invention include the cationic lipids as described in International Patent Publication WO 2016/004202, which is incorporated herein by reference. In some embodiments, the compositions and methods of the present invention include a cationic lipid having the compound structure:

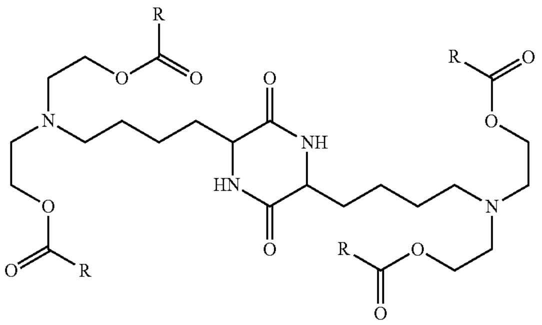

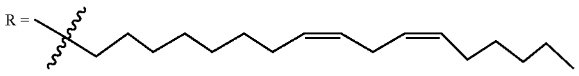

or a pharmaceutically acceptable salt thereof. In some embodiments, the compositions and methods of the present invention include a cationic lipid having the compound structure:

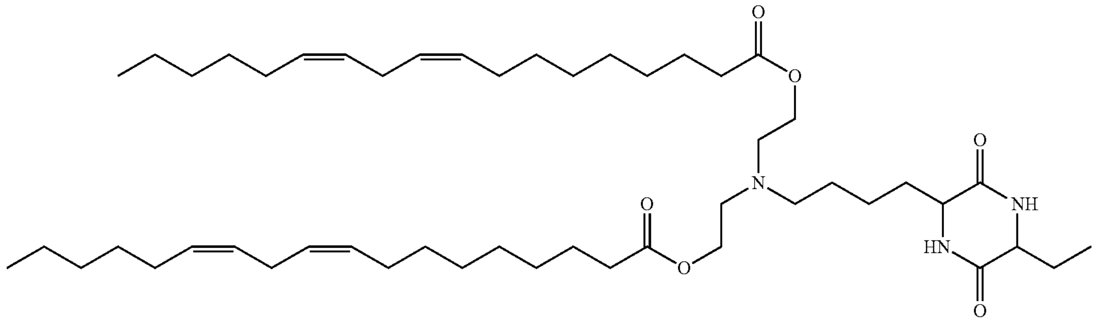 [SMILES: CCCCC/C=C\C/C=C\CCCCCCCC(=O)OCCN(CCCCC1NC(=O)C(CC)NC1=O)CCOC(=O)CCCCCCC/C=C\C/C=C\CCCCC]

or a pharmaceutically acceptable salt thereof. In some embodiments, the compositions and methods of the present invention include a cationic lipid having the compound structure:

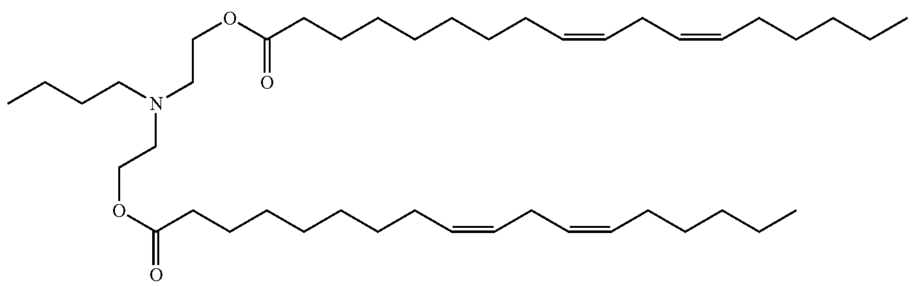 [SMILES: CCCCC/C=C\C/C=C\CCCCCCCC(=O)OCCN(CCCC)CCOC(=O)CCCCCCC/C=C\C/C=C\CCCCC]

or a pharmaceutically acceptable salt thereof.

Other suitable cationic lipids for use in the compositions and methods of the present invention include cationic lipids as described in U.S. Provisional Patent Application Ser. No. 62/758,179, which is incorporated herein by reference. In some embodiments, the compositions and methods of the present invention include a cationic lipid of the following formula:

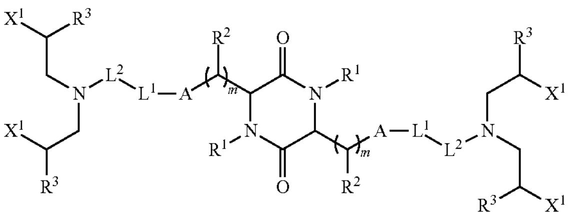

or a pharmaceutically acceptable salt thereof, wherein each $R^1$ and $R^2$ is independently H or $C_1$-$C_6$ aliphatic; each m is independently an integer having a value of 1 to 4; each A is independently a covalent bond or arylene; each $L^1$ is independently an ester, thioester, disulfide, or anhydride group; each $L^2$ is independently $C_2$-$C_{10}$ aliphatic; each $X^1$ is independently H or OH; and each $R^3$ is independently $C_6$-$C_{20}$ aliphatic. In some embodiments, the compositions and methods of the present invention include a cationic lipid of the following formula:

(Compound 1)

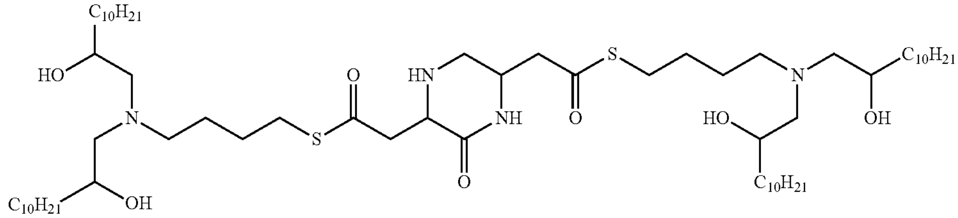

or a pharmaceutically acceptable salt thereof. In some embodiments, the compositions and methods of the present invention include a cationic lipid of the following formula:

(Compound 2)

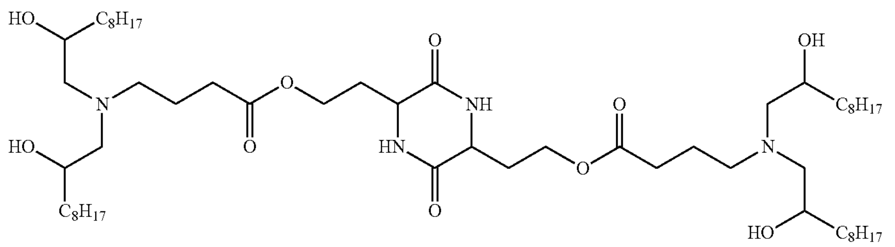

or a pharmaceutically acceptable salt thereof. In some embodiments, the compositions and methods of the present invention include a cationic lipid of the following formula:

(Compound 3)

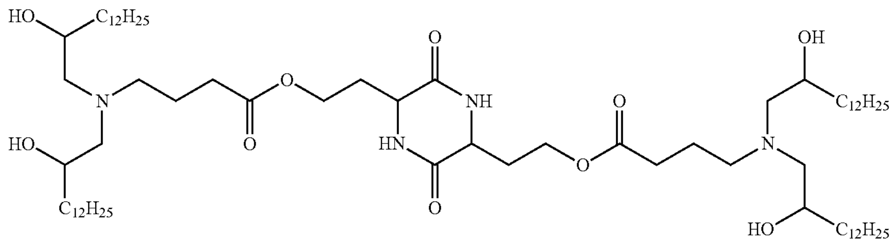

or a pharmaceutically acceptable salt thereof.

Other suitable cationic lipids for use in the compositions and methods of the present invention include the cationic lipids as described in J. McClellan, M. C. King, Cell 2010, 141, 210-217 and in Whitehead et al., Nature Communications (2014) 5:4277, which is incorporated herein by reference. In certain embodiments, the cationic lipids of the compositions and methods of the present invention include a cationic lipid having a compound structure of:

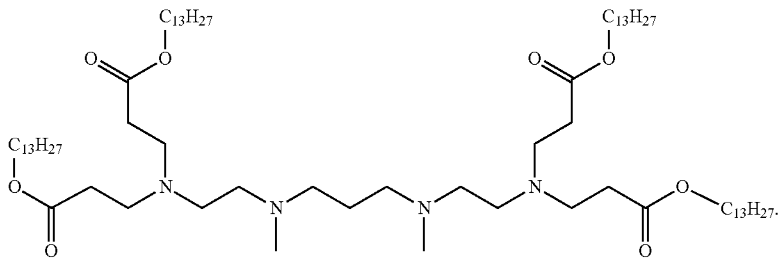

and pharmaceutically acceptable salts thereof.

Other suitable cationic lipids for use in the compositions and methods of the invention include the cationic lipids as described in International Patent Publication WO 2015/199952, which is incorporated herein by reference. In some embodiments, the compositions and methods of the present invention include a cationic lipid having the compound structure:

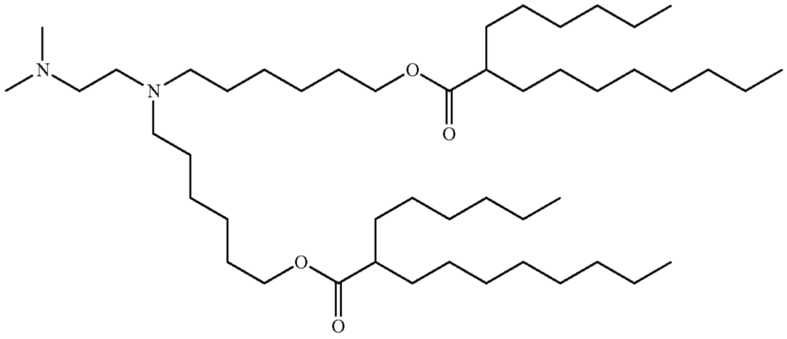 [SMILES: CCCCCCCCC(CCCCCC)C(=O)OCCCCCCN(CCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

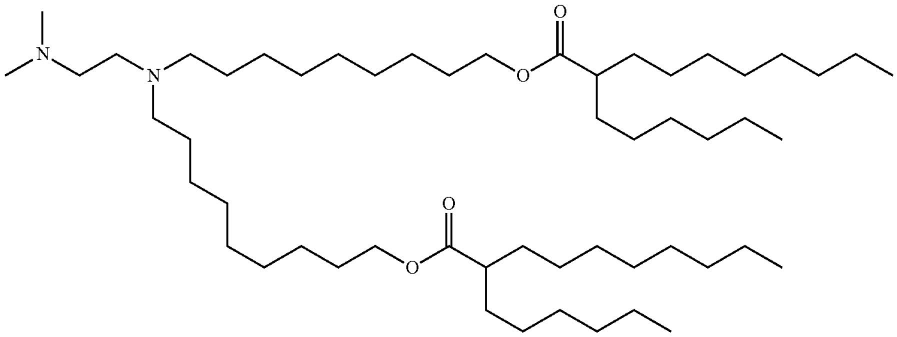 [SMILES: CCCCCCCCC(CCCCCC)C(=O)OCCCCCCCCCN(CCCCCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

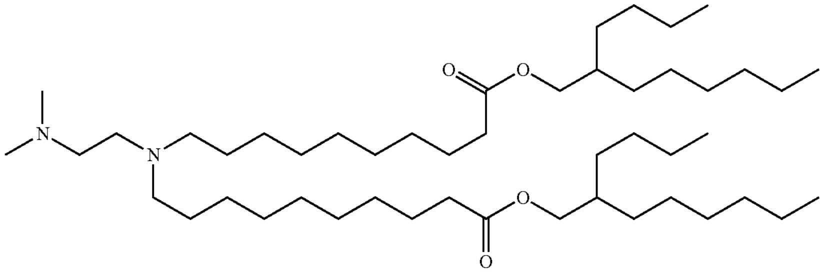 [SMILES: CCCCCCC(CCCC)COC(=O)CCCCCCCCCN(CCCCCCCCCC(=O)OCC(CCCC)CCCCCC)CCN(C)C]

and pharmaceutically acceptable salts thereof. In some embodiments, the compositions and methods of the present invention include a cationic lipid having the compound structure:

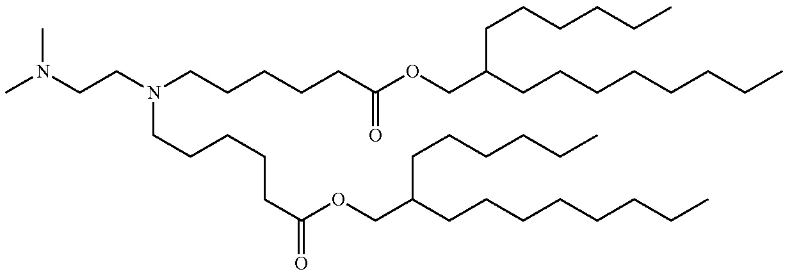 [SMILES: CCCCCCCCC(CCCCCC)COC(=O)CCCCCN(CCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

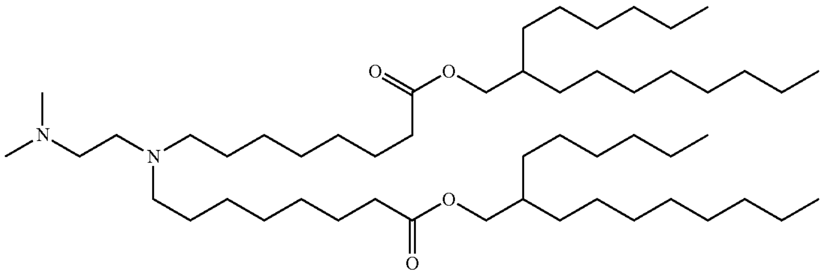 [SMILES: CCCCCCCCC(CCCCCC)COC(=O)CCCCCCCN(CCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

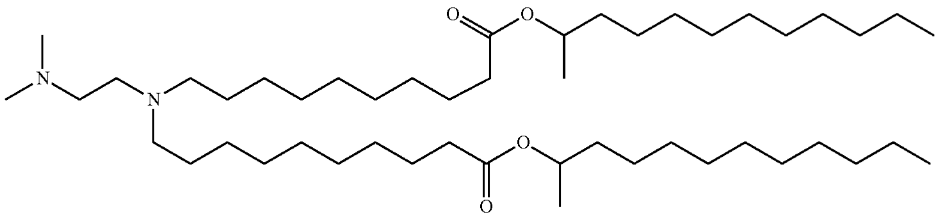 [SMILES: CCCCCCCCCCC(C)OC(=O)CCCCCCCCCN(CCCCCCCCCC(=O)OC(C)CCCCCCCCCC)CCN(C)C]

and pharmaceutically acceptable salts thereof. In some embodiments, the compositions and methods of the present invention include a cationic lipid having the compound structure:

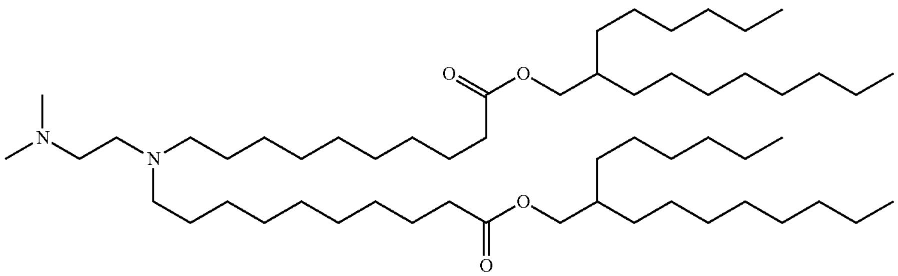 [SMILES: CCCCCCCCC(CCCCCC)COC(=O)CCCCCCCCCN(CCCCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

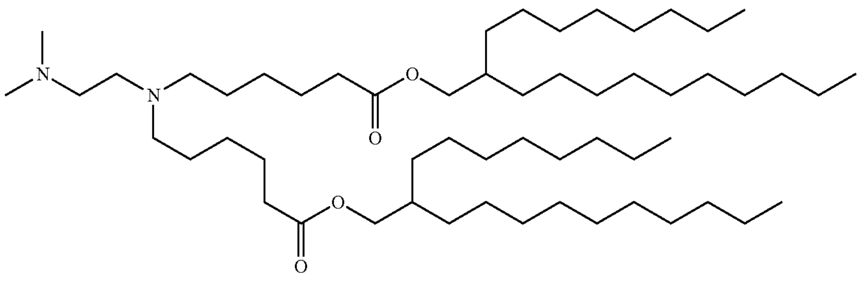 [SMILES: CCCCCCCCCCC(CCCCCCCC)COC(=O)CCCCCN(CCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

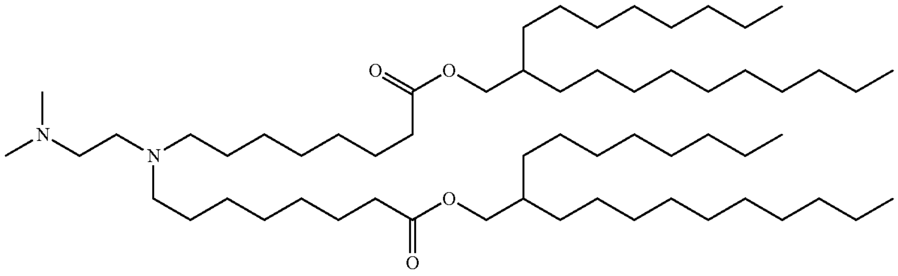 [SMILES: CCCCCCCCCCC(CCCCCCCC)COC(=O)CCCCCCCN(CCCCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

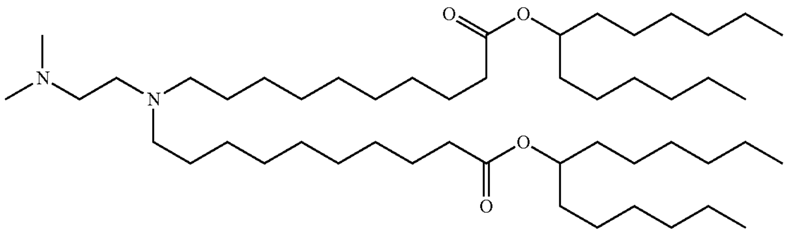 [SMILES: CCCCCCC(CCCCCC)OC(=O)CCCCCCCCCN(CCCCCCCCCC(=O)OC(CCCCCC)CCCCCC)CCN(C)C]

and pharmaceutically acceptable salts thereof. In some embodiments, the compositions and methods of the present invention include a cationic lipid having the compound structure:

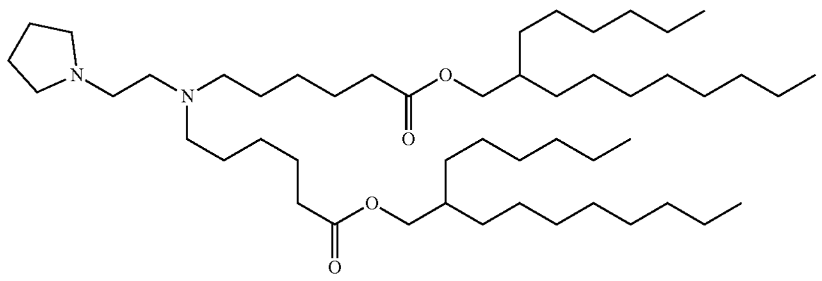 [SMILES: CCCCCCCCC(CCCCCC)COC(=O)CCCCCN(CCCCCC(=O)OCC(CCCCCC)CCCCCCCC)CCN1CCCC1]

and pharmaceutically acceptable salts thereof. In some embodiments, the compositions and methods of the present invention include a cationic lipid having the compound structure:

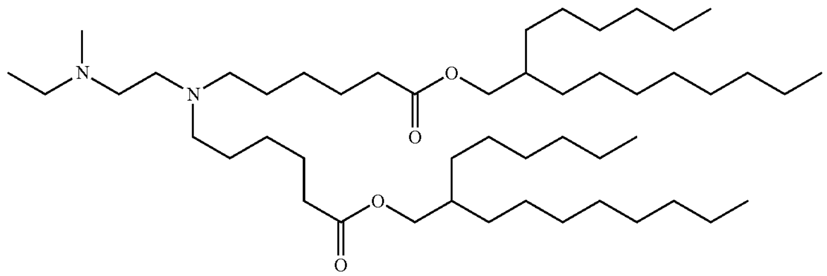 [SMILES: CCCCCCCCC(CCCCCC)COC(=O)CCCCCN(CCCCCC(=O)OCC(CCCCCC)CCCCCCCC)CCN(C)CC]

and pharmaceutically acceptable salts thereof. In some embodiments, the compositions and methods of the present invention include a cationic lipid having the compound structure:

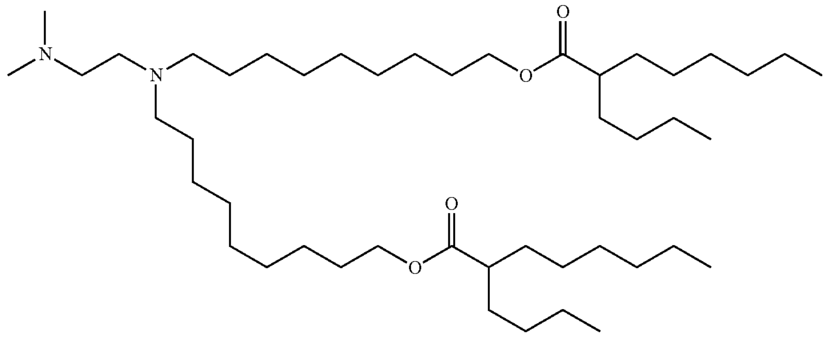 [SMILES: CCCCCCC(CCCC)C(=O)OCCCCCCCCCN(CCCCCCCCCOC(=O)C(CCCC)CCCCCC)CCN(C)C]

and pharmaceutically acceptable salts thereof.

Other suitable cationic lipids for use in the compositions and methods of the invention include the cationic lipids as described in International Patent Publication WO 2017/004143, which is incorporated herein by reference. In some embodiments, the compositions and methods of the present invention include a cationic lipid having the compound structure:

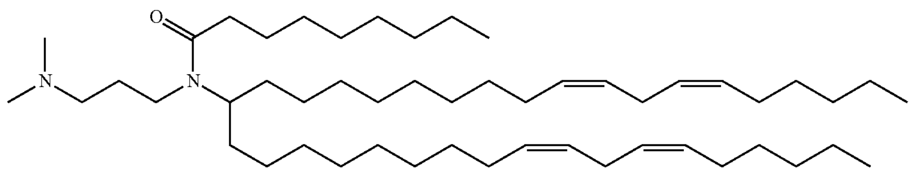 [SMILES: CCCCC/C=C\C/C=C\CCCCCCCCC(CCCCCCCC/C=C\C/C=C\CCCCC)N(CCCN(C)C)C(=O)CCCCCCCC]

and pharmaceutically acceptable salts thereof. In some embodiments, the compositions and methods of the present invention include a cationic lipid having the compound structure:

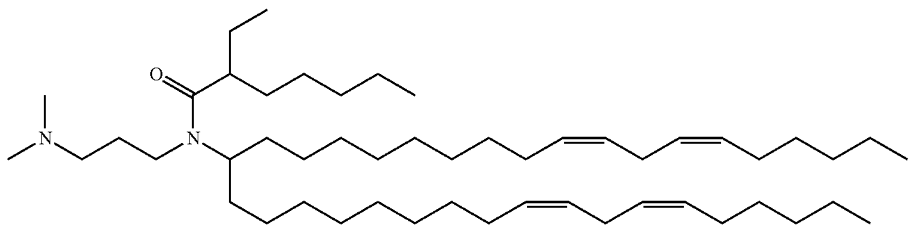 [SMILES: CCCCC/C=C\C/C=C\CCCCCCCCC(CCCCCCCC/C=C\C/C=C\CCCCC)N(CCCN(C)C)C(=O)C(CC)CCCCC]

and pharmaceutically acceptable salts thereof. In some embodiments, the compositions and methods of the present invention include a cationic lipid having the compound structure:

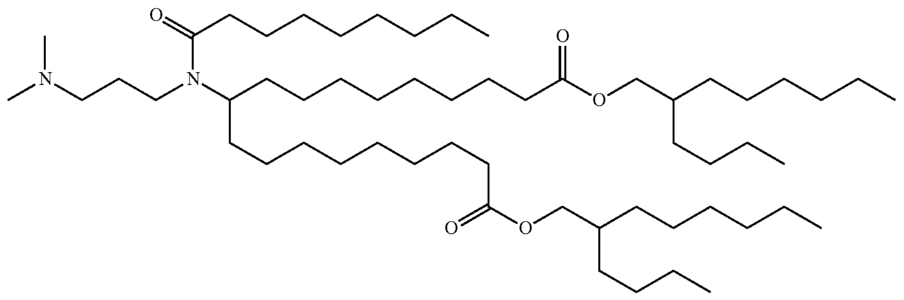 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

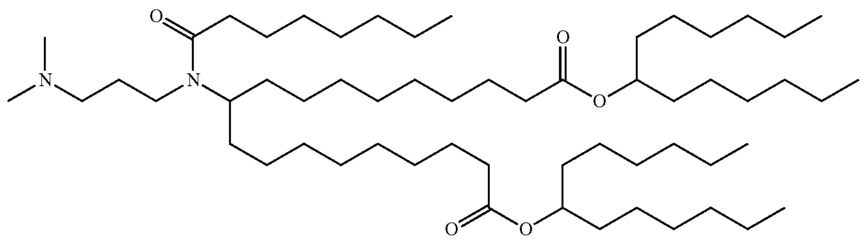 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

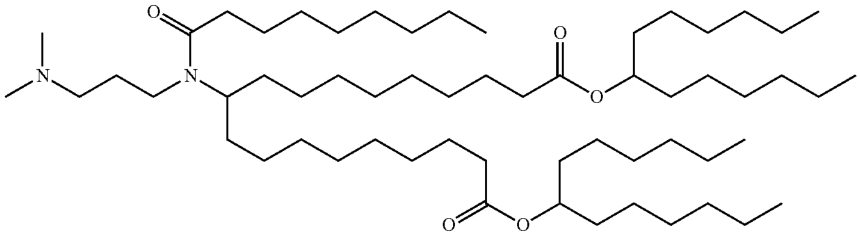 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

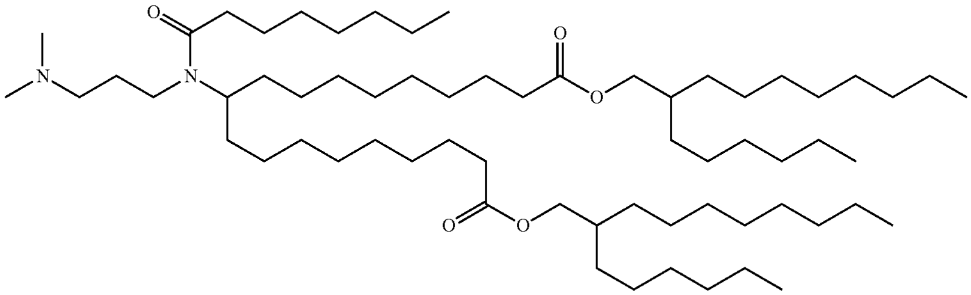 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

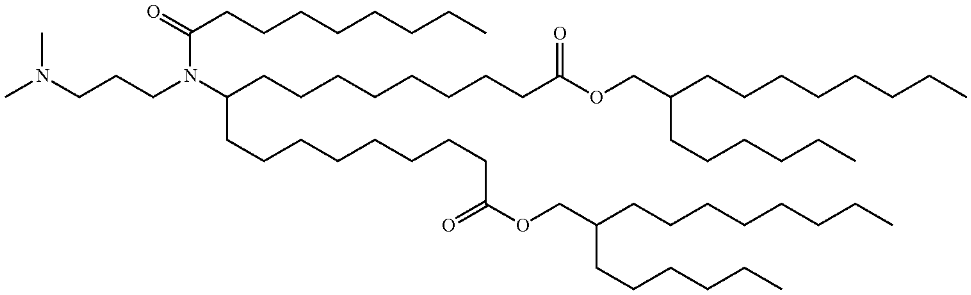 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC]

and pharmaceutically acceptable salts thereof. In some embodiments, the compositions and methods of the present invention include a cationic lipid having the compound structure:

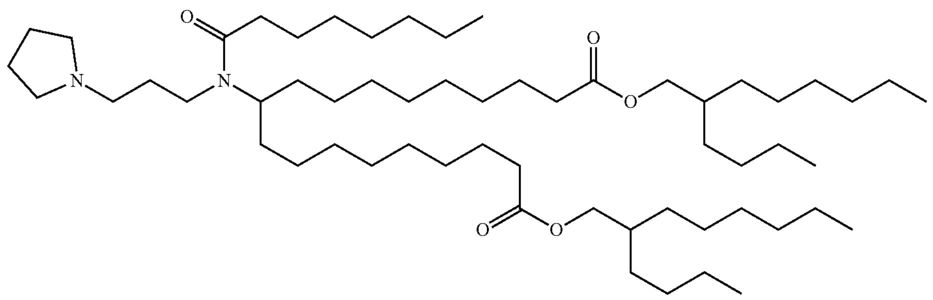 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

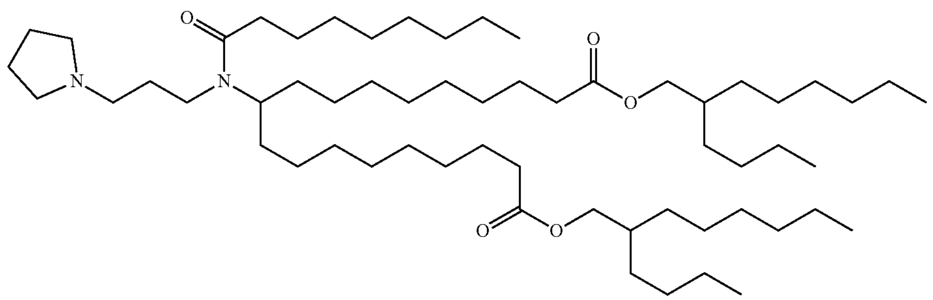 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

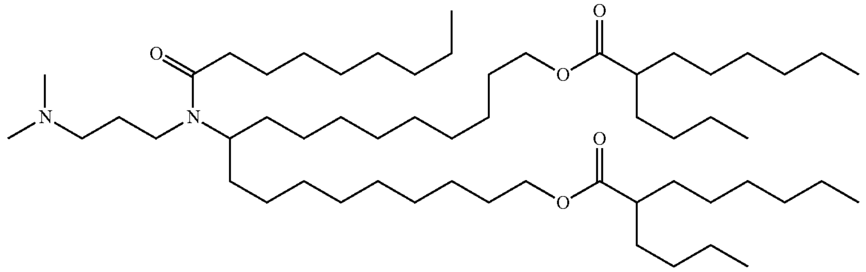 [SMILES: CCCCCCCCC(=O)N(CCCN(C)C)C(CCCCCCCCCOC(=O)C(CCCC)CCCCCC)CCCCCCCCCOC(=O)C(CCCC)CCCCCC]

and pharmaceutically acceptable salts thereof. In some embodiments, the compositions and methods of the present invention include a cationic lipid having the compound structure:

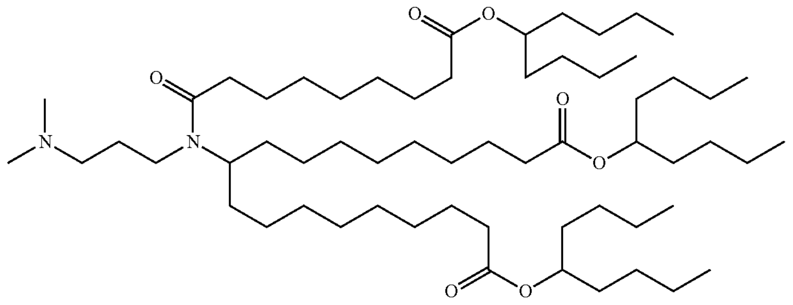 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC]

and pharmaceutically acceptable salts thereof. In some embodiments, the compositions and methods of the present invention include a cationic lipid having the compound structure:

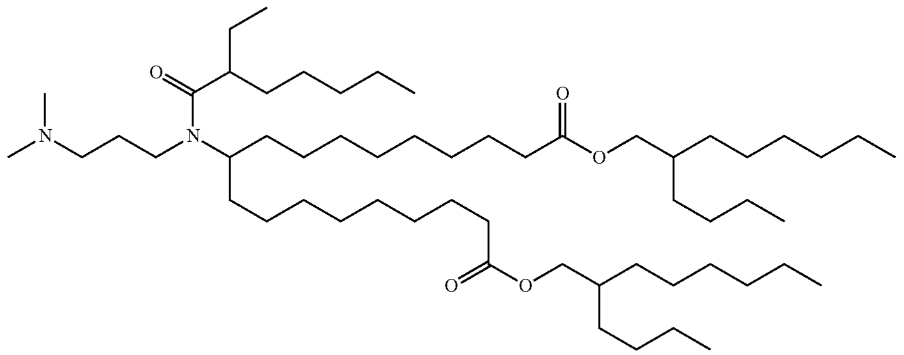 [SMILES: CCCCCCC(CCCC)COC(=O)CCCCCCCCC(CCCCCCCCC(=O)OCC(CCCC)CCCCCC)N(CCCN(C)C)C(=O)C(CC)CCCCC]

and pharmaceutically acceptable salts thereof. In some embodiments, the compositions and methods of the present invention include a cationic lipid having the compound structure:

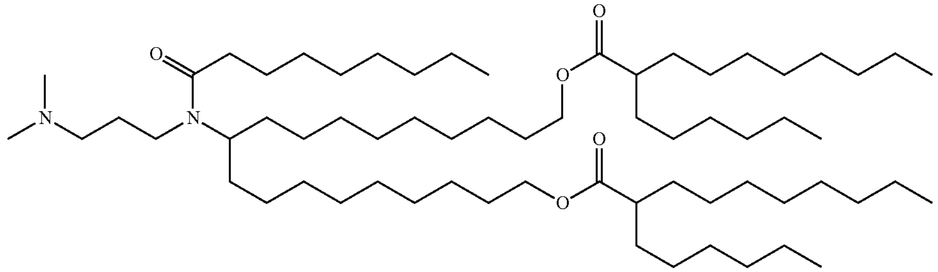 [SMILES: CCCCCCCCC(=O)N(CCCN(C)C)C(CCCCCCCCCOC(=O)C(CCCCCC)CCCCCCCC)CCCCCCCCCOC(=O)C(CCCCCC)CCCCCCCC]

and pharmaceutically acceptable salts thereof. In some embodiments, the compositions and methods of the present invention include a cationic lipid having the compound structure:

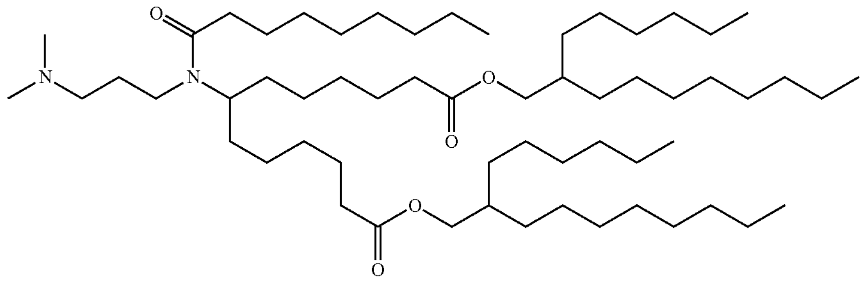 [SMILES: CCCCCCCCC(=O)N(CCCN(C)C)C(CCCCCC(=O)OCC(CCCCCC)CCCCCCCC)CCCCCC(=O)OCC(CCCCCC)CCCCCCCC]

and pharmaceutically acceptable salts thereof. In some embodiments, the compositions and methods of the present invention include a cationic lipid having the compound structure:

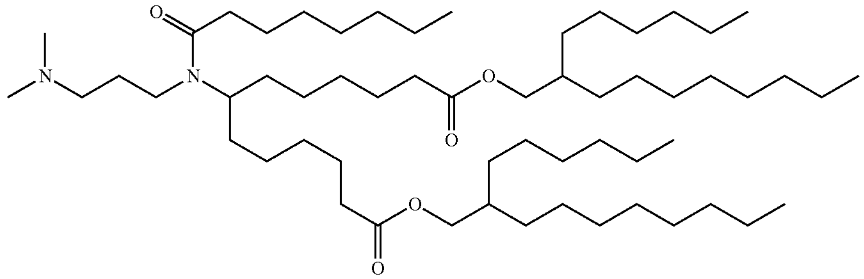 [SMILES: CCCCCCCCC(CCCCCC)COC(=O)CCCCCC(CCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

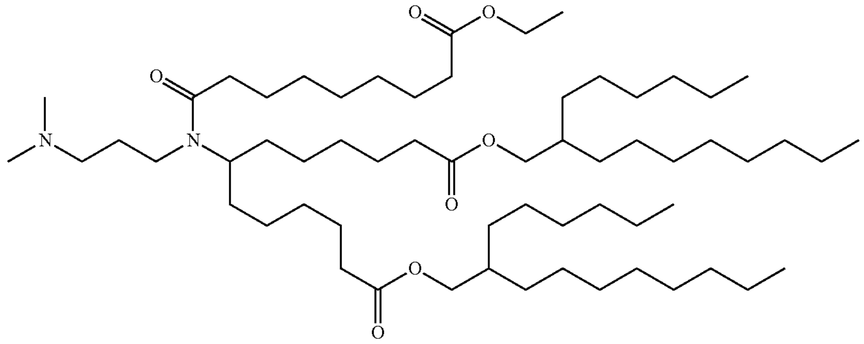 [SMILES: CCCCCCCCC(CCCCCC)COC(=O)CCCCCC(CCCCCC(=O)OCC(CCCCCC)CCCCCCCC)N(CCCN(C)C)C(=O)CCCCCCCC(=O)OCC]

and pharmaceutically acceptable salts thereof. In some embodiments, the compositions and methods of the present invention include a cationic lipid having the compound structure:

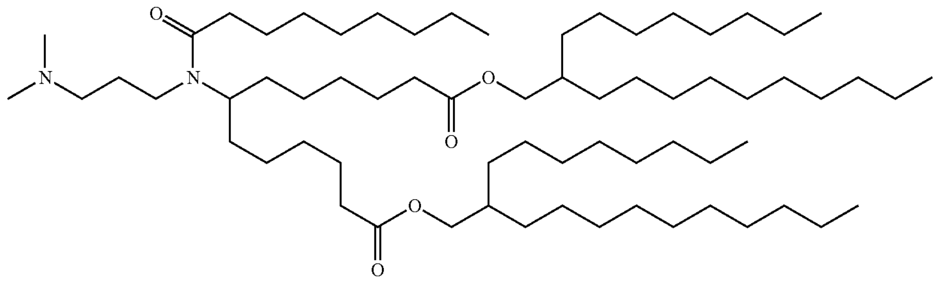 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC]

and pharmaceutically acceptable salts thereof.

Other suitable cationic lipids for use in the compositions and methods of the invention include the cationic lipids as described in International Patent Publication WO 2017/075531, which is incorporated herein by reference. In some embodiments, the compositions and methods of the present invention include a cationic lipid of the following formula:

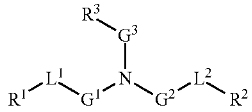

or a pharmaceutically acceptable salt thereof, wherein one of $L^1$ or $L^2$ is —O(C═O)—, —(C═O)O—, —C(═O)—, —O—, —S(O)$_x$, —S—S—, —C(═O)S—, —SC(═O)—, —NR$^a$C(═O)—, —C(═O)NR$^a$—, NR$^a$C(═O)NR$^a$—, —OC(═O)NR$^a$—, or —NR$^a$C(═O)O—; and the other of $L^1$ or $L^2$ is —O(C═O)—, —(C═O)O—, —C(═O)—, —O—, —S(O)$_x$, —S—S—, —C(═O)S—, SC(═O)—, —NR$^a$C(═O)—, —C(═O)NR$^a$—, NR$^a$C(═O)NR$^a$—, —OC(═O)NR$^a$— or —NR$^a$C(═O)O— or a direct bond; $G^1$ and $G^2$ are each independently unsubstituted $C_1$-$C_{12}$ alkylene or $C_1$-$C_{12}$ alkenylene; $G^3$ is $C_1$-$C_{24}$ alkylene, $C_1$-$C_{24}$ alkenylene, $C_3$-$C_8$ cycloalkylene, $C_3$-$C_8$ cycloalkenylene; Ra is H or $C_1$-$C_{12}$ alkyl; $R^1$ and $R^2$ are each independently $C_6$-$C_{24}$ alkyl or $C_6$-$C_{24}$ alkenyl; $R^3$ is H, $OR^5$, CN, —C(═O)OR$^4$, —OC(═O)R$^4$ or —NR$^5$ C(═O)R$^4$; $R^4$ is $C_1$-$C_{12}$ alkyl; $R^5$ is H or $C_1$-$C_6$ alkyl; and x is 0, 1 or 2.

Other suitable cationic lipids for use in the compositions and methods of the invention include the cationic lipids as described in International Patent Publication WO 2017/117528, which is incorporated herein by reference. In some embodiments, the compositions and methods of the present invention include a cationic lipid having the compound structure:

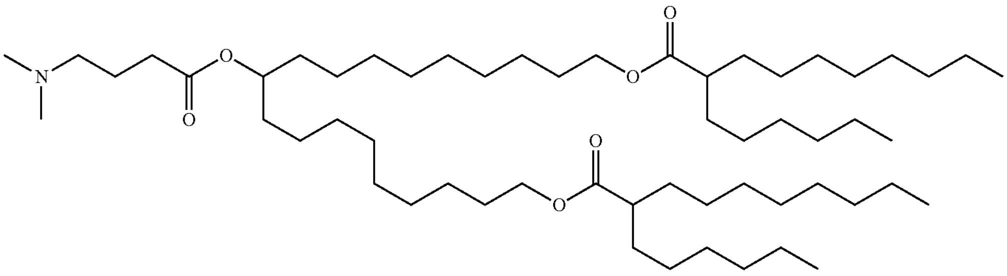 [SMILES: CCCCCCCCC(CCCCCC)C(=O)OCCCCCCCCCC(CCCCCCCCCOC(=O)C(CCCCCC)CCCCCCCC)OC(=O)CCCN(C)C]

and pharmaceutically acceptable salts thereof. In some embodiments, the compositions and methods of the present invention include a cationic lipid having the compound structure:

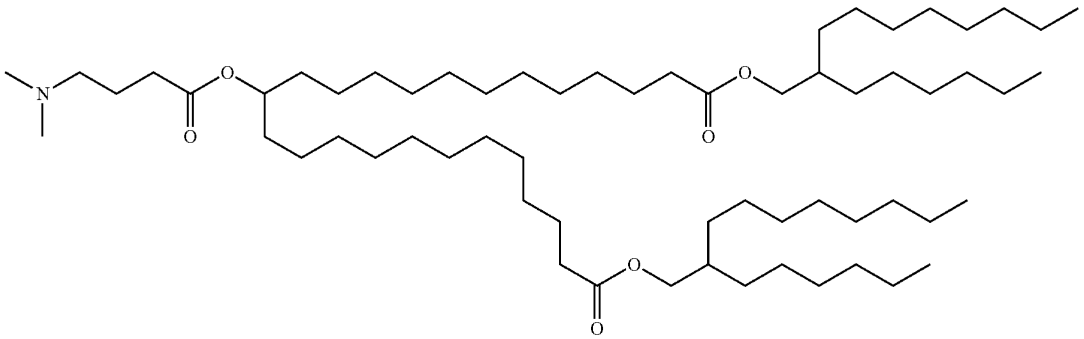 [SMILES: CCCCCCCCC(CCCCCC)COC(=O)CCCCCCCCCCCC(CCCCCCCCCCCC(=O)OCC(CCCCCC)CCCCCCCC)OC(=O)CCCN(C)C]

and pharmaceutically acceptable salts thereof. In some embodiments, the compositions and methods of the present invention include a cationic lipid having the compound structure:

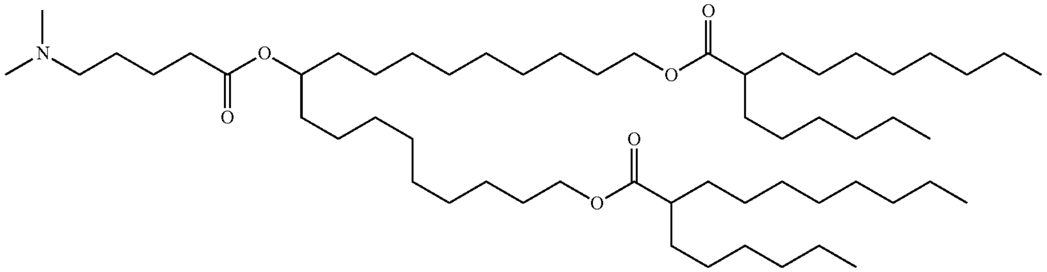 [SMILES: CCCCCCCCC(CCCCCC)C(=O)OCCCCCCCCCC(CCCCCCCCCOC(=O)C(CCCCCC)CCCCCCCC)OC(=O)CCCCN(C)C]

and pharmaceutically acceptable salts thereof.

Other suitable cationic lipids for use in the compositions and methods of the invention include the cationic lipids as described in International Patent Publication WO 2017/049245, which is incorporated herein by reference. In some embodiments, the cationic lipids of the compositions and methods of the present invention include a compound of one of the following formulas:

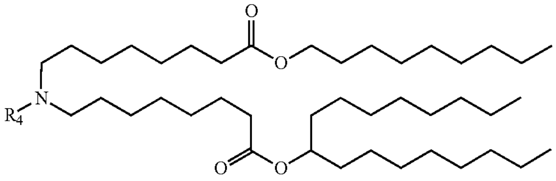

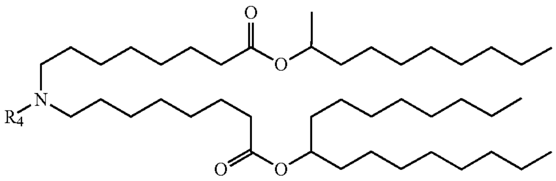

-continued

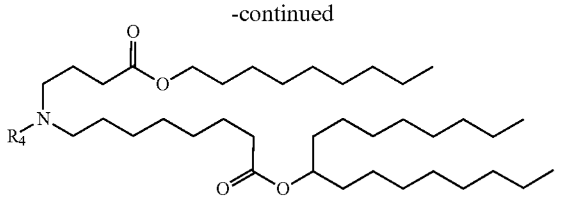

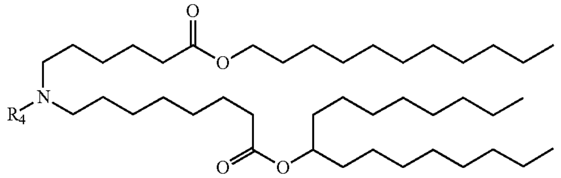

and pharmaceutically acceptable salts thereof. For any one of these four formulas, $R_4$ is independently selected from —$(CH_2)_nQ$ and —$(CH_2)_nCHQR$; Q is selected from the group consisting of —OR, —OH, —$O(CH_2)_nN(R)_2$, —OC(O)R, —$CX_3$, —CN, —N(R)C(O)R, —N(H)C(O)R, —$N(R)S(O)_2R$, —$N(H)S(O)_2R$, —$N(R)C(O)N(R)_2$, —$N(H)C(O)N(R)_2$, —N(H)C(O)N(H)(R), —$N(R)C(S)N(R)_2$, —$N(H)C(S)N(R)_2$, —N(H)C(S)N(H)(R), and a heterocycle; and n is 1, 2, or 3. In certain embodiments, the compositions and methods of the present invention include a cationic lipid having a compound structure of:

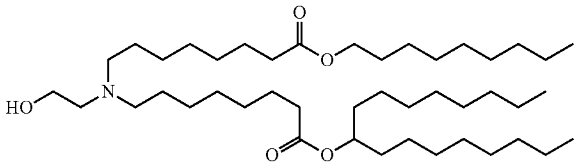 [SMILES: CCCCCCCCCOC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

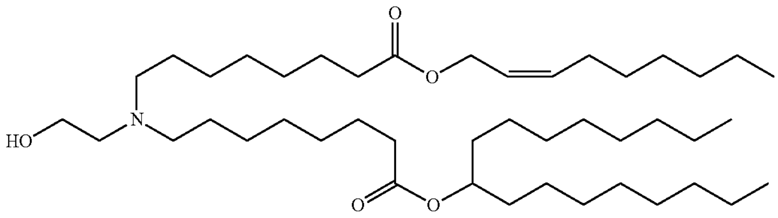 [SMILES: CCCCCC/C=C\COC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

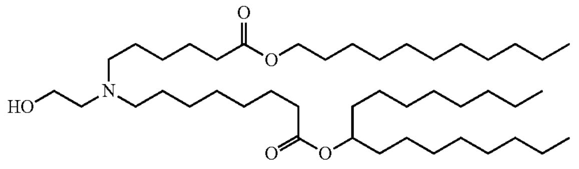 [SMILES: CCCCCCCCCCCOC(=O)CCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

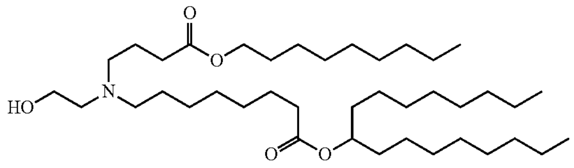 [SMILES: CCCCCCCCCOC(=O)CCCN(CCO)CCCCCCCC(=O)OC(CCCCCCCC)CCCCCCCC]

and pharmaceutically acceptable salts thereof.

Other suitable cationic lipids for use in the compositions and methods of the invention include the cationic lipids as described in International Patent Publication WO 2017/173054 and WO 2015/095340, each of which is incorporated herein by reference. In certain embodiments, the compositions and methods of the present invention include a cationic lipid having a compound structure of:

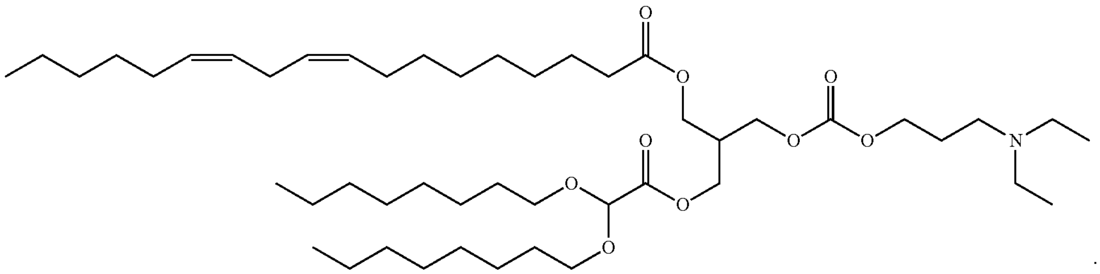 [SMILES: CCCCC/C=C\C/C=C\CCCCCCCC(=O)OCC(COC(=O)OCCCN(CC)CC)COC(=O)C(OCCCCCCCC)OCCCCCCCC]

and pharmaceutically acceptable salts thereof. In certain embodiments, the compositions and methods of the present invention include a cationic lipid having a compound structure of:

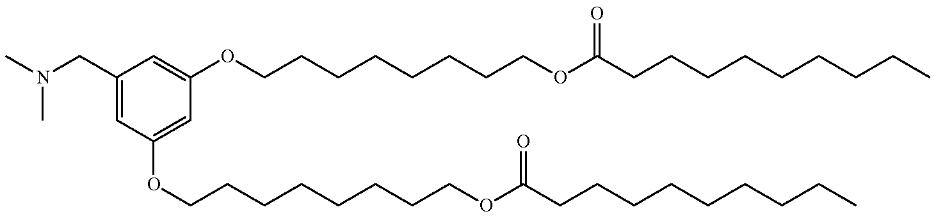 [SMILES: CCCCCCCCCC(=O)OCCCCCCCCOc1cc(CN(C)C)cc(OCCCCCCCCOC(=O)CCCCCCCCC)c1]

and pharmaceutically acceptable salts thereof. In certain embodiments, the compositions and methods of the present invention include a cationic lipid having a compound structure of:

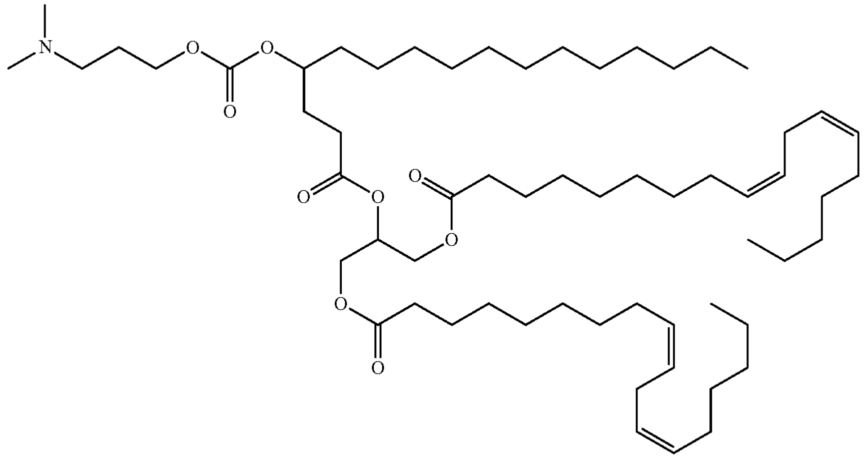 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C]

and pharmaceutically acceptable salts thereof. In certain embodiments, the compositions and methods of the present invention include a cationic lipid having a compound structure of:

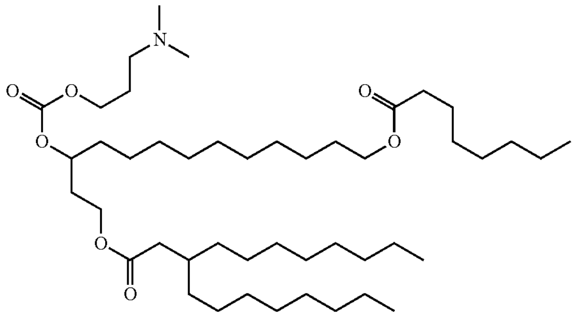 [SMILES: CCCCCCCCC(CCCCCCCC)CC(=O)OCCC(CCCCCCCCCCOC(=O)CCCCCCC)OC(=O)OCCCN(C)C]

and pharmaceutically acceptable salts thereof.

Other suitable cationic lipids for use in the compositions and methods of the present invention include cleavable cationic lipids as described in International Patent Publication WO 2012/170889, which is incorporated herein by reference. In some embodiments, the compositions and methods of the present invention include a cationic lipid of the following formula:

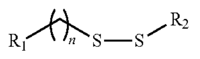

wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is selected from the group consisting of one of the following two formulas:

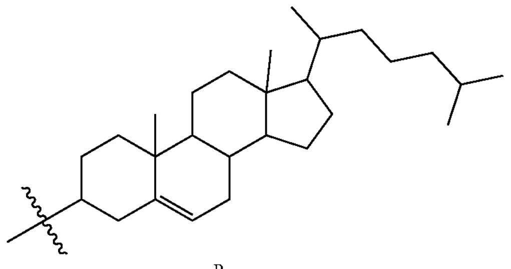

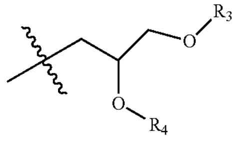

and wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl; and wherein n is zero or any positive integer (e.g., one, two, three, four, five, six, seven, eight, nine, ten, eleven, twelve, thirteen, fourteen, fifteen, sixteen, seventeen, eighteen, nineteen, twenty or more). In certain embodiments, the compositions and methods of the present invention include a cationic lipid, "HGT4001", having a compound structure of:

(HGT4001)

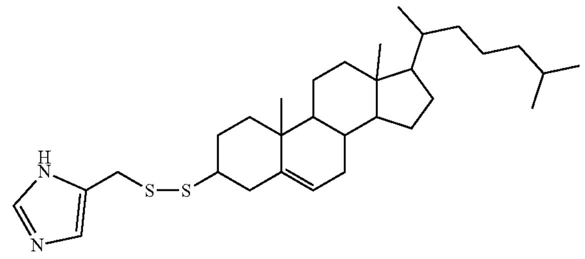

and pharmaceutically acceptable salts thereof. In certain embodiments, the compositions and methods of the present invention include a cationic lipid, "HGT4002", having a compound structure of:

(HGT4002)

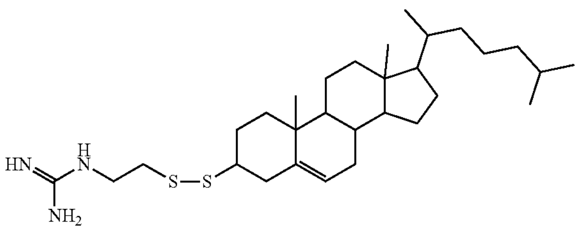

and pharmaceutically acceptable salts thereof. In certain embodiments, the compositions and methods of the present invention include a cationic lipid, "HGT4003", having a compound structure of:

(HGT4003)

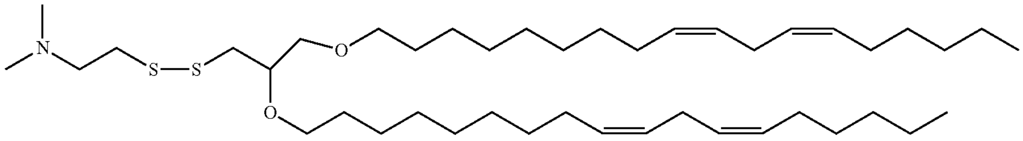

and pharmaceutically acceptable salts thereof. In certain embodiments, the compositions and methods of the present invention include a cationic lipid, "HGT4004", having a compound structure of:

(HGT4004)

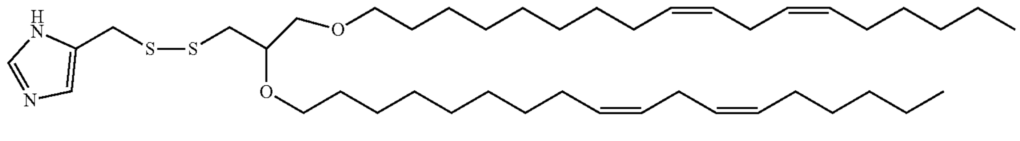

and pharmaceutically acceptable salts thereof. In certain embodiments, the compositions and methods of the present invention include a cationic lipid "HGT4005", having a compound structure of:

(HGT4005)

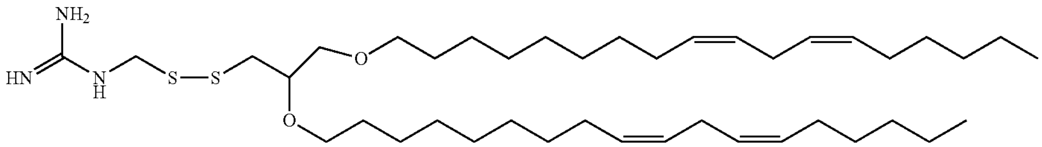

and pharmaceutically acceptable salts thereof.

Other suitable cationic lipids for use in the compositions and methods of the present invention include cleavable cationic lipids as described in U.S. Provisional Application No. 62/672,194, filed May 16, 2018, and incorporated herein by reference. In certain embodiments, the compositions and methods of the present invention include a cationic lipid that is any of general formulas or any of structures (1a)-(21a) and (1b)-(21b) and (22)-(237) described in U.S. Provisional Application No. 62/672,194. In certain embodiments, the compositions and methods of the present invention include a cationic lipid that has a structure according to Formula (I'),

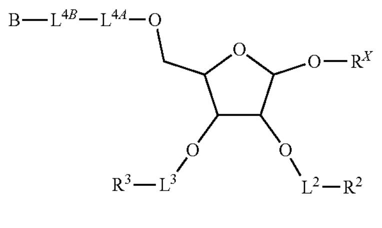

wherein:

$R^X$ is independently —H, $-L^1-R^1$, or $-L^{5A}-L^{5B}-B'$;

each of $L^1$, $L^2$, and $L^3$ is independently a covalent bond, —C(O)—, —C(O)O—, —C(O)S—, or —C(O)$NR^L$—;

each $L^{4A}$ and $L^{5A}$ is independently —C(O)—, —C(O)O—, or —C(O)$NR^L$—;

each $L^{4B}$ and $L^{5B}$ is independently $C_1$-$C_{20}$ alkylene; $C_2$-$C_{20}$ alkenylene; or $C_2$-$C_{20}$ alkynylene;

each B and B' is $NR^4R^5$ or a 5- to 10-membered nitrogen-containing heteroaryl;

each $R^1$, $R^2$, and $R^3$ is independently $C_6$-$C_{30}$ alkyl, $C_6$-$C_{30}$ alkenyl, or $C_6$-$C_{30}$ alkynyl;

each $R^4$ and $R^5$ is independently hydrogen, $C_1$-$C_{10}$ alkyl; $C_2$-$C_{10}$ alkenyl; or $C_2$-$C_{10}$ alkynyl; and each $R^L$ is independently hydrogen, $C_1$-$C_{20}$ alkyl, $C_2$-$C_{20}$ alkenyl, or $C_2$-$C_{20}$ alkynyl.

In certain embodiments, the compositions and methods of the present invention include a cationic lipid that is Compound (139) of 62/672,194, having a compound structure of:

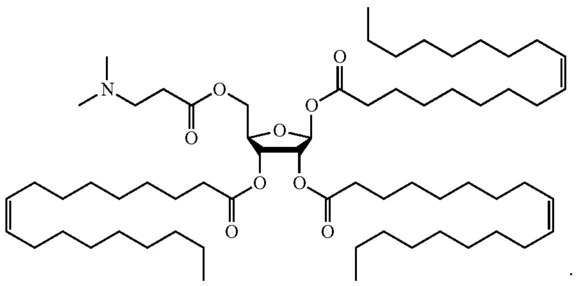

("18:1 Carbon tail-ribose lipid")

In some embodiments, the compositions and methods of the present invention include the cationic lipid, N-[1-(2,3-dioleyloxy)propyl]-N,N,N-trimethylammonium chloride ("DOTMA"). (Feigner et al. (Proc. Nat'l Acad. Sci. 84, 7413 (1987); U.S. Pat. No. 4,897,355, which is incorporated herein by reference). Other cationic lipids suitable for the compositions and methods of the present invention include, for example, 5-carboxyspermylglycinedioctadecylamide ("DOGS"); 2,3-dioleyloxy-N-[2(spermine-carboxamido)ethyl]-N,N-dimethyl-1-propanaminium ("DOSPA") (Behr et al. Proc. Nat.'l Acad. Sci. 86, 6982 (1989), U.S. Pat. Nos. 5,171,678; 5,334,761); 1,2-Dioleoyl-3-Dimethylammonium-Propane ("DODAP"); 1,2-Dioleoyl-3-Trimethylammonium-Propane ("DOTAP").

Additional exemplary cationic lipids suitable for the compositions and methods of the present invention also include: 1,2-distearyloxy-N,N-dimethyl-3-aminopropane ("DSDMA"); 1,2-dioleyloxy-N,N-dimethyl-3-aminopropane ("DODMA"); 1,2-dilinoleyloxy-N,N-dimethyl-3-aminopropane ("DLinDMA"); 1,2-dilinolenyloxy-N,N-dimethyl-3-aminopropane ("DLenDMA"); N-dioleyl-N,N-dimethylammonium chloride ("DODAC"); N,N-distearyl-N,N-dimethylammonium bromide ("DDAB"); N-(1,2-dimyristyloxyprop-3-yl)-N,N-dimethyl-N-hydroxyethyl ammonium bromide ("DMRIE"); 3-dimethylamino-2-(cholest-5-en-3-beta-oxybutan-4-oxy)-1-(cis,cis-9,12-octadecadienoxy)propane ("CLinDMA"); 2-[5'-(cholest-5-en-3-beta-oxy)-3'-oxapentoxy)-3-dimethy 1-1-(cis,cis-9', 1-2'-octadecadienoxy)propane ("CpLinDMA"); N,N-dimethyl-3,4-dioleyloxybenzylamine ("DMOBA"); 1,2-N,N'-dioleylcarbamyl-3-dimethylaminopropane ("DOcarbDAP"); 2,3-Dilinoleoyloxy-N,N-dimethylpropylamine ("DLinDAP"); 1,2-N,N'-Dilinoleylcarbamyl-3-dimethylaminopropane ("DLincarbDAP"); 1,2-Dilinoleoylcarbamyl-3-dimethylaminopropane ("DLinCDAP"); 2,2-dilinoleyl-4-dimethylaminomethyl-[1,3]-dioxolane ("DLin-K-DMA"); 2-((8-[(3P)-cholest-5-en-3-yloxy]octyl)oxy)-N,N-dimethyl-3-[(9Z, 12Z)-octadeca-9, 12-dien-1-yloxy]propane-1-amine ("Octyl-CLinDMA"); (2R)-2-((8-[(3beta)-cholest-5-en-3-yloxy]octyl)oxy)-N, N-dimethyl-3-[(9Z, 12Z)-octadeca-9, 12-dien-1-yloxy]propan-1-amine ("Octyl-CLinDMA (2R)"); (2S)-2-((8-[(3P)-cholest-5-en-3-yloxy]octyl)oxy)-N, fsl-dimethyh3-[(9Z, 12Z)-octadeca-9, 12-dien-1-yloxy]propan-1-amine ("Octyl-CLinDMA (2S)"); 2,2-dilinoleyl-4-dimethylaminoethyl-[1,3]-dioxolane ("DLin-K-XTC2-DMA"); and 2-(2,2-di((9Z,12Z)-octadeca-9,1 2-dien-1-yl)-1,3-dioxolan-4-yl)-N,N-dimethylethanamine ("DLin-KC2-DMA") (see, WO 2010/042877, which is incorporated herein by reference; Semple et al., Nature Biotech. 28: 172-176 (2010)). (Heyes, J., et al., J Controlled Release 107: 276-287 (2005); Morrissey, D V., et al., Nat. Biotechnol. 23(8): 1003-1007 (2005); International Patent Publication WO 2005/121348). In some embodiments, one or more of the cationic lipids comprise at least one of an imidazole, dialkylamino, or guanidinium moiety.

In some embodiments, one or more cationic lipids suitable for the compositions and methods of the present invention include 2,2-Dilinoleyl-4-dimethylaminoethyl-[1,3]-dioxolane ("XTC"); (3aR,5s,6aS)-N,N-dimethyl-2,2-di((9Z,12Z)-octadeca-9,12-dienyl)tetrahydro-3aH-cyclopenta[d][1,3]dioxol-5-amine ("ALNY-100") and/or 4,7,13-tris(3-oxo-3-(undecylamino)propyl)-N1,N16-diundecyl-4,7,10,13-tetraazahexadecane-1,16-diamide ("NC98-5").

In some embodiments, the compositions of the present invention include one or more cationic lipids that constitute at least about 5%, 10%, 20%, 30%, 35%, 40%, 45%, 50%, 55%, 60%, 65%, or 70%, measured by weight, of the total lipid content in the composition, e.g., a lipid nanoparticle. In some embodiments, the compositions of the present invention include one or more cationic lipids that constitute at least about 5%, 10%, 20%, 30%, 35%, 40%, 45%, 50%, 55%, 60%, 65%, or 70%, measured as a mol %, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured by weight, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured as mol %, of the total lipid content in the composition, e.g., a lipid nanoparticle.

Non-Cationic Helper Lipids

In some embodiments, provided liposomes contain one or more non-cationic ("helper") lipids. As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), phosphatidylserine, sphingolipids, cerebrosides, gangliosides, 16-O-monomethyl PE, 16-O-dimethyl PE, 18-1-trans PE, 1-stearoyl-2-oleoyl-phosphatidyethanolamine (SOPE), or a mixture thereof.

In some embodiments, such non-cationic lipids may be used alone, but are preferably used in combination with other lipids, for example, cationic lipids. In some embodiments, the non-cationic lipid may comprise a molar ratio of about 5% to about 90%, or about 10% to about 70% of the total lipid present in a liposome. In some embodiments, a non-cationic lipid is a neutral lipid, i.e., a lipid that does not carry a net charge in the conditions under which the composition is formulated and/or administered. In some embodiments, the percentage of non-cationic lipid in a liposome may be greater than 5%, greater than 10%, greater than 20%, greater than 30%, or greater than 40%.

Cholesterol-Based Lipids

In some embodiments, provided liposomes comprise one or more cholesterol-based lipids. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, the cholesterol-based lipid may comprise a molar ration of about 2% to about 30%, or about 5% to about 20% of the total lipid present in a liposome. In some embodiments, the percentage of cholesterol-based lipid in the lipid nanoparticle may be greater than 5%, greater than 10%, greater than 20%, greater than 30%, or greater than 40%.

PEG-Modified Lipids

The use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention, either alone or preferably in combination with other lipid formulations together which comprise the transfer vehicle (e.g., a lipid nanoparticle). Contemplated PEG-modified lipids include, but are not limited to, a polyethylene glycol chain of up to S kDa in length covalently attached to a lipid with alkyl chain(s) of $C_6$-$C_{20}$ length. The addition of such components may prevent complex aggregation and may also provide a means for increasing circulation lifetime and increasing the delivery of the lipid-nucleic acid composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., C14 or C18). The PEG-modified phospholipid and derivatized lipids of the present invention may comprise a molar ratio from about 0% to about 20%, about 0.5% to about 20%, about 1% to about 15%, about 4% to about 10%, or about 2% of the total lipid present in the liposomal transfer vehicle.

According to various embodiments, the selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the MCNA to be delivered. Additional considerations include, for example, the saturation of the alkyl chain, as well as the size, charge, pH, pKa, fusogenicity and toxicity of the selected lipid(s). Thus the molar ratios may be adjusted accordingly.

Polymers

In some embodiments, a suitable delivery vehicle is formulated using a polymer as a carrier, alone or in combination with other carriers including various lipids described herein. Thus, in some embodiments, liposomal delivery vehicles, as used herein, also encompass nanoparticles comprising polymers. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDa, e.g., 25 kDa branched PEI (Sigma #408727).

A suitable liposome for the present invention may include one or more of any of the cationic lipids, non-cationic lipids, cholesterol lipids, PEG-modified lipids and/or polymers described herein at various ratios. As non-limiting examples, a suitable liposome formulation may include a combination selected from cKK-E12, DOPE, cholesterol and DMG-PEG2K; C12-200, DOPE, cholesterol and DMG-PEG2K; HGT4003, DOPE, cholesterol and DMG-PEG2K; ICE, DOPE, cholesterol and DMG-PEG2K; or ICE, DOPE, and DMG-PEG2K.

In various embodiments, cationic lipids (e.g., cKK-E12, C12-200, ICE, and/or HGT4003) constitute about 30-60% (e.g., about 30-55%, about 30-50%, about 30-45%, about 30-40%, about 35-50%, about 35-45%, or about 35-40%) of the liposome by molar ratio. In some embodiments, the percentage of cationic lipids (e.g., cKK-E12, C12-200, ICE, and/or HGT4003) is or greater than about 30%, about 35%, about 40%, about 45%, about 50%, about 55%, or about 60% of the liposome by molar ratio.

In some embodiments, the ratio of cationic lipid(s) to non-cationic lipid(s) to cholesterol-based lipid(s) to PEG-modified lipid(s) may be between about 30-60:25-35:20-30:1-15, respectively. In some embodiments, the ratio of cationic lipid(s) to non-cationic lipid(s) to cholesterol-based lipid(s) to PEG-modified lipid(s) is approximately 40:30:20:10, respectively. In some embodiments, the ratio of cationic lipid(s) to non-cationic lipid(s) to cholesterol-based lipid(s) to PEG-modified lipid(s) is approximately 40:30:25:5, respectively. In some embodiments, the ratio of cationic lipid(s) to non-cationic lipid(s) to cholesterol-based lipid(s) to PEG-modified lipid(s) is approximately 40:32:25:3, respectively. In some embodiments, the ratio of cationic lipid(s) to non-cationic lipid(s) to cholesterol-based lipid(s) to PEG-modified lipid(s) is approximately 50:25:20:5.

Ratio of Distinct Lipid Components

In embodiments where a lipid nanoparticle comprises three and no more than three distinct components of lipids, the ratio of total lipid content (i.e., the ratio of lipid component (1):lipid component (2):lipid component (3)) can be represented as x:y:z, wherein $$(y+z)=100-x.$$

In some embodiments, each of “x,” “y,” and “z” represents molar percentages of the three distinct components of lipids, and the ratio is a molar ratio.

In some embodiments, each of “x,” “y,” and “z” represents weight percentages of the three distinct components of lipids, and the ratio is a weight ratio.

In some embodiments, lipid component (1), represented by variable “x,” is a sterol-based cationic lipid.

In some embodiments, lipid component (2), represented by variable “y,” is a helper lipid.

In some embodiments, lipid component (3), represented by variable “z” is a PEG lipid.

In some embodiments, variable “x,” representing the molar percentage of lipid component (1) (e.g., a sterol-based cationic lipid), is at least about 10%, about 20%, about 30%, about 40%, about 50%, about 55%, about 60%, about 65%, about 70%, about 75%, about 80%, about 85%, about 90%, or about 95%.

In some embodiments, variable “x,” representing the molar percentage of lipid component (1) (e.g., a sterol-based cationic lipid), is no more than about 95%, about 90%, about 85%, about 80%, about 75%, about 70%, about 65%, about 60%, about 55%, about 50%, about 40%, about 30%, about 20%, or about 10%. In embodiments, variable “x” is no more than about 65%, about 60%, about 55%, about 50%, about 40%.

In some embodiments, variable “x,” representing the molar percentage of lipid component (1) (e.g., a sterol-based cationic lipid), is: at least about 50% but less than about 95%; at least about 50% but less than about 90%; at least about 50% but less than about 85%; at least about 50% but less than about 80%; at least about 50% but less than about 75%; at least about 50% but less than about 70%; at least about 50% but less than about 65%; or at least about 50% but less than about 60%. In embodiments, variable “x” is at least about 50% but less than about 70%; at least about 50% but less than about 65%; or at least about 50% but less than about 60%.

In some embodiments, variable “x,” representing the weight percentage of lipid component (1) (e.g., a sterol-based cationic lipid), is at least about 10%, about 20%, about 30%, about 40%, about 50%, about 55%, about 60%, about 65%, about 70%, about 75%, about 80%, about 85%, about 90%, or about 95%.

In some embodiments, variable “x,” representing the weight percentage of lipid component (1) (e.g., a sterol-based cationic lipid), is no more than about 95%, about 90%, about 85%, about 80%, about 75%, about 70%, about 65%, about 60%, about 55%, about 50%, about 40%, about 30%, about 20%, or about 10%. In embodiments, variable “x” is no more than about 65%, about 60%, about 55%, about 50%, about 40%.

In some embodiments, variable “x,” representing the weight percentage of lipid component (1) (e.g., a sterol-based cationic lipid), is: at least about 50% but less than about 95%; at least about 50% but less than about 90%; at least about 50% but less than about 85%; at least about 50% but less than about 80%; at least about 50% but less than about 75%; at least about 50% but less than about 70%; at least about 50% but less than about 65%; or at least about 50% but less than about 60%. In embodiments, variable “x” is at least about 50% but less than about 70%; at least about 50% but less than about 65%; or at least about 50% but less than about 60%.

In some embodiments, variable “z,” representing the molar percentage of lipid component (3) (e.g., a PEG lipid) is no more than about 1%, 2%, 3%, 4%, 5%, 6%, 7%, 8%, 9%, 10%, 15%, 20%, or 25%. In embodiments, variable “z,” representing the molar percentage of lipid component (3) (e.g., a PEG lipid) is about 1%, 2%, 3%, 4%, 5%, 6%, 7%, 8%, 9%, 10%. In embodiments, variable “z,” representing the molar percentage of lipid component (3) (e.g., a PEG lipid) is about 1% to about 10%, about 2% to about 10%, about 3% to about 10%, about 4% to about 10%, about 1% to about 7.5%, about 2.5% to about 10%, about 2.5% to about 7.5%, about 2.5% to about 5%, about 5% to about 7.5%, or about 5% to about 10%.

In some embodiments, variable “z,” representing the weight percentage of lipid component (3) (e.g., a PEG lipid) is no more than about 1%, 2%, 3%, 4%, 5%, 6%, 7%, 8%, 9%, 10%, 15%, 20%, or 25%. In embodiments, variable “z,” representing the weight percentage of lipid component (3) (e.g., a PEG lipid) is about 1%, 2%, 3%, 4%, 5%, 6%, 7%, 8%, 9%, 10%. In embodiments, variable “z,” representing the weight percentage of lipid component (3) (e.g., a PEG lipid) is about 1% to about 10%, about 2% to about 10%, about 3% to about 10%, about 4% to about 10%, about 1% to about 7.5%, about 2.5% to about 10%, about 2.5% to about 7.5%, about 2.5% to about 5%, about 5% to about 7.5%, or about 5% to about 10%.

For compositions having three and only three distinct lipid components, variables “x,” “y,” and “z” may be in any combination so long as the total of the three variables sums to 100% of the total lipid content.

Formation of Liposomes Encapsulating mRNA

The liposomal transfer vehicles for use in the compositions of the invention can be prepared by various techniques which are presently known in the art. The liposomes for use in provided compositions can be prepared by various techniques which are presently known in the art. For example, multilamellar vesicles (MLV) may be prepared according to conventional techniques, such as by depositing a selected lipid on the inside wall of a suitable container or vessel by dissolving the lipid in an appropriate solvent, and then evaporating the solvent to leave a thin film on the inside of the vessel or by spray drying. An aqueous phase may then be added to the vessel with a vortexing motion which results in the formation of MLVs. Unilamellar vesicles (ULV) can then be formed by homogenization, sonication or extrusion of the multilamellar vesicles. In addition, unilamellar vesicles can be formed by detergent removal techniques.

In certain embodiments, provided compositions comprise a liposome wherein the mRNA is associated on both the surface of the liposome and encapsulated within the same liposome. For example, during preparation of the compositions of the present invention, cationic liposomes may associate with the mRNA through electrostatic interactions. For example, during preparation of the compositions of the present invention, cationic liposomes may associate with the mRNA through electrostatic interactions.

In some embodiments, the compositions and methods of the invention comprise mRNA encapsulated in a liposome. In some embodiments, the one or more mRNA species may be encapsulated in the same liposome. In some embodiments, the one or more mRNA species may be encapsulated in different liposomes. In some embodiments, the mRNA is encapsulated in one or more liposomes, which differ in their lipid composition, molar ratio of lipid components, size, charge (zeta potential), targeting ligands and/or combinations thereof. In some embodiments, the one or more liposome may have a different composition of sterol-based cationic lipids, neutral lipid, PEG-modified lipid and/or combinations thereof. In some embodiments the one or more liposomes may have a different molar ratio of cholesterol-based cationic lipid, neutral lipid, and PEG-modified lipid used to create the liposome.

The process of incorporation of a desired mRNA into a liposome is often referred to as "loading". Exemplary methods are described in Lasic, et al., FEBS Lett., 312: 255-258, 1992, which is incorporated herein by reference. The liposome-incorporated nucleic acids may be completely or partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome. The purpose of incorporating an mRNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and/or facilitate the delivery of mRNA to the target cell or tissue.

Suitable liposomes in accordance with the present invention may be made in various sizes. In some embodiments, provided liposomes may be made smaller than previously known mRNA encapsulating liposomes. In some embodiments, decreased size of liposomes is associated with more efficient delivery of mRNA. Selection of an appropriate liposome size may take into consideration the site of the target cell or tissue and to some extent the application for which the liposome is being made.

In some embodiments, an appropriate size of liposome is selected to facilitate systemic distribution of antibody encoded by the mRNA. In some embodiments, it may be desirable to limit transfection of the mRNA to certain cells or tissues. For example, to target hepatocytes a liposome may be sized such that its dimensions are smaller than the fenestrations of the endothelial layer lining hepatic sinusoids in the liver; in such cases the liposome could readily penetrate such endothelial fenestrations to reach the target hepatocytes.

Alternatively or additionally, a liposome may be sized such that the dimensions of the liposome are of a sufficient diameter to limit or expressly avoid distribution into certain cells or tissues.

A variety of alternative methods known in the art are available for sizing of a population of liposomes. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomes may be determined by quasi-electric light scattering (QELS) as described in Bloomfield, Ann. Rev. Biophys. Bioeng., 10:421-150 (1981), incorporated herein by reference. Average liposome diameter may be reduced by sonication of formed liposomes. Intermittent sonication cycles may be alternated with QELS assessment to guide efficient liposome synthesis.

Therapeutic Use of Compositions

In one aspect, the present invention, among other things, provide a method of inducing CFTR expression in vivo by administration of nucleic acids encoding a modified CFTR protein, or by administration of a modified CFTR protein. In some embodiments, a composition comprises nucleic acids encapsulated or complexed with a delivery vehicle. In some embodiments, the delivery vehicle is selected from the group consisting of liposomes, lipid nanoparticles, solid-lipid nanoparticles, polymers, viruses, sol-gels, and nanogels. In some embodiments, nucleic acids encoding a modified CFTR protein are packaged in a viral particle.

Gene Therapy

In some embodiments, a pharmaceutical composition comprising nucleic acids encoding a modified CFTR protein is used to treat subjects in need thereof. In some embodiments, a pharmaceutical composition comprising a rAAV vector described herein is used to treat subjects in need thereof. The pharmaceutical composition containing a rAAV vector or particle of the invention contains a pharmaceutically acceptable excipient, diluent or carrier. Examples of suitable pharmaceutical carriers are well known in the art and include phosphate buffered saline solutions, water, emulsions, such as oil/water emulsions, various types of wetting agents, sterile solutions and the like. The pharmaceutical composition can be in a lyophilized form. Such carriers can be formulated by conventional methods and are administered to the subject at a therapeutically effective amount.

The rAAV vector is administered to a subject in need thereof via a suitable route. In some embodiments, the rAAV vector is administered by intravenous, intraperitoneal, subcutaneous, or intradermal routes. In one embodiment, the rAAV vector is administered intravenously. In embodiments, the intradermal administration comprises administration by use of a "gene gun" or biolistic particle delivery system. In some embodiments, the rAAV vector is administered via a non-viral lipid nanoparticle. For example, a composition comprising the rAAV vector may comprise one or more diluents, buffers, liposomes, a lipid, a lipid complex. In some embodiments, the rAAV vector is comprised within a microsphere or a nanoparticle, such as a lipid nanoparticle or an inorganic nanoparticle.

In some embodiments, a rAAV is pseudotyped. A pseudotyped rAAV is an infectious virus comprising any combination of an AAV capsid protein and a rAAV genome. Pseudotyped rAAV are useful to alter the tissue or cell specificity of rAAV, and may be employed alone or in conjunction with non-pseudotyped rAAV to transfer one or more genes to a cell, e.g., a mammalian cell. For example, pseudotyped rAAV may be employed subsequent to administration with non-pseudotyped rAAV in a mammal which has developed an immune response to the non-pseudotyped rAAV. Capsid proteins from any AAV serotype may be employed with a rAAV genome which is derived or obtainable from a wild-type AAV genome of a different serotype or which is a chimeric genome, i.e., formed from AAV DNA from two or more different serotypes, e.g., a chimeric genome having 2 ITRs, each ITR from a different serotype or chimeric ITRs. The use of chimeric genomes such as those comprising ITRs from two AAV serotypes or chimeric ITRs can result in directional recombination which may further enhance the production of transcriptionally active intermolecular concatamers. Thus, the 5' and 3' JTRs within a rAAV vector of the invention may be homologous, i.e., from the same serotype, heterologous, i.e., from different serotypes, or chimeric, i.e., an ITR which has ITR sequences from more than one AAV serotype.

In some embodiments, the rAAV vector is an AAV1, AAV2, AAV3, AAV4, AAV5, AAV6, AAV7, AAV8, AAV9, AAV10, or AAV11 vector. In some embodiments, the rAAV vector is AAV1. In some embodiments, the rAAV vector is AAV2. In some embodiments, the rAAV vector is AAV3. In some embodiments, the rAAV vector is AAV4. In some embodiments, the rAAV vector is AAV5. In some embodiments, the rAAV vector is AAV6. In some embodiments, the rAAV vector is AAV7. In some embodiments, the rAAV vector is AAV8. In some embodiments, the rAAV vector is AAV9. In some embodiments, the rAAV vector is AAV10. In some embodiments, the rAAV vector is AAV11. In some embodiments, the rAAV vector is sequence optimized. In some embodiments, the rAAV capsid is modified. For example, in some embodiments, the rAAV8 capsid is modified.

Protein Replacement Therapy

The term "protein replacement" refers to the introduction of a non-native, purified protein into an individual having a deficiency in such protein. In some embodiments, a modified CFTR protein of the present invention can be used to treat subjects suffering from CFTR protein insufficiency.

A modified CFTR protein can be administered as a pure compound, but is advantageously presented in the form of a pharmaceutical preparation. In some embodiments, a modified CFTR protein is administered in a pharmaceutically acceptable carrier. In some embodiments, a modified CFTR protein can be formulated for oral, parenteral or rectal administration, or in forms suited to administrations by inhalation or insufflation (either via the mouth or nose).

For oral administrations, the pharmaceutical preparations are in the form of, for example, tablets or capsules prepared by known methods with pharmaceutically acceptable excipients such as binders (for example pregelatinized maize starch, polyvinylpyrrolidone, or methyl cellulose); fillers (for example lactose, microcrystalline cellulose or calcium hydrogen phosphate); additives (for example magnesium stearate, talc, silica); disintegrants (for example potato starch); and/or lubricants (for example sodium lauryl sulphate). The tablets can be coated using known methods. Liquid preparations for oral administration have the form, for example, of solutions, syrups or suspensions, or can be in the form of a dry product that can be dissolved in water or another liquid prior to use. Said preparations are prepared by known methods with pharmaceutically acceptable additives such as suspending agents (for example sorbitol, cellulose derivatives, edible hydrogenated fats); emulsifying agents (for example lecithin or acacia); non-aqueous liquids (for example almond oil, oily esters, ethyl alcohol or fractionated vegetable oils); and/or preservatives (for example methyl or propylhydroxybenzoates, sorbic acid or ascorbic acid). The preparations can also contain, in appropriate cases, buffering salts, colouring agents, flavouring agents and/or sweeteners.

Preparations for oral administration are formulated in a known manner, in order to provide a controlled release of the active compound.

In some embodiments, a modified CFTR protein is formulated, in a known manner, for parenteral administration, by injection or continuous administration. Formulations for injection are, advantageously, in the form of dosage units, for example in ampoules or multi-dose containers containing preservatives. The composition can be in the form of a suspension, in aqueous or oily liquids, and can contain elements of the formulation as dispersing and stabilizing agents. Alternatively, the active compound can be in powder form to be dissolved just before use in a liquid as needed, such as sterile water.

In some embodiments, a modified CFTR protein can be formulated for rectal administration as suppositories or enemas, for example, containing suppository excipients of known type such as cocoa butter or other glycerides.

In some embodiments, a modified CFTR protein is also formulated, in a known manner, in extended release compositions. These extended release compositions are, for example, administered by means of an implant (for example subcutaneous or intramuscular) or an intramuscular injection. Therefore, for example, a modified CFTR protein is formulated with suitable polymer or hydrophobic materials (such as an emulsion or an oil) or ion exchange resins, or relatively poorly soluble derivatives, such as relatively poorly soluble salts.

In some embodiments, a modified CFTR protein is administered by intranasal delivery. In some embodiments, a modified CFTR protein is formulated by administrations via a (known) device, such as in a powder with a suitable vehicle. In some embodiments, a modified CFTR protein is administered by pulmonary delivery.

In certain embodiments, a modified CFTR protein is administered on a suitable dosage schedule, for example, weekly, twice weekly, monthly, twice monthly, etc. In certain embodiments, the modified CFTR protein is administered once weekly by inhalation. The activated CFTR protein can be administered in any therapeutically effective amount.

EXAMPLES

While certain compounds, compositions and methods of the present invention have been described with specificity in accordance with certain embodiments, the following examples serve only to illustrate the compounds of the invention and are not intended to limit the same.

Example 1. Schematic Model of Regulation of Cystic Fibrosis Transmembrane Conductance Regulator (CFTR) Channel Activity This example illustrates a schematic model for the regulation of CFTR channel activity (FIG. 1).

Briefly, CFTR is a chloride channel located in the apical membrane of epithelia and comprises 5 domains: two membrane spanning domains (TMD1 and TMD2) with six transmembrane segments each which form the chloride channel pore, two nucleotide binding domains (NBD1 and NBD2) that interact with and hydrolyze ATP, and a fifth unique unstructured regulatory domain called the R domain.

NBD1-NBD2 dimerization is promoted by cAMP-dependent Protein kinase A (PKA) phosphorylation of the unique R domain. Additionally, phosphorylation of the R domain regulates the CFTR activity through mechanisms independent of ATP-induced NBD dimerization.

CFTR is the only known ion channel in the ATP binding cassette (ABC) transporter superfamily. The binding of ATP to each of two sites in the nucleotide binding domains (NBD1 and NBD2 dimer interface) of CFTR drive conformational rearrangements of the transmembrane domains linked to cytosolic loops resulting in opening of the CFTR chloride channel (FIG. 1). ATP hydrolysis at the NBD2 site results in closing of the channel.

Example 2. Engineering CFTR Activation/Stability Mutant Proteins

This example illustrates CFTR amino acid residues mutated in the CFTR gene that results in activation and opening of the CFTR chloride channel. For example, shown here are activating mutations that are R domain phosphomimetics, ATP-gating mutations and CFTR protein stability/expression-enhancing mutations.

The unstructured regulatory domain (R domain) of CFTR contains multiple protein kinase A (PKA) sites that when phosphorylated allow chloride channel gating by PKA.

Figure 2A:
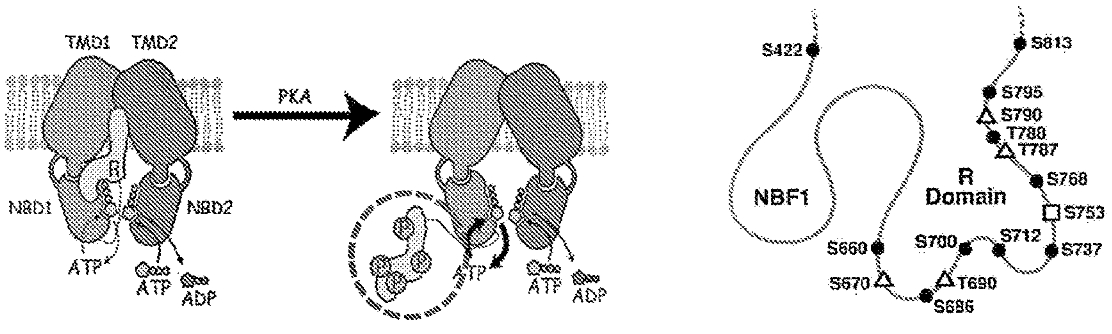
FIG. 2A and FIG. 2B show schematics of exemplary engineered CFTR proteins with mutations that activate and/or stabilize and/or enhance CFTR protein expression.

In this example, R domain phosphomimetics were generated by mutating residues described in Table 5 where X is any amino acid. R domain phosphomimetics included CFTR mutants such as S-Quad-D (S660D, S737D, S795D, S813D) and S-Hex-D (S660D, S685D, S700D, S737D, S795D, S813D), which are amino acid substitutions that mimic a phosphorylated CFTR, thereby resulting in activation (FIG. 2A, Table 3).

TABLE 5

CFTR Protein Activation Mutations: R-domain phosphomimetics

| | S422 | S660 | S670 | S686 | T690 | S700 | S712 | S737 | S753 | S768 | T787 | T788 | S790 | S795 | S813 |
|---|---|---|---|---|---|---|---|---|---|---|---|---|---|---|---|
| S-Quad-D (4D) | | D | | | | | | D | | | | | | D | D |
| S-Hex-D (6D) | | D | | D | | D | | D | | | | | | D | D |
| 8-D | | D | | D | | D | D | D | | D | | | | D | D |
| 15-D | D | D | D | D | D | D | D | D | D | D | D | D | D | D | D |
| 15-A | A | A | A | A | A | A | A | A | A | A | A | A | A | A | A |
| 13-D | D | D | D | D | D | D | D | | D | | D | D | D | D | D |
| S-Oct-D | | D | | D | | D | D | D | | D | | | | D | D |
| S-Quad-X | | X | | | | | | X | | | | | | X | X |
| S-Hex-X | | X | | X | | X | | X | | | | | | X | X |
| 15-X | X | X | X | X | X | X | X | X | X | X | X | X | X | X | X |
| 13-X | X | X | X | X | X | X | X | | X | | X | X | X | X | X |
| S-Oct-X | | X | | X | | X | X | X | | X | | | | X | X |

Figure 2B:
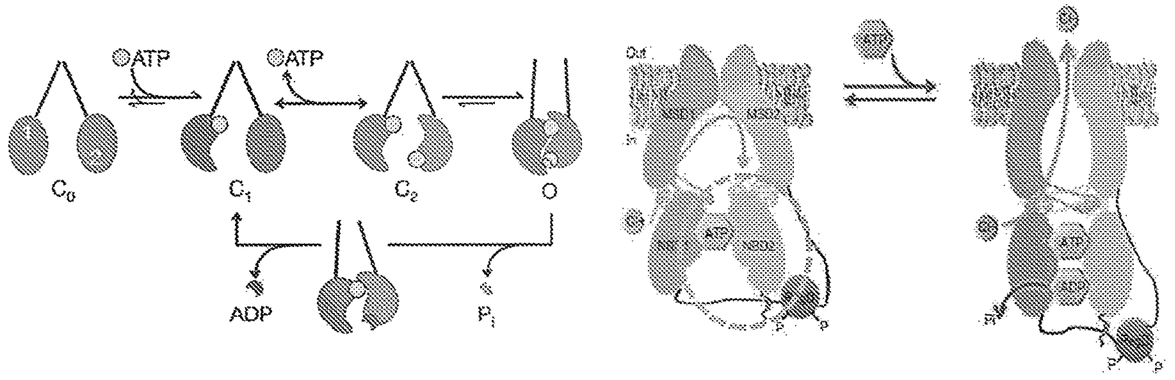

Another strategy used to engineer activation mutants of CFTR involved mutating residues involved in ATP gating to any other amino acid depicted by X as exemplified in Table 6. As one example, mutations K978C and E1371Q resulted in activation (FIG. 2B).

TABLE 6

CFTR Protein Activation Mutations: ATP-hydrolysis

| | S422 | S660 | S670 | S686 | T690 | S700 | S712 | S737 | S753 | S768 | T787 | T788 | S790 | S795 | S813 | K978 | E1371 |
|---|---|---|---|---|---|---|---|---|---|---|---|---|---|---|---|---|---|
| K978C | | | | | | | | | | | | | | | | C | |
| E1371Q | | | | | | | | | | | | | | | | | Q |
| 15-A E1371Q | A | A | A | A | A | A | A | A | A | A | A | A | A | A | A | | Q |
| 15-D E1371Q | D | D | D | D | D | D | D | D | D | D | D | D | D | D | D | | Q |
| K978X | | | | | | | | | | | | | | | | X | |
| E1371X | | | | | | | | | | | | | | | | | X |
| 15-X E1371X | X | X | X | X | X | X | X | X | X | X | X | X | X | X | X | | X |

Figure 2C:
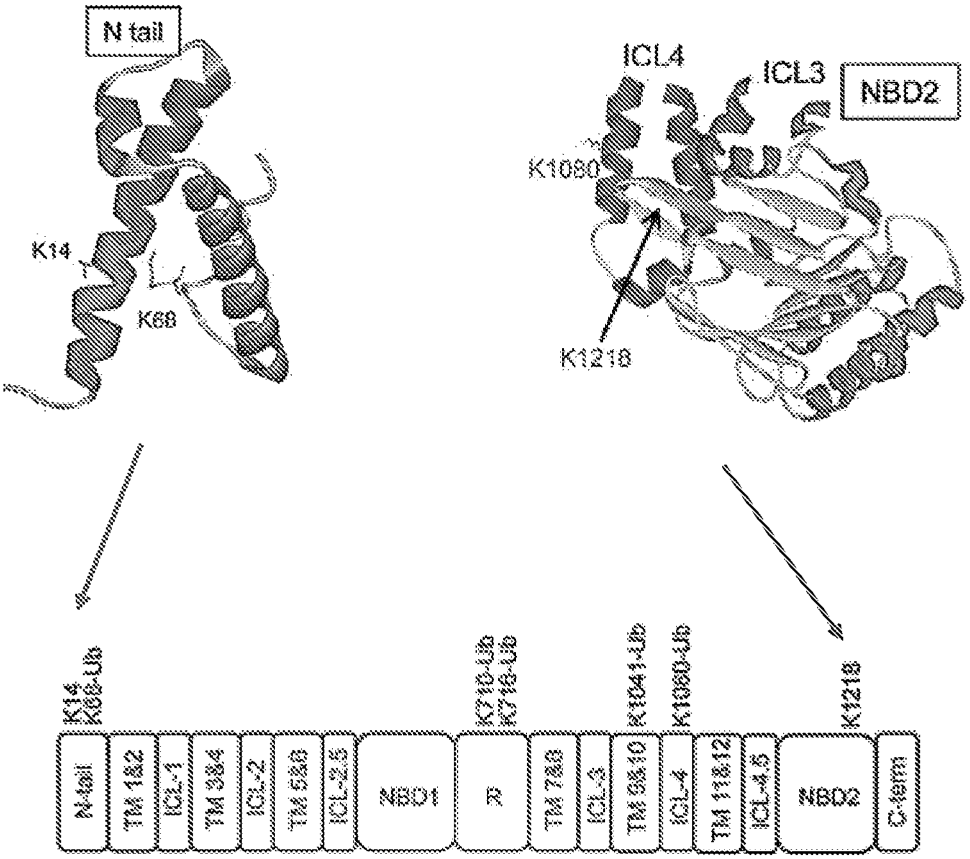
FIG. 2C shows exemplary stability/expression-enhancing mutations.
Figure 2D:
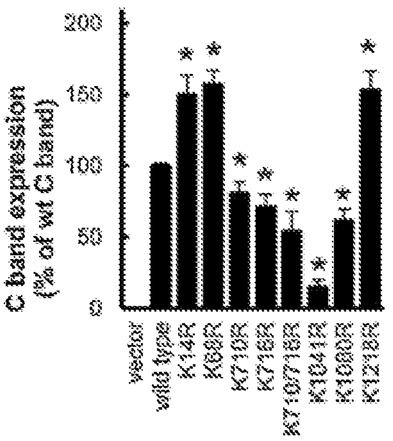
FIG. 2D shows exemplary engineered CFTR stability mutant protein expression relative to WT.

CFTR proteins undergo ubiquitination at lysine residues. Amino acid mutations at lysine residues that result in a substitution of the lysine to another amino acid residue results in enhanced stability and protein expression of the CFTR protein (FIG. 2C). Exemplary mutant CFTR proteins were engineered as listed in Table 7. CFTR expression was measured as a proportion of WT CFTR (FIG. 2D)).

TABLE 7

| Stability/Expression-enhancing engineered CFTR Proteins | | | | | | |
|---|---|---|---|---|---|---|
| | K14 | K68 | K710 | K716 | K1041 | K1218 |
| 1 | R | | | | | |
| 2 | | R | | | | |
| 3 | R | R | | | | |
| 4 | | | | | | R |
| 5 | | R | | | | R |
| 6 | R | | | | | R |
| 7 | R | R | | | | R |
| 8 | | | R | | | |
| 9 | | | | R | | |
| 10 | | | | | R | |
| 11 | | | R | R | | |
| 12 | | | R | R | R | |
| 13 | X | | | | | |
| 14 | | X | | | | |
| 15 | X | X | | | | |
| 16 | | | | | | X |
| 17 | | X | | | | X |
| 18 | X | | | | | X |
| 19 | X | X | | | | X |
| 20 | | | X | | | |
| 21 | | | | X | | |
| 22 | | | | | X | |
| 23 | | | X | X | | |
| 23 | | | X | X | X | |

Example 3. Evaluating Response of Activated CFTR Constructs in Ussing Chamber Assay at a High Concentration In this example, mutant CFTR proteins were assessed for chloride ion transport using the Ussing assay. These assessments determined the activity of the mutant CFTR proteins.

TABLE 8

| Activated CFTR Constructs | | | | | | | | |
|---|---|---|---|---|---|---|---|---|
| Engineered | Activated CFTR Mutation | | | | | | | |
| CFTR | S660 | S686 | S700 | S737 | S795 | S813 | K978 | E1371 |
| A | | | | | | | | |
| B | D | | | D | D | D | | |
| C | D | D | D | D | D | D | | |
| D | | | | | | | C | |
| E | | | | | | | | Q |

Figure 3A:
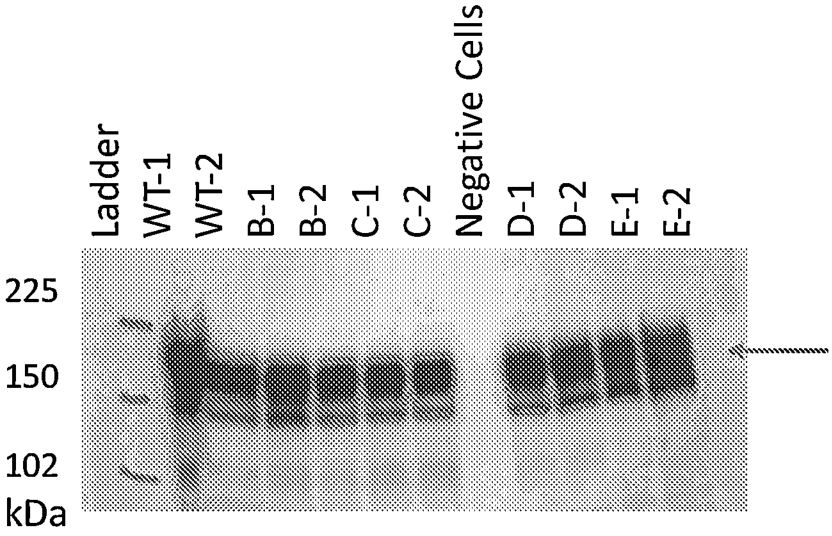
FIG. 3A is a gel that shows mutated CFTR constructs are expressed to similar levels as compared with wild type CFTR in cultured HEK cells.

Wild type construct (CFTR Protein A in Table 8) and all mutant constructs (Engineered Proteins B-E in Table 8) were highly translated in BTEK293 cells and provided high CFTR expression as observed in a protein gel. The CFTR band is depicted by an arrow (FIG. 3A).

Chloride ion transport was measured by an Ussing chamber. This assay provides an indication of chloride flux based on the principle that the epithelium pumps ions from one side to another and ions leak back through tight junctions situated between epithelial cells. The voltage difference between two sides of the epithelium is measured using two voltage electrodes placed near the tissue/epithelium. The voltage is cancelled out by injecting current, using two other electrodes placed away from the epithelium. The short circuit current is measured as net chloride ion transport.

Figure 3B:
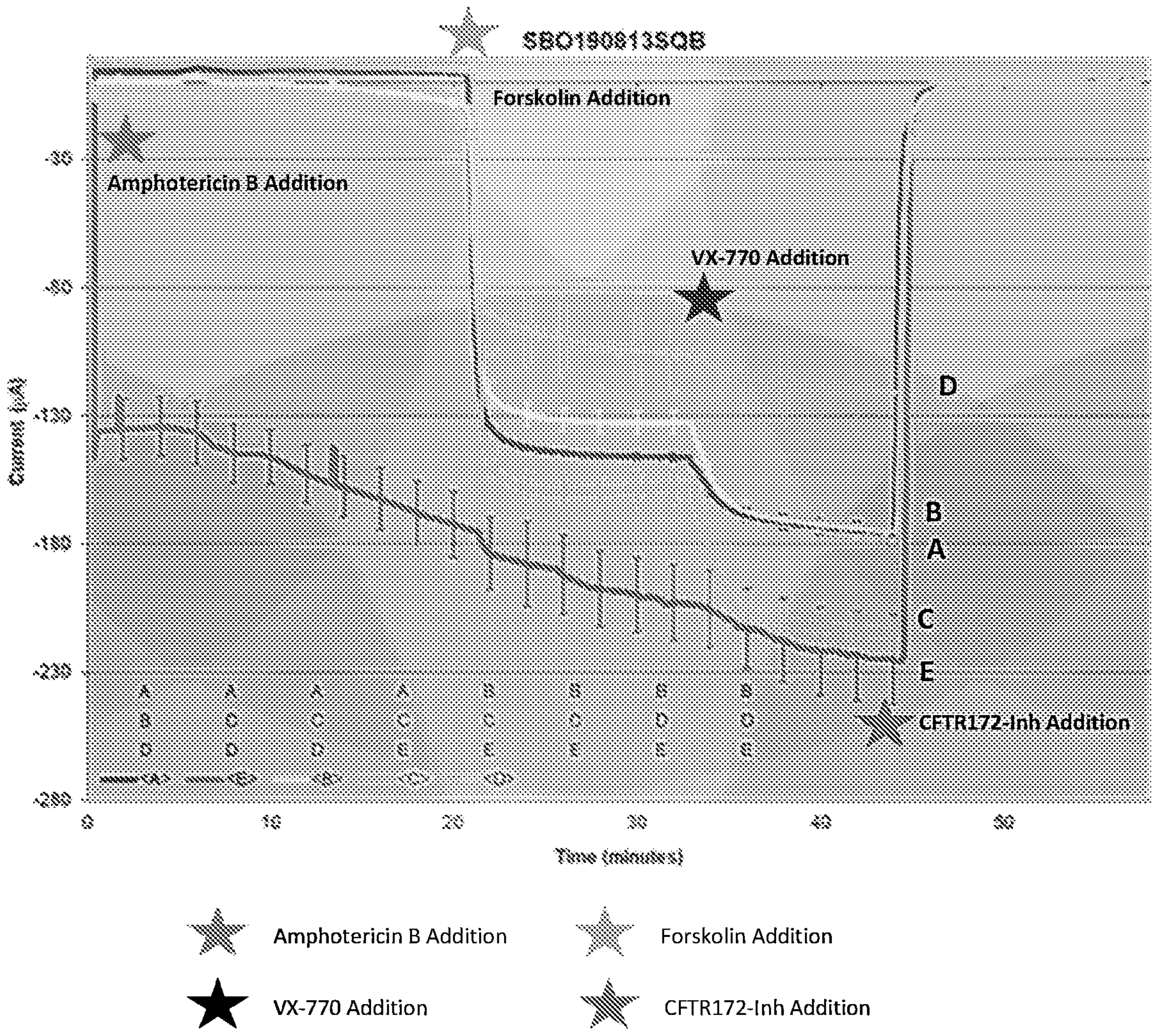
FIG. 3B shows an exemplary graph of short circuit current depicting chloride ion flux over time through WT CFTR and engineered CFTR mutant protein channels in an Ussing Chamber Assay at a high dose of 0.5 μg.

Traces in FIG. 3B show short-circuit current measurements measuring current over time, comparing WT CFTR (Protein A) relative to engineered CFTR mutant Protein B (R domain phosphomimetic S-Quad-D), engineered CFTR mutant Protein C (R domain phosphomimetic S-Hex-D), engineered CFTR mutant Protein D (K978C ATP independent activity), engineered CFTR mutant Protein E (E1371Q ATP hydrolysis deficient) at a concentration of 0.5 μg CFTR ("high concentration").

Traces show short-circuit current measurements during sequential additions of forskolin, an activator of CFTR-mediated chloride secretion, and VX-770 (ivacaftor), a potentiator compound that directly increases phosphorylation-dependent CFTR channel opening on amphotericin B-permeabilized membranes. CFTR proteins A-D responded to forskolin activation resulting in increased chloride ion conductance. Forskolin activation was not observed for CFTR Protein E, the ATP hydrolysis deficient E1371Q mutant. Further addition of VX-770 increased conductance in CFTR Proteins B-D.

Conductance in all cases was lost upon inhibition of CFTR by treatment with the CFTR172-Inhibitor.

Varying profiles of response were observed at the high concentration of 0.5 μg of engineered CFTR proteins tested. (FIG. 3B)

Figure 4:
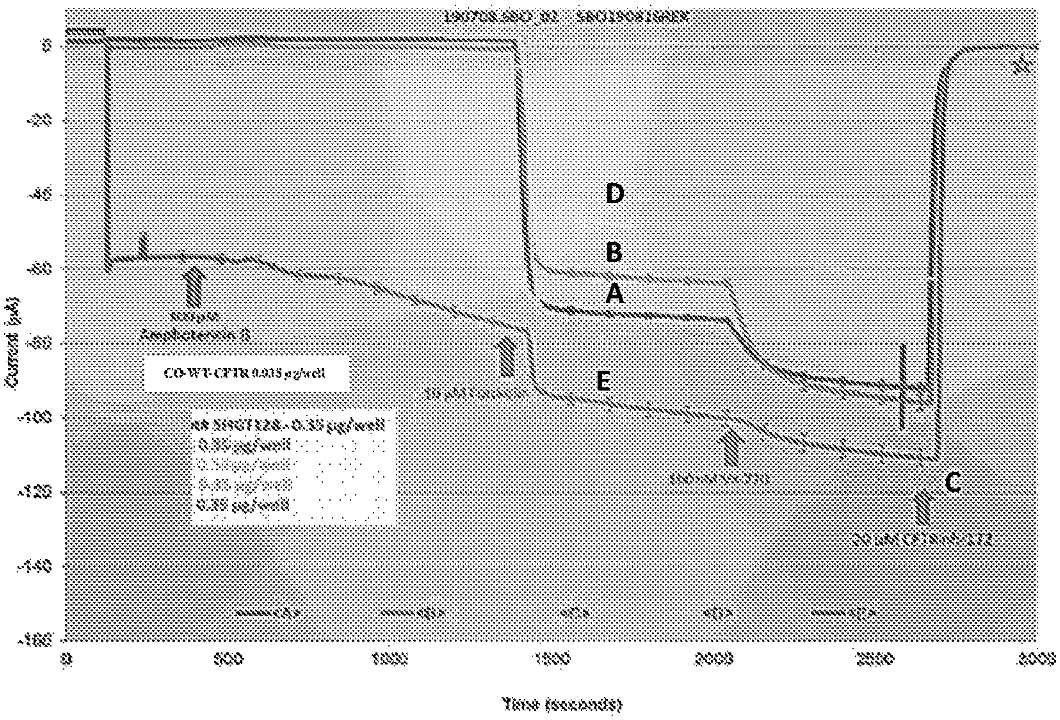
FIG. 4 shows an exemplary graph of short circuit current depicting chloride ion flux over time through WT CFTR and engineered CFTR mutant protein channels in an Ussing Chamber Assay at a low dose of 0.35 μg.

Example 4. Evaluating Response of Activated CFTR Constructs in Ussing Chamber Assay at a Low Concentration In this example, activation of various engineered CFTR protein mutants (proteins B-E, discussed above) were compared with the activation of wild type CFTR (protein A) using the Ussing assay as described in Example 3. In this example the engineered CFTR protein activity was tested at a low concentration of 0.35 μg (FIG. 4).

Using a lower concentration (i.e., 0.35 μg) of the tested CFTR proteins showed improved reproducibility of current in the Ussing chamber analysis.

The results showed consistent trends in rank-ordered response to forskolin activation. Of the mutants tested, engineered CFTR mutant protein E showed forskolin activation at a lower dose in comparison to other constructs tested. Additionally, FIG. 4 demonstrate two distinct effects. Substitutions of cysteine for a particular lysine in cytosolic loop 3 (e.g., CFTR mutant D in Table 8) yielded a channel with overall reduced activity as compared to wild-type CFTR, though it did demonstrate slight conductance prior to forskolin addition. In contrast, substituting glutamine for a specific glutamic acid in NBD-2 (e.g., CFTR mutant E in Table 8) produced significant pre-forskolin conductance, as well as overall increased activity in FRT cells.

Furthermore, the data showed that addition of ivacaftor resulted in a stronger activation response in all of the constructs tested. Engineered CFTR mutant protein C had a more pronounced response to ivacaftor in comparison to the other constructs tested.

Example 5. Dose Response Assessment of Engineered CFTR Protein E in Ussing Chamber Assay In this example, engineered CFTR protein E1371Q was tested for activation using various doses ranging from 0.05-

Figure 5:
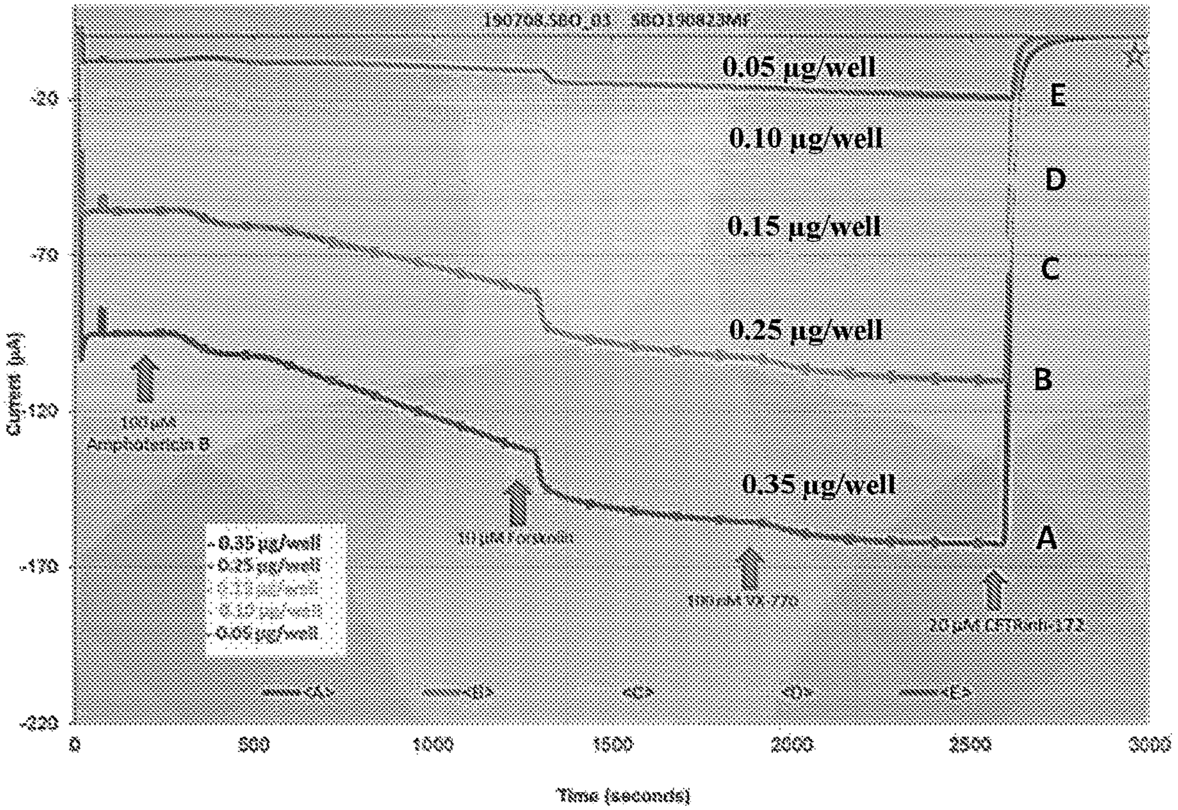
FIG. 5 shows exemplary results of a graph of a time course of short-circuit current, a measure of chloride ion transport through engineered CFTR protein E at doses ranging from 0.05-0.35 μg.

0.35 µg/well using the Ussing assay (FIG. 5). FIG. 5 illustrates chloride flux from a cell expressing the mutant CFTR protein.

The data showed a consistent activity pattern across treatments at the different doses of tested.

Example 6. Optimization of Escin Permeabilization for ATP Depletion Using WT CFTR at Different Doses In this example, the effect of escin permeabilization for ATP depletion was assessed using wild type CFTR protein. The Ussing assay was used for these studies.

For these studies, the saponin escin was used as a perforating agent, which permits permeation of larger molecules including nucleotides and modulators of ion channel activity.

Ecsin treatment was carried out at doses of 10 µM, 15 µM, 20 µM, 25 µM in the presence and absence of ATP.

Figure 6:
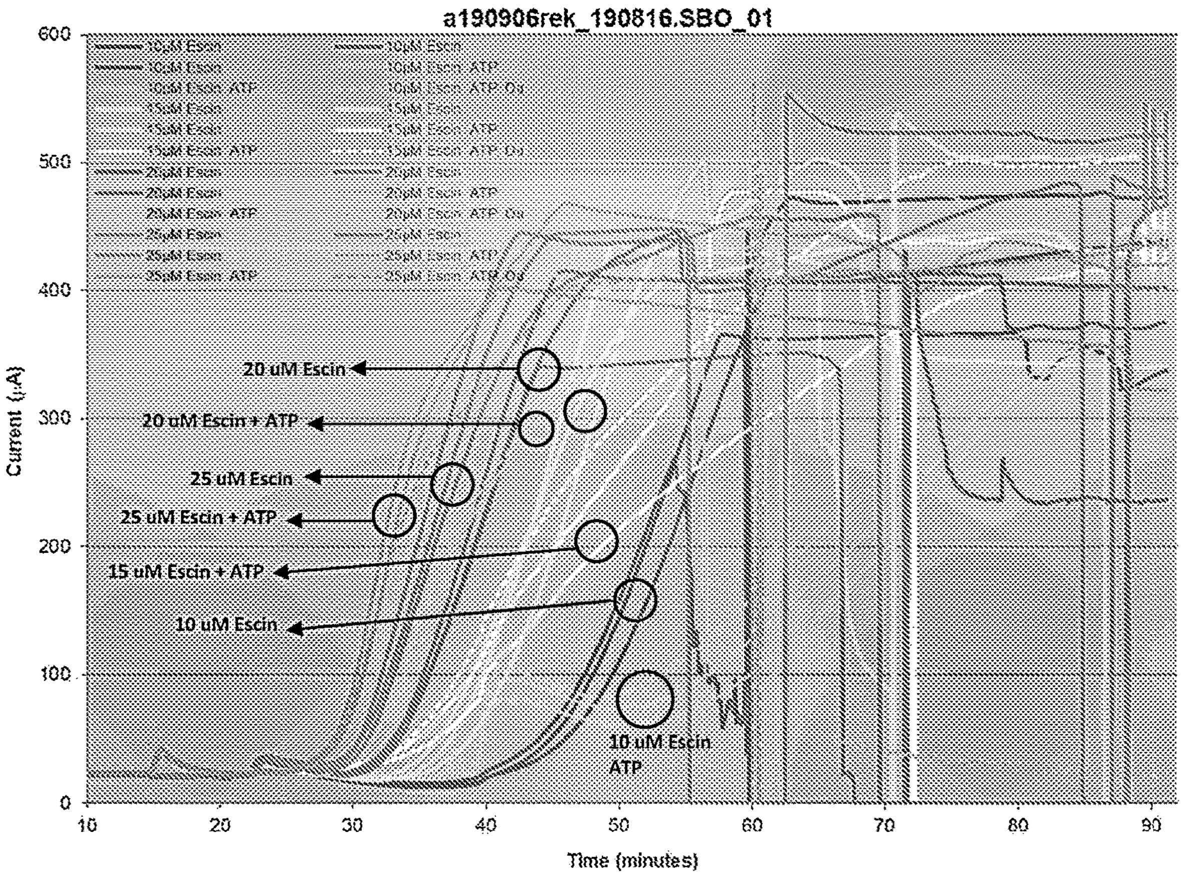
FIG. 6 shows exemplary results of a graph of a time course of short-circuit current, a measure of chloride ion transport through WT CFTR protein upon ecsin permeabilization of the membrane using doses from 10-25 μM ecsin in the presence and absence of ATP.

The results showed that ecsin permeabilization resulted in loss of membrane integrity at all levels tested in a dose and time dependent manner (FIG. 6). It was observed that that 10 µM ecsin yielded only a short window of time in which measurements with and without ATP could be compared, leading to additional optimizations.

Figure 7:
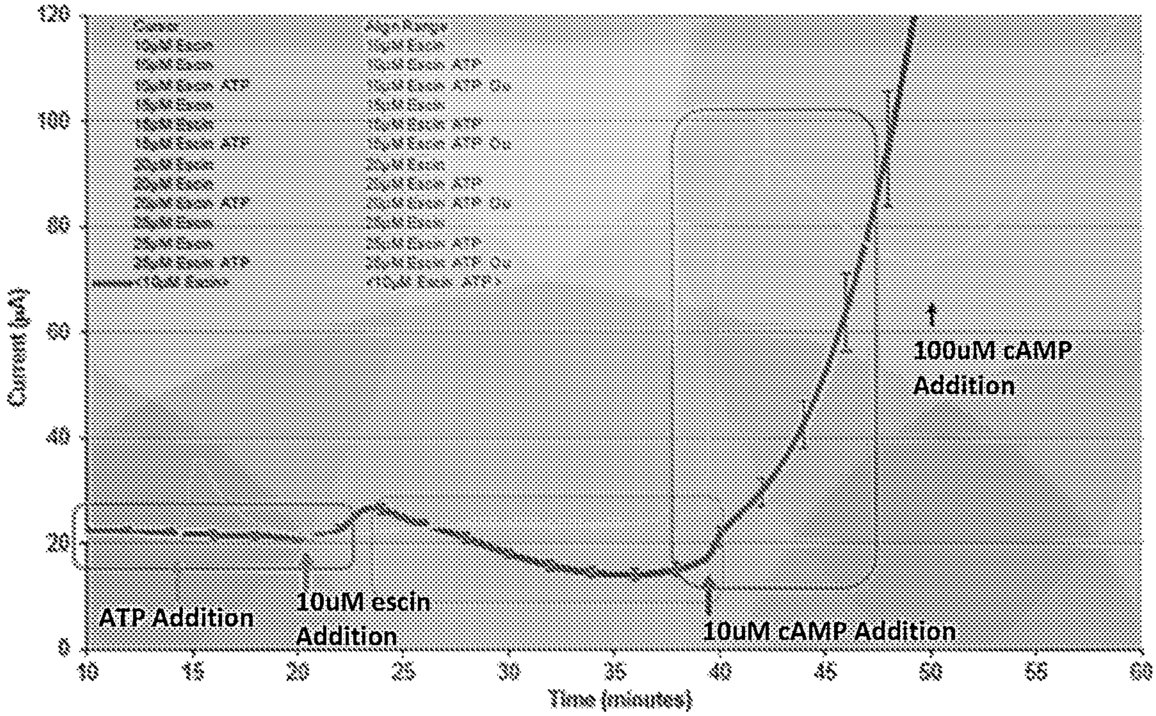
FIG. 7 shows exemplary results of a graph of a time course of short-circuit current, a measure of chloride ion transport through WT CFTR protein at a dose of 10 μM ecsin in an Ussing Chamber Assay.

Further analysis was conducted to optimize ecsin permeabilization for ATP depletion (FIG. 7).

Example 7. Evaluating Response of Phosphomimetic CFTR Constructs in Ussing Chamber Assay In this example, activities of various engineered phosphomimetic CFTR protein mutants (Table. 9) were compared with the activity of wild-type CFTR using the Ussing chamber assay as described in Example 3.

TABLE 9

Phosphomimetic CFTR Constructs

| Engineered CFTR | Mutations |
|---|---|
| WT | Wild-type |
| 4D | S660D, S737D, S795D, S813D |
| 6D | S660D, S686D, S700D, S737D, S795D, S813D |
| 8D | S660D, S686D, S700D, S712D, S737D, S768D, S795D, S813D |
| 13D | S422D, S660D, S670D, S686D, T690D, S700D, S712D, S753D, T787D, T788D, T790D, S795D, S813D |
| 15D | S422D, S660D, S670D, S686D, T690D, S700D, S712D, S737D, S753D, S768D, T787D, T788D, T790D, S795D, S813D |

Figure 8:
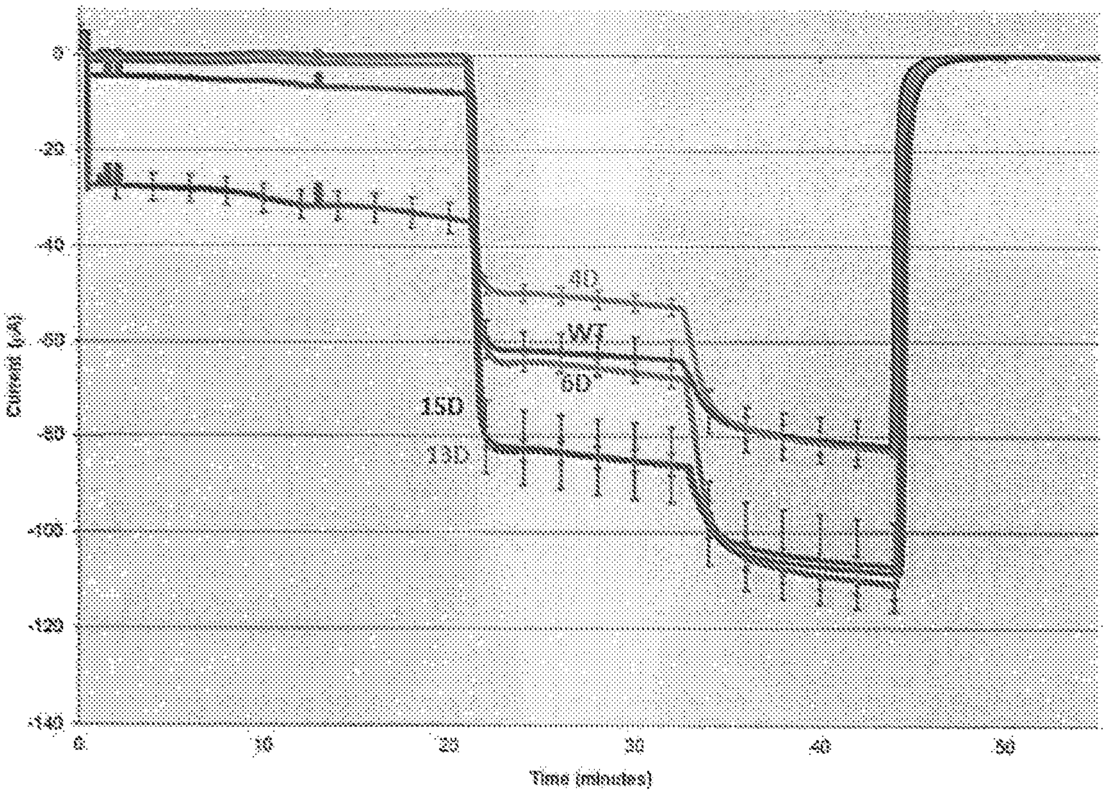
FIG. 8 shows an exemplary graph of short circuit current depicting chloride ion flux over time through WT CFTR and engineered phosphomimetic CFTR mutant protein channels in an Ussing Chamber Assay.

As shown in FIG. 8, combinations of S/T to D mutations in the R domain of CFTR impart various alterations to the channel functioning. 4D and 6D channels demonstrate greater responsiveness to VX-770, while 13D and 15D display forskolin-independent chloride transport, as well as increased overall activity as compared to wild-type CFTR channels. All phosphomimetic CFTR mutants, with an exception of the 4D mutant, showed higher overall activity as compared to the wild-type CFTR. The data also showed that increasing the number of phosphomimetic sites in the CFTR protein can increase the overall activity in Ussing chamber activity.

Figure 9A:
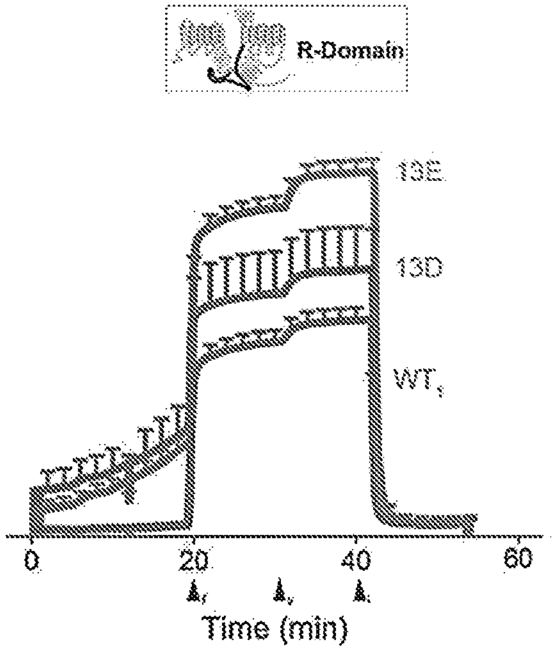
FIG. 9A shows exemplary graph of short-circuit conductivity measured by Ussing chamber using FRT cells transfected with wild-type, 13D, and 13E CFTR mRNA.
Figure 9B:
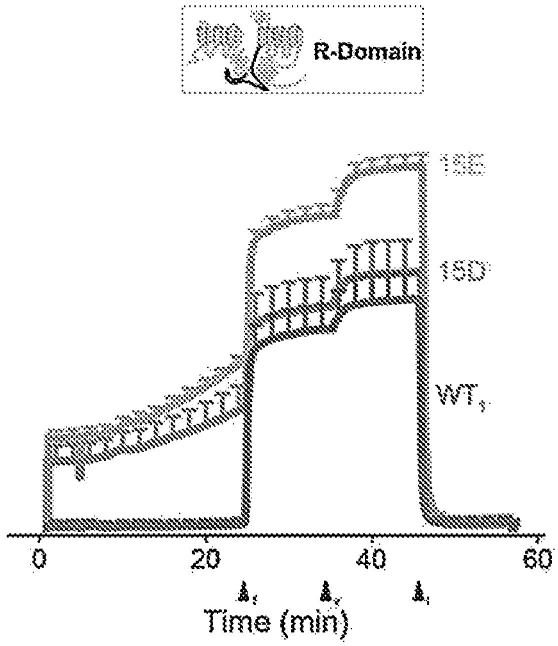
FIG. 9B shows exemplary graph of short-circuit conductivity measured by Ussing chamber using FRT cells transfected with wild-type, 15D, and 15E CFTR mRNA. Arrowheads indicate addition of forskolin (f), VX-770 Ivacaftor (v), or CFTR inhibitor 172. Error bars represent s.e.m. with N=3 or 4.

Next, several combinations of serine and threonine in the R-domain were replaced with negatively charged amino acids, either glutamic acid or aspartic acid, in order to mimic the electrostatic nature of phosphorylation. Two combinations were found to significantly impact chloride current—one containing 13 amino acid changes and the other with 15 amino acid changes. FIG. 9A shows a comparison of CFTR mutants containing 13 amino acid changes to either aspartate or glutamate in the R-domain. FIG. 9B shows comparison of CFTR mutants containing 15 amino acid changes to either aspartate or glutamate in the R-domain. In both cases, glutamate (E) substitutions were more effective than aspartate (D) substitutions.

The results showed that the phosphomimetic CFTR mutants were responsive to both forskolin and VX-700. The phosphomimetic CFTR mutants also showed increased current compared to the wild-type CFTR in the absence of forskolin (post-amphotericin) (FIG. 8, FIG. 9A and FIG. 9 B). Without being bound by a particular theory, this may be due a reduced threshold for cAMP gating, consistent with the expected phosphomimetic effect. While opening of wild-type channels depends on cAMP activation of PKA and downstream R-domain phosphorylation, the aspartate point mutations partially mimic constitutive phosphorylation such that the open-state conformation is adopted even in the absence of cAMP.

Example 8. Evaluating Response of Stability/Trafficking CFTR Constructs in Ussing Chamber Assay In this example, activities of various engineered stability/trafficking CFTR protein mutants (Table. 10) were compared with the activity of wild-type CFTR using the Ussing chamber assay as described in Example 3.

CFTR proteins undergo ubiquitination at multiple lysines in the protein. Ubiquitination is a reversible process due to the presence of deubiquitinating enzymes that can cleave ubiquitin from modified proteins. Ubiquitination is involved in regulation of both membrane trafficking and protein degradation. For example, the ubiquitinated K710, K716, and K1041 residues stabilize the wild-type CFTR, protecting it from proteolysis. Modifications of K14R and K68R lead to increased mature band C CFTR, which can be augmented by proteasomal inhibition allowing trafficking to the surface.

TABLE 10

Stability/Trafficking CFTR Constructs

| Engineered CFTR | Mutations |
|---|---|
| WT | Wild-type |
| A | K14R |
| B | K68R |
| C | K14R, K68R |
| D | K1218R |
| E | K68R, K1218R |
| F | K14R, K1218R |
| G | K14R, K68R, K1218R |

Figure 10:
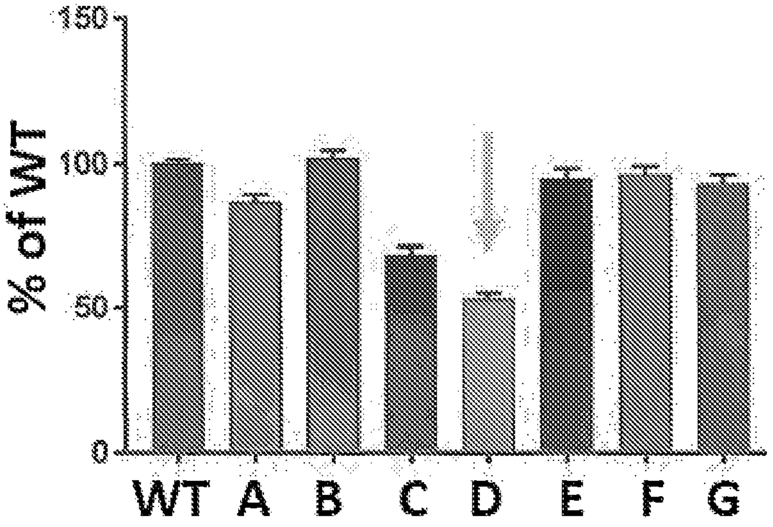
FIG. 10 shows an exemplary bar graph depicting maximum activated current for various trafficking CFTR mutant proteins listed in Table 10, as determined by an Ussing Chamber assay.

As shown in FIG. 10, no significant increase in activity was observed for the CFTR mutants in Table. 10, compared to the wild-type CFTR. The CFTR mutants A (K14R), C (K14R, K68R) and D (K1218R) showed decreased activity as compared to the wild-type CFTR as determined by Ussing chamber assay.

Example 9. Evaluating Response of Phosphomimetic CFTR Constructs in Combination with K14R or E1371Q Mutation in Ussing Chamber Assay In this example, activities of various engineered CFTR protein mutants (Table. 11) were compared using the Ussing chamber assay as described in Example 3. In particular, various combinations of K14R, E1371Q, and phosphomimetic mutations were tested.

To examine whether a synergistic effect can be achieved by combining phosphomimetic mutations with a trafficking mutation (K14R) or an ATP hydrolysis-deficient (E1371Q) mutation, CFTR mutant constructs shown in Table. 11 were prepared.

TABLE 11

Various CFTR Mutant Constructs

| Engineered CFTR | Mutations |
|---|---|
| WT | Wild-type |
| 13D | S422D, S660D, S670D, S686D, T690D, S700D, S712D, S753D, T787D, T788D, T790D, S795D, S813D |
| 13D/K14R | K14R, S422D, S660D, S670D, S686D, T690D, S700D, S712D, S753D, T787D, T788D, T790D, S795D, S813D |
| 13E | S422E, S660E, S670E, S686E, T690E, S700E, S712E, S753E, T787E, T788E, T790E, S795E, S813E |
| 13E/K14R | K14R, S422E, S660E, S670E, S686E, T690E, S700E, S712E, S753E, T787E, T788E, T790E, S795E, S813E |
| 15E | S422E, S660E, S670E, S686E, T690E, S700E, S712E, S737E, S753E, S768E, T787E, T788E, T790E, S795E, S813E |
| 15E/K14R | K14R, S422E, S660E, S670E, S686E, T690E, S700E, S712E, S737E, S753E, S768E, T787E, T788E, T790E, S795E, S813E |
| 15A | S422A, S660A, S670A, S686A, T690A, S700A, S712A, S737A, S753A, S768A, T787A, T788A, T790A, S795A, S813A |
| 15A/E1371Q | S422A, S660A, S670A, S686A, T690A, S700A, S712A, S737A, S753A, S768A, T787A, T788A, T790A, S795A, S813A, E1371Q |
| 15D/E1371Q | S422D, S660D, S670D, S686D, T690D, S700D, S712D, S737D, S753D, S768D, T787D, T788D, T790D, S795D, S813D, E1371Q |

Figure 11A:
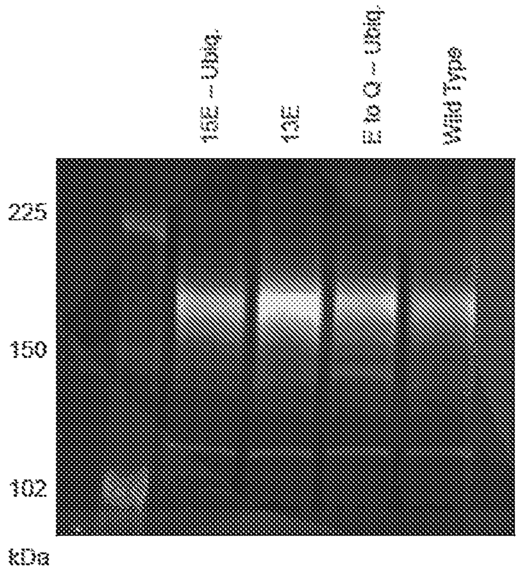
FIG. 11A shows an exemplary a Western blot illustrating expression of CFTR proteins (15E, 13E, E1371Q variants, and wild-type CFTR) in HEK293 cells.
Figure 11B:
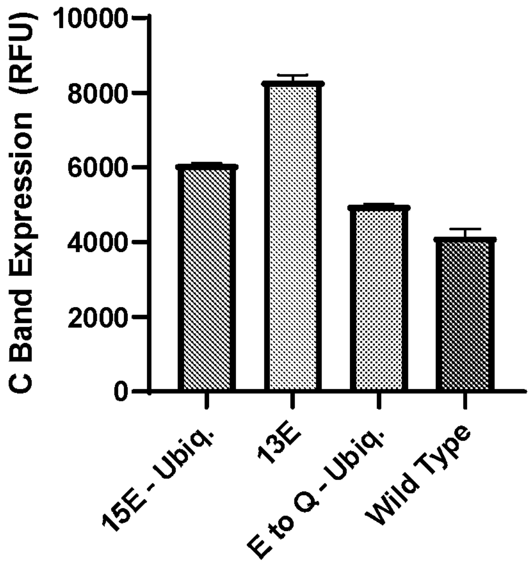
FIG. 11B is a quantification of expression levels as shown in FIG. 11A

To examine the expression of CFTR mutants, expression of the wild-type CFTR, 15E, 13E, and E1371Q mutants was quantified as shown in FIG. 11A and FIG. 11B. Quantification of Western blot demonstrated an increased C-band expression from three variant CFTRs, with 13E showing a greater than 2-fold increase in protein.

Figure 11C:
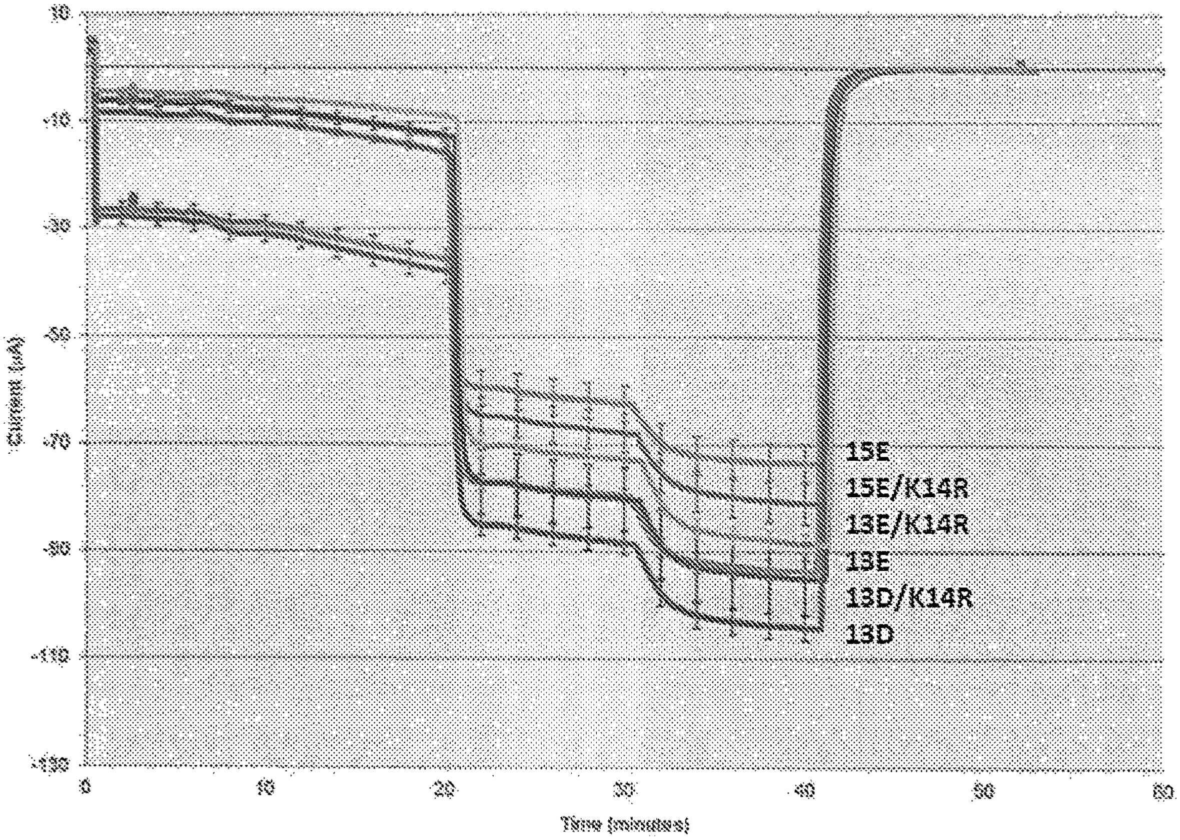
FIG. 11C shows exemplary graph of short-circuit conductivity measured by Ussing chamber using FRT cells transfected with wild-type, 15E, 15E/K14R, 13D, 13D/K14R, 13E and 13E/K14R CFTR mRNAs.
Figure 11D:
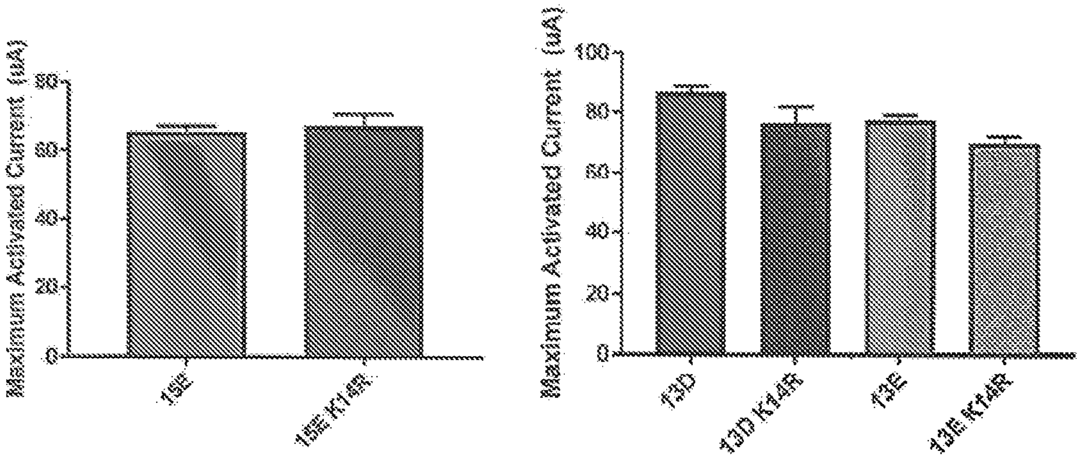
FIG. 11D is a bar graph representation of maximum activated current for various CFTR constructs tested in FIG. 11C.

As shown in FIG. 11C, the K14R mutation did not further increase the activity of the phosphomimetic CFTR mutants. FIG. 11D is a bar graph representation of maximum activated current for each mutant. FIG. 11D shows that when K14R mutation was combined with 15E, 13D, or 13E phosphomimetic mutants, there was no significant increase in the activity of the CFTR proteins.

Figure 11E:
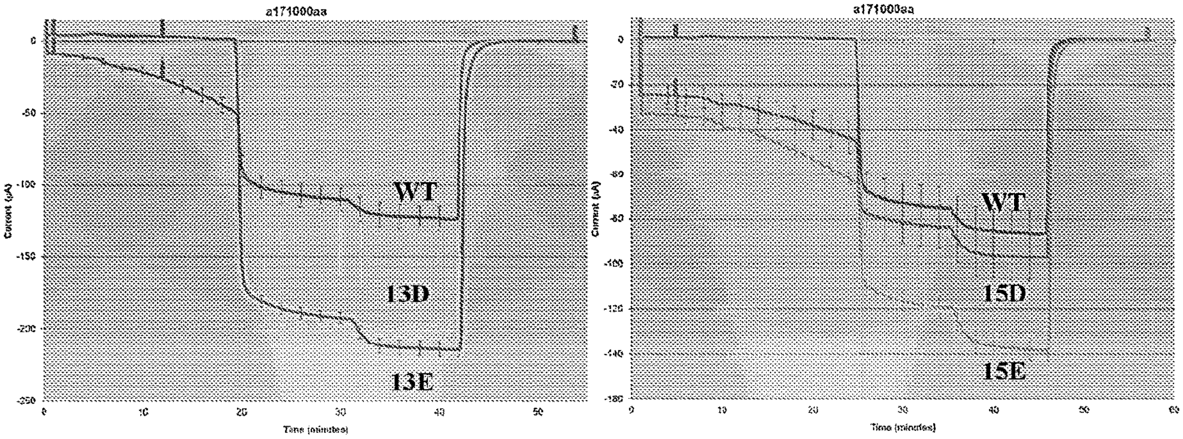
FIG. 11E is a series of graphs that show short-circuit conductivity measured by Ussing chamber using FRT cells that were transfected with WT, 13D, 13E, 15D or 15E CFTR mRNAs as indicated.

Studies were also performed to assess whether there were any differences in CFTR activity following S to D amino acid substitutions in comparison to S to E amino acid substitutions. For these studies, the activity of CFTR mutant 13D was compared to the activity of 13E using Ussing chamber. The activity of CFTR mutant 15D was compared to the activity of 15E using the Ussing chamber. The data from these studies showed that E substitutions produced CFTR that had increased activity in comparison to those that had D substitutions (FIG. 11E). Thus, E amino acid substitutions can be used to further increase CFTR activity. For example, S13E and S15E substitutions have greater CFTR activity than S13D and S15D substitutions, respectively.

FIG. 12A and FIG. 12B show that the CFTR mutant protein 15A has a decreased activity compared to the wild-type CFTR. Analysis in Ussing chamber showed 85% reduction in short circuit current after forskolin addition when compared to wild-type CFTR, consistent with the known role of pKa-mediated channel activation. Additionally, CFTR mutant proteins (15A/E1371Q and 15D/E1371Q mutants) containing the E1371Q mutation have an increased pre-activation current. Surprisingly, this forskolin-independent effect was observed even more prominently with the E1371Q mutation (as compared to the phosphomimetic mutations), which falls in the ATP binding region of NBD2. The E1371Q mutation showed overall higher conductance than the wild-type CFTR, especially before forskolin addition. Additionally, a significant forskolin activation and an increased activity by the addition of VX-770 were not observed for the CFTR mutants containing E1371Q mutation. The minimal response to VX-770 likely reflects E1371Q's open probability having approached the theoretical, fully open maximum. The CFTR mutants of 15A, 15A/E1371Q, and 15D/E1371Q did not show an increased activity as compared to the wild-type CFTR protein.

Example 10. Evaluating Response of E1371Q CFTR Construct in Combination with K14R Mutation in Ussing Chamber Assay In this example, activity of E1371Q CFTR mutant was tested in combination with the K14R mutation using the Ussing chamber assay as described in Example 3.

Figure 13A:
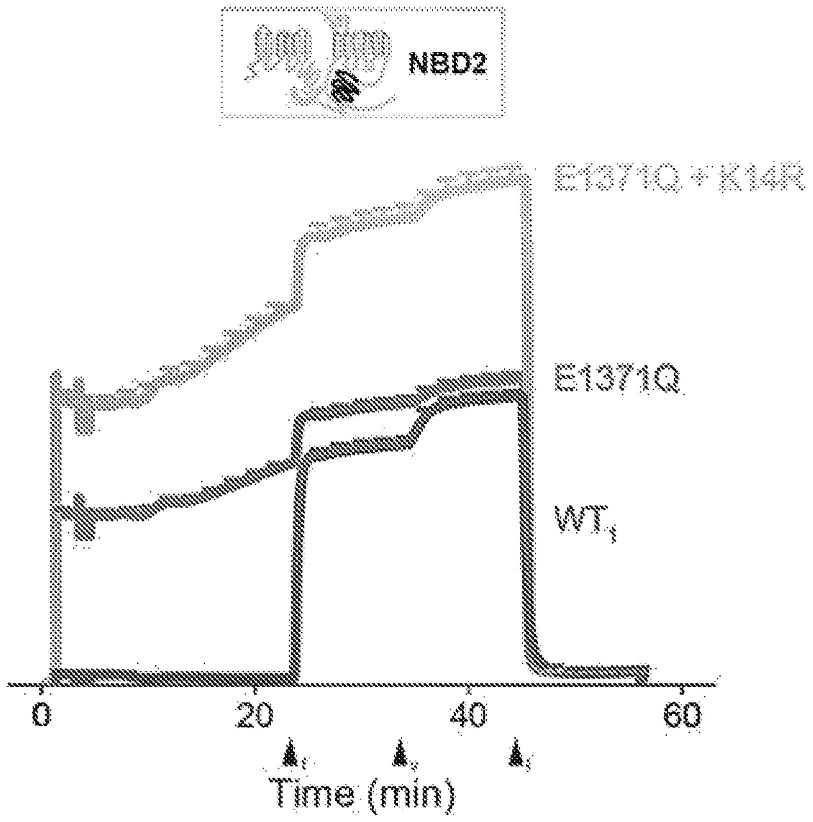
FIG. 13A shows exemplary graph of short-circuit conductivity measured by Ussing chamber using FRT cells transfected with wild-type, E1371Q and E1371Q/K14R CFTR mRNAs. Arrowheads indicate addition of forskolin (f), VX-770 Ivacaftor (v), or CFTR inhibitor 172. Error bars represent s.e.m. with N=3 or 4.
Figure 13B:
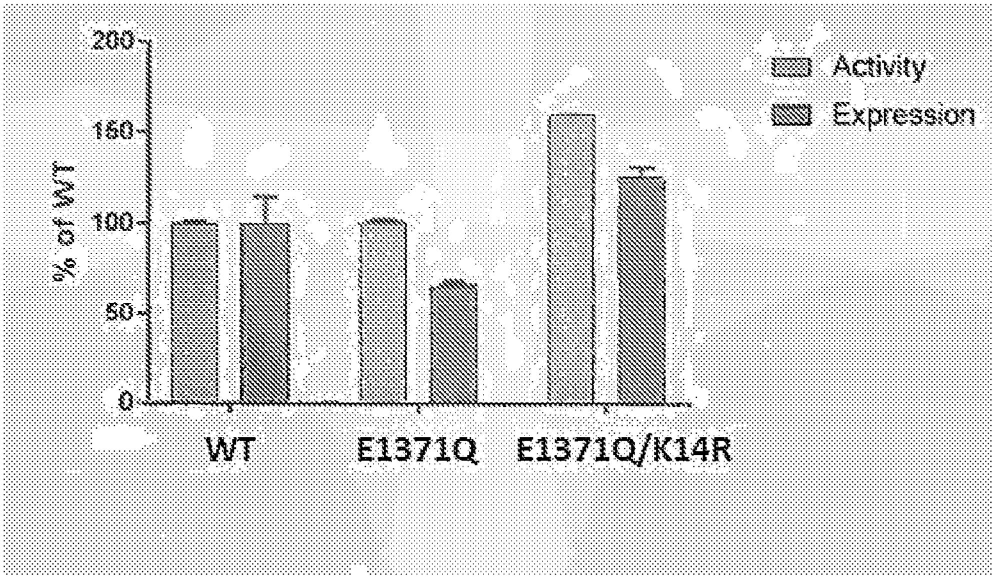
FIG. 13B is a bar graph representation of activity and expression of E1371Q CFTR mutant and E1371Q/K14R CFTR mutant compared to the wild-type CFTR protein.

Our results also showed that E1371Q could be further augmented by introducing an additional variant, K14R, which represents a putative ubiquitination site (FIG. 13A). FIG. 13B shows that the E13Q/K14R CFTR mutant has an increased activity and an increased expression compared to both wild-type CFTR protein and the CFTR protein having only the E1371Q point mutation. These data suggest the possibility of generating a CFTR variant that is both more active (increased open probability) and more stable (increased copy number).

Example 11. Evaluating Duration of Activity of CFTR Construct in Time-Course Ussing Chamber Assay In this example, duration of activity of various phosphomimetic CFTR mutants were tested in combination with the K14R mutation using a time-course Ussing chamber assay as described in Example 3. The CFTR mutants tested in this example is listed in Table 12.

TABLE 12

CFTR Mutants tested in time-course Ussing Assay

| Engineered CFTR | Mutations |
|---|---|
| WT | Wild-type |
| 13E | S422E, S660E, S670E, S686E, T690E, S700E, S712E, S753E, T787E, T788E, T790E, S795E, S813E |
| 13E/K14R | K14R, S422E, S660E, S670E, S686E, T690E, S700E, S712E, S753E, T787E, T788E, T790E, S795E, S813E |
| 15E | S422E, S660E, S670E, S686E, T690E, S700E, S712E, S737E, S753E, S768E, T787E, T788E, T790E, S795E, S813E |
| 15E/K14R | K14R, S422E, S660E, S670E, S686E, T690E, S700E, S712E, S737E, S753E, S768E, T787E, T788E, T790E, S795E, S813E |

Figure 14A:
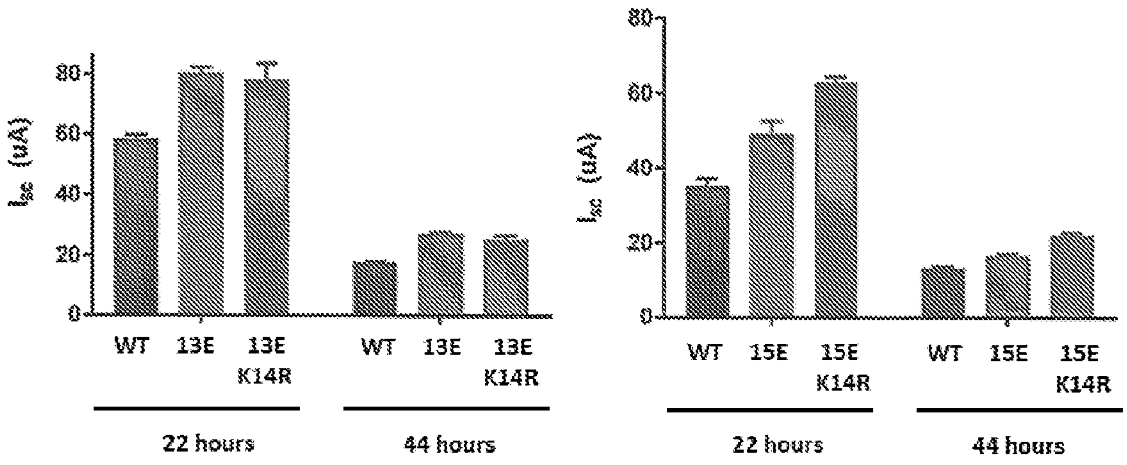
FIG. 14A and FIG. 14B is a bar graph representation of maximum activation current for various CFTR constructs in Ussing chamber assay at 22 and 44 hours.
Figure 14B:
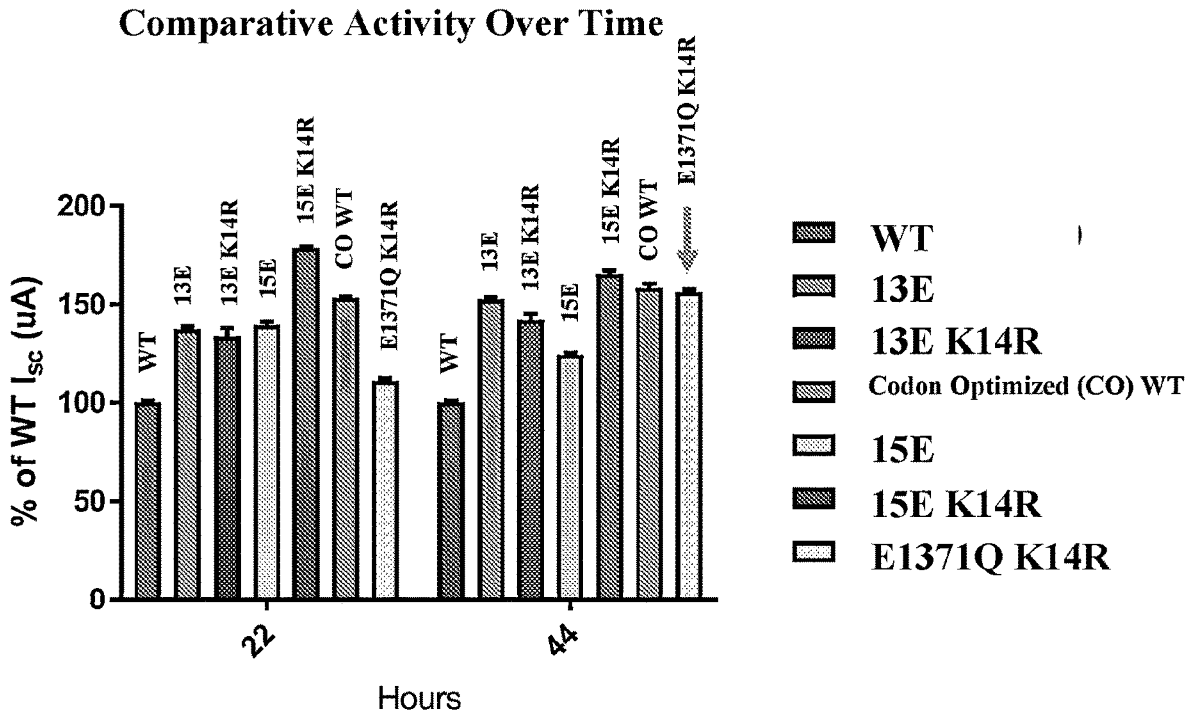

Activity of various CFTR proteins listed in Table 12 were measured at 22 and 44 hours. Short-circuit current ($I_{sc}$), the movement of ions as measured in the Ussing chamber from active transport, was plotted for each CFTR protein at 22 and 44 hours. FIG. 14A shows that highest remaining activity at 44 hours was observed with the 15E/K14R mutant and 13E mutant proteins. FIG. 14B shows that the E1371Q K14R mutant had high remaining activity at 44 hours.

Figure 14C:
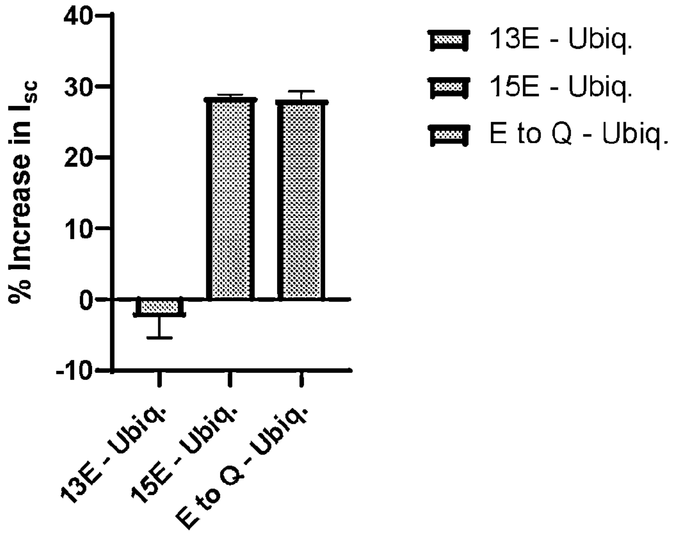
FIG. 14C is an exemplary bar graphs showing that removal of ubiquitination site at N terminus alters channel activity when combined with other substitutions.

Three engineered CFTR proteins (13E, 15E, and E to Q gating) were further designed to alter ubiquitination patterns in the N-terminus by substituting K14 with arginine. As shown in FIG. 14C, the additional substitution (K14R) had no effect on the chloride conductance when combined with the 13E phosphomimetic protein, in contrast with the 15E and E to Q gating variant proteins, both of which showed greater than about 25% increase in activity.

Example 12. CFTR Mutations that Modulate the ATP Gating Cycle

In this example, mutations were made at CFTR amino acid residues that modulate the ATP gating cycle.

Mutations that destabilize or shorten the open state (e.g., mutations at W401, F409, F430, and/or K464) may modulate the effects of E1371Q to create an intermediate phenotype. Table 13, below, shows exemplary mutations that were assessed.

TABLE 13

Select CFTR Mutations that Modulate ATP Gating Cycle

| W401 | F409 | F430 | K464 | K978 | E1371 |
|---|---|---|---|---|---|
| | | | | C | |
| | | | | | Q |
| G | | | | | Q |
| G | G | | | | Q |
| G | G | G | | | Q |
| | | | A | | Q |

Figure 15A:
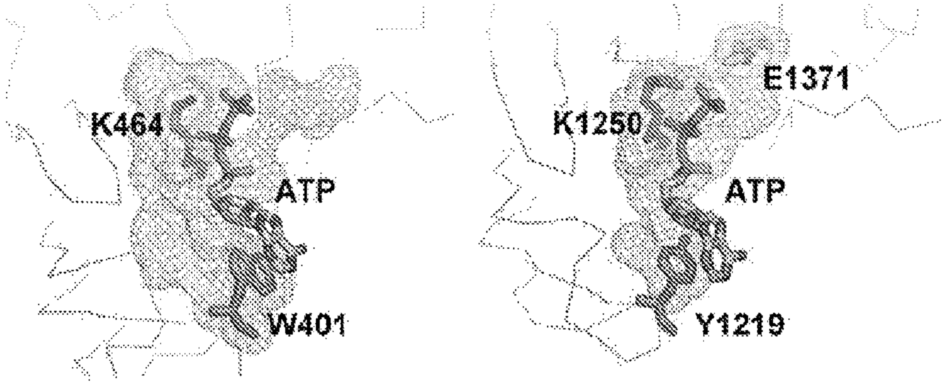
FIG. 15A depicts a schematic that shows CFTR that contains mutations at the indicated amino acid residues.
Figure 15B:
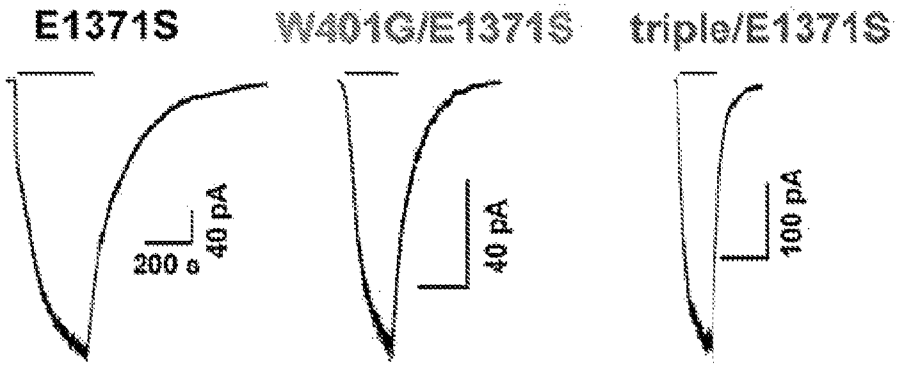
FIG. 15B depicts a series of graphs that shows channel relaxation times for the indicated CFTR mutants.

FIG. 15A shows a schematic of CFTR that contains mutations at the indicated residues. CFTR containing mutations that modulate the ATP gating cycle were assessed for CFTR channel relaxation times. The data shows that alterations in certain amino acid residues result in modulations of channel relation times (FIG. 15B).

Additional variants for E1371Q were assessed by measurement of short-circuit conductivity measured by Ussing chamber. The data showed that K1218R mutation decreases activity in both WT and E1371Q CFTR proteins (FIG. 15C).

Example 13. Phosphomimetic CFTR mRNAs Show Varying Sensitivity to Forskolin Activation In this example, various phosphomimetic CFTR mRNAs were tested for their sensitivity to forskolin activation.

In one study, varying numbers of phosphomimetic mutations were introduced into CFTR mRNAs. The number of phosphomimetic mutations that were introduced into CFTR mRNAs were 0, 4, 6, 8, 13 and 15. These CFTR mRNAs were then assessed for forskolin activation, by the successive addition of 10, 30, 100, 300, 1,000 and 10,000 nM forskolin. The activity of the different CFTR mRNAs having varying numbers of phosphomimetic mutations was assessed by measurement of short-circuit conductivity measured by Ussing chamber of FRT cells that had been transfected with CFTR mRNAs having a specific number of mutations.

Figure 16A:
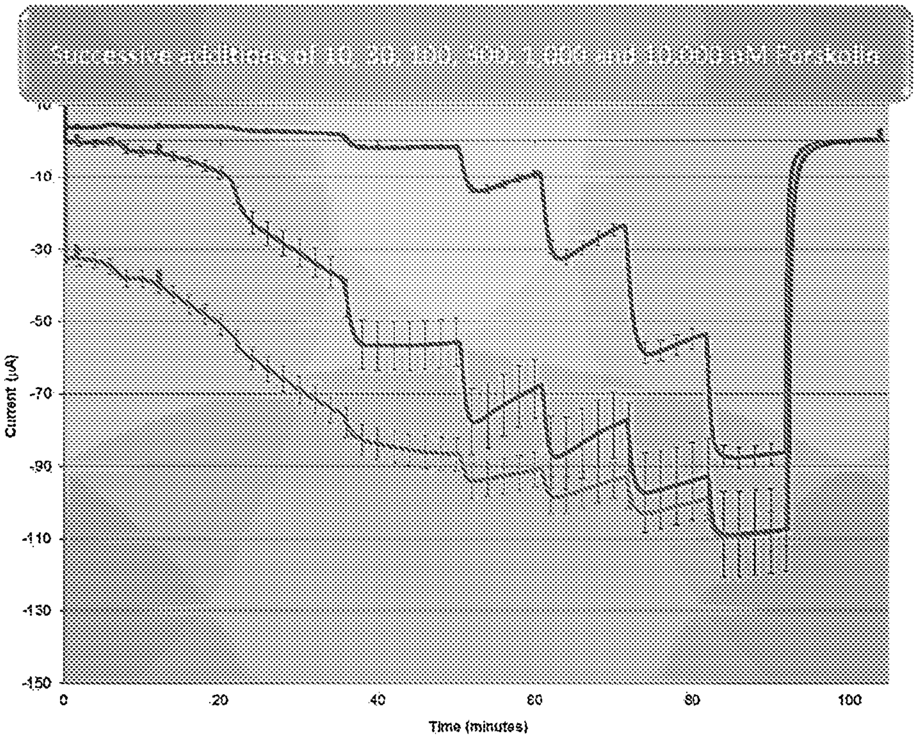
FIG. 16A depicts a graph that shows short-circuit conductivity measured by Ussing chamber using FRT cells that were transfected with CFTR mRNAs that had phosphomimetic CFTR mutations.
Figure 16B:
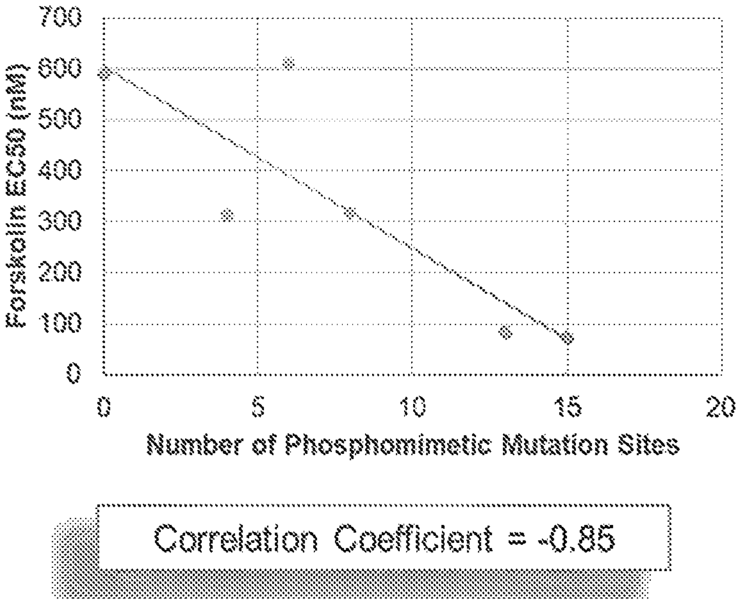
FIG. 16B is a graph that shows forskolin EC50 (nM) in CFTR mRNAs that had varying number of phosphomimetic mutations.

As shown in FIG. 16A, modifying typical Ussing chamber procedure to include successive escalating doses of forskolin demonstrates varying forskolin sensitivity of engineered CFTR variant channels. The data obtained from these experiments showed that with increasing amounts of phosphomimetic CFTR mutations, there was a corresponding increased sensitivity to forskolin activation (FIGS. 16A and 16B). The forskolin EC50 (nM) with respect to the number of mutations in the CFTR mRNA shown in Table 14 below.

TABLE 14

Phosphomimetic CFTR mRNAs have varying sensitivity to forskolin activation

| Number of CFTR Mutations | Forskolin EC50 (NM) |
|---|---|
| 0 | 588.1 |
| 4 | 313.7 |
| 6 | 610.2 |
| 8 | 317.2 |
| 13 | 82.4 |
| 15 | 70.3 |

Figure 17:
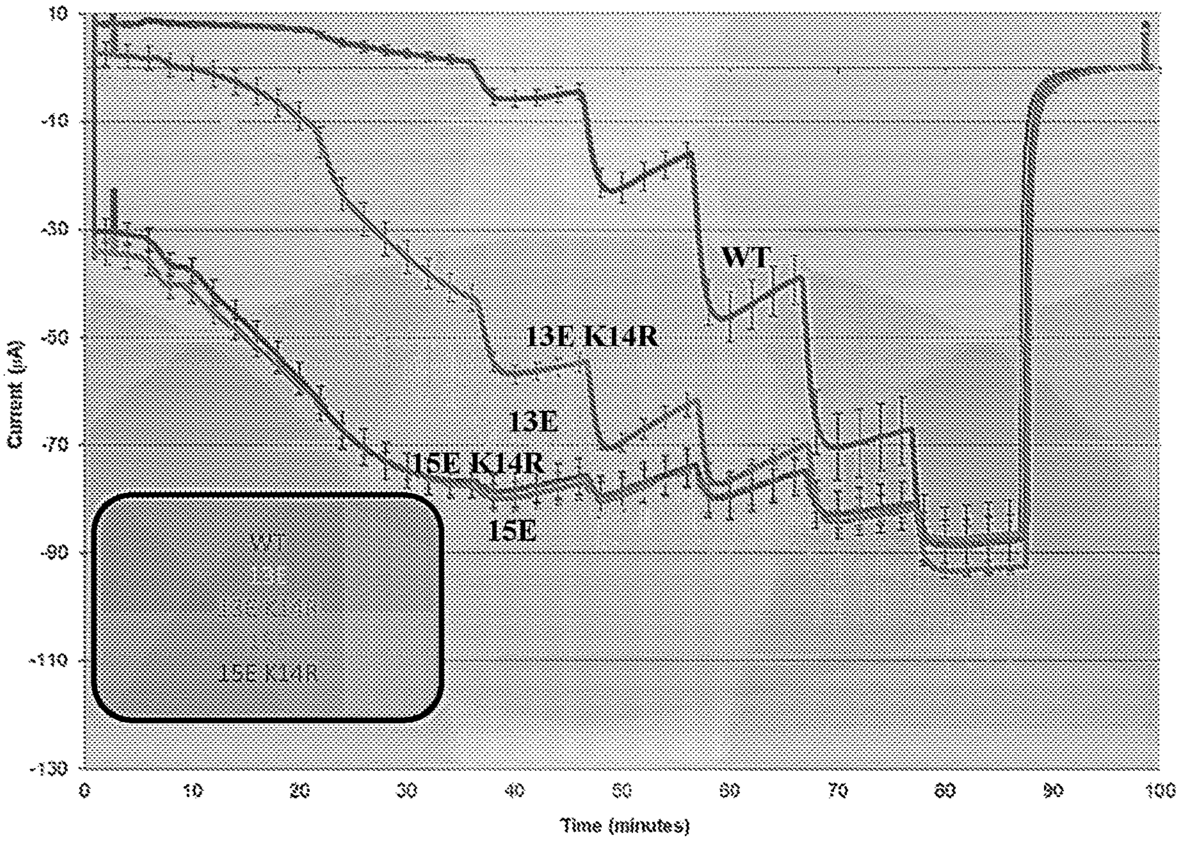
FIG. 17 depicts a graph that shows forskolin sensitivity of CFTR mRNAs that had specific amino acid substitutions as assessed by short-circuit conductivity measured by Ussing chamber using FRT cells that were transfected with CFTR mRNAs identified in the graph.

Studies were also conducted to determine whether amino acid substitutions 13S to 13D in comparison to 13 S to 13D showed any difference with regard to forskolin sensitivity. The data showed that both types of amino acid substitutions displayed similar changes in forskolin sensitivity as assessed by measurements of short-circuit conductivity measured by Ussing chamber of FRT cells that had been transfected with CFTR mRNAs having the specific amino acid substitutions (FIG. 17). The forskolin EC50 (nM) with these CFTR mutants is shown in Table 15 below.

TABLE 15

CFTR mRNA mutants 13S to 13D, and 13S to 13E showed similar changes in forskolin sensitivity

| Construct | Forskolin EC50 (nM) |
|---|---|
| WT | 588.1 |
| 13D | 82.4 |
| 13E | 54.72 |
| 13E K14R | 54.84 |

Example 14. In Silico Prediction of T Cell and B Cell Epitopes and In Vitro Translation and Tolerability EpiQuest® software was used to predict T cell and B cell epitopes with regard to the CFTR mutants. Analysis using this software showed that all of the mutations assessed (i.e., K14R, 13D, 13E, 15D, 15E, K68R, K1218R, and E1371Q) were all outside of potential cytotoxic T lymphocyte (CTL) regions.

The data obtained from the assays showed that all assessed peptide sequences showed low or no immunogenicity potential. Furthermore, epitopes with humoral immunogenicity potential were not readily accessible and/or not on the surface. The data also showed that no mutations were predicted to create or enhance the potential of CTL epitopes. Moreover, ActivSite® software predicts that all mutations tested would fall outside critical regions of the CFTR molecule involved in functional and structural integrity.

Collectively, these data showed that the mutations would had low or no immunogenicity potential and that the mutations would not negatively impact CFTR functional and structural integrity.

Figure 18A:
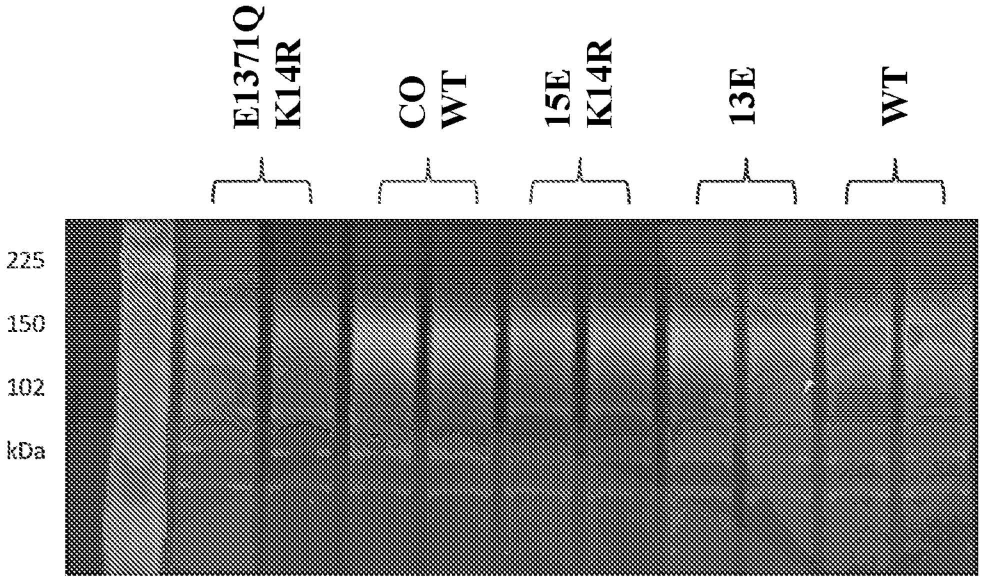
FIG. 18A is a gel that depicts the banding patterns of various CFTR sequences.
Figure 18B:
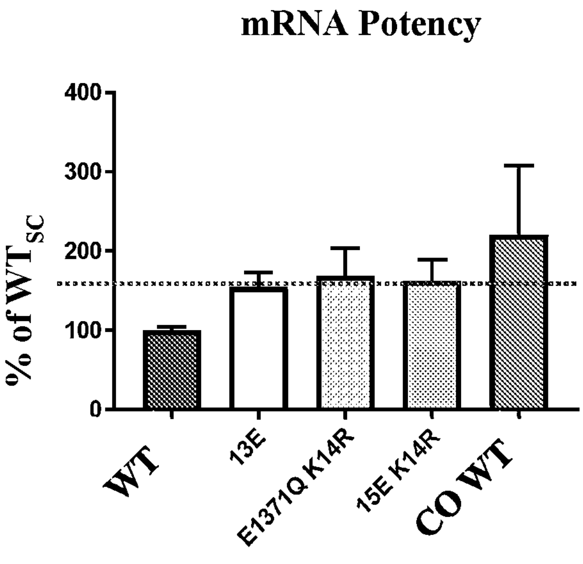
FIG. 18B is a bar graph that depicts CFTR mRNA potency of various CFTR sequences.
Figure 18C:
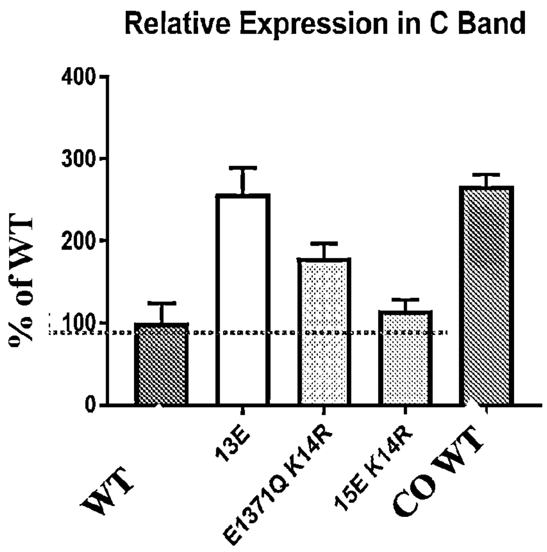
FIG. 18C is a bar graph that depicts the relative expression of various CFTR sequences in the C band.

Studies were also performed to assess in vitro translation and tolerability of CFTR mutants. The data from these studies showed that codon optimized WT sequence, 13E and E1371Q K14R variants showed increased expression in the C band of HEK293 lysates (FIGS. 18A, 18B, and 18C). The "C band" refers to mature complex glycosylated form of CFTR.

Figure 19:
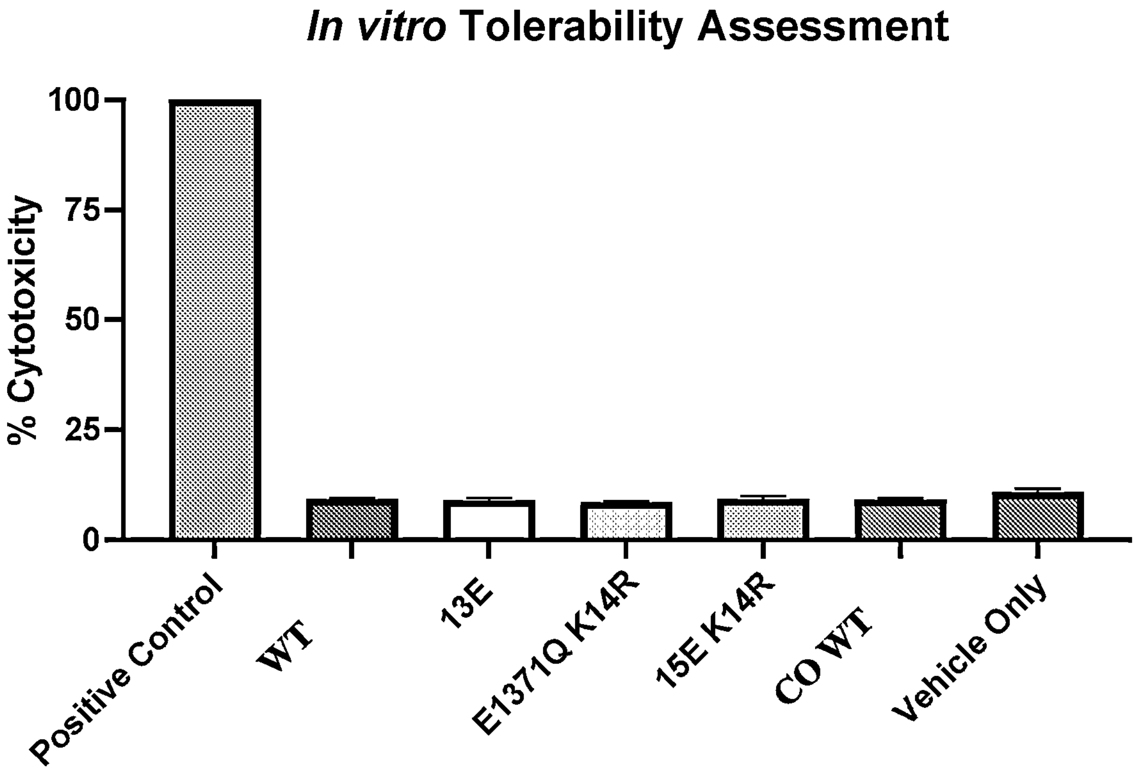
FIG. 19 is a bar graph that depicts the results of an assay to assess cytotoxicity of various CFTR mRNA sequences.

In vitro tolerability of the mutant CFTR mRNAs was also assessed in HEK293 cells using a commercially available cytotoxicity assay. The data from these studies showed that none of the CFTR variants demonstrated increased cytotoxicity when compared to vehicle control in HEK293 cells (FIG. 19).

Example 15. CFTR Codon Optimization Increases Total Activity in Ussing Chamber for Tested CFTR Proteins In this example, total activity of CFTR sequences that had been codon optimized ("CO") in comparison to the non-codon optimized counterpart was assessed. A listing of codon-optimized CFTR sequences are shown in Table 4. For these assays, the following CFTR mutants were assessed WT, E1271Q/K14R, 13E/K14R, 15E/K14R, and 13E. The assessments included activity measurements between non-codon optimized CFTR mutants and codon-optimized CFTR mutants.

The data from these assays showed that codon-optimized constructs had increased activity in Ussing Chamber assays for all variants that were tested (FIGS. 20A, 20B, 20C, 20E and 20F) in comparison to the non-codon optimized counterpart.

Figure 20A:
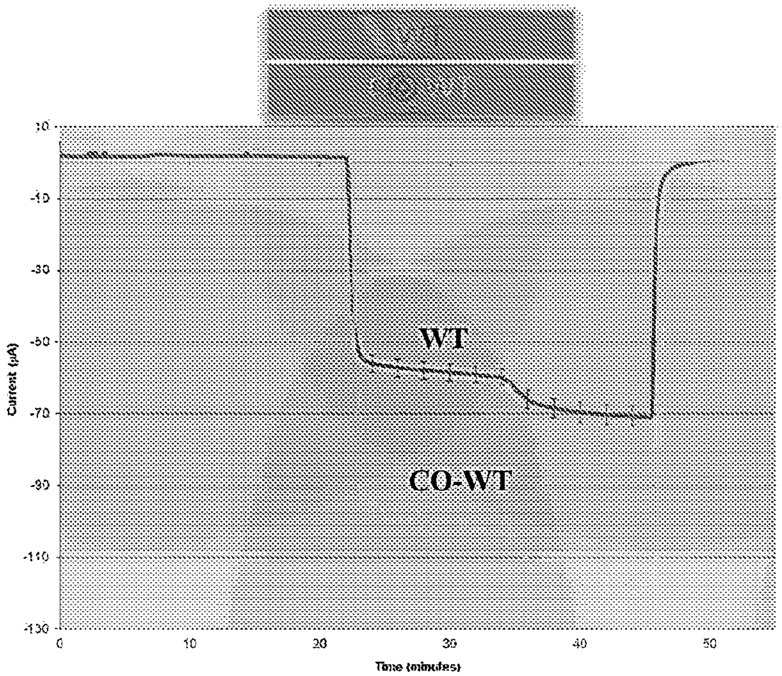
FIGS. 20A, 20B, 20C, 20D, 20E, and 20F are a series of graphs that show short-circuit conductivity measured by Ussing chamber of various codon-optimized and non-codon optimized CFTR constructs.
Figure 20B:
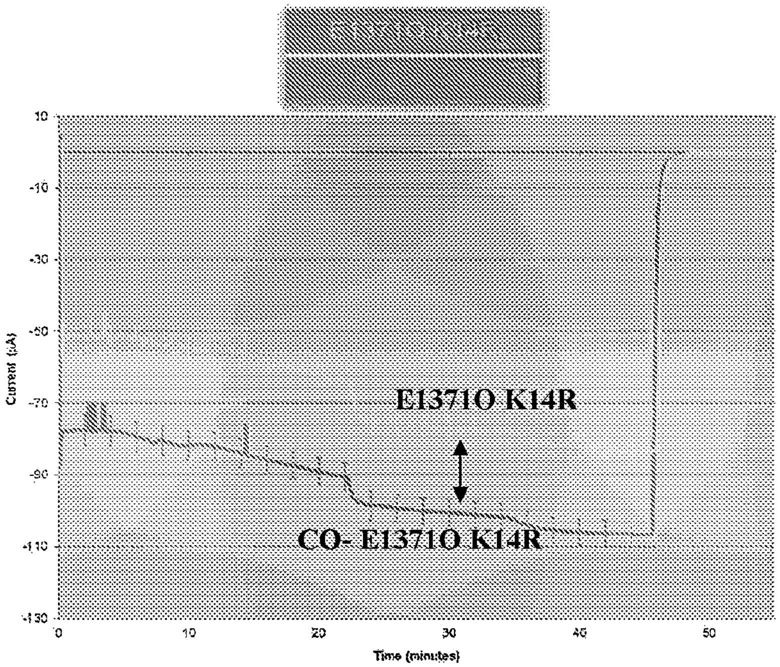
Figure 20C:
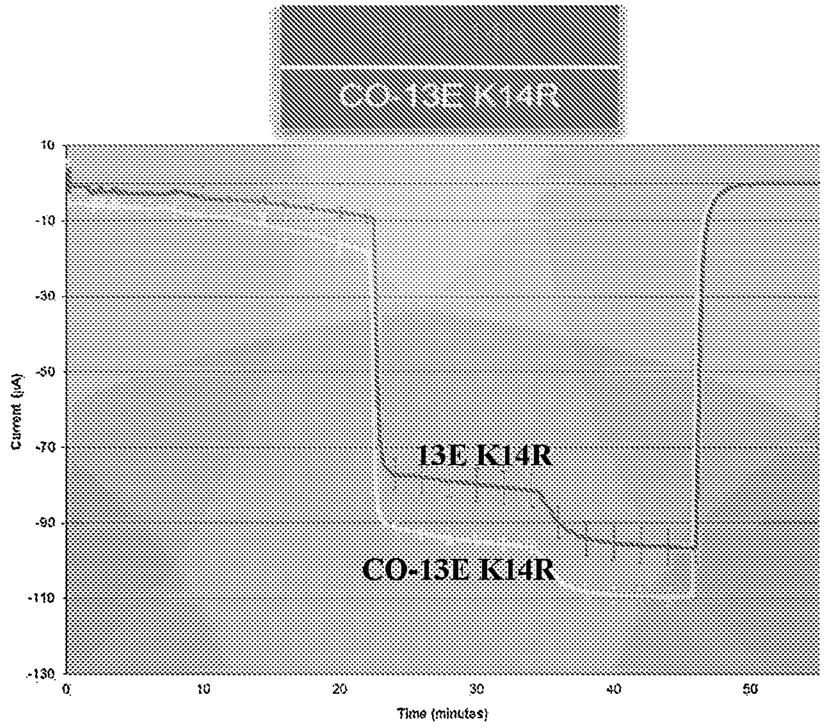
Figure 20D:
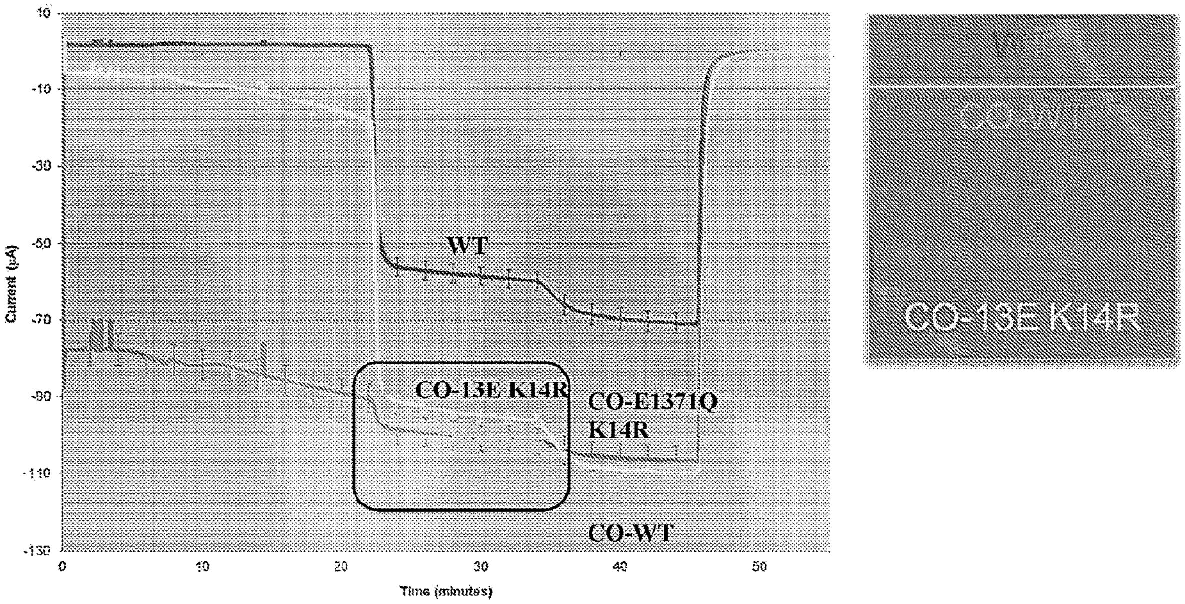
Figure 20E:
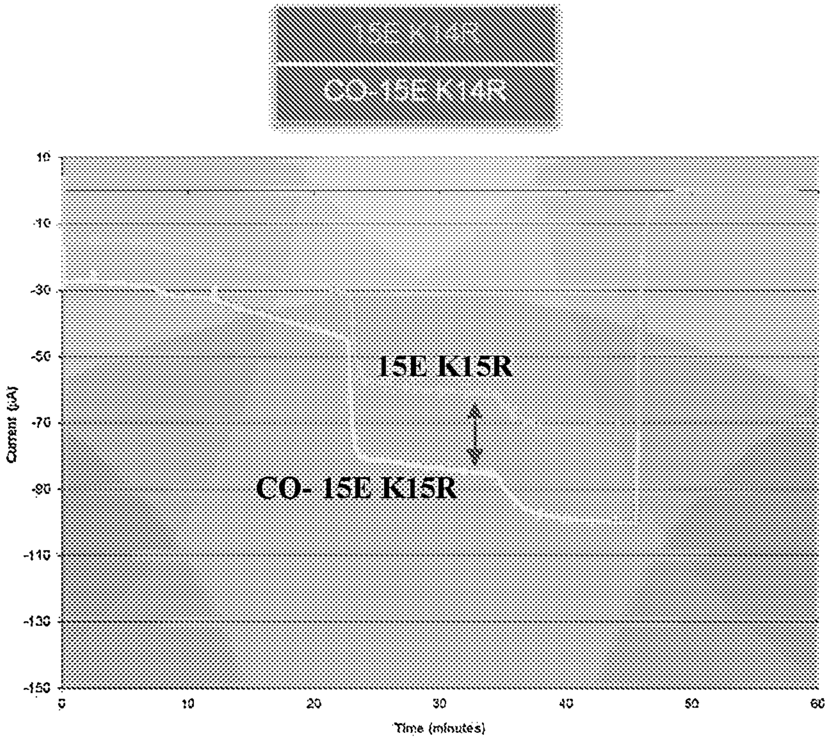
Figure 20F:
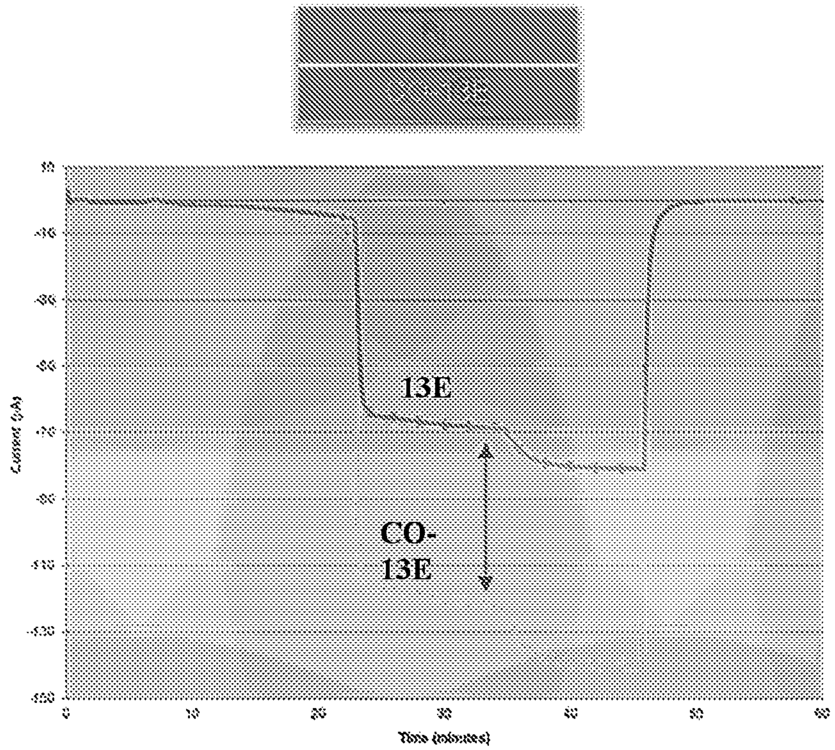

In another study, the codon-optimized sequences each demonstrated comparable activity in comparison to other codon-optimized sequences regardless of the nature of the mutation contained in the codon-optimized sequence (FIG. 20D).

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

We claim:

1. A pharmaceutical composition for treating cystic fibrosis, comprising an mRNA encoding a Cystic Fibrosis Transmembrane Conductance Regulator (CFTR), wherein the CFTR comprises the amino acid substitutions:

(i) S422D/S660D/S670D/S686D/T690D/S700D/S712D/S753D/T787D/T788D/S790D/S795D/S813D;

(ii) S422D/S660D/S670D/S686D/T690D/S700D/S712D/S737D/S753D/S768D/T787D/T788D/S790D/S795D/S813D;

(iii) S422E/S660E/S670E/S686E/T690E/S700E/S712E/S753E/T787E/T788E/S790E/S795E/S813E; or (iv) S422E/S660E/S670E/S686E/T690E/S700E/S712E/S737E/S753E/S768E/T787E/T788E/S790E/S795E/S813E, wherein said mutations produce an activated CFTR protein.

2. The pharmaceutical composition of claim 1, wherein the CFTR further comprises K14R mutation and/or E1371Q mutation.

3. The pharmaceutical composition of claim 1, wherein the mRNA encoding CFTR is codon optimized.

4. The pharmaceutical composition of claim 3, wherein the codon optimized CFTR mRNA further comprises a 5' untranslated region (UTR) sequence set forth by SEQ ID NO: 4 and/or a 3' untranslated region (UTR) sequence set forth by SEQ ID NO: 5 or SEQ ID NO: 6.

5. The pharmaceutical composition of claim 3, wherein the codon optimized CFTR mRNA is encapsulated within a nanoparticle.

6. The pharmaceutical composition of claim 5, wherein the nanoparticle comprises one or more cationic lipids, one or more non-cationic lipids, one or more cholesterol-based lipids and one or more PEG-modified lipids.

7. The pharmaceutical composition of claim 6, wherein the nanoparticle has a size of less than about 100 nm.

8. A nucleic acid encoding a modified Cystic Fibrosis Transmembrane Conductance Regulator (CFTR) protein, wherein the modified CFTR protein comprises the amino acid substitutions:

(i) S422D/S660D/S670D/S686D/T690D/S700D/S712D/S753D/T787D/T788D/S790D/S795D/S813D;

(ii) S422D/S660D/S670D/S686D/T690D/S700D/S712D/S737D/S753D/S768D/T787D/T788D/S790D/S795D/S813D;

(iii) S422E/S660E/S670E/S686E/T690E/S700E/S712E/S753E/T787E/T788E/S790E/S795E/S813E; or (iv) S422E/S660E/S670E/S686E/T690E/S700E/S712E/S737E/S753E/S768E/T787E/T788E/S790E/S795E/S813E.

9. The nucleic acid of claim 8, wherein the modified CFTR protein further comprises K14R mutation and/or E1371Q mutation.

10. The nucleic acid of claim 8, wherein the nucleic acid is DNA, cDNA, RNA, mRNA or PNA.

* * * * *

SEQUENCE LISTING

```
<160> NUMBER OF SEQ ID NOS: 52

<210> SEQ ID NO 1
<211> LENGTH: 4443
<212> TYPE: RNA
<213> ORGANISM: Artificial Sequence
<220> FEATURE:
<223> OTHER INFORMATION: Synthetic polynucleotide

<400> SEQUENCE: 1

augcaacgcu cuccucuuga aaaggccucg guggugucca agcucuucuu cucguggacu     60

agacccaucc ugagaaaggg guacagacag cgcuuggagc uguccgauau cuaucaaauc    120

ccuuccgugg acuccgcgga caaccugucc gagaagcucg agagagaaug ggacagagaa    180

cucgccucaa agaagaaccc gaagcugauu aaugcgcuua ggcggugcuu uuucuggcgg    240

uucauguucu acggcaucuu ccucuaccug ggagagguca ccaaggccgu gcagccccug    300

uugcugggac ggauuauugc cuccuacgac cccgacaaca aggaagaaag aagcaucgcu    360

aucuacuugg gcaucggucu gugccugcuu uucaucgucc ggacccucuu guugcauccu    420

gcuauuuucg gccugcauca cauuggcaug cagaugagaa uugccauguu uucccugauc    480

uacaagaaaa cucugaagcu cucgagccgc gugcuugaca agauuuccau cggccagcuc    540

guguccugc ucuccaacaa ucugaacaag uucgacgagg gccucgcccu ggcccacuuc    600

guguggaucg ccccucugca aguggcgcuu cugaugggcc ugaucuggga gcugcugcaa    660

gccucggcau ucugugggcu uggauuccug aucgugcugg cacuguucca ggccggacug    720

gggcggauga ugaugaagua cagggaccag agagccggaa agauuuccga acggcuggug    780

aucacuucgg aaaugaucga aaacauccag ucagugaagg ccuacugcug ggaagaggcc    840

auggaaaaga ugauugaaaa ccuccggcaa accgagcuga agcugacccg caaggccgcu    900

uacgugcgcu auuucaacuc guccgcuuuc uucuucuccg gguucuucgu ggguguuucuc    960

uccgugcucc ccuacgcccu gauuaaggga aucauccuca ggaagaucuu caccaccauu   1020

uccuucugua ucgugcuccg cauggccgug acccggcagu ucccaugggc cgugcagacu   1080

ugguacgacu cccugggagc cauuaacaag auccaggacu uccuucaaaa gcaggaguac   1140

aagacccucg aguacaaccu gacuacuacc gaggucguga uggaaaacgu caccgccuuu   1200
```

-continued

```
ugggaggagg gauuuggcga acuguucgag aaggccaagc agaacaacaa caaccgcaag   1260
accucgaacg gugacgacuc ccucuucuuu ucaaacuuca gccugcucgg gacgcccgug   1320
cugaaggaca uuaacuucaa gaucgaaaga ggacagcucc uggcgguggc cggaucgacc   1380
ggagccggaa agacuucccu gcugauggug aucaugggag agcuugaacc uagcgaggga   1440
aagaucaagc acuccggccg caucagcuuc uguagccagu uuuccuggau caugcccgga   1500
accauuaagg aaaacaucau cuucggcgug uccuacgaug aauaccgcua ccgguccgug   1560
aucaaagccu gccagcugga agaggauauu ucaaaguucg cggagaaaga uaacaucgug   1620
cugggcgaag gggguauuac cuugucgggg ggccagcggg cuagaaucuc gcuggccaga   1680
gccguguaua aggacgccga ccuguaucuc cuggacuccc ccuucggaua ccuggacguc   1740
cugaccgaaa aggagaucuu cgaaucgugc gugugcaagc ugauggcuaa caagacucgc   1800
auccucguga ccuccaaaau ggagcaccug aagaaggcag acaagauucu gauucugcau   1860
gaggggucuu ccuacuuuua cggcaccuuc ucggaguugc agaacuugca gcccgacuuc   1920
ucaucgaagc ugaugggguug cgacagcuuc gaccaguucu ccgccgaaag aaggaacucg   1980
auccugacgg aaaccuugca ccgcuucucu uuggaaggcg acgccccugu gucauggacc   2040
gagacuaaga agcagagcuu caagcagacc ggggaauucg gcgaaaagag gaagaacagc   2100
aucuugaacc ccauuaacuc cauccgcaag uucucaaucg ugcaaaagac gccacugcag   2160
augaacggca uugaggagga cuccgacgaa ccccuugaga ggcgccuguc ccuggugccg   2220
gacagcgagc agggagaagc cauccugccu cggauuuccg ugaucuccac ugguccgacg   2280
cuccaagccc ggcggcggca guccgugcug aaccugauga cccacagcgu gaaccagggc   2340
caaaacauuc accgcaagac uaccgcaucc acccggaaag ugucccuggc accucaagcg   2400
aaucuuaccg agcucgacau cuacucccgg agacugucgc aggaaaccgg gcucgaaauu   2460
uccgaagaaa ucaacgagga ggaucugaaa gagugcuucu ucgacgauau ggagucgaua   2520
cccgccguga cgacuuggaa cacuuaucug cgguacauca cugugcacaa gucauugauc   2580
uucgugcuga uuuggugccu ggugauuuuc cuggccgagg ucgcggccuc acuggugug   2640
cucuggcugu ugggaaacac gccucugcaa gacaagggaa acuccacgca cucgagaaac   2700
aacagcuaug ccgugauuau cacuuccacc uccucuuauu acguguucua caucuacguc   2760
ggaguggcgg auacccugcu cgcgaugggu uucuucagag gacugccgcu gguccacacc   2820
uugaucaccg ucagcaagau ucuucaccac aagauguugc auagcgugcu gcaggccccc   2880
auguccaccc ucaacacucu gaaggccgga ggcauucuga acagauucuc caaggacauc   2940
gcuauccugg acgaucuccu gccgcuuacc aucuuugacu ucauccagcu gcugcugauc   3000
gugauuggag caaucgcagu gguggcggug cugcagccuu acauuuucgu ggccacugug   3060
ccggucauug uggcguucau caugcugcgg gccuacuucc uccaaaccag ccagcagcug   3120
aagcaacugg aauccgaggg acgaucccc aucuucacuc accuugugac gucguugaag   3180
ggacugugga cccuccgggc uuucggacgg cagcccuacu ucgaaacccu cuuccacaag   3240
gcccugaacc uccacaccgc caauugguuc cuguaccugu ccacccugcg gugguuccag   3300
augcgcaucg agaugauuuu cgucaucuuc uucaucgcgg ucacauucau cagcauccug   3360
acuaccggag agggagaggg acgggucgga auaaauccuga cccucgccau gaacauuaug   3420
agcacccugc agugggcagu gaacagcucg aucgacgugg acagccugau gcgaagcguc   3480
agccgcgugu ucaaguucau cgacaugccu acugagggaa aacccacuaa guccacuaag   3540
cccuacaaaa auggccagcu gagcaagguc augaucaucg aaaacuccca cgugaagaag   3600
```

gacgauauuu ggcccuccgg aggucaaaug accgugaagg accugaccgc aaaguacacc 3660
gagggaggaa acgccauucu cgaaaacauc agcuucucca uuucgccggg acagcggguc 3720
ggccuucucg ggcggaccgg uuccgggaag ucaacucugc ugucggcuuu ccuccggcug 3780
cugaauaccg agggggaaau ccaaauugac ggcgugucuu gggauuccau uacucugcag 3840
caguggcgga aggccuucgg cgugaucccc cagaaggugu ucaucuucuc ggguaccuuc 3900
cggaagaacc uggauccuua cgagcagugg agcgaccaag aaaucuggaa ggucgccgac 3960
gaggucggcc ugcgcuccgu gauugaacaa uuuccuggaa agcuggacuu cgugcucguc 4020
gacgggggau guguccuguc gcacggacau aagcagcuca ugugccucgc acgguccgug 4080
cucuccaagg ccaagauucu gcugcuggac gaaccuucgg cccaccugga uccggucacc 4140
uaccagauca ucaggaggac ccugaagcag gccuuugccg auugcaccgu gauucucugc 4200
gagcaccgca ucgaggccau gcuggagugc cagcaguucc uggucaucga ggagaacaag 4260
guccgccaau acgacuccau ucaaaagcuc cucaacgagc ggucgcuguu cagacaagcu 4320
auuucaccgu ccgauagagu gaagcucuuc ccgcaucgga acagcucaaa gugcaaaucg 4380
aagccgcaga ucgcagccuu gaaggaagag acugaggaag aggugcagga cacccggcuu 4440
uaa 4443

<210> SEQ ID NO 2
<211> LENGTH: 4443
<212> TYPE: RNA
<213> ORGANISM: Artificial Sequence
<220> FEATURE:
<223> OTHER INFORMATION: Synthetic polynucleotide

<400> SEQUENCE: 2
augcagcggu ccccgcucga aaaggccagu gucgugucca aacucuucuu cucauggacu 60
cggccuaucc uuagaaaggg guaucggcag aggcuugagu ugucugacau cuaccagauc 120
cccucgguag auucggcgga uaaccucucg gagaagcucg aacgggaaug ggaccgcgaa 180
cucgcgucua agaaaaaccc gaagcucauc aacgcacuga gaaggugcuu cuucuggcgg 240
uucauguucu acgguaucuu cuuguaucuc ggggagguca caaaagcagu ccaaccccug 300
uuguuggguc gcauuaucgc cucguacgac cccgauaaca aagaagaacg gagcaucgcg 360
aucuaccucg ggaucggacu guguuugcuu uucaucguca gaacacuuuu guugcaucca 420
gcaaucuucg gccuccauca caucgguaug cagaugcgaa ucgcuauguu uagcuugauc 480
uacaaaaaga cacugaaacu cucgucgcgg guguuggaua agauuuccau cggucaguug 540 guguccccugc uuaguaauaa ccucaacaaa uucgaugagg gacuggcgcu ggcacauuuc 600
guguggauug ccccguugca agucgcccuu uugaugggcc uuauuuggga gcuguugcag 660
gcaucugccu uuuguggccu gggauuucug auuguguugg cauuguuuca ggcugggcuu 720
gggcggauga ugaugaagua ucgcgaccag agagcgggua aaaucucgga aagacucguc 780
aucacuucgg aaaugaucga aaacauccag ucggucaaag ccuauugcug ggaagaagcu 840
auggagaaga ugauugaaaa ccuccgccaa acugagcuga aacugacccg caaggcggcg 900
uauguccggu auuucaauuc gucagcguuc uucuuuuccg gguucuucgu ugucuuucuc 960
ucgguuuugc cuuaugccuu gauuaagggg auuauccucc gcaagauuuu caccacgauu 1020
ucguucugca uuguauugcg cauggcagug acacggcaau uuccgugggc cgugcagaca 1080
ugguaugacu cgcuuggagc gaucaacaaa auccaagacu ucuugcaaaa gcaagaguac 1140

-continued

```
aagacccugg aguacaaucu uacuacuacg gagguaguaa uggagaaugu gacggcuuuu   1200
ugggaagagg guuuuggaga acuguuugag aaagcaaagc agaauaacaa caaccgcaag   1260
accucaaaug gggacgauuc ccuguuuuuc ucgaacuucu cccugcucgg aacacccgug   1320
uugaaggaca ucaauuucaa gauugagagg ggacagcuuc ucgcgguagc gggaagcacu   1380
ggugcgggaa aaacuagccu cuugauggug auuauggggg agcuugagcc cagcgagggg   1440
aagauuaaac acuccgggcg uaucucauuc uguagccagu uucauggau caugcccgga   1500
accauuaaag agaacaucau uuucggagua uccuaugaug aguaccgaua cagaucgguc   1560
auuaaggcgu gccaguugga agaggacauu ucuaaguucg ccgagaagga uaacaucguc   1620
uugggagaag gggguauuac auugucggga gggcagcgag cgcggaucag ccucgcgaga   1680
gcgguauaca aagaugcaga uuuguaucug cuugauucac cguuuggaua ccucgacgua   1740
uugacagaaa aagaaaucuu cgagucgugc guguguaaac uuauggcuaa uaagacgaga   1800
auccugguga caucaaaaau ggaacaccuu aagaaggcgg acaagauccu gauccuccac   1860
gaaggaucgu ccuacuuuua cggcacuuuc ucagaguugc aaaacuugca gccggacuuc   1920
ucaagcaaac ucaugggggug ugacucauuc gaccaguuca gcgcggaacg gcggaacucg   1980
aucuugacgg aaacgcugca ccgauucucg cuugagggug augccccggu aucguggacc   2040
gagacaaaga agcagucguu uaagcagaca ggagaauuug gugagaaaag aaagaacagu   2100
aucuugaauc cuauuaacuc aauucgcaag uucucaaucg uccagaaaac uccacugcag   2160
augaauggaa uugaagagga uucggacgaa ccccuggagc gcaggcuuag ccucgugccg   2220
gauucagagc aaggggaggc cauucuuccc cggauuucgg ugauuucaac cggaccuaca   2280
cuucaggcga ggcgaaggca auccgugcuc aaccucauga cgcauucggu aaaccagggg   2340
caaaacauuc accgcaaaac gacggccuca acgagaaaag ugucacuugc accccaggcg   2400
aauuugacug aacucgacau cuacagccgu aggcuuucgc aagaaaccgg acuugagauc   2460
agcgaagaaa ucaaugaaga agauuugaaa gaguguuucu uugaugacau ggaaucaauc   2520
ccagcgguga caacguggaa cacauacuug cguuacauca cggugcacaa guccuugauu   2580
uucguccuca ucuggugucu cgugaucuuu cucgcugagg ucgcagcguc acuuguggc   2640
cucuggcugc uugguaauac gcccuugcaa gacaaaggca auucuacaca cucaagaaac   2700
aauuccuaug ccgugauuau cacuucuaca agcucguauu acguguuuua caucuacgua   2760
ggaguggccg acacucugcu cgcgaugggu uucuuccgag gacucccacu cguucacacg   2820
cuuaucacug ucuccaagau ucuccaccau aagaugcuuc auagcguacu gcaggcuccc   2880
auguccaccu ugaauacgcu caaggcggga gguauuuuga aucgcuucuc aaaagauauu   2940
gcaauuuugg augaccuucu gccccugacg aucuucgacu ucauccaguu guugcugauc   3000
gugauugggg cuauugcagu agucgcuguc cuccagccuu acauuuuugu cgcgaccguu   3060
ccggugaucg uggcguuuau caugcugcgg gccuauuucu ugcagacguc acagcagcuu   3120
aagcaacugg agucugaagg gaggucgccu aucuuuacgc aucuugugac caguuugaag   3180
ggauugugga cguugcgcgc cuuuggcagg cagcccuacu uugaaacacu guuccacaaa   3240
gcgcugaauc uccauacggc aaauugguuu uuguauuuga guacccuccg augguuucag   3300
augcgcauug agaugauuuu ugugaucuuc uuuaucgcgg ugacuuuuau cuccaucuug   3360
accacgggag agggcgaggg acgggucggu auuauccuga cacucgccau gaacauuaug   3420
agcacuuugc aguggggcagu gaacagcucg auugaugugg auagccugau gagguccguu   3480
ucgagggucu uuaaguucau cgacaugccg acggagggaa agcccacaaa aaguacgaaa   3540
```

-continued

```
cccuauaaga augggcaauu gaguaaggua augaucaucg agaacaguca cgugaagaag   3600

gaugacaucu ggccuagcgg gggucagaug accgugaagg accugacggc aaaauacacc   3660

gagggaggga acgcaauccu ugaaaacauc ucguucagca uuagccccgg ucagcgugug   3720

ggguugcucg ggaggaccgg gucaggaaaa ucgacguugc ugucggccuu cuugagacuu   3780

cugaauacag agggugagau ccagaucgac ggcguuucgu gggauagcau caccuugcag   3840

caguggcgga aagcguuugg aguaaucccc caaaaggucu uuaucuuuag cggaaccuuc   3900

cgaaagaauc ucgauccuua ugaacagugg ucagaucaag agauuuggaa agucgcggac   3960

gagguuggcc uucggagugu aaucgagcag uuuccgggaa aacucgacuu uguccuugua   4020

gaugggggau gcguccuguc gcaugggcac aagcagcuca ugugccuggc gcgauccguc   4080

cucucuaaag cgaaaauucu ucucuuggau gaaccuucgg cccaucugga cccgguaacg   4140

uaucagauca ucagaaggac acuuaagcag gcguuugccg acugcacggu gauucucugu   4200

gagcaucgua ucgaggccau gcucgaaugc cagcaauuuc uugucaucga agagaauaag   4260

guccgccagu acgacuccau ccagaagcug cuuaaugaga gaucauuguu ccggcaggcg   4320

auuucaccau ccgauagggu gaaacuuuuu ccacacagaa auucgucgaa gugcaagucc   4380

aaaccgcaga ucgcggccuu gaaagaagag acugaagaag aaguucaaga cacgcgucuu   4440

uaa                                                                 4443
```

```
<210> SEQ ID NO 3
<211> LENGTH: 1480
<212> TYPE: PRT
<213> ORGANISM: Homo sapiens

<400> SEQUENCE: 3

Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205
```

-continued

```
Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Val Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
        515                 520                 525

Asp Ile Ser Lys Phe Ala Glu Lys Asp Asn Ile Val Leu Gly Glu Gly
    530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu His Glu Gly Ser Ser
    610                 615                 620
```

-continued

```
Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
        675                 680                 685

Gln Thr Gly Glu Phe Gly Glu Lys Arg Lys Asn Ser Ile Leu Asn Pro
    690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
        755                 760                 765

Val Leu Asn Leu Met Thr His Ser Val Asn Gln Gly Gln Asn Ile His
    770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
            820                 825                 830

Phe Phe Asp Asp Met Glu Ser Ile Pro Ala Val Thr Thr Trp Asn Thr
        835                 840                 845

Tyr Leu Arg Tyr Ile Thr Val His Lys Ser Leu Ile Phe Val Leu Ile
    850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
        915                 920                 925

Met Gly Phe Phe Arg Gly Leu Pro Leu Val His Thr Leu Ile Thr Val
    930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile  Val Ile Gly Ala Ile  Ala Val Val
        995                 1000                 1005

Ala Val  Leu Gln Pro Tyr Ile  Phe Val Ala Thr Val  Pro Val Ile
    1010                 1015                 1020

Val Ala  Phe Ile Met Leu Arg  Ala Tyr Phe Leu Gln  Thr Ser Gln
    1025                 1030                 1035

Gln Leu  Lys Gln Leu Glu Ser  Glu Gly Arg Ser Pro  Ile Phe Thr
```

```
    1040                1045                1050

His Leu  Val Thr Ser Leu Lys  Gly Leu Trp Thr Leu  Arg Ala Phe
    1055                1060                1065

Gly Arg  Gln Pro Tyr Phe Glu  Thr Leu Phe His Lys  Ala Leu Asn
    1070                1075                1080

Leu His  Thr Ala Asn Trp Phe  Leu Tyr Leu Ser Thr  Leu Arg Trp
    1085                1090                1095

Phe Gln  Met Arg Ile Glu Met  Ile Phe Val Ile Phe  Phe Ile Ala
    1100                1105                1110

Val Thr  Phe Ile Ser Ile Leu  Thr Thr Gly Glu Gly  Glu Gly Arg
    1115                1120                1125

Val Gly  Ile Ile Leu Thr Leu  Ala Met Asn Ile Met  Ser Thr Leu
    1130                1135                1140

Gln Trp  Ala Val Asn Ser Ser  Ile Asp Val Asp Ser  Leu Met Arg
    1145                1150                1155

Ser Val  Ser Arg Val Phe Lys  Phe Ile Asp Met Pro  Thr Glu Gly
    1160                1165                1170

Lys Pro  Thr Lys Ser Thr Lys  Pro Tyr Lys Asn Gly  Gln Leu Ser
    1175                1180                1185

Lys Val  Met Ile Ile Glu Asn  Ser His Val Lys Lys  Asp Asp Ile
    1190                1195                1200

Trp Pro  Ser Gly Gly Gln Met  Thr Val Lys Asp Leu  Thr Ala Lys
    1205                1210                1215

Tyr Thr  Glu Gly Gly Asn Ala  Ile Leu Glu Asn Ile  Ser Phe Ser
    1220                1225                1230

Ile Ser  Pro Gly Gln Arg Val  Gly Leu Leu Gly Arg  Thr Gly Ser
    1235                1240                1245

Gly Lys  Ser Thr Leu Leu Ser  Ala Phe Leu Arg Leu  Leu Asn Thr
    1250                1255                1260

Glu Gly  Glu Ile Gln Ile Asp  Gly Val Ser Trp Asp  Ser Ile Thr
    1265                1270                1275

Leu Gln  Gln Trp Arg Lys Ala  Phe Gly Val Ile Pro  Gln Lys Val
    1280                1285                1290

Phe Ile  Phe Ser Gly Thr Phe  Arg Lys Asn Leu Asp  Pro Tyr Glu
    1295                1300                1305

Gln Trp  Ser Asp Gln Glu Ile  Trp Lys Val Ala Asp  Glu Val Gly
    1310                1315                1320

Leu Arg  Ser Val Ile Glu Gln  Phe Pro Gly Lys Leu  Asp Phe Val
    1325                1330                1335

Leu Val  Asp Gly Gly Cys Val  Leu Ser His Gly His  Lys Gln Leu
    1340                1345                1350

Met Cys  Leu Ala Arg Ser Val  Leu Ser Lys Ala Lys  Ile Leu Leu
    1355                1360                1365

Leu Asp  Glu Pro Ser Ala His  Leu Asp Pro Val Thr  Tyr Gln Ile
    1370                1375                1380

Ile Arg  Arg Thr Leu Lys Gln  Ala Phe Ala Asp Cys  Thr Val Ile
    1385                1390                1395

Leu Cys  Glu His Arg Ile Glu  Ala Met Leu Glu Cys  Gln Gln Phe
    1400                1405                1410

Leu Val  Ile Glu Glu Asn Lys  Val Arg Gln Tyr Asp  Ser Ile Gln
    1415                1420                1425

Lys Leu  Leu Asn Glu Arg Ser  Leu Phe Arg Gln Ala  Ile Ser Pro
    1430                1435                1440
```

```
Ser Asp  Arg Val Lys Leu Phe  Pro His Arg Asn Ser  Ser Lys Cys
    1445                1450                1455

Lys Ser  Lys Pro Gln Ile Ala  Ala Leu Lys Glu Glu  Thr Glu Glu
    1460                1465                1470

Glu Val  Gln Asp Thr Arg Leu
    1475                1480


<210> SEQ ID NO 4
<211> LENGTH: 140
<212> TYPE: RNA
<213> ORGANISM: Artificial Sequence
<220> FEATURE:
<223> OTHER INFORMATION: Synthetic polynucleotide

<400> SEQUENCE: 4

ggacagaucg ccuggagacg ccauccacgc uguuuugacc uccauagaag acaccgggac     60

cgauccagcc uccgcggccg ggaacggugc auuggaacgc ggauuccccg ugccaagagu    120

gacucaccgu ccuugacacg                                                140


<210> SEQ ID NO 5
<211> LENGTH: 105
<212> TYPE: RNA
<213> ORGANISM: Artificial Sequence
<220> FEATURE:
<223> OTHER INFORMATION: Synthetic polynucleotide

<400> SEQUENCE: 5

cggguggcau cccugugacc ccuccccagu gccucuccug gcccuggaag uugccacucc     60

agugcccacc agccuugucc uaauaaaauu aaguugcauc aagcu                    105


<210> SEQ ID NO 6
<211> LENGTH: 105
<212> TYPE: RNA
<213> ORGANISM: Artificial Sequence
<220> FEATURE:
<223> OTHER INFORMATION: Synthetic polynucleotide

<400> SEQUENCE: 6

ggguggcauc ccugugaccc cuccccagug ccucuccugg cccuggaagu ugccacucca     60

gugcccacca gccuuguccu aauaaaauua aguugcauca aagcu                    105


<210> SEQ ID NO 7
<211> LENGTH: 4688
<212> TYPE: RNA
<213> ORGANISM: Artificial Sequence
<220> FEATURE:
<223> OTHER INFORMATION: Synthetic polynucleotide

<400> SEQUENCE: 7

ggacagaucg ccuggagacg ccauccacgc uguuuugacc uccauagaag acaccgggac     60

cgauccagcc uccgcggccg ggaacggugc auuggaacgc ggauuccccg ugccaagagu    120

gacucaccgu ccuugacacg augcaacgcu cuccucuuga aaaggccucg guggugucca    180

agcucuucuu cucguggacu agacccaucc ugagaaaggg guacagacag cgcuuggagc    240

uguccgauau cuaucaaauc ccuuccgugg acuccgcgga caaccugucc gagaagcucg    300

agagagaaug ggacagagaa cucgccucaa agaagaaccc gaagcugauu aaugcgcuua    360

ggcggugcuu uuucuggcgg uucauguucu acggcaucuu ccucuaccug ggagagguca    420

ccaaggccgu gcagccccug uugcugggac ggauuauugc cuccuacgac cccgacaaca    480
```

```
aggaagaaag aagcaucgcu aucuacuugg gcaucggucu gugccugcuu uucaucgucc    540
ggacccucuu guugcauccu gcuauuuucg gccugcauca cauuggcaug cagaugagaa    600
uugccauguu uucccugauc uacaagaaaa cucugaagcu cucgagccgc gugcuugaca    660
agauuuccau cggccagcuc gugucccugc ucuccaacaa ucugaacaag uucgacgagg    720
gccucgcccu ggcccacuuc guguggaucg ccccucugca aguggcgcuu cugaugggcc    780
ugaucuggga gcugcugcaa gccucggcau ucugugggcu uggauuccug aucgugcugg    840
cacuguucca ggccggacug gggcggauga ugaugaagua cagggaccag agagccggaa    900
agauuuccga acggcuggug aucacuucgg aaaugaucga aaacauccag ucagugaagg    960
ccuacugcug ggaagaggcc auggaaaaga ugauugaaaa ccuccggcaa accgagcuga   1020
agcugacccg caaggccgcu uacgugcgcu auuucaacuc guccgcuuuc uucuucuccg   1080
gguucuucgu gguguuucuc uccgugcucc ccuacgcccu gauuaaggga aucauccuca   1140
ggaagaucuu caccaccauu uccuucugua ucgugcuccg cauggccgug acccggcagu   1200
ucccaugggc cgugcagacu ugguacgacu cccugggagc cauuaacaag auccaggacu   1260
uccuucaaaa gcaggaguac aagacccucg aguacaaccu gacuacuacc gaggucguga   1320
uggaaaacgu caccgccuuu ugggaggagg gauuuggcga acuguucgag aaggccaagc   1380
agaacaacaa caaccgcaag accucgaacg gugacgacuc ccucuucuuu ucaaacuuca   1440
gccugcucgg gacgcccgug cugaaggaca uuaacuucaa gaucgaaaga ggacagcucc   1500
uggcgguggc cggaucgacc ggagccggaa agacuucccu gcugauggug aucaugggag   1560
agcuugaacc uagcgaggga aagaucaagc acuccggccg caucagcuuc uguagccagu   1620
uuuccuggau caugcccgga accauuaagg aaaacaucau cuucggcgug uccuacgaug   1680
aauaccgcua ccgguccgug aucaaagccu gccagcugga agaggauauu ucaaaguucg   1740
cggagaaaga uaacaucgug cugggcgaag gggguauuac cuugucgggg ggccagcggg   1800
cuagaaucuc gcuggccaga gccguguaua aggacgccga ccuguaucuc cuggacuccc   1860
ccuucggaua ccuggacguc cugaccgaaa aggagaucuu cgaaucgugc gugugcaagc   1920
ugauggcuaa caagacucgc auccucguga ccuccaaaau ggagcaccug aagaaggcag   1980
acaagauucu gauucugcau gaggggguccu ccuacuuuua cggcaccuuc ucggaguugc   2040
agaacuugca gcccgacuuc ucaucgaagc ugauggguug cgacagcuuc gaccaguucu   2100
ccgccgaaag aaggaacucg auccugacgg aaaccuugca ccgcuucucu uuggaaggcg   2160
acgccccugu gucauggacc gagacuaaga agcagagcuu caagcagacc ggggaauucg   2220
gcgaaaagag gaagaacagc aucuugaacc ccauuaacuc cauccgcaag uucucaaucg   2280
ugcaaaagac gccacugcag augaacggca uugaggagga cuccgacgaa ccccuugaga   2340
ggcgccuguc ccuggugccg gacagcgagc agggagaagc cauccugccu cggauuuccg   2400
ugaucuccac ugguccgacg cuccaagccc ggcggcggca guccgugcug aaccugauga   2460
cccacagcgu gaaccagggc caaaacauuc accgcaagac uaccgcaucc acccggaaag   2520
ugucccuggc accucaagcg aaucuuaccg agcucgacau cuacucccgg agacugucgc   2580
aggaaaccgg gcucgaaauu uccgaagaaa ucaacgagga ggaucugaaa gagugcuucu   2640
ucgacgauau ggagucgaua cccgccguga cgacuuggaa cacuuaucug cgguacauca   2700
cugugcacaa gucauugauc uucgugcuga uuuggugccu ggugauuuuc cuggccgagg   2760
ucgcggccuc acugguggug cucuggcugu ugggaaacac gccucugcaa gacaagggaa   2820
```

acuccacgca cucgagaaac aacagcuaug ccgugauuau cacuuccacc uccucuuauu 2880
acguguucua caucuacguc ggaguggcgg auacccugcu cgcgaugggu uucuucagag 2940
gacugccgcu gguccacacc uugaucaccg ucagcaagau ucuucaccac aagauguugc 3000
auagcgugcu gcaggccccc auguccaccc ucaacacucu gaaggccgga ggcauucuga 3060
acagauucuc caaggacauc gcuauccugg acgaucuccu gccgcuuacc aucuuugacu 3120
ucauccagcu gcugcugauc gugauuggag caaucgcagu gguggcggug cugcagccuu 3180
acauuuucgu ggccacugug ccggucauug uggcguucau caugcugcgg gccuacuucc 3240
uccaaaccag ccagcagcug aagcaacugg aauccgaggg acgauccccc aucuucacuc 3300
accuugugac gucguugaag ggacugugga cccuccgggc uuucggacgg cagcccuacu 3360
ucgaaacccu cuuccacaag gcccugaacc uccacaccgc caauugguuc cuguaccugu 3420
ccacccugcg gugguuccag augcgcaucg agaugauuuu cgucaucuuc uucaucgcgg 3480
ucacauucau cagcauccug acuaccggag agggagaggg acgggucgga auaauccuga 3540
cccucgccau gaacauuaug agcacccugc agugggcagu gaacagcucg aucgacgugg 3600
acagccugau gcgaagcguc agccgcgugu ucaaguucau cgacaugccu acugagggaa 3660
aacccacuaa guccacuaag cccuacaaaa auggccagcu gagcaagguc augaucaucg 3720
aaaacuccca cgugaagaag gacgauauuu ggcccuccgg aggucaaaug accgugaagg 3780
accugaccgc aaaguacacc gagggaggaa acgccauucu cgaaaacauc agcuucucca 3840
uuucgccggg acagcggguc ggccuucucg ggcggaccgg uuccgggaag ucaacucugc 3900
ugucggcuuu ccuccggcug cugaauaccg aggggggaaau ccaaauugac ggcgugucuu 3960
gggauuccau uacucugcag caguggcgga aggccuucgg cgugaucccc cagaaggugu 4020
ucaucuucuc ggguaccuuc cggaagaacc uggauccuua cgagcagugg agcgaccaag 4080
aaaucuggaa ggucgccgac gaggucggcc ugcgcuccgu gauugaacaa uuuccuggaa 4140
agcuggacuu cgugcucguc gacgggggau guguccuguc gcacggacau aagcagcuca 4200
ugugccucgc acgguccgug cucuccaagg ccaagauucu gcugcuggac gaaccuucgg 4260
cccaccugga uccggucacc uaccagauca ucaggaggac ccugaagcag gccuuugccg 4320
auugcaccgu gauucucugc gagcaccgca ucgaggccau gcuggagugc cagcaguucc 4380
uggucaucga ggagaacaag guccgccaau acgacuccau ucaaaagcuc cucaacgagc 4440
ggucgcuguu cagacaagcu auuucaccgu ccgauagagu gaagcucuuc ccgcaucgga 4500
acagcucaaa gugcaaaucg aagccgcaga ucgcagccuu gaaggaagag acugaggaag 4560
aggugcagga cacccggcuu uaacgggugg cauccccugug accccucccc agugccucuc 4620
cuggcccugg aaguugccac uccagugccc accagccuug uccuaauaaa auuaaguugc 4680
aucaagcu 4688

<210> SEQ ID NO 8
<211> LENGTH: 4688
<212> TYPE: RNA
<213> ORGANISM: Artificial Sequence
<220> FEATURE:
<223> OTHER INFORMATION: Synthetic polynucleotide

<400> SEQUENCE: 8
ggacagaucg ccuggagacg ccauccacgc uguuuugacc uccauagaag acaccgggac 60
cgauccagcc uccgcggccg ggaacggugc auuggaacgc ggauuccccg ugccaagagu 120
gacucaccgu ccuugacacg augcaacgcu cuccucuuga aaaggccucg guggugucca 180

-continued

```
agcucuucuu cucguggacu agacccaucc ugagaaaggg guacagacag cgcuuggagc    240
uguccgauau cuaucaaauc ccuuccgugg acuccgcgga caaccugucc gagaagcucg    300
agagagaaug ggacagagaa cucgccucaa agaagaaccc gaagcugauu aaugcgcuua    360
ggcggugcuu uuucuggcgg uucauguucu acggcaucuu ccucuaccug ggagagguca    420
ccaaggccgu gcagccccug uugcugggac ggauuauugc cuccuacgac cccgacaaca    480
aggaagaaag aagcaucgcu aucuacuugg gcaucggucu gugccugcuu uucaucgucc    540
ggacccucuu guugcauccu gcuauuuucg gccugcauca cauuggcaug cagaugagaa    600
uugccauguu uucccugauc uacaagaaaa cucugaagcu cucgagccgc gugcuugaca    660
agauuuccau cggccagcuc guguccccugc ucuccaacaa ucugaacaag uucgacgagg    720
gccucgcccu ggcccacuuc guguggaucg ccccucugca aguggcgcuu cugaugggcc    780
ugaucuggga gcugcugcaa gccucggcau ucugugggcu uggauuccug aucgugcugg    840
cacuguucca ggccggacug ggcggauga ugaugaagua cagggaccag agagccggaa    900
agauuuccga acggcuggug aucacuucgg aaaugaucga aaacauccag ucagugaagg    960
ccuacugcug ggaagaggcc auggaaaaga ugauugaaaa ccuccggcaa accgagcuga   1020
agcugacccg caaggccgcu uacgugcgcu auuucaacuc guccgcuuuc uucuucuccg   1080
gguucuucgu gguguuucuc uccgugcucc ccuacgcccu gauuaaggga aucauccuca   1140
ggaagaucuu caccaccauu uccuucugua ucgugcuccg cauggccgug acccggcagu   1200
ucccaugggc cgugcagacu ugguacgacu cccugggagc cauuaacaag auccaggacu   1260
uccuucaaaa gcaggaguac aagacccucg aguacaaccu gacuacuacc gaggucguga   1320
uggaaaacgu caccgccuuu ugggaggagg gauuuggcga acuguucgag aaggccaagc   1380
agaacaacaa caaccgcaag accucgaacg gugacgacuc ccucuucuuu ucaaacuuca   1440
gccugcucgg gacgcccgug cugaaggaca uuaacuucaa gaucgaaaga ggacagcucc   1500
uggcggugge cggaucgacc ggagccggaa agacuucccu gcugauggug aucaugggag   1560
agcuugaacc uagcgaggga aagaucaagc acuccggccg caucagcuuc uguagccagu   1620
uuuccuggau caugcccgga accauuaagg aaaacaucau cuucggcgug uccuacgaug   1680
aauaccgcua ccgguccgug aucaaagccu gccagcugga agaggauauu ucaaaguucg   1740
cggagaaaga uaacaucgug cugggcgaag gggguauuac cuugucgggg ggccagcggg   1800
cuagaaucuc gcuggccaga gccguguaua aggacgccga ccuguaucuc cuggacuccc   1860
ccuucggaua ccuggacguc cugaccgaaa aggagaucuu cgaaucgugc gugugcaagc   1920
ugauggcuaa caagacucgc auccucguga ccuccaaaau ggagcaccug aagaaggcag   1980
acaagauucu gauucugcau gagggguccu ccuacuuuua cggcaccuuc ucggaguugc   2040
agaacuugca gcccgacuuc ucaucgaagc ugauggguug cgacagcuuc gaccaguucu   2100
ccgccgaaag aaggaacucg auccugacgg aaaccuugca ccgcuucucu uuggaaggcg   2160
acgccccugu gucauggacc gagacuaaga agcagagcuu caagcagacc ggggaauucg   2220
gcgaaaagag gaagaacagc aucuugaacc ccauuaacuc cauccgcaag uucucaaucg   2280
ugcaaaagac gccacugcag augaacggca uugaggagga cuccgacgaa ccccuugaga   2340
ggcgccuguc ccuggugccg gacagcgagc agggagaagc cauccugccu cggauuuccg   2400
ugaucuccac ugguccgacg cuccaagccc ggcggcggca guccgugcug aaccugauga   2460
cccacagcgu gaaccagggc caaaacauuc accgcaagac uaccgcaucc acccggaaag   2520
```

```
uguccuggc accucaagcg aaucuuaccg agcucgacau cuacucccgg agacugucgc   2580
aggaaaccgg gcucgaaauu uccgaagaaa ucaacgagga ggaucugaaa gagugcuucu   2640
ucgacgauau ggagucgaua cccgccguga cgacuuggaa cacuuaucug cgguacauca   2700
cugugcacaa gucauugauc uucgugcuga uuuggugccu ggugauuuuc cuggccgagg   2760
ucgcggccuc acugguggug cucuggcugu ugggaaacac gccucugcaa gacaagggaa   2820
acuccacgca cucgagaaac aacagcuaug ccgugauuau cacuuccacc uccucuuauu   2880
acguguucua caucuacguc ggaguggcgg auacccugcu cgcgaugggu uucuucagag   2940
gacugccgcu gguccacacc uugaucaccg ucagcaagau ucuucaccac aagauguugc   3000
auagcgugcu gcaggccccc auguccaccc ucaacacucu gaaggccgga ggcauucuga   3060
acagauucuc caaggacauc gcuauccugg acgaucuccu gccgcuuacc aucuuugacu   3120
ucauccagcu gcugcugauc gugauuggag caaucgcagu gguggcggug cugcagccuu   3180
acauuuucgu ggccacugug ccggucauug uggcguucau caugcugcgg gccuacuucc   3240
uccaaaccag ccagcagcug aagcaacugg aauccgaggg acgauccccc aucuucacuc   3300
accuugugac gucguugaag ggacugugga cccuccgggc uuucggacgg cagcccuacu   3360
ucgaaacccu cuuccacaag gcccugaacc uccacaccgc caauugguuc cuguaccugu   3420
ccacccugcg gugguuccag augcgcaucg agaugauuuu cgucaucuuc uucaucgcgg   3480
ucacauucau cagcauccug acuaccggag agggagaggg acgggucgga auaauccuga   3540
cccucgccau gaacauuaug agcacccugc agugggcagu gaacagcucg aucgacgugg   3600
acagccugau gcgaagcguc agccgcgugu ucaaguucau cgacaugccu acugagggaa   3660
aacccacuaa guccacuaag cccuacaaaa auggccagcu gagcaagguc augaucaucg   3720
aaaacuccca cgugaagaag gacgauauuu ggcccuccgg aggucaaaug accgugaagg   3780
accugaccgc aaaguacacc gagggaggaa acgccauucu cgaaaacauc agcuucucca   3840
uuucgccggg acagcggguc ggccuucucg ggcggaccgg uuccgggaag ucaacucugc   3900
ugucggcuuu ccuccggcug cugaauaccg agggggaaau ccaaauugac ggcgugucuu   3960
gggauuccau uacucugcag caguggcgga aggccuucgg cgugaucccc cagaaggugu   4020
ucaucuucuc ggguaccuuc cggaagaacc uggauccuua cgagcagugg agcgaccaag   4080
aaaucuggaa ggucgccgac gaggucggcc ugcgcuccgu gauugaacaa uuuccuggaa   4140
agcuggacuu cgugcucguc gacgggggau guguccuguc gcacggacau aagcagcuca   4200
ugugccucgc acgguccgug cucuccaagg ccaagauucu gcugcuggac gaaccuucgg   4260
cccaccugga uccggucacc uaccagauca ucaggaggac ccugaagcag gccuuugccg   4320
auugcaccgu gauucucugc gagcaccgca ucgaggccau gcuggagugc cagcaguucc   4380
uggucaucga ggagaacaag guccgccaau acgacuccau ucaaaagcuc cucaacgagc   4440
ggucgcuguu cagacaagcu auuucaccgu ccgauagagu gaagcucuuc ccgcaucgga   4500
acagcucaaa gugcaaaucg aagccgcaga ucgcagccuu gaaggaagag acugaggaag   4560
aggugcagga cacccggcuu uaagggugcc aucccuguga ccccuccca gugccucucc    4620
uggcccugga aguugccacu ccagugccca ccagccuugu ccuaauaaaa uuaaguugca   4680
ucaaagcu                                                            4688
```

<210> SEQ ID NO 9
<211> LENGTH: 874
<212> TYPE: PRT
<213> ORGANISM: Unknown

<220> FEATURE:
<223> OTHER INFORMATION: bacterial

<400> SEQUENCE: 9

```
Met Gln Asp Leu His Ala Ile Gln Leu Gln Leu Glu Glu Glu Met Phe
1               5                   10                  15

Asn Gly Gly Ile Arg Arg Phe Glu Ala Asp Gln Gln Arg Gln Ile Ala
            20                  25                  30

Ala Gly Ser Glu Ser Asp Thr Ala Trp Asn Arg Arg Leu Leu Ser Glu
        35                  40                  45

Leu Ile Ala Pro Met Ala Glu Gly Ile Gln Ala Tyr Lys Glu Glu Tyr
    50                  55                  60

Glu Gly Lys Lys Gly Arg Ala Pro Arg Ala Leu Ala Phe Leu Gln Cys
65                  70                  75                  80

Val Glu Asn Glu Val Ala Ala Tyr Ile Thr Met Lys Val Val Met Asp
                85                  90                  95

Met Leu Asn Thr Asp Ala Thr Leu Gln Ala Ile Ala Met Ser Val Ala
            100                 105                 110

Glu Arg Ile Glu Asp Gln Val Arg Phe Ser Lys Leu Glu Gly His Ala
        115                 120                 125

Ala Lys Tyr Phe Glu Lys Val Lys Lys Ser Leu Lys Ala Ser Arg Thr
    130                 135                 140

Lys Ser Tyr Arg His Ala His Asn Val Ala Val Val Ala Glu Lys Ser
145                 150                 155                 160

Val Ala Glu Lys Asp Ala Asp Phe Asp Arg Trp Glu Ala Trp Pro Lys
                165                 170                 175

Glu Thr Gln Leu Gln Ile Gly Thr Thr Leu Leu Glu Ile Leu Glu Gly
            180                 185                 190

Ser Val Phe Tyr Asn Gly Glu Pro Val Phe Met Arg Ala Met Arg Thr
        195                 200                 205

Tyr Gly Gly Lys Thr Ile Tyr Tyr Leu Gln Thr Ser Glu Ser Val Gly
    210                 215                 220

Gln Trp Ile Ser Ala Phe Lys Glu His Val Ala Gln Leu Ser Pro Ala
225                 230                 235                 240

Tyr Ala Pro Cys Val Ile Pro Pro Arg Pro Trp Arg Thr Pro Phe Asn
                245                 250                 255

Gly Gly Phe His Thr Glu Lys Val Ala Ser Arg Ile Arg Leu Val Lys
            260                 265                 270

Gly Asn Arg Glu His Val Arg Lys Leu Thr Gln Lys Gln Met Pro Lys
        275                 280                 285

Val Tyr Lys Ala Ile Asn Ala Leu Gln Asn Thr Gln Trp Gln Ile Asn
    290                 295                 300

Lys Asp Val Leu Ala Val Ile Glu Glu Val Ile Arg Leu Asp Leu Gly
305                 310                 315                 320

Tyr Gly Val Pro Ser Phe Lys Pro Leu Ile Asp Lys Glu Asn Lys Pro
                325                 330                 335

Ala Asn Pro Val Pro Val Glu Phe Gln His Leu Arg Gly Arg Glu Leu
            340                 345                 350

Lys Glu Met Leu Ser Pro Glu Gln Trp Gln Gln Phe Ile Asn Trp Lys
        355                 360                 365

Gly Glu Cys Ala Arg Leu Tyr Thr Ala Glu Thr Lys Arg Gly Ser Lys
    370                 375                 380

Ser Ala Ala Val Val Arg Met Val Gly Gln Ala Arg Lys Tyr Ser Ala
385                 390                 395                 400
```

-continued

```
Phe Glu Ser Ile Tyr Phe Val Tyr Ala Met Asp Ser Arg Ser Arg Val
                405                 410                 415

Tyr Val Gln Ser Ser Thr Leu Ser Pro Gln Ser Asn Asp Leu Gly Lys
            420                 425                 430

Ala Leu Leu Arg Phe Thr Glu Gly Arg Pro Val Asn Gly Val Glu Ala
        435                 440                 445

Leu Lys Trp Phe Cys Ile Asn Gly Ala Asn Leu Trp Gly Trp Asp Lys
    450                 455                 460

Lys Thr Phe Asp Val Arg Val Ser Asn Val Leu Asp Glu Glu Phe Gln
465                 470                 475                 480

Asp Met Cys Arg Asp Ile Ala Ala Asp Pro Leu Thr Phe Thr Gln Trp
                485                 490                 495

Ala Lys Ala Asp Ala Pro Tyr Glu Phe Leu Ala Trp Cys Phe Glu Tyr
            500                 505                 510

Ala Gln Tyr Leu Asp Leu Val Asp Glu Gly Arg Ala Asp Glu Phe Arg
        515                 520                 525

Thr His Leu Pro Val His Gln Asp Gly Ser Cys Ser Gly Ile Gln His
    530                 535                 540

Tyr Ser Ala Met Leu Arg Asp Glu Val Gly Ala Lys Ala Val Asn Leu
545                 550                 555                 560

Lys Pro Ser Asp Ala Pro Gln Asp Ile Tyr Gly Ala Val Ala Gln Val
                565                 570                 575

Val Ile Lys Lys Asn Ala Leu Tyr Met Asp Ala Asp Asp Ala Thr Thr
            580                 585                 590

Phe Thr Ser Gly Ser Val Thr Leu Ser Gly Thr Glu Leu Arg Ala Met
        595                 600                 605

Ala Ser Ala Trp Asp Ser Ile Gly Ile Thr Arg Ser Leu Thr Lys Lys
    610                 615                 620

Pro Val Met Thr Leu Pro Tyr Gly Ser Thr Arg Leu Thr Cys Arg Glu
625                 630                 635                 640

Ser Val Ile Asp Tyr Ile Val Asp Leu Glu Glu Lys Glu Ala Gln Lys
                645                 650                 655

Ala Val Ala Glu Gly Arg Thr Ala Asn Lys Val His Pro Phe Glu Asp
            660                 665                 670

Asp Arg Gln Asp Tyr Leu Thr Pro Gly Ala Ala Tyr Asn Tyr Met Thr
        675                 680                 685

Ala Leu Ile Trp Pro Ser Ile Ser Glu Val Val Lys Ala Pro Ile Val
    690                 695                 700

Ala Met Lys Met Ile Arg Gln Leu Ala Arg Phe Ala Ala Lys Arg Asn
705                 710                 715                 720

Glu Gly Leu Met Tyr Thr Leu Pro Thr Gly Phe Ile Leu Glu Gln Lys
                725                 730                 735

Ile Met Ala Thr Glu Met Leu Arg Val Arg Thr Cys Leu Met Gly Asp
            740                 745                 750

Ile Lys Met Ser Leu Gln Val Glu Thr Asp Ile Val Asp Glu Ala Ala
        755                 760                 765

Met Met Gly Ala Ala Ala Pro Asn Phe Val His Gly His Asp Ala Ser
    770                 775                 780

His Leu Ile Leu Thr Val Cys Glu Leu Val Asp Lys Gly Val Thr Ser
785                 790                 795                 800

Ile Ala Val Ile His Asp Ser Phe Gly Thr His Ala Asp Asn Thr Leu
                805                 810                 815
```

-continued

```
Thr Leu Arg Val Ala Leu Lys Gly Gln Met Val Ala Met Tyr Ile Asp
            820                 825                 830

Gly Asn Ala Leu Gln Lys Leu Leu Glu Glu His Glu Val Arg Trp Met
        835                 840                 845

Val Asp Thr Gly Ile Glu Val Pro Glu Gln Gly Glu Phe Asp Leu Asn
    850                 855                 860

Glu Ile Met Asp Ser Glu Tyr Val Phe Ala
865                 870


<210> SEQ ID NO 10
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 10

atttaggtga cactatag                                                   18


<210> SEQ ID NO 11
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 11

atttagggga cactatagaa gag                                             23


<210> SEQ ID NO 12
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 12

atttagggga cactatagaa gg                                              22


<210> SEQ ID NO 13
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 13

atttagggga cactatagaa ggg                                             23


<210> SEQ ID NO 14
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 14

atttaggtga cactatagaa                                                 20


<210> SEQ ID NO 15
<211> LENGTH: 22
<212> TYPE: DNA
<213> ORGANISM: Artificial Sequence
<220> FEATURE:
<223> OTHER INFORMATION: Synthetic polynucleotide
```

<400> SEQUENCE: 15
atttaggtga cactatagaa ga 22

<210> SEQ ID NO 16
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 16
atttaggtga cactatagaa gag 23

<210> SEQ ID NO 17
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 17
atttaggtga cactatagaa gg 22

<210> SEQ ID NO 18
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 18
atttaggtga cactatagaa ggg 23

<210> SEQ ID NO 19
<211> LENGTH: 23
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (22)..(22)
<223> OTHER INFORMATION: n is a, c, g, or t

<400> SEQUENCE: 19
atttaggtga cactatagaa gng 23

<210> SEQ ID NO 20
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 20
catacgattt aggtgacact atag 24

<210> SEQ ID NO 21
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 21

-continued

```
atgcagagga gcccactgga gaaagcctcc gtggtgagta aactcttttt tagttggacc     60
agacccatcc tgcgaaaagg atacaggcag cgcctcgagt tgtcagatat ctaccagatt    120
ccttctgtgg actcagctga caatttgagt gagaagctgg agcgggagtg ggatagagag    180
ctggcgagca aaaaaaaccc caagcttatc aatgctctgc gccgctgctt tttctggagg    240
ttcatgtttt atgggatctt cctgtacctg ggggaggtca ccaaagctgt tcagccgctc    300
cttcttggcc gcatcatcgc cagctatgac cctgataata aagaagaaag gtctattgct    360
atttatctgg gaattggcct ctgcttgctc ttcatcgtcc gcacccttct gctgcaccct    420
gccatttttg gccttcacca catcggcatg caaatgagaa ttgccatgtt ctccctcatt    480
tacaaaaaga ccctgaaact ttcctcaaga gtgttagata aaatatccat tggtcagctg    540
gtcagcctgc tgtccaacaa tcttaacaaa tttgatgaag gcttggcgct ggcccacttc    600
gtgtggattg cacctctgca ggtggccctg ttgatgggac ttatatggga gctgcttcaa    660
gcctctgctt tctgtgggct gggctttttg attgtactgg cactttttca ggctgggctc    720
ggaagaatga tgatgaaata cagagatcag cgggccggga agatatcaga gcgacttgtg    780
atcaccagtg aaatgattga aaatattcag agcgtgaaag cctactgctg ggaagaagcc    840
atggagaaga tgattgagaa cctgaggcag acagagctca agctcactcg gaaggctgct    900
tatgttcgct atttcaacag cagcgccttc ttcttcagtg gcttctttgt tgtcttcctg    960
tctgttctgc catatgcact gataaaaggc attattttac gaaagatctt caccaccatc   1020
agtttttgca tcgttctcag gatggccgtc acaagacagt tcccctgggc tgtgcagacc   1080
tggtacgatt ccttgggggc catcaacaag attcaagatt tcttgcaaaa acaagaatat   1140
aaaactttag aatacaacct caccaccact gaagtggtca tggaaaatgt gacagccttt   1200
tgggaggagg gttttggaga attgttcgag aaggcaaagc agaataacaa caacaggaag   1260
acgagcaatg ggacgactc tctcttcttc agcaactttt cactgctcgg gacccctgtg    1320
ttgaaagata taaacttcaa gatcgagagg ggccagctct tggctgtggc aggctccact   1380
ggagctggta aaacatctct tctcatggtg atcatggggg aactggagcc ttccgaagga   1440
aaaatcaagc acagtgggag aatctcattc tgcagccagt ttcctggat catgcccggc    1500
accattaagg aaaacatcat atttggagtg tcctatgatg agtaccgcta ccggtcagtc   1560
atcaaagcct gtcagttgga ggaggacatc tccaagtttg cagagaaaga caacattgtg   1620
cttggagagg ggggtatcac tctttctgga ggacaaagag ccaggatctc tttggcccgg   1680
gcagtctaca aggatgcaga cctctacttg ttggacagtc ccttcggcta cctcgacgtg   1740
ctgactgaaa aagaaatttt tgaaagctgt gtgtgcaaac tgatggcaaa caagaccagg   1800
attcttgtca ccagcaagat ggaacatctg aagaaagcgg acaaaattct gattctgcat   1860
gaagggagct cctacttcta tggaacattt agcgagcttc agaacctaca gccagacttc   1920
tcctccaaat taatgggctg tgactccttc gaccagttct ctgcagaaag aagaaactct   1980
atactcacag agaccctcca ccgcttctcc cttgagggag atgccccagt ttcttggaca   2040
gaaaccaaga agcagtcctt taagcagact ggcgagtttg gtgaaaagag gaaaaattca   2100
attctcaatc caattaacag tattcgcaag ttcagcattg tccagaagac acccctccag   2160
atgaatggca tcgaagaaga tagtgacgag ccgctggaga gacggctgag tctggtgcca   2220
gattcagaac agggggaggc catcctgccc cggatcagcg tcatttccac aggcccccaca   2280
ttacaagcac ggcgccggca gagtgtttta aatctcatga cccattcagt gaaccagggc   2340
caaaatatcc acaggaagac tacagcttct acccggaaag tgtctctggc ccctcaggcc   2400
```

-continued

```
aatctgaccg agctggacat ctacagcagg aggctctccc aggaaacagg gctggaaata   2460
tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
tttgtcctca tctggtgcct ggttattttc ctcgctgagg tggcggccag tcttgttgtg   2640
ctctggctgc tgggcaacac tcctctccag gacaagggca atagtactca cagcagaaat   2700
aattcttatg ccgtcatcat tacaagcacc tccagctact acgtgttcta catctatgtg   2760
ggcgtggctg acaccctcct ggccatgggt ttcttccggg gcctgccttt ggtgcacacc   2820
ctcatcacag tgtcaaaaat tctgcaccat aaaatgcttc attctgtcct gcaggcaccc   2880
atgagcactt tgaacacatt gaaggctggc ggcatcctca acagattttc taaagatatt   2940
gctatcctgg atgatctcct ccccctgaca atctttgact ttatccagct tctgctgatc   3000
gtgattggag ccatagcagt ggttgctgtc ctgcagccct acatttttgt ggccaccgtg   3060
cccgtgattg ttgcctttat tatgctcaga gcttacttcc tgcaaacttc tcaacagctc   3120
aaacagctag aatctgaggg ccggagcccc atttttaccc acctggtgac ttccctgaag   3180
ggactgtgga ctctgagagc attcgggcga cagccttact ttgagacact gttccacaag   3240
gccctgaact tgcacactgc caactggttt ctttacctga gcacactccg ctggttccag   3300
atgcggatag agatgatctt cgtcatcttt tttatagctg taaccttcat ttctatcctt   3360
acaacaggag aaggagaggg cagggtggga atcatcctca cgctggctat gaacataatg   3420
tccaccttgc agtgggccgt gaattccagt atagatgtgg attctctaat gaggagtgtc   3480
tcccgggtgt ttaaattcat tgatatgcct actgagggga aacccaccaa gtcaacaaaa   3540
ccttataaga atggacagct gagcaaggtg atgataattg agaacagcca cgtgaagaag   3600
gatgacattt ggcccagcgg gggccagatg actgtgaagg acctgacggc caagtacacc   3660
gaaggtggaa atgccatttt ggaaaacatc agcttctcaa tctctcctgg gcagagagtt   3720
ggattgctgg gtcgcacggg cagcggcaaa tcaaccctgc tcagtgcctt ccttcggctc   3780
ctgaatacag aaggcgaaat ccaaattgac ggggtgagct gggacagcat caccctgcag   3840
cagtggagaa aagcatttgg ggtcattcca cagaaagttt tcatcttctc tggcactttc   3900
agaaagaacc tggaccccta tgagcagtgg agcgaccagg agatctggaa ggttgcagat   3960
gaagttggcc tgcggagtgt gatagaacaa tttcctggca agctggattt tgtgctggta   4020
gatggaggct gcgtgctgtc ccacggccac aaacagctga tgtgcctcgc ccgctccgtt   4080
ctttcaaagg ccaaaatctt gcttttggat gagcccagtg ctcacctcga cccagtgacc   4140
tatcagataa tccgcaggac cttaaagcaa gcttttgccg actgcaccgt catactgtgt   4200
gagcaccgga ttgaagcaat gctggaatgc cagcagtttc tggtgatcga ggagaataag   4260
gtccggcagt acgacagcat ccagaagttg ttgaatgagc gcagcctttt ccgccaggcc   4320
atctccccat ctgacagagt caagctgttt ccacatagga actcctctaa gtgcaagtcc   4380
aagccccaga tcgctgccct caaggaggaa actgaggaag aggtgcagga tacccgcctg   4440
tga                                                                 4443
```

<210> SEQ ID NO 22
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 22

```
atgcagagga gcccactgga gaaagcctcc gtggtgagta aactcttttt tagttggacc     60
agacccatcc tgcgaaaagg atacaggcag cgcctcgagt tgtctgatat ctaccagatt    120
ccttctgtgg actcagctga caatttgagt gagaagctgg agcgggagtg ggatagagag    180
ctggcgagca aaaaaaaccc caagcttatc aatgctctgc gccgctgctt tttctggagg    240
ttcatgtttt atgggatctt cctgtacctg gggggaggtca ccaaagctgt tcagccgctc    300
cttcttggcc gcatcatcgc cagctatgac cctgataata aagaagaaag gtctattgct    360
atttatctgg gaattggcct ctgcttgctc ttcatcgtcc gcacccttct gctgcaccct    420
gccatttttg gccttcacca catcggcatg caaatgagaa ttgccatgtt ctccctcatt    480
tacaaaaaga ccctgaaact ttcctcaaga gtgttagata aaatatccat tggtcagctg    540
gtcagcctgc tgtccaacaa tcttaacaaa tttgatgaag gcttggcgct ggcccacttc    600
gtgtggattg cacctctgca ggtggccctg ttgatgggac ttatatggga gctgcttcaa    660
gcctctgctt tctgtgggct gggctttttg attgtactgg cactttttca ggctgggctc    720
ggaagaatga tgatgaaata cagagatcag cgggccggga agatttcaga gcgacttgtg    780
atcaccagtg aaatgattga aaatattcag agcgtgaaag cctactgctg ggaagaagcc    840
atggagaaga tgattgagaa cctgaggcag acagagctca agctcactcg gaaggctgct    900
tatgttcgct atttcaacag cagcgccttc ttcttcagtg gcttctttgt tgtcttcctg    960
tctgttctgc catatgcact gataaaaggc attattttac gaaagatctt caccaccatc   1020
agtttttgca tcgttctcag gatggccgtc acaagacagt tcccctgggc tgtgcagacc   1080
tggtacgatt ccttgggggc catcaacaag attcaagatt tcttgcaaaa acaagaatat   1140
aaaactttag aatacaacct caccaccact gaagtggtca tggaaaatgt gacagccttt   1200
tgggaggagg gttttggaga attgttcgag aaggcaaagc agaataacaa caacaggaag   1260
acgagcaatg gggacgactc tctcttcttc agcaactttt cactgctcgg gacccctgtg   1320
ttgaaagata taaacttcaa gatcgagagg ggccagctct tggctgtggc aggctccact   1380
ggagctggta aaacatctct tctcatggtg atcatggggg aactggagcc ttccgaagga   1440
aaaatcaagc acagtgggag aatctcattc tgcagccagt tttcctggat catgcccggc   1500
accattaagg aaaacatcat atttggagtg tcctatgatg agtaccgcta ccggtcagtc   1560
atcaaagcct gtcagttgga ggaggacatc tccaagtttg cagagaaaga caacattgtg   1620
cttggagagg ggggtatcac tctttctgga ggacaaagag ccaggatctc tttggcccgg   1680
gcagtctaca aggatgcaga cctctacttg ttggacagtc ccttcggcta cctcgacgtg   1740
ctgactgaaa aagaaatttt tgaaagctgt gtgtgcaaac tgatggcaaa caagaccagg   1800
attcttgtca ccagcaagat ggaacatctg aagaaagcgg acaaaattct gattctgcat   1860
gaagggagct cctacttcta tggaacattt agcgagcttc agaacctaca gccagacttc   1920
tcctccaaat taatgggctg tgactccttc gaccagttct ctgcagaaag aagaaactct   1980
atactcacag agaccctcca ccgcttctcc cttgagggag atgccccagt ttcttggaca   2040
gaaaccaaga agcagtcctt taagcagact ggcgagtttg gtgaaaagag gaaaaattca   2100
attctcaatc caattaacag tattcgcaag ttcagcattg tccagaagac acccctccag   2160
atgaatggca tcgaagaaga tagtgacgag ccgctggaga gacggctgag tctggtgcca   2220
gattcagaac agggggaggc catcctgccc cggatcagcg tcatttccac aggccccaca   2280
ttacaagcac ggcgccggca gagtgtttta aatctcatga cccattcagt gaaccagggc   2340
```

```
caaaatatcc acaggaagac tacagcttct acccggaaag tgtctctggc ccctcaggcc   2400
aatctgaccg agctggacat ctacagcagg aggctctccc aggaaacagg gctggaaata   2460
tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
tttgtcctca tctggtgcct ggttattttc ctcgctgagg tggcggccag tcttgttgtg   2640
ctctggctgc tgggcaacac tcctctccag gacaagggca atagtactca cagcagaaat   2700
aattcttatg ccgtcatcat tacaagcacc tccagctact acgtgttcta catctatgtg   2760
ggcgtggctg acaccctcct ggccatgggt ttcttccggg gcctgccttt ggtgcacacc   2820
ctcatcacag tgtcaaaaat tctgcaccat aaaatgcttc attctgtcct gcaggcaccc   2880
atgagcactt tgaacacatt gaaggctggc ggcatcctca acagattttc taaagatatt   2940
gctatcctgg atgatctcct cccccctgaca atctttgact ttatccagct tctgctgatc   3000
gtgattggag ccatagcagt ggttgctgtc ctgcagccct acatttttgt ggccaccgtg   3060
cccgtgattg ttgcctttat tatgctcaga gcttacttcc tgcaaacttc tcaacagctc   3120
aaacagctag aatctgaggg ccggagcccc atttttaccc acctggtgac ttccctgaag   3180
ggactgtgga ctctgagagc attcgggcga cagccttact ttgagacact gttccacaag   3240
gccctgaact tgcacactgc caactggttt ctttacctga gcacactccg ctggttccag   3300
atgcggatag agatgatctt cgtcatcttt tttatagctg taaccttcat ttctatcctt   3360
acaacaggag aaggagaggg cagggtggga atcatcctca cgctggctat gaacataatg   3420
tccaccttgc agtgggccgt gaattccagt atagatgtgg attctctaat gaggagtgtc   3480
tcccgggtgt ttaaattcat tgatatgcct actgagggga aacccaccaa gtcaacaaaa   3540
ccttataaga atggacagct gagcaaggtg atgataattg agaacagcca cgtgaagaag   3600
gatgacattt ggcccagcgg gggccagatg actgtgaagg acctgacggc caagtacacc   3660
gaaggtggaa atgccatttt ggaaaacatc agcttctcaa tctctcctgg gcagagagtt   3720
ggattgctgg gtcgcacggg cagcggcaaa tcaaccctgc tcagtgcctt ccttcggctc   3780
ctgaatacag aaggcgaaat ccaaattgac ggggtgagct gggacagcat caccctgcag   3840
cagtggagaa aagcatttgg ggtcattcca cagaaagttt tcatcttctc tggcactttc   3900
agaaagaacc tggaccccta tgagcagtgg agcgaccagg agatctggaa ggttgcagat   3960
gaagttggcc tgcggagtgt gatagaacaa tttcctggca agctggattt tgtgctggta   4020
gatggaggct gcgtgctgtc ccacggccac aaacagctga tgtgcctcgc ccgctccgtt   4080
ctttcaaagg ccaaaatctt gcttttggat gagcccagtg ctcaccttga cccagtgacc   4140
tatcagataa tccgcaggac cttaaagcaa gcttttgccg actgcaccgt catactgtgt   4200
gagcaccgga ttgaagcaat gctggaatgc cagcagtttc tggtgatcga ggagaataag   4260
gtccggcagt acgacagcat ccagaagttg ttgaatgagc gcagcctttt ccgccaggcc   4320
atctccccat ctgacagagt caagctgttt ccacatagga actcctctaa gtgcaagtcc   4380
aagccccaga tcgctgccct caaggaggaa actgaggaag aggtgcagga tacccgcctg   4440
tga                                                                 4443
```

<210> SEQ ID NO 23
<211> LENGTH: 4443
<212> TYPE: DNA
<213> ORGANISM: Artificial Sequence
<220> FEATURE:

<223> OTHER INFORMATION: Synthetic polynucleotide

<400> SEQUENCE: 23

```
atgcagagga gcccactgga gaaagcctcc gtggtgagta aactcttttt tagttggacc     60
agacccatcc tgcgaaaagg atacaggcag cgcctcgagt tgtcagatat ctaccagatt    120
ccttctgtgg actcagctga caatttgagt gagaagctgg agcgggagtg ggatagagag    180
ctggcgagca aaaaaaaccc caagcttatc aatgctctgc gccgctgctt tttctggagg    240
ttcatgtttt atgggatctt cctgtacctg gggaggtca ccaaagctgt tcagccgctc     300
cttcttggcc gcatcatcgc cagctatgac cctgataata aagaagaaag gtctattgct    360
atttatctgg gaattggcct ctgcttgctc ttcatcgtcc gcacccttct gctgcaccct    420
gccatttttg gccttcacca catcggcatg caaatgagaa ttgccatgtt ctccctcatt    480
tacaaaaaga ccctgaaact ttcctcaaga gtgttagata aaatatccat tggtcagctg    540
gtcagcctgc tgtccaacaa tcttaacaaa tttgatgaag gcttggcgct ggcccacttc    600
gtgtggattg cacctctgca ggtggccctg ttgatgggac ttatatggga gctgcttcaa    660
gcctctgctt tctgtgggct gggcttttg attgtactgg cactttttca ggctgggctc     720
ggaagaatga tgatgaaata cagagatcag cgggccggga agatatcaga gcgacttgtg    780
atcaccagtg aaatgattga aaatattcag agcgtgaaag cctactgctg ggaagaagcc    840
atggagaaga tgattgagaa cctgaggcag acagagctca agctcactcg gaaggctgct    900
tatgttcgct atttcaacag cagcgccttc ttcttcagtg gcttctttgt tgtcttcctg    960
tctgttctgc catatgcact gataaaaggc attattttac gaaagatctt caccaccatc   1020
agtttttgca tcgttctcag gatggccgtc acaagacagt tcccctgggc tgtgcagacc   1080
tggtacgatt ccttgggggc catcaacaag attcaagatt tcttgcaaaa acaagaatat   1140
aaaactttag aatacaacct caccaccact gaagtggtca tggaaaatgt gacagccttt   1200
tgggaggagg gttttggaga attgttcgag aaggcaaagc agaataacaa caacaggaag   1260
acgagcaatg ggacgactc tctcttcttc agcaactttt cactgctcgg gacccctgtg    1320
ttgaaagata taaacttcaa gatcgagagg ggccagctct tggctgtggc aggctccact   1380
ggagctggta aaacatctct tctcatggtg atcatggggg aactggagcc ttccgaagga   1440
aaaatcaagc acagtgggag aatctcattc tgcagccagt ttcctggat catgcccggc    1500
accattaagg aaaacatcat atttggagtg tcctatgatg agtaccgcta ccggtcagtc   1560
atcaaagcct gtcagttgga ggaggacatc tccaagtttg cagagaaaga caacattgtg   1620
cttggagagg ggggtatcac tctttctgga ggacaaagag ccaggatctc tttggcccgg   1680
gcagtctaca aggatgcaga cctctacttg ttggacagtc ccttcggcta cctcgacgtg   1740
ctgactgaaa aagaaatttt tgaaagctgt gtgtgcaaac tgatggcaaa caagaccagg   1800
attcttgtca ccagcaagat ggaacatctg aagaaagcgg acaaaattct gattctgcat   1860
gaagggagct cctacttcta tggaacattt agcgagcttc agaacctaca gccagacttc   1920
tcctccaaat taatgggctg tgactccttc gaccagttct ctgcagaaag aagaaactct   1980
atactcacag agaccctcca ccgcttctcc cttgagggag atgccccagt ttcttggaca   2040
gaaaccaaga agcagtcctt taagcagact ggcgagtttg gtgaaaagag gaaaaattca   2100
attctcaatc caattaacag tattcgcaag ttcagcattg tccagaagac accctccag    2160
atgaatggca tcgaagaaga tagtgacgag ccgctggaga gacggctgag tctggtgcca   2220
gattcagaac agggggaggc catcctgccc cggatcagcg tcatttccac aggccccaca   2280
```

ttacaagcac ggcgccggca gagtgtttta aatctcatga cccattcagt gaaccagggc 2340
caaaatatcc acaggaagac tacagcttct acccggaaag tgtctctggc ccctcaggcc 2400
aatctgaccg agctggacat ctacagcagg aggctctccc aggaaacagg gcttgaaata 2460
tctgaagaga ttaatgaaga ggatcttaaa gagtgcttct ttgatgacat ggagagcatc 2520
cccgcggtga ccacatggaa cacctacctt agatatatta ctgtccacaa gagcctcata 2580
tttgtcctca tctggtgcct ggttattttc ctcgctgagg tggcggccag tcttgttgtg 2640
ctctggctgc tgggcaacac tcctctccag gacaagggca atagtacaca cagcagaaat 2700
aattcttatg ccgtcatcat tacaagcacc tccagctact acgtgttcta catctatgtg 2760
ggcgtggctg acaccctcct ggccatgggt ttcttccggg gcctgccttt ggtgcacacc 2820
ctcatcacag tgtcaaaaat tctgcaccat aaaatgcttc attctgtcct gcaggcaccc 2880
atgagcactt tgaacacatt gaaggctggc ggcatcctca acagattttc taaagatatt 2940
gctatcctgg atgatctcct ccccctgaca atctttgact ttatccagct tctgctgatc 3000
gtgattggag ccatagcagt ggttgctgtc ctgcagccct acatttttgt ggccaccgtg 3060
cccgtgattg ttgcctttat tatgctcaga gcttacttcc tgcaaacttc tcaacagctc 3120
aaacagctag aatctgaggg ccggagcccc atttttaccc acctggtgac ttccctgaag 3180
ggactgtgga ctctgagagc attcgggcga cagccttact ttgagacact gttccacaag 3240
gccctgaact tgcacactgc caactggttt ctttacctga gcacactccg ctggttccag 3300
atgcggatag agatgatctt cgtcatcttt tttatagctg taaccttcat ttctatcctt 3360
acaacaggag aaggagaggg cagggtggga atcatcctca cgctggctat gaacataatg 3420
tccaccttgc agtgggccgt gaattccagt atagatgtgg attctctaat gaggagtgtc 3480
tcccgggtgt ttaaattcat tgatatgcct actgagggga aacccaccaa gtcaacaaaa 3540
ccttataaga atggacagct gagcaaggtg atgataattg agaacagcca cgtgaagaag 3600
gatgacattt ggcccagcgg gggccagatg actgtgaagg acctgacggc caagtacacc 3660
gaaggtggaa atgccatttt ggaaaacatc agcttctcaa tctctcctgg gcagagagtt 3720
ggattgctgg gtcgcacggg cagcggcaaa tcaaccctgc tcagtgcctt ccttcggctc 3780
ctgaatacag aaggcgaaat ccaaattgac ggggtgagct gggacagcat caccctgcag 3840
cagtggagaa aagcatttgg ggtcattcca cagaaagttt tcatcttctc tggcactttc 3900
agaaagaacc tggaccccta tgagcagtgg agcgaccagg agatctggaa ggttgcagat 3960
gaagttggcc tgcggagtgt gatagaacaa tttcctggca agctggattt tgtgctggta 4020
gatggaggct gcgtgctgtc ccacggccac aaacagctga tgtgcctcgc ccgctccgtt 4080
ctttcaaagg ccaaaatctt gcttttggat gagcccagtg ctcaccttga cccagtgacc 4140
tatcagataa tccgcaggac cttaaagcaa gcttttgccg actgcaccgt catactgtgt 4200
gagcaccgga ttgaagcaat gctggaatgc cagcagtttc tggtgatcga ggagaataag 4260
gtccggcagt acgacagcat ccagaagttg ttgaatgagc gcagcctttt ccgccaggcc 4320
atctccccat ctgacagagt caagctgttt ccacatagga actcctctaa gtgcaagtcc 4380
aagccccaga tcgctgccct caaggaggaa actgaggaag aggtgcagga tacccgcctg 4440
tga 4443

<210> SEQ ID NO 24
<211> LENGTH: 4443
<212> TYPE: DNA

-continued

<213> ORGANISM: Artificial Sequence
<220> FEATURE:
<223> OTHER INFORMATION: Synthetic polynucleotide

<400> SEQUENCE: 24
atgcagagga gcccactgga gaaagcctcc gtggtgagta aactcttttt tagttggacc 60
agacccatcc tgcgaaaagg atacaggcag cgcctcgagt tgtcagatat ctaccagatt 120
ccttctgtgg actcagctga caatttgagt gagaagctgg agcgggagtg ggatagagag 180
ctggcgagca aaaaaaaccc caagcttatc aatgctctgc gccgctgctt tttctggagg 240
ttcatgtttt atgggatctt cctgtacctg ggggaggtca ccaaagctgt tcagccgctc 300
cttcttggcc gcatcatcgc cagctatgac cctgataata aagaagaaag gtctattgct 360
atttatctgg gaattggcct ctgcttgctc ttcatcgtcc gcacccttct gctgcaccct 420
gccatttttg gccttcacca catcggcatg caaatgagaa ttgccatgtt ctccctcatt 480
tacaaaaaga ccctgaaact ttcctcaaga gtgttagata aaatatccat tggtcagctg 540
gtcagcctgc tgtccaacaa tcttaacaaa tttgatgaag gcttggcgct ggcccacttc 600
gtgtggattg cacctctgca ggtggccctg ttgatgggac ttatatggga gctgcttcaa 660
gcctctgctt tctgtgggct gggctttttg attgtactgg cactttttca ggctgggctc 720
ggaagaatga tgatgaaata cagagatcag cgggccggga agatatcaga gcgacttgtg 780
atcaccagtg aaatgattga aaatattcag agcgtgaaag cctactgctg ggaagaagcc 840
atggagaaga tgattgagaa cctgaggcag acagagctca agctcactcg gaaggctgct 900
tatgttcgct atttcaacag cagcgccttc ttcttcagtg gcttctttgt tgtcttcctg 960
tctgttctgc catatgcact gataaaaggc attattttac gaaagatctt caccaccatc 1020
agtttttgca tcgttctcag gatggccgtc acaagacagt tcccctgggc tgtgcagacc 1080
tggtacgatt ccttgggggc catcaacaag attcaagatt tcttgcaaaa acaagaatat 1140
aaaactttag aatacaacct caccaccact gaagtggtca tggaaaatgt gacagccttt 1200
tgggaggagg gttttggaga attgttcgag aaggcaaagc agaataacaa caacaggaag 1260
acgagcaatg ggacgactc tctcttcttc agcaactttt cactgctcgg gacccctgtg 1320
ttgaaagata taaacttcaa gatcgagagg ggccagctct tggctgtggc aggctccact 1380
ggagctggta aaacatctct tctcatggtg atcatggggg aactggagcc ttccgaagga 1440
aaaatcaagc acagtgggag aatctcattc tgcagccagt tttcctggat catgcccggc 1500
accattaagg aaaacatcat atttggagtg tcctatgatg agtaccgcta ccggtcagtc 1560
atcaaagcct gtcagttgga ggaggacatc tccaagtttg cagagaaaga caacattgtg 1620
cttggagagg ggggtatcac tctttctgga ggacaaagag ccaggatctc tttggcccgg 1680
gcagtctaca aggatgcaga cctctacttg ttggacagtc ccttcggcta cctcgacgtg 1740
ctgactgaaa aagaaatttt tgaaagctgt gtgtgcaaac tgatggcaaa caagaccagg 1800
attcttgtca ccagcaagat ggaacatctg aagaaagcgg acaaaattct gattctgcat 1860
gaagggagct cctacttcta tggaacattt agcgagcttc agaacctaca gccagacttc 1920
tcctccaaat taatgggctg tgactccttc gaccagttct ctgcagaaag aagaaactct 1980
atactcacag agaccctcca ccgcttctcc cttgagggag atgccccagt ttcttggaca 2040
gaaaccaaga agcagtcctt taagcagact ggcgagtttg gtgaaaagag gaaaaattca 2100
attctcaatc caattaacag tattcgcaag ttcagcattg tccagaagac acccctccag 2160
atgaatggca tcgaagaaga tagtgacgag ccgctggaga gacggctgag tctggtgcca 2220

-continued gattcagaac aggggaggc catcctgccc cggatcagcg tcatttccac aggccccaca 2280
ttacaagcac ggcgccggca gagtgtttta aatctcatga cccattcagt gaaccagggc 2340
caaaatatcc acaggaagac tacagcttct acccggaaag tgtctctggc ccctcaggcc 2400
aatctgaccg agctggacat ctacagcagg aggctctccc aggaaacagg gctggaaata 2460
tctgaagaga ttaatgaaga ggatcttaaa gagtgcttct ttgatgacat ggagagcatc 2520
cccgcggtga ccacatggaa cacctacctt agatatatta ctgtccacaa gagcctcata 2580
tttgtcctca tctggtgcct ggttatttc ctcgctgagg tggcggccag tcttgttgtg 2640
ctctggctgc tgggcaacac tcctctccag gacaagggca atagtactca cagcagaaat 2700
aattcttatg ccgtcatcat tacaagcacc tccagctact acgtgttcta catctatgtg 2760
ggcgtggctg acaccctcct ggccatgggt ttcttccggg gcctgccttt ggtgcacacc 2820
ctcatcacag tgtcaaaaat tctgcaccat aaaatgcttc attctgtcct gcaggcaccc 2880
atgagcactt tgaacacatt gaaggctggc ggcatcctca acagattttc taaagatatt 2940
gctatcctgg atgatctcct cccccctgaca atctttgact ttatccagct tctgctgatc 3000
gtgattggag ccatagcagt ggttgctgtc ctgcagccct acatttttgt ggccaccgtg 3060
cccgtgattg ttgcctttat tatgctcaga gcttacttcc tgcaaacttc tcaacagctc 3120
aaacagctag aatctgaggg ccggagcccc atttttaccc acctggtgac ttccctgaag 3180
ggactgtgga ctctgagagc attcgggcga cagccttact ttgagacact gttccacaag 3240
gccctgaact tgcacactgc caactggttt ctttacctga gcacactccg ctggttccag 3300
atgcggatag agatgatctt cgtcatcttt tttatagctg taaccttcat ttctatcctt 3360
acaacaggag aaggagaggg cagggtggga atcatcctca cgctggctat gaacataatg 3420
tccaccttgc agtgggccgt gaattccagt atagatgtgg attctctaat gaggagtgtc 3480
tcccgggtgt ttaaattcat tgatatgcca actgagggga aacccaccaa gtcaacaaaa 3540
ccttataaga atggacagct gagcaaggtg atgataattg agaacagcca cgtgaagaag 3600
gatgacattt ggcccagcgg gggccagatg actgtgaagg acctgacggc caagtacacc 3660
gaaggtggaa atgccatttt ggaaaacatc agcttctcaa tctctcctgg gcagagagtt 3720
ggattgctgg gtcgcacggg cagcggcaaa tcaaccctgc tcagtgcctt ccttcggctc 3780
ctgaatacag aaggcgaaat ccaaattgac ggggtgagct gggacagcat caccctgcag 3840
cagtggagaa aagcatttgg ggtcattcca cagaaagttt tcatcttctc tggcactttc 3900
agaaagaacc tggaccccta tgagcagtgg agcgaccagg agatctggaa ggttgcagat 3960
gaagttggcc tgcggagtgt gatagaacaa tttcctggca agctggattt tgtgctggta 4020
gatggaggct gcgtgctgtc ccacggccac aaacagctga tgtgcctcgc ccgctccgtt 4080
ctttcaaagg ccaaaatctt gcttttggat gagcccagtg ctcacctcga cccagtgacc 4140
tatcagataa tccgcaggac cttaaagcaa gcttttgccg actgcaccgt catactgtgt 4200
gagcaccgga ttgaagcaat gctggaatgc cagcagtttc tggtgatcga ggagaataag 4260
gtccggcagt acgacagcat ccagaagttg ttgaatgagc gcagcctttt ccgccaggcc 4320
atctccccat ctgacagagt caagctgttt ccacatagga actcctctaa gtgcaagtcc 4380
aagccccaga tcgctgccct caaggaggaa actgaggaag aggtgcagga tacccgcctg 4440
tga 4443

<210> SEQ ID NO 25

<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 25
atgcagagga gcccactgga gaaagcctcc gtggtgagta aactcttttt tagttggacc 60
agacccatcc tgcgaaaagg atacaggcag cgcctcgagt tgtcagatat ctaccagatt 120
ccttctgtgg actcagctga caatttgagt gagaagctgg agcgggagtg ggatagagag 180
ctggcgagca aaaaaaaccc caagcttatc aatgctctgc gccgctgctt tttctggagg 240
ttcatgtttt atgggatctt cctgtacctg ggggaggtca ccaaagctgt tcagccgctc 300
cttcttggcc gcatcatcgc cagctatgac cctgataata aagaagaaag gtctattgct 360
atttatctgg gaattggcct ctgcttgctc ttcatcgtcc gcacccttct gctgcaccct 420
gccatttttg gccttcacca catcggcatg caaatgagaa ttgccatgtt ctccctcatt 480
tacaaaaaga ccctgaaact ttcctcaaga gtgttagata aaatatccat tggtcagctg 540
gtcagcctgc tgtccaacaa tcttaacaaa tttgatgaag gcttggcgct ggcccacttc 600
gtgtggattg cacctctgca ggtggccctg ttgatgggac ttatatggga gctgcttcaa 660
gcctctgctt tctgtgggct gggctttttg attgtactgg cactttttca ggctgggctc 720
ggaagaatga tgatgaaata cagagatcag cgggccggga agatatcaga gcgacttgtg 780
atcaccagtg aaatgattga aaatattcag agcgtgaaag cctactgctg ggaagaagcc 840
atggagaaga tgattgagaa cctgaggcag acagagctca agctcactcg gaaggctgct 900
tatgttcgct atttcaacag cagcgccttc ttcttcagtg gcttctttgt tgtcttcctg 960
tctgttctgc catatgcact gataaaaggc attattttac gaaagatctt caccaccatc 1020
agtttttgca tcgttctcag gatggccgtc acaagacagt tcccctgggc tgtgcagacc 1080
tggtacgatt ccttgggggc catcaacaag attcaagatt tcttgcaaaa acaagaatat 1140
aaaactttag aatacaacct caccaccact gaagtggtca tggaaaatgt gacagccttt 1200
tgggaggagg gttttggaga attgttcgag aaggcaaagc agaataacaa caacaggaag 1260
acgagcaatg gggacgactc tctcttcttc agcaactttt cactgctcgg gacccctgtg 1320
ttgaaagata taaacttcaa gatcgagagg ggccagctct tggctgtggc aggctccact 1380
ggagctggta aaacatctct tctcatggtg atcatggggg aactggagcc ttccgaagga 1440
aaaatcaagc acagtgggag aatctcattc tgcagccagt ttcctggat catgcccggc 1500 accattaagg aaaacatcat atttggagtg tcctatgatg agtaccgcta ccggtcagtc 1560
atcaaagcct gtcagttgga ggaggacatc tccaagtttg cagagaaaga caacattgtg 1620
cttggagagg ggggtatcac tctttctgga ggacaaagag ccaggatctc tttggcccgg 1680
gcagtctaca aggatgcaga cctctacttg ttggacagtc ccttcggcta cctcgacgtg 1740
ctgactgaaa aagaaatttt tgaaagctgt gtgtgcaaac tgatggcaaa caagaccagg 1800
attcttgtca ccagcaagat ggaacatctg aagaaagcgg acaaaattct gattctgcat 1860
gaagggagct cctacttcta tggaacattt agcgagcttc agaacctaca gccagacttc 1920
tcctccaaat taatgggctg tgactccttc gaccagttct ctgcagaaag aagaaactct 1980
atactcacag agaccctcca ccgcttctcc cttgagggag atgccccagt ttcttggaca 2040
gaaaccaaga agcagtcctt taagcagact ggcgagtttg gtgaaaagag gaaaaattca 2100
attctcaatc ctattaacag tattcgcaag ttcagcattg tccagaagac acccctccag 2160

-continued

```
atgaatggca tcgaagaaga tagtgacgag ccgctggaga gacggctgag tctggtgcca   2220
gattcagaac agggggaggc catcctgccc cggatcagcg tcatttccac aggcccccaca   2280
ttacaagcac ggcgccggca gagtgtttta aatctcatga cccattcagt gaaccagggc   2340
caaaatatcc acaggaagac tacagcttct acccggaaag tgtctctggc ccctcaggcc   2400
aatctgaccg agctggacat ctacagcagg aggctctccc aggaaacagg gcttgaaata   2460
tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
tttgtcctca tctggtgcct ggttatttttc ctcgctgagg tggcggccag tcttgttgtg   2640
ctctggctgc tgggcaacac tcctctccag gacaagggca atagtactca cagcagaaat   2700
aattcttatg ccgtcatcat tacaagcacc tccagctact acgtgttcta catctatgtg   2760
ggcgtggctg acaccctcct ggccatgggt ttcttccggg gcctgccttt ggtgcacacc   2820
ctcatcacag tgtcaaaaat tctgcaccat aaaatgcttc attctgtcct gcaggcaccc   2880
atgagcactt tgaacacatt gaaggctggc ggcatcctca acagattttc taaagatatt   2940
gctatcctgg atgatctcct ccccctgaca atctttgact ttatccagct tctgctgatc   3000
gtgattggag ccatagcagt ggttgctgtc ctgcagccct acatttttgt ggccaccgtg   3060
cccgtgattg ttgcctttat tatgctcaga gcttacttcc tgcaaacttc tcaacagctc   3120
aaacagctag aatctgaggg ccggagcccc atttttaccc acctggtgac ttccctgaag   3180
ggactgtgga ctctgagagc attcgggcga cagccttact ttgagacact gttccacaag   3240
gccctgaact tgcacactgc caactggttt ctttacctga gcacactccg ctggttccag   3300
atgcggatag agatgatctt cgtcatcttt tttatagctg taaccttcat ttctatcctt   3360
acaacaggag aaggagaggg cagggtggga atcatcctca cgctggctat gaacataatg   3420
tccaccttgc agtgggccgt gaattccagt atagatgtgg attctctaat gaggagtgtc   3480
tcccgggtgt ttaaattcat tgatatgcct actgagggga aacccaccaa gtcaacaaaa   3540
ccttataaga atggacagct gagcaaggtg atgataattg agaacagcca cgtgaagaag   3600
gatgacattt ggcccagcgg gggccagatg actgtgaagg acctgacggc caagtacacc   3660
gaaggtggaa atgccatttt ggaaaacatc agcttctcaa tctctcctgg gcagagagtt   3720
ggattgctgg gtcgcacggg cagcggcaaa tcaaccctgc tcagtgcctt ccttcggctc   3780
ctgaatacag aaggcgaaat ccaaattgac ggggtgagct gggacagcat caccctgcag   3840
cagtggagaa aagcatttgg ggtcattcca cagaaagttt tcatcttctc tggcactttc   3900
agaaagaacc tggaccccta tgagcagtgg agcgaccagg agatctggaa ggttgcagat   3960
gaagttggcc tgcggagtgt gatagaacaa tttcctggca agctggattt tgtgctggta   4020
gatggaggct gcgtgctgtc ccacggccac aaacagctga tgtgcctcgc ccgctccgtt   4080
ctttcaaagg ccaaaatctt gcttttggat gagcccagtg ctcacctcga cccagtgacc   4140
tatcagataa tccgcaggac cttaaagcaa gcttttgccg actgcaccgt catactgtgt   4200
gagcaccgga ttgaagcaat gctggaatgc cagcagtttc tggtgatcga ggagaataag   4260
gtccggcagt acgacagcat ccagaagttg ttgaatgagc gcagcctttt ccgccaggcc   4320
atctccccat ctgacagagt caagctgttt ccacatagga actcctctaa gtgcaagtcc   4380
aagccccaga tcgctgccct caaggaggaa actgaggaag aggtgcagga tacccgcctg   4440
tga                                                                 4443
```

<210> SEQ ID NO 26
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 26
atgcagagga gcccactgga gaaagcctcc gtggtgagta aactcttttt tagttggacc 60
agacccatcc tgcgaaaagg atacaggcag cgcctcgagt tgtcagatat ctaccagatt 120
ccttctgtgg actcagctga caatttgagt gagaagctgg agcgggagtg ggatagagag 180
ctggcgagca aaaaaaaccc caagcttatc aatgctctgc gccgctgctt tttctggagg 240
ttcatgtttt atgggatctt cctgtacctg gggggaggtca ccaaagctgt tcagccgctc 300
cttcttggcc gcatcatcgc cagctatgac cctgataata aagaagaaag gtctattgct 360
atttatctgg gaattggcct ctgcttgctc ttcatcgtcc gcacccttct gctgcaccct 420
gccatttttg gccttcacca catcggcatg caaatgagaa ttgccatgtt ctccctcatt 480
tacaaaaaga ccctgaaact ttcctcaaga gtgttagata aaatatccat tggtcagctg 540
gtcagcctgc tgtccaacaa tcttaacaaa tttgatgaag gcttggcgct ggcccacttc 600
gtgtggattg cacctctgca ggtggccctg ttgatgggac ttatatggga gctgcttcaa 660
gcctctgctt tctgtgggct gggctttttg attgtactgg cactttttca ggctgggctc 720
ggaagaatga tgatgaaata cagagatcag cgggccggga agatttcaga gcgacttgtg 780
atcaccagtg aaatgattga aaatattcag agcgtgaaag cctactgctg ggaagaagcc 840
atggagaaga tgattgagaa cctgaggcag acagagctca agctcactcg gaaggctgct 900
tatgttcgct atttcaacag cagcgccttc ttcttcagtg gcttctttgt tgtcttcctg 960
tctgttctgc catatgcact gataaaaggc attattttac gaaagatctt caccaccatc 1020
agtttttgca tcgttctcag gatggccgtc acaagacagt tcccctgggc tgtgcagacc 1080
tggtacgatt ccttgggggc catcaacaag attcaagatt tcttgcaaaa acaagaatat 1140
aaaactttag aatacaacct caccaccact gaagtggtca tggaaaatgt gacagccttt 1200
tgggaggagg gttttggaga attgttcgag aaggcaaagc agaataacaa caacaggaag 1260
acgagcaatg ggacgactc tctcttcttc agcaactttt cactgctcgg gacccctgtg 1320
ttgaaagata taaacttcaa gatcgagagg ggccagctct tggctgtggc aggctccact 1380
ggagctggta aaacatctct tctcatggtg atcatggggg aactggagcc ttccgaagga 1440
aaaatcaagc acagtgggag aatctcattc tgcagccagt tttcctggat catgcccggc 1500
accattaagg aaaacatcat atttggagtg tcctatgatg agtaccgcta ccggtcagtc 1560
atcaaagcct gtcagttgga ggaggacatc tccaagtttg cagagaaaga caacattgtg 1620
cttggagagg ggggtatcac tctttctgga ggacaaagag ccaggatctc tttggcccgg 1680
gcagtctaca aggatgcaga cctctacttg ttggacagtc ccttcggcta cctcgacgtg 1740
ctgactgaaa aagaaatttt tgaaagctgt gtgtgcaaac tgatggcaaa caagaccagg 1800
attcttgtca ccagcaagat ggaacatctg aagaaagcgg acaaaattct gattctgcat 1860
gaagggagct cctacttcta tggaacattt agcgagcttc agaacctaca gccagacttc 1920
tcctccaaat taatgggctg tgactccttc gaccagttct ctgcagaaag aagaaactct 1980
atactcacag agaccctcca ccgcttctcc cttgagggag atgccccagt ttcttggaca 2040
gaaaccaaga agcagtcctt taagcagact ggcgagtttg gtgaaaagag gaaaaattca 2100

-continued

```
attctcaatc caattaacag tattcgcaag ttcagcattg tccagaagac acccctccag   2160
atgaatggca tcgaagaaga tagtgacgag ccgctggaga gacggctgag tctggtgcca   2220
gattcagaac agggggaggc catcctgccc cggatcagcg tcatttccac aggcccccaca   2280
ttacaagcac ggcgccggca gagtgtttta aatctcatga cccattcagt gaaccagggc   2340
caaaatatcc acaggaagac tacagcttct acccggaaag tgtctctggc ccctcaggcc   2400
aatctgaccg agctggacat ctacagcagg aggctctccc aggaaacagg gctggaaata   2460
tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
tttgtcctca tctggtgcct ggttattttc ctcgctgagg tggcggccag tcttgttgtg   2640
ctctggctgc tgggcaacac tcctctccag gacaagggca atagtactca cagcagaaat   2700
aattcttatg ccgtcatcat tacaagcacc tccagctact acgtgttcta catctatgtg   2760
ggcgtggctg acaccctcct ggccatgggt ttcttccggg gcctgccttt ggtgcacacc   2820
ctcatcacag tgtcaaaaat tctgcaccat aaaatgcttc attctgtcct gcaggcaccc   2880
atgagcactt tgaacacatt gaaggctggc ggcatcctca acagattttc taaagatatt   2940
gctatcctgg atgatctcct cccccctgaca atctttgact ttatccagct tctgctgatc   3000
gtgattggag ccatagcagt ggttgctgtc ctgcagccct acatttttgt ggccaccgtg   3060
cccgtgattg ttgcctttat tatgctcaga gcttacttcc tgcaaacttc tcaacagctc   3120
aaacagctag aatctgaggg ccggagcccc atttttaccc acctggtgac ttccctgaag   3180
ggactgtgga ctctgagagc attcgggcga cagccttact ttgagacact gttccacaag   3240
gccctgaact tgcacactgc caactggttt ctttacctga gcacactccg ctggttccag   3300
atgcggatag agatgatctt cgtcatcttt tttatagctg taaccttcat ttctatcctt   3360
acaacaggag aaggagaggg cagggtggga atcatcctca cgctggctat gaacataatg   3420
tccaccttgc agtgggccgt gaattccagt atagatgtgg attctctaat gaggagtgtc   3480
tcccgggtgt ttaaattcat tgatatgcca actgagggga aacccaccaa gtcaacaaaa   3540
ccttataaga atggacagct gagcaaggtg atgataattg agaacagcca cgtgaagaag   3600
gatgacattt ggcccagcgg gggccagatg actgtgaagg acctgacggc caagtacacc   3660
gaaggtggaa atgccatttt ggaaaacatc agcttctcaa tctctcctgg gcagagagtt   3720
ggattgctgg gtcgcacggg cagcggcaaa tcaaccctgc tcagtgcctt ccttcggctc   3780
ctgaatacag aaggcgaaat ccaaattgac ggggtgagct gggacagcat caccctgcag   3840
cagtggagaa aagcatttgg ggtcattcca cagaaagttt tcatcttctc tggcactttc   3900
agaaagaacc tggaccccta tgagcagtgg agcgaccagg agatctggaa ggttgcagat   3960
gaagttggcc tgcggagtgt gatagaacaa tttcctggca agctggattt tgtgctggta   4020
gatggaggct gcgtgctgtc ccacggccac aaacagctga tgtgcctcgc ccgctccgtt   4080
ctttcaaagg ccaaaatctt gcttttggat gagcccagtg ctcacctcga cccagtgacc   4140
tatcagataa tccgcaggac cttaaagcaa gcttttgccg actgcaccgt catactgtgt   4200
gagcaccgga ttgaagcaat gctggaatgc cagcagtttc tggtgatcga ggagaataag   4260
gtccggcagt acgacagcat ccagaagttg ttgaatgagc gcagcctttt ccgccaggcc   4320
atctccccat ctgacagagt caagctgttt ccacatagga actcctctaa gtgcaagtcc   4380
aagccccaga tcgctgccct caaggaggaa actgaggaag aggtgcagga tacccgcctg   4440
```

tga 4443

<210> SEQ ID NO 27
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 27
atgcagagga gcccactgga gaaagcctcc gtggtgagta aactcttttt tagttggacc 60
agacccatcc tgcgaaaagg atacaggcag cgcctcgagt tgtctgatat ctaccagatt 120
ccttctgtgg actcagctga caatttgagt gagaagctgg agcgggagtg ggatagagag 180
ctggcgagca aaaaaaaccc caagcttatc aatgctctgc gccgctgctt tttctggagg 240
ttcatgtttt atgggatctt cctgtacctg gggggaggtca ccaaagctgt tcagccgctc 300
cttcttggcc gcatcatcgc cagctatgac cctgataata aagaagaaag gtctattgct 360
atttatctgg gaattggcct ctgcttgctc ttcatcgtcc gcacccttct gctgcaccct 420
gccatttttg gccttcacca catcggcatg caaatgagaa ttgccatgtt ctccctcatt 480
tacaaaaaga ccctgaaact ttcctcaaga gtgttagata aaatatccat tggtcagctg 540
gtcagcctgc tgtccaacaa tcttaacaaa tttgatgaag gcttggcgct ggcccacttc 600
gtgtggattg cacctctgca ggtggccctg ttgatgggac ttatatggga gctgcttcaa 660
gcctctgctt tctgtgggct gggctttttg attgtactgg cactttttca ggctgggctc 720
ggaagaatga tgatgaaata cagagatcag cgggccggga agatatcaga gcgacttgtg 780
atcaccagtg aaatgattga aaatattcag agcgtgaaag cctactgctg ggaagaagcc 840
atggagaaga tgattgagaa cctgaggcag acagagctca agctcactcg gaaggctgct 900
tatgttcgct atttcaacag cagcgccttc ttcttcagtg gcttctttgt tgtcttcctg 960
tctgttctgc catatgcact gataaaaggc attattttac gaaagatctt caccaccatc 1020
agtttttgca tcgttctcag gatggccgtc acaagacagt tcccctgggc tgtgcagacc 1080
tggtacgatt ccttgggggc catcaacaag attcaagatt tcttgcaaaa acaagaatat 1140
aaaactttag aatacaacct caccaccact gaagtggtca tggaaaatgt gacagccttt 1200
tgggaggagg gttttggaga attgttcgag aaggcaaagc agaataacaa caacaggaag 1260
acgagcaatg gggacgactc tctcttcttc agcaactttt cactgctcgg gacccctgtg 1320
ttgaaagata taaacttcaa gatcgagagg ggccagctct tggctgtggc aggctccact 1380
ggagctggta aaacatctct tctcatggtg atcatggggg aactggagcc ttccgaagga 1440
aaaatcaagc acagtgggag aatctcattc tgcagccagt tttcctggat catgcccggc 1500
accattaagg aaaacatcat atttggagtg tcctatgatg agtaccgcta ccggtccgtc 1560
atcaaagcct gtcagttgga ggaggacatc tccaagtttg cagagaaaga caacattgtg 1620
cttggagagg ggggtatcac tctttctgga ggacaaagag ccaggatctc tttggcccgg 1680
gcagtctaca aggatgcaga cctctacttg ttggacagtc ccttcggcta cctcgacgtg 1740
ctgactgaaa aagaaatttt tgaaagctgt gtgtgcaaac tgatggcaaa caagaccagg 1800
attcttgtca ccagcaagat ggaacatctg aagaaagcgg acaaaattct gattctgcat 1860
gaagggagct cctacttcta tggaacattt agcgagcttc agaacctaca gccagacttc 1920
tcctccaaat taatgggctg tgactccttc gaccagttct ctgcagaaag aagaaactct 1980
atactcacag agaccctcca ccgcttctcc cttgagggag atgccccagt ttcttggaca 2040

-continued

```
gaaaccaaga agcagtcctt taagcagact ggcgagtttg gtgaaaagag gaaaaattca   2100
attctcaatc caattaacag tattcgcaag ttcagcattg tccagaagac acccctccag   2160
atgaatggca tcgaagaaga tagtgacgag ccgctggaga gacggctgag tctggtgcca   2220
gattcagaac agggggaggc catcctgccc cggatcagcg tcatttccac aggccccaca   2280
ttacaagcac ggcgccggca gagtgtttta aatctcatga cccattcagt gaaccagggc   2340
caaaatatcc acaggaagac tacagcttct acccggaaag tgtctctggc ccctcaggcc   2400
aatctgaccg agctggacat ctacagcagg aggctctccc aggaaacagg gcttgaaata   2460
tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
tttgtcctca tctggtgcct ggttatttc ctcgctgagg tggcggccag tcttgttgtg   2640
ctctggctgc tgggcaacac tcctctccag gacaagggca atagtactca cagcagaaat   2700
aattcttatg ccgtcatcat tacaagcacc tccagctact acgtgttcta catctatgtg   2760
ggcgtggctg acaccctcct ggccatgggt ttcttccggg gcctgccttt ggtgcacacc   2820
ctcatcacag tgtcaaaaat tctgcaccat aaaatgcttc attctgtcct gcaggcaccc   2880
atgagcactt tgaacacatt gaaggctggc ggcatcctca acagattttc taaagatatt   2940
gctatcctgg atgatctcct ccccctgaca atctttgact ttatccagct tctgctgatc   3000
gtgattggag ccatagcagt ggttgctgtc ctgcagccct acatttttgt ggccaccgtg   3060
cccgtgattg ttgcctttat tatgctcaga gcttacttcc tgcaaacttc tcaacagctc   3120
aaacagctag aatctgaggg ccggagcccc atttttaccc acctggtgac ttccctgaag   3180
ggactgtgga ctctgagagc attcgggcga cagccttact ttgagacact gttccacaag   3240
gccctgaact tgcacactgc caactggttt ctttacctga gcacactccg ctggttccag   3300
atgcggatag agatgatctt cgtcatcttt tttatagctg taaccttcat ttctatcctt   3360
acaacaggag aaggagaggg cagggtggga atcatcctca cgctggctat gaacataatg   3420
tccaccttgc agtgggccgt gaattccagt atagatgtgg attctctaat gaggagtgtc   3480
tcccgggtgt ttaaattcat tgatatgcct actgagggga aacccaccaa gtcaacaaag   3540
ccttataaga atggacagct gagcaaggtg atgataattg agaacagcca cgtgaagaag   3600
gatgacattt ggcccagcgg ggccagatg actgtgaagg acctgacggc caagtacacc   3660
gaaggtggaa atgccatttt ggaaaacatc agcttctcaa tctctcctgg gcagagagtt   3720
ggattgctgg gtcgcacggg cagcggcaaa tcaaccctgc tcagtgcctt ccttcggctc   3780
ctgaatacag aaggcgaaat ccaaattgac ggggtgagct gggacagcat caccctgcag   3840
cagtggagaa aagcatttgg ggtcattcca cagaaagttt tcatcttctc tggcactttc   3900
agaaagaacc tggaccccta tgagcagtgg agcgaccagg agatctggaa ggttgcagat   3960
gaagttggcc tgcggagtgt gatagaacaa tttcctggca agctggattt tgtgctggta   4020
gatggaggct gcgtgctgtc ccacggccac aaacagctga tgtgcctcgc ccgctccgtt   4080
ctttcaaagg ccaaaatctt gcttttggat gagcccagtg ctcacctcga cccagtgacc   4140
tatcagataa tccgcaggac cttaaagcaa gcttttgccg actgcaccgt catactgtgt   4200
gagcaccgga ttgaagcaat gctggaatgc cagcagtttc tggtgatcga ggagaataag   4260
gtccggcagt acgacagcat ccagaagttg ttgaatgagc gcagcctttt ccgccaggcc   4320
atctccccat ctgacagagt caagctgttt ccacatagga actcctctaa gtgcaagtcc   4380
```

-continued

```
aagccccaga tcgctgccct caaggaggaa actgaggaag aggtgcagga tacccgcctg   4440

tga                                                                 4443


<210> SEQ ID NO 28
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 28

atgcagagga gcccactgga gaaagcctcc gtggtgagta aactcttttt tagttggacc     60

agacccatcc tgcgaaaagg atacaggcag cgcctcgagt tgtcagatat ctaccagatt    120

ccttctgtgg actcagctga caatttgagt gagaagctgg agcgggagtg ggatagagag    180

ctggcgagca aaaaaaaccc caagcttatc aatgctctgc gccgctgctt tttctggagg    240

ttcatgtttt atgggatctt cctgtacctg gggaggtca ccaaagctgt tcagccgctc     300

cttcttggcc gcatcatcgc cagctatgac cctgataata aagaagaaag gtctattgct    360

atttatctgg gaattggcct ctgcttgctc ttcatcgtcc gcacccttct gctgcaccct    420

gccatttttg gccttcacca catcggcatg caaatgagaa ttgccatgtt ctccctcatt    480

tacaaaaaga ccctgaaact ttcctcaaga gtgttagata aaatatccat tggtcagctg    540

gtcagcctgc tgtccaacaa tcttaacaaa tttgatgaag gcttggcgct ggcccacttc    600

gtgtggattg cacctctgca ggtggccctg ttgatgggac ttatatggga gctgcttcaa    660

gcctctgctt tctgtgggct gggctttttg attgtactgg cactttttca ggctgggctc    720

ggaagaatga tgatgaaata cagagatcag cgggccggga agatatcaga gcgacttgtg    780

atcaccagtg aaatgattga aaatattcag agcgtgaaag cctactgctg ggaagaagcc    840

atggagaaga tgattgagaa cctgaggcag acagagctca agctcactcg gaaggctgct    900

tatgttcgct atttcaacag cagcgccttc ttcttcagtg gcttctttgt tgtcttcctg    960

tctgttctgc catatgcact gataaaaggc attattttac gaaagatctt caccaccatc   1020

agtttttgca tcgttctcag gatggccgtc acaagacagt tcccctgggc tgtgcagacc   1080

tggtacgatt ccttgggggc catcaacaag attcaagatt tcttgcaaaa acaagaatat   1140

aaaactttag aatacaacct caccaccact gaagtggtca tggaaaatgt gacagccttt   1200

tgggaggagg gttttggaga attgttcgag aaggcaaagc agaataacaa caacaggaag   1260

acgagcaatg gggacgactc tctcttcttc agcaactttt cactgctcgg gacccctgtg   1320

ttgaaagata taaacttcaa gatcgagagg ggccagctct tggctgtggc aggctccact   1380

ggagctggta aaacatctct tctcatggtg atcatggggg aactggagcc ttccgaagga   1440

aaaatcaagc acagtgggag aatctcattc tgcagccagt tttcctggat catgcccggc   1500

accattaagg aaaacatcat atttggagtg tcctatgatg agtaccgcta ccggtcagtc   1560

atcaaagcct gtcagttgga ggaggacatc tccaagtttg cagagaaaga caacattgtg   1620

cttggagagg ggggtatcac tctttctgga ggacaaagag ccaggatctc tttggcccgg   1680

gcagtctaca aggatgcaga cctctacttg ttggacagtc ccttcggcta cctcgacgtg   1740

ctgactgaaa aagaaatttt tgaaagctgt gtgtgcaaac tgatggcaaa caagaccagg   1800

attcttgtca ccagcaagat ggaacatctg aagaaagcgg acaaaattct gattctgcat   1860

gaagggagct cctacttcta tggaacattt agcgagcttc agaacctaca gccagacttc   1920

tcctccaaat taatgggctg tgactccttc gaccagttct ctgcagaaag aagaaactct   1980
```

-continued

```
atactcacag agaccctcca ccgcttctcc cttgagggag atgccccagt ttcttggaca   2040
gaaaccaaga agcagtcctt taagcagact ggcgagtttg gtgaaaagag gaaaaattca   2100
attctcaatc ctattaacag tattcgcaag ttcagcattg tccagaagac acccctccag   2160
atgaatggca tcgaagaaga tagtgacgag ccgctggaga gacggctgag tctggtgcca   2220
gattcagaac agggggaggc catcctgccc cggatcagcg tcatttccac aggccccaca   2280
ttacaagcac ggcgccggca gagtgtttta aatctcatga cccattcagt gaaccagggc   2340
caaaatatcc acaggaagac tacagcttct acccggaaag tgtctctggc ccctcaggcc   2400
aatctgaccg agctggacat ctacagcagg aggctctccc aggaaacagg gcttgaaata   2460
tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
tttgtcctca tctggtgcct ggttattttc ctcgctgagg tggcggccag tcttgttgtg   2640
ctctggctgc tgggcaacac tcctctccag gacaagggca atagtacaca cagcagaaat   2700
aattcttatg ccgtcatcat tacaagcacc tccagctact acgtgttcta catctatgtg   2760
ggcgtggctg acaccctcct ggccatgggt ttcttccggg gcctgccttt ggtgcacacc   2820
ctcatcacag tgtcaaaaat tctgcaccat aaaatgcttc attctgtcct gcaggcaccc   2880
atgagcactt tgaacacatt gaaggctggc ggcatcctca acagattttc taaagatatt   2940
gctatcctgg atgatctcct ccccctgaca atctttgact ttatccagct tctgctgatc   3000
gtgattggag ccatagcagt ggttgctgtc ctgcagccct acatttttgt ggccaccgtg   3060
cccgtgattg ttgcctttat tatgctcaga gcttacttcc tgcaaacttc tcaacagctc   3120
aaacagctag aatctgaggg ccggagcccc atttttaccc acctggtgac ttccctgaag   3180
ggactgtgga ctctgagagc attcgggcga cagccttact ttgagacact gttccacaag   3240
gccctgaact tgcacactgc caactggttt ctttacctga gcacactccg ctggttccag   3300
atgcggatag agatgatctt cgtcatcttt tttatagctg taaccttcat ttctatcctt   3360
acaacaggag aaggagaggg cagggtggga atcatcctca cgctggctat gaacataatg   3420
tccaccttgc agtgggccgt gaattccagt atagatgtgg attctctaat gaggagtgtc   3480
tcccgggtgt ttaaattcat tgatatgcct actgagggga aacccaccaa gtcaacaaaa   3540
ccttataaga atggacagct gagcaaggtg atgataattg agaacagcca cgtgaagaag   3600
gatgacattt ggcccagcgg gggccagatg actgtgaagg acctgacggc caagtacacc   3660
gaaggtggaa atgccatttt ggaaaacatc agcttctcaa tctctcctgg gcagagagtt   3720
ggattgctgg gtcgcacggg cagcggcaaa tcaaccctgc tcagtgcctt ccttcggctc   3780
ctgaatacag aaggcgaaat ccaaattgac ggggtgagct gggacagcat caccctgcag   3840
cagtggagaa aagcatttgg ggtcattcca cagaaagttt tcatcttctc tggcactttc   3900
agaaagaacc tggaccccta tgagcagtgg agcgaccagg agatctggaa ggttgcagat   3960
gaagttggcc tgcggagtgt gatagaacaa tttcctggca agctggattt tgtgctggta   4020
gatggaggct gcgtgctgtc ccacggccac aaacagctga tgtgcctcgc ccgctccgtt   4080
ctttcaaagg ccaaaatctt gcttttggat gagcccagtg ctcacctcga cccagtgacc   4140
tatcagataa tccgcaggac cttaaagcaa gcttttgccg actgcaccgt catactgtgt   4200
gagcaccgga ttgaagcaat gctggaatgc cagcagtttc tggtgatcga ggagaataag   4260
gtccggcagt acgacagcat ccagaagttg ttgaatgagc gcagcctttt ccgccaggcc   4320
```

```
atctccccat ctgacagagt caagctgttt ccacatagga actcctctaa gtgcaagtcc   4380

aagccccaga tcgctgccct caaggaggaa actgaggaag aggtgcagga tacccgcctg   4440

tga                                                                  4443
```

<210> SEQ ID NO 29
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 29

```
atgcagagga gcccactgga gaaagcctcc gtggtgagta aactcttttt tagttggacc     60

agacccatcc tgcgaaaagg atacaggcag cgcctcgagt tgtcagatat ctaccagatt    120

ccttctgtgg actcagctga caatttgagt gagaagctgg agcgggagtg ggatagagag    180

ctggcgagca aaaaaaaccc caagcttatc aatgctctgc gccgctgctt tttctggagg    240

ttcatgtttt atgggatctt cctgtacctg gggggaggtca ccaaagctgt tcagccgctc   300

cttcttggcc gcatcatcgc cagctatgac cctgataata aagaagaaag gtctattgct    360

atttatctgg gaattggcct ctgcttgctc ttcatcgtcc gcacccttct gctgcaccct    420

gccatttttg gccttcacca catcggcatg caaatgagaa ttgccatgtt ctccctcatt    480

tacaaaaaga ccctgaaact ttcctcaaga gtgttagata aaatatccat tggtcagctg    540

gtcagcctgc tgtccaacaa tcttaacaaa tttgatgaag gcttggcgct ggcccacttc    600

gtgtggattg cacctctgca ggtggccctg ttgatgggac ttatatggga gctgcttcaa    660

gcctctgctt tctgtgggct gggcttttg attgtactgg cactttttca ggctgggctc     720

ggaagaatga tgatgaaata cagagatcag cgggccggga agatatcaga gcgacttgtg    780

atcaccagtg aaatgattga aaatattcag agcgtgaaag cctactgctg ggaagaagcc    840

atggagaaga tgattgagaa cctgaggcag acagagctca agctcactcg gaaggctgct    900

tatgttcgct atttcaacag cagcgccttc ttcttcagtg gcttctttgt tgtcttcctg    960

tctgttctgc catatgcact gataaaaggc attattttac gaaagatctt caccaccatc   1020

agtttttgca tcgttctcag gatggccgtc acaagacagt tcccctgggc tgtgcagacc   1080

tggtacgatt ccttgggggc catcaacaag attcaagatt tcttgcaaaa acaagaatat   1140

aaaactttag aatacaacct caccaccact gaagtggtca tggaaaatgt gacagccttt   1200

tgggaggagg gttttggaga attgttcgag aaggcaaagc agaataacaa caacaggaag   1260

acgagcaatg ggacgactc tctcttcttc agcaactttt cactgctcgg gacccctgtg    1320

ttgaaagata taaacttcaa gatcgagagg ggccagctct tggctgtggc aggctccact   1380

ggagctggta aaacatctct tctcatggtg atcatggggg aactggagcc ttccgaagga   1440

aaaatcaagc acagtgggag aatctcattc tgcagccagt tttcctggat catgcccggc   1500

accattaagg aaaacatcat atttggagtg tcctatgatg agtaccgcta ccggtccgtc   1560

atcaaagcct gtcagttgga ggaggacatc tccaagtttg cagagaaaga caacattgtg   1620

cttggagagg ggggtatcac tctttctgga ggacaaagag ccaggatctc tttggcccgg   1680

gcagtctaca aggatgcaga cctctacttg ttggacagtc ccttcggcta cctcgacgtg   1740

ctgactgaaa aagaaatttt tgaaagctgt gtgtgcaaac tgatggcaaa caagaccagg   1800

attcttgtca ccagcaagat ggaacatctg aagaaagcgg acaaaattct gattctgcat   1860

gaagggagct cctacttcta tggaacattt agcgagcttc agaacctaca gccagacttc   1920
```

-continued

```
tcctccaaat taatgggctg tgactccttc gaccagttct ctgcagaaag aagaaactct   1980
atactcacag agaccctcca ccgcttctcc cttgagggag atgccccagt ttcttggaca   2040
gaaaccaaga agcagtcctt taagcagact ggcgagtttg gtgaaaagag gaaaaattca   2100
attctcaatc caattaacag tattcgcaag ttcagcattg tccagaagac acccctccag   2160
atgaatggca tcgaagaaga tagtgacgag ccgctggaga gacggctgag tctggtgcca   2220
gattcagaac agggggaggc catcctgccc cggatcagcg tcatttccac aggccccaca   2280
ttacaagcac ggcgccggca gagtgtttta aatctcatga cccattcagt gaaccagggc   2340
caaaatatcc acaggaagac tacagcttct acccggaaag tgtctctggc ccctcaggcc   2400
aatctgaccg agctggacat ctacagcagg aggctctccc aggaaacagg gctggaaata   2460
tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
tttgtcctca tctggtgcct ggttatttc ctcgctgagg tggcggccag tcttgttgtg    2640
ctctggctgc tgggcaacac tcctctccag gacaagggca atagtactca cagcagaaat   2700
aattcttatg ccgtcatcat tacaagcacc tccagctact acgtgttcta catctatgtg   2760
ggcgtggctg acaccctcct ggccatgggt ttcttccggg gcctgccttt ggtgcacacc   2820
ctcatcacag tgtcaaaaat tctgcaccat aaaatgcttc attctgtcct gcaggcaccc   2880
atgagcactt tgaacacatt gaaggctggc ggcatcctca acagattttc taaagatatt   2940
gctatcctgg atgatctcct ccccctgaca atctttgact ttatccagct tctgctgatc   3000
gtgattggag ccatagcagt ggttgctgtc ctgcagccct acatttttgt ggccaccgtg   3060
cccgtgattg ttgcctttat tatgctcaga gcttacttcc tgcaaacttc tcaacagctc   3120
aaacagctag agtctgaggg ccggagcccc atttttaccc acctggtgac ttccctgaag   3180
ggactgtgga ctctgagagc attcgggcga cagccttact ttgagacact gttccacaag   3240
gccctgaact tgcacactgc caactggttt ctttacctga gcacactccg ctggttccag   3300
atgcggatag agatgatctt cgtcatcttt tttatagctg taaccttcat ttctatcctt   3360
acaacaggag aaggagaggg cagggtggga atcatcctca cgctggctat gaacataatg   3420
tccaccttgc agtgggccgt gaattccagt atagatgtgg attctctaat gaggagtgtc   3480
tcccgggtgt ttaaattcat tgatatgcct actgagggga aacccaccaa gtcaacaaaa   3540
ccttataaga atggacagct gagcaaggtg atgataattg agaacagcca cgtgaagaag   3600
gatgacattt ggcccagcgg gggccagatg actgtgaagg acctgacggc caagtacacc   3660
gaaggtggaa atgccatttt ggaaaacatc agcttctcaa tctctcctgg gcagagagtt   3720
ggattgctgg gtcgcacggg cagcggcaaa tcaaccctgc tcagtgcctt ccttcggctc   3780
ctgaatacag aaggcgaaat ccaaattgac ggggtgagct gggacagcat caccctgcag   3840
cagtggagaa aagcatttgg ggtcattcca cagaaagttt tcatcttctc tggcactttc   3900
agaaagaacc tggaccccta tgagcagtgg agcgaccagg agatctggaa ggttgcagat   3960
gaagttggcc tgcggagtgt gatagaacaa tttcctggca agctggattt tgtgctggta   4020
gatggaggct gcgtgctgtc ccacggccac aaacagctga tgtgcctcgc ccgctccgtt   4080
ctttcaaagg ccaaaatctt gcttttggat gagcccagtg ctcacctcga cccagtgacc   4140
tatcagataa tccgcaggac cttaaagcaa gcttttgccg actgcaccgt catactgtgt   4200
gagcaccgga ttgaagcaat gctggaatgc cagcagtttc tggtgatcga ggagaataag   4260
```

-continued

```
gtccggcagt acgacagcat ccagaagttg ttgaatgagc gcagcctttt ccgccaggcc   4320

atctccccat ctgacagagt caagctgttt ccacatagga actcctctaa gtgcaagtcc   4380

aagccccaga tcgctgccct caaggaggaa actgaggaag aggtgcagga tacccgcctg   4440

tga                                                                 4443
```

<210> SEQ ID NO 30
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 30

```
atgcagagga gcccactgga gaaagcctcc gtggtgagta aactcttttt tagttggacc     60

agacccatcc tgcgaaaagg atacaggcag cgcctcgagt tgtctgatat ctaccagatt    120

ccttctgtgg actcagctga caatttgagt gagaagctgg agcgggagtg ggatagagag    180

ctggcgagca aaaaaaaccc caagcttatc aatgctctgc gccgctgctt tttctggagg    240

ttcatgtttt atgggatctt cctgtacctg ggggaggtca ccaaagctgt tcagccgctc    300

cttcttggcc gcatcatcgc cagctatgac cctgataata aagaagaaag gtctattgct    360

atttatctgg gaattggcct ctgcttgctc ttcatcgtcc gcacccttct gctgcaccct    420

gccatttttg gccttcacca catcggcatg caaatgagaa ttgccatgtt ctccctcatt    480

tacaaaaaga ccctgaaact ttcctcaaga gtgttagata aaatatccat tggtcagctg    540

gtcagcctgc tgtccaacaa tcttaacaaa tttgatgaag gcttggcgct ggcccacttc    600

gtgtggattg cacctctgca ggtggccctg ttgatgggac ttatatggga gctgcttcaa    660

gcctctgctt tctgtgggct gggctttttg attgtactgg cactttttca ggctgggctc    720

ggaagaatga tgatgaaata cagagatcag cgggccggga agatttcaga gcgacttgtg    780

atcaccagtg aaatgattga aaatattcag agcgtgaaag cctactgctg ggaagaagcc    840

atggagaaga tgattgagaa cctgaggcag acagagctca agctcactcg gaaggctgct    900

tatgttcgct atttcaacag cagcgccttc ttcttcagtg gcttctttgt tgtcttcctg    960

tctgttctgc catatgcact gataaaaggc attattttac gaaagatctt caccaccatc   1020

agtttttgca tcgttctcag gatggccgtc acaagacagt tcccctgggc tgtgcagacc   1080

tggtacgatt ccttgggggc catcaacaag attcaagatt tcttgcaaaa acaagaatat   1140

aaaactttag aatacaacct caccaccact gaagtggtca tggaaaatgt gacagccttt   1200

tgggaggagg gttttggaga attgttcgag aaggcaaagc agaataacaa caacaggaag   1260

acgagcaatg ggacgactc tctcttcttc agcaactttt cactgctcgg gacccctgtg   1320

ttgaaagata taaacttcaa gatcgagagg ggccagctct tggctgtggc aggctccact   1380

ggagctggta aaacatctct tctcatggtg atcatggggg aactggagcc ttccgaagga   1440

aaaatcaagc acagtgggag aatctcattc tgcagccagt tttcctggat catgcccggc   1500

accattaagg aaaacatcat atttggagtg tcctatgatg agtaccgcta ccggtcagtc   1560

atcaaagcct gtcagttgga ggaggacatc tccaagtttg cagagaaaga caacattgtg   1620

cttggagagg ggggtatcac tctttctgga ggacaaagag ccaggatctc tttggcccgg   1680

gcagtctaca aggatgcaga cctctacttg ttggacagtc ccttcggcta cctcgacgtg   1740

ctgactgaaa aagaaatttt tgaaagctgt gtgtgcaaac tgatggcaaa caagaccagg   1800

attcttgtca ccagcaagat ggaacatctg aagaaagcgg acaaaattct gattctgcat   1860
```

```
gaagggagct cctacttcta tggaacattt agcgagcttc agaacctaca gccagacttc   1920
tcctccaaat taatgggctg tgactccttc gaccagttct ctgcagaaag aagaaactct   1980
atactcacag agaccctcca ccgcttctcc cttgagggag atgccccagt ttcttggaca   2040
gaaaccaaga agcagtcctt taagcagact ggcgagtttg gtgaaaagag gaaaaattca   2100
attctcaatc ctattaacag tattcgcaag ttcagcattg tccagaagac acccctccag   2160
atgaatggca tcgaagaaga tagtgacgag ccgctggaga gacggctgag tctggtgcca   2220
gattcagaac agggggaggc catcctgccc cggatcagcg tcatttccac aggcccccaca   2280
ttacaagcac ggcgccggca gagtgtttta aatctcatga cccattcagt gaaccagggc   2340
caaaatatcc acaggaagac tacagcttct acccggaaag tgtctctggc ccctcaggcc   2400
aatctgaccg agctggacat ctacagcagg aggctctccc aggaaacagg gctggaaata   2460
tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
tttgtcctca tctggtgcct ggttattttc ctcgctgagg tggcggccag tcttgttgtg   2640
ctctggctgc tgggcaacac tcctctccag gacaagggca atagtacaca cagcagaaat   2700
aattcttatg ccgtcatcat tacaagcacc tccagctact acgtgttcta catctatgtg   2760
ggcgtggctg acaccctcct ggccatgggt ttcttccggg gcctgccttt ggtgcacacc   2820
ctcatcacag tgtcaaaaat tctgcaccat aaaatgcttc attctgtcct gcaggcaccc   2880
atgagcactt tgaacacatt gaaggctggc ggcatcctca acagattttc taaagatatt   2940
gctatcctgg atgatctcct ccccctgaca atctttgact ttatccagct tctgctgatc   3000
gtgattggag ccatagcagt ggttgctgtc ctgcagccct acatttttgt ggccaccgtg   3060
cccgtgattg ttgcctttat tatgctcaga gcttacttcc tgcaaacttc tcaacagctc   3120
aaacagctag aatctgaggg ccggagcccc atttttaccc acctggtgac ttccctgaag   3180
ggactgtgga ctctgagagc attcgggcga cagccttact ttgagacact gttccacaag   3240
gccctgaact tgcacactgc caactggttt ctttacctga gcacactccg ctggttccag   3300
atgcggatag agatgatctt cgtcatcttt tttatagctg taaccttcat ttctatcctt   3360
acaacaggag aaggagaggg cagggtggga atcatcctca cgctggctat gaacataatg   3420
tccaccttgc agtgggccgt gaattccagt atagatgtgg attctctaat gaggagtgtc   3480
tcccgggtgt ttaaattcat tgatatgcct actgagggga aacccaccaa gtcaacaaaa   3540
ccttataaga atggacagct gagcaaggtg atgataattg agaacagcca cgtgaagaag   3600
gatgacattt ggcccagcgg gggccagatg actgtgaagg acctgacggc caagtacacc   3660
gaaggtggaa atgccatttt ggaaaacatc agcttctcaa tctctcctgg gcagagagtt   3720
ggattgctgg gtcgcacggg cagcggcaaa tcaaccctgc tcagtgcctt ccttcggctc   3780
ctgaatacag aaggcgaaat ccaaattgac ggggtgagct gggacagcat caccctgcag   3840
cagtggagaa aagcatttgg ggtcattcca cagaaagttt tcatcttctc tggcactttc   3900
agaaagaacc tggaccccta tgagcagtgg agcgaccagg agatctggaa ggttgcagat   3960
gaagttggcc tgcggagtgt gatagaacaa tttcctggca agctggattt tgtgctggta   4020
gatggaggct gcgtgctgtc ccacggccac aaacagctga tgtgcctcgc ccgctccgtt   4080
ctttcaaagg ccaaaatctt gcttttggat gagcccagtg ctcacctcga cccagtgacc   4140
tatcagataa tccgcaggac cttaaagcaa gcttttgccg actgcaccgt catactgtgt   4200
```

gagcaccgga ttgaagcaat gctggaatgc cagcagtttc tggtgatcga ggagaataag 4260
gtccggcagt acgacagcat ccagaagttg ttgaatgagc gcagcctttt ccgccaggcc 4320
atctccccat ctgacagagt caagctgttt ccacatagga actcctctaa gtgcaagtcc 4380
aagccccaga tcgctgccct caaggaggaa actgaggaag aggtgcagga tacccgcctg 4440
tga 4443

<210> SEQ ID NO 31
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 31
atgcagagaa gccccctgga gaaggcctct gtggtgagca agctgttctt cagctggacc 60
agacccatcc tgagaaaggg ctacagacag agactggagc tgtctgacat ctaccagatc 120
ccctctgtgg actctgccga caacctgtct gagaagctgg agagagagtg ggacagagag 180
ctggccagca agaagaaccc caagctgatc aatgccctga gaagatgctt cttctggaga 240
ttcatgttct atggcatctt cctgtacctg ggagaggtga ccaaggccgt gcagcccctg 300
ctgctgggca ggatcattgc cagctatgac cctgacaaca aggaggagag aagcattgcc 360
atctacctgg gcattggcct gtgcctgctg ttcattgtga gaaccctgct gctgcaccct 420
gccatctttg gcctgcacca cattggcatg cagatgagaa ttgccatgtt cagcctgatc 480
tacaagaaga ccctgaagct gagcagcaga gtgctggaca agatcagcat tggccagctg 540
gtgagcctgc tgagcaacaa cctgaacaag tttgatgagg gcctggccct ggcccacttt 600
gtgtggattg ccccctgca ggtggccctg ctgatgggcc tgatctggga gctgctgcag 660
gcctctgcct tctgtggcct gggcttcctg attgtgctgg ccctgttcca ggccggcctg 720
ggcagaatga tgatgaagta cagagaccag agagccggca agatctctga gagactggtg 780
atcacctctg agatgattga gaacatccag tctgtgaagg cctactgctg ggaggaggcc 840
atggagaaga tgattgagaa cctgagacag acagagctga agctgaccag gaaggccgcc 900
tatgtgagat acttcaacag ctctgccttc ttcttctctg gcttctttgt ggtgttcctg 960
tctgtgctgc cctatgccct gatcaagggc atcatcctga ggaagatctt caccaccatc 1020
agcttctgca ttgtgctgag gatggccgtg accaggcagt tcccctgggc cgtgcagacc 1080
tggtatgaca gcctgggggc catcaacaag atccaggact tcctgcagaa gcaggagtac 1140
aagaccctgg agtacaacct gaccaccaca gaggtggtga tggagaatgt gacagccttc 1200
tgggaggagg gctttggaga gctgtttgag aaggccaagc agaacaacaa caacagaaag 1260
accagcaatg gagatgacag cctgttcttc agcaacttca gcctgctggg caccccctgtg 1320 ctgaaggaca tcaacttcaa gattgagagg ggccagctgc tggccgtggc cggcagcaca 1380
ggagccggca agaccagcct gctgatggtg atcatgggag agctggagcc ctctgagggc 1440
aagatcaagc actctggcag aatcagcttc tgcagccagt tcagctggat catgcctggc 1500
accatcaagg agaacatcat ctttggggtg agctatgatg agtacaggta cagatctgtg 1560
atcaaggcct gccagctgga ggaggacatc tccaagtttg ccgagaagga caacattgtg 1620
ctgggggagg gaggcatcac cctgtctggg ggccagagag ccagaatcag cctggccaga 1680
gccgtgtaca aggatgccga cctgtacctg ctggacagcc cctttggcta cctggatgtg 1740
ctgacagaga aggagatctt tgagagctgt gtgtgcaagc tgatggccaa caagaccagg 1800
atcctggtga ccagcaagat ggagcacctg aagaaggccg acaagatcct gatcctgcat 1860
gagggcagca gctacttcta tggcaccttc tctgagctgc agaacctgca gcctgacttc 1920
agcagcaagc tgatgggctg tgacagcttt gaccagttct ctgctgagag aagaaacagc 1980
atcctgacag agaccctgca caggttcagc ctggaggggg atgcccctgt gagctggaca 2040
gagaccaaga agcagagctt caagcagaca ggagagtttg gggagaagag gaagaacagc 2100
atcctgaacc ccatcaacag catcaggaag ttcagcattg tgcagaagac ccccctgcag 2160
atgaatggca ttgaggagga ctctgatgag cccctggaga gaagactgag cctggtgcca 2220
gactctgagc agggagaggc catcctgccc aggatctctg tgatcagcac aggcccccacc 2280
ctgcaggcca gaagaagaca gtctgtgctg aacctgatga cccactctgt gaaccagggc 2340
cagaatatcc acagaaagac cacagccagc accagaaagg tgagcctggc cccccaggcc 2400
aacctgacag agctggacat ctacagcaga aggctgagcc aggagacagg cctggagatc 2460
tctgaggaga tcaatgagga ggacctgaag gagtgcttct ttgatgacat ggagagcatc 2520
cctgccgtga ccacctggaa cacctacctg agatacatca cagtgcacaa gagcctgatc 2580
tttgtgctga tctggtgcct ggtgatcttc ctggccgagg tggccgccag cctggtggtg 2640
ctgtggctgc tgggcaacac cccccctgcag gacaagggca acagcaccca cagcagaaac 2700
aacagctatg ctgtgatcat caccagcacc agcagctact atgtgttcta catctatgtg 2760
ggagtggctg acaccctgct ggccatgggc ttcttcagag gcctgcccct ggtgcacacc 2820
ctgatcacag tgagcaagat cctgcaccac aagatgctgc actctgtgct gcaggccccc 2880
atgagcaccc tgaacaccct gaaggctgga ggcatcctga acagattcag caaggacatt 2940
gccatcctgg atgacctgct gcccctgacc atctttgact tcatccagct gctgctgatt 3000
gtgattggag ccattgccgt ggtggccgtg ctgcagccct acatctttgt ggccacagtg 3060
cctgtgattg tggccttcat catgctgagg gcctacttcc tgcagaccag ccagcagctg 3120
aagcagctgg agtctgaggg cagaagcccc atcttcaccc acctggtgac cagcctgaag 3180
ggcctgtgga ccctgagggc ctttggcaga cagccctact ttgagaccct gttccacaag 3240
gccctgaacc tgcacacagc caactggttc ctgtacctga gcaccctgag atggttccag 3300
atgaggattg agatgatctt tgtgatcttc ttcattgccg tgaccttcat cagcatcctg 3360
accacagggg agggcgaggg cagagtgggc atcatcctga ccctggccat gaacatcatg 3420
agcaccctgc agtgggccgt gaacagcagc attgatgtgg acagcctgat gagatctgtg 3480
agcagagtgt tcaagttcat tgacatgccc acagagggca agcccaccaa gagcaccaag 3540
ccctacaaga atggccagct gagcaaggtg atgatcattg agaacagcca tgtgaagaag 3600
gatgacatct ggccctctgg aggccagatg acagtgaagg acctgacagc caagtacaca 3660
gagggggggca atgccatcct ggagaacatc agcttcagca tcagccctgg ccagagggtg 3720
ggcctgctgg gcagaacagg ctctggcaag agcaccctgc tgtctgcctt cctgaggctg 3780
ctgaacacag agggagagat ccagattgat ggggtgagct gggacagcat caccctgcag 3840
cagtggagga aggcctttgg ggtgatcccc cagaaggtgt tcatcttctc tggcaccttc 3900
aggaagaacc tggaccccta tgagcagtgg tctgaccagg agatctggaa ggtggccgat 3960
gaggtgggcc tgagatctgt gattgagcag ttccctggca agctggactt tgtgctggtg 4020
gatggaggct gtgtgctgag ccatggccac aagcagctga tgtgcctggc cagatctgtg 4080
ctgagcaagg ccaagatcct gctgctggat gagccctctg cccacctgga ccctgtgacc 4140
taccagatca tcagaagaac cctgaagcag gcctttgccg actgcacagt gatcctgtgt 4200
gagcacagaa ttgaggccat gctggagtgc cagcagttcc tggtgattga ggagaacaag 4260
gtgaggcagt atgacagcat ccagaagctg ctgaatgaga gaagcctgtt cagacaggcc 4320
atcagcccct ctgacagagt gaagctgttc ccccacagga acagcagcaa gtgcaagagc 4380
aagccccaga ttgccgccct gaaggaggag acagaggagg aggtgcagga caccagactg 4440
tga 4443

<210> SEQ ID NO 32
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 32
atgcagagga gccccctgga gaaggccagc gtggtgagca agctgttctt cagctggacc 60
aggcccatcc tgaggaaggg ctacaggcag aggctggagc tgagcgacat ctaccagatc 120
cccagcgtgg acagcgccga caacctgagc gagaagctgg agagggagtg ggacagggag 180
ctggccagca agaagaaccc caagctgatc aacgccctga ggaggtgctt cttctggagg 240
ttcatgttct acggcatctt cctgtacctg ggcgaggtga ccaaggccgt gcagcccctg 300
ctgctgggca ggatcatcgc cagctacgac cccgacaaca aggaggagag gagcatcgcc 360
atctacctgg gcatcggcct gtgcctgctg ttcatcgtga ggaccctgct gctgcacccc 420
gccatcttcg gcctgcacca catcggcatg cagatgagga tcgccatgtt cagcctgatc 480
tacaagaaga ccctgaagct gagcagcagg gtgctggaca agatcagcat cggccagctg 540
gtgagcctgc tgagcaacaa cctgaacaag ttcgacgagg gcctggccct ggcccacttc 600
gtgtggatcg ccccccctgca ggtggccctg ctgatgggcc tgatctggga gctgctgcag 660
gccagcgcct tctgcggcct gggcttcctg atcgtgctgg ccctgttcca ggccggcctg 720
ggcaggatga tgatgaagta cagggaccag agggccggca agatcagcga gaggctggtg 780
atcaccagcg agatgatcga gaacatccag agcgtgaagg cctactgctg ggaggaggcc 840
atggagaaga tgatcgagaa cctgaggcag accgagctga agctgaccag gaaggccgcc 900
tacgtgaggt acttcaacag cagcgccttc ttcttcagcg gcttcttcgt ggtgttcctg 960
agcgtgctgc cctacgccct gatcaagggc atcatcctga ggaagatctt caccaccatc 1020
agcttctgca tcgtgctgag gatggccgtg accaggcagt tcccctgggc cgtgcagacc 1080
tggtacgaca gcctgggcgc catcaacaag atccaggact tcctgcagaa gcaggagtac 1140
aagaccctgg agtacaacct gaccaccacc gaggtggtga tggagaacgt gaccgccttc 1200
tgggaggagg gcttcggcga gctgttcgag aaggccaagc agaacaacaa caacaggaag 1260
accagcaacg gcgacgacag cctgttcttc agcaacttca gcctgctggg cacccccgtg 1320
ctgaaggaca tcaacttcaa gatcgagagg ggccagctgc tggccgtggc cggcagcacc 1380
ggcgccggca agaccagcct gctgatggtg atcatgggcg agctggagcc cagcgagggc 1440
aagatcaagc acagcggcag gatcagcttc tgcagccagt tcagctggat catgcccggc 1500
accatcaagg agaacatcat cttcggcgtg agctacgacg agtacaggta caggagcgtg 1560
atcaaggcct gccagctgga ggaggacatc agcaagttcg ccgagaagga caacatcgtg 1620
ctgggcgagg gcggcatcac cctgagcggc ggccagaggg ccaggatcag cctggccagg 1680
gccgtgtaca aggacgccga cctgtacctg ctggacagcc ccttcggcta cctggacgtg 1740

-continued

```
ctgaccgaga aggagatctt cgagagctgc gtgtgcaagc tgatggccaa caagaccagg   1800
atcctggtga ccagcaagat ggagcacctg aagaaggccg acaagatcct gatcctgcac   1860
gagggcagca gctacttcta cggcaccttc agcgagctgc agaacctgca gcccgacttc   1920
agcagcaagc tgatgggctg cgacagcttc gaccagttca gcgccgagag gaggaacagc   1980
atcctgaccg agaccctgca caggttcagc ctggagggcg acgcccccgt gagctggacc   2040
gagaccaaga agcagagctt caagcagacc ggcgagttcg gcgagaagag gaagaacagc   2100
atcctgaacc ccatcaacag catcaggaag ttcagcatcg tgcagaagac ccccctgcag   2160
atgaacggca tcgaggagga cagcgacgag cccctggaga ggaggctgag cctggtgccc   2220
gacagcgagc agggcgaggc catcctgccc aggatcagcg tgatcagcac cggccccacc   2280
ctgcaggcca ggaggaggca gagcgtgctg aacctgatga cccacagcgt gaaccagggc   2340
cagaacatcc acaggaagac caccgccagc accaggaagg tgagcctggc cccccaggcc   2400
aacctgaccg agctggacat ctacagcagg aggctgagcc aggagaccgg cctggagatc   2460
agcgaggaga tcaacgagga ggacctgaag gagtgcttct tcgacgacat ggagagcatc   2520
cccgccgtga ccacctggaa cacctacctg aggtacatca ccgtgcacaa gagcctgatc   2580
ttcgtgctga tctggtgcct ggtgatcttc ctggccgagg tggccgccag cctggtggtg   2640
ctgtggctgc tgggcaacac cccccctgcag gacaagggca acagcaccca cagcaggaac   2700
aacagctacg ccgtgatcat caccagcacc agcagctact acgtgttcta catctacgtg   2760
ggcgtggccg acaccctgct ggccatgggc ttcttcaggg gcctgcccct ggtgcacacc   2820
ctgatcaccg tgagcaagat cctgcaccac aagatgctgc acagcgtgct gcaggccccc   2880
atgagcaccc tgaacaccct gaaggccggc ggcatcctga acaggttcag caaggacatc   2940
gccatcctgg acgacctgct gcccctgacc atcttcgact tcatccagct gctgctgatc   3000
gtgatcggcg ccatcgccgt ggtggccgtg ctgcagccct acatcttcgt ggccaccgtg   3060
cccgtgatcg tggccttcat catgctgagg gcctacttcc tgcagaccag ccagcagctg   3120
aagcagctgg agagcgaggg caggagcccc atcttcaccc acctggtgac cagcctgaag   3180
ggcctgtgga ccctgagggc cttcggcagg cagccctact tcgagaccct gttccacaag   3240
gccctgaacc tgcacaccgc caactggttc ctgtacctga gcaccctgag gtggttccag   3300
atgaggatcg agatgatctt cgtgatcttc ttcatcgccg tgaccttcat cagcatcctg   3360
accaccggcg agggcgaggg cagggtgggc atcatcctga ccctggccat gaacatcatg   3420
agcaccctgc agtgggccgt gaacagcagc atcgacgtgg acagcctgat gaggagcgtg   3480
agcagggtgt tcaagttcat cgacatgccc accgagggca agcccaccaa gagcaccaag   3540
ccctacaaga acggccagct gagcaaggtg atgatcatcg agaacagcca cgtgaagaag   3600
gacgacatct ggcccagcgg cggccagatg accgtgaagg acctgaccgc caagtacacc   3660
gagggcggca acgccatcct ggagaacatc agcttcagca tcagccccgg ccagagggtg   3720
ggcctgctgg gcaggaccgg cagcggcaag agcaccctgc tgagcgcctt cctgaggctg   3780
ctgaacaccg agggcgagat ccagatcgac ggcgtgagct gggacagcat caccctgcag   3840
cagtggagga aggccttcgg cgtgatcccc cagaaggtgt tcatcttcag cggcaccttc   3900
aggaagaacc tggaccccta cgagcagtgg agcgaccagg agatctggaa ggtggccgac   3960
gaggtgggcc tgaggagcgt gatcgagcag ttccccggca agctggactt cgtgctggtg   4020
gacggcggct gcgtgctgag ccacggccac aagcagctga tgtgcctggc caggagcgtg   4080
```

-continued

```
ctgagcaagg ccaagatcct gctgctggac gagcccagcg cccacctgga ccccgtgacc   4140

taccagatca tcaggaggac cctgaagcag gccttcgccg actgcaccgt gatcctgtgc   4200

gagcacagga tcgaggccat gctggagtgc cagcagttcc tggtgatcga ggagaacaag   4260

gtgaggcagt acgacagcat ccagaagctg ctgaacgaga ggagcctgtt caggcaggcc   4320

atcagcccca gcgacagggt gaagctgttc ccccacagga acagcagcaa gtgcaagagc   4380

aagccccaga tcgccgccct gaaggaggag accgaggagg aggtgcagga caccaggctg   4440

tga                                                                 4443
```

```
<210> SEQ ID NO 33
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 33
```

```
atgcagagat cccctctgga gaaggcctca gtggtgtcca agcttttctt ctcctggacc     60

aggcccattt taagaaaggg ctacaggcag agacttgagc tgtctgacat ctatcagatc    120

ccttctgtgg attctgctga caatcttagt gaaaaattgg aaagggagtg ggacagagag    180

ctggcaagta aaaagaaccc caagctgatt aatgccctga ggcgctgctt tttttggaga    240

ttcatgttct atggcatatt cctctacctt ggagaagtaa ccaaagctgt acagcctctc    300

ctccttggca gaatcattgc ctcctatgat cctgataaca aggaggagag aagcatagcc    360

atctacctgg gcattgggct gtgcctcttg tttattgtga ggacccttct cttgcaccct    420

gccatctttg gccttcatca cattggcatg caaatgagaa tagcaatgtt tagtcttatt    480

tacaaaaaaa cattaaaact ctcttccagg gtgttggaca agatcagtat tggacaactg    540

gtcagcctgc tgagcaacaa cctgaacaag tttgatgaag gactggccct ggcccacttt    600

gtctggattg ccccccttca ggtggctctt ttgatgggcc tgatctggga actcctgcag    660

gcctctgcct tctgtgggtt aggcttcctg atagtgctag ctctctttca ggcagggttg    720

ggtagaatga tgatgaagta cagagaccag agggctggga agatatctga gaggctggtc    780

attacttctg aaatgataga aaacatccag tctgttaaag cttactgctg ggaggaggct    840

atggaaaaga tgattgagaa cttgaggcaa acagagctca agctgactag gaaggcagcc    900

tatgtcaggt atttcaacag cagtgctttc ttcttctcag gctttttcgt ggtcttcttg    960

agtgttctgc cctatgccct catcaagggg ataattttga gaaagatttt caccactatt   1020

tccttttgca ttgtcctgag gatggctgtc accaggcaat tcccctgggc tgtgcagaca   1080

tggtatgact ctctgggggc catcaacaaa atccaagatt tcctgcagaa gcaggagtac   1140

aagaccctgg aatacaacct caccaccaca gaagttgtga tggagaatgt gactgcattc   1200

tgggaggaag gatttgggga gctgtttgag aaagcaaaac aaaacaataa taacaggaaa   1260

accagcaatg gagatgactc cctgttcttt tccaacttct ctttgttggg cacccctgtc   1320

ctgaaagata taaactttaa aattgaaaga gggcagctgt tggcagttgc tggctccaca   1380

ggagctggaa aaacttcact actgatggtg atcatggggg agttagaacc ctctgaaggg   1440

aaaataaaac attctgggag gattagtttc tgcagccagt tcagctggat catgcctggg   1500

accattaaag aaaatattat atttggagtg agctatgatg aatatagata taggagtgtc   1560

atcaaagcct gtcagttgga ggaagacatc agcaaatttg cagagaaaga caacattgtt   1620

ctgggtgaag gtggcatcac cctgtcagga gggcaaaggg ccaggatcag cttggccaga   1680
```

```
gcagtctata aagatgctga tctgtacctc ctggatagcc cttttggcta tctggatgtt   1740
ttgacagaga aggaaatttt tgagtcctgt gtctgcaagt taatggcaaa taaaacaagg   1800
atacttgtga cctcaaaaat ggaacacctg aagaaggctg acaaaattct gatcctgcat   1860
gagggcagca gctactttta tggaacattt tctgaactgc agaatttgca accagacttt   1920
tcatcaaagc tcatgggatg tgacagtttt gatcagtttt ctgcagaaag gagaaactcc   1980
attttgactg agaccctgca caggttcagt ctggaggggg atgccccagt gagttggact   2040
gagacaaaga aacagagctt caagcagact ggagagtttg gagaaaagag gaaaaactca   2100
attctcaatc ccatcaatag catcaggaag ttcagcatag ttcagaagac tcctttgcag   2160
atgaatggga ttgaagagga ctcagatgag cccctggaaa ggagactctc cttggtgcca   2220
gattcagagc agggggaagc catactgcca aggatctctg tgatttctac agggcccacc   2280
ctccaagcaa gaaggagaca gtcagtttta aacctgatga cccactctgt caaccaggga   2340
cagaacattc atagaaagac aacagcatct acaagaaaag tttcactggc ccctcaagcc   2400
aatttaactg aactagatat ctacagcagg aggctcagcc aagaaacagg cctggagatc   2460
tcagaagaaa taaatgagga ggatttgaag gaatgcttct ttgatgatat ggagagcatc   2520
ccagctgtca caacctggaa cacctacctg agatacatca cagtgcacaa atccctcatc   2580
tttgtactta tatggtgcct tgtcatcttc ttagctgagg tggctgcttc cctggtggtg   2640
ctgtggctgc tgggaaacac acccctccag gataaaggga actctactca cagcaggaac   2700
aacagttatg ctgtgatcat caccagtacc tcctcctact atgtgttcta catttatgtt   2760
ggagttgcag acacattgct tgccatgggt ttttttagag gactccccct ggtgcatact   2820
ctcatcactg tttccaaaat ccttcaccac aagatgctgc acagtgtact acaggctccc   2880
atgagcaccc tcaacactct taaagcagga ggaatcttga acagatttag caaggacatt   2940
gcaattcttg atgacctgct tccactgacc atctttgact tcatccagct tctgctcatt   3000
gtaattggtg ccattgctgt ggtagcagtg ctccagccat atatttttgt ggccactgtg   3060
cctgttattg tggccttcat tatgttgaga gcctacttcc tgcagacctc tcagcagctc   3120
aagcaacttg aaagtgaggg caggagcccc atatttacac acttggtcac ttccctcaaa   3180
ggcctctgga cactcagagc ttttggaaga caaccttatt ttgaaactct cttccacaag   3240
gctctgaatc tccacacagc caactggttt ctgtatcttt caacactgcg ctggttccag   3300
atgaggattg agatgatctt tgttatcttc ttcatagctg ttaccttcat ctctattctg   3360
acaactggtg agggggaagg gagagtaggc atcatcctca cactagccat gaacataatg   3420
tctaccttac aatgggccgt gaacagctcc atagatgtgg acagcctcat gagaagtgtg   3480
tcaagagttt tcaaattcat tgacatgccc acagaaggca aaccaaccaa gagcacaaaa   3540
ccctacaaga atggccagct gagtaaggtc atgatcattg aaaattctca tgtgaagaag   3600
gatgatattt ggcccagtgg gggccagatg acagtcaagg acctcactgc caaatacaca   3660
gagggtggaa atgctatcct agagaacatc tccttctcca tctccccagg ccaaagagtt   3720
ggcttgctgg gcaggactgg cagtggcaag tccaccttgc tctcagcatt tctcaggctt   3780
ttaaatacag agggagagat tcaaattgat ggggtgtctt gggatagtat aacacttcaa   3840
cagtggagga aagcctttgg tgtgattcct cagaaagtgt ttatcttctc tggcactttc   3900
agaaaaaatc tggaccccta tgaacagtgg agtgaccagg aaatctggaa ggtggcagat   3960
gaagtgggcc taagatcagt catagagcag tttcctggaa agttggattt tgtgcttgta   4020
```

-continued gatggaggct gtgtgctgtc ccatggccat aaacagctaa tgtgcctggc taggtcagtg 4080
ctgagcaagg ccaagatcct gctgttagat gagccttcag cccatctgga ccctgtgaca 4140
taccagatta tcagaagaac tctgaagcag gcctttgctg actgcactgt catcctgtgt 4200
gagcacagaa ttgaggccat gctggagtgc cagcagttcc ttgttataga agagaataag 4260
gttaggcagt atgacagcat tcagaaactg ctaaatgaaa gatctctctt caggcaagct 4320
atttcaccat ctgatagagt gaaacttttt ccccacagaa attcctctaa atgtaaatct 4380
aagccccaga tagctgcctt gaaagaggag actgaagaag aagtccagga caccagactg 4440
tga 4443

<210> SEQ ID NO 34
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 34
atgcagagat ccccgctgga gaaggcatct gtggtgtcaa aactgttctt tagctggaca 60
aggcccatcc ttaggaaagg gtacagacag aggttggagc tgtcagacat atatcagatc 120
ccttcagtgg actctgcaga caacctctct gaaaagctgg agagggaatg ggacagggaa 180
ctggccagca aaaaaaaccc taaactgatt aatgccctga ggaggtgctt cttttggaga 240
ttcatgttct atgggatctt cctttacctg ggggaggtga ctaaagctgt tcagcctctt 300
cttctgggga ggattattgc ctcctatgac ccagacaaca aagaagaaag aagcatagcc 360
atttacttag gcataggcct ctgcttgctc ttcatagtta gaaccctcct actccaccca 420
gccatctttg gtctccacca cataggtatg cagatgagaa tagcaatgtt ctccttgatc 480
tacaagaaga ccctcaagct gtccagcagg gtgctggaca agatctccat aggccagtta 540
gtcagtctac tgtccaataa cttaaataag tttgatgagg gactggcact ggcacatttt 600
gtgtggattg ccccccctcca agtggccctt cttatgggcc ttatctggga gctgttgcag 660
gcctctgctt tctgtggcct gggtttcctc atagtcctag ccttattcca ggctggactg 720
ggcagaatga tgatgaagta tagggaccaa agagcaggga agatttctga aaggctggtt 780
ataacttctg agatgattga gaacattcag tcagtgaaag cttactgctg ggaagaagct 840
atggaaaaaa tgattgaaaa tctcagacag actgaattaa agttgaccag gaaagctgct 900
tatgtcagat acttcaactc ctcagccttc ttttttttctg gcttctttgt tgtattcctt 960
tcagtcctcc cctatgccct gattaagggc attatcttga ggaaaatttt cacaaccatc 1020
tccttttgta ttgtcctcag gatggctgtt acaaggcaat ttccttgggc tgtgcaaact 1080
tggtatgata gccttggagc aatcaacaag atccaggatt tcctgcaaaa gcaggagtac 1140
aagacattgg aatacaacct taccaccact gaggtggtga tggaaaatgt gactgccttc 1200
tgggaggagg ggtttggaga gctgtttgag aaagccaaac agaacaacaa caatagaaag 1260
acctctaatg gtgatgattc cctgttcttt tctaacttta gtcttctggg gaccccagtt 1320
ctgaaagata ttaactttaa aattgaaagg ggacagttgc tggctgtggc tgggtccact 1380
ggggctggga agacaagcct gctcatggtg atcatgggag agctggaacc cagtgaagga 1440
aagatcaaac actcaggcag gatctccttc tgcagccagt tctcatggat tatgccaggc 1500
actattaaag aaaatatcat ctttggtgta agctatgatg agtacaggta tagatctgta 1560
attaaagcct gccagctgga ggaagacatc tctaagtttg ctgagaagga taacattgtg 1620
ttgggggaag gggcatcac cctttctggt gggcagaggg ctaggatctc ccttgctagg 1680
gcagtataca aggatgctga cttgtacctc ttggatagtc cttttggcta cctagatgtg 1740
ctgacagaga aagaaatatt tgaaagctgt gtgtgtaagc tcatggctaa caagaccagg 1800
atcctggtca ccagtaaaat ggaacacctc aaaaaagcag acaagatcct tattctccat 1860
gagggctcct cctacttcta tgggaccttc agtgagctgc agaatctgca gccagacttc 1920
tcctcaaaac ttatgggctg tgactccttt gaccaattct ctgcagaaag aaggaatagc 1980
atactgacag aaacactgca tagattctcc ctggaaggag atgccccagt gagttggaca 2040
gaaaccaaaa agcagagctt caagcagact ggtgagtttg gtgaaaagag gaagaattct 2100
atcctgaacc ccatcaatag catcaggaaa tttagcatag tccaaaagac ccccctccag 2160
atgaatggaa tagaggagga tagtgatgag cctcttgaga gaaggctgtc cctggttcca 2220
gacagtgaac agggtgaagc cattcttccg aggatcagtg tcatctccac tgggcccaca 2280
ttgcaggcca gaagaagaca gtctgttctg aatttgatga cacattctgt gaatcaaggc 2340
cagaatatcc atagaaaaac cactgccagc accagaaaag tttctctagc cccccaggct 2400
aacctgactg agttagacat ctacagcaga aggctgagcc aagagactgg cttggaaata 2460
tctgaggaga tcaatgagga ggacctcaag gagtgcttct ttgatgacat ggagtcaatc 2520
cctgcagtca ctacatggaa cacttaccta aggtacatca cagttcataa gagcctcatc 2580
tttgtcctca tatggtgtct ggtcatcttt ttagcagaag tggctgccag cctagttgtg 2640
ctgtggttac tgggcaatac acctcttcag gacaaaggca atagcacaca cagcagaaac 2700
aactcctatg cagtgatcat cacctctaca agctcttact atgtattcta tatatatgtg 2760
ggagtggcag atactctcct ggccatggga ttcttcaggg gattacctct agttcacaca 2820
ttgatcacag tgtcaaaaat tctccaccac aagatgttac acagtgtcct gcaagcccca 2880
atgtctactc tgaacacact taaggcaggt ggaattttga ataggtttag caaggacata 2940
gctatcctgg atgatctcct ccctctgacc atctttgact tcatccagtt actgctcatt 3000
gtaattggag ccattgcagt ggtagcagtc ctacagcctt acatttttgt ggctactgtt 3060
cctgttattg tggccttcat tatgctaaga gcttacttcc tgcaaacaag ccaacagttg 3120
aaacagctag aaagtgaggg aaggtccccc atcttcaccc acctggtgac atcactcaag 3180
gggctatgga ctcttagggc ttttgggaga cagccgtact ttgagacctt attccataag 3240
gcccttaacc tccatacagc aaactggttc ttatacctga gtactctgag gtggtttcaa 3300
atgaggattg aaatgatttt tgtgatcttc ttcattgctg tgaccttcat ctcaatcttg 3360
accacaggag agggggaggg cagggtgggc atcatactga ccttggccat gaacattatg 3420
tcaaccctgc agtgggctgt caatagctcc attgatgtgg acagtctgat gaggagtgtc 3480
tccagggtct tcaagtttat tgacatgcca actgagggca aacccaccaa aagcactaag 3540
ccatataaaa atggccaact gtccaaagtg atgatcattg aaaattcaca tgtaaagaag 3600
gatgatatct ggccctctgg aggacagatg acagtgaaag acctgactgc caagtacaca 3660
gagggtggta atgccattct tgagaacatt agtttcagta tttccccggg gcaaagggtg 3720
ggcctccttg gcagaacagg ctctggcaag agtaccctgc tgtcagcctt tttaagactg 3780
ttgaacactg agggagaaat tcagattgat ggtgtctcct gggatagcat caccctccag 3840
cagtggagaa aagcttttgg agtgatcccg caaaaggttt tcatcttttc aggcaccttc 3900
cggaagaacc tggaccccta tgagcagtgg tctgaccagg aaatatggaa ggtagctgat 3960

-continued

```
gaagttgggc ttaggtcagt catagagcag ttcccaggca aactggactt tgtcctggtg   4020

gatggtggat gtgtactgag tcatgggcac aaacagctga tgtgcctagc caggtctgtg   4080

ctcagcaagg caaagatatt gctgcttgat gaacccagtg cccatctgga cccagtcaca   4140

tatcagatca tcagaagaac attgaagcag gcctttgctg attgcacagt tatcctctgt   4200

gagcacagga ttgaggccat gctggagtgc cagcagtttc tggtgattga ggagaataaa   4260

gtaaggcagt atgactccat ccagaagctg ctcaatgaaa gaagcctctt tagacaagct   4320

atctcccccct cagacagggt caaattgttc cctcacagaa acagcagcaa gtgcaagagc   4380

aagccccaaa ttgcagcctt gaaagaggag acagaggaag aggtgcagga caccagactc   4440

tga                                                                 4443
```

<210> SEQ ID NO 35
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 35

```
atgcagagaa gccccctgga gaaggccagc gtggtgagca agctgttctt cagctggacc     60

agacccatcc tgagaaaggg ctacagacag agactggagc tgagcgacat ctaccagatc    120

cccagcgtgg acagcgccga caacctgagc gagaagctgg agagagagtg ggacagagag    180

ctggccagca agaagaaccc caagctgatc aacgccctga gaagatgctt cttctggaga    240

ttcatgttct acggcatctt cctgtacctg ggcgaggtga ccaaggccgt gcagcccctg    300

ctgctgggca gaatcatcgc cagctacgac cccgacaaca aggaggagag aagcatcgcc    360

atctacctgg gcatcggcct gtgcctgctg ttcatcgtga gaaccctgct gctgcacccc    420

gccatcttcg gcctgcacca catcggcatg cagatgagaa tcgccatgtt cagcctgatc    480

tacaagaaga ccctgaagct gagcagcaga gtgctggaca agatcagcat cggccagctg    540

gtgagcctgc tgagcaacaa cctgaacaag ttcgacgagg gcctggccct ggcccacttc    600

gtgtggatcg ccccccctgca ggtggccctg ctgatgggcc tgatctggga gctgctgcag    660

gccagcgcct tctgcggcct gggcttcctg atcgtgctgg ccctgttcca ggccggcctg    720

ggcagaatga tgatgaagta cagagaccag agagccggca agatcagcga gagactggtg    780

atcaccagcg agatgatcga gaacatccag agcgtgaagg cctactgctg ggaggaggcc    840

atggagaaga tgatcgagaa cctgagacag accgagctga agctgaccag aaaggccgcc    900

tacgtgagat acttcaacag cagcgccttc ttcttcagcg gcttcttcgt ggtgttcctg    960

agcgtgctgc cctacgccct gatcaagggc atcatcctga gaaagatctt caccaccatc   1020

agcttctgca tcgtgctgag aatggccgtg accagacagt tcccctgggc cgtgcagacc   1080

tggtacgaca gcctgggcgc catcaacaag atccaggact tcctgcagaa gcaggagtac   1140

aagaccctgg agtacaacct gaccaccacc gaggtggtga tggagaacgt gaccgccttc   1200

tgggaggagg gcttcggcga gctgttcgag aaggccaagc agaacaacaa caacagaaag   1260

accagcaacg gcgacgacag cctgttcttc agcaacttca gcctgctggg cacccccgtg   1320

ctgaaggaca tcaacttcaa gatcgagaga ggccagctgc tggccgtggc cggcagcacc   1380

ggcgccggca agaccagcct gctgatggtg atcatgggcg agctggagcc cagcgagggc   1440

aagatcaagc acagcggcag aatcagcttc tgcagccagt tcagctggat catgcccggc   1500

accatcaagg agaacatcat cttcggcgtg agctacgacg agtacagata cagaagcgtg   1560
```

```
atcaaggcct gccagctgga ggaggacatc agcaagttcg ccgagaagga caacatcgtg   1620
ctgggcgagg gcggcatcac cctgagcggc ggccagagag ccagaatcag cctggccaga   1680
gccgtgtaca aggacgccga cctgtacctg ctggacagcc ccttcggcta cctggacgtg   1740
ctgaccgaga aggagatctt cgagagctgc gtgtgcaagc tgatggccaa caagaccaga   1800
atcctggtga ccagcaagat ggagcacctg aagaaggccg acaagatcct gatcctgcac   1860
gagggcagca gctacttcta cggcaccttc agcgagctgc agaacctgca gcccgacttc   1920
agcagcaagc tgatgggctg cgacagcttc gaccagttca gcgccgagag aagaaacagc   1980
atcctgaccg agaccctgca cagattcagc ctggagggcg acgcccccgt gagctggacc   2040
gagaccaaga agcagagctt caagcagacc ggcgagttcg gcgagaagag aaagaacagc   2100
atcctgaacc ccatcaacag catcagaaag ttcagcatcg tgcagaagac cccccctgcag   2160
atgaacggca tcgaggagga cagcgacgag cccctggaga gaagactgag cctggtgccc   2220
gacagcgagc agggcgaggc catcctgccc agaatcagcg tgatcagcac cggccccacc   2280
ctgcaggcca gaagaagaca gagcgtgctg aacctgatga cccacagcgt gaaccagggc   2340
cagaacatcc acagaaagac caccgccagc accagaaagg tgagcctggc cccccaggcc   2400
aacctgaccg agctggacat ctacagcaga agactgagcc aggagaccgg cctggagatc   2460
agcgaggaga tcaacgagga ggacctgaag gagtgcttct tcgacgacat ggagagcatc   2520
cccgccgtga ccacctggaa cacctacctg agatacatca ccgtgcacaa gagcctgatc   2580
ttcgtgctga tctggtgcct ggtgatcttc ctggccgagg tggccgccag cctggtggtg   2640
ctgtggctgc tgggcaacac cccccctgcag gacaagggca acagcaccca cagcagaaac   2700
aacagctacg ccgtgatcat caccagcacc agcagctact acgtgttcta catctacgtg   2760
ggcgtggccg acaccctgct ggccatgggc ttcttcagag gcctgcccct ggtgcacacc   2820
ctgatcaccg tgagcaagat cctgcaccac aagatgctgc acagcgtgct gcaggccccc   2880
atgagcaccc tgaacaccct gaaggccggc ggcatcctga acagattcag caaggacatc   2940
gccatcctgg acgacctgct gcccctgacc atcttcgact tcatccagct gctgctgatc   3000
gtgatcggcg ccatcgccgt ggtggccgtg ctgcagccct acatcttcgt ggccaccgtg   3060
cccgtgatcg tggccttcat catgctgaga gcctacttcc tgcagaccag ccagcagctg   3120
aagcagctgg agagcgaggg cagaagcccc atcttcaccc acctggtgac cagcctgaag   3180
ggcctgtgga ccctgagagc cttcggcaga cagccctact tcgagaccct gttccacaag   3240
gccctgaacc tgcacaccgc caactggttc ctgtacctga gcaccctgag atggttccag   3300
atgagaatcg agatgatctt cgtgatcttc ttcatcgccg tgaccttcat cagcatcctg   3360
accaccggcg agggcgaggg cagagtgggc atcatcctga ccctggccat gaacatcatg   3420
agcaccctgc agtgggccgt gaacagcagc atcgacgtgg acagcctgat gagaagcgtg   3480
agcagagtgt tcaagttcat cgacatgccc accgagggca agcccaccaa gagcaccaag   3540
ccctacaaga acggccagct gagcaaggtg atgatcatcg agaacagcca cgtgaagaag   3600
gacgacatct ggcccagcgg cggccagatg accgtgaagg acctgaccgc caagtacacc   3660
gagggcggca acgccatcct ggagaacatc agcttcagca tcagccccgg ccagagagtg   3720
ggcctgctgg gcagaaccgg cagcggcaag agcaccctgc tgagcgcctt cctgagactg   3780
ctgaacaccg agggcgagat ccagatcgac ggcgtgagct gggacagcat caccctgcag   3840
cagtggagaa aggccttcgg cgtgatcccc cagaaggtgt tcatcttcag cggcaccttc   3900
```

-continued agaaagaacc tggaccccta cgagcagtgg agcgaccagg agatctggaa ggtggccgac 3960
gaggtgggcc tgagaagcgt gatcgagcag ttccccggca agctggactt cgtgctggtg 4020
gacggcggct gcgtgctgag ccacggccac aagcagctga tgtgcctggc cagaagcgtg 4080
ctgagcaagg ccaagatcct gctgctggac gagcccagcg cccacctgga ccccgtgacc 4140
taccagatca tcagaagaac cctgaagcag gccttcgccg actgcaccgt gatcctgtgc 4200
gagcacagaa tcgaggccat gctggagtgc cagcagttcc tggtgatcga ggagaacaag 4260
gtgagacagt acgacagcat ccagaagctg ctgaacgaga gaagcctgtt cagacaggcc 4320
atcagcccca gcgacagagt gaagctgttc ccccacagaa acagcagcaa gtgcaagagc 4380
aagccccaga tcgccgccct gaaggaggag accgaggagg aggtgcagga caccagactg 4440
tga 4443

<210> SEQ ID NO 36
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 36
atgcagcgca gcccccctgga gaaggccagc gtggtgagca agctgttctt cagctggacc 60
cgccccatcc tgcgcaaggg ctaccgccag cgcctggagc tgagcgacat ctaccagatc 120
cccagcgtgg acagcgccga caacctgagc gagaagctgg agcgcgagtg ggaccgcgag 180
ctggccagca agaagaaccc caagctgatc aacgccctgc gccgctgctt cttctggcgc 240
ttcatgttct acggcatctt cctgtacctg ggcgaggtga ccaaggccgt gcagcccctg 300
ctgctgggcc gcatcatcgc cagctacgac cccgacaaca aggaggagcg cagcatcgcc 360
atctacctgg gcatcggcct gtgcctgctg ttcatcgtgc gcaccctgct gctgcacccc 420
gccatcttcg gcctgcacca catcggcatg cagatgcgca tcgccatgtt cagcctgatc 480
tacaagaaga ccctgaagct gagcagccgc gtgctggaca agatcagcat cggccagctg 540
gtgagcctgc tgagcaacaa cctgaacaag ttcgacgagg gcctggccct ggcccacttc 600
gtgtggatcg cccccctgca ggtggccctg ctgatgggcc tgatctggga gctgctgcag 660
gccagcgcct tctgcggcct gggcttcctg atcgtgctgg ccctgttcca ggccggcctg 720
ggccgcatga tgatgaagta ccgcgaccag cgcgccggca agatcagcga gcgcctggtg 780
atcaccagcg agatgatcga gaacatccag agcgtgaagg cctactgctg ggaggaggcc 840
atggagaaga tgatcgagaa cctgcgccag accgagctga agctgacccg caaggccgcc 900
tacgtgcgct acttcaacag cagcgccttc ttcttcagcg gcttcttcgt ggtgttcctg 960
agcgtgctgc cctacgccct gatcaagggc atcatcctgc gcaagatctt caccaccatc 1020
agcttctgca tcgtgctgcg catggccgtg acccgccagt tcccctgggc cgtgcagacc 1080
tggtacgaca gcctgggcgc catcaacaag atccaggact tcctgcagaa gcaggagtac 1140
aagaccctgg agtacaacct gaccaccacc gaggtggtga tggagaacgt gaccgccttc 1200
tgggaggagg gcttcggcga gctgttcgag aaggccaagc agaacaacaa caaccgcaag 1260
accagcaacg gcgacgacag cctgttcttc agcaacttca gcctgctggg caccccccgtg 1320 ctgaaggaca tcaacttcaa gatcgagcgc ggccagctgc tggccgtggc cggcagcacc 1380
ggcgccggca agaccagcct gctgatggtg atcatgggcg agctggagcc cagcgagggc 1440
aagatcaagc acagcggccg catcagcttc tgcagccagt tcagctggat catgcccggc 1500

```
accatcaagg agaacatcat cttcggcgtg agctacgacg agtaccgcta ccgcagcgtg   1560
atcaaggcct gccagctgga ggaggacatc agcaagttcg ccgagaagga caacatcgtg   1620
ctgggcgagg gcggcatcac cctgagcggc ggccagcgcg cccgcatcag cctggcccgc   1680
gccgtgtaca aggacgccga cctgtacctg ctggacagcc ccttcggcta cctggacgtg   1740
ctgaccgaga aggagatctt cgagagctgc gtgtgcaagc tgatggccaa caagacccgc   1800
atcctggtga ccagcaagat ggagcacctg aagaaggccg acaagatcct gatcctgcac   1860
gagggcagca gctacttcta cggcaccttc agcgagctgc agaacctgca gcccgacttc   1920
agcagcaagc tgatgggctg cgacagcttc gaccagttca gcgccgagcg ccgcaacagc   1980
atcctgaccg agaccctgca ccgcttcagc ctggagggcg acgcccccgt gagctggacc   2040
gagaccaaga agcagagctt caagcagacc ggcgagttcg gcgagaagcg caagaacagc   2100
atcctgaacc ccatcaacag catccgcaag ttcagcatcg tgcagaagac cccccctgcag   2160
atgaacggca tcgaggagga cagcgacgag cccctggagc gccgcctgag cctggtgccc   2220
gacagcgagc agggcgaggc catcctgccc cgcatcagcg tgatcagcac cggccccacc   2280
ctgcaggccc gccgccgcca gagcgtgctg aacctgatga cccacagcgt gaaccagggc   2340
cagaacatcc accgcaagac caccgccagc acccgcaagg tgagcctggc cccccaggcc   2400
aacctgaccg agctggacat ctacagccgc cgcctgagcc aggagaccgg cctggagatc   2460
agcgaggaga tcaacgagga ggacctgaag gagtgcttct tcgacgacat ggagagcatc   2520
cccgccgtga ccacctggaa cacctacctg cgctacatca ccgtgcacaa gagcctgatc   2580
ttcgtgctga tctggtgcct ggtgatcttc ctggccgagg tggccgccag cctggtggtg   2640
ctgtggctgc tgggcaacac cccctgcag gacaagggca acagcaccca cagccgcaac   2700
aacagctacg ccgtgatcat caccagcacc agcagctact acgtgttcta catctacgtg   2760
ggcgtggccg acaccctgct ggccatgggc ttcttccgcg gcctgcccct ggtgcacacc   2820
ctgatcaccg tgagcaagat cctgcaccac aagatgctgc acagcgtgct gcaggccccc   2880
atgagcaccc tgaacaccct gaaggccggc ggcatcctga accgcttcag caaggacatc   2940
gccatcctgg acgacctgct gcccctgacc atcttcgact tcatccagct gctgctgatc   3000
gtgatcggcg ccatcgccgt ggtggccgtg ctgcagccct acatcttcgt ggccaccgtg   3060
cccgtgatcg tggccttcat catgctgcgc gcctacttcc tgcagaccag ccagcagctg   3120
aagcagctgg agagcgaggg ccgcagcccc atcttcaccc acctggtgac cagcctgaag   3180
ggcctgtgga ccctgcgcgc cttcggccgc cagccctact tcgagaccct gttccacaag   3240
gccctgaacc tgcacaccgc caactggttc ctgtacctga gcaccctgcg ctggttccag   3300
atgcgcatcg agatgatctt cgtgatcttc ttcatcgccg tgaccttcat cagcatcctg   3360
accaccggcg agggcgaggg ccgcgtgggc atcatcctga ccctggccat gaacatcatg   3420
agcaccctgc agtgggccgt gaacagcagc atcgacgtgg acagcctgat gcgcagcgtg   3480
agccgcgtgt tcaagttcat cgacatgccc accgagggca agcccaccaa gagcaccaag   3540
ccctacaaga acggccagct gagcaaggtg atgatcatcg agaacagcca cgtgaagaag   3600
gacgacatct ggcccagcgg cggccagatg accgtgaagg acctgaccgc caagtacacc   3660
gagggcggca acgccatcct ggagaacatc agcttcagca tcagccccgg ccagcgcgtg   3720
ggcctgctgg gccgcaccgg cagcggcaag agcaccctgc tgagcgcctt cctgcgcctg   3780
ctgaacaccg agggcgagat ccagatcgac ggcgtgagct gggacagcat caccctgcag   3840
```

cagtggcgca aggccttcgg cgtgatcccc cagaaggtgt tcatcttcag cggcaccttc 3900
cgcaagaacc tggaccccta cgagcagtgg agcgaccagg agatctggaa ggtggccgac 3960
gaggtgggcc tgcgcagcgt gatcgagcag ttccccggca agctggactt cgtgctggtg 4020
gacggcggct gcgtgctgag ccacggccac aagcagctga tgtgcctggc ccgcagcgtg 4080
ctgagcaagg ccaagatcct gctgctggac gagcccagcg cccacctgga ccccgtgacc 4140
taccagatca tccgccgcac cctgaagcag gccttcgccg actgcaccgt gatcctgtgc 4200
gagcaccgca tcgaggccat gctggagtgc cagcagttcc tggtgatcga ggagaacaag 4260
gtgcgccagt acgacagcat ccagaagctg ctgaacgagc gcagcctgtt ccgccaggcc 4320
atcagcccca gcgaccgcgt gaagctgttc ccccaccgca acagcagcaa gtgcaagagc 4380
aagccccaga tcgccgccct gaaggaggag accgaggagg aggtgcagga cacccgcctg 4440
taa 4443

<210> SEQ ID NO 37
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 37
atgcagagaa gcccccctgga gaaggccagc gtggtgagca agctgttctt cagctggacc 60
agacccatcc tgagaaaggg ctacagacag agactggagc tgagcgacat ctaccagatc 120
cccagcgtgg acagcgccga caacctgagc gagaagctgg agagagagtg ggacagagag 180
ctggccagca agaagaaccc caagctgatc aacgccctga gaagatgctt cttctggaga 240
ttcatgttct acggcatctt cctgtacctg ggcgaggtga ccaaggccgt gcagcccctg 300
ctgctgggca gaatcatcgc cagctacgac cccgacaaca aggaggagag aagcatcgcc 360
atctacctgg gcatcggcct gtgcctgctg ttcatcgtga gaaccctgct gctgcacccc 420
gccatcttcg gcctgcacca catcggcatg cagatgagaa tcgccatgtt cagcctgatc 480
tacaagaaga ccctgaagct gagcagcaga gtgctggaca agatcagcat cggccagctg 540
gtgagcctgc tgagcaacaa cctgaacaag ttcgacgagg gcctggccct ggcccacttc 600
gtgtggatcg cccccctgca ggtggccctg ctgatgggcc tgatctggga gctgctgcag 660
gccagcgcct tctgcggcct gggcttcctg atcgtgctgg ccctgttcca ggccggcctg 720
ggcagaatga tgatgaagta cagggaccag agagccggca agatcagcga gagactggtg 780
atcaccagcg agatgatcga gaacatccag agcgtgaagg cctactgctg ggaggaggcc 840
atggagaaga tgatcgagaa cctgagacag accgagctga agctgaccag aaaggccgcc 900
tacgtgagat acttcaacag cagcgccttc ttcttcagcg gcttcttcgt ggtgttcctg 960
agcgtgctgc cctacgccct gatcaagggc atcatcctga gaaagatctt caccaccatc 1020
agcttctgca tcgtgctgag aatggccgtg accagacagt tcccctgggc cgtgcagacc 1080
tggtacgaca gcctgggcgc catcaacaag atccaggact tcctgcagaa gcaggagtac 1140
aagaccctgg agtacaacct gaccaccacc gaggtggtga tggagaacgt gaccgccttc 1200
tgggaggagg gcttcggcga gctgttcgag aaggccaagc agaacaacaa caacagaaag 1260
accagcaacg gcgacgacag cctgttcttc agcaacttca gcctgctggg cacccccgtg 1320
ctgaaggaca tcaacttcaa gatcgagaga ggccagctgc tggccgtggc cggcagcacc 1380
ggcgccggca agaccagcct gctgatggtg atcatgggcg agctggagcc cagcgagggc 1440
aagatcaagc acagcggcag aatcagcttc tgcagccagt tcagctggat catgcccggc 1500
accatcaagg agaacatcat cttcggcgtg agctacgacg agtacagata cagaagcgtg 1560
atcaaggcct gccagctgga ggaggacatc agcaagttcg ccgagaagga caacatcgtg 1620
ctgggcgagg gcggcatcac cctgagcggc ggccagagag ccagaatcag cctggccaga 1680
gccgtgtaca aggacgccga cctgtacctg ctggacagcc ccttcggcta cctggacgtg 1740
ctgaccgaga aggagatctt cgagagctgc gtgtgcaagc tgatggccaa caagaccaga 1800
atcctggtga ccagcaagat ggagcacctg aagaaggccg acaagatcct gatcctgcac 1860
gagggcagca gctacttcta cggcaccttc agcgagctgc agaacctgca gcccgacttc 1920
agcagcaagc tgatgggctg cgacagcttc gaccagttca gcgccgagag aagaaacagc 1980
atcctgaccg agaccctgca cagattcagc ctggagggcg acgcccccgt gagctggacc 2040
gagaccaaga agcagagctt caagcagacc ggcgagttcg gcgagaagag aaagaacagc 2100
atcctgaacc ccatcaacag catcagaaag ttcagcatcg tgcagaagac cccccctgcag 2160
atgaacggca tcgaggagga cagcgacgag cccctggaga gaagactgag cctggtgccc 2220
gacagcgagc agggcgaggc catcctgccc agaatcagcg tgatcagcac cggccccacc 2280
ctgcaggcca gaagaagaca gagcgtgctg aacctgatga cccacagcgt gaaccagggc 2340
cagaacatcc acagaaagac caccgccagc accagaaagg tgagcctggc cccccaggcc 2400
aacctgaccg agctggacat ctacagcaga agactgagcc aggagaccgg cctggagatc 2460
agcgaggaga tcaacgagga ggacctgaag gagtgcttct tcgacgacat ggagagcatc 2520
cccgccgtga ccacctggaa cacctacctg agatacatca ccgtgcacaa gagcctgatc 2580
ttcgtgctga tctggtgcct ggtgatcttc ctggccgagg tggccgccag cctggtggtg 2640
ctgtggctgc tgggcaacac ccccctgcag gacaagggca acagcaccca cagcagaaac 2700
aacagctacg ccgtgatcat caccagcacc agcagctact acgtgttcta catctacgtg 2760
ggcgtggccg acaccctgct ggccatgggc ttcttcagag gcctgcccct ggtgcacacc 2820
ctgatcaccg tgagcaagat cctgcaccac aagatgctgc acagcgtgct gcaggccccc 2880
atgagcaccc tgaacaccct gaaggccggc ggcatcctga acagattcag caaggacatc 2940
gccatcctgg acgacctgct gcccctgacc atcttcgact tcatccagct gctgctgatc 3000
gtgatcggcg ccatcgccgt ggtggccgtg ctgcagccct acatcttcgt ggccaccgtg 3060
cccgtgatcg tggccttcat catgctgaga gcctacttcc tgcagaccag ccagcagctg 3120
aagcagctgg agagcgaggg caggagcccc atcttcaccc acctggtgac cagcctgaag 3180
ggcctgtgga ccctgagagc cttcggcaga cagccctact tcgagaccct gttccacaag 3240
gccctgaacc tgcacaccgc caactggttc ctgtacctga gcaccctgag atggttccag 3300
atgagaatcg agatgatctt cgtgatcttc ttcatcgccg tgaccttcat cagcatcctg 3360
accaccggcg agggcgaggg cagagtgggc atcatcctga ccctggccat gaacatcatg 3420
agcaccctgc agtgggccgt gaacagcagc atcgacgtgg acagcctgat gagaagcgtg 3480
agcagagtgt tcaagttcat cgacatgccc accgagggca agcccaccaa gagcaccaag 3540
ccctacaaga acggccagct gagcaaggtg atgatcatcg agaacagcca cgtgaagaag 3600
gacgacatct ggcccagcgg cggccagatg accgtgaagg acctgaccgc caagtacacc 3660
gagggcggca acgccatcct ggagaacatc agcttcagca tcagccccgg ccagagagtg 3720
ggcctgctgg gcagaaccgg cagcggcaag agcaccctgc tgagcgcctt cctgagactg 3780

-continued ctgaacaccg agggcgagat ccagatcgac ggcgtgagct gggacagcat caccctgcag 3840
cagtggagaa aggccttcgg cgtgatcccc cagaaggtgt tcatcttcag cggcaccttc 3900
agaaagaacc tggaccccta cgagcagtgg agcgaccagg agatctggaa ggtggccgac 3960
gaggtgggcc tgagaagcgt gatcgagcag ttccccggca agctggactt cgtgctggtg 4020
gacggcggct gcgtgctgag ccacggccac aagcagctga tgtgcctggc cagaagcgtg 4080
ctgagcaagg ccaagatcct gctgctggac gagcccagcg cccacctgga ccccgtgacc 4140
taccagatca tcagaagaac cctgaagcag gccttcgccg actgcaccgt gatcctgtgc 4200
gagcacagaa tcgaggccat gctggagtgc cagcagttcc tggtgatcga ggagaacaag 4260
gtgagacagt acgacagcat ccagaagctg ctgaacgaga gaagcctgtt cagacaggcc 4320
atcagcccca gcgacagagt gaagctgttc ccccacagaa acagcagcaa gtgcaagagc 4380
aagccccaga tcgccgccct gaaggaggag accgaggagg aggtgcagga caccagactg 4440
tga 4443

<210> SEQ ID NO 38
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 38
atgcagaggt cacctctgga aaaggctagc gtggtcagca agctattttt ttcctggacc 60 cgccccgatac tcaggaaggg ctaccgacag cggctggagc tgagtgacat ttatcagatt 120
ccctccgtcg attccgctga caacctgtct gagaaactgg agcgggaatg ggatagggaa 180
ctggcgtcca aaaaaaaccc caaactcatc aatgcactcc gcagatgctt cttctggcgg 240
tttatgtttt atggcatatt cctgtatctg ggggaggtga cgaaagccgt gcagccgctg 300
ctgcttggtc gcattatcgc gtcatacgat ccagataaca aggaggaaag aagtatcgct 360
atctatctcg ggatagggct gtgcctgctc ttcattgtgc ggactcttct cttgcacccc 420
gccattttcg gtctgcatca tataggtatg cagatgagaa ttgcgatgtt ctcattgatt 480
tacaaaaaaa cgcttaagct aagttcaagg gtgctagata agatatcgat cggccagctg 540
gtgtctctgc ttagcaacaa cctcaataaa ttcgacgaag gccttgcact ggcccacttc 600
gtgtggatcg cccctctgca ggtggctctg ctgatggggt taatatggga gctgttgcag 660
gcctccgctt tttgtggcct ggggtttctc atcgtgttgg ccttgtttca ggcagggctg 720
ggacgtatga tgatgaaata tagggatcag agggctggca aaatctctga gcgcctggtt 780
attacgagtg aaatgattga gaacatccag tcagtgaagg cctattgctg ggaggaggcc 840
atggaaaaaa tgattgagaa cctacgccag actgagctga agttaaccag aaaagccgcc 900
tatgtgcgct actttaacag tagcgcattt ttcttctccg gtttttttcgt ggtgtttctt 960 agtgtgttgc cgtatgcctt aatcaaggga ataatactcc ggaagatttt cactaccatc 1020
agcttctgta tcgtgttgcg gatggccgtc acccggcagt ttccctgggc agtacagact 1080
tggtacgatt ctctcggagc aattaacaaa atccaagact ttctacaaaa gcaggagtac 1140
aagaccctgg agtacaatct gaccaccaca gaagtcgtaa tggagaatgt aactgccttc 1200
tgggaagagg gctttggcga actctttgaa aaggccaagc agaacaataa caaccggaag 1260
acctccaacg gggacgacag cttatttttc agcaattttt ctttgctcgg gacccctgta 1320
ctgaaagata ttaactttaa gatcgagcgc ggacaactcc tggctgtcgc cggcagcact 1380

-continued

```
ggagctggaa aaacatcact gcttatggtg ataatgggag aactcgaacc aagcgaggga   1440
aaaataaagc actctggacg gattagtttt tgctcccagt tctcgtggat aatgcctggc   1500
accattaagg agaatatcat ctttggagtg agttacgacg aataccggta ccggtccgtt   1560
atcaaggctt gtcaactcga ggaggacatt tctaaattcg ccgaaaaaga taatatagtg   1620
ctgggcgaag gaggcattac actgagcggg ggtcagagag ctcgaattag cctcgcccga   1680
gcagtctata aagacgccga tctttacctg ctggattccc cttttgggta tttggatgtt   1740
ctgacagaga aggaaatctt tgaatcatgt gtctgtaaac tgatggccaa taagactagg   1800
attctagtga cttcgaaaat ggagcacctg aaaaaagcgg acaaaattct gatactccat   1860
gaagggtctt cctacttcta cggcaccttc tcagagttgc agaacttaca acctgatttt   1920
tcatctaagc ttatggggtg cgactcgttt gaccagttct ccgctgaaag acgaaacagc   1980
atcttaacgg aaactcttca caggttctca ttagagggag atgcgccggt gtcctggaca   2040
gagacaaaaa aacagtcttt caaacagaca ggagagtttg gcgagaagag aaaaaactca   2100
atcctcaatc ccatcaattc tattagaaag tttagcatcg tccaaaaaac accattgcag   2160
atgaatggga ttgaggagga cagtgatgag cctttggaac gaagactgtc cctggtaccc   2220
gatagcgaac agggtgaggc catccttcct aggatctcgg tcataagtac agggcccaca   2280
ctgcaggcca ggcgacgtca aagtgtcctc aatcttatga cgcacagtgt gaatcagggg   2340
cagaacatcc atcgtaagac gacagcttca actcgaaagg tcagtctagc tccacaagcc   2400
aatcttacag agctggacat ttattcccgc cgcctcagtc aggagaccgg attggaaata   2460
tcagaggaaa ttaatgaaga ggatctgaag gaatgcttct ttgatgacat ggaatcgatc   2520
cccgctgtta ctacctggaa cacatatctg agatatatta ccgtccataa gagcttaatc   2580
tttgtactga tatggtgctt ggtgattttc ctggcagagg ttgcggcgag tttggtcgtg   2640
ctatggctcc ttggaaacac tcccctgcag gataagggga actccactca tagcaggaat   2700
aacagctatg ccgtgatcat cacctctacc tcctcttatt acgtgtttta catatacgtc   2760
ggtgttgcgg ataccctgtt ggcaatgggg ttctttagag gactacccct agttcacacc   2820
ctgatcaccg tttcgaagat cttgcaccac aagatgcttc atagcgttct ccaagctcct   2880
atgagcaccc ttaatacact gaaagcagga ggtatcctta accgcttttc caaagacatc   2940
gctatactcg acgatttgct cccattgacc atcttcgact tcattcagct gctcctcatt   3000
gtgatcggcg ccattgccgt ggtcgcagtg ttacagccat atattttcgt agccaccgtg   3060
cccgtcatcg tggcatttat catgctgcgc gcatatttct tacagacatc tcagcaactg   3120
aagcagctgg aatctgaggg cagatctcct atttttacac acctggttac cagcctgaag   3180
ggcctgtgga ccctgcgtgc tttcggtcgc caaccctact ttgagactct cttccataag   3240
gctctgaatt tacatactgc caattggttc ctatacctta gtacccttcg gtggttccag   3300
atgcggatag aaatgatctt cgtgattttc ttcatcgcag tcactttcat ctctattttg   3360
acgaccggtg agggcgaggg cagggtgggc atcattctga ctttggccat gaacattatg   3420
tcaacactcc agtgggccgt taattcaagc attgatgtgg attccttgat gcgttccgtc   3480
agcagggtat ttaaattcat agacatgccc accgagggca agccaacaaa atctaccaag   3540
ccatacaaaa atggccaact aagcaaggtc atgattatcg agaattctca tgtgaaaaag   3600
gacgacattt ggccttccgg gggtcaaatg actgtaaagg acctgacggc taaatacact   3660
gagggcggta atgctatctt ggagaacatc tctttcagca tctcccctgg ccagagagtg   3720
```

ggactgctcg ggcggacagg ctccggaaag tctacgctcc tttcagcatt ccttagactt 3780
ctgaacaccg aaggtgagat tcagattgac ggggtctctt gggactccat cacacttcag 3840
caatggagga aggcattcgg tgtaatcccc caaaaggttt ttatcttctc cggaacattt 3900
cgtaagaatc tggacccgta cgagcagtgg tcagatcagg agatctggaa agtagcagac 3960
gaggtcgggc tacggagcgt tattgaacag tttcctggca aactggactt cgttttggtg 4020
gacggaggct gtgtgctgag tcacggccat aaacaactga tgtgcttagc taggtctgtt 4080
ctcagcaagg caaagatttt actgctggat gaaccaagcg cccaccttga tccagtgaca 4140
tatcaaatca tcagaagaac tcttaaacag gcgttcgccg actgcacagt gatcctgtgt 4200
gagcacagaa tagaagccat gctggaatgt caacagtttc tcgtgattga ggagaacaag 4260
gtgcgccagt acgatagcat ccagaagtta ctcaatgaaa ggtcactctt caggcaggcc 4320
atctcaccca gcgaccgcgt taagctgttt ccacaccgaa acagttccaa gtgcaaaagt 4380
aagccacaga ttgctgcact gaaggaagag acagaagaag aagttcagga cactcggctc 4440
tga 4443

<210> SEQ ID NO 39
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 39
atgcagagga gcccactgga gaaagcctcc gtggtgagta aactcttttt tagttggacc 60
agacccatcc tgcgaaaagg atacaggcag cgcctcgagt tgtcagatat ctaccagatt 120
ccttctgtgg actcagctga caatttgagt gagaagctgg agcgggagtg ggatagagag 180
ctggcgagca aaaaaaaccc caagcttatc aatgctctgc gccgctgctt tttctggagg 240
ttcatgtttt atgggatctt cctgtacctg ggggaggtca ccaaagctgt tcagccgctc 300
cttcttggcc gcatcatcgc cagctatgac cctgataata aagaagaaag gtctattgct 360
atttatctgg gaattggcct ctgcttgctc ttcatcgtcc gcacccttct gctgcaccct 420
gccatttttg gccttcacca catcggcatg caaatgagaa ttgccatgtt ctccctcatt 480
tacaaaaaga ccctgaaact ttcctcaaga gtgttagata aaatatccat tggtcagctg 540
gtcagcctgc tgtccaacaa tcttaacaaa tttgatgaag gcttggcgct ggcccacttc 600
gtgtggattg cacctctgca ggtggccctg ttgatgggac ttatatggga gctgcttcaa 660
gcctctgctt tctgtgggct gggctttttg attgtactgg cactttttca ggctgggctc 720
ggaagaatga tgatgaaata cagagatcag cgggccggga agatatcaga gcgacttgtg 780
atcaccagtg aaatgattga aaatattcag agcgtgaaag cctactgctg ggaagaagcc 840
atggagaaga tgattgagaa cctgaggcag acagagctca agctcactcg gaaggctgct 900
tatgttcgct atttcaacag cagcgccttc ttcttcagtg gcttctttgt tgtcttcctg 960
tctgttctgc catatgcact gataaaaggc attattttac gaaagatctt caccaccatc 1020
agtttttgca tcgttctcag gatggccgtc acaagacagt tcccctgggc tgtgcagacc 1080
tggtacgatt ccttgggggc catcaacaag attcaagatt tcttgcaaaa acaagaatat 1140
aaaactttag aatacaacct caccaccact gaagtggtca tggaaaatgt gacagccttt 1200
tgggaggagg gttttggaga attgttcgag aaggcaaagc agaataacaa caacaggaag 1260
acgagcaatg ggacgactc tctcttcttc agcaactttt cactgctcgg gacccctgtg 1320

-continued

```
ttgaaagata taaacttcaa gatcgagagg ggccagctct tggctgtggc aggctccact   1380
ggagctggta aaacatctct tctcatggtg atcatggggg aactggagcc ttccgaagga   1440
aaaatcaagc acagtgggag aatctcattc tgcagccagt tttcctggat catgcccggc   1500
accattaagg aaaacatcat atttggagtg tcctatgatg agtaccgcta ccggtcagtc   1560
atcaaagcct gtcagttgga ggaggacatc tccaagtttg cagagaaaga caacattgtg   1620
cttggagagg ggggtatcac tctttctgga ggacaaagag ccaggatctc tttggcccgg   1680
gcagtctaca aggatgcaga cctctacttg ttggacagtc ccttcggcta cctcgacgtg   1740
ctgactgaaa aagaaatttt tgaaagctgt gtgtgcaaac tgatggcaaa caagaccagg   1800
attcttgtca ccagcaagat ggaacatctg aagaaagcgg acaaaattct gattctgcat   1860
gaagggagct cctacttcta tggaacattt agcgagcttc agaacctaca gccagacttc   1920
tcctccaaat taatgggctg tgactccttc gaccagttct ctgcagaaag aagaaactct   1980
atactcacag agaccctcca ccgcttctcc cttgagggag atgccccagt ttcttggaca   2040
gaaaccaaga agcagtcctt taagcagact ggcgagtttg gtgaaaagag gaaaaattca   2100
attctcaatc caattaacag tattcgcaag ttcagcattg tccagaagac acccctccag   2160
atgaatggca tcgaagaaga tagtgacgag ccgctggaga gacggctgag tctggtgcca   2220
gattcagaac agggggaggc catcctgccc cggatcagcg tcatttccac aggccccaca   2280
ttacaagcac ggcgccggca gagtgtttta aatctcatga cccattcagt gaaccagggc   2340
caaaatatcc acaggaagac tacagcttct acccggaaag tgtctctggc ccctcaggcc   2400
aatctgaccg agctggacat ctacagcagg aggctctccc aggaaacagg gctggaaata   2460
tctgaagaga ttaatgaaga ggatcttaaa gagtgcttct ttgatgacat ggagagcatc   2520
cccgcggtga ccacatggaa cacctacctt agatatatta ctgtccacaa gagcctcata   2580
tttgtcctca tctggtgcct ggttatttc ctcgctgagg tggcggccag tcttgttgtg    2640
ctctggctgc tgggcaacac tcctctccag gacaagggca atagtactca cagcagaaat   2700
aattcttatg ccgtcatcat tacaagcacc tccagctact acgtgttcta catctatgtg   2760
ggcgtggctg acaccctcct ggccatgggt ttcttccggg gcctgccttt ggtgcacacc   2820
ctcatcacag tgtcaaaaat tctgcaccat aaaatgcttc attctgtcct gcaggcaccc   2880
atgagcactt tgaacacatt gaaggctggc ggcatcctca acagattttc taaagatatt   2940
gctatcctgg atgatctcct cccccctgaca atctttgact ttatccagct tctgctgatc  3000
gtgattggag ccatagcagt ggttgctgtc ctgcagccct acatttttgt ggccaccgtg   3060
cccgtgattg ttgcctttat tatgctcaga gcttacttcc tgcaaacttc tcaacagctc   3120
aaacagctag aatctgaggg ccggagcccc atttttaccc acctggtgac ttccctgaag   3180
ggactgtgga ctctgagagc attcgggcga cagccttact ttgagacact gttccacaag   3240
gccctgaact tgcacactgc caactggttt ctttacctga gcacactccg ctggttccag   3300
atgcggatag agatgatctt cgtcatcttt tttatagctg taaccttcat ttctatcctt   3360
acaacaggag aaggagaggg cagggtggga atcatcctca cgctggctat gaacataatg   3420
tccaccttgc agtgggccgt gaattccagt atagatgtgg attctctaat gaggagtgtc   3480
tcccgggtgt ttaaattcat tgatatgcct actgagggga aacccaccaa gtcaacaaaa   3540
ccttataaga atggacagct gagcaaggtg atgataattg agaacagcca cgtgaagaag   3600
gatgacattt ggcccagcgg gggccagatg actgtgaagg acctgacggc caagtacacc   3660
```

-continued

```
gaaggtggaa atgccatttt ggaaaacatc agcttctcaa tctctcctgg gcagagagtt   3720

ggattgctgg gtcgcacggg cagcggcaaa tcaaccctgc tcagtgcctt ccttcggctc   3780

ctgaatacag aaggcgaaat ccaaattgac ggggtgagct gggacagcat caccctgcag   3840

cagtggagaa aagcatttgg ggtcattcca cagaaagttt tcatcttctc tggcactttc   3900

agaaagaacc tggaccccta tgagcagtgg agcgaccagg agatctggaa ggttgcagat   3960

gaagttggcc tgcggagtgt gatagaacaa tttcctggca agctggattt tgtgctggta   4020

gatggaggct gcgtgctgtc ccacggccac aaacagctga tgtgcctcgc ccgctccgtt   4080

ctttcaaagg ccaaaatctt gcttttggat gagcccagtg ctcacctcga cccagtgacc   4140

tatcagataa tccgcaggac cttaaagcaa gcttttgccg actgcaccgt catactgtgt   4200

gagcaccgga ttgaagcaat gctggaatgc cagcagtttc tggtgatcga ggagaataag   4260

gtccggcagt acgacagcat ccagaagttg ttgaatgagc gcagcctttt ccgccaggcc   4320

atctccccat ctgacagagt caagctgttt ccacatagga actcctctaa gtgcaagtcc   4380

aagccccaga tcgctgccct caaggaggaa actgaggaag aggtgcagga tacccgcctg   4440

tga                                                                 4443
```

```
<210> SEQ ID NO 40
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 40

atgcaacgga gtcctctgga aaaagcctct gtcgtatcta agcttttctt cagttggaca     60

cgcccgattt tgagaaaggg ttatcggcaa cgcttggaac ttagtgacat ctaccaaatt    120

ccaagtgtag actcagccga taacttgagc gaaaagctcg aacgagagtg ggatcgagaa    180

ctggctagca aaaaaaatcc caaactcata aatgccctgc gacgctgttt cttttggcga    240

tttatgtttt acggtatttt cctttatttg ggtgaggtca cgaaggctgt acagccactg    300

ctgctgggtc gcatcattgc ctcttacgac cctgacaaca aagaggagcg gtcaatagct    360

atctaccttg gtataggact ttgcttgctc ttcatagtcc gcacgttgct tctccaccct    420

gctatatttg gtctccatca cattgggatg caaatgcgga tcgcgatgtt cagtcttata    480

tataaaaaga ctcttaaact ttccagccgg gttctggata agatctctat tggtcaactg    540

gtatctcttt tgtctaacaa cctgaataag ttcgacgagg gccttgcatt ggcccatttt    600

gtatggattg ccccttttgca agtcgccctc ctgatgggat tgatctggga actcctgcaa    660

gctagtgctt tttgcggatt gggattcctc atagtccttg cgctctttca ggcgggactt    720

ggacgcatga tgatgaagta tcgcgaccaa cgagctggca agatcagtga acggcttgta    780

ataaccagtg aaatgataga gaacatccag agcgtaaaag cttactgttg ggaagaagcg    840

atggaaaaga tgattgagaa ccttcgccag acagaactta aacttacacg aaaggccgct    900

tatgtccggt acttcaactc ttcagcattt ttttttagtg gcttctttgt agtgttcctg    960

tccgtccttc cgtatgcact tatcaagggt ataatactta ggaaaatctt cacaacaatc   1020

agtttttgca tagtccttcg catggcagta actcgccaat ttccctgggc agttcagacg   1080

tggtacgact cacttggcgc aattaacaaa attcaagatt tcctccaaaa gcaagagtat   1140

aaaaccttgg aatacaacct taccaccaca gaagttgtaa tggaaaatgt cacagccttc   1200

tgggaggaag gtttcggcga actttttgag aaggcgaagc aaaataacaa taatcggaaa   1260
```

```
acatcaaacg gtgacgattc actgttcttt tctaacttta gccttcttgg gacgcccgtc   1320
ctgaaggaca taaactttaa gattgaacgg ggtcaacttc tcgcggtcgc agggagtact   1380
ggagcgggga aaacgagcct gctgatggtg ataatggggg agttggagcc ctcagaaggc   1440
aagatcaagc atagtggtag aattagcttc tgcagtcaat ttagttggat tatgccgggc   1500
acgatcaaag aaaatataat ctttggggta tcctacgatg aatacaggta ccgatcagtg   1560
ataaaagcgt gccagcttga agaagacatt tcaaagtttg ctgagaagga taatatcgta   1620
cttggagaag gaggtatcac cctgtctggg ggtcaacgag cgaggatctc cctggcacgc   1680
gccgtctaca aggacgcgga cctctatctg ttggattcac cgttcggata tttggacgtg   1740
cttacggaga aagaaatatt tgagagctgt gtttgcaagc tcatggcaaa taaaaccaga   1800
atattggtta caagcaagat ggagcatctt aagaaagcag ataaaatcct gatattgcac   1860
gagggctctt catacttcta cgggacgttt tctgagttgc agaacctcca gccggatttc   1920
agctctaagc tgatgggctg tgattccttt gatcagttta gtgcggaaag acgaaacagt   1980
atactcaccg aaacactgca caggttctct ctggagggcg acgccccggt ttcctggaca   2040
gagacgaaga agcagtcctt caaacagaca ggcgagtttg gggagaaaag gaaaaatagc   2100
atactcaacc cgattaacag cattcgcaag ttcagtatag tacaaaagac cccgttgcag   2160
atgaacggta tagaggaaga ttctgatgag ccactggaaa gacggctttc tctcgttccg   2220
gacagtgaac agggagaggc aatactgcct cggatcagcg ttatctctac aggacctact   2280
ttgcaagctc ggcgccgaca gtcagtcttg aatcttatga ctcatagtgt taatcaaggc   2340
cagaatatcc atcgcaagac caccgcaagt acaaggaaag tgagcttggc acctcaagca   2400
aaccttactg aacttgatat ctactcacgg cgactttcac aggagaccgg acttgaaatt   2460
agtgaagaaa ttaacgagga ggacctcaag gagtgcttct tcgatgacat ggaatcaatc   2520
cccgcagtca caacctggaa cacttatctg aggtatataa cagttcacaa gagcctcatt   2580
tttgtactta tttggtgttt ggtaattttc ctggcggagg ttgctgcttc tttggtcgtc   2640
ctttggctcc tcgggaatac accgctccaa gacaaaggca actctaccca tagtaggaac   2700
aattcatatg cagtgattat aaccagtaca tcatcttatt acgttttcta tatttatgtc   2760
ggggtagctg acacgctgtt ggcgatgggc ttctttaggg gcctcccctt ggtacacacc   2820
cttatcacgg tgagtaaaat cctgcatcac aaaatgcttc attctgtact ccaagcgccg   2880
atgagtacgc ttaatacgct gaaagcagga gggatactga atcggttcag caaggacatc   2940
gccattctgg atgacctgct tccattgaca atatttgatt tcattcagct ccttctcata   3000
gttattggag ccatagcggt ggtggctgtg cttcagcctt atatattcgt tgccacagtt   3060
cccgttatag tggcatttat aatgctcagg gcctactttc tccagacttc ccagcagttg   3120
aagcaactcg aatcagaagg aaggtcacct attttcacac atcttgtgac ttccttgaag   3180
ggcttgtgga cgctgcgggc cttcggaaga caaccatatt ttgaaactct cttccacaaa   3240
gctttgaatc ttcatactgc gaactggttc ctgtatttga gtactttgcg ctggttccag   3300
atgaggatag aaatgatatt cgttatcttc tttatcgcgg ttacgttcat aagtatcctc   3360
actacggggg agggtgaggg tagagtgggc ataatactga ccctcgccat gaacattatg   3420
tccaccctgc agtgggcggt aaacagcagc atagatgtgg attctttgat gcgcagtgtg   3480
agcagggttt ttaagtttat cgatatgccg acggaaggaa agcccactaa aagcacgaaa   3540
ccctataaaa atggacagct tagcaaagta atgataatcg agaatagcca tgtgaaaaag   3600
```

-continued

```
gatgacatat ggccttccgg aggccaaatg actgttaaag atctgaccgc taaatatacc   3660

gagggcggca acgcaatact cgaaaacata agcttttcca taagccccgg ccaacgcgtg   3720

ggtcttctgg ggaggactgg ctccggaaaa tcaacgttgc ttagcgcgtt tttgcggctc   3780

cttaacactg aaggtgagat ccaaatagat ggcgttagtt gggactctat aacactgcaa   3840

caatggcgga aagctttcgg cgtcatacct cagaaggtgt tcatctttag cggaacgttc   3900

aggaagaact tggatcccta cgaacaatgg agtgatcaag aaatatggaa agtggcagat   3960

gaggtaggct tgcgcagtgt cattgaacaa ttcccaggga aactcgactt tgtactggtg   4020

gacggcggtt gcgtcttgtc acacgggcac aaacagttga tgtgtttggc ccgcagtgtt   4080

ttgtctaagg cgaagattct gttgctcgac gaaccgagtg ctcatcttga tcccgtcacc   4140

taccaaatca tcagaaggac gttgaagcaa gctttcgccg actgcactgt aatcctttgt   4200

gagcatagga tcgaagcaat gctcgagtgc caacagttct tggttataga ggagaataag   4260

gttcggcaat acgactcaat acagaaactg cttaatgagc ggtcactctt tcgacaagct   4320

atctctccta gtgacagggt aaagcttttt cctcatcgga attccagcaa gtgtaagagt   4380

aaaccacaga tcgccgccct taaagaggag accgaagaag aggtgcagga tacgagactt   4440

tag                                                                  4443
```

<210> SEQ ID NO 41
<211> LENGTH: 1480
<212> TYPE: PRT
<213> ORGANISM: Artificial Sequence
<220> FEATURE:
<223> OTHER INFORMATION: Synthetic polypeptide

<400> SEQUENCE: 41

```
Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205
```

-continued

```
Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Val Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
        515                 520                 525

Asp Ile Ser Lys Phe Ala Glu Lys Asp Asn Ile Val Leu Gly Glu Gly
    530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu His Glu Gly Ser Ser
    610                 615                 620

Tyr Phe Tyr Gly Thr Phe Ser Glu Leu Gln Asn Leu Gln Pro Asp Phe
```

```
625                 630                 635                 640

Ser Ser Lys Leu Met Gly Cys Asp Ser Phe Asp Gln Phe Ser Ala Glu
                645                 650                 655

Arg Arg Asn Asp Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
        675                 680                 685

Gln Thr Gly Glu Phe Gly Glu Lys Arg Lys Asn Ser Ile Leu Asn Pro
    690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Asp Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
        755                 760                 765

Val Leu Asn Leu Met Thr His Ser Val Asn Gln Gly Gln Asn Ile His
    770                 775                 780

Arg Lys Thr Thr Ala Ser Thr Arg Lys Val Asp Leu Ala Pro Gln Ala
785                 790                 795                 800

Asn Leu Thr Glu Leu Asp Ile Tyr Ser Arg Arg Leu Asp Gln Glu Thr
                805                 810                 815

Gly Leu Glu Ile Ser Glu Glu Ile Asn Glu Glu Asp Leu Lys Glu Cys
            820                 825                 830

Phe Phe Asp Asp Met Glu Ser Ile Pro Ala Val Thr Thr Trp Asn Thr
        835                 840                 845

Tyr Leu Arg Tyr Ile Thr Val His Lys Ser Leu Ile Phe Val Leu Ile
    850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
        915                 920                 925

Met Gly Phe Phe Arg Gly Leu Pro Leu Val His Thr Leu Ile Thr Val
    930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile  Val Ile Gly Ala Ile  Ala Val Val
        995                 1000                 1005

Ala Val  Leu Gln Pro Tyr Ile  Phe Val Ala Thr Val  Pro Val Ile
    1010                 1015                 1020

Val Ala  Phe Ile Met Leu Arg  Ala Tyr Phe Leu Gln  Thr Ser Gln
    1025                 1030                 1035

Gln Leu  Lys Gln Leu Glu Ser  Glu Gly Arg Ser Pro  Ile Phe Thr
    1040                 1045                 1050
```

-continued

His Leu Val Thr Ser Leu Lys Gly Leu Trp Thr Leu Arg Ala Phe
1055 1060 1065

Gly Arg Gln Pro Tyr Phe Glu Thr Leu Phe His Lys Ala Leu Asn
1070 1075 1080

Leu His Thr Ala Asn Trp Phe Leu Tyr Leu Ser Thr Leu Arg Trp
1085 1090 1095

Phe Gln Met Arg Ile Glu Met Ile Phe Val Ile Phe Phe Ile Ala
1100 1105 1110

Val Thr Phe Ile Ser Ile Leu Thr Thr Gly Glu Gly Glu Gly Arg
1115 1120 1125

Val Gly Ile Ile Leu Thr Leu Ala Met Asn Ile Met Ser Thr Leu
1130 1135 1140

Gln Trp Ala Val Asn Ser Ser Ile Asp Val Asp Ser Leu Met Arg
1145 1150 1155

Ser Val Ser Arg Val Phe Lys Phe Ile Asp Met Pro Thr Glu Gly
1160 1165 1170

Lys Pro Thr Lys Ser Thr Lys Pro Tyr Lys Asn Gly Gln Leu Ser
1175 1180 1185

Lys Val Met Ile Ile Glu Asn Ser His Val Lys Lys Asp Asp Ile
1190 1195 1200

Trp Pro Ser Gly Gly Gln Met Thr Val Lys Asp Leu Thr Ala Lys
1205 1210 1215

Tyr Thr Glu Gly Gly Asn Ala Ile Leu Glu Asn Ile Ser Phe Ser
1220 1225 1230

Ile Ser Pro Gly Gln Arg Val Gly Leu Leu Gly Arg Thr Gly Ser
1235 1240 1245

Gly Lys Ser Thr Leu Leu Ser Ala Phe Leu Arg Leu Leu Asn Thr
1250 1255 1260

Glu Gly Glu Ile Gln Ile Asp Gly Val Ser Trp Asp Ser Ile Thr
1265 1270 1275

Leu Gln Gln Trp Arg Lys Ala Phe Gly Val Ile Pro Gln Lys Val
1280 1285 1290

Phe Ile Phe Ser Gly Thr Phe Arg Lys Asn Leu Asp Pro Tyr Glu
1295 1300 1305

Gln Trp Ser Asp Gln Glu Ile Trp Lys Val Ala Asp Glu Val Gly
1310 1315 1320

Leu Arg Ser Val Ile Glu Gln Phe Pro Gly Lys Leu Asp Phe Val
1325 1330 1335

Leu Val Asp Gly Gly Cys Val Leu Ser His Gly His Lys Gln Leu
1340 1345 1350

Met Cys Leu Ala Arg Ser Val Leu Ser Lys Ala Lys Ile Leu Leu
1355 1360 1365

Leu Asp Glu Pro Ser Ala His Leu Asp Pro Val Thr Tyr Gln Ile
1370 1375 1380

Ile Arg Arg Thr Leu Lys Gln Ala Phe Ala Asp Cys Thr Val Ile
1385 1390 1395

Leu Cys Glu His Arg Ile Glu Ala Met Leu Glu Cys Gln Gln Phe
1400 1405 1410

Leu Val Ile Glu Glu Asn Lys Val Arg Gln Tyr Asp Ser Ile Gln
1415 1420 1425

Lys Leu Leu Asn Glu Arg Ser Leu Phe Arg Gln Ala Ile Ser Pro
1430 1435 1440

Ser Asp Arg Val Lys Leu Phe Pro His Arg Asn Ser Ser Lys Cys
1445 1450 1455

Lys Ser Lys Pro Gln Ile Ala Ala Leu Lys Glu Glu Thr Glu Glu
1460 1465 1470

Glu Val Gln Asp Thr Arg Leu
1475 1480

<210> SEQ ID NO 42
<211> LENGTH: 1480
<212> TYPE: PRT
<213> ORGANISM: Artificial Sequence
<220> FEATURE:
<223> OTHER INFORMATION: Synthetic polypeptide

<400> SEQUENCE: 42

Met Gln Arg Ser Pro Leu Glu Lys Ala Ser Val Val Ser Lys Leu Phe
1 5 10 15

Phe Ser Trp Thr Arg Pro Ile Leu Arg Lys Gly Tyr Arg Gln Arg Leu
20 25 30

Glu Leu Ser Asp Ile Tyr Gln Ile Pro Ser Val Asp Ser Ala Asp Asn
35 40 45

Leu Ser Glu Lys Leu Glu Arg Glu Trp Asp Arg Glu Leu Ala Ser Lys
50 55 60

Lys Asn Pro Lys Leu Ile Asn Ala Leu Arg Arg Cys Phe Phe Trp Arg
65 70 75 80

Phe Met Phe Tyr Gly Ile Phe Leu Tyr Leu Gly Glu Val Thr Lys Ala
85 90 95

Val Gln Pro Leu Leu Leu Gly Arg Ile Ile Ala Ser Tyr Asp Pro Asp
100 105 110

Asn Lys Glu Glu Arg Ser Ile Ala Ile Tyr Leu Gly Ile Gly Leu Cys
115 120 125

Leu Leu Phe Ile Val Arg Thr Leu Leu Leu His Pro Ala Ile Phe Gly
130 135 140

Leu His His Ile Gly Met Gln Met Arg Ile Ala Met Phe Ser Leu Ile
145 150 155 160

Tyr Lys Lys Thr Leu Lys Leu Ser Ser Arg Val Leu Asp Lys Ile Ser
165 170 175

Ile Gly Gln Leu Val Ser Leu Leu Ser Asn Asn Leu Asn Lys Phe Asp
180 185 190

Glu Gly Leu Ala Leu Ala His Phe Val Trp Ile Ala Pro Leu Gln Val
195 200 205

Ala Leu Leu Met Gly Leu Ile Trp Glu Leu Leu Gln Ala Ser Ala Phe
210 215 220

Cys Gly Leu Gly Phe Leu Ile Val Leu Ala Leu Phe Gln Ala Gly Leu
225 230 235 240

Gly Arg Met Met Met Lys Tyr Arg Asp Gln Arg Ala Gly Lys Ile Ser
245 250 255

Glu Arg Leu Val Ile Thr Ser Glu Met Ile Glu Asn Ile Gln Ser Val
260 265 270

Lys Ala Tyr Cys Trp Glu Glu Ala Met Glu Lys Met Ile Glu Asn Leu
275 280 285

Arg Gln Thr Glu Leu Lys Leu Thr Arg Lys Ala Ala Tyr Val Arg Tyr
290 295 300

Phe Asn Ser Ser Ala Phe Phe Phe Ser Gly Phe Phe Val Val Phe Leu
305 310 315 320

-continued

```
Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Val Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
        515                 520                 525

Asp Ile Ser Lys Phe Ala Glu Lys Asp Asn Ile Val Leu Gly Glu Gly
    530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu His Glu Gly Ser Ser
    610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Asp Ile Leu Thr Glu Thr Leu His Arg Phe Ser Leu Glu
            660                 665                 670

Gly Asp Ala Pro Val Ser Trp Thr Glu Thr Lys Lys Gln Asp Phe Lys
        675                 680                 685

Gln Thr Gly Glu Phe Gly Glu Lys Arg Lys Asn Asp Ile Leu Asn Pro
    690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Asp Leu Val Pro Asp Ser Glu Gln Gly Glu Ala Ile Leu Pro Arg Ile
```

```
            740                 745                 750

Ser Val Ile Ser Thr Gly Pro Thr Leu Gln Ala Arg Arg Arg Gln Ser
        755                 760                 765

Val Leu Asn Leu Met Thr His Ser Val Asn Gln Gly Gln Asn Ile His
    770                 775                 780

Arg Lys Thr Thr Ala Ser Thr Arg Lys Val Asp Leu Ala Pro Gln Ala
785                 790                 795                 800

Asn Leu Thr Glu Leu Asp Ile Tyr Ser Arg Arg Leu Asp Gln Glu Thr
                805                 810                 815

Gly Leu Glu Ile Ser Glu Glu Ile Asn Glu Glu Asp Leu Lys Glu Cys
            820                 825                 830

Phe Phe Asp Asp Met Glu Ser Ile Pro Ala Val Thr Thr Trp Asn Thr
        835                 840                 845

Tyr Leu Arg Tyr Ile Thr Val His Lys Ser Leu Ile Phe Val Leu Ile
    850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
        915                 920                 925

Met Gly Phe Phe Arg Gly Leu Pro Leu Val His Thr Leu Ile Thr Val
    930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile  Val Ile Gly Ala Ile  Ala Val Val
        995                 1000                1005

Ala Val  Leu Gln Pro Tyr Ile  Phe Val Ala Thr Val  Pro Val Ile
    1010                1015                1020

Val Ala  Phe Ile Met Leu Arg  Ala Tyr Phe Leu Gln  Thr Ser Gln
    1025                1030                1035

Gln Leu  Lys Gln Leu Glu Ser  Glu Gly Arg Ser Pro  Ile Phe Thr
    1040                1045                1050

His Leu  Val Thr Ser Leu Lys  Gly Leu Trp Thr Leu  Arg Ala Phe
    1055                1060                1065

Gly Arg  Gln Pro Tyr Phe Glu  Thr Leu Phe His Lys  Ala Leu Asn
    1070                1075                1080

Leu His  Thr Ala Asn Trp Phe  Leu Tyr Leu Ser Thr  Leu Arg Trp
    1085                1090                1095

Phe Gln  Met Arg Ile Glu Met  Ile Phe Val Ile Phe  Phe Ile Ala
    1100                1105                1110

Val Thr  Phe Ile Ser Ile Leu  Thr Thr Gly Glu Gly  Glu Gly Arg
    1115                1120                1125

Val Gly  Ile Ile Leu Thr Leu  Ala Met Asn Ile Met  Ser Thr Leu
    1130                1135                1140

Gln Trp  Ala Val Asn Ser Ser  Ile Asp Val Asp Ser  Leu Met Arg
    1145                1150                1155
```

```
Ser Val  Ser Arg Val Phe Lys  Phe Ile Asp Met Pro  Thr Glu Gly
    1160                 1165                 1170

Lys Pro  Thr Lys Ser Thr Lys  Pro Tyr Lys Asn Gly  Gln Leu Ser
    1175                 1180                 1185

Lys Val  Met Ile Ile Glu Asn  Ser His Val Lys Lys  Asp Asp Ile
    1190                 1195                 1200

Trp Pro  Ser Gly Gly Gln Met  Thr Val Lys Asp Leu  Thr Ala Lys
    1205                 1210                 1215

Tyr Thr  Glu Gly Gly Asn Ala  Ile Leu Glu Asn Ile  Ser Phe Ser
    1220                 1225                 1230

Ile Ser  Pro Gly Gln Arg Val  Gly Leu Leu Gly Arg  Thr Gly Ser
    1235                 1240                 1245

Gly Lys  Ser Thr Leu Leu Ser  Ala Phe Leu Arg Leu  Leu Asn Thr
    1250                 1255                 1260

Glu Gly  Glu Ile Gln Ile Asp  Gly Val Ser Trp Asp  Ser Ile Thr
    1265                 1270                 1275

Leu Gln  Gln Trp Arg Lys Ala  Phe Gly Val Ile Pro  Gln Lys Val
    1280                 1285                 1290

Phe Ile  Phe Ser Gly Thr Phe  Arg Lys Asn Leu Asp  Pro Tyr Glu
    1295                 1300                 1305

Gln Trp  Ser Asp Gln Glu Ile  Trp Lys Val Ala Asp  Glu Val Gly
    1310                 1315                 1320

Leu Arg  Ser Val Ile Glu Gln  Phe Pro Gly Lys Leu  Asp Phe Val
    1325                 1330                 1335

Leu Val  Asp Gly Gly Cys Val  Leu Ser His Gly His  Lys Gln Leu
    1340                 1345                 1350

Met Cys  Leu Ala Arg Ser Val  Leu Ser Lys Ala Lys  Ile Leu Leu
    1355                 1360                 1365

Leu Asp  Glu Pro Ser Ala His  Leu Asp Pro Val Thr  Tyr Gln Ile
    1370                 1375                 1380

Ile Arg  Arg Thr Leu Lys Gln  Ala Phe Ala Asp Cys  Thr Val Ile
    1385                 1390                 1395

Leu Cys  Glu His Arg Ile Glu  Ala Met Leu Glu Cys  Gln Gln Phe
    1400                 1405                 1410

Leu Val  Ile Glu Glu Asn Lys  Val Arg Gln Tyr Asp  Ser Ile Gln
    1415                 1420                 1425

Lys Leu  Leu Asn Glu Arg Ser  Leu Phe Arg Gln Ala  Ile Ser Pro
    1430                 1435                 1440

Ser Asp  Arg Val Lys Leu Phe  Pro His Arg Asn Ser  Ser Lys Cys
    1445                 1450                 1455

Lys Ser  Lys Pro Gln Ile Ala  Ala Leu Lys Glu Glu  Thr Glu Glu
    1460                 1465                 1470

Glu Val  Gln Asp Thr Arg Leu
    1475                 1480
```

<210> SEQ ID NO 43
<211> LENGTH: 1480
<212> TYPE: PRT
<213> ORGANISM: Artificial Sequence
<220> FEATURE:
<223> OTHER INFORMATION: Synthetic polypeptide

<400> SEQUENCE: 43

```
Met Gln Arg Ser Pro Leu Glu Lys Ala Ser Val Val Ser Lys Leu Phe
1               5                   10                  15
```

-continued

```
Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430
```

```
Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Val Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
        515                 520                 525

Asp Ile Ser Lys Phe Ala Glu Lys Asp Asn Ile Val Leu Gly Glu Gly
    530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu His Glu Gly Ser Ser
    610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
        675                 680                 685

Gln Thr Gly Glu Phe Gly Glu Lys Arg Lys Asn Ser Ile Leu Asn Pro
    690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
        755                 760                 765

Val Leu Asn Leu Met Thr His Ser Val Asn Gln Gly Gln Asn Ile His
    770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
            820                 825                 830

Phe Phe Asp Asp Met Glu Ser Ile Pro Ala Val Thr Thr Trp Asn Thr
        835                 840                 845

Tyr Leu Arg Tyr Ile Thr Val His Lys Ser Leu Ile Phe Val Leu Ile
```

-continued

```
    850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
        915                 920                 925

Met Gly Phe Phe Arg Gly Leu Pro Leu Val His Thr Leu Ile Thr Val
    930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Cys Asp Ile Ala Ile Leu Asp Asp Leu Leu Pro Leu Thr Ile Phe
            980                 985                 990

Asp Phe Ile Gln Leu Leu Leu Ile  Val Ile Gly Ala Ile  Ala Val Val
        995                 1000                1005

Ala Val  Leu Gln Pro Tyr Ile  Phe Val Ala Thr Val  Pro Val Ile
    1010                1015                1020

Val Ala  Phe Ile Met Leu Arg  Ala Tyr Phe Leu Gln  Thr Ser Gln
    1025                1030                1035

Gln Leu  Lys Gln Leu Glu Ser  Glu Gly Arg Ser Pro  Ile Phe Thr
    1040                1045                1050

His Leu  Val Thr Ser Leu Lys  Gly Leu Trp Thr Leu  Arg Ala Phe
    1055                1060                1065

Gly Arg  Gln Pro Tyr Phe Glu  Thr Leu Phe His Lys  Ala Leu Asn
    1070                1075                1080

Leu His  Thr Ala Asn Trp Phe  Leu Tyr Leu Ser Thr  Leu Arg Trp
    1085                1090                1095

Phe Gln  Met Arg Ile Glu Met  Ile Phe Val Ile Phe  Phe Ile Ala
    1100                1105                1110

Val Thr  Phe Ile Ser Ile Leu  Thr Thr Gly Glu Gly  Glu Gly Arg
    1115                1120                1125

Val Gly  Ile Ile Leu Thr Leu  Ala Met Asn Ile Met  Ser Thr Leu
    1130                1135                1140

Gln Trp  Ala Val Asn Ser Ser  Ile Asp Val Asp Ser  Leu Met Arg
    1145                1150                1155

Ser Val  Ser Arg Val Phe Lys  Phe Ile Asp Met Pro  Thr Glu Gly
    1160                1165                1170

Lys Pro  Thr Lys Ser Thr Lys  Pro Tyr Lys Asn Gly  Gln Leu Ser
    1175                1180                1185

Lys Val  Met Ile Ile Glu Asn  Ser His Val Lys Lys  Asp Asp Ile
    1190                1195                1200

Trp Pro  Ser Gly Gly Gln Met  Thr Val Lys Asp Leu  Thr Ala Lys
    1205                1210                1215

Tyr Thr  Glu Gly Gly Asn Ala  Ile Leu Glu Asn Ile  Ser Phe Ser
    1220                1225                1230

Ile Ser  Pro Gly Gln Arg Val  Gly Leu Leu Gly Arg  Thr Gly Ser
    1235                1240                1245

Gly Lys  Ser Thr Leu Leu Ser  Ala Phe Leu Arg Leu  Leu Asn Thr
    1250                1255                1260
```

```
Glu Gly  Glu Ile Gln Ile Asp  Gly Val Ser Trp Asp  Ser Ile Thr
    1265                 1270                 1275

Leu Gln  Gln Trp Arg Lys Ala  Phe Gly Val Ile Pro  Gln Lys Val
    1280                 1285                 1290

Phe Ile  Phe Ser Gly Thr Phe  Arg Lys Asn Leu Asp  Pro Tyr Glu
    1295                 1300                 1305

Gln Trp  Ser Asp Gln Glu Ile  Trp Lys Val Ala Asp  Glu Val Gly
    1310                 1315                 1320

Leu Arg  Ser Val Ile Glu Gln  Phe Pro Gly Lys Leu  Asp Phe Val
    1325                 1330                 1335

Leu Val  Asp Gly Gly Cys Val  Leu Ser His Gly His  Lys Gln Leu
    1340                 1345                 1350

Met Cys  Leu Ala Arg Ser Val  Leu Ser Lys Ala Lys  Ile Leu Leu
    1355                 1360                 1365

Leu Asp  Glu Pro Ser Ala His  Leu Asp Pro Val Thr  Tyr Gln Ile
    1370                 1375                 1380

Ile Arg  Arg Thr Leu Lys Gln  Ala Phe Ala Asp Cys  Thr Val Ile
    1385                 1390                 1395

Leu Cys  Glu His Arg Ile Glu  Ala Met Leu Glu Cys  Gln Gln Phe
    1400                 1405                 1410

Leu Val  Ile Glu Glu Asn Lys  Val Arg Gln Tyr Asp  Ser Ile Gln
    1415                 1420                 1425

Lys Leu  Leu Asn Glu Arg Ser  Leu Phe Arg Gln Ala  Ile Ser Pro
    1430                 1435                 1440

Ser Asp  Arg Val Lys Leu Phe  Pro His Arg Asn Ser  Ser Lys Cys
    1445                 1450                 1455

Lys Ser  Lys Pro Gln Ile Ala  Ala Leu Lys Glu Glu  Thr Glu Glu
    1460                 1465                 1470

Glu Val  Gln Asp Thr Arg Leu
    1475                 1480


<210> SEQ ID NO 44
<211> LENGTH: 1480
<212> TYPE: PRT
<213> ORGANISM: Artificial Sequence
<220> FEATURE:
<223> OTHER INFORMATION: Synthetic polypeptide

<400> SEQUENCE: 44

Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125
```

-continued

```
Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Val Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
        515                 520                 525

Asp Ile Ser Lys Phe Ala Glu Lys Asp Asn Ile Val Leu Gly Glu Gly
    530                 535                 540
```

-continued

```
Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu His Glu Gly Ser Ser
    610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
        675                 680                 685

Gln Thr Gly Glu Phe Gly Glu Lys Arg Lys Asn Ser Ile Leu Asn Pro
    690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
        755                 760                 765

Val Leu Asn Leu Met Thr His Ser Val Asn Gln Gly Gln Asn Ile His
    770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
            820                 825                 830

Phe Phe Asp Asp Met Glu Ser Ile Pro Ala Val Thr Thr Trp Asn Thr
        835                 840                 845

Tyr Leu Arg Tyr Ile Thr Val His Lys Ser Leu Ile Phe Val Leu Ile
    850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
        915                 920                 925

Met Gly Phe Phe Arg Gly Leu Pro Leu Val His Thr Leu Ile Thr Val
    930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
```

-continued

```
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile  Val Ile Gly Ala Ile  Ala Val Val
        995                 1000                1005

Ala Val  Leu Gln Pro Tyr Ile  Phe Val Ala Thr Val  Pro Val Ile
    1010                1015                1020

Val Ala  Phe Ile Met Leu Arg  Ala Tyr Phe Leu Gln  Thr Ser Gln
    1025                1030                1035

Gln Leu  Lys Gln Leu Glu Ser  Glu Gly Arg Ser Pro  Ile Phe Thr
    1040                1045                1050

His Leu  Val Thr Ser Leu Lys  Gly Leu Trp Thr Leu  Arg Ala Phe
    1055                1060                1065

Gly Arg  Gln Pro Tyr Phe Glu  Thr Leu Phe His Lys  Ala Leu Asn
    1070                1075                1080

Leu His  Thr Ala Asn Trp Phe  Leu Tyr Leu Ser Thr  Leu Arg Trp
    1085                1090                1095

Phe Gln  Met Arg Ile Glu Met  Ile Phe Val Ile Phe  Phe Ile Ala
    1100                1105                1110

Val Thr  Phe Ile Ser Ile Leu  Thr Thr Gly Glu Gly  Glu Gly Arg
    1115                1120                1125

Val Gly  Ile Ile Leu Thr Leu  Ala Met Asn Ile Met  Ser Thr Leu
    1130                1135                1140

Gln Trp  Ala Val Asn Ser Ser  Ile Asp Val Asp Ser  Leu Met Arg
    1145                1150                1155

Ser Val  Ser Arg Val Phe Lys  Phe Ile Asp Met Pro  Thr Glu Gly
    1160                1165                1170

Lys Pro  Thr Lys Ser Thr Lys  Pro Tyr Lys Asn Gly  Gln Leu Ser
    1175                1180                1185

Lys Val  Met Ile Ile Glu Asn  Ser His Val Lys Lys  Asp Asp Ile
    1190                1195                1200

Trp Pro  Ser Gly Gly Gln Met  Thr Val Lys Asp Leu  Thr Ala Lys
    1205                1210                1215

Tyr Thr  Glu Gly Gly Asn Ala  Ile Leu Glu Asn Ile  Ser Phe Ser
    1220                1225                1230

Ile Ser  Pro Gly Gln Arg Val  Gly Leu Leu Gly Arg  Thr Gly Ser
    1235                1240                1245

Gly Lys  Ser Thr Leu Leu Ser  Ala Phe Leu Arg Leu  Leu Asn Thr
    1250                1255                1260

Glu Gly  Glu Ile Gln Ile Asp  Gly Val Ser Trp Asp  Ser Ile Thr
    1265                1270                1275

Leu Gln  Gln Trp Arg Lys Ala  Phe Gly Val Ile Pro  Gln Lys Val
    1280                1285                1290

Phe Ile  Phe Ser Gly Thr Phe  Arg Lys Asn Leu Asp  Pro Tyr Glu
    1295                1300                1305

Gln Trp  Ser Asp Gln Glu Ile  Trp Lys Val Ala Asp  Glu Val Gly
    1310                1315                1320

Leu Arg  Ser Val Ile Glu Gln  Phe Pro Gly Lys Leu  Asp Phe Val
    1325                1330                1335

Leu Val  Asp Gly Gly Cys Val  Leu Ser His Gly His  Lys Gln Leu
    1340                1345                1350

Met Cys  Leu Ala Arg Ser Val  Leu Ser Lys Ala Lys  Ile Leu Leu
    1355                1360                1365
```

```
Leu Asp  Gln Pro Ser Ala His  Leu Asp Pro Val Thr  Tyr Gln Ile
    1370                 1375                 1380

Ile Arg  Arg Thr Leu Lys Gln  Ala Phe Ala Asp Cys  Thr Val Ile
    1385                 1390                 1395

Leu Cys  Glu His Arg Ile Glu  Ala Met Leu Glu Cys  Gln Gln Phe
    1400                 1405                 1410

Leu Val  Ile Glu Glu Asn Lys  Val Arg Gln Tyr Asp  Ser Ile Gln
    1415                 1420                 1425

Lys Leu  Leu Asn Glu Arg Ser  Leu Phe Arg Gln Ala  Ile Ser Pro
    1430                 1435                 1440

Ser Asp  Arg Val Lys Leu Phe  Pro His Arg Asn Ser  Ser Lys Cys
    1445                 1450                 1455

Lys Ser  Lys Pro Gln Ile Ala  Ala Leu Lys Glu Glu  Thr Glu Glu
    1460                 1465                 1470

Glu Val  Gln Asp Thr Arg Leu
    1475                 1480


<210> SEQ ID NO 45
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 45

atgcaacgct ctcctcttga aaaggcctcg gtggtgtcca agctcttctt ctcgtggact     60

agacccatcc tgagaaaggg gtacagacag cgcttggagc tgtccgatat ctatcaaatc    120

ccttccgtgg actccgcgga caacctgtcc gagaagctcg agagagaatg ggacagagaa    180

ctcgcctcaa agaagaaccc gaagctgatt aatgcgctta ggcggtgctt tttctggcgg    240

ttcatgttct acggcatctt cctctacctg ggagaggtca ccaaggccgt gcagcccctg    300

ttgctgggac ggattattgc ctcctacgac cccgacaaca aggaagaaag aagcatcgct    360

atctacttgg gcatcggtct gtgcctgctt ttcatcgtcc ggaccctctt gttgcatcct    420

gctattttcg gcctgcatca cattggcatg cagatgagaa ttgccatgtt ttccctgatc    480

tacaagaaaa ctctgaagct ctcgagccgc gtgcttgaca agatttccat cggccagctc    540

gtgtccctgc tctccaacaa tctgaacaag ttcgacgagg gcctcgccct ggcccacttc    600

gtgtggatcg cccctctgca agtggcgctt ctgatgggcc tgatctggga gctgctgcaa    660

gcctcggcat tctgtgggct tggattcctg atcgtgctgg cactgttcca ggccggactg    720

gggcggatga tgatgaagta cagggaccag agagccggaa agatttccga acggctggtg    780

atcacttcgg aaatgatcga aaacatccag tcagtgaagg cctactgctg ggaagaggcc    840

atggaaaaga tgattgaaaa cctccggcaa accgagctga agctgacccg caaggccgct    900

tacgtgcgct atttcaactc gtccgctttc ttcttctccg ggttcttcgt ggtgtttctc    960

tccgtgctcc cctacgccct gattaaggga atcatcctca ggaagatctt caccaccatt   1020

tccttctgta tcgtgctccg catggccgtg acccggcagt tcccatgggc cgtgcagact   1080

tggtacgact ccctgggagc cattaacaag atccaggact tccttcaaaa gcaggagtac   1140

aagaccctcg agtacaacct gactactacc gaggtcgtga tggaaaacgt caccgccttt   1200

tgggaggagg gatttggcga actgttcgag aaggccaagc agaacaacaa caaccgcaag   1260

acctcgaacg gtgacgactc cctcttcttt tcaaacttca gcctgctcgg gacgcccgtg   1320
```

-continued

```
ctgaaggaca ttaacttcaa gatcgaaaga ggacagctcc tggcggtggc cggatcgacc   1380
ggagccggaa agacttccct gctgatggtg atcatgggag agcttgaacc tagcgaggga   1440
aagatcaagc actccggccg catcagcttc tgtagccagt tttcctggat catgcccgga   1500
accattaagg aaaacatcat cttcggcgtg tcctacgatg aataccgcta ccggtccgtg   1560
atcaaagcct gccagctgga agaggatatt tcaaagttcg cggagaaaga taacatcgtg   1620
ctgggcgaag gggtattac cttgtcgggg ggccagcggg ctagaatctc gctggccaga    1680
gccgtgtata aggacgccga cctgtatctc ctggactccc ccttcggata cctggacgtc   1740
ctgaccgaaa aggagatctt cgaatcgtgc gtgtgcaagc tgatggctaa caagactcgc   1800
atcctcgtga cctccaaaat ggagcacctg aagaaggcag acaagattct gattctgcat   1860
gaggggtcct cctactttta cggcaccttc tcggagttgc agaacttgca gcccgacttc   1920
tcatcgaagc tgatgggttg cgacagcttc gaccagttct ccgccgaaag aaggaacgat   1980
atcctgacgg aaaccttgca ccgcttctct ttggaaggcg acgcccctgt gtcatggacc   2040
gagactaaga agcagagctt caagcagacc ggggaattcg gcgaaaagag gaagaacagc   2100
atcttgaacc ccattaactc catccgcaag ttctcaatcg tgcaaaagac gccactgcag   2160
atgaacggca ttgaggagga ctccgacgaa ccccttgaga ggcgcctgga tctggtgccg   2220
gacagcgagc agggagaagc catcctgcct cggatttccg tgatctccac tggtccgacg   2280
ctccaagccc ggcggcggca gtccgtgctg aacctgatga cccacagcgt gaaccagggc   2340
caaaacattc accgcaagac taccgcatcc acccggaaag tggatctggc acctcaagcg   2400
aatcttaccg agctcgacat ctactcccgg agactggatc aggaaaccgg gctcgaaatt   2460
tccgaagaaa tcaacgagga ggatctgaaa gagtgcttct tcgacgatat ggagtcgata   2520
cccgccgtga cgacttggaa cacttatctg cggtacatca ctgtgcacaa gtcattgatc   2580
ttcgtgctga tttggtgcct ggtgattttc ctggccgagg tcgcggcctc actggtggtg   2640
ctctggctgt tgggaaacac gcctctgcaa gacaagggaa actccacgca ctcgagaaac   2700
aacagctatg ccgtgattat cacttccacc tcctcttatt acgtgttcta catctacgtc   2760
ggagtggcgg ataccctgct cgcgatgggt ttcttcagag gactgccgct ggtccacacc   2820
ttgatcaccg tcagcaagat tcttcaccac aagatgttgc atagcgtgct gcaggccccc   2880
atgtccaccc tcaacactct gaaggccgga ggcattctga acagattctc caaggacatc   2940
gctatcctgg acgatctcct gccgcttacc atctttgact tcatccagct gctgctgatc   3000
gtgattggag caatcgcagt ggtggcggtg ctgcagcctt acattttcgt ggccactgtg   3060
ccggtcattg tggcgttcat catgctgcgg gcctacttcc tccaaaccag ccagcagctg   3120
aagcaactgg aatccgaggg acgatccccc atcttcactc accttgtgac gtcgttgaag   3180
ggactgtgga ccctccgggc tttcggacgg cagccctact tcgaaaccct cttccacaag   3240
gccctgaacc tccacaccgc caattggttc ctgtacctgt ccaccctgcg gtggttccag   3300
atgcgcatcg agatgatttt cgtcatcttc ttcatcgcgg tcacattcat cagcatcctg   3360
actaccggag agggagaggg acgggtcgga ataatcctga ccctcgccat gaacattatg   3420
agcaccctgc agtgggcagt gaacagctcg atcgacgtgg acagcctgat gcgaagcgtc   3480
agccgcgtgt tcaagttcat cgacatgcct actgagggaa aacccactaa gtccactaag   3540
ccctacaaaa atggccagct gagcaaggtc atgatcatcg aaaactccca cgtgaagaag   3600
gacgatattt ggccctccgg aggtcaaatg accgtgaagg acctgaccgc aaagtacacc   3660
gagggaggaa acgccattct cgaaaacatc agcttctcca tttcgccggg acagcgggtc   3720
```

```
ggccttctcg ggcggaccgg ttccgggaag tcaactctgc tgtcggcttt cctccggctg   3780

ctgaataccg agggggaaat ccaaattgac ggcgtgtctt gggattccat tactctgcag   3840

cagtggcgga aggccttcgg cgtgatcccc cagaaggtgt tcatcttctc gggtaccttc   3900

cggaagaacc tggatcctta cgagcagtgg agcgaccaag aaatctggaa ggtcgccgac   3960

gaggtcggcc tgcgctccgt gattgaacaa tttcctggaa agctggactt cgtgctcgtc   4020

gacgggggat gtgtcctgtc gcacggacat aagcagctca tgtgcctcgc acggtccgtg   4080

ctctccaagg ccaagattct gctgctggac gaaccttcgg cccacctgga tccggtcacc   4140

taccagatca tcaggaggac cctgaagcag gcctttgccg attgcaccgt gattctctgc   4200

gagcaccgca tcgaggccat gctggagtgc cagcagttcc tggtcatcga ggagaacaag   4260

gtccgccaat acgactccat tcaaaagctc ctcaacgagc ggtcgctgtt cagacaagct   4320

atttcaccgt ccgatagagt gaagctcttc ccgcatcgga acagctcaaa gtgcaaatcg   4380

aagccgcaga tcgcagcctt gaaggaagag actgaggaag aggtgcagga cacccggctt   4440

taa                                                                 4443
```

<210> SEQ ID NO 46
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 46

```
atgcaacgct ctcctcttga aaaggcctcg gtggtgtcca agctcttctt ctcgtggact     60

agacccatcc tgagaaaggg gtacagacag cgcttggagc tgtccgatat ctatcaaatc    120

ccttccgtgg actccgcgga caacctgtcc gagaagctcg agagagaatg ggacagagaa    180

ctcgcctcaa agaagaaccc gaagctgatt aatgcgctta ggcggtgctt tttctggcgg    240

ttcatgttct acggcatctt cctctacctg ggagaggtca ccaaggccgt gcagcccctg    300

ttgctgggac ggattattgc ctcctacgac cccgacaaca aggaagaaag aagcatcgct    360

atctacttgg gcatcggtct gtgcctgctt ttcatcgtcc ggaccctctt gttgcatcct    420

gctattttcg gcctgcatca cattggcatg cagatgagaa ttgccatgtt ttccctgatc    480

tacaagaaaa ctctgaagct ctcgagccgc gtgcttgaca agatttccat cggccagctc    540

gtgtccctgc tctccaacaa tctgaacaag ttcgacgagg gcctcgccct ggcccacttc    600

gtgtggatcg cccctctgca agtggcgctt ctgatgggcc tgatctggga gctgctgcaa    660

gcctcggcat tctgtgggct tggattcctg atcgtgctgg cactgttcca ggccggactg    720

gggcggatga tgatgaagta cagggaccag agagccggaa agatttccga acggctggtg    780

atcacttcgg aaatgatcga aaacatccag tcagtgaagg cctactgctg ggaagaggcc    840

atggaaaaga tgattgaaaa cctccggcaa accgagctga agctgacccg caaggccgct    900

tacgtgcgct atttcaactc gtccgctttc ttcttctccg ggttcttcgt ggtgtttctc    960

tccgtgctcc cctacgccct gattaaggga atcatcctca ggaagatctt caccaccatt   1020

tccttctgta tcgtgctccg catggccgtg acccggcagt tcccatgggc cgtgcagact   1080

tggtacgact ccctgggagc cattaacaag atccaggact tccttcaaaa gcaggagtac   1140

aagaccctcg agtacaacct gactactacc gaggtcgtga tggaaaacgt caccgccttt   1200

tgggaggagg gatttggcga actgttcgag aaggccaagc agaacaacaa caaccgcaag   1260
```

-continued

```
acctcgaacg gtgacgactc cctcttcttt tcaaacttca gcctgctcgg gacgcccgtg   1320
ctgaaggaca ttaacttcaa gatcgaaaga ggacagctcc tggcggtggc cggatcgacc   1380
ggagccggaa agacttccct gctgatggtg atcatgggag agcttgaacc tagcgaggga   1440
aagatcaagc actccggccg catcagcttc tgtagccagt tttcctggat catgcccgga   1500
accattaagg aaaacatcat cttcggcgtg tcctacgatg aataccgcta ccggtccgtg   1560
atcaaagcct gccagctgga agaggatatt tcaaagttcg cggagaaaga taacatcgtg   1620
ctgggcgaag gggtattac cttgtcgggg ggccagcggg ctagaatctc gctggccaga   1680
gccgtgtata aggacgccga cctgtatctc ctggactccc ccttcggata cctggacgtc   1740
ctgaccgaaa aggagatctt cgaatcgtgc gtgtgcaagc tgatggctaa caagactcgc   1800
atcctcgtga cctccaaaat ggagcacctg aagaaggcag acaagattct gattctgcat   1860
gaggggtcct cctactttta cggcaccttc tcggagttgc agaacttgca gcccgacttc   1920
tcatcgaagc tgatgggttg cgacagcttc gaccagttct ccgccgaaag aaggaacgat   1980
atcctgacgg aaaccttgca ccgcttctct ttggaaggcg acgcccctgt gtcatggacc   2040
gagactaaga agcaggattt caagcagacc ggggaattcg gcgaaaagag gaagaacgac   2100
atcttgaacc ccattaactc catccgcaag ttctcaatcg tgcaaaagac gccactgcag   2160
atgaacggca ttgaggagga ctccgacgaa ccccttgaga ggcgcctgga tctggtgccg   2220
gacagcgagc agggagaagc catcctgcct cggatttccg tgatctccac tggtccgacg   2280
ctccaagccc ggcggcggca gtccgtgctg aacctgatga cccacagcgt gaaccagggc   2340
caaaacattc accgcaagac taccgcatcc acccggaaag tggatctggc acctcaagcg   2400
aatcttaccg agctcgacat ctactcccgg agactggatc aggaaaccgg gctcgaaatt   2460
tccgaagaaa tcaacgagga ggatctgaaa gagtgcttct tcgacgatat ggagtcgata   2520
cccgccgtga cgacttggaa cacttatctg cggtacatca ctgtgcacaa gtcattgatc   2580
ttcgtgctga tttggtgcct ggtgattttc ctggccgagg tcgcggcctc actggtggtg   2640
ctctggctgt tgggaaacac gcctctgcaa gacaagggaa actccacgca ctcgagaaac   2700
aacagctatg ccgtgattat cacttccacc tcctcttatt acgtgttcta catctacgtc   2760
ggagtggcgg ataccctgct cgcgatgggt ttcttcagag gactgccgct ggtccacacc   2820
ttgatcaccg tcagcaagat tcttcaccac aagatgttgc atagcgtgct gcaggccccc   2880
atgtccaccc tcaacactct gaaggccgga ggcattctga acagattctc caaggacatc   2940
gctatcctgg acgatctcct gccgcttacc atctttgact tcatccagct gctgctgatc   3000
gtgattggag caatcgcagt ggtggcggtg ctgcagcctt acattttcgt ggccactgtg   3060
ccggtcattg tggcgttcat catgctgcgg gcctacttcc tccaaaccag ccagcagctg   3120
aagcaactgg aatccgaggg acgatccccc atcttcactc accttgtgac gtcgttgaag   3180
ggactgtgga ccctccgggc tttcggacgg cagccctact tcgaaaccct cttccacaag   3240
gccctgaacc tccacaccgc caattggttc ctgtacctgt ccaccctgcg gtggttccag   3300
atgcgcatcg agatgatttt cgtcatcttc ttcatcgcgg tcacattcat cagcatcctg   3360
actaccggag agggagaggg acgggtcgga ataatcctga ccctcgccat gaacattatg   3420
agcaccctgc agtgggcagt gaacagctcg atcgacgtgg acagcctgat gcgaagcgtc   3480
agccgcgtgt tcaagttcat cgacatgcct actgagggaa aacccactaa gtccactaag   3540
ccctacaaaa atggccagct gagcaaggtc atgatcatcg aaaactccca cgtgaagaag   3600
gacgatattt ggccctccgg aggtcaaatg accgtgaagg acctgaccgc aaagtacacc   3660
```

gagggaggaa acgccattct cgaaaacatc agcttctcca tttcgccggg acagcgggtc 3720
ggccttctcg ggcggaccgg ttccgggaag tcaactctgc tgtcggcttt cctccggctg 3780
ctgaataccg agggggaaat ccaaattgac ggcgtgtctt gggattccat tactctgcag 3840
cagtggcgga aggccttcgg cgtgatcccc cagaaggtgt tcatcttctc gggtaccttc 3900
cggaagaacc tggatcctta cgagcagtgg agcgaccaag aaatctggaa ggtcgccgac 3960
gaggtcggcc tgcgctccgt gattgaacaa tttcctggaa agctggactt cgtgctcgtc 4020
gacgggggat gtgtcctgtc gcacggacat aagcagctca tgtgcctcgc acggtccgtg 4080
ctctccaagg ccaagattct gctgctggac gaaccttcgg cccacctgga tccggtcacc 4140
taccagatca tcaggaggac cctgaagcag gcctttgccg attgcaccgt gattctctgc 4200
gagcaccgca tcgaggccat gctggagtgc cagcagttcc tggtcatcga ggagaacaag 4260
gtccgccaat acgactccat tcaaaagctc ctcaacgagc ggtcgctgtt cagacaagct 4320
atttcaccgt ccgatagagt gaagctcttc ccgcatcgga acagctcaaa gtgcaaatcg 4380
aagccgcaga tcgcagcctt gaaggaagag actgaggaag aggtgcagga cacccggctt 4440
taa 4443

<210> SEQ ID NO 47
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 47
atgcaacgct ctcctcttga aaaggcctcg gtggtgtcca agctcttctt ctcgtggact 60
agacccatcc tgagaaaggg gtacagacag cgcttggagc tgtccgatat ctatcaaatc 120
ccttccgtgg actccgcgga caacctgtcc gagaagctcg agagagaatg ggacagagaa 180
ctcgcctcaa agaagaaccc gaagctgatt aatgcgctta ggcggtgctt tttctggcgg 240
ttcatgttct acggcatctt cctctacctg ggagaggtca ccaaggccgt gcagcccctg 300
ttgctgggac ggattattgc ctcctacgac cccgacaaca aggaagaaag aagcatcgct 360
atctacttgg gcatcggtct gtgcctgctt ttcatcgtcc ggaccctctt gttgcatcct 420
gctattttcg gcctgcatca cattggcatg cagatgagaa ttgccatgtt ttccctgatc 480
tacaagaaaa ctctgaagct ctcgagccgc gtgcttgaca agatttccat cggccagctc 540
gtgtccctgc tctccaacaa tctgaacaag ttcgacgagg gcctcgccct ggcccacttc 600
gtgtggatcg cccctctgca agtggcgctt ctgatgggcc tgatctggga gctgctgcaa 660
gcctcggcat tctgtgggct tggattcctg atcgtgctgg cactgttcca ggccggactg 720
gggcggatga tgatgaagta cagggaccag agagccggaa agatttccga acggctggtg 780
atcacttcgg aaatgatcga aaacatccag tcagtgaagg cctactgctg ggaagaggcc 840
atggaaaaga tgattgaaaa cctccggcaa accgagctga agctgacccg caaggccgct 900
tacgtgcgct atttcaactc gtccgctttc ttcttctccg ggttcttcgt ggtgtttctc 960
tccgtgctcc cctacgccct gattaaggga atcatcctca ggaagatctt caccaccatt 1020
tccttctgta tcgtgctccg catggccgtg acccggcagt tcccatgggc cgtgcagact 1080
tggtacgact ccctgggagc cattaacaag atccaggact tccttcaaaa gcaggagtac 1140
aagaccctcg agtacaacct gactactacc gaggtcgtga tggaaaacgt caccgccttt 1200

-continued

```
tgggaggagg gatttggcga actgttcgag aaggccaagc agaacaacaa caaccgcaag   1260
acctcgaacg gtgacgactc cctcttcttt tcaaacttca gcctgctcgg gacgcccgtg   1320
ctgaaggaca ttaacttcaa gatcgaaaga ggacagctcc tggcggtggc cggatcgacc   1380
ggagccggaa agacttccct gctgatggtg atcatgggag agcttgaacc tagcgaggga   1440
aagatcaagc actccggccg catcagcttc tgtagccagt tttcctggat catgcccgga   1500
accattaagg aaaacatcat cttcggcgtg tcctacgatg aataccgcta ccggtccgtg   1560
atcaaagcct gccagctgga agaggatatt tcaaagttcg cggagaaaga taacatcgtg   1620
ctgggcgaag gggtattac cttgtcgggg ggccagcggg ctagaatctc gctggccaga    1680
gccgtgtata aggacgccga cctgtatctc ctggactccc ccttcggata cctggacgtc   1740
ctgaccgaaa aggagatctt cgaatcgtgc gtgtgcaagc tgatggctaa caagactcgc   1800
atcctcgtga cctccaaaat ggagcacctg aagaaggcag acaagattct gattctgcat   1860
gaggggtcct cctactttta cggcaccttc tcggagttgc agaacttgca gcccgacttc   1920
tcatcgaagc tgatgggttg cgacagcttc gaccagttct ccgccgaaag aaggaactcg   1980
atcctgacgg aaaccttgca ccgcttctct ttggaaggcg acgcccctgt gtcatggacc   2040
gagactaaga agcagagctt caagcagacc ggggaattcg gcgaaaagag gaagaacagc   2100
atcttgaacc ccattaactc catccgcaag ttctcaatcg tgcaaaagac gccactgcag   2160
atgaacggca ttgaggagga ctccgacgaa ccccttgaga ggcgcctgtc cctggtgccg   2220
gacagcgagc agggagaagc catcctgcct cggatttccg tgatctccac tggtccgacg   2280
ctccaagccc ggcggcggca gtccgtgctg aacctgatga cccacagcgt gaaccagggc   2340
caaaacattc accgcaagac taccgcatcc acccggaaag tgtccctggc acctcaagcg   2400
aatcttaccg agctcgacat ctactcccgg agactgtcgc aggaaaccgg gctcgaaatt   2460
tccgaagaaa tcaacgagga ggatctgaaa gagtgcttct tcgacgatat ggagtcgata   2520
cccgccgtga cgacttggaa cacttatctg cggtacatca ctgtgcacaa gtcattgatc   2580
ttcgtgctga tttggtgcct ggtgattttc ctggccgagg tcgcggcctc actggtggtg   2640
ctctggctgt tgggaaacac gcctctgcaa gacaagggaa actccacgca ctcgagaaac   2700
aacagctatg ccgtgattat cacttccacc tcctcttatt acgtgttcta catctacgtc   2760
ggagtggcgg ataccctgct cgcgatgggt ttcttcagag gactgccgct ggtccacacc   2820
ttgatcaccg tcagcaagat tcttcaccac aagatgttgc atagcgtgct gcaggccccc   2880
atgtccaccc tcaacactct gaaggccgga ggcattctga acagattctc ctgcgacatc   2940
gctatcctgg acgatctcct gccgcttacc atctttgact tcatccagct gctgctgatc   3000
gtgattggag caatcgcagt ggtggcggtg ctgcagcctt acattttcgt ggccactgtg   3060
ccggtcattg tggcgttcat catgctgcgg gcctacttcc tccaaaccag ccagcagctg   3120
aagcaactgg aatccgaggg acgatccccc atcttcactc accttgtgac gtcgttgaag   3180
ggactgtgga ccctccgggc tttcggacgg cagccctact tcgaaaccct cttccacaag   3240
gccctgaacc tccacaccgc caattggttc ctgtacctgt ccaccctgcg gtggttccag   3300
atgcgcatcg agatgatttt cgtcatcttc ttcatcgcgg tcacattcat cagcatcctg   3360
actaccggag agggagaggg acgggtcgga ataatcctga ccctcgccat gaacattatg   3420
agcaccctgc agtgggcagt gaacagctcg atcgacgtgg acagcctgat gcgaagcgtc   3480
agccgcgtgt tcaagttcat cgacatgcct actgagggaa aacccactaa gtccactaag   3540
ccctacaaaa atggccagct gagcaaggtc atgatcatcg aaaactccca cgtgaagaag   3600
```

```
gacgatattt ggccctccgg aggtcaaatg accgtgaagg acctgaccgc aaagtacacc   3660

gagggaggaa acgccattct cgaaaacatc agcttctcca tttcgccggg acagcgggtc   3720

ggccttctcg ggcggaccgg ttccgggaag tcaactctgc tgtcggcttt cctccggctg   3780

ctgaataccg agggggaaat ccaaattgac ggcgtgtctt gggattccat tactctgcag   3840

cagtggcgga aggccttcgg cgtgatcccc cagaaggtgt tcatcttctc gggtaccttc   3900

cggaagaacc tggatcctta cgagcagtgg agcgaccaag aaatctggaa ggtcgccgac   3960

gaggtcggcc tgcgctccgt gattgaacaa tttcctggaa agctggactt cgtgctcgtc   4020

gacgggggat gtgtcctgtc gcacggacat aagcagctca tgtgcctcgc acggtccgtg   4080

ctctccaagg ccaagattct gctgctggac gaaccttcgg cccacctgga tccggtcacc   4140

taccagatca tcaggaggac cctgaagcag gcctttgccg attgcaccgt gattctctgc   4200

gagcaccgca tcgaggccat gctggagtgc cagcagttcc tggtcatcga ggagaacaag   4260

gtccgccaat acgactccat tcaaaagctc ctcaacgagc ggtcgctgtt cagacaagct   4320

atttcaccgt ccgatagagt gaagctcttc ccgcatcgga acagctcaaa gtgcaaatcg   4380

aagccgcaga tcgcagcctt gaaggaagag actgaggaag aggtgcagga cacccggctt   4440

taa                                                                 4443
```

<210> SEQ ID NO 48
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 48

```
atgcaacgct ctcctcttga aaaggcctcg gtggtgtcca agctcttctt ctcgtggact     60

agacccatcc tgagaaaggg gtacagacag cgcttggagc tgtccgatat ctatcaaatc    120

ccttccgtgg actccgcgga caacctgtcc gagaagctcg agagagaatg ggacagagaa    180

ctcgcctcaa agaagaaccc gaagctgatt aatgcgctta ggcggtgctt tttctggcgg    240

ttcatgttct acggcatctt cctctacctg ggagaggtca ccaaggccgt gcagcccctg    300

ttgctgggac ggattattgc ctcctacgac cccgacaaca aggaagaaag aagcatcgct    360

atctacttgg gcatcggtct gtgcctgctt ttcatcgtcc ggaccctctt gttgcatcct    420

gctattttcg gcctgcatca cattggcatg cagatgagaa ttgccatgtt ttccctgatc    480

tacaagaaaa ctctgaagct ctcgagccgc gtgcttgaca agatttccat cggccagctc    540

gtgtccctgc tctccaacaa tctgaacaag ttcgacgagg gcctcgccct ggcccacttc    600

gtgtggatcg cccctctgca agtggcgctt ctgatgggcc tgatctggga gctgctgcaa    660

gcctcggcat tctgtgggct tggattcctg atcgtgctgg cactgttcca ggccggactg    720

gggcggatga tgatgaagta cagggaccag agagccggaa agatttccga acggctggtg    780

atcacttcgg aaatgatcga aaacatccag tcagtgaagg cctactgctg ggaagaggcc    840

atggaaaaga tgattgaaaa cctccggcaa accgagctga agctgacccg caaggccgct    900

tacgtgcgct atttcaactc gtccgctttc ttcttctccg ggttcttcgt ggtgtttctc    960

tccgtgctcc cctacgccct gattaaggga atcatcctca ggaagatctt caccaccatt   1020

tccttctgta tcgtgctccg catggccgtg acccggcagt tcccatgggc cgtgcagact   1080

tggtacgact ccctgggagc cattaacaag atccaggact tccttcaaaa gcaggagtac   1140
```

-continued

```
aagaccctcg agtacaacct gactactacc gaggtcgtga tggaaaacgt caccgccttt   1200
tgggaggagg gatttggcga actgttcgag aaggccaagc agaacaacaa caaccgcaag   1260
acctcgaacg gtgacgactc cctcttcttt tcaaacttca gcctgctcgg gacgcccgtg   1320
ctgaaggaca ttaacttcaa gatcgaaaga ggacagctcc tggcggtggc cggatcgacc   1380
ggagccggaa agacttccct gctgatggtg atcatgggag agcttgaacc tagcgaggga   1440
aagatcaagc actccggccg catcagcttc tgtagccagt tttcctggat catgcccgga   1500
accattaagg aaaacatcat cttcggcgtg tcctacgatg aataccgcta ccggtccgtg   1560
atcaaagcct gccagctgga agaggatatt tcaaagttcg cggagaaaga taacatcgtg   1620
ctgggcgaag gggtattac cttgtcgggg ggccagcggg ctagaatctc gctggccaga   1680
gccgtgtata aggacgccga cctgtatctc ctggactccc ccttcggata cctggacgtc   1740
ctgaccgaaa aggagatctt cgaatcgtgc gtgtgcaagc tgatggctaa caagactcgc   1800
atcctcgtga cctccaaaat ggagcacctg aagaaggcag acaagattct gattctgcat   1860
gaggggtcct cctactttta cggcaccttc tcggagttgc agaacttgca gcccgacttc   1920
tcatcgaagc tgatgggttg cgacagcttc gaccagttct ccgccgaaag aaggaactcg   1980
atcctgacgg aaaccttgca ccgcttctct ttggaaggcg acgcccctgt gtcatggacc   2040
gagactaaga agcagagctt caagcagacc ggggaattcg gcgaaaagag gaagaacagc   2100
atcttgaacc ccattaactc catccgcaag ttctcaatcg tgcaaaagac gccactgcag   2160
atgaacggca ttgaggagga ctccgacgaa ccccttgaga ggcgcctgtc cctggtgccg   2220
gacagcgagc agggagaagc catcctgcct cggatttccg tgatctccac tggtccgacg   2280
ctccaagccc ggcggcggca gtccgtgctg aacctgatga cccacagcgt gaaccagggc   2340
caaaacattc accgcaagac taccgcatcc acccggaaag tgtccctggc acctcaagcg   2400
aatcttaccg agctcgacat ctactcccgg agactgtcgc aggaaaccgg gctcgaaatt   2460
tccgaagaaa tcaacgagga ggatctgaaa gagtgcttct tcgacgatat ggagtcgata   2520
cccgccgtga cgacttggaa cacttatctg cggtacatca ctgtgcacaa gtcattgatc   2580
ttcgtgctga tttggtgcct ggtgattttc ctggccgagg tcgcggcctc actggtggtg   2640
ctctggctgt tgggaaacac gcctctgcaa gacaagggaa actccacgca ctcgagaaac   2700
aacagctatg ccgtgattat cacttccacc tcctcttatt acgtgttcta catctacgtc   2760
ggagtggcgg ataccctgct cgcgatgggt ttcttcagag gactgccgct ggtccacacc   2820
ttgatcaccg tcagcaagat tcttcaccac aagatgttgc atagcgtgct gcaggccccc   2880
atgtccaccc tcaacactct gaaggccgga ggcattctga acagattctc caaggacatc   2940
gctatcctgg acgatctcct gccgcttacc atctttgact tcatccagct gctgctgatc   3000
gtgattggag caatcgcagt ggtggcggtg ctgcagcctt acattttcgt ggccactgtg   3060
ccggtcattg tggcgttcat catgctgcgg gcctacttcc tccaaaccag ccagcagctg   3120
aagcaactgg aatccgaggg acgatccccc atcttcactc accttgtgac gtcgttgaag   3180
ggactgtgga ccctccgggc tttcggacgg cagccctact tcgaaaccct cttccacaag   3240
gccctgaacc tccacaccgc caattggttc ctgtacctgt ccaccctgcg gtggttccag   3300
atgcgcatcg agatgatttt cgtcatcttc ttcatcgcgg tcacattcat cagcatcctg   3360
actaccggag agggagaggg acgggtcgga ataatcctga ccctcgccat gaacattatg   3420
agcaccctgc agtgggcagt gaacagctcg atcgacgtgg acagcctgat gcgaagcgtc   3480
agccgcgtgt tcaagttcat cgacatgcct actgagggaa aacccactaa gtccactaag   3540
```

-continued ccctacaaaa atggccagct gagcaaggtc atgatcatcg aaaactccca cgtgaagaag 3600
gacgatattt ggccctccgg aggtcaaatg accgtgaagg acctgaccgc aaagtacacc 3660
gagggaggaa acgccattct cgaaaacatc agcttctcca tttcgccggg acagcgggtc 3720
ggccttctcg ggcggaccgg ttccgggaag tcaactctgc tgtcggcttt cctccggctg 3780
ctgaataccg agggggaaat ccaaattgac ggcgtgtctt gggattccat tactctgcag 3840
cagtggcgga aggccttcgg cgtgatcccc cagaaggtgt tcatcttctc gggtaccttc 3900
cggaagaacc tggatcctta cgagcagtgg agcgaccaag aaatctggaa ggtcgccgac 3960
gaggtcggcc tgcgctccgt gattgaacaa tttcctggaa agctggactt cgtgctcgtc 4020
gacgggggat gtgtcctgtc gcacggacat aagcagctca tgtgcctcgc acggtccgtg 4080
ctctccaagg ccaagattct gctgctggac caaccttcgg cccacctgga tccggtcacc 4140
taccagatca tcaggaggac cctgaagcag gcctttgccg attgcaccgt gattctctgc 4200
gagcaccgca tcgaggccat gctggagtgc cagcagttcc tggtcatcga ggagaacaag 4260
gtccgccaat acgactccat tcaaaagctc ctcaacgagc ggtcgctgtt cagacaagct 4320
atttcaccgt ccgatagagt gaagctcttc ccgcatcgga acagctcaaa gtgcaaatcg 4380
aagccgcaga tcgcagcctt gaaggaagag actgaggaag aggtgcagga cacccggctt 4440
taa 4443

<210> SEQ ID NO 49
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 49
atgcagcgct cgcctctgga aaaggcgagc gtcgtgtcac ggctattctt ttcttggacc 60
cggcccattc tcaggaaggg ctacaggcag aggctggagt tgagcgacat ctatcagatt 120
ccttccgtgg acagcgccga caacctgagc gagaagctgg aaagggagtg ggaccgcgaa 180
ctggcaagca aaaagaaccc caagctgatc aatgccctga gaaggtgttt cttttggaga 240
ttcatgttct acgggatctt tctgtatctg ggcgaggtta caaaggctgt gcagcccctg 300
ctgctcggca gaatcatcgc ctcatacgat ccagacaaca aggaagaaag aagcatcgcc 360
atctacctgg gcattggcct ctgcctcctg tttattgtgc ggactctgct gctgcaccca 420
gcaattttcg ggttgcatca tattggcatg cagatgcgca ttgctatgtt ttccctcatc 480
tacaaaaaga cactgaaact cagctcccgg gtgctggaca agatctccat cggccaactg 540
gtgtctctcc tgagcaataa cttgaataag ttcgacgaag ggctggccct ggcacacttc 600
gtgtggattg ccccccctgca ggtggccctg ctgatgggac tgatttggga actgctgcag 660
gctagcgctt tctgcggcct ggggttcctg atcgtgctgg cactgtttca ggcaggcctg 720
ggccgtatga tgatgaagta cagagaccag agggccggga agatctccga acggctcgtt 780
attacctctg agatgatcga gaacattcag tctgtgaaag cctactgctg ggaggaggct 840
atggagaaga tgatcgagaa tctgagacag accgagctga agctgaccag aaaggccgcc 900
tacgtgaggt acttcaacag cagtgccttc ttcttctctg gcttcttcgt tgtgtttctg 960
agcgtgctgc catacgctct catcaaaggc atcatcctgc ggaagatctt caccaccatc 1020
agcttttgca tcgtgcttag aatggccgtg acccggcagt tcccatgggc cgtgcaaact 1080

-continued

```
tggtatgatt ccctgggcgc catcaacaaa atccaggatt tcctgcagaa gcaggaatac   1140
aagacactcg aatataatct cacaactact gaggtggtta tggagaacgt gactgccttc   1200
tgggaggagg ggttcggaga gctttttgag aaggcaaaac agaataacaa caaccgcaaa   1260
accagcaacg gcgacgacag cctgttcttc tccaattttt ctctcctggg aacacccgtc   1320
ctcaaagaca tcaactttaa gatcgagagg ggacagctgc tcgcagtcgc cggatccaca   1380
ggcgccggca agacctctct gctgatggtt atcatgggcg aactggagcc atccgagggc   1440
aagattaagc acagtggaag aatctccttt tgtagccagt tcagttggat tatgcccggc   1500
actattaagg agaatatcat ttttggggtg agctatgatg agtatcggta tcggagcgtt   1560
atcaaagcct gtcagctgga ggaggatatc agcaaattcg cagagaagga taatatcgtg   1620
ctgggggagg ggggaatcac cctgagcgga ggccagagag ccagaatctc actggcccgg   1680
gccgtctaca aggacgccga cctttacctt ctggacagtc cctttggata tctggatgtg   1740
ctgactgaaa aggagatctt cgagtcttgt gtgtgcaagc tgatggctaa taagacccgg   1800
atcctagtga ccagtaagat ggagcacctg aagaaggcag acaagatctt gattctgcac   1860
gagggatcct cttactttta cggcaccttt agcgagctgc agaatctcca gcccgatttc   1920
tcatctaagc tgatgggctg tgatagcttc gaccagttct ctgccgagcg cagaaacagc   1980
atcctgacag agacactgca ccggttttca ctggagggcg acgcccctgt cagctggacc   2040
gagaccaaaa agcagtcttt caagcagaca ggcgagttcg gcgagaagcg caaaaacagc   2100
atcctgaatc caatcaactc tataaggaag tttagcatcg tgcagaagac acccctccag   2160
atgaacggca tcgaagagga cagtgacgag cccctggagc ggcgcctgag cctcgtgcct   2220
gacagcgaac agggcgaggc catcctgcct aggatcagcg tgatttcaac cgggccaaca   2280
ctgcaggcta ggagaagaca gtcagtgctt aacctgatga cacatagcgt gaatcaggga   2340
cagaacatcc atcgaaaaac cacagcctct actcgcaaag tgtcactggc tcctcaggct   2400
aatctgacag agctggacat ctatagcagg aggctgagcc aggagacagg cctggagatc   2460
agtgaggaga tcaacgaaga ggacctgaag gagtgctttt tcgatgacat ggagagtatc   2520
cccgccgtca ccacctggaa tacctacctc cggtacatca cagtgcacaa gtccctcatc   2580
tttgtgctga tttggtgcct cgtgatcttt ctcgcagaag tggccgcctc cctggtggtg   2640
ctgtggctgt tggggaatac tccactgcag gacaaaggca attctacaca cagcaggaat   2700
aattcctatg ccgtgattat caccagcaca tcctcttact acgtgttcta catctacgtg   2760
ggagtggcag atactctgct tgcaatgggc ttcttcaggg ggctgcccct ggtgcacaca   2820
ctgatcacag tgtccaagat cctccaccat aaaatgctcc acagcgtgct gcaggcaccc   2880
atgagcaccc tgaacacact gaaggccggc ggcatcctga atcgcttttc caaagacatc   2940
gccatcctcg acgatctcct gccactgacc atcttcgatt ttatccagct gctgctgatc   3000
gtgatcgggg ccatcgccgt ggtggccgtg ctgcagccat acattttcgt ggctacagtg   3060
cccgtgatcg ttgcctttat catgctgaga gcctacttcc tgcagacttc tcagcagctg   3120
aagcagctgg agagcgaagg gagaagcccc atcttcactc acctggtgac aagcctgaag   3180
ggactctgga ccctgagagc cttcggccgg cagccctatt tcgagaccct gtttcacaag   3240
gccctcaacc tgcacacagc caactggttt ctctacctgt ccaccctgag gtggttccag   3300
atgaggattg aaatgatctt cgtgattttt ttcatcgccg tgacattcat tagcattctg   3360
accaccggcg agggggaggg gagagtgggc atcatcctga cccttgccat gaacattatg   3420
tccacactgc agtgggccgt gaatagttca atcgacgtgg acagtctgat gaggtccgtg   3480
```

agccgggtgt tcaagttcat tgacatgccc acagagggga aacccaccaa aagcaccaag 3540
ccctacaaga acgggcagct gtccaaggtt atgatcatcg agaactctca cgtgaagaag 3600
gacgacattt ggcccagcgg cggccagatg acagtgaaag atctgaccgc caaatacacc 3660
gagggaggca acgccatcct cgaaaacatt agcttctcta tcagccctgg acagagggtg 3720
ggcctgctgg gccggacagg ctcagggaag agtactctgc tgtcagcatt cctgaggctc 3780
ctgaacacag agggcgagat ccagattgac ggcgtgtcct gggactccat caccctgcag 3840
cagtggcgga aggctttcgg ggtgatcccc cagaaggtgt tcatctttag cggcactttc 3900
agaaagaatc tggaccctta tgagcagtgg agtgaccagg agatctggaa agtggccgat 3960
gaggtcggac tgaggagcgt gatcgagcag tttccaggga agctggactt tgtgctggtg 4020
gatggcggat gcgtgctgtc tcacggccat aaacagctga tgtgtctggc ccggtccgtg 4080
ctgtctaagg ccaagatcct gctgctggac caaccctccg cccacctgga ccccgtgaca 4140
taccagatca tcaggagaac tctcaagcag gccttcgccg actgtaccgt gattctgtgc 4200
gagcaccgca ttgaagctat gctggagtgt cagcagttcc tggtgatcga ggaaaataag 4260
gtgaggcagt acgacagcat ccagaagctg ctgaacgagc gctccctgtt ccgccaggct 4320
atctccccat cagaccgggt gaagctcttt ccccacagaa actcctcaaa gtgcaagtcc 4380
aagccccaga tcgccgccct gaaggaggag accgaggagg aggtgcagga caccaggctg 4440
tga 4443

<210> SEQ ID NO 50
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 50
atgcagcgct cgcctctgga aaaggcgagc gtcgtgtcac ggctattctt ttcttggacc 60
cggcccattc tcaggaaggg ctacaggcag aggctggagt tgagcgacat ctatcagatt 120
ccttccgtgg acagcgccga caacctgagc gagaagctgg aaagggagtg ggaccgcgaa 180
ctggcaagca aaaagaaccc caagctgatc aatgccctga gaaggtgttt cttttggaga 240
ttcatgttct acgggatctt tctgtatctg ggcgaggtta caaaggctgt gcagcccctg 300
ctgctcggca gaatcatcgc ctcatacgat ccagacaaca aggaagaaag aagcatcgcc 360
atctacctgg gcattggcct ctgcctcctg tttattgtgc ggactctgct gctgcaccca 420
gcaattttcg ggttgcatca tattggcatg cagatgcgca ttgctatgtt ttccctcatc 480
tacaaaaaga cactgaaact cagctcccgg gtgctggaca agatctccat cggccaactg 540
gtgtctctcc tgagcaataa cttgaataag ttcgacgaag ggctggccct ggcacacttc 600
gtgtggattg ccccccctgca ggtggccctg ctgatgggac tgatttggga actgctgcag 660
gctagcgctt tctgcggcct ggggttcctg atcgtgctgg cactgtttca ggcaggcctg 720
ggccgtatga tgatgaagta cagagaccag agggccggga agatctccga acggctcgtt 780
attacctctg agatgatcga gaacattcag tctgtgaaag cctactgctg ggaggaggct 840
atggagaaga tgatcgagaa tctgagacag accgagctga agctgaccag aaaggccgcc 900
tacgtgaggt acttcaacag cagtgccttc ttcttctctg gcttcttcgt tgtgtttctg 960
agcgtgctgc catacgctct catcaaaggc atcatcctgc ggaagatctt caccaccatc 1020

-continued

```
agcttttgca tcgtgcttag aatggccgtg acccggcagt tcccatgggc cgtgcaaact   1080
tggtatgatt ccctgggcgc catcaacaaa atccaggatt tcctgcagaa gcaggaatac   1140
aagacactcg aatataatct cacaactact gaggtggtta tggagaacgt gactgccttc   1200
tgggaggagg ggttcggaga gctttttgag aaggcaaaac agaataacaa caaccgcaaa   1260
accgagaacg gcgacgacag cctgttcttc tccaattttt ctctcctggg aacacccgtc   1320
ctcaaagaca tcaactttaa gatcgagagg ggacagctgc tcgcagtcgc cggatccaca   1380
ggcgccggca agacctctct gctgatggtt atcatgggcg aactggagcc atccgagggc   1440
aagattaagc acagtggaag aatctccttt tgtagccagt tcagttggat tatgcccggc   1500
actattaagg agaatatcat ttttggggtg agctatgatg agtatcggta tcggagcgtt   1560
atcaaagcct gtcagctgga ggaggatatc agcaaattcg cagagaagga taatatcgtg   1620
ctgggggagg ggggaatcac cctgagcgga ggccagagag ccagaatctc actggcccgg   1680
gccgtctaca aggacgccga cctttacctt ctggacagtc cctttggata tctggatgtg   1740
ctgactgaaa aggagatctt cgagtcttgt gtgtgcaagc tgatggctaa taagacccgg   1800
atcctagtga ccagtaagat ggagcacctg aagaaggcag acaagatctt gattctgcac   1860
gagggatcct cttactttta cggcaccttt agcgagctgc agaatctcca gcccgatttc   1920
tcatctaagc tgatgggctg tgatagcttc gaccagttct ctgccgagcg cagaaacgaa   1980
atcctgacag agacactgca ccggtttgag ctggagggcg acgcccctgt cagctggacc   2040
gagaccaaaa agcaggaatt caagcaggag ggcgagttcg gcgagaagcg caaaaacgaa   2100
atcctgaatc caatcaactc tataaggaag tttgaaatcg tgcagaagac acccctccag   2160
atgaacggca tcgaagagga cagtgacgag cccctggagc ggcgcctgag cctcgtgcct   2220
gacagcgaac agggcgaggc catcctgcct aggatcgagg tgatttcaac cgggccaaca   2280
ctgcaggcta ggagaagaca gtcagtgctt aacctgatga cacatagcgt gaatcaggga   2340
cagaacatcc atcgaaaaga agaagccgaa actcgcaaag tggagctggc tcctcaggct   2400
aatctgacag agctggacat ctatagcagg aggctggaac aggagacagg cctggagatc   2460
agtgaggaga tcaacgaaga ggacctgaag gagtgctttt tcgatgacat ggagagtatc   2520
cccgccgtca ccacctggaa tacctacctc cggtacatca cagtgcacaa gtccctcatc   2580
tttgtgctga tttggtgcct cgtgatcttt ctcgcagaag tggccgcctc cctggtggtg   2640
ctgtggctgt tggggaatac tccactgcag gacaaaggca attctacaca cagcaggaat   2700
aattcctatg ccgtgattat caccagcaca tcctcttact acgtgttcta catctacgtg   2760
ggagtggcag atactctgct tgcaatgggc ttcttcaggg ggctgcccct ggtgcacaca   2820
ctgatcacag tgtccaagat cctccaccat aaaatgctcc acagcgtgct gcaggcaccc   2880
atgagcaccc tgaacacact gaaggccggc ggcatcctga atcgcttttc caaagacatc   2940
gccatcctcg acgatctcct gccactgacc atcttcgatt ttatccagct gctgctgatc   3000
gtgatcgggg ccatcgccgt ggtggccgtg ctgcagccat acattttcgt ggctacagtg   3060
cccgtgatcg ttgcctttat catgctgaga gcctacttcc tgcagacttc tcagcagctg   3120
aagcagctgg agagcgaagg gagaagcccc atcttcactc acctggtgac aagcctgaag   3180
ggactctgga ccctgagagc cttcggccgg cagccctatt tcgagaccct gtttcacaag   3240
gccctcaacc tgcacacagc caactggttt ctctacctgt ccaccctgag gtggttccag   3300
atgaggattg aaatgatctt cgtgattttt ttcatcgccg tgacattcat tagcattctg   3360
accaccggcg agggggaggg gagagtgggc atcatcctga cccttgccat gaacattatg   3420
```

tccacactgc agtgggccgt gaatagttca atcgacgtgg acagtctgat gaggtccgtg 3480
agccgggtgt tcaagttcat tgacatgccc acagagggga aacccaccaa aagcaccaag 3540
ccctacaaga acgggcagct gtccaaggtt atgatcatcg agaactctca cgtgaagaag 3600
gacgacattt ggcccagcgg cggccagatg acagtgaaag atctgaccgc caaatacacc 3660
gagggaggca acgccatcct cgaaaacatt agcttctcta tcagccctgg acagagggtg 3720
ggcctgctgg gccggacagg ctcagggaag agtactctgc tgtcagcatt cctgaggctc 3780
ctgaacacag agggcgagat ccagattgac ggcgtgtcct gggactccat caccctgcag 3840
cagtggcgga aggctttcgg ggtgatcccc cagaaggtgt tcatctttag cggcactttc 3900
agaaagaatc tggaccctta tgagcagtgg agtgaccagg agatctggaa agtggccgat 3960
gaggtcggac tgaggagcgt gatcgagcag tttccaggga agctggactt tgtgctggtg 4020
gatggcggat gcgtgctgtc tcacggccat aaacagctga tgtgtctggc ccggtccgtg 4080
ctgtctaagg ccaagatcct gctgctggac gaaccctccg cccacctgga ccccgtgaca 4140
taccagatca tcaggagaac tctcaagcag gccttcgccg actgtaccgt gattctgtgc 4200
gagcaccgca ttgaagctat gctggagtgt cagcagttcc tggtgatcga ggaaaataag 4260
gtgaggcagt acgacagcat ccagaagctg ctgaacgagc gctccctgtt ccgccaggct 4320
atctccccat cagaccgggt gaagctcttt ccccacagaa actcctcaaa gtgcaagtcc 4380
aagccccaga tcgccgccct gaaggaggag accgaggagg aggtgcagga caccaggctg 4440
tga 4443

<210> SEQ ID NO 51
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 51
atgcagcgct cgcctctgga aaaggcgagc gtcgtgtcac ggctattctt ttcttggacc 60
cggcccattc tcaggaaggg ctacaggcag aggctggagt tgagcgacat ctatcagatt 120
ccttccgtgg acagcgccga caacctgagc gagaagctgg aaagggagtg ggaccgcgaa 180
ctggcaagca aaaagaaccc caagctgatc aatgccctga gaaggtgttt cttttggaga 240
ttcatgttct acgggatctt tctgtatctg ggcgaggtta caaaggctgt gcagcccctg 300
ctgctcggca gaatcatcgc ctcatacgat ccagacaaca aggaagaaag aagcatcgcc 360
atctacctgg gcattggcct ctgcctcctg tttattgtgc ggactctgct gctgcaccca 420
gcaattttcg ggttgcatca tattggcatg cagatgcgca ttgctatgtt ttccctcatc 480
tacaaaaaga cactgaaact cagctcccgg gtgctggaca agatctccat cggccaactg 540
gtgtctctcc tgagcaataa cttgaataag ttcgacgaag ggctggccct ggcacacttc 600
gtgtggattg ccccccctgca ggtggccctg ctgatgggac tgatttggga actgctgcag 660
gctagcgctt tctgcggcct ggggttcctg atcgtgctgg cactgtttca ggcaggcctg 720
ggccgtatga tgatgaagta cagagaccag agggccggga agatctccga acggctcgtt 780
attacctctg agatgatcga gaacattcag tctgtgaaag cctactgctg ggaggaggct 840
atggagaaga tgatcgagaa tctgagacag accgagctga agctgaccag aaaggccgcc 900
tacgtgaggt acttcaacag cagtgccttc ttcttctctg gcttcttcgt tgtgtttctg 960

-continued

```
agcgtgctgc catacgctct catcaaaggc atcatcctgc ggaagatctt caccaccatc   1020
agcttttgca tcgtgcttag aatggccgtg acccggcagt tcccatgggc cgtgcaaact   1080
tggtatgatt ccctgggcgc catcaacaaa atccaggatt tcctgcagaa gcaggaatac   1140
aagacactcg aatataatct cacaactact gaggtggtta tggagaacgt gactgccttc   1200
tgggaggagg ggttcggaga gctttttgag aaggcaaaac agaataacaa caaccgcaaa   1260
accgagaacg gcgacgacag cctgttcttc tccaattttt ctctcctggg aacacccgtc   1320
ctcaaagaca tcaactttaa gatcgagagg ggacagctgc tcgcagtcgc cggatccaca   1380
ggcgccggca agacctctct gctgatggtt atcatgggcg aactggagcc atccgagggc   1440
aagattaagc acagtggaag aatctccttt tgtagccagt tcagttggat tatgcccggc   1500
actattaagg agaatatcat ttttggggtg agctatgatg agtatcggta tcggagcgtt   1560
atcaaagcct gtcagctgga ggaggatatc agcaaattcg cagagaagga taatatcgtg   1620
ctgggggagg ggggaatcac cctgagcgga ggccagagag ccagaatctc actggcccgg   1680
gccgtctaca aggacgccga cctttacctt ctggacagtc cctttggata tctggatgtg   1740
ctgactgaaa aggagatctt cgagtcttgt gtgtgcaagc tgatggctaa taagacccgg   1800
atcctagtga ccagtaagat ggagcacctg aagaaggcag acaagatctt gattctgcac   1860
gagggatcct cttactttta cggcaccttt agcgagctgc agaatctcca gcccgatttc   1920
tcatctaagc tgatgggctg tgatagcttc gaccagttct ctgccgagcg cagaaacgaa   1980
atcctgacag agacactgca ccggtttgag ctggagggcg acgcccctgt cagctggacc   2040
gagaccaaaa agcaggaatt caagcaggag ggcgagttcg gcgagaagcg caaaaacgaa   2100
atcctgaatc caatcaactc tataaggaag tttgaaatcg tgcagaagac acccctccag   2160
atgaacggca tcgaagagga cagtgacgag cccctggagc ggcgcctgga actcgtgcct   2220
gacagcgaac agggcgaggc catcctgcct aggatcgagg tgatttcaac cgggccaaca   2280
ctgcaggcta ggagaagaca ggaagtgctt aacctgatga cacatagcgt gaatcaggga   2340
cagaacatcc atcgaaaaga agaagccgaa actcgcaaag tggagctggc tcctcaggct   2400
aatctgacag agctggacat ctatagcagg aggctggaac aggagacagg cctggagatc   2460
agtgaggaga tcaacgaaga ggacctgaag gagtgctttt tcgatgacat ggagagtatc   2520
cccgccgtca ccacctggaa tacctacctc cggtacatca cagtgcacaa gtccctcatc   2580
tttgtgctga tttggtgcct cgtgatcttt ctcgcagaag tggccgcctc cctggtggtg   2640
ctgtggctgt tggggaatac tccactgcag gacaaaggca attctacaca cagcaggaat   2700
aattcctatg ccgtgattat caccagcaca tcctcttact acgtgttcta catctacgtg   2760
ggagtggcag atactctgct tgcaatgggc ttcttcaggg ggctgcccct ggtgcacaca   2820
ctgatcacag tgtccaagat cctccaccat aaaatgctcc acagcgtgct gcaggcaccc   2880
atgagcaccc tgaacacact gaaggccggc ggcatcctga atcgcttttc caaagacatc   2940
gccatcctcg acgatctcct gccactgacc atcttcgatt ttatccagct gctgctgatc   3000
gtgatcgggg ccatcgccgt ggtggccgtg ctgcagccat acattttcgt ggctacagtg   3060
cccgtgatcg ttgcctttat catgctgaga gcctacttcc tgcagacttc tcagcagctg   3120
aagcagctgg agagcgaagg gagaagcccc atcttcactc acctggtgac aagcctgaag   3180
ggactctgga ccctgagagc cttcggccgg cagccctatt tcgagaccct gtttcacaag   3240
gccctcaacc tgcacacagc caactggttt ctctacctgt ccaccctgag gtggttccag   3300
atgaggattg aaatgatctt cgtgattttt ttcatcgccg tgacattcat tagcattctg   3360
```

accaccggcg aggggggaggg gagagtgggc atcatcctga cccttgccat gaacattatg 3420
tccacactgc agtgggccgt gaatagttca atcgacgtgg acagtctgat gaggtccgtg 3480
agccgggtgt tcaagttcat tgacatgccc acagagggga aacccaccaa aagcaccaag 3540
ccctacaaga acgggcagct gtccaaggtt atgatcatcg agaactctca cgtgaagaag 3600
gacgacattt ggcccagcgg cggccagatg acagtgaaag atctgaccgc caaatacacc 3660
gagggaggca acgccatcct cgaaaacatt agcttctcta tcagccctgg acagagggtg 3720
ggcctgctgg gccggacagg ctcagggaag agtactctgc tgtcagcatt cctgaggctc 3780
ctgaacacag agggcgagat ccagattgac ggcgtgtcct gggactccat caccctgcag 3840
cagtggcgga aggctttcgg ggtgatcccc cagaaggtgt tcatctttag cggcactttc 3900
agaaagaatc tggaccctta tgagcagtgg agtgaccagg agatctggaa agtggccgat 3960
gaggtcggac tgaggagcgt gatcgagcag tttccaggga agctggactt tgtgctggtg 4020
gatggcggat gcgtgctgtc tcacggccat aaacagctga tgtgtctggc ccggtccgtg 4080
ctgtctaagg ccaagatcct gctgctggac gaaccctccg cccacctgga ccccgtgaca 4140
taccagatca tcaggagaac tctcaagcag gccttcgccg actgtaccgt gattctgtgc 4200
gagcaccgca ttgaagctat gctggagtgt cagcagttcc tggtgatcga ggaaaataag 4260
gtgaggcagt acgacagcat ccagaagctg ctgaacgagc gctccctgtt ccgccaggct 4320
atctccccat cagaccgggt gaagctcttt ccccacagaa actcctcaaa gtgcaagtcc 4380
aagccccaga tcgccgccct gaaggaggag accgaggagg aggtgcagga caccaggctg 4440
tga 4443

<210> SEQ ID NO 52
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 52
atgcagcgct cgcctctgga aaaggcgagc gtcgtgtcaa agctattctt ttcttggacc 60
cggcccattc tcaggaaggg ctacaggcag aggctggagt tgagcgacat ctatcagatt 120
ccttccgtgg acagcgccga caacctgagc gagaagctgg aaagggagtg ggaccgcgaa 180
ctggcaagca aaaagaaccc caagctgatc aatgccctga gaaggtgttt cttttggaga 240
ttcatgttct acgggatctt tctgtatctg ggcgaggtta caaaggctgt gcagcccctg 300
ctgctcggca gaatcatcgc ctcatacgat ccagacaaca aggaagaaag aagcatcgcc 360
atctacctgg gcattggcct ctgcctcctg tttattgtgc ggactctgct gctgcaccca 420
gcaattttcg ggttgcatca tattggcatg cagatgcgca ttgctatgtt ttccctcatc 480
tacaaaaaga cactgaaact cagctcccgg gtgctggaca agatctccat cggccaactg 540
gtgtctctcc tgagcaataa cttgaataag ttcgacgaag ggctggccct ggcacacttc 600
gtgtggattg cccccctgca ggtggccctg ctgatgggac tgatttggga actgctgcag 660
gctagcgctt tctgcggcct ggggttcctg atcgtgctgg cactgtttca ggcaggcctg 720
ggccgtatga tgatgaagta cagagaccag agggccggga agatctccga acggctcgtt 780
attacctctg agatgatcga gaacattcag tctgtgaaag cctactgctg ggaggaggct 840
atggagaaga tgatcgagaa tctgagacag accgagctga agctgaccag aaaggccgcc 900

-continued

```
tacgtgaggt acttcaacag cagtgccttc ttcttctctg gcttcttcgt tgtgtttctg    960
agcgtgctgc catacgctct catcaaaggc atcatcctgc ggaagatctt caccaccatc   1020
agcttttgca tcgtgcttag aatggccgtg acccggcagt tcccatgggc cgtgcaaact   1080
tggtatgatt ccctgggcgc catcaacaaa atccaggatt tcctgcagaa gcaggaatac   1140
aagacactcg aatataatct cacaactact gaggtggtta tggagaacgt gactgccttc   1200
tgggaggagg ggttcggaga gctttttgag aaggcaaaac agaataacaa caaccgcaaa   1260
accgagaacg gcgacgacag cctgttcttc tccaattttt ctctcctggg aacacccgtc   1320
ctcaaagaca tcaactttaa gatcgagagg ggacagctgc tcgcagtcgc cggatccaca   1380
ggcgccggca agacctctct gctgatggtt atcatgggcg aactggagcc atccgagggc   1440
aagattaagc acagtggaag aatctccttt tgtagccagt tcagttggat tatgcccggc   1500
actattaagg agaatatcat ttttggggtg agctatgatg agtatcggta tcggagcgtt   1560
atcaaagcct gtcagctgga ggaggatatc agcaaattcg cagagaagga taatatcgtg   1620
ctgggggagg ggggaatcac cctgagcgga ggccagagag ccagaatctc actggcccgg   1680
gccgtctaca aggacgccga cctttacctt ctggacagtc cctttggata tctggatgtg   1740
ctgactgaaa aggagatctt cgagtcttgt gtgtgcaagc tgatggctaa taagacccgg   1800
atcctagtga ccagtaagat ggagcacctg aagaaggcag acaagatctt gattctgcac   1860
gagggatcct cttactttta cggcaccttt agcgagctgc agaatctcca gcccgatttc   1920
tcatctaagc tgatgggctg tgatagcttc gaccagttct ctgccgagcg cagaaacgaa   1980
atcctgacag agacactgca ccggtttgag ctggagggcg acgcccctgt cagctggacc   2040
gagaccaaaa agcaggaatt caagcaggag ggcgagttcg gcgagaagcg caaaaacgaa   2100
atcctgaatc caatcaactc tataaggaag tttgaaatcg tgcagaagac accccctccag  2160
atgaacggca tcgaagagga cagtgacgag cccctggagc ggcgcctgag cctcgtgcct   2220
gacagcgaac agggcgaggc catcctgcct aggatcgagg tgatttcaac cgggccaaca   2280
ctgcaggcta ggagaagaca gtcagtgctt aacctgatga cacatagcgt gaatcaggga   2340
cagaacatcc atcgaaaaga agaagccgaa actcgcaaag tggagctggc tcctcaggct   2400
aatctgacag agctggacat ctatagcagg aggctggaac aggagacagg cctggagatc   2460
agtgaggaga tcaacgaaga ggacctgaag gagtgctttt tcgatgacat ggagagtatc   2520
cccgccgtca ccacctggaa tacctacctc cggtacatca cagtgcacaa gtccctcatc   2580
tttgtgctga tttggtgcct cgtgatcttt ctcgcagaag tggccgcctc cctggtggtg   2640
ctgtggctgt tggggaatac tccactgcag gacaaaggca attctacaca cagcaggaat   2700
aattcctatg ccgtgattat caccagcaca tcctcttact acgtgttcta catctacgtg   2760
ggagtggcag atactctgct tgcaatgggc ttcttcaggg ggctgcccct ggtgcacaca   2820
ctgatcacag tgtccaagat cctccaccat aaaatgctcc acagcgtgct gcaggcaccc   2880
atgagcaccc tgaacacact gaaggccggc ggcatcctga atcgcttttc caaagacatc   2940
gccatcctcg acgatctcct gccactgacc atcttcgatt ttatccagct gctgctgatc   3000
gtgatcgggg ccatcgccgt ggtggccgtg ctgcagccat acattttcgt ggctacagtg   3060
cccgtgatcg ttgcctttat catgctgaga gcctacttcc tgcagacttc tcagcagctg   3120
aagcagctgg agagcgaagg gagaagcccc atcttcactc acctggtgac aagcctgaag   3180
ggactctgga ccctgagagc cttcggccgg cagccctatt tcgagaccct gtttcacaag   3240
gccctcaacc tgcacacagc caactggttt ctctacctgt ccaccctgag gtggttccag   3300
```

-continued

```
atgaggattg aaatgatctt cgtgattttt ttcatcgccg tgacattcat tagcattctg   3360

accaccggcg agggggaggg gagagtgggc atcatcctga cccttgccat gaacattatg   3420

tccacactgc agtgggccgt gaatagttca atcgacgtgg acagtctgat gaggtccgtg   3480

agccgggtgt tcaagttcat tgacatgccc acagagggga aacccaccaa aagcaccaag   3540

ccctacaaga acgggcagct gtccaaggtt atgatcatcg agaactctca cgtgaagaag   3600

gacgacattt ggcccagcgg cggccagatg acagtgaaag atctgaccgc caaatacacc   3660

gagggaggca acgccatcct cgaaaacatt agcttctcta tcagccctgg acagagggtg   3720

ggcctgctgg gccggacagg ctcagggaag agtactctgc tgtcagcatt cctgaggctc   3780

ctgaacacag agggcgagat ccagattgac ggcgtgtcct gggactccat caccctgcag   3840

cagtggcgga aggctttcgg ggtgatcccc cagaaggtgt tcatctttag cggcactttc   3900

agaaagaatc tggaccctta tgagcagtgg agtgaccagg agatctggaa agtggccgat   3960

gaggtcggac tgaggagcgt gatcgagcag tttccaggga agctggactt tgtgctggtg   4020

gatggcggat gcgtgctgtc tcacggccat aaacagctga tgtgtctggc ccggtccgtg   4080

ctgtctaagg ccaagatcct gctgctggac gaaccctccg cccacctgga ccccgtgaca   4140

taccagatca tcaggagaac tctcaagcag gccttcgccg actgtaccgt gattctgtgc   4200

gagcaccgca ttgaagctat gctggagtgt cagcagttcc tggtgatcga ggaaaataag   4260

gtgaggcagt acgacagcat ccagaagctg ctgaacgagc gctccctgtt ccgccaggct   4320

atctccccat cagaccgggt gaagctcttt ccccacagaa actcctcaaa gtgcaagtcc   4380

aagccccaga tcgccgccct gaaggaggag accgaggagg aggtgcagga caccaggctg   4440

tga                                                                 4443
```